US010899769B2

(12) United States Patent
Le et al.

(10) Patent No.: US 10,899,769 B2
(45) Date of Patent: Jan. 26, 2021

(54) IMIDAZOPIPERAZINONE INHIBITORS OF TRANSCRIPTION ACTIVATING PROTEINS

(71) Applicant: Board of Regents, The University of Texas System, Austin, TX (US)

(72) Inventors: Kang Le, Sugar Land, TX (US); Michael J. Soth, Sugar Land, TX (US); Gang Liu, Sugar Land, TX (US); Philip Jones, Houston, TX (US); Jason Bryant Cross, Pearland, TX (US); Timothy Joseph Mcafoos, Pearland, TX (US); Christopher L. Carroll, Houston, TX (US); Richard T. Lewis, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/378,309

(22) Filed: Apr. 8, 2019

(65) Prior Publication Data

US 2019/0308978 A1 Oct. 10, 2019

Related U.S. Application Data

(60) Provisional application No. 62/653,643, filed on Apr. 6, 2018.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................. C07D 487/04
USPC ........................................................ 544/35
See application file for complete search history.

(56) References Cited

U.S. PATENT DOCUMENTS

| | | | | |
|---|---|---|---|---|
| 7,732,603 | B2 | 6/2010 | Mc Kenna | |
| 8,772,279 | B2 | 7/2014 | Mirizzi | |
| 9,145,418 | B2 | 9/2015 | Casuscelli | |
| 9,695,176 | B2 | 7/2017 | Degnan | |
| 2007/0004736 | A1* | 1/2007 | Kubo | C07D 401/04 514/249 |
| 2009/0149450 | A1 | 6/2009 | Beckett | |
| 2010/0093740 | A1 | 4/2010 | Aissaoui | |
| 2011/0190292 | A1 | 8/2011 | Dhar | |
| 2012/0220766 | A1 | 8/2012 | Tang | |
| 2016/0113893 | A1 | 4/2016 | Mulvany | |
| 2019/0298729 | A1 | 10/2019 | Le | |

FOREIGN PATENT DOCUMENTS

| | | |
|---|---|---|
| CN | 103087067 | 5/2013 |
| WO | 2016055028 | 4/2016 |
| WO | 2016086200 | 6/2016 |
| WO | 2016170323 | 10/2016 |
| WO | 2016170324 | 10/2016 |
| WO | 2017184462 | 10/2017 |
| WO | 2017205536 | 11/2017 |
| WO | 2017205538 | 11/2017 |
| WO | 2019191667 | 10/2019 |
| WO | 2019195846 | 10/2019 |

OTHER PUBLICATIONS

Dorwald F. A. Side Reactions in Organic Synthesis, 2005, Wiley: VCH, Weinheim p. IX of Preface p. 1-15.*
Venkatesh., J. Pharm. Sci. 89, 145-54 (2000) (p. 146, left column).*
CA Registry No. 1069782-59-7 entered into the CA Registry File on Nov. 2, 2008 supplied by ChemBridge Corporation. (Year: 2008).
ChemBridge Product Guide, 2 pages, retrieved from the internet at http://www.chembridge.com/screening_libraries/ on Aug. 9, 2015. (Year: 2015).
International Application No. PCT/US2019/022727; International Search Report and Written Opinion of the International Searching Authority, dated May 14, 2019; 8 pages.
International Application No. PCT/US2019/026379; International Search Report and Written Opinion of the International Searching Authority, dated Jul. 30, 2019; 8 pages.
Machine Translation for CN 103087067 (May 8, 2013). (Year: 2013).
PubChem CID: 89233298, Compound Summary ZNFWDQVOYHEDS 0-UHFFFAOYSA-N Create Date: Feb. 13, 2015, 8 pages.
U.S. Appl. No. 16/370,404; Non-Final Office Action, dated Dec. 12, 2019; pages.
Bronner, S. et al., "A Unique Approach to Design Potent and Selective Cyclic Adenosine Monophosphate Response Element Binding Protein (CBP) Inhibitors", J Med Chem., 60(24):10151-71, (2017).
Crawford, T. et al., "Discovery of a Potent and Selective In Vivo Probe (GNE-272) for the Bromodomains of CBP/EP300", J Med Chem., 59(23):10549-63, (2016).
International Application No. PCT/US2019/024976; International Search Report and Written Opinion of the International Searching Authority, dated Jul. 22, 2019; 11 pages.
Lai, K. et al., "Design and Synthesis of a Biaryl Series as Inhibitors for the Bromodomains of CBP/P300", Bioorg Med Chem Lett., 28(1):15-23, (2018).
Romero, F. et al., "GNE-781, A Highly Advanced Potent and Selective Bromodomain Inhibitor of Cyclic Adenosine Monophosphate Response Element Binding Protein, Binding Protein (CBP)", J Med Chem., 60(22):9162-83, (2017).
Taylor, A.M. et al., "Fragment-Based Discovery of a Selective and Cell-Active Benzodiazepinone CBP/EP300 Bromodomain Inhibitor (CPI-637)", ACS. Med. Chem. Lett., 7:531-6, (2016).
U.S. Appl. No. 16/370,404; Application as filed, filed Mar. 29, 2019; 231 pages.

* cited by examiner

*Primary Examiner* — Nizal S Chandrakumar
(74) *Attorney, Agent, or Firm* — Dennis A. Bennett; Cynthia Hathaway; John Desper

(57) ABSTRACT

The present disclosure relates to heterocyclic compounds and methods which may be useful as inhibitors of transcription activating proteins such as CBP and P300 for the treatment or prevention of diseases such as proliferative diseases, inflammatory disorders, autoimmune diseases, and fibrotic diseases.

26 Claims, No Drawings

IMIDAZOPIPERAZINONE INHIBITORS OF TRANSCRIPTION ACTIVATING PROTEINS

This application claims the benefit of priority of U.S. Provisional Application No. 62/653,643, filed Apr. 6, 2018, the disclosure of which is hereby incorporated by reference as if written herein in its entirety.

Disclosed herein are new imidazopiperazinone compounds and compositions and their application as pharmaceuticals for the treatment of disease. Methods of inhibition of the activity of transcription activating proteins such as CBP and P300 in a human or animal subject are also provided for the treatment of diseases such as cancer.

Chromatin is a combination of DNA and protein, found in eukaryotic nuclei, that makes up chromosomes. Chromatin can be classified as either heterochromatin (condensed) or euchromatin (extended) forms. The major protein components of chromatin are termed histones, which serve as scaffolds on which DNA is packaged and compacted into a smaller volume to fit in the nucleus. Histones are implicated in the processes of mitosis and meiosis, and are thought to play important roles in the expression and replication of DNA. Importantly, histones undergo post-translational modification ("PTM") at various amino acid sites, which modulates chromatin structure and thereby affects transcription. This modification provides a mechanism for "epigenetics", or the control of gene activity and expression that does not arise from the direct alteration of the DNA sequence.

Acetylation of lysine residues is a PTM with broad relevance to cellular signaling and disease biology. Lysine acetylation, which is particularly abundant in nuclear macromolecular complexes, plays a key role in chromatin regulation and transcriptional control. In cells, the principal 'readers' of the acetyl-lysine marks are the bromodomains (BRDs), which are a diverse family of evolutionary conserved protein-protein interaction modules that specifically recognize and bind to acetylated lysine residues. The bromodomains, together with the enzymes that 'write' (Histone acetyl transferases, HATs) and 'erase' (histone deacetylases, HDACs) acetylated lysine residues on histone and non-histone proteins, critically control the regulation of gene expression and thereby cell phenotype including proliferation, cell differentiation and metabolism. Besides chromatin, many other proteins are also post-translationally modified such as p53, which could also be potentially recognized by bromodomain proteins. Because chromatin-mediated processes are often deregulated in cancer, targeting epigenetic reader proteins like BET (dual-BRD4 containing proteins), CREBBP, ATAD2A, SMARCA2/4 and Tripartite Motif-containing 24 (TRIM24) represent promising targets for drug discovery. As illustrated by the development of selective inhibitors of the BET family of bromodomains, the conserved BRD fold represents a promising pocket for the development of small pharmaceutically active molecules.

The histone acetyltransferase paralogues, cyclic adenosine monophosphate response element binding protein, binding protein (CBP, CREBBP, or CREB-binding protein) and adenoviral E1A binding protein of 300 kDa (P300 or EP300), are highly homologous and are two closely related multi-domain transcription activating proteins containing both a histone acetyl transferase (HAT) as well as a bromodomain, and have important roles in histone acetylation. They are key transcriptional co-activators that are essential for a multitude of cellular processes, and have also been implicated in several human pathological conditions, including cancer.

CBP and P300 bind to chromatin via their bromodomains, and once associated with chromatin, this complex recruits additional transcriptional machinery to modulate gene expression leading to the recruitment of various transcriptional proteins to modulate gene expression. In addition to chromatin, CBP/P300 have been shown to bind non-histone proteins; for instance, CBP has been described to recognize acetylated p53 at K382 following DNA damage. Several studies have implicated CBP/P300 in the development, maintenance, and/or progression of cancer and tumor immunity, and therefore CBP/P300 inhibitors are the target of current efforts to develop anti-cancer agents. In particular, CBP has been found to regulate expression of MYC, a transcription factor and oncogene widely up-regulated in many human cancers, which suggests a potential therapeutic strategy for targeting multiple myeloma and other lymphoid malignancies, and solid tumors.

In addition, CBP and P300 are known co-activators of the androgen receptor (AR), and have been implicated in enhancing the response to androgen. Consistent with this, CBP/P300 have been proposed to play an oncogenic role in prostate cancer, and up-regulation of both proteins has been observed in tumors. CBP inhibitors selectively inhibit proliferation in lineage-specific tumour types, including several hematological malignancies and androgen receptor-positive prostate cancer. CBP inhibitors inhibit the androgen receptor transcriptional program in both androgen-sensitive and castration-resistant prostate cancer and inhibit tumour growth in prostate cancer xenograft models.

CBP also has relevance to cancer immunotherapy, and the ability of CBP bromodomain inhibitors to impair Treg differentiation and suppressive function has been described. This activity could constitute a novel small molecule approach to enhance the response to cancer immunotherapy.

Compounds and pharmaceutical compositions, certain of which have been found to bind to and inhibit interactions of CBP and P300 have been discovered, together with methods of synthesizing and using the compounds including methods for the treatment of CBP- and P300-mediated diseases in a patient by administering the compounds.

DETAILED DESCRIPTION

Provided herein is Embodiment 1: a compound having structural Formula I:

(I)

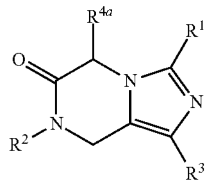

or a salt thereof, wherein:

$R^1$ is H or is chosen from alkyl, amino, alkoxy, heteroalkyl, cycloalkyl, heterocycloalkyl, halo, haloalkyl, sulfonylalkyl, aryl, and heteroaryl, any of which is optionally substituted with 1, 2, or 3 $R^5$ groups;

$R^2$ is H or is chosen from alkyl, cycloalkyl, heterocycloalkyl, and haloalkyl, any of which is optionally substituted with 1, 2, or 3 $R^6$ groups;

$R^3$ is chosen from alkyl, amino, alkoxy, heteroalkyl, cycloalkyl, heterocycloalkyl, alkylcarbonyl, alkylsulfonyl, arylcarbonyl, arylsulfonyl, aryl, and heteroaryl, any of which is:

(a) optionally substituted with 1, 2, or 3 $R^7$ groups, and
(b) optionally substituted with 1 $R^8$ group;

$R^{4a}$ is chosen from H, halo, alkyl, heteroalkyl, cycloalkyl and heterocycloalkyl, any of which is optionally substituted with 1, 2, or 3 $R^9$ groups;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ and $R^7$ is independently chosen from alkyl, alkoxy, cyano, carboxy, halo, haloalkoxy, haloalkyl, hydroxy, and oxo;

$R^8$ is chosen from heterocycloalkyl, aryl and heteroaryl, either of which is optionally substituted with 1, 2, or 3 $R^{10}$ groups;

each $R^9$ is independently chosen from alkyl, alkoxy, cyano, carboxy, halo, haloalkyl, hydroxy, and oxo; and each $R^{10}$ is independently chosen from alkyl, alkoxy, cyano, carboxy, halo, haloalkyl, and hydroxy.

Certain compounds disclosed herein may possess useful inhibiting activity for CBP or P300, and may be used in the treatment or prophylaxis of a disease or condition in which CBP or P300 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting CBP or P300. Other embodiments provide methods for treating a disorder mediated by CBP or P300 in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of CBP and P300.

In certain embodiments, $R^1$ is chosen from alkyl, alkoxy, amino, heteroalkyl, cycloalkyl, heterocycloalkyl, aryl, and heteroaryl, any of which is optionally substituted with 1, 2, or 3 $R^5$ groups.

In certain embodiments, $R^1$ is chosen from alkyl, cycloalkyl, and heterocycloalkyl, any of which is optionally substituted with 1 or 2 $R^5$ groups.

In certain embodiments, $R^1$ is chosen from alkyl, cycloalkyl, and heterocycloalkyl.

In certain embodiments, $R^1$ is cycloalkyl, and is optionally substituted with 1 or 2 $R^5$ groups.

In certain embodiments, $R^1$ is chosen from $C_{1-4}$alkyl, $C_{3-7}$cycloalkyl, tetrahydro-2H-pyran-4-yl, and tetrahydrofuranyl.

In certain embodiments, $R^1$ is tetrahydro-2H-pyran-4-yl.

In some embodiments, $R^1$ is chosen from $C_{1-4}$alkyl and $C_{3-7}$cycloalkyl.

In certain embodiments, $R^1$ is cyclopropyl.

In certain embodiments, $R^2$ is is chosen from alkyl, heteroalkyl, cycloalkyl, and heterocycloalkyl, any of which is optionally substituted with 1 or 2 $R^6$ groups.

In certain embodiments, $R^2$ is chosen from alkyl and cycloalkyl, either of which is optionally substituted with 1 or 2 $R^6$ groups.

In certain embodiments, $R^2$ is chosen from alkyl and cycloalkyl.

In certain embodiments, $R^2$ is $C_{1-4}$alkyl.

In certain embodiments, $R^2$ is methyl.

In certain embodiments, $R^3$ is chosen from alkyl, amino, alkoxy, heteroalkyl, cycloalkyl, heterocycloalkyl, alkylcarbonyl, alkylsulfonyl, arylcarbonyl, arylsulfonyl, aryl, and heteroaryl, any of which is:

(a) optionally substituted with 1, 2, or 3 $R^7$ groups, and
(b) substituted with 1 $R^8$ group.

In certain embodiments, $R^3$ is chosen from alkyl, amino, alkoxy, heteroalkyl, cycloalkyl, heterocycloalkyl, alkylcarbonyl, alkylsulfonyl, arylcarbonyl, arylsulfonyl, aryl, and heteroaryl, any of which is:

(a) optionally substituted with 1, 2, or 3 $R^7$ groups, and
(b) substituted with 1 $R^8$ group.

In certain embodiments, $R^3$ is chosen from aryl and heteroaryl, either of which is:

(a) optionally substituted with 1, 2, or 3 $R^7$ groups, and
(b) substituted with 1 $R^8$ group.

In certain embodiments, $R^3$ is heteroaryl, and is:

(a) optionally substituted with 1 or 2 $R^7$ groups, and
(b) substituted with 1 $R^8$ group;

In certain embodiments, $R^3$ is a nitrogen-containing heteroaryl, and is:

(a) optionally substituted with 1 or 2 $R^7$ groups, and
(b) substituted with 1 $R^8$ group.

In certain embodiments, $R^3$ is a bicyclic nitrogen-containing heteroaryl, and is:

(a) optionally substituted with 1 or 2 $R^7$ groups, and
(b) substituted with 1 $R^8$ group.

In certain embodiments, $R^3$ is a bicyclic heteroaryl containing 1 or 2 nitrogens, and is:

(a) optionally substituted with 1 or 2 $R^7$ groups, and
(b) substituted with 1 $R^8$ group.

In certain embodiments, $R^3$ is chosen from quinolinyl, isoquinolinyl, 1,2,3,4-tetrahydroquinolinyl, 1,2,3,4-tetrahydroisoquinolinyl, indolyl, indazolyl, purinyl, and 7-deazapurinyl.

In certain embodiments, each $R^5$, $R^6$, and $R^7$ is independently chosen from alkyl, alkoxy, halo, haloalkyl, hydroxy, and oxo.

In certain embodiments, $R^3$ is substituted with 1 $R^8$ group.

In certain embodiments, $R^{4a}$ is chosen from H, halo, alkyl, and heteroalkyl, any of which is optionally substituted with 1 or 2 $R^9$ groups.

In certain embodiments, $R^{4a}$ is H or is alkyl, which is optionally substituted with 1 or 2 $R^9$ groups.

In certain embodiments, $R^{4a}$ is alkyl and is optionally substituted with 1 or 2 $R^9$ groups.

In certain embodiments, $R^{4a}$ is unsubstituted alkyl.

In certain embodiments, $R^{4a}$ is chosen from H, fluoro, methyl, and ethyl.

In certain embodiments, $R^{4a}$ is chosen from H and alkyl.

In certain embodiments, $R^{4a}$ is chosen from H and methyl.

In certain embodiments, $R^{4a}$ is H.

In certain embodiments, $R^8$ is a monocyclic aryl or heteroaryl, either of which is optionally substituted with 1 or 2 $R^{10}$ groups.

In certain embodiments, $R^8$ is a nitrogen-containing heteroaryl, and is optionally substituted with 1 or 2 $R^{10}$ groups.

In certain embodiments, $R^8$ is a monocyclic nitrogen-containing heteroaryl, and is optionally substituted with 1 or 2 $R^{10}$ groups.

In certain embodiments, $R^8$ is chosen from pyrrolyl, imidazolyl, and pyrazolyl, any of which is optionally substituted with 1 or 2 $R^{10}$ groups.

In certain embodiments, $R^8$ is a monocyclic heteroaryl, and is optionally substituted with 1 or 2 $R^{10}$ groups.

In certain embodiments, $R^8$ is chosen from pyrrolyl, pyrazolyl, and imidazolyl, and is optionally substituted with 1 or 2 $R^{10}$ groups.

In certain embodiments, $R^8$ is pyrazol-4-yl, and is optionally substituted with 1 or 2 $R^{10}$ groups.

In certain embodiments, each $R^{10}$ is independently chosen from alkyl and alkoxy.

In certain embodiments, each $R^{10}$ is $C_{1-4}$alkyl.

In certain embodiments, $R^3$ is substituted with 1, 2, or 3 $R^7$ groups.

Provided herein is Embodiment 2: a compound having structural Formula II:

(II)

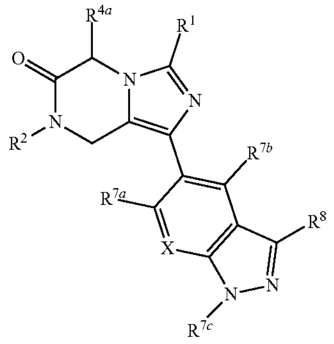

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, cycloalkyl, heterocycloalkyl, and haloalkyl, any of which is optionally substituted with 1, 2, or 3 $R^6$ groups;

$R^{4a}$ is chosen from H, halo, alkyl, heteroalkyl, cycloalkyl and heterocycloalkyl, any of which is optionally substituted with 1, 2, or 3 $R^9$ groups;

X is chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$, $R^{7b}$, and $R^{7c}$ are independently chosen from H, alkyl, alkoxy, cyano, carboxy, halo, haloalkyl, and hydroxy;

$R^8$ is chosen from heterocycloalkyl, aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

In certain embodiments of the compounds of Formula II, $R^{7a}$, $R^{7b}$, and $R^{7c}$ are H.

Embodiment 3: the compound of Embodiment 2, wherein $R^{7a}$, $R^{7b}$, and $R^{7c}$ are independently chosen from H, alkyl, alkoxy, and haloalkyl.

Embodiment 4: the compound of either one of Embodiments 2 and 3, wherein at least one of $R^{7a}$, $R^{7b}$, and $R^{7c}$ is H.

Embodiment 5: the compound of any one of Embodiments 2-4, wherein at least two of $R^{7a}$, $R^{7b}$, and $R^{7c}$ are H.

Embodiment 6: the compound of Embodiment 5, wherein $R^{7c}$ is alkyl.

Embodiment 7: the compound of Embodiment 6, wherein $R^{7c}$ is methyl.

Embodiment 8: the compound of any one of Embodiments 2-5, wherein $R^{7a}$, $R^{7b}$, and $R^{7c}$ are H.

Embodiment 9: the compound of any one of Embodiments 2-8, wherein X is CH.

Embodiment 10: the compound of any one of Embodiments 2-8, wherein X is N.

Provided herein is Embodiment 11: a compound having structural Formula III:

(III)

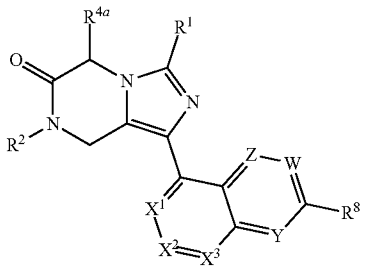

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, cycloalkyl, heterocycloalkyl, and haloalkyl, any of which is optionally substituted with 1, 2, or 3 $R^6$ groups;

$R^{4a}$ is chosen from H, halo, alkyl, heteroalkyl, cycloalkyl and heterocycloalkyl, any of which is optionally substituted with 1, 2, or 3 $R^9$ groups;

W is chosen from $C(R^{7a})$ and N;

$X^1$ is independently chosen from $C(R^{7b})$ and N;

$X^2$ and $X^3$ are independently chosen from C(H) and N;

Y and Z are independently chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, hydroxy, and oxo;

$R^{7b}$ is chosen from H and fluoro;

$R^8$ is chosen from heterocycloalkyl, aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

Embodiment 12: the compound of Embodiment 11, wherein $R^{7b}$ is H.

Embodiment 13: the compound of Embodiment 11, wherein $R^{7b}$ is fluoro.

Embodiment 14: the compound of any one of Embodiments 11-13, wherein at least one of $X^1$, $X^2$, and $X^3$ is N.

Embodiment 15: the compound of any one of Embodiments 11-13, wherein at most one of $X^1$, $X^2$, and $X^3$ is N.

Embodiment 16: the compound of any one of Embodiments 11-13, wherein exactly one of $X^1$, $X^2$, and $X^3$ is N.

Embodiment 17: the compound of Embodiment 16, wherein:

$X^1$ is N, $X^2$ is C(H), and $X^3$ is C(H).

Embodiment 18: the compound of Embodiment 16, wherein:

$X^1$ is $C(R^{7b})$, $X^2$ is N, and $X^3$ is C(H).

Embodiment 19: the compound of Embodiment 16, wherein:

$X^1$ is $C(R^{7b})$, $X^2$ is C(H), and $X^3$ is N.

Embodiment 20: the compound of any one of Embodiments 11-19, wherein at most two of W, Y, and Z is N.

Embodiment 21: the compound of Embodiment 20, wherein exactly one of W, Y and Z is N.

Embodiment 22: the compound of any one of Embodiments 11-21, wherein W is $C(R^{7a})$.

Embodiment 23: the compound of Embodiment 22, wherein Y is CH.

Embodiment 24: the compound of Embodiment 22, wherein Z is CH.

Embodiment 25: the compound of any one of Embodiments 22-24, wherein $R^{7a}$ is chosen from H, alkyl, alkoxy, cyano, and haloalkyl.

Embodiment 26: the compound of Embodiment 25, wherein $R^{7a}$ is H.

Embodiment 27: the compound of Embodiment 25, wherein $R^{7a}$ is methyl.

Embodiment 28: the compound of Embodiment 25, wherein $R^{7a}$ is cyano.

Embodiment 29: the compound of Embodiment 25, wherein $R^{7a}$ is haloalkyl.

Embodiment 30: the compound of Embodiment 29, wherein $R^{7a}$ is difluoromethyl.

Embodiment 31: the compound of Embodiment 29, wherein $R^{7a}$ is trifluoromethyl.

Embodiment 32: the compound of any one of Embodiments 11-21, wherein W is N.

Provided herein is Embodiment 33: a compound having structural Formula IIIa:

(IIIa)

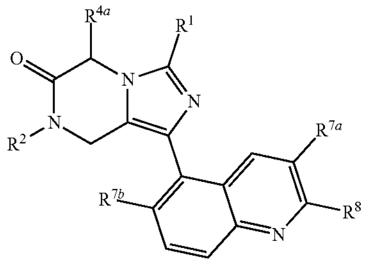

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, cycloalkyl, heterocycloalkyl, and haloalkyl, any of which is optionally substituted with 1, 2, or 3 $R^6$ groups;

$R^{4a}$ is chosen from H, halo, alkyl, heteroalkyl, cycloalkyl and heterocycloalkyl, any of which is optionally substituted with 1, 2, or 3 $R^9$ groups;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, hydroxy, and oxo;

$R^{7b}$ is chosen from H and fluoro;

$R^8$ is chosen from heterocycloalkyl, aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

Embodiment 34: the compound of Embodiment 33, wherein $R^{7b}$ is H.

Embodiment 35: the compound of Embodiment 33, wherein $R^{7b}$ is fluoro.

Embodiment 36: the compound of any one of Embodiments 33-35, wherein $R^{7a}$ is chosen from H, alkyl, alkoxy, cyano, and haloalkyl.

Embodiment 37: the compound of Embodiment 36, wherein $R^{7a}$ is H.

Embodiment 38: the compound of Embodiment 36, wherein $R^{7a}$ is methyl.

Embodiment 39: the compound of Embodiment 36, wherein $R^{7a}$ is cyano.

Embodiment 40: the compound of Embodiment 36, wherein $R^{7a}$ is haloalkyl.

Embodiment 41: the compound of Embodiment 40, wherein $R^{7a}$ is difluoromethyl.

Embodiment 42: the compound of Embodiment 40, wherein $R^{7a}$ is trifluoromethyl.

Provided herein is Embodiment 43: a compound having structural Formula IV:

(IV)

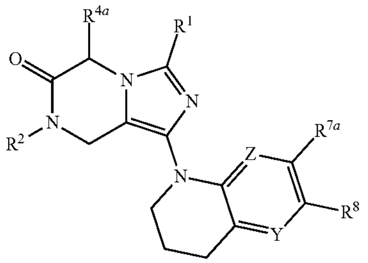

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, cycloalkyl, heterocycloalkyl, and haloalkyl, any of which is optionally substituted with 1 or 2 $R^6$ groups;

$R^{4a}$ is chosen from H, halo, alkyl, cycloalkyl and heterocycloalkyl;

Y and Z are independently chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, and hydroxy;

$R^{8a}$ is chosen from aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

In certain embodiments of the compounds of Formula IV, $R^{7a}$ is chosen from alkyl, alkoxy, and haloalkyl.

Embodiment 44: the compound of Embodiment 43, wherein exactly one of Y and Z is N.

Embodiment 45: the compound of Embodiment 43, wherein Y and Z are CH.

Embodiment 46: the compound of any one of Embodiments 43-45, wherein $R^{7a}$ is chosen from H, alkyl, alkoxy, cyano, and haloalkyl.

Embodiment 47: the compound of any one of Embodiments 43-45, wherein $R^{7a}$ is chosen from alkyl, alkoxy, and haloalkyl.

Embodiment 48: the compound of Embodiment 47, wherein $R^{7a}$ is H.

Embodiment 49: the compound of Embodiment 47, wherein $R^{7a}$ is haloalkyl.

Embodiment 50: the compound of Embodiment 49, wherein $R^{7a}$ is difluoromethyl.

Embodiment 51: the compound of Embodiment 49, wherein $R^{7a}$ is trifluoromethyl.

Embodiment 52: the compound of Embodiment 1, wherein $R^3$ is chosen from aryl and heteroaryl, either of which is:

(a) optionally substituted with 1, 2, or 3 $R^7$ groups, and (b) substituted with 1 $R^8$ group.

Embodiment 53: the compound of Embodiment 52, wherein $R^3$ is heteroaryl, and is:

(a) optionally substituted with 1 or 2 $R^7$ groups, and (b) substituted with 1 $R^8$ group;

Embodiment 54: the compound of Embodiment 53, wherein $R^3$ is a nitrogen-containing heteroaryl, and is:

(a) optionally substituted with 1 or 2 $R^7$ groups, and (b) substituted with 1 $R^8$ group.

Embodiment 55: the compound of Embodiment 54, wherein $R^3$ is a bicyclic nitrogen-containing heteroaryl, and is:

(a) optionally substituted with 1 or 2 $R^7$ groups, and (b) substituted with 1 $R^8$ group.

Embodiment 56: the compound of Embodiment 55, wherein $R^3$ is a bicyclic heteroaryl containing 1 or 2 nitrogens, and is:

(a) optionally substituted with 1 or 2 $R^7$ groups, and (b) substituted with 1 $R^8$ group.

Embodiment 57: the compound of Embodiment 56, wherein $R^3$ is chosen from quinolinyl, isoquinolinyl, 1,2,3,4-tetrahydroquinolinyl, 1,2,3,4-tetrahydroisoquinolinyl, indolyl, indazolyl, purinyl, and 7-deazapurinyl.

Embodiment 58: the compound of Embodiment 56, wherein $R^3$ is chosen from naphthalenyl, benzothiophenyl, quinolinyl, isoquinolinyl, naphthyridinyl, 1,2,3,4-tetrahydroquinolinyl, and indazolyl, any of which is:

(a) optionally substituted with 1, 2, or 3 $R^7$ groups, and (b) optionally substituted with 1 $R^8$ group.

Embodiment 59: a compound of Embodiment 58, wherein $R^3$ is chosen from quinolinyl, isoquinolinyl, 1,2,3,4-tetrahydroquinolinyl, and indazolyl, any of which is:

(a) optionally substituted with 1, 2, or 3 $R^7$ groups, and (b) optionally substituted with 1 $R^8$ group.

Embodiment 60: a compound of Embodiment 59, wherein $R^3$ is chosen from quinolin-5-yl, isoquinolin-8-yl, 1,2,3,4-tetrahydroquinolin-1-yl, and indazol-5-yl, any of which is:

(a) optionally substituted with 1, 2, or 3 $R^7$ groups, and (b) optionally substituted with 1 $R^8$ group.

Embodiment 61: a compound of Embodiment 59, wherein $R^3$ is quinolin-5-yl and is:

(a) optionally substituted with 1, 2, or 3 $R^7$ groups, and (b) optionally substituted with 1 $R^8$ group.

Embodiment 62: a compound of Embodiment 59, wherein $R^3$ is isoquinolin-8-yl and is:

(a) optionally substituted with 1, 2, or 3 $R^7$ groups, and (b) optionally substituted with 1 $R^8$ group.

Embodiment 63: a compound of Embodiment 59, wherein $R^3$ is 1,2,3,4-tetrahydroquinolin-1-yl and is:

(a) optionally substituted with 1, 2, or 3 $R^7$ groups, and (b) optionally substituted with 1 $R^8$ group.

Embodiment 64: a compound of Embodiment 59, wherein $R^3$ is indazol-5-yl and is:

(a) optionally substituted with 1, 2, or 3 $R^7$ groups, and (b) optionally substituted with 1 $R^8$ group.

Embodiment 65: a compound of Embodiment 1, wherein $R^3$ is chosen from:

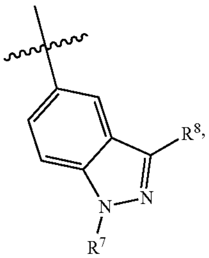
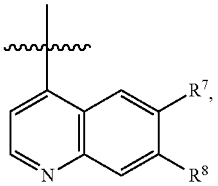
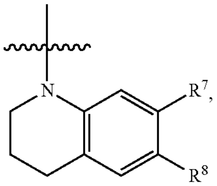
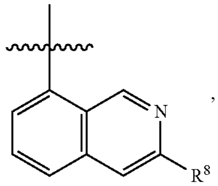
,
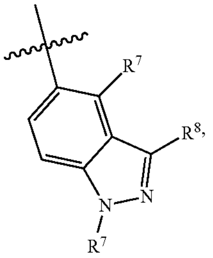
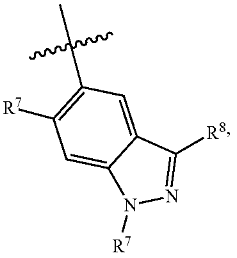
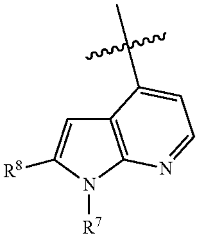
,
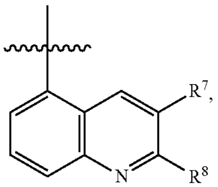
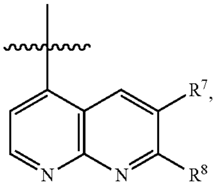
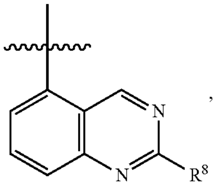
, -continued

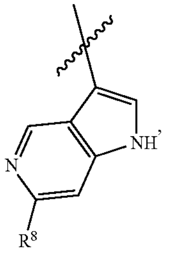
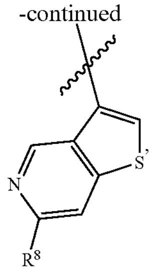
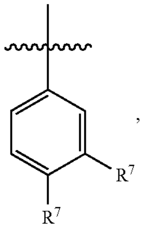
,
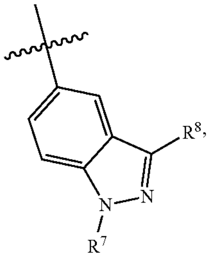
and
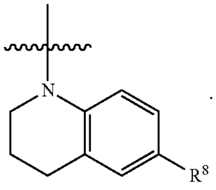
.

Embodiment 66: a compound of any one of Embodiments 1-65, wherein $R^3$ is substituted with 1 $R^8$ group.

Embodiment 67: a compound of Embodiment 66 wherein $R^8$ is optionally substituted with 1 or 2 $R^{10}$ groups.

Embodiment 68: a compound of Embodiment 67 wherein $R^8$ is substituted with 1 or 2 $R^{10}$ groups.

Embodiment 69: a compound of Embodiment 68 wherein $R^8$ is substituted with 1 $R^{10}$ group.

Embodiment 70: a compound of Embodiment 67 wherein $R^8$ is optionally substituted with 1 $R^{10}$ group.

Embodiment 71: a compound of any one of Embodiments 66-70 wherein each $R^{10}$ is independently chosen from alkyl, cyclopropyl, cyclobutyl, (cycloalkyl)methyl, heterocycloalkyl, aryl, (aryl)methyl, (heteroaryl)methyl, methoxy, cyano, halo, difluoromethyl, trifluoromethyl, trifluoromethoxy, hydroxy, hydroxyalkyl, oxo, $CONH_2$, and $CONHCH_3$.

Embodiment 72: a compound of Embodiment 71 wherein each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

Embodiment 73: a compound of Embodiment 72 wherein each $R^{10}$ is alkyl.

Embodiment 74: a compound of Embodiment 73 wherein each $R^{10}$ is methyl.

Embodiment 75: a compound of Embodiment 70 wherein $R^8$ is not substituted with an $R^{10}$ group.

Embodiment 76: a compound of any one of Embodiments 66-75, wherein $R^8$ is heteroaryl.

Embodiment 77: a compound of Embodiment 76, wherein $R^8$ is 5-membered monocyclic heteroaryl.

Embodiment 78: a compound of Embodiment 77, wherein $R^8$ is chosen from pyrrolyl, pyrazolyl, imidazolyl, oxazolyl, isoxazolyl, furyl, thienyl, and thiazolyl.

Embodiment 79: a compound of Embodiment 76, wherein $R^8$ is 6-membered monocyclic heteroaryl.

Embodiment 80: a compound of Embodiment 79, wherein $R^8$ is chosen from pyridinyl, pyridazinyl, pyrimidinyl, and pyrazinyl.

Embodiment 81: a compound of any one of Embodiments 66-75, wherein $R^8$ is aryl.

Embodiment 82: a compound of Embodiment 81, wherein $R^8$ is phenyl.

Embodiment 83: a compound of Embodiment 66, wherein $R^8$ is chosen from:

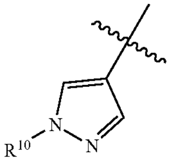
,
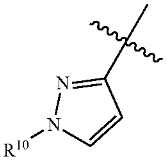
,
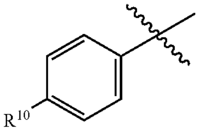
,
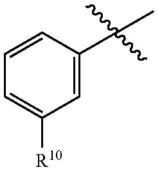
,
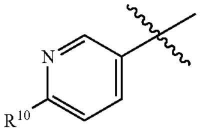
,
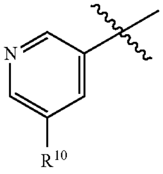
,
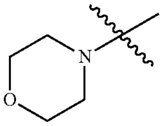
,
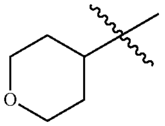
,
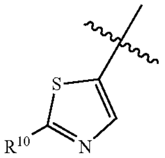
,
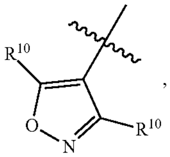
, and
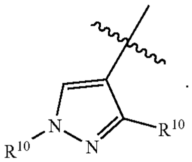
.

Embodiment 85: a compound of Embodiment 83, wherein $R^8$ is

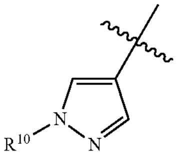
.

Embodiment 85: a compound of Embodiment 83, wherein $R^8$ is

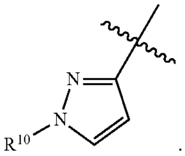
.

Embodiment 86: a compound of Embodiment 83, wherein $R^8$ is

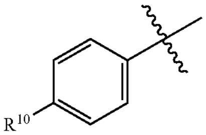
.

Embodiment 87: a compound of Embodiment 83, wherein $R^8$ is

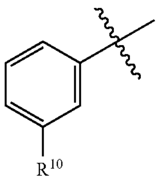
.

Embodiment 88: a compound of Embodiment 83, wherein $R^8$ is

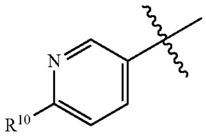
.

Embodiment 89: a compound of Embodiment 83, wherein $R^8$ is

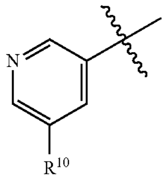
.

Embodiment 90: a compound of Embodiment 83, wherein $R^8$ is

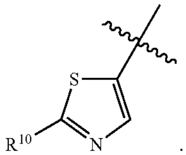
.

Embodiment 91: a compound of Embodiment 83, wherein $R^8$ is

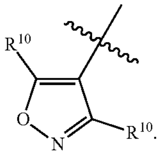

Embodiment 92: a compound of Embodiment 83, wherein $R^8$ is

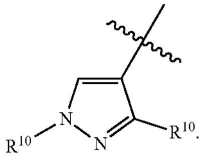

Embodiment 93: a compound of any one of Embodiments 83-92 wherein each $R^{10}$ is independently chosen from alkyl, cyclopropyl, cyclobutyl, (cycloalkyl)methyl, heterocycloalkyl, aryl, (aryl)methyl, (heteroaryl)methyl, methoxy, cyano, halo, difluoromethyl, trifluoromethyl, trifluoromethoxy, hydroxy, hydroxyalkyl, oxo, $CONH_2$, and $CONHCH_3$.

Embodiment 94: a compound of Embodiment 93 wherein each $R^{10}$ is independently chosen from alkyl, cyclopropyl, methoxy, cyano, halo, difluoromethyl, trifluoromethyl, trifluoromethoxy, hydroxy, $CONH_2$, and $CONHCH_3$.

Embodiment 95: a compound of Embodiment 94 wherein each $R^{10}$ is alkyl.

Embodiment 96: a compound of Embodiment 95 wherein each $R^{10}$ is methyl.

Embodiment 97: a compound of Embodiment 83, wherein $R^8$ is

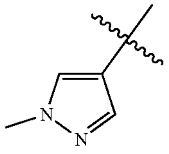
.

Embodiment 98: a compound of Embodiment 83, wherein $R^8$ is

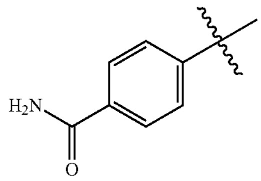
.

Embodiment 99: a compound of Embodiment 83, wherein $R^8$ is

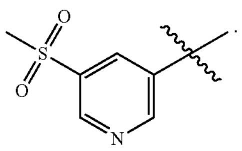 [SMILES: *c1cncc(S(C)(=O)=O)c1]

Embodiment 100: a compound of Embodiment 83, wherein $R^8$ is

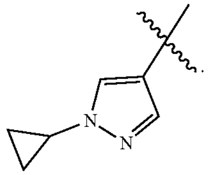 [SMILES: *c1cnn(C2CC2)c1]

Embodiment 101: a compound of Embodiment 83, wherein $R^8$ is

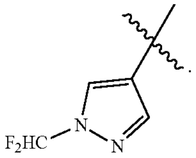 [SMILES: *c1cnn(C(F)F)c1]

Embodiment 102: a compound of Embodiment 83, wherein $R^8$ is

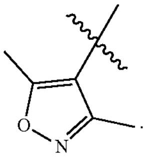

Embodiment 103: a compound of Embodiment 83, wherein $R^8$ is

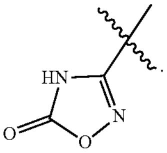 [SMILES: *c1noc(=O)[nH]1]

Embodiment 104: a compound of Embodiment 83, wherein $R^8$ is

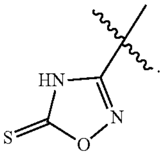 [SMILES: *c1noc(=S)[nH]1]

Embodiment 105: a compound of Embodiment 83, wherein $R^8$ is

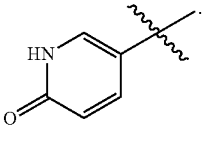 [SMILES: *c1ccc(=O)[nH]c1]

Embodiment 106: a compound of Embodiment 83, wherein $R^8$ is

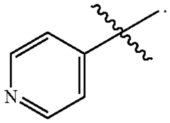 [SMILES: *c1ccncc1]

Embodiment 107: a compound of Embodiment 83, wherein $R^8$ is

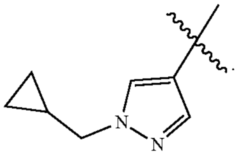 [SMILES: *c1cnn(CC2CC2)c1]

Embodiment 108: a compound of Embodiment 83, wherein $R^8$ is

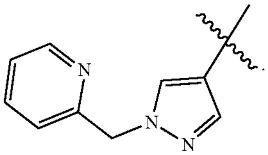 [SMILES: *c1cnn(Cc2ccccn2)c1]

Embodiment 109: a compound of Embodiment 83, wherein $R^8$ is

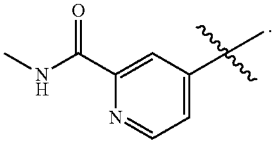 [SMILES: *c1ccnc(C(=O)NC)c1]

Embodiment 110: a compound of Embodiment 83, wherein $R^8$ is

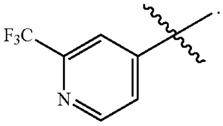 [SMILES: *c1ccnc(C(F)(F)F)c1]

Embodiment 111: a compound of Embodiment 83, wherein $R^8$ is

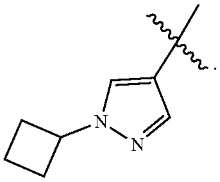 [SMILES: *c1cnn(C2CCC2)c1]

Embodiment 112: a compound of Embodiment 83, wherein $R^8$ is

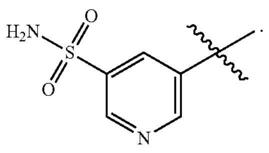 [SMILES: *c1cncc(S(N)(=O)=O)c1]

Embodiment 113: a compound of Embodiment 83, wherein $R^8$ is

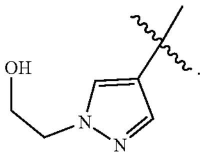 [SMILES: *c1cnn(CCO)c1]

Embodiment 114: a compound of Embodiment 83, wherein $R^8$ is

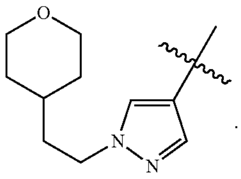 [SMILES: *c1cnn(CCC2CCOCC2)c1]

Embodiment 115: a compound of Embodiment 83, wherein $R^8$ is

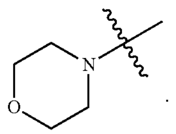 [SMILES: *N1CCOCC1]

Embodiment 116: a compound of Embodiment 83, wherein $R^8$ is

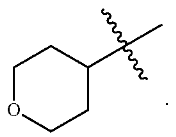 [SMILES: *C1CCOCC1]

Embodiment 117: a compound of a compound of any one of Embodiments 1-65, wherein $R^3$ is unsubstituted with an $R^8$ group.

Embodiment 118: a compound of any one of Embodiments 1-117, wherein $R^1$ is H or is chosen from alkyl, cycloalkyl, and heterocycloalkyl, any of which is optionally substituted with 1, 2, or 3 $R^5$ groups.

Embodiment 119: a compound of Embodiment 118, wherein $R^1$ is chosen from alkyl, cycloalkyl, and heterocycloalkyl, any of which is optionally substituted with 1, 2, or 3 $R^5$ groups.

Embodiment 120: a compound of Embodiment 118, wherein $R^1$ is H.

Embodiment 121: a compound of any one of Embodiments 1-119, wherein $R^1$ is optionally substituted with 1 or 2 $R^5$ groups.

Embodiment 122: a compound of Embodiment 121, wherein $R^1$ is substituted with 1 or 2 $R^5$ groups.

Embodiment 123: a compound of Embodiment 122, wherein $R^1$ is substituted with 1 $R^5$ group.

Embodiment 124: a compound of Embodiment 121, wherein $R^1$ is optionally substituted with 1 $R^5$ group.

Embodiment 125: a compound of Embodiment 121, wherein $R^1$ is not substituted with an $R^5$ group.

Embodiment 126: a compound of Embodiment 125, wherein $R^1$ is chosen from:

$—CH_3$, $—CH(CH_3)_2$,

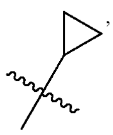, 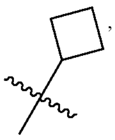, 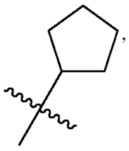, 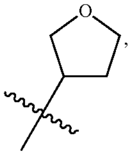,

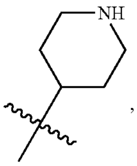, and 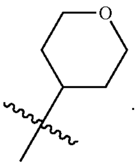 [SMILES: *C1CCOCC1].

Embodiment 127: a compound of Embodiment 126, wherein $R^1$ is

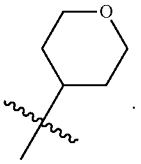

Embodiment 128: a compound of Embodiment 126, wherein $R^1$ is

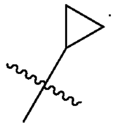

Embodiment 129: the compound of any one of Embodiments 1-128, wherein $R^2$ is H or is chosen from alkyl, cycloalkyl, and heterocycloalkyl, any of which is optionally substituted with 1 or 2 $R^6$ groups.

Embodiment 130: the compound of Embodiment 129, wherein $R^2$ is chosen from alkyl and cycloalkyl, either of which is optionally substituted with 1 or 2 $R^6$ groups.

Embodiment 131: the compound of Embodiment 130, wherein $R^2$ is alkyl and is optionally substituted with 1 or 2 $R^6$ groups Embodiment 132: the compound of any one of Embodiments 1-131, wherein each $R^6$ is independently chosen from alkoxy, cyano, halo, haloalkyl, and hydroxy.

Embodiment 133: the compound of Embodiment 131, wherein $R^2$ is chosen from $—CH_3$, $—CH_2F$, amino, and $—OCH_3$.

Embodiment 134: the compound of Embodiment 133, wherein $R^2$ is chosen from $—CH_3$, $—CH_2F$, $—NH_2$, $—NHCH_3$, and $—OCH_3$.

Embodiment 135: the compound of Embodiment 134, wherein $R^2$ is chosen from —$CH_3$ and —$NHCH_3$.

Embodiment 136: the compound of Embodiment 135, wherein $R^2$ is —$CH_3$.

Embodiment 137: the compound of any one of Embodiments 1-136, wherein each $R^7$ is independently chosen from methyl, ethyl, methoxy, cyano, $NH_2$, halo, difluoromethyl, trifluoromethyl, and trifluoromethoxy.

Embodiment 138: the compound of Embodiment 137, wherein each $R^7$ is independently chosen from methyl, methoxy, cyano, fluoro, difluoromethyl, trifluoromethyl, and trifluoromethoxy.

Embodiment 139: the compound of Embodiment 138, wherein each $R^7$ is independently chosen from methyl, fluoro, and difluoromethyl.

Embodiment 140: the compound of any one of 1-139, wherein at least one $R^7$ is is methyl.

Embodiment 141: the compound of any one of 1-140, wherein at least one $R^7$ is is fluoro.

Embodiment 142: the compound of any one of 1-141, wherein at least one $R^7$ is is difluoromethyl.

Embodiment 143: the compound of any one of Embodiments 1-142, wherein $R^{4a}$ is chosen from H, halo, and alkyl, any of which is optionally substituted with 1, 2, or 3 $R^9$ groups.

Embodiment 144: the compound of any one of Embodiments 1-143, wherein $R^{4a}$ is alkyl and is optionally substituted with 1, 2, or 3 $R^9$ groups.

Embodiment 145: the compound of Embodiment 144, wherein $R^{4a}$ is alkyl and is optionally substituted with 1 $R^9$ group.

Embodiment 146: the compound of any one of Embodiments 1-145, wherein each $R^9$ is independently chosen from cyano, halo, hydroxy, and oxo.

Embodiment 147: the compound of Embodiment 143, wherein $R^{4a}$ is chosen from H, fluoro, methyl, and ethyl.

Embodiment 148: the compound of Embodiment 147, wherein $R^{4a}$ is chosen from H, fluoro, and methyl.

Embodiment 149: the compound of Embodiment 148, wherein $R^{4a}$ is H.

Embodiment 150: the compound of Embodiment 148, wherein $R^{4a}$ is fluoro.

Embodiment 151: the compound of Embodiment 148, wherein $R^{4a}$ is methyl.

Embodiment 152: the compound of Embodiment 1, chosen from:

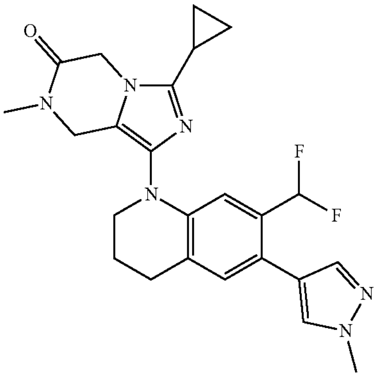

,

-continued

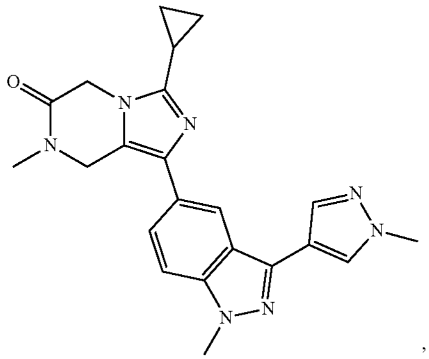

,

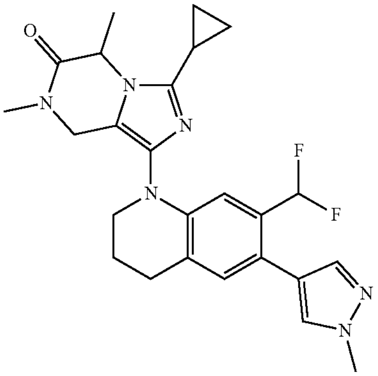

,

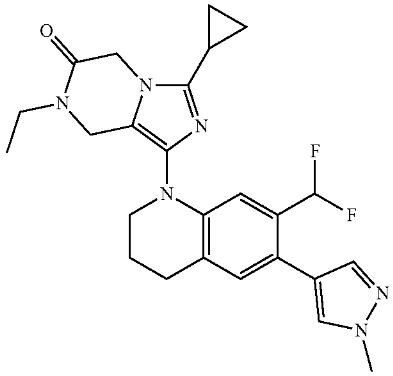

,

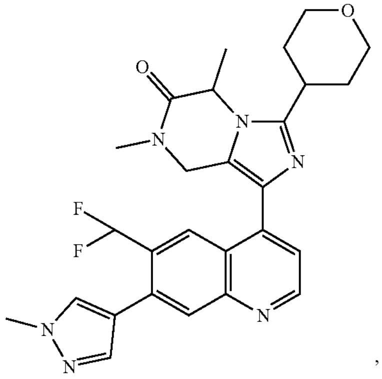

,

-continued
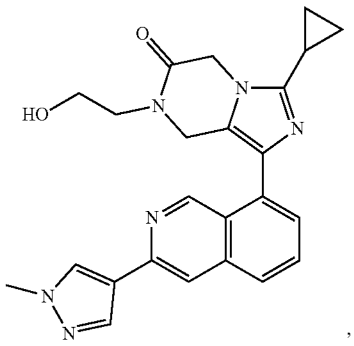
,
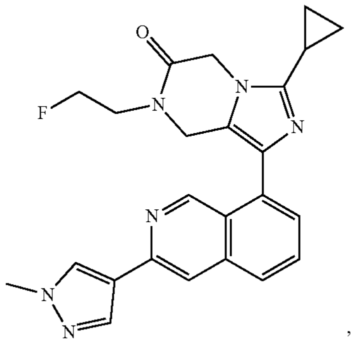
,
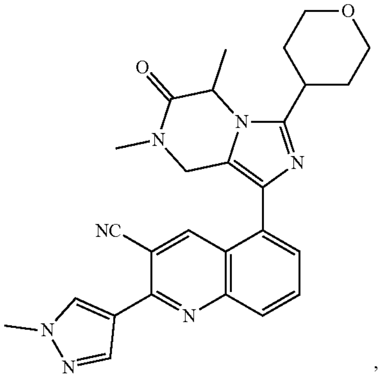
,
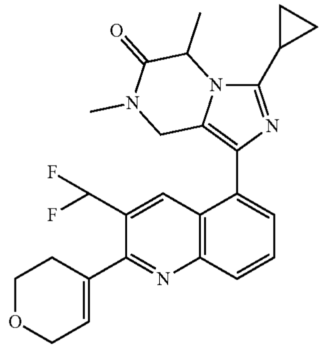
,
-continued
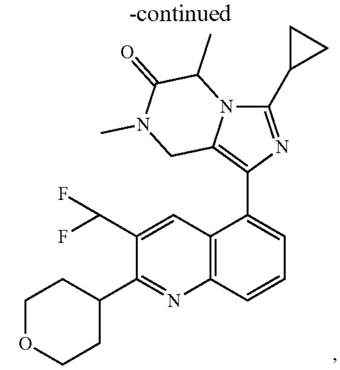
,
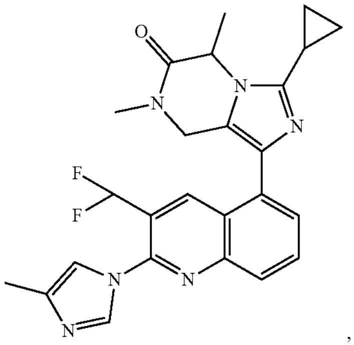 [SMILES: Cc1cn(-c2nc3cccc(-c4nc(C5CC5)n5c4CN(C)C(=O)C5C)c3cc2C(F)F)cn1]
,
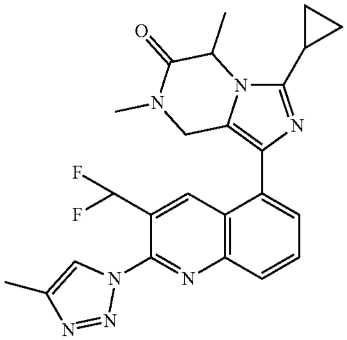
,
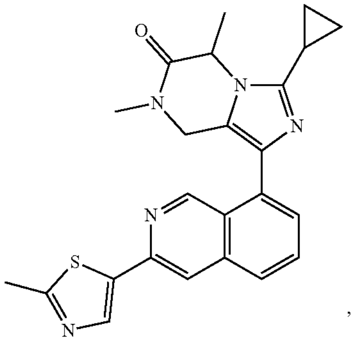
,
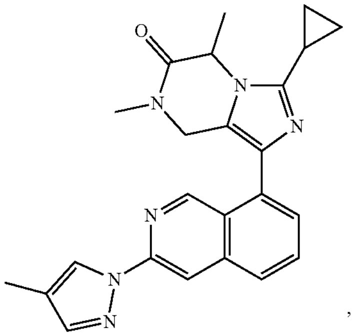
, -continued
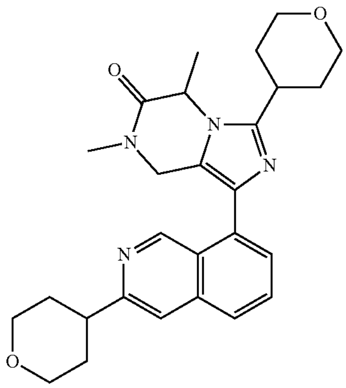
,
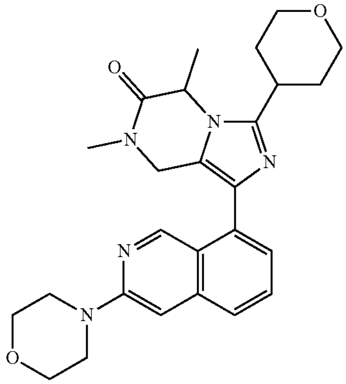
,
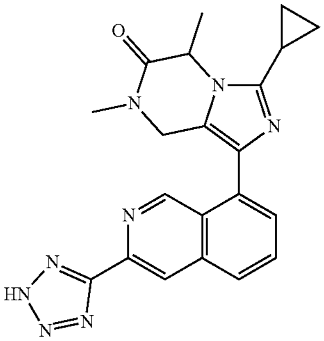
,
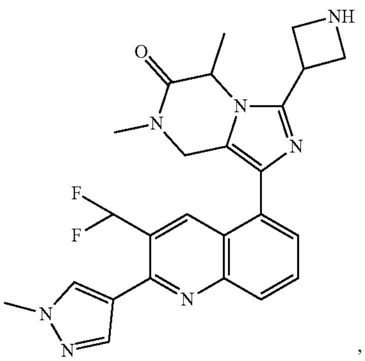
,
-continued
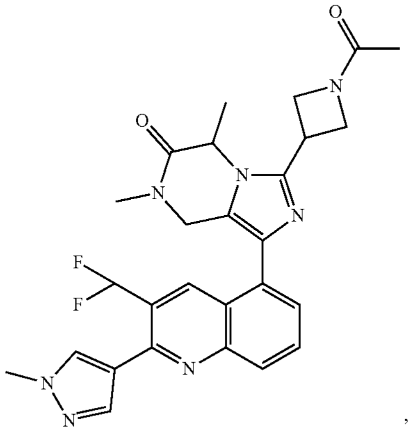
,
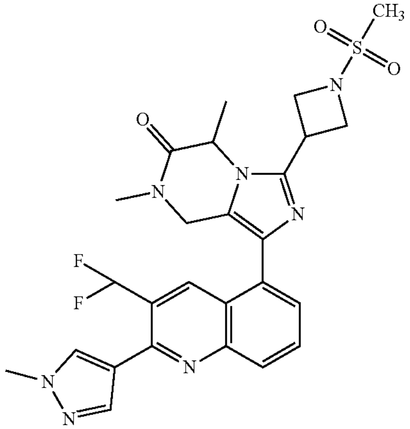
,
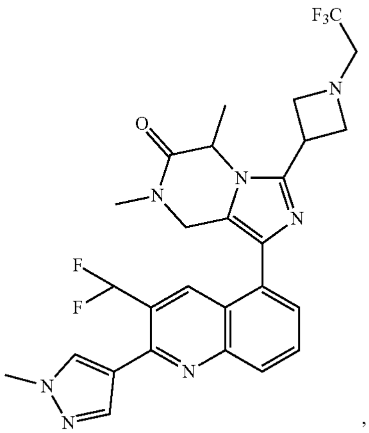
,
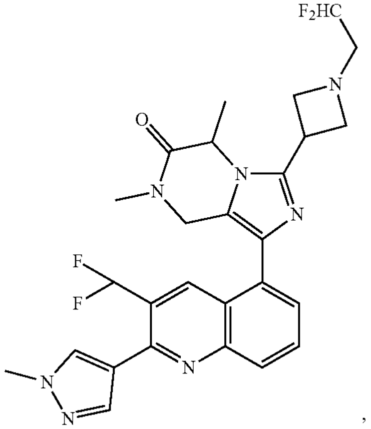
, -continued
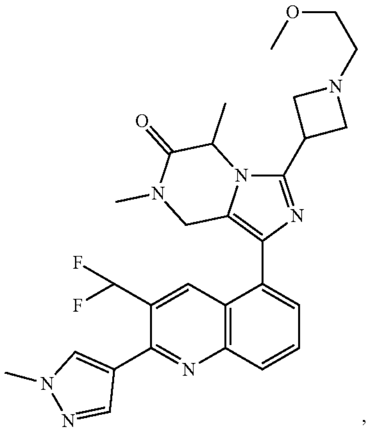
,
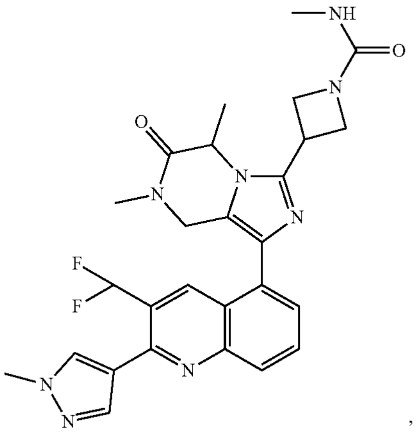
,
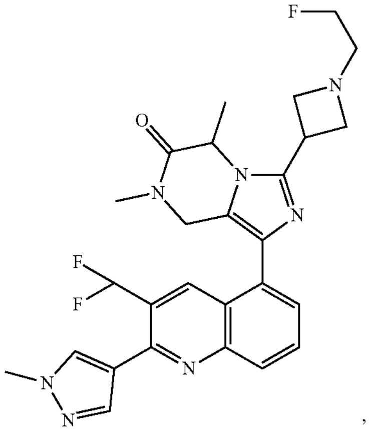
,
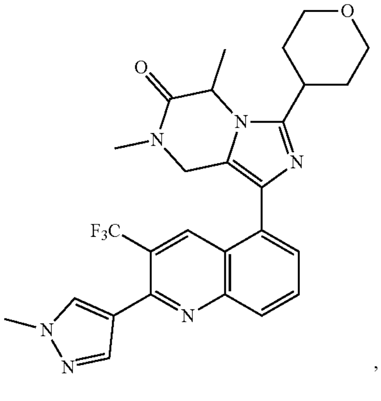
,
-continued
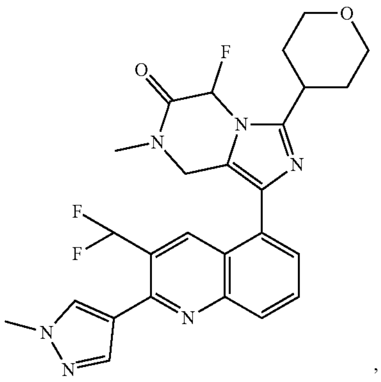
,
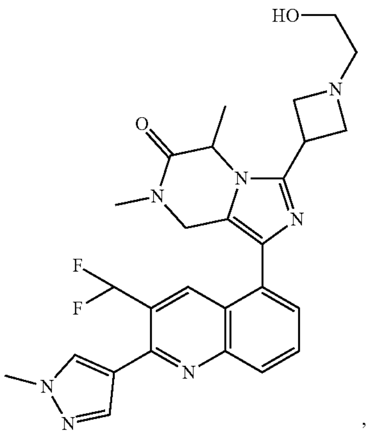
,
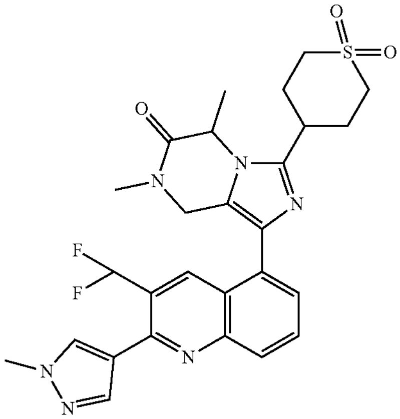
,
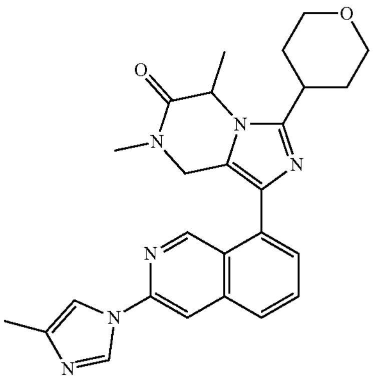
, -continued
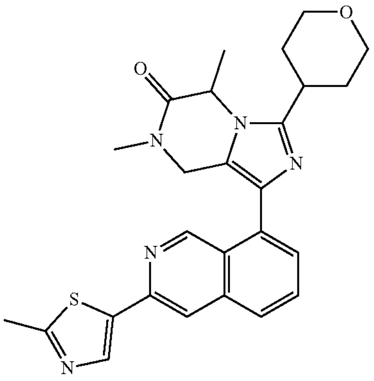
,
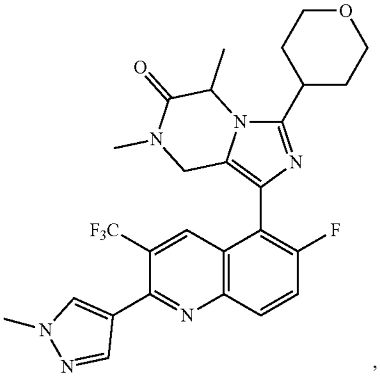
,
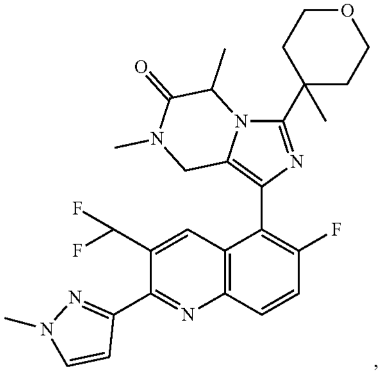
,
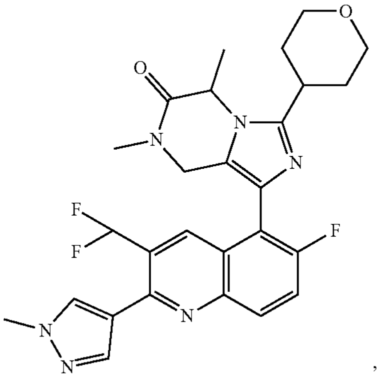
,
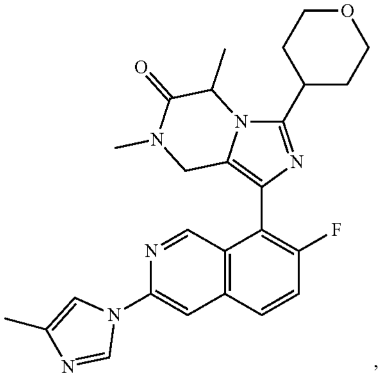
,
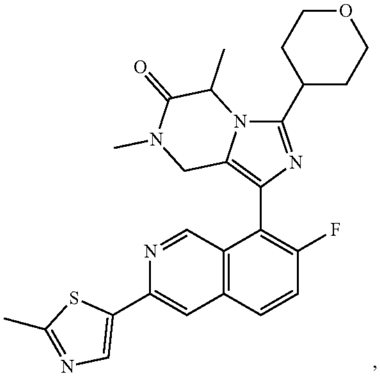
,
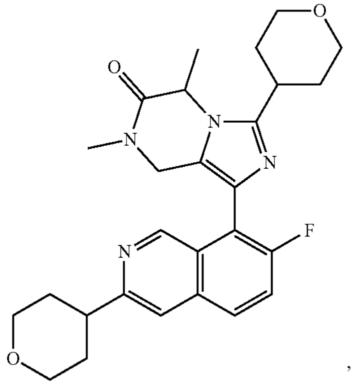
,
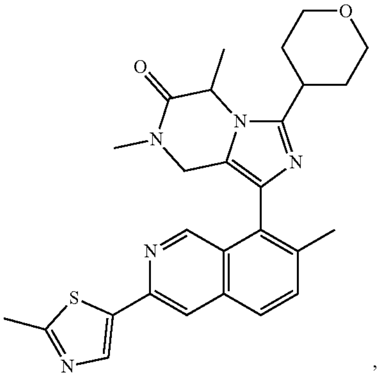 [SMILES: Cc1ncc(-c2cc3ccc(C)c(-c4nc(C5CCOCC5)n5c4CN(C)C(=O)C5C)c3cn2)s1]
, -continued
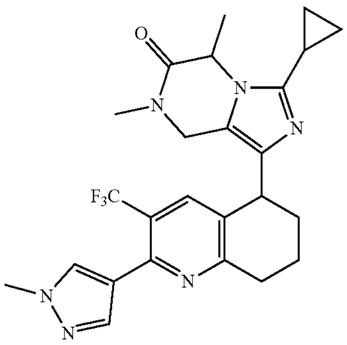
,
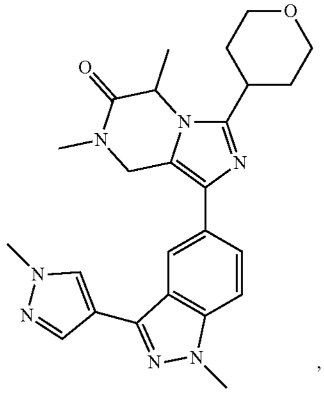
,
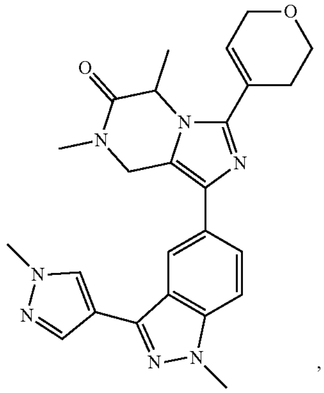
,
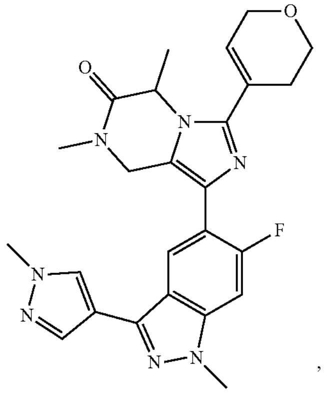
,
-continued
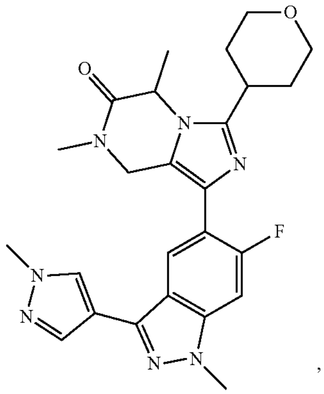
,
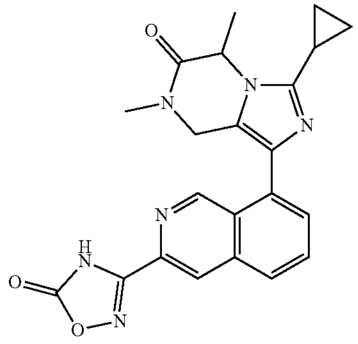
,
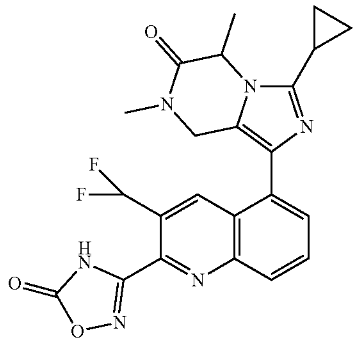
,
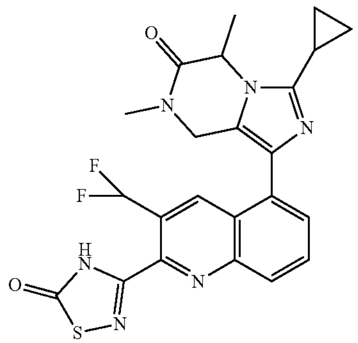
, -continued
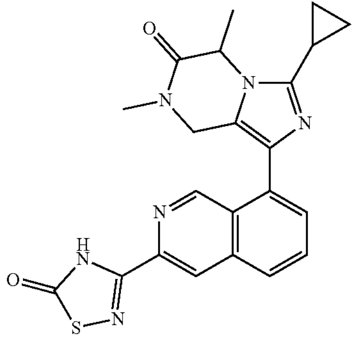
,
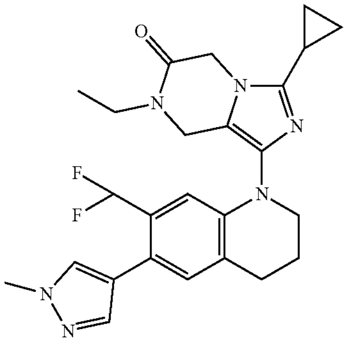
,
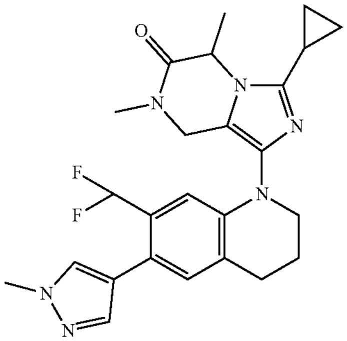
,
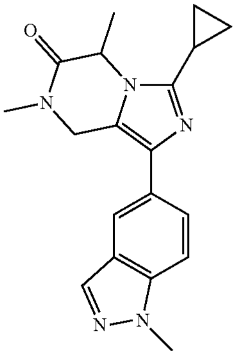
,
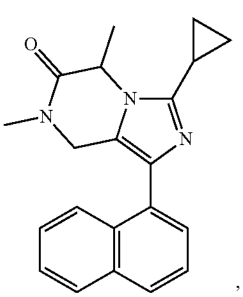
,
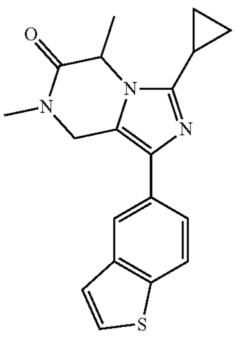
,
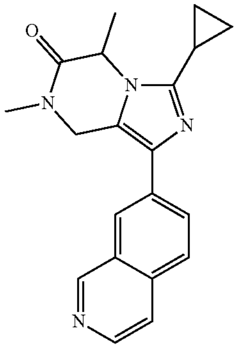
,
-continued
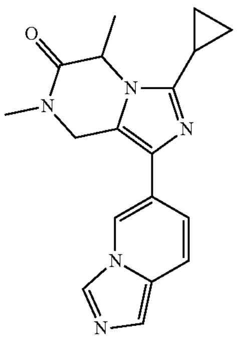
,
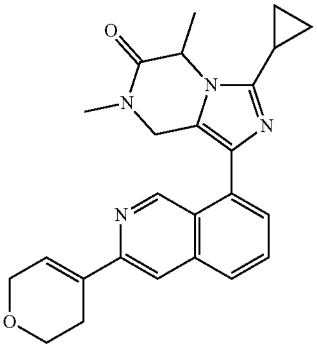
,
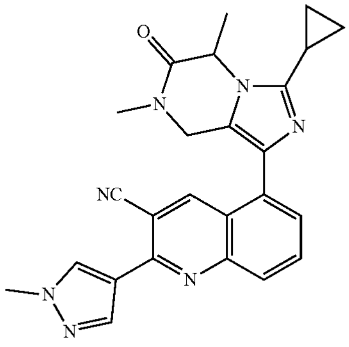
,
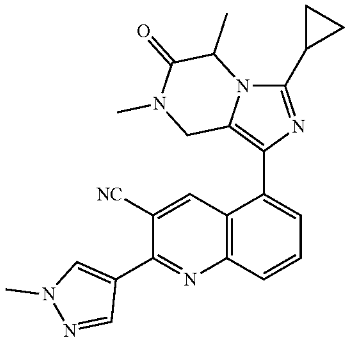
,
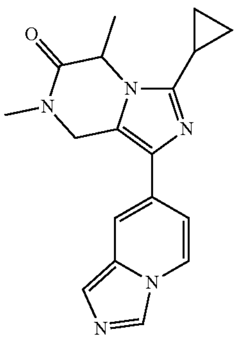
,
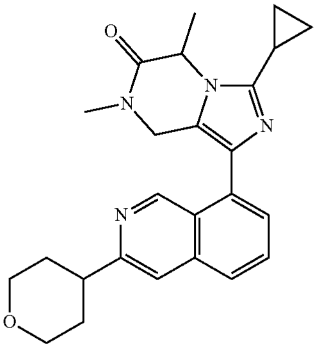
,
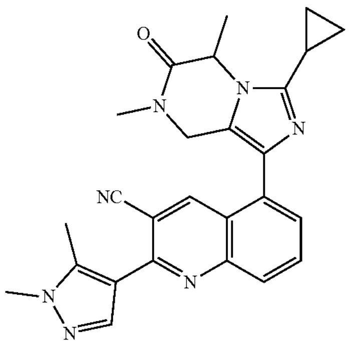
, -continued
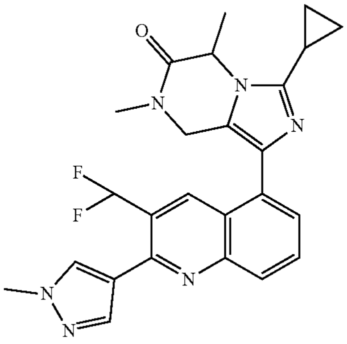
,
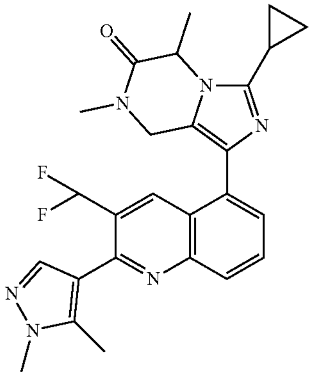
,
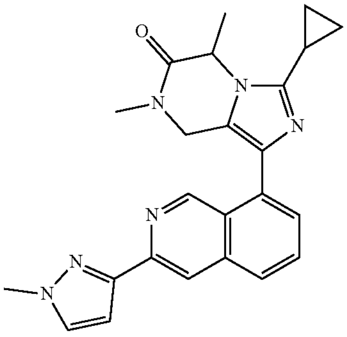
,
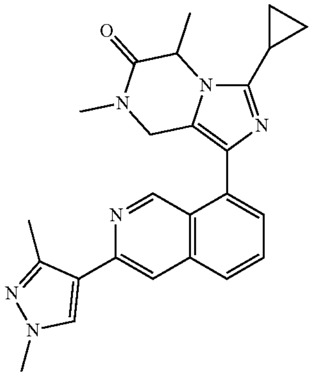
,
-continued
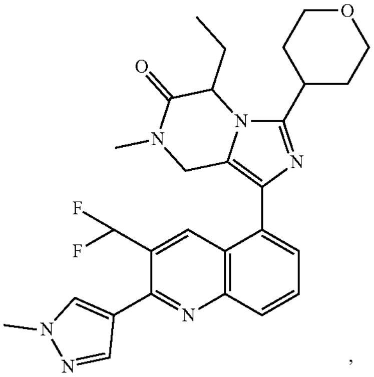
,
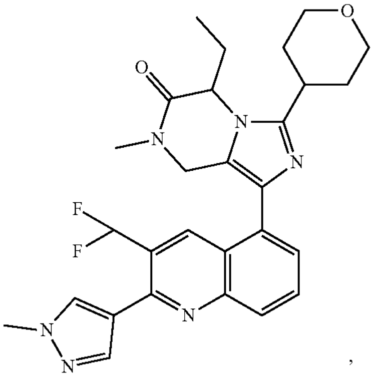
,
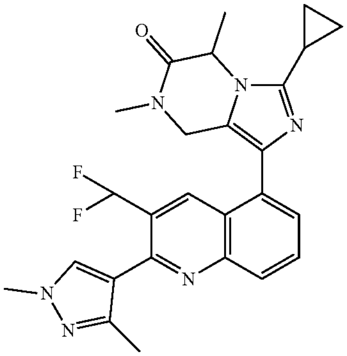
,
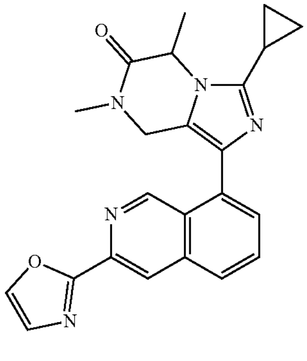
, -continued
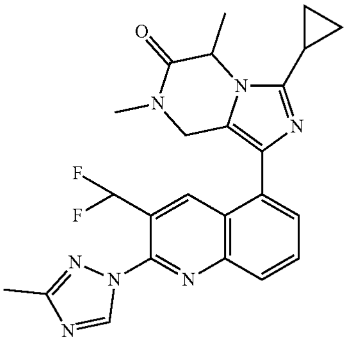
,
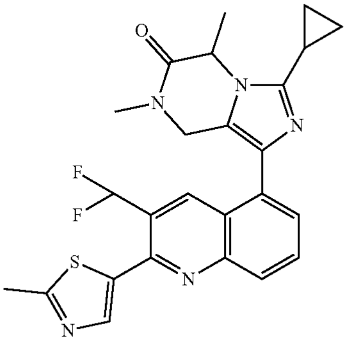
,
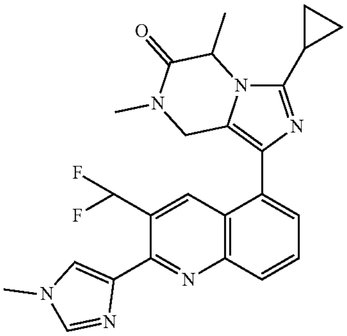
,
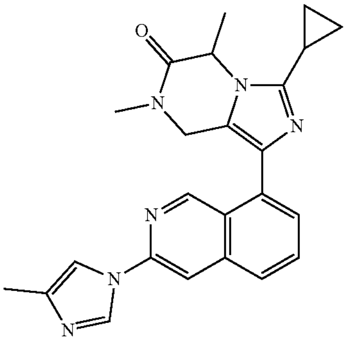
,
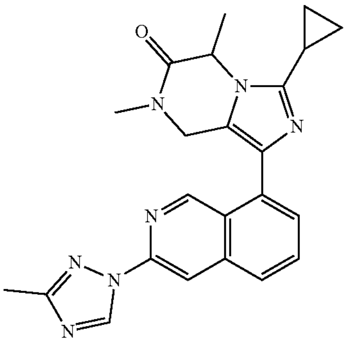
,
-continued
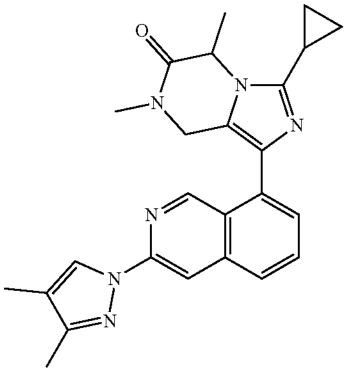
,
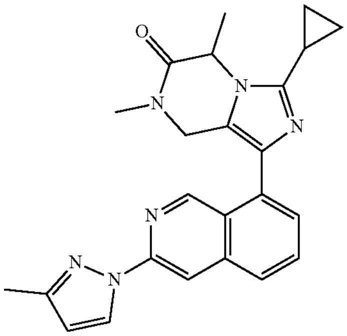
,
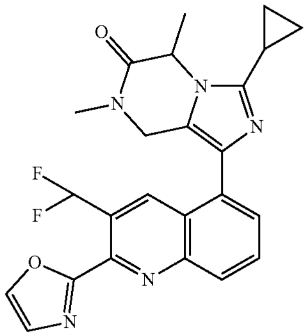
,
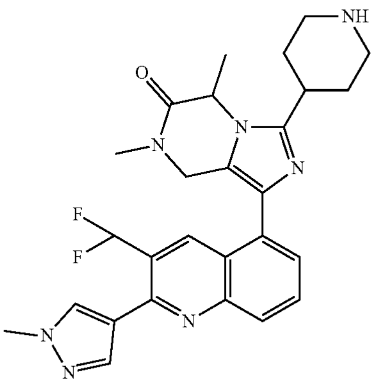
, -continued
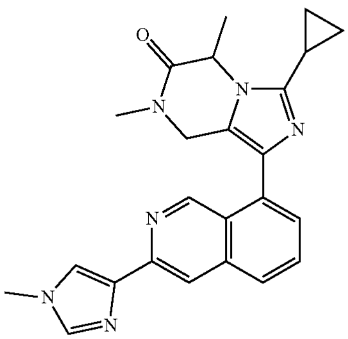
,
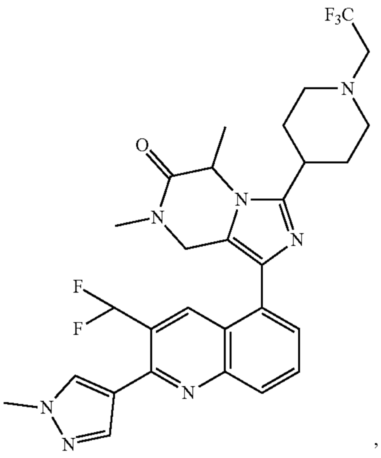
,
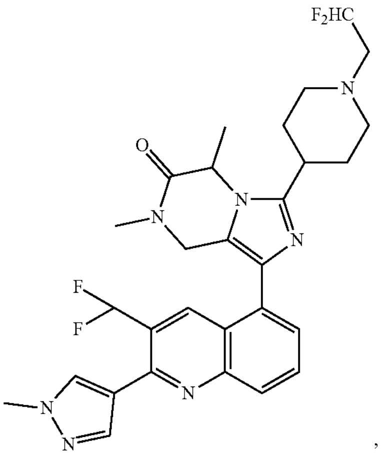
,
-continued
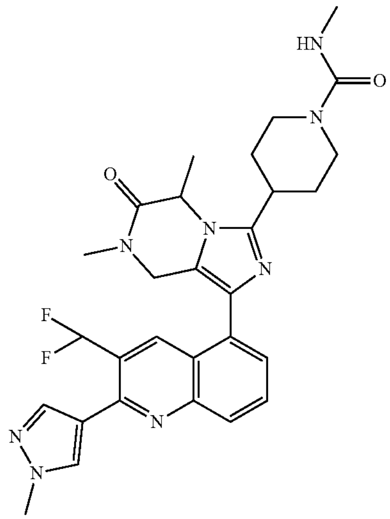
,
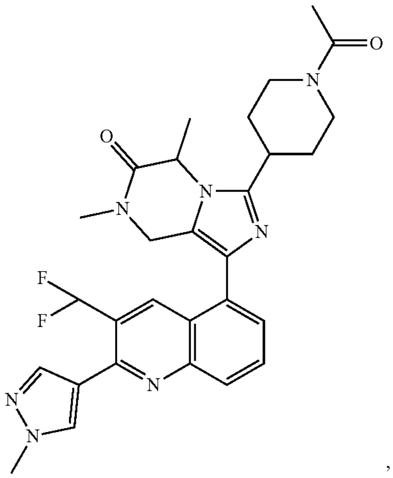
,
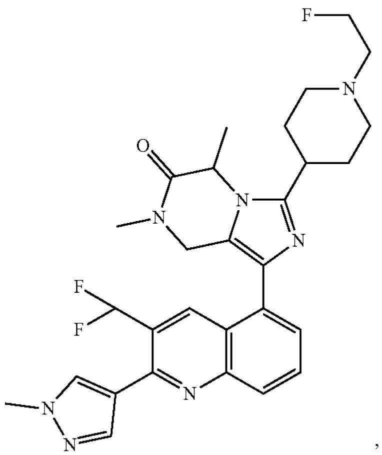
, -continued
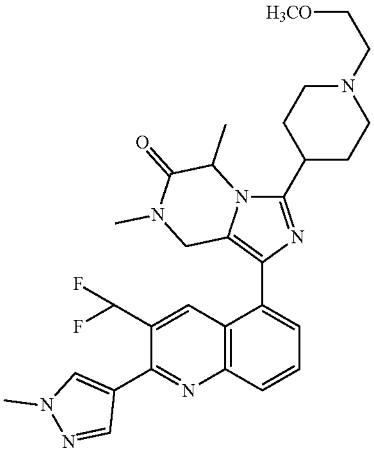
,
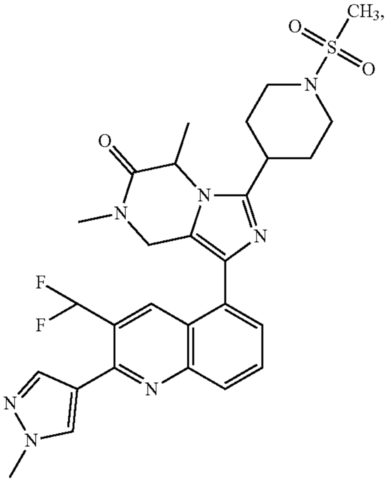
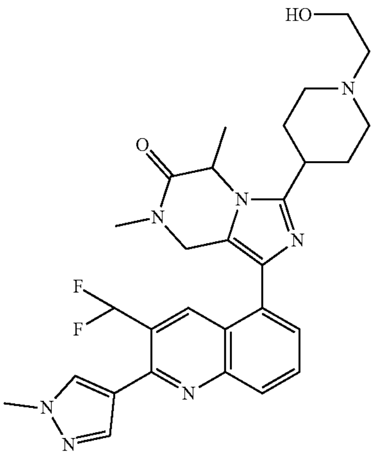
,
-continued
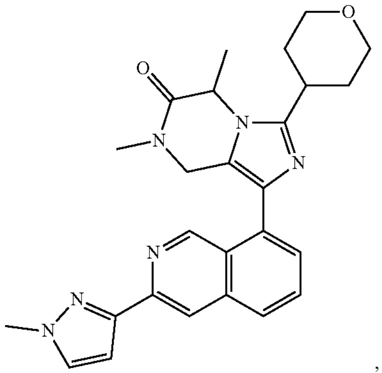
,
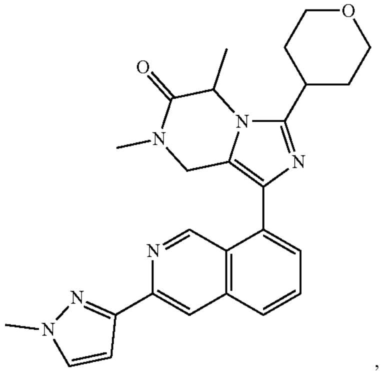
,
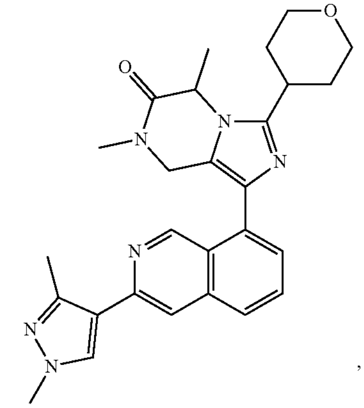
,
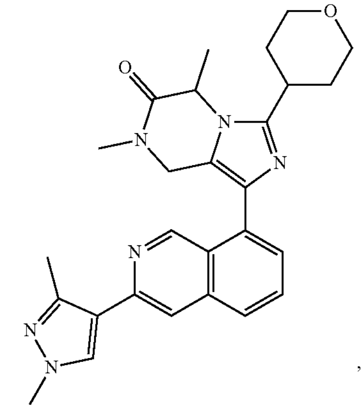
, -continued
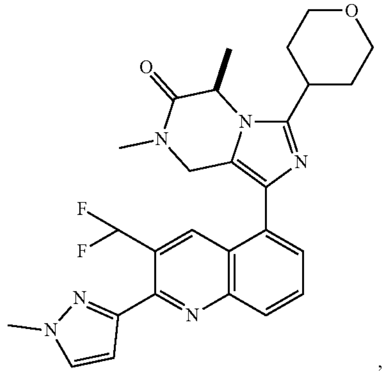
,
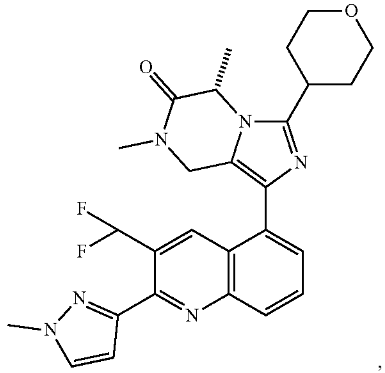
,
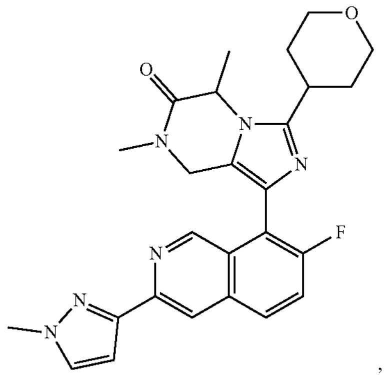
,
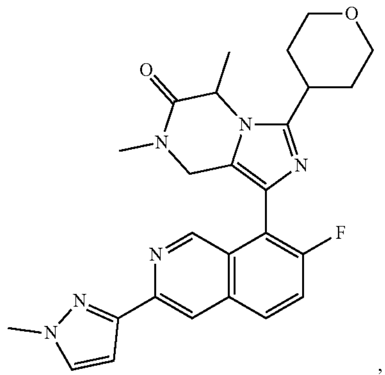
,
-continued
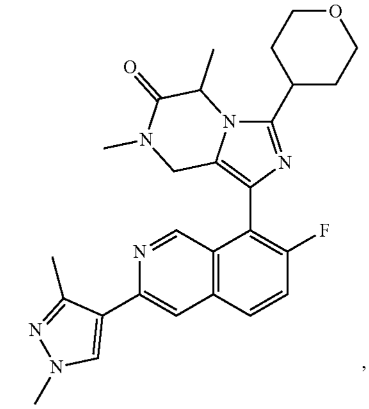
,
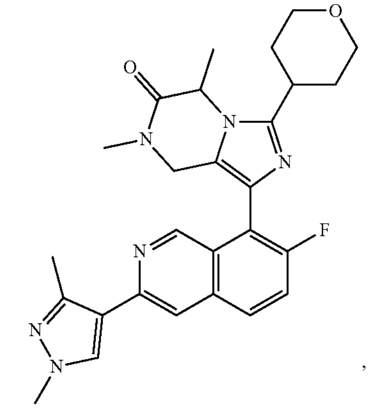
,
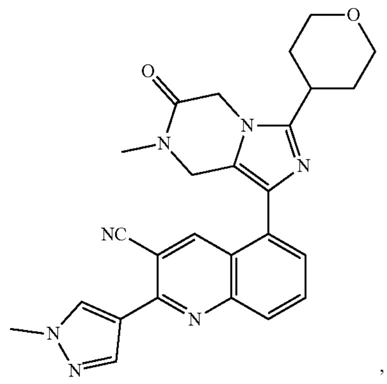
,
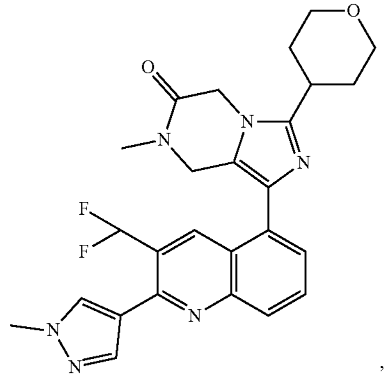
, -continued
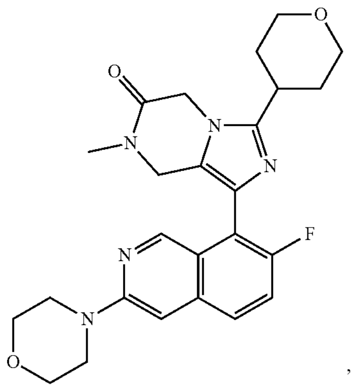
,
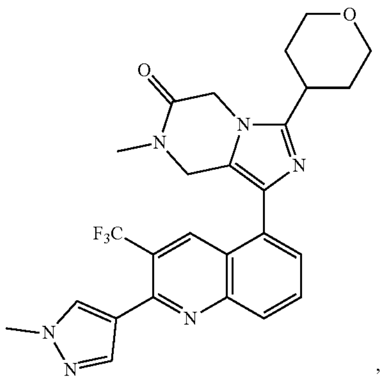
,
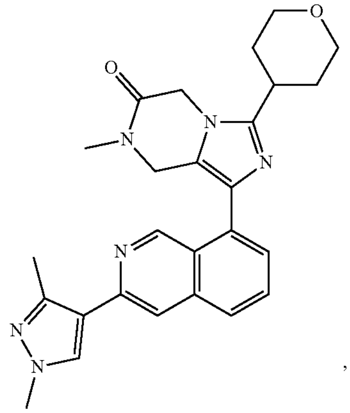
,
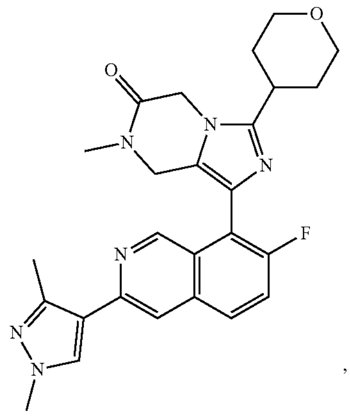
,
-continued
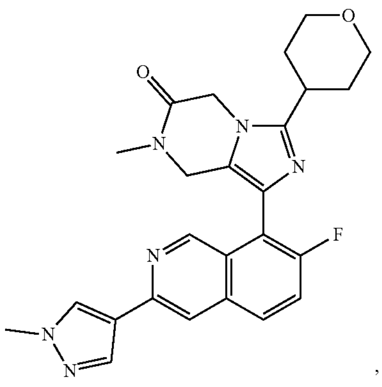
,
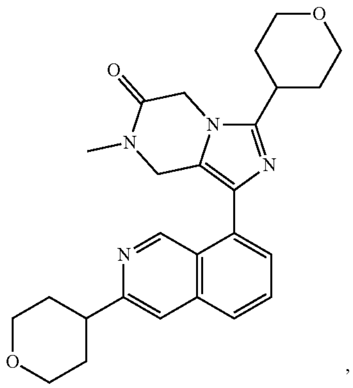
,
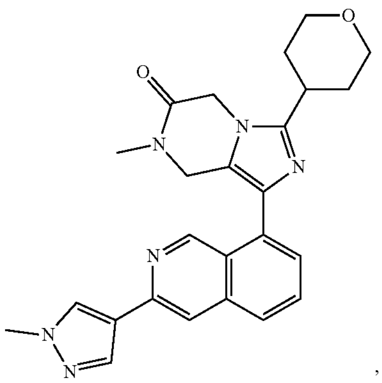
,
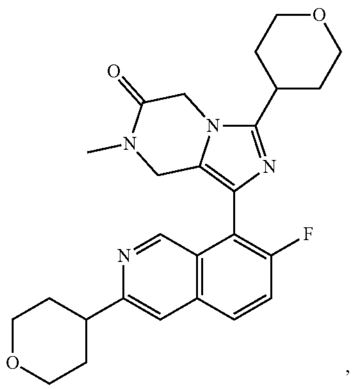
, -continued
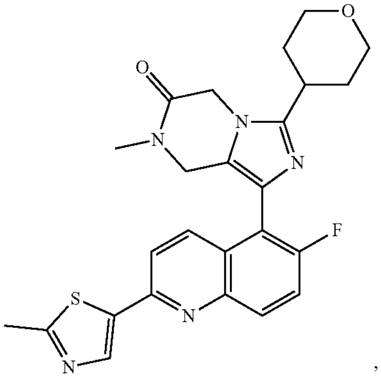
,
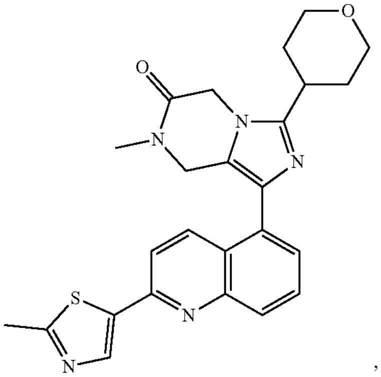
,
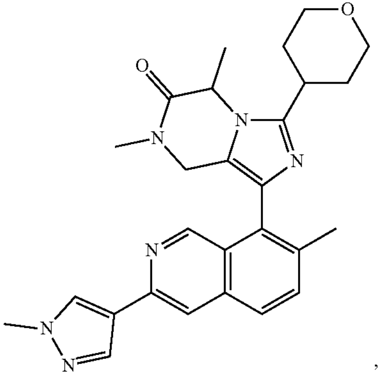
,
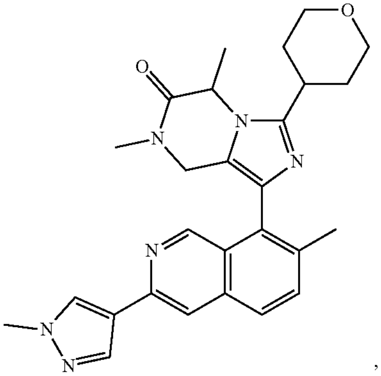
,
-continued
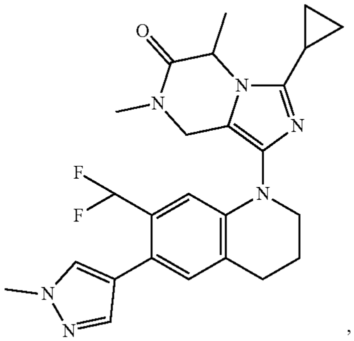
,
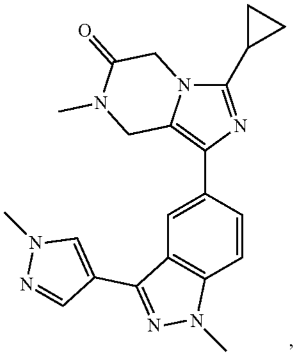
,
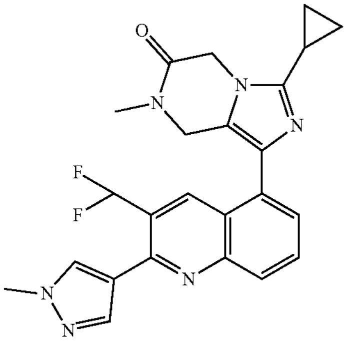
,
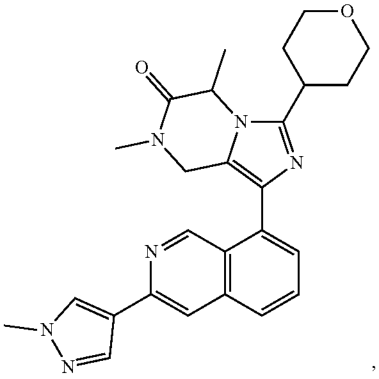
, -continued
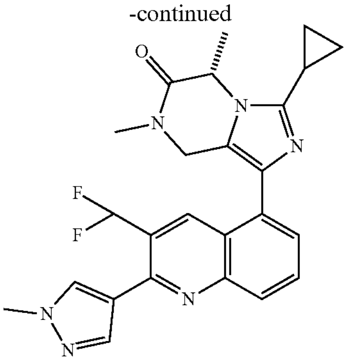
,
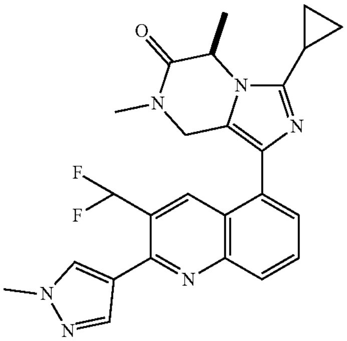
,
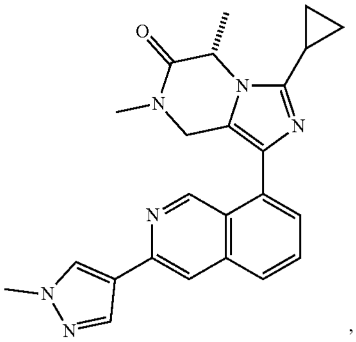 [SMILES: C[C@@H]1C(=O)N(C)Cc2c(-c3cccc4cc(-c5cnn(C)c5)ncc34)nc(C3CC3)n21]
, and
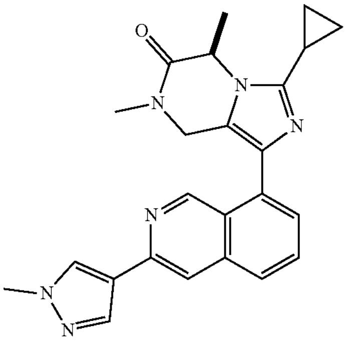
,
or a salt thereof.
Embodiment 153: the compound of Embodiment 1, chosen from:
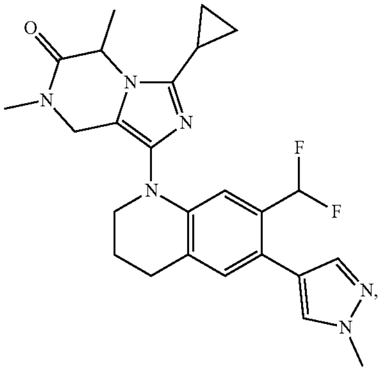
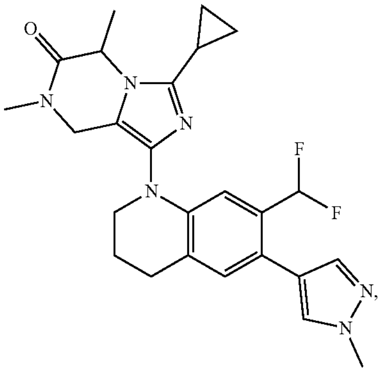
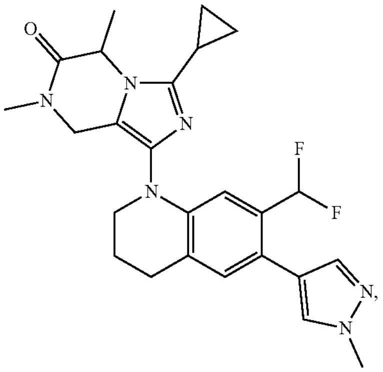
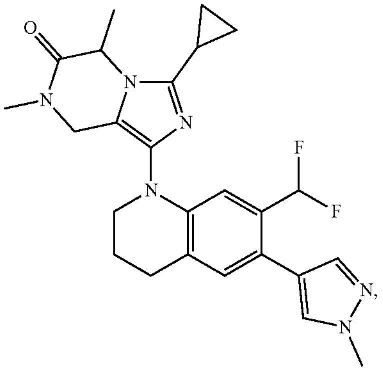

-continued
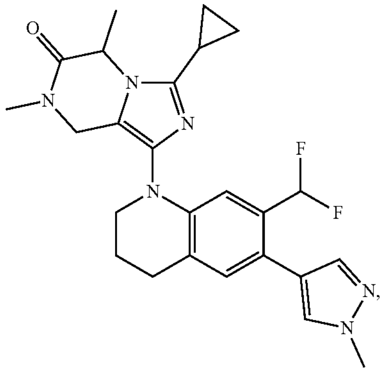
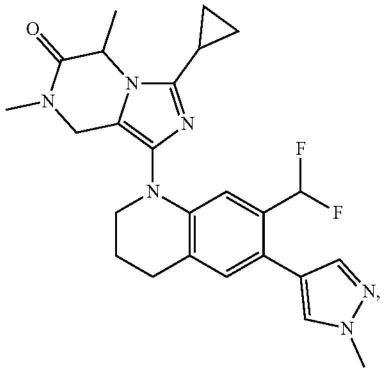
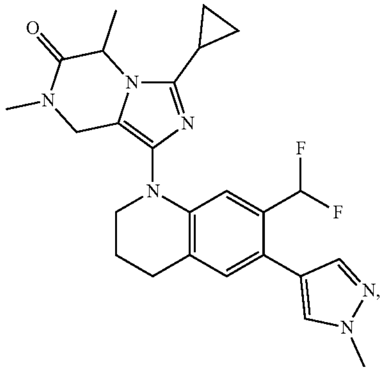
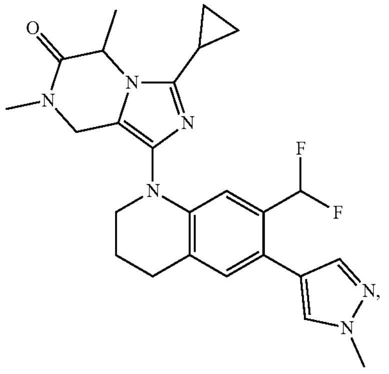
-continued
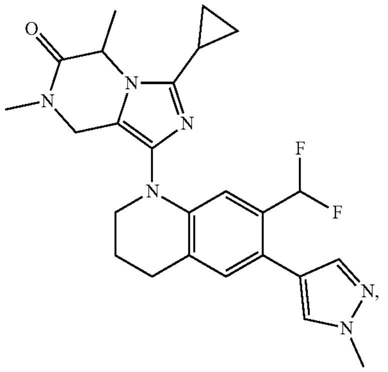
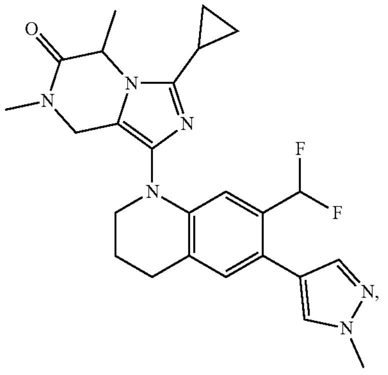
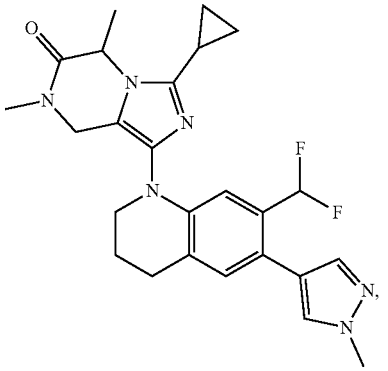
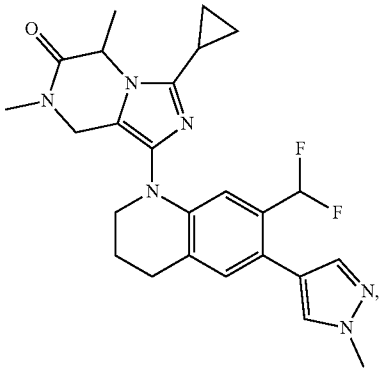

-continued
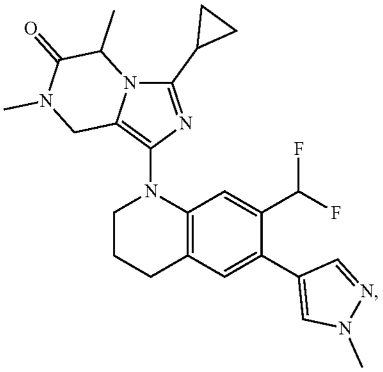
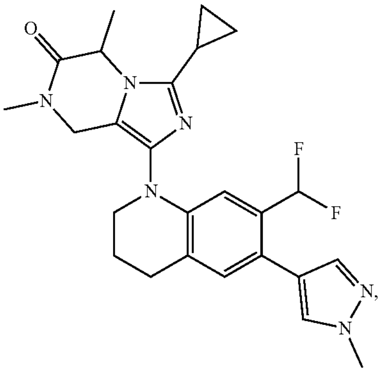
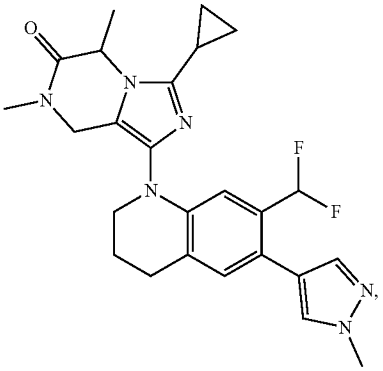
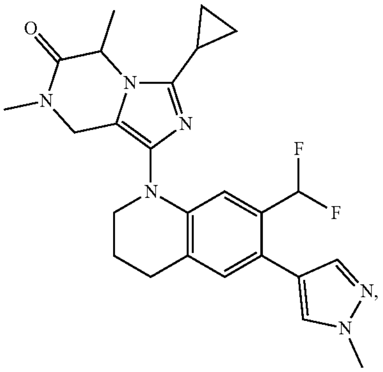
-continued
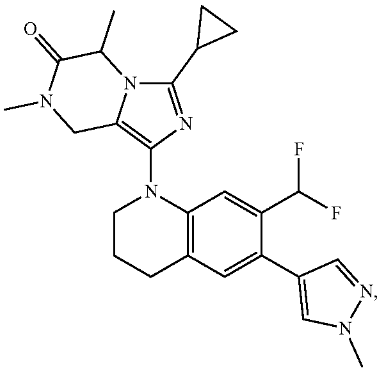
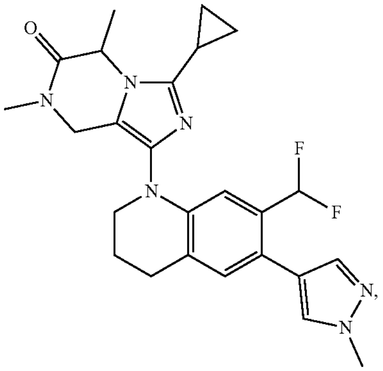
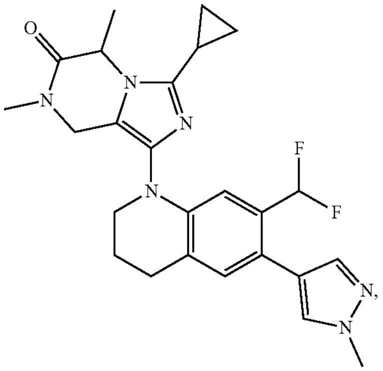
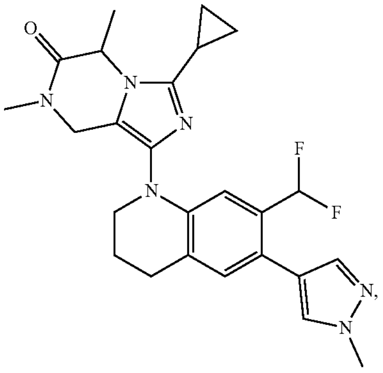

-continued
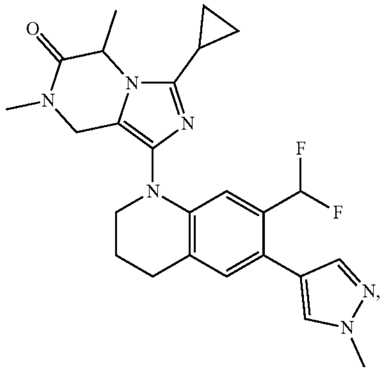
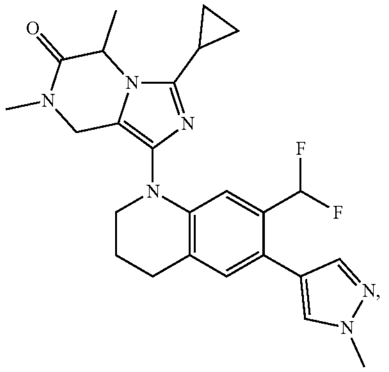
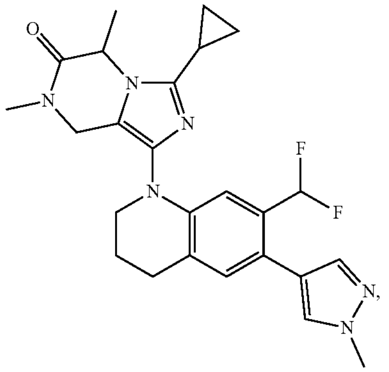
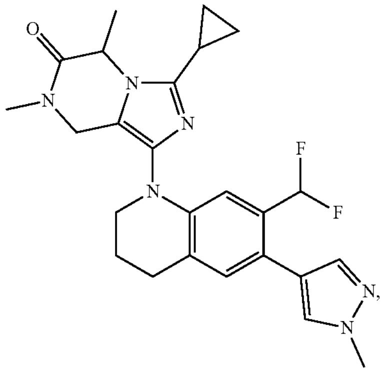
-continued
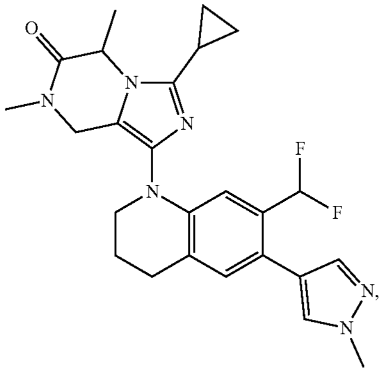
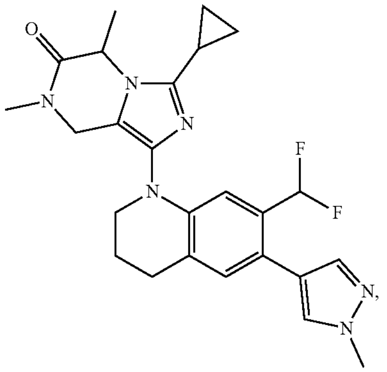
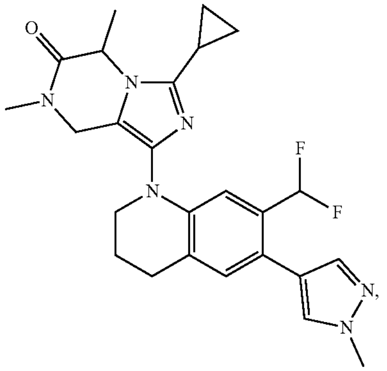
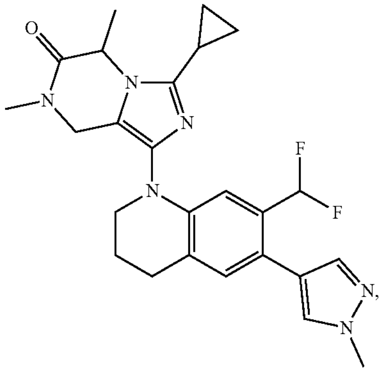

-continued
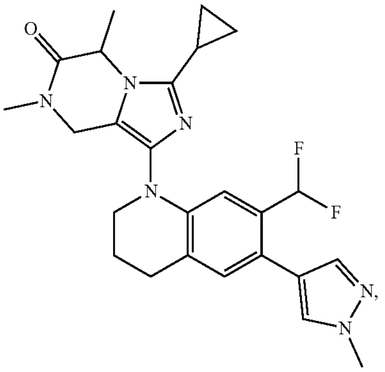
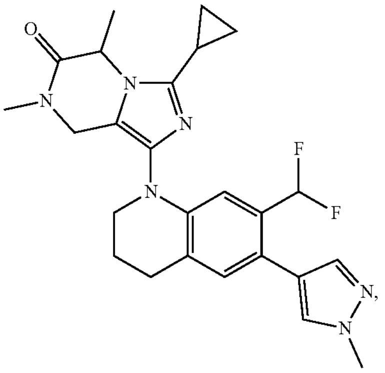
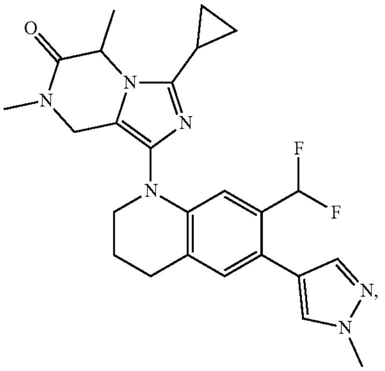
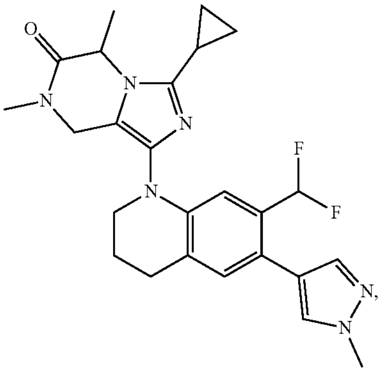
-continued
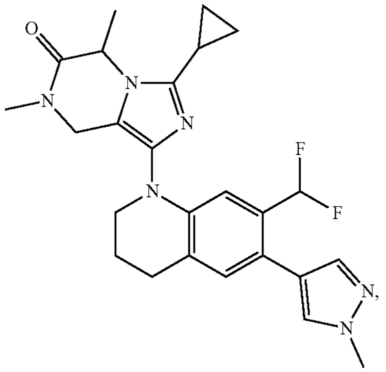
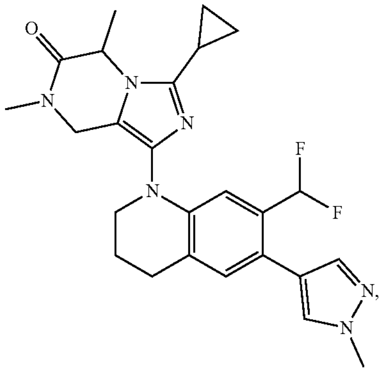
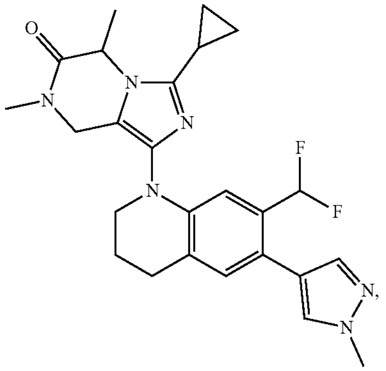
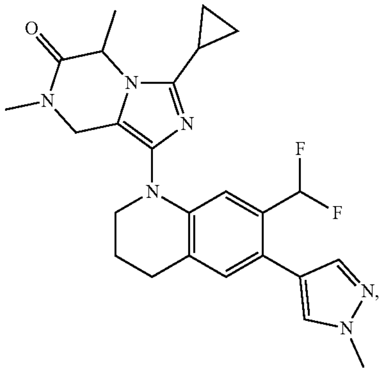

-continued
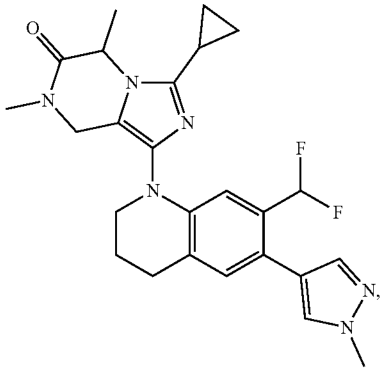
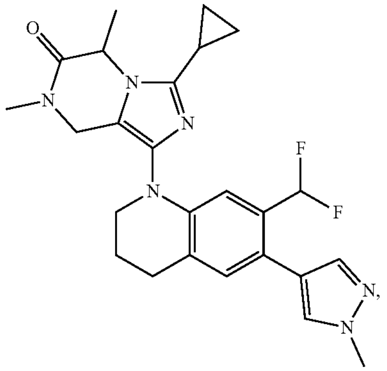
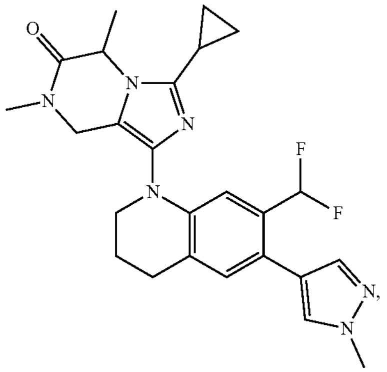
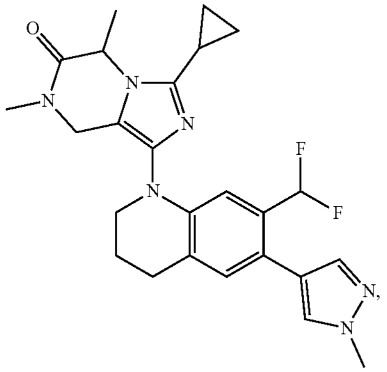
-continued
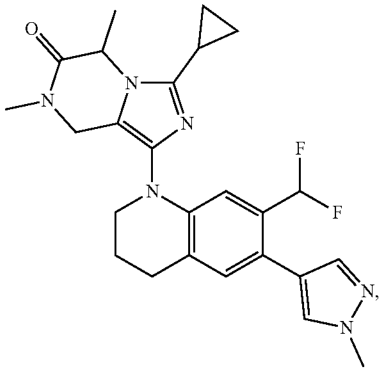
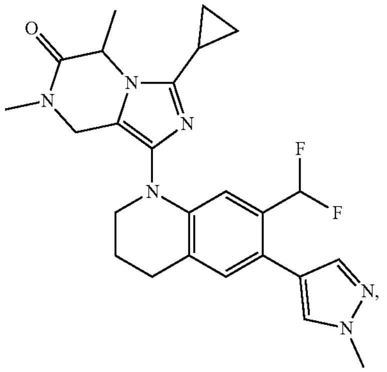
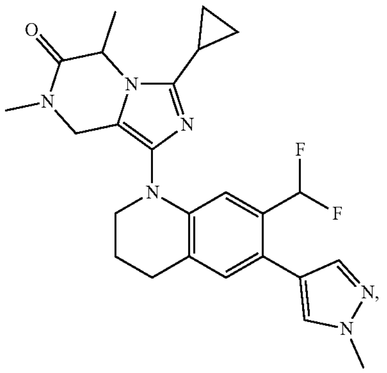
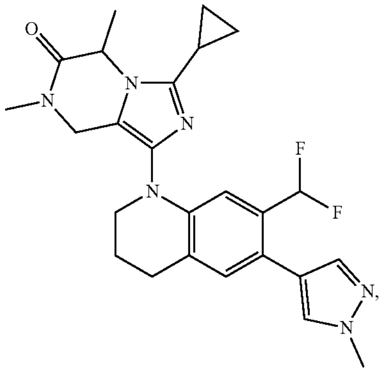

-continued
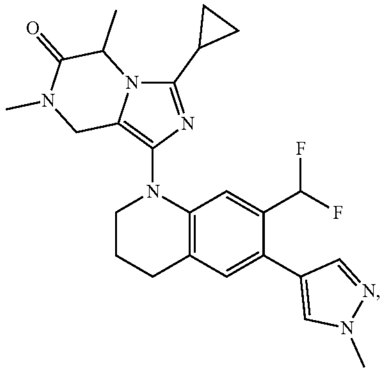
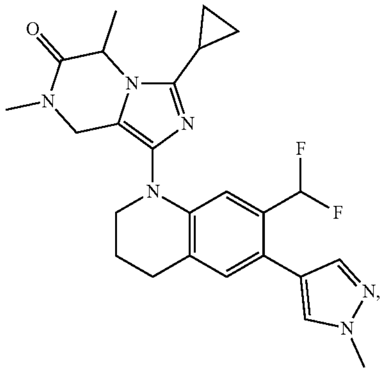
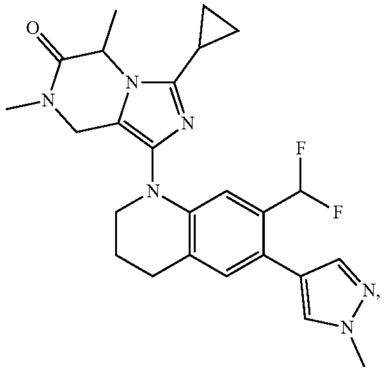
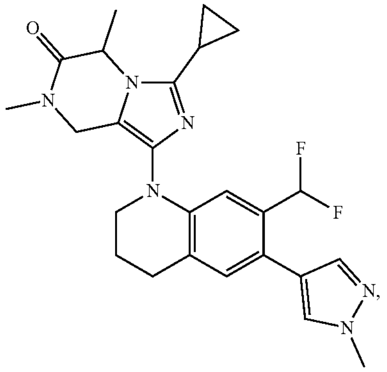
-continued
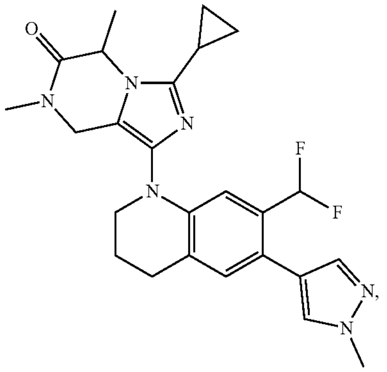
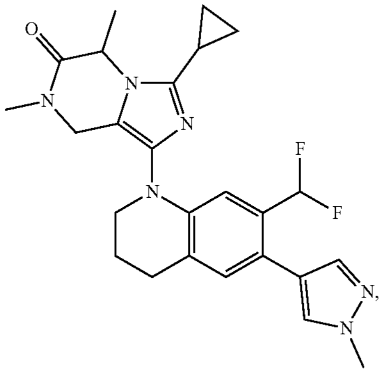
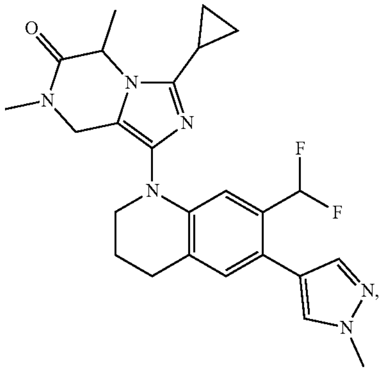
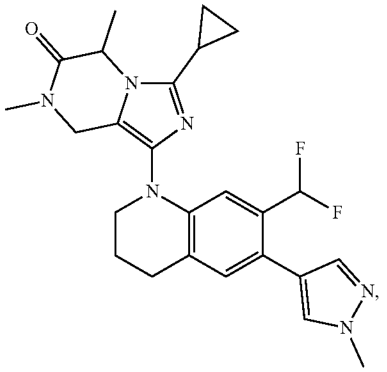

-continued
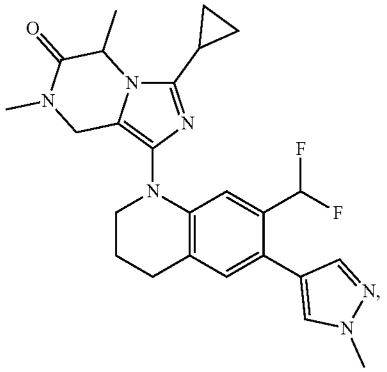
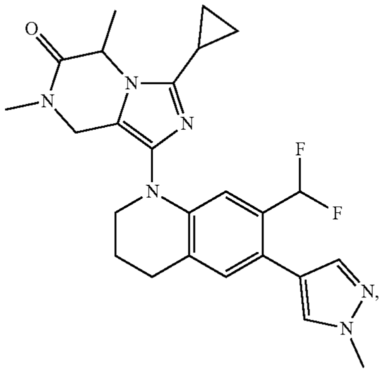
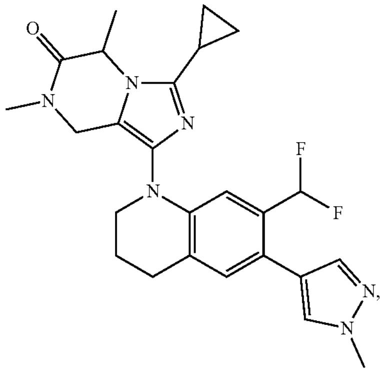
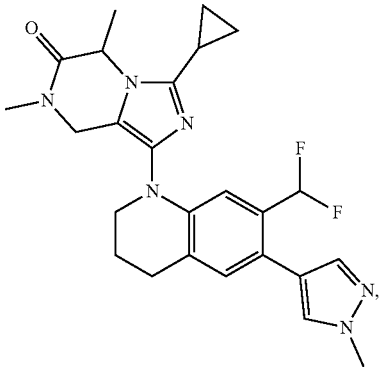
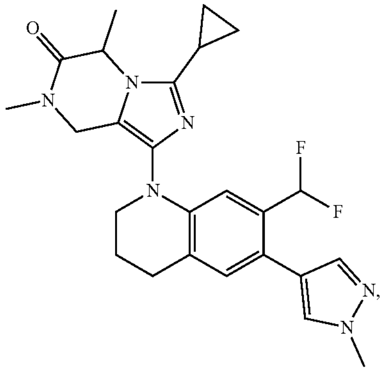
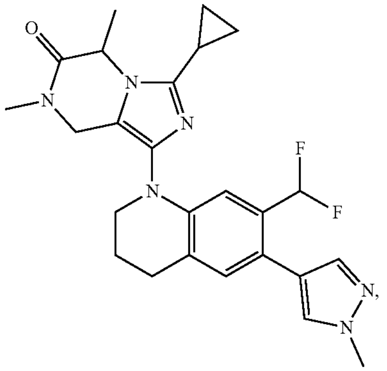
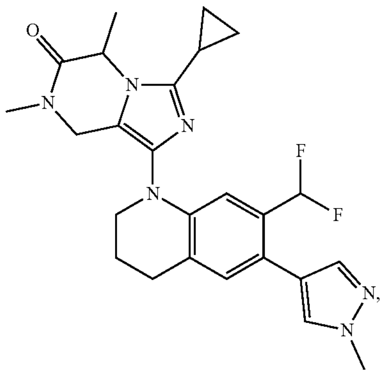
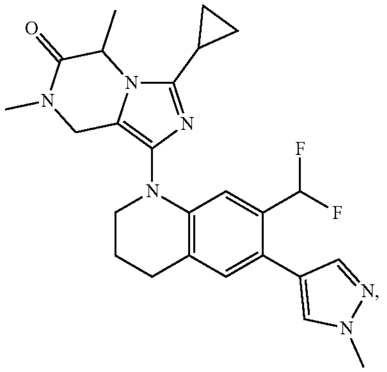

-continued
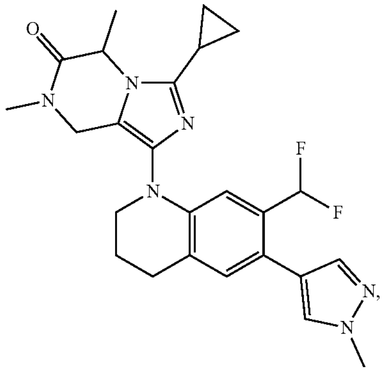
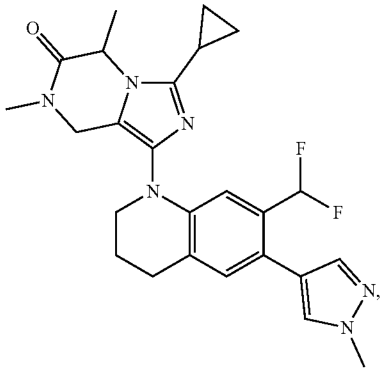
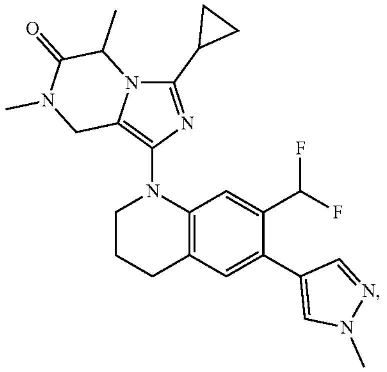
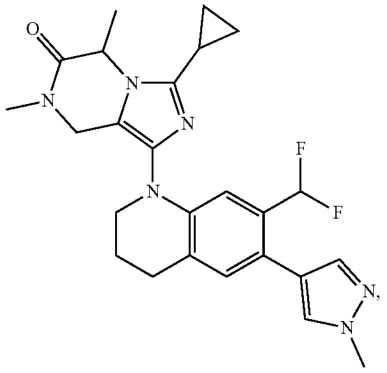
-continued
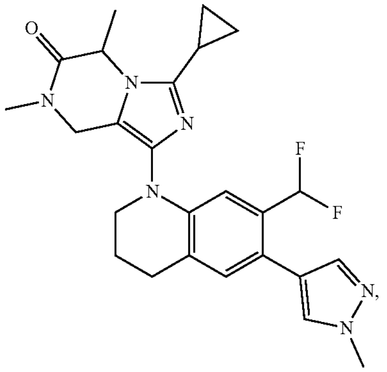
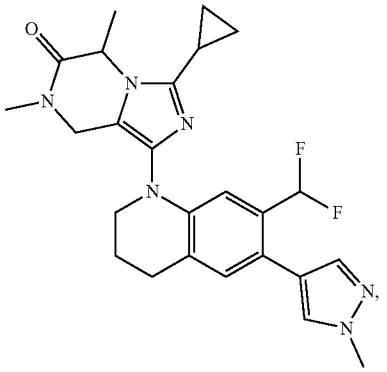
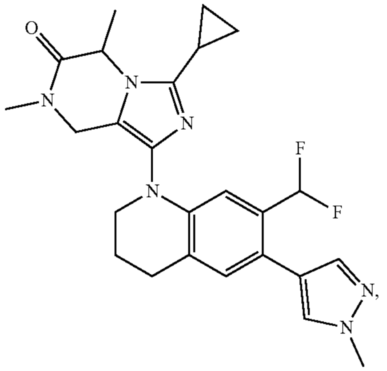
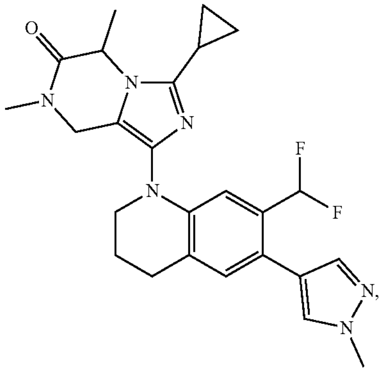

-continued
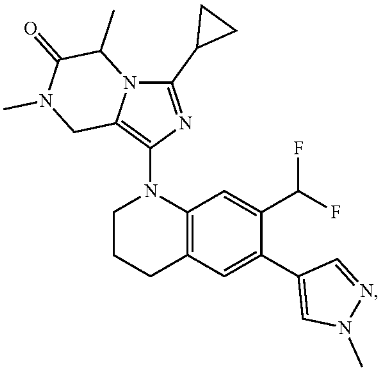
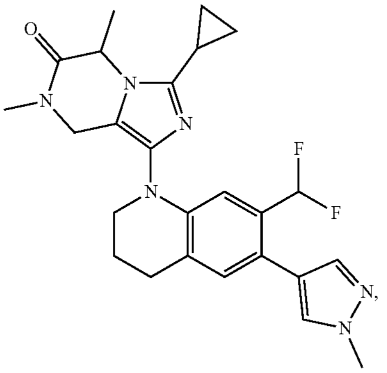
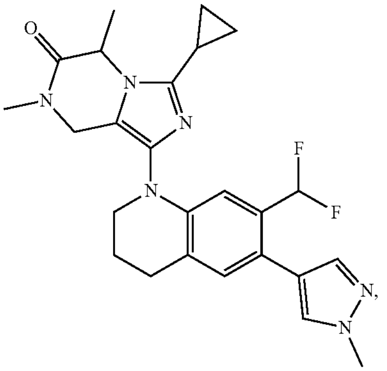
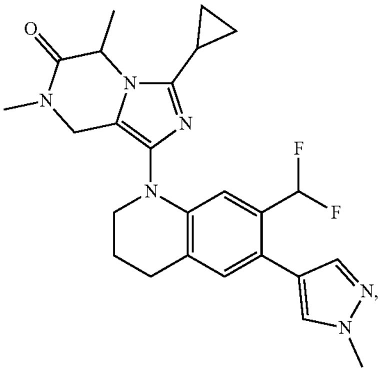
-continued
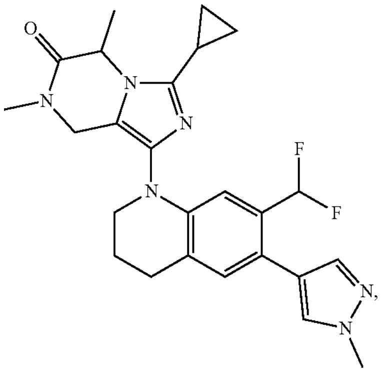
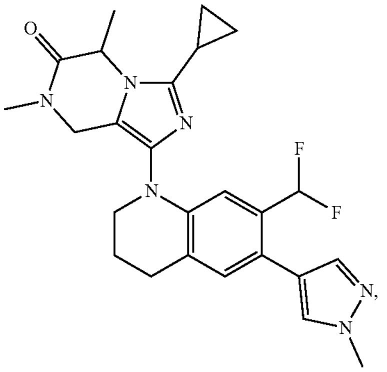
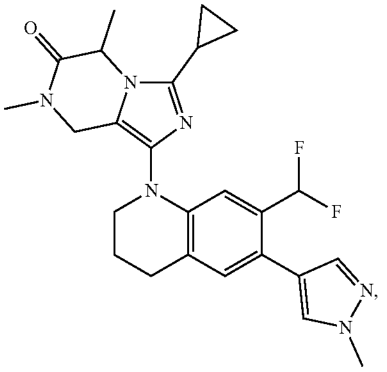
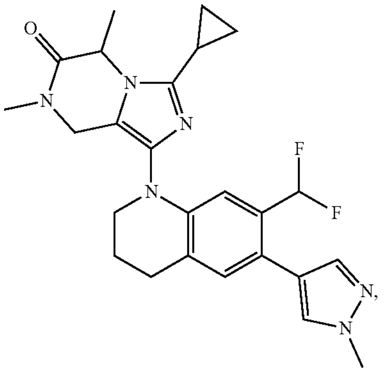

-continued
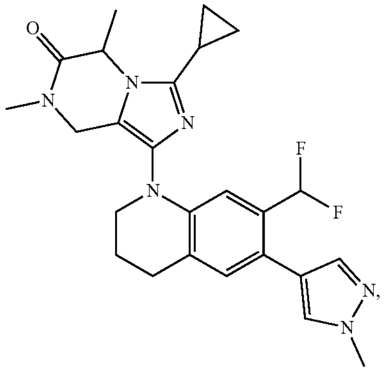
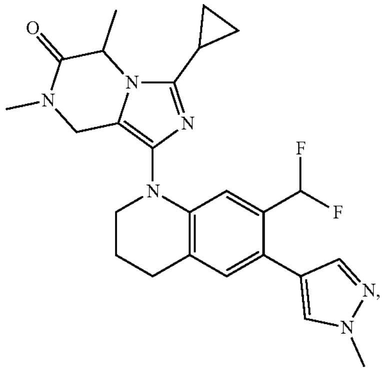
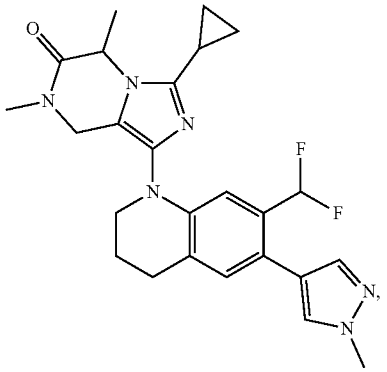
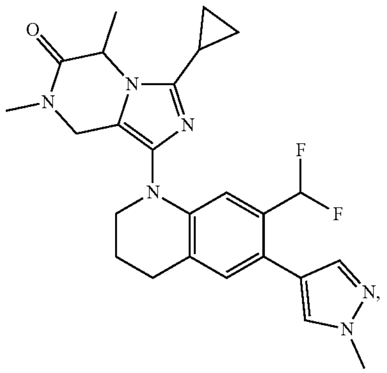
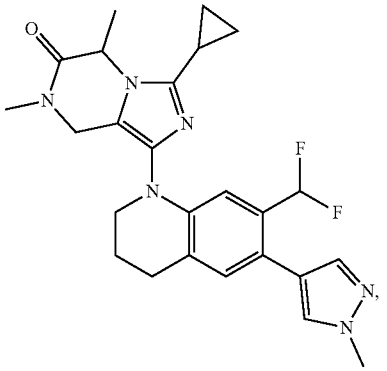
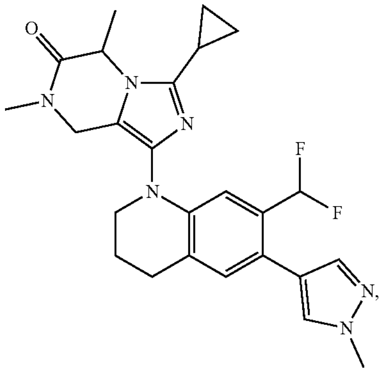
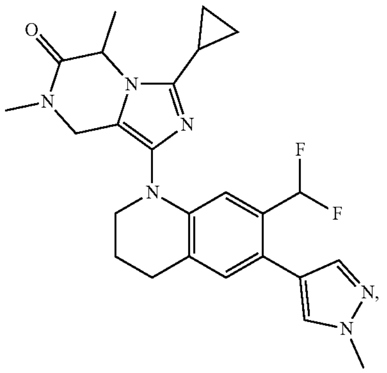
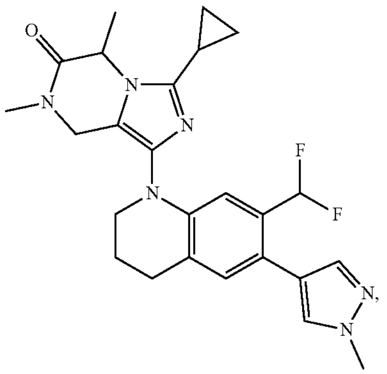
-continued -continued
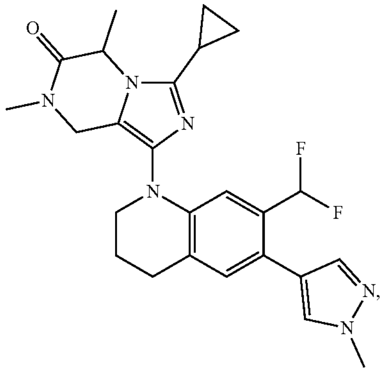
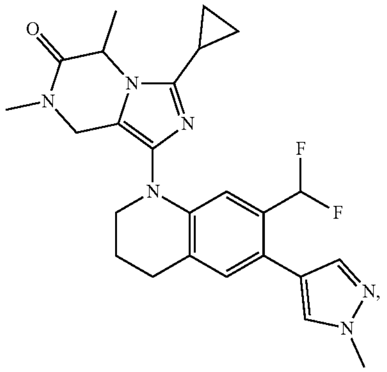
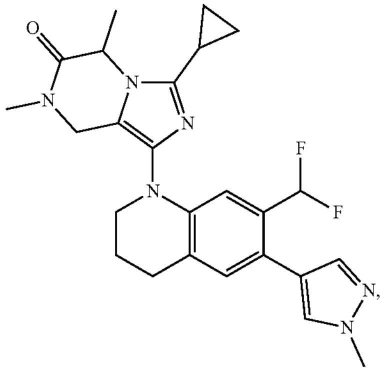
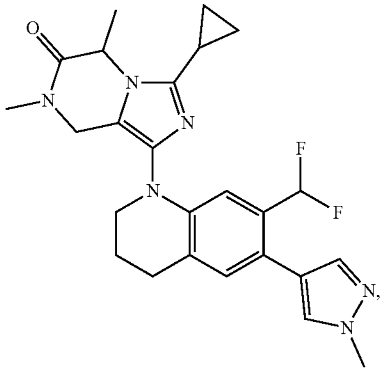
-continued
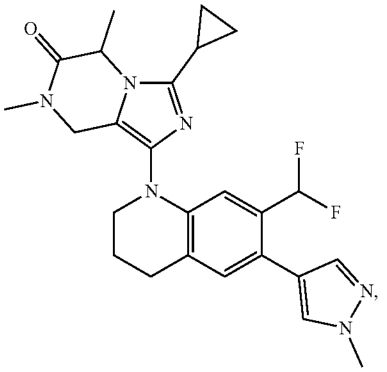
and
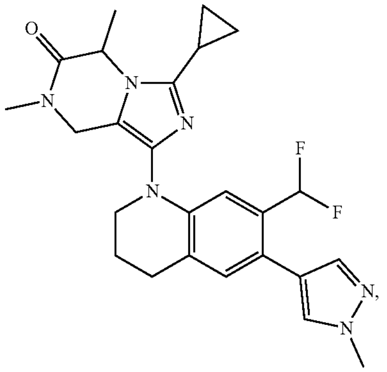
or a salt thereof.
Embodiment 154: the compound of Embodiment 1, chosen from:
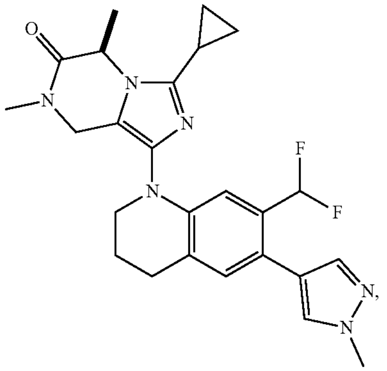
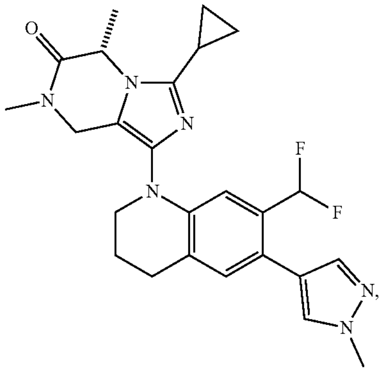

-continued
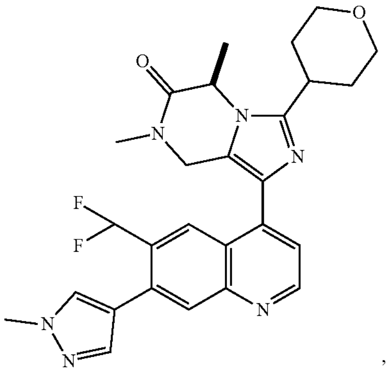
,
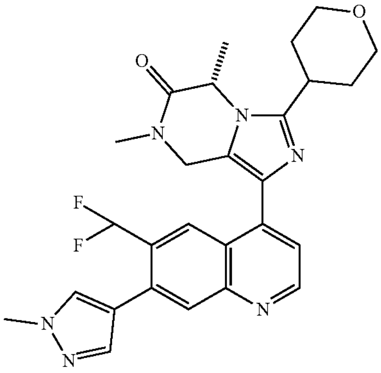
,
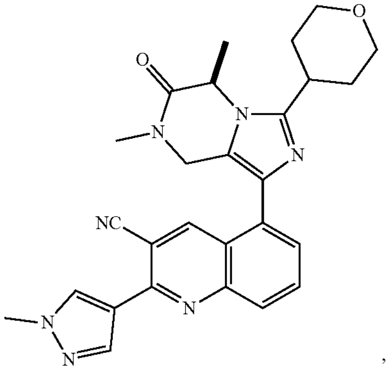
,
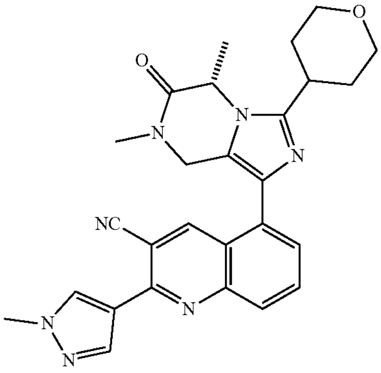
,
-continued
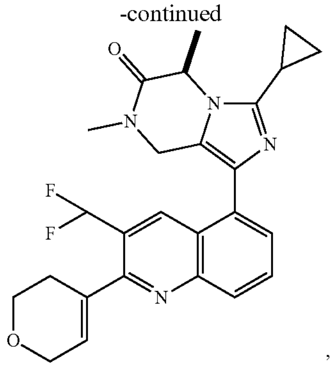
,
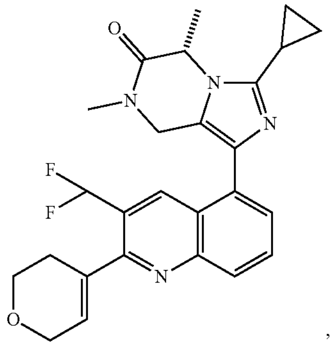
,
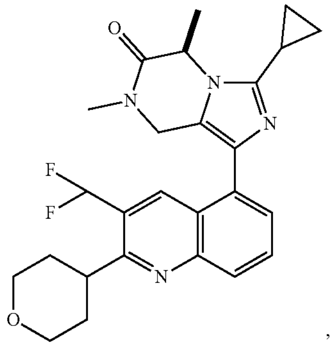
,
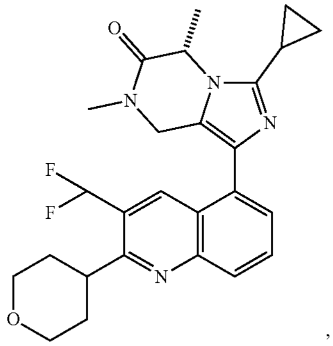
,
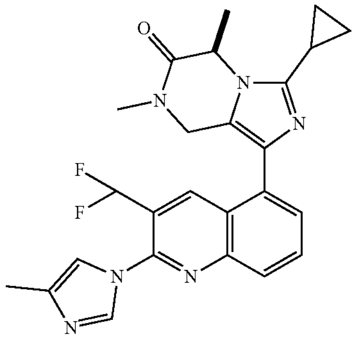
, -continued
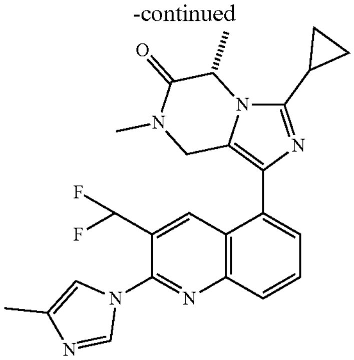
,
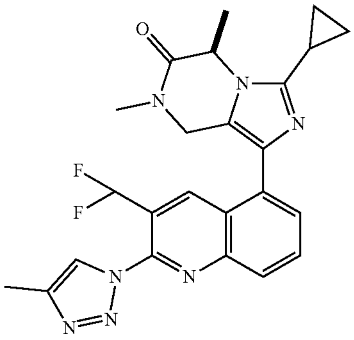
,
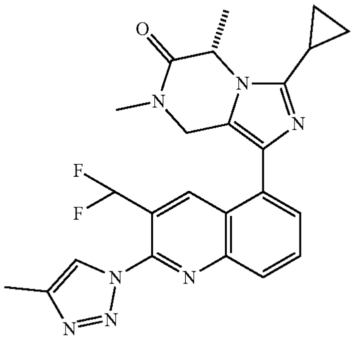
,
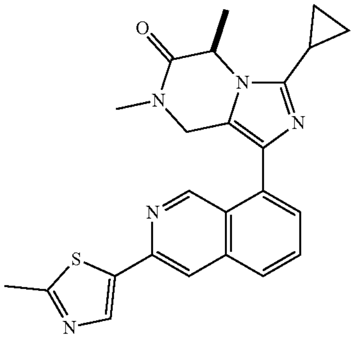
,
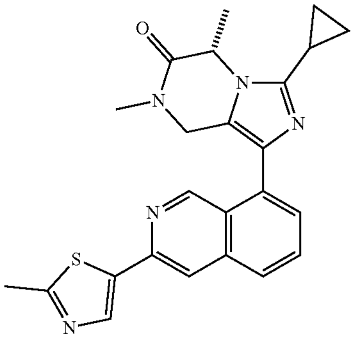
,
-continued
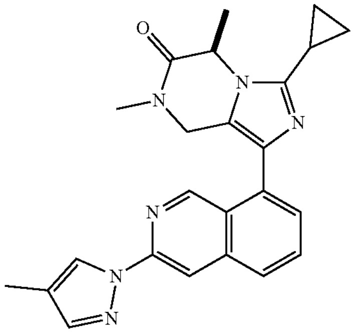
,
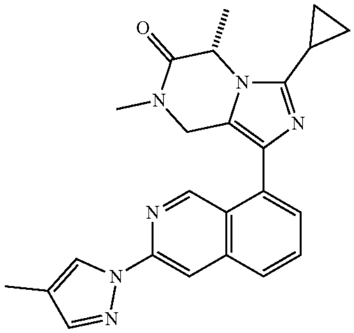
,
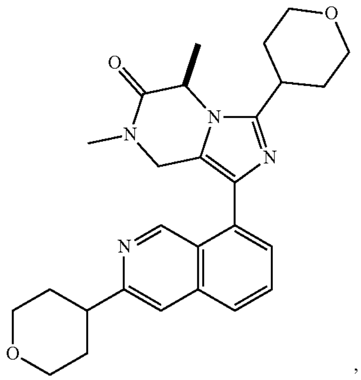
,
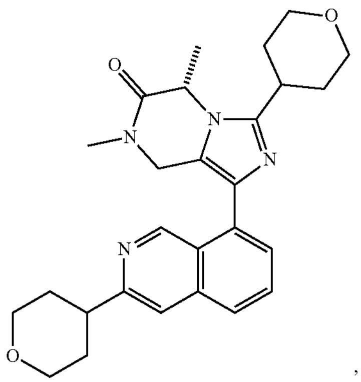
, -continued
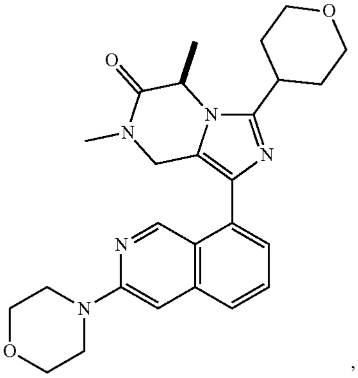
,
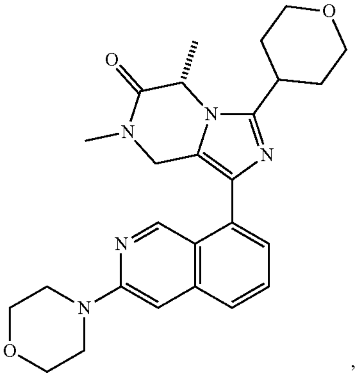
,
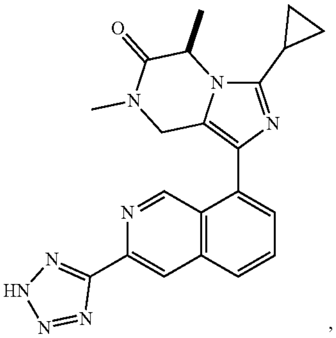
,
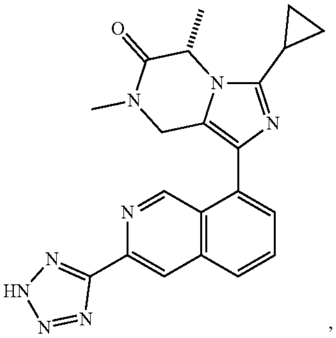
,
-continued
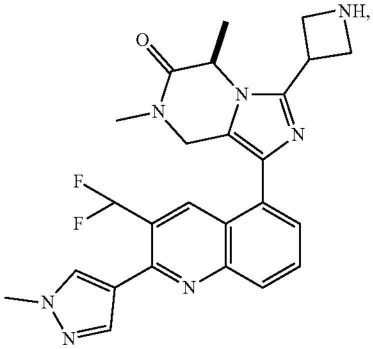
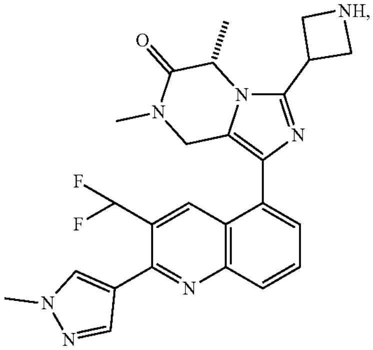
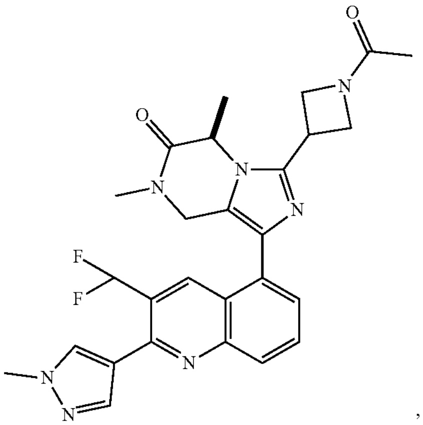
,
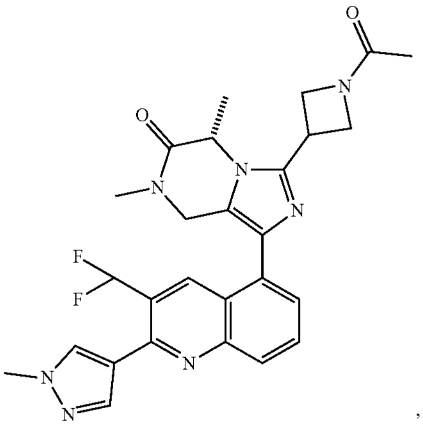
, -continued
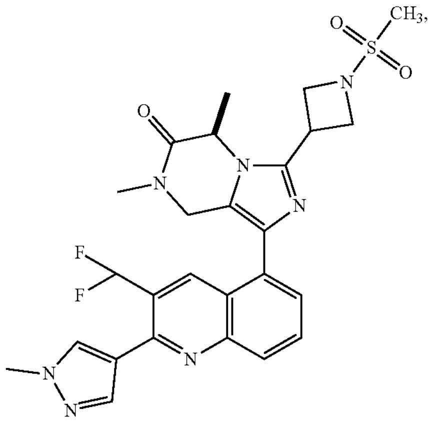
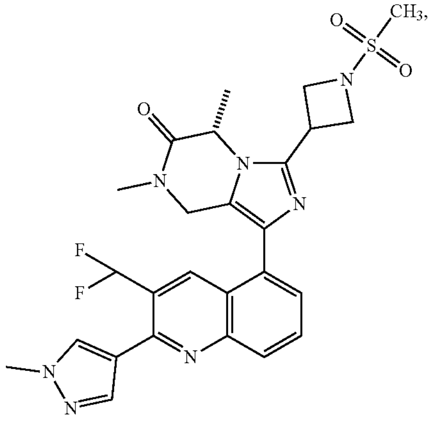
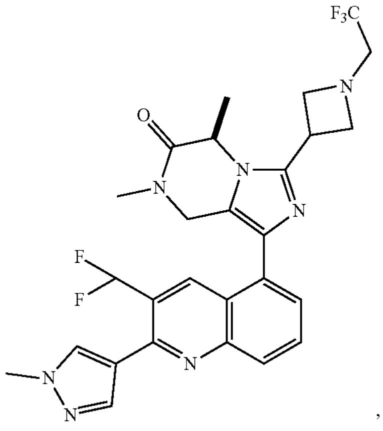
,
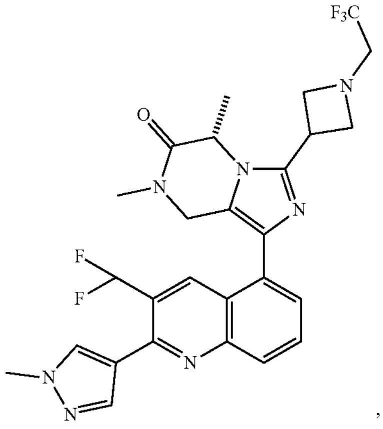
,
-continued
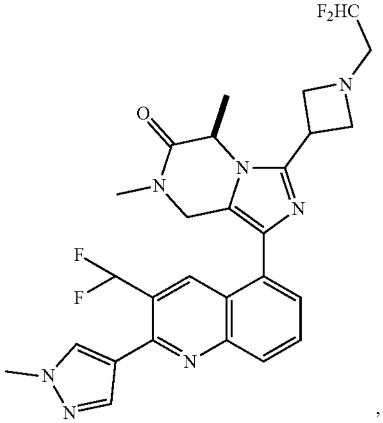
,
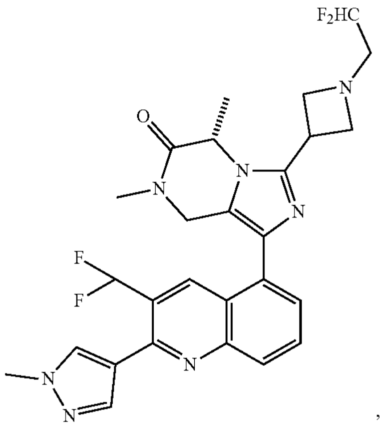
,
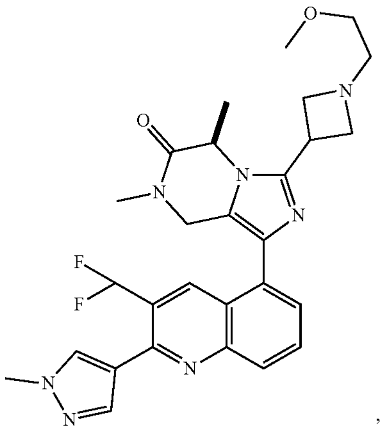
,
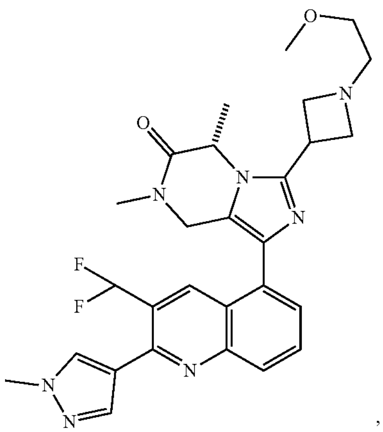
, -continued
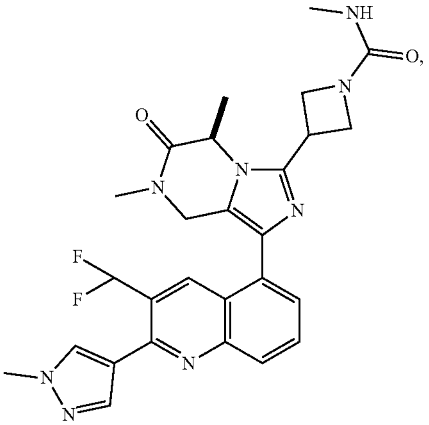
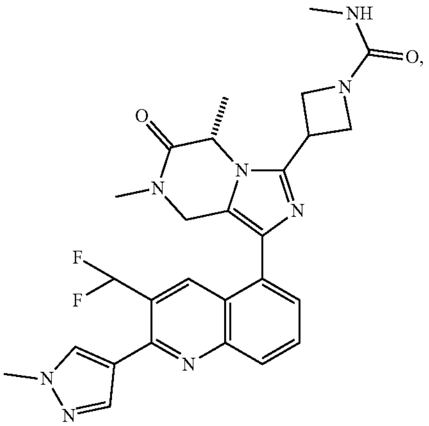
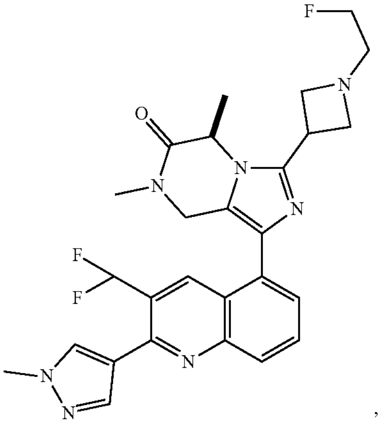
,
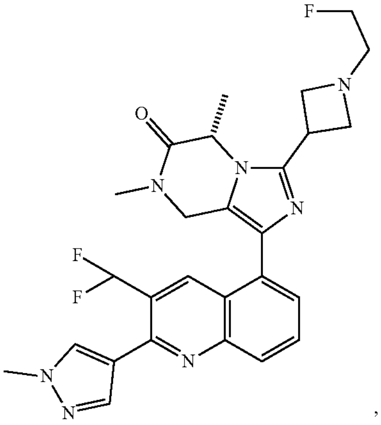
,
-continued
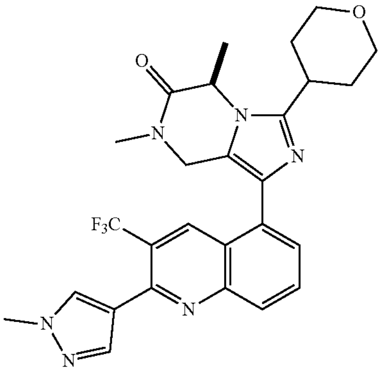
,
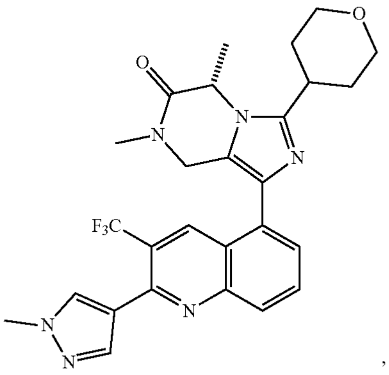
,
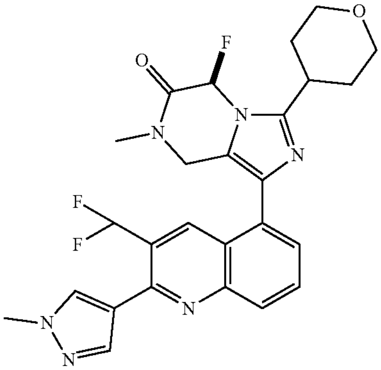
,
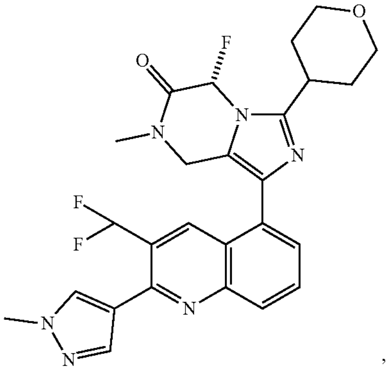
, -continued
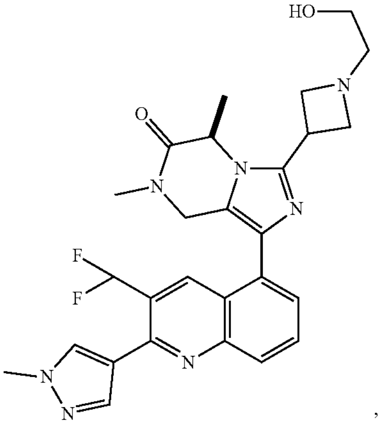
,
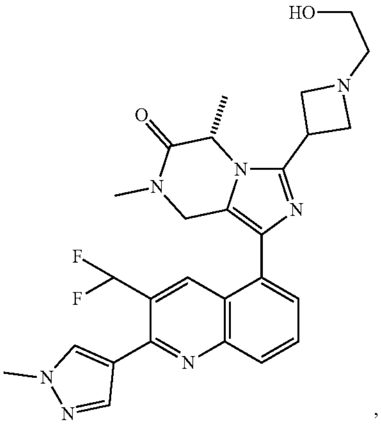
,
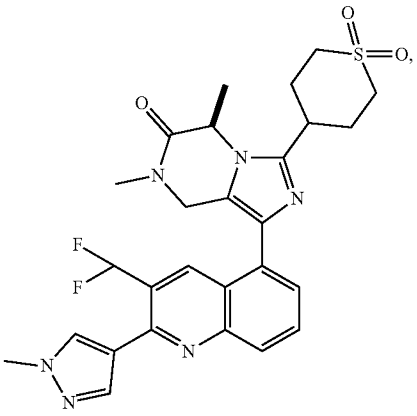
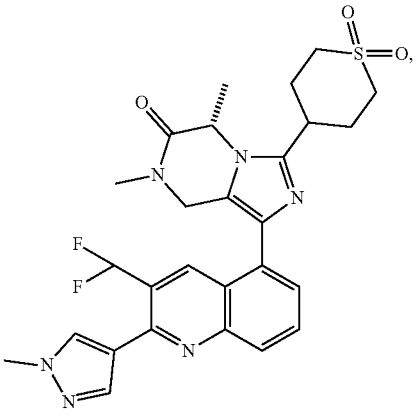
-continued
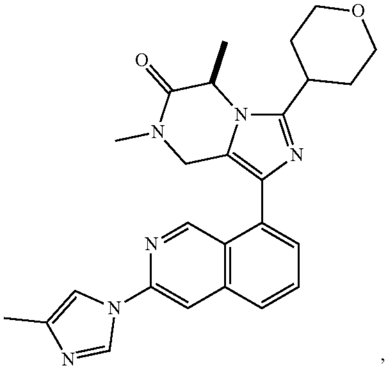
,
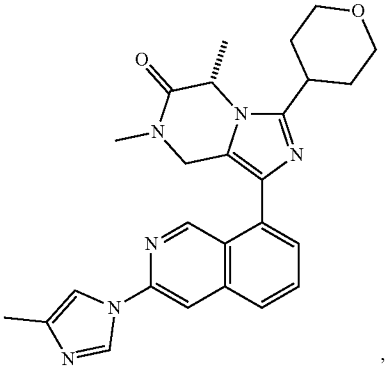
,
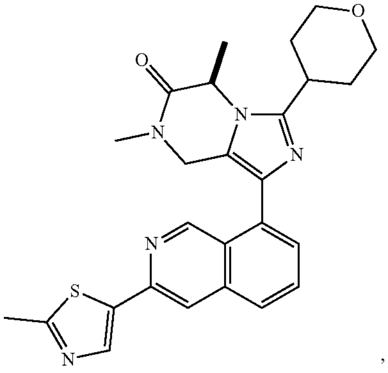
,
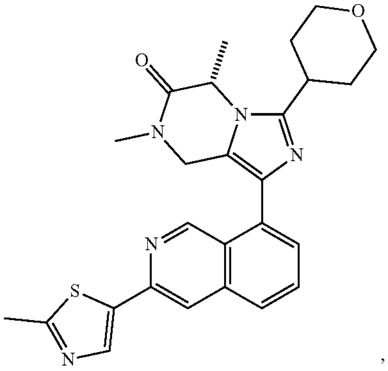
, -continued
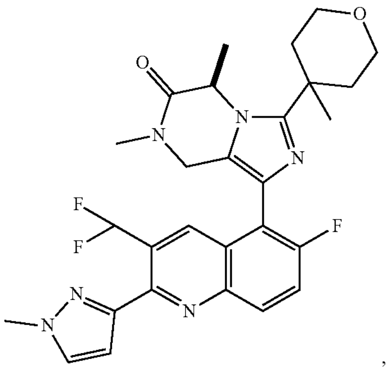
,
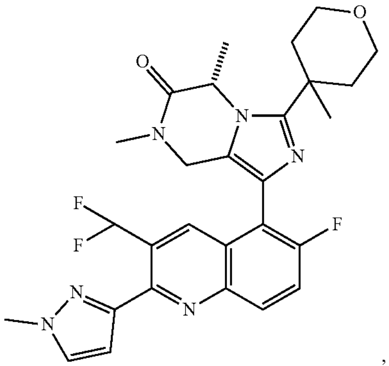
,
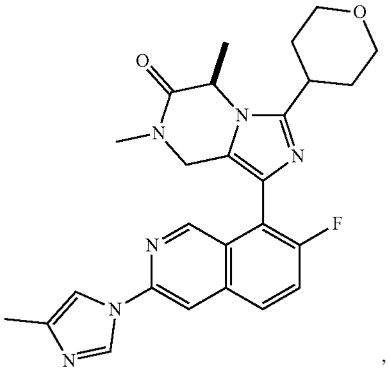
,
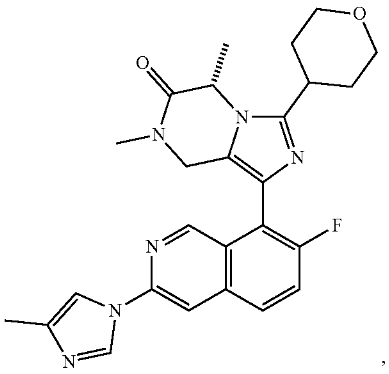
,
-continued
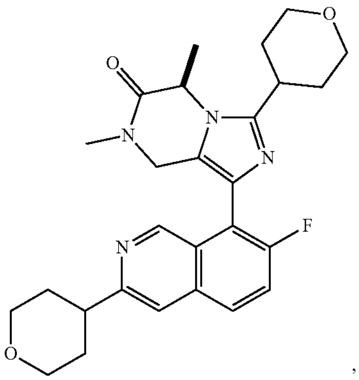
,
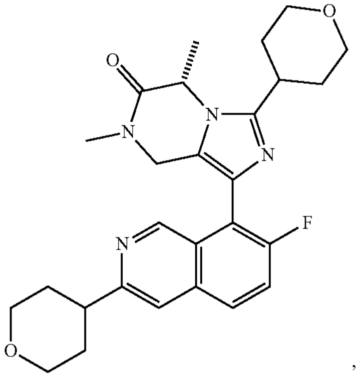
,
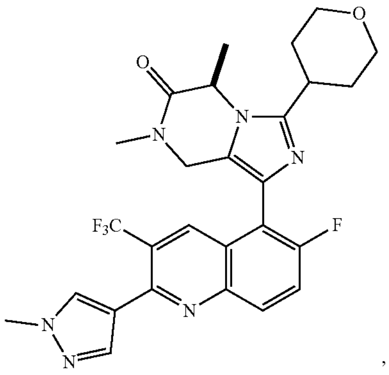
,
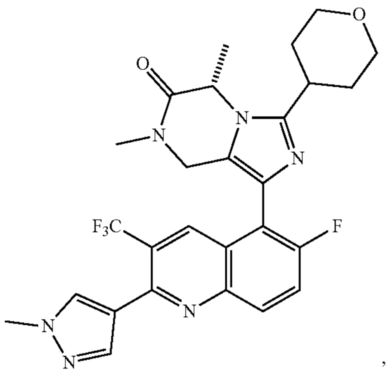
,

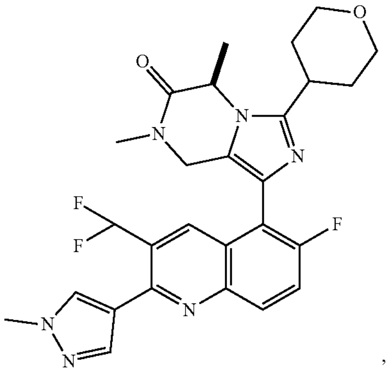
,
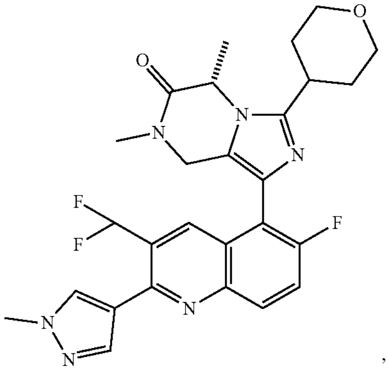
,
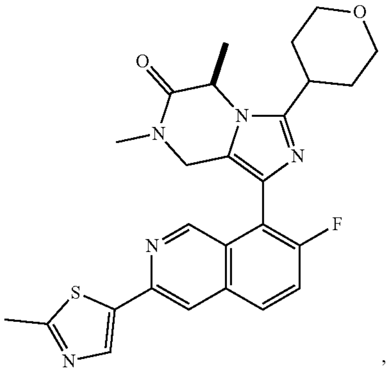
,
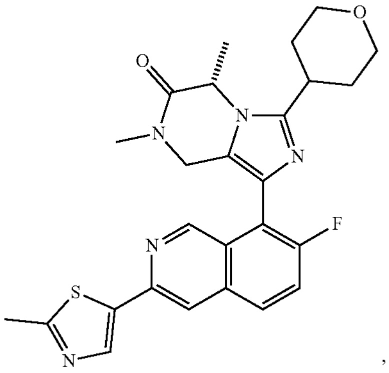
,
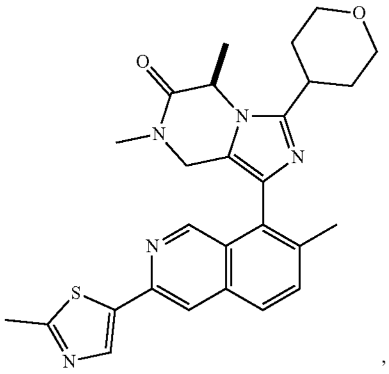
,
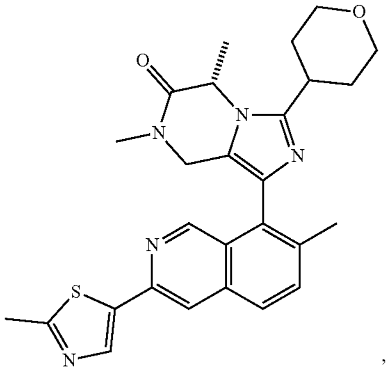
,
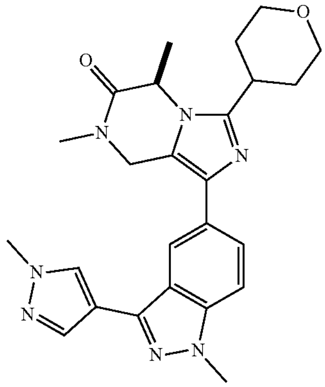
,
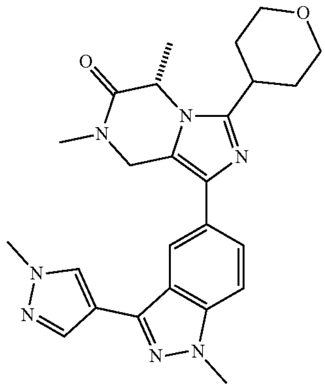
, -continued
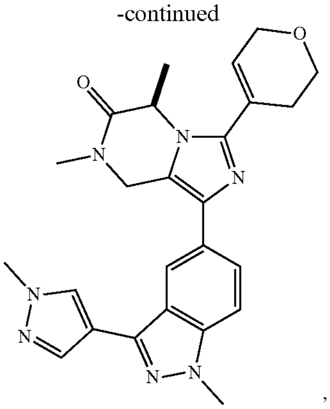
,
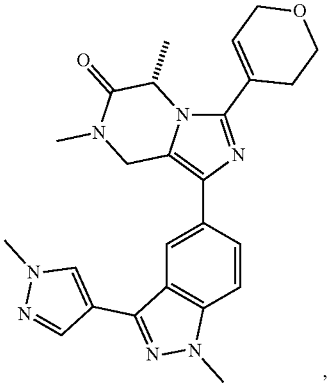
,
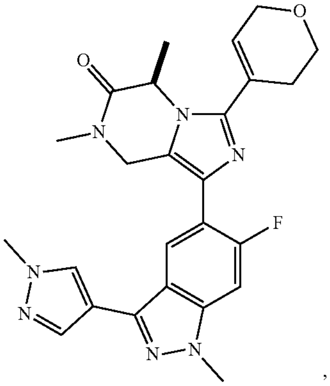
,
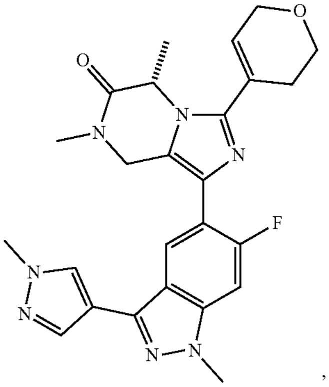
,
-continued
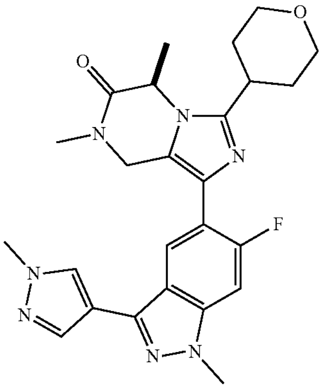
,
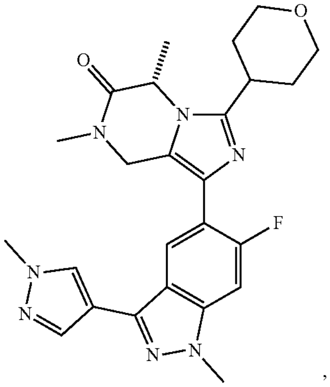
,
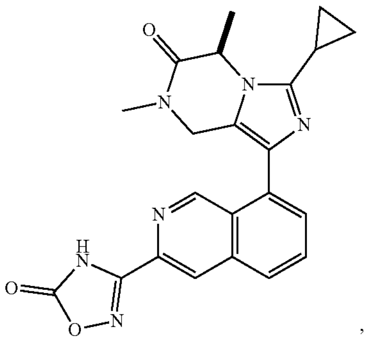
,
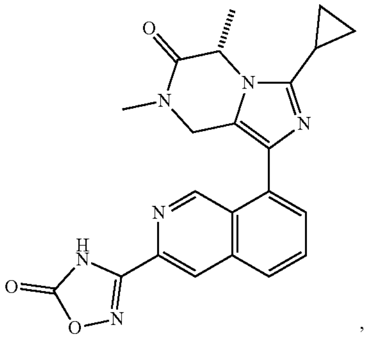
, -continued
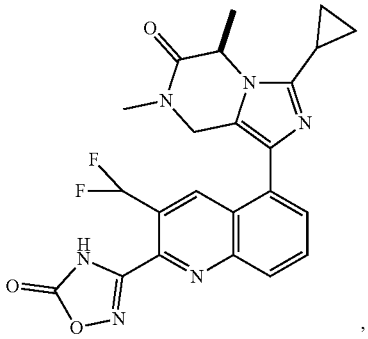
,
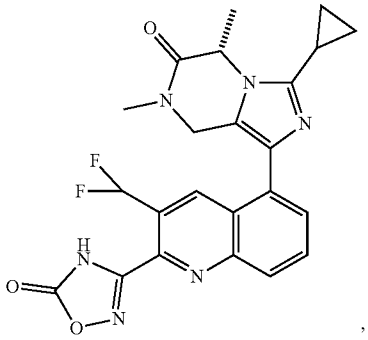
,
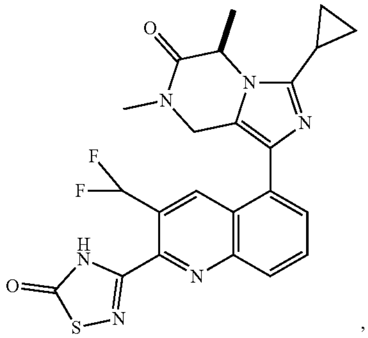
,
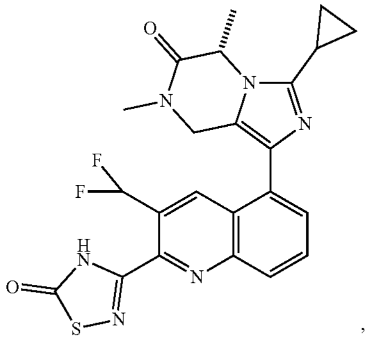
,
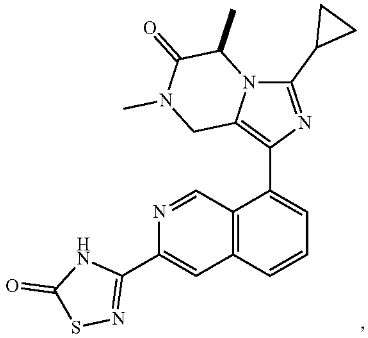
,
-continued
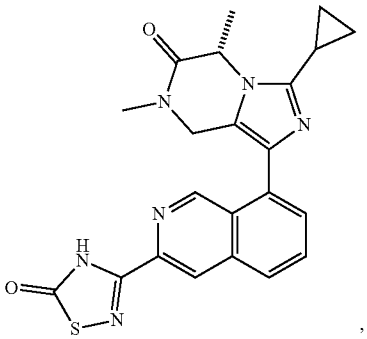
,
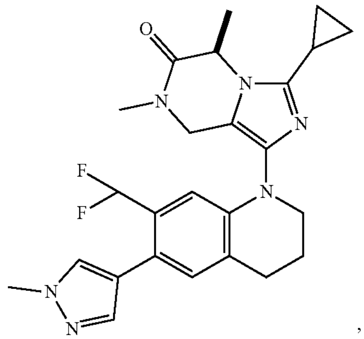
,
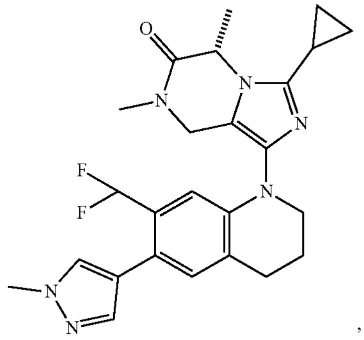
,
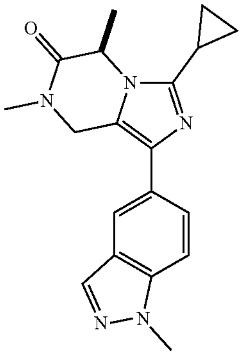
,
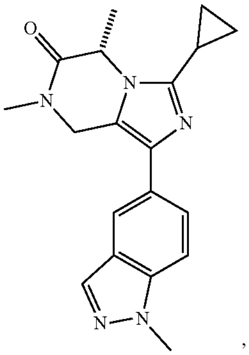
,
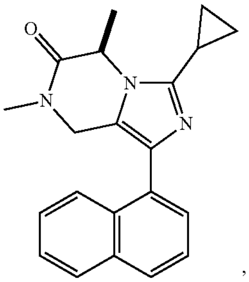
,
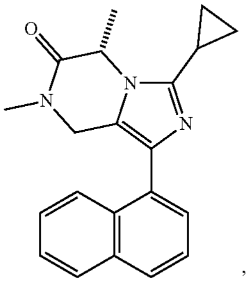
, -continued
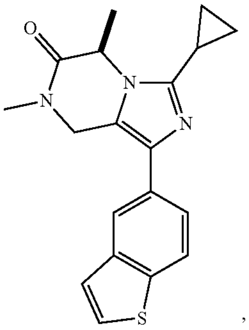,
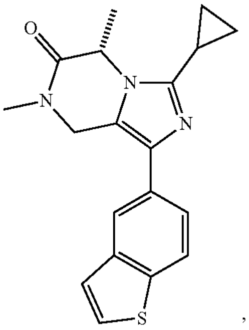,
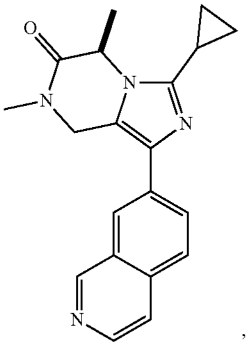,
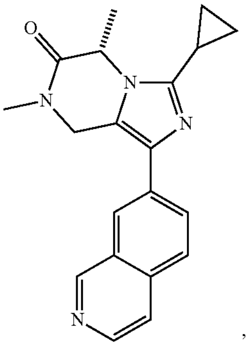,
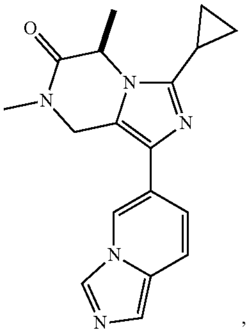,
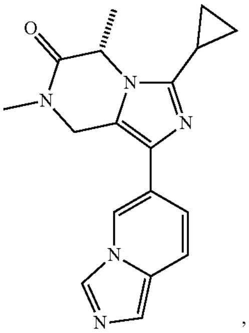,
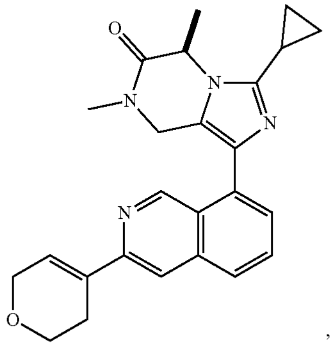,
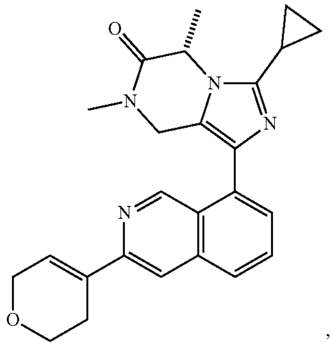,
-continued
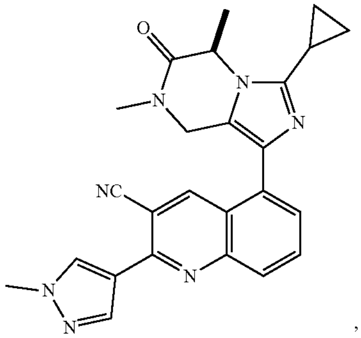,
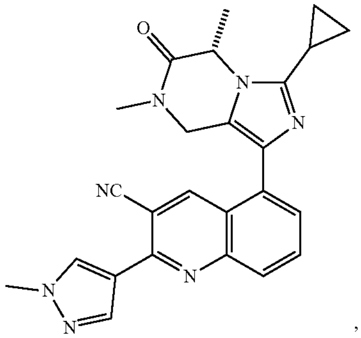,
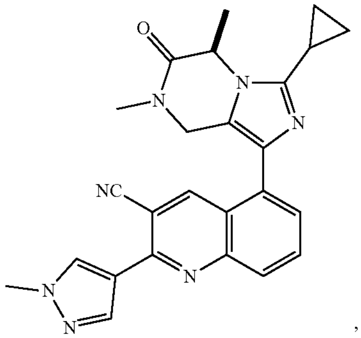,
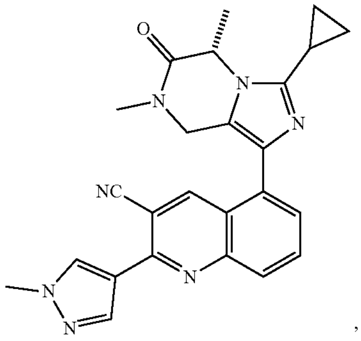,
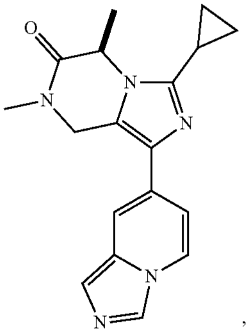,
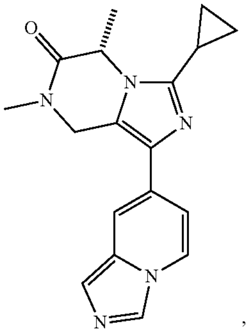, -continued
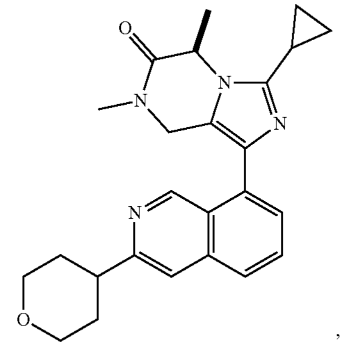
,
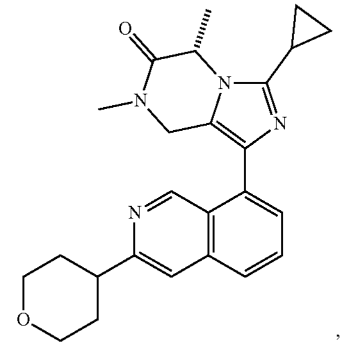
,
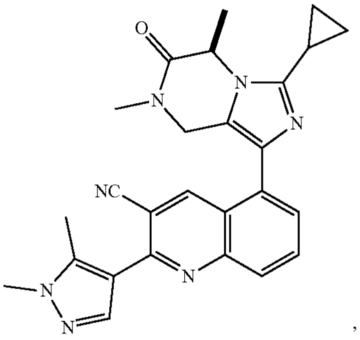
,
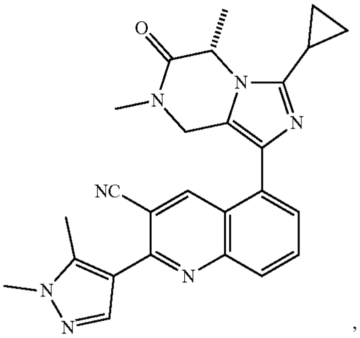
,
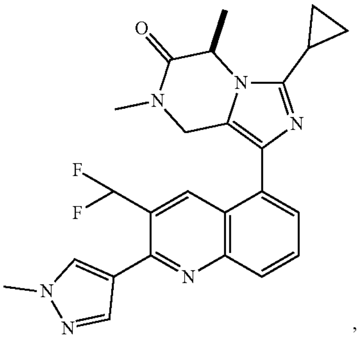
,
-continued
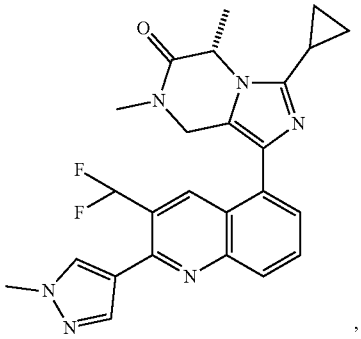
,
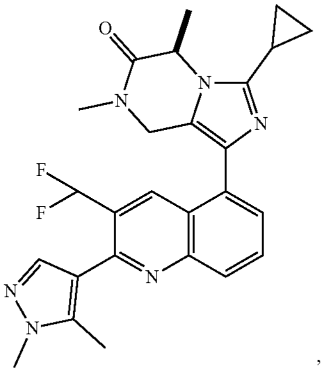
,
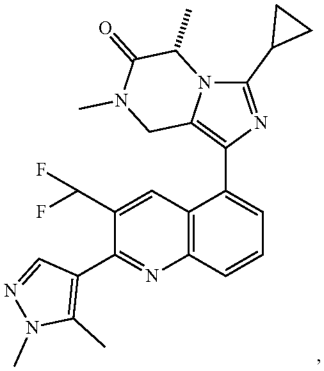
,
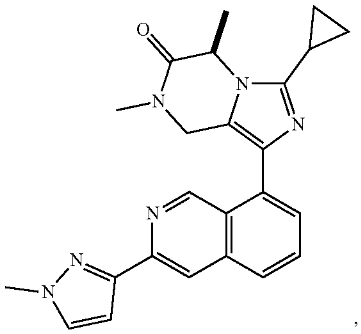
, -continued
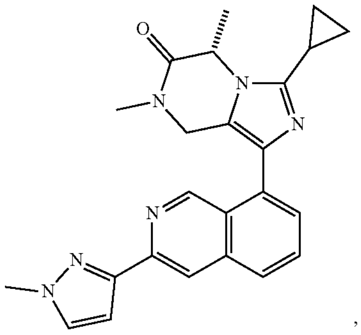
,
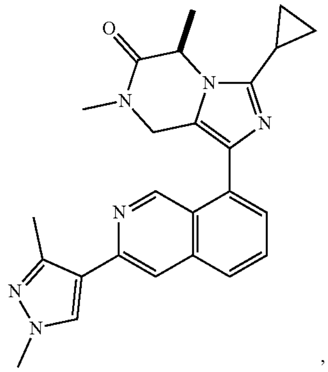
,
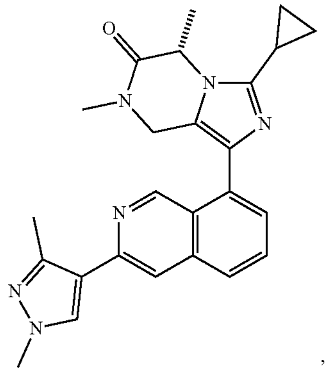
,
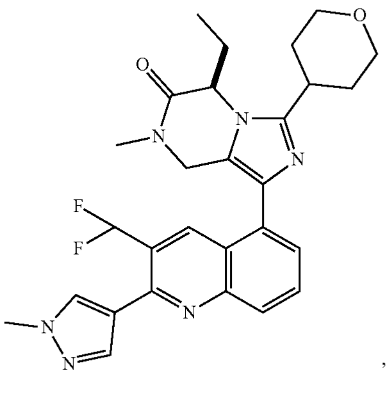
,
-continued
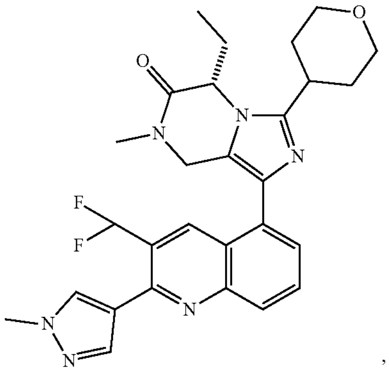
,
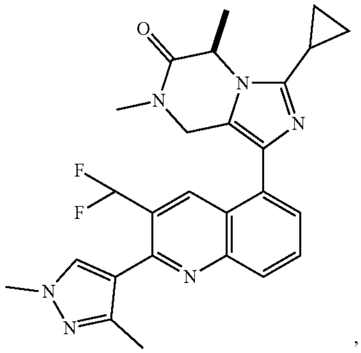
,
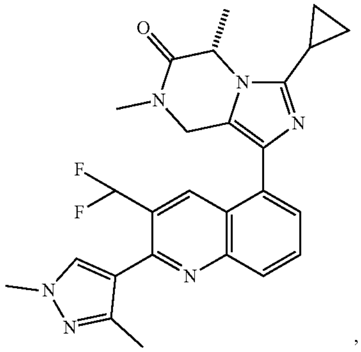
,
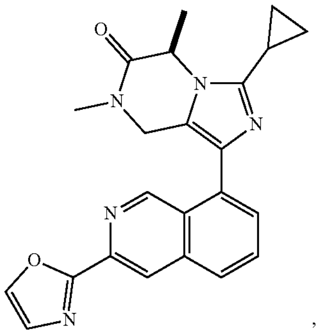
, -continued
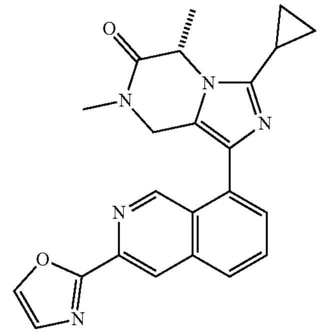
,
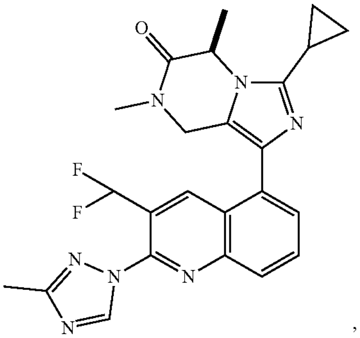
,
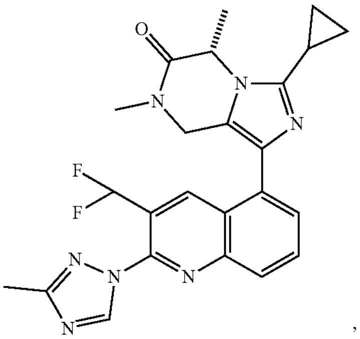
,
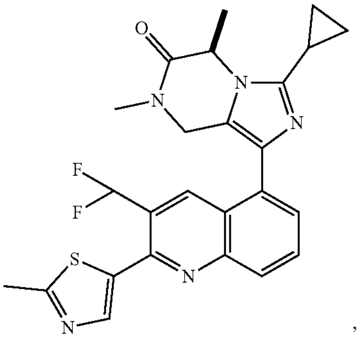
,
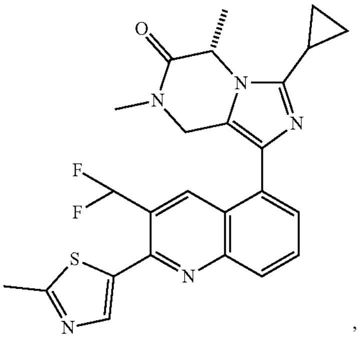
,
-continued
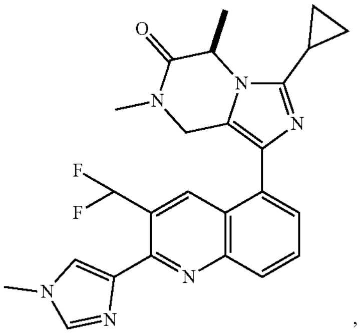
,
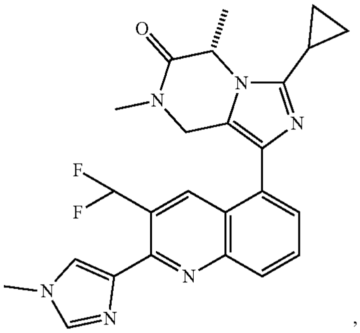
,
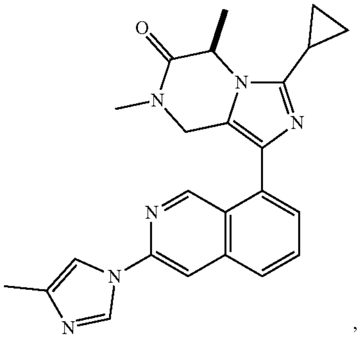
,
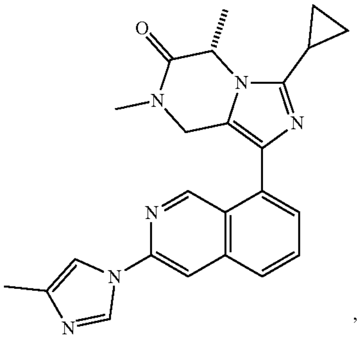
,
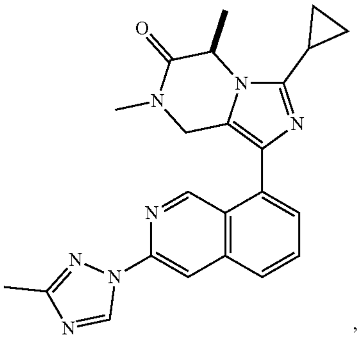
, -continued
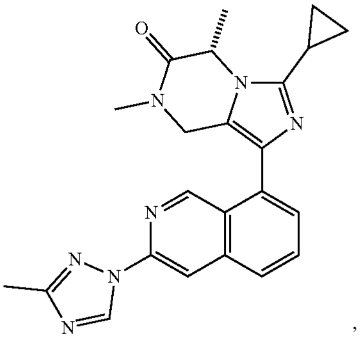
,
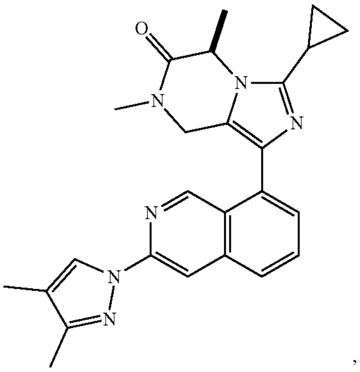
,
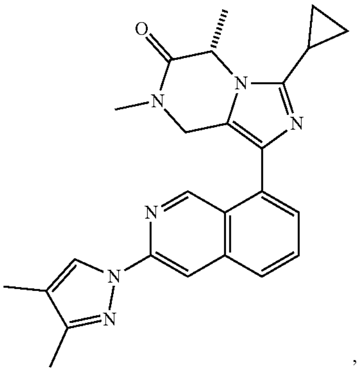
,
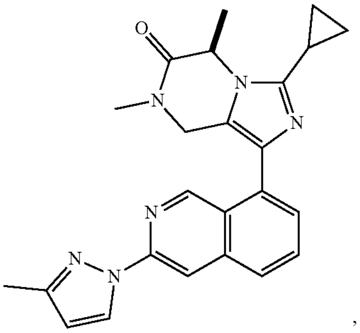
,
-continued
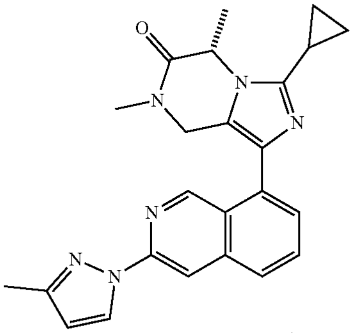
,
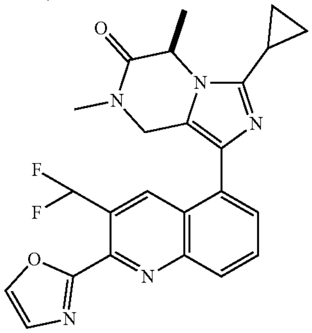
,
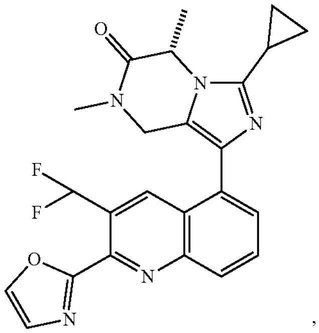
,
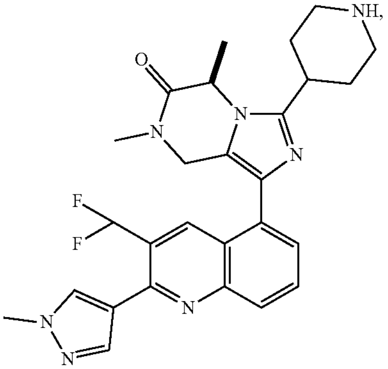
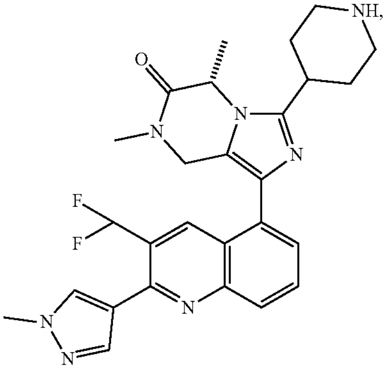

-continued
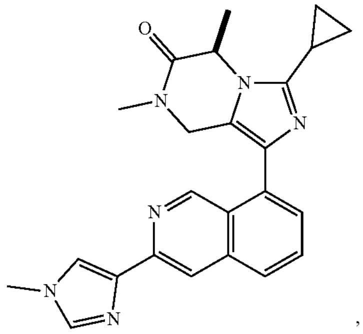
,
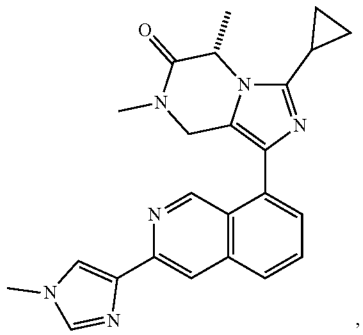
,
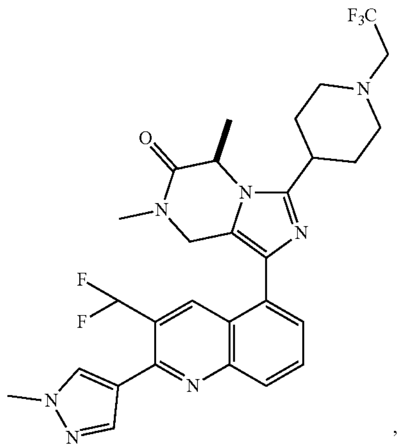
,
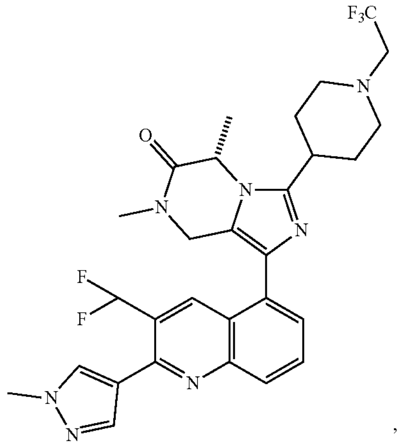
,
-continued
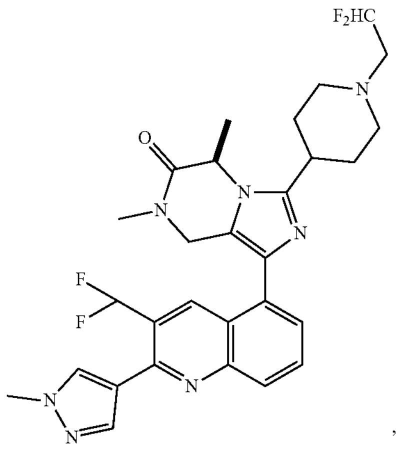
,
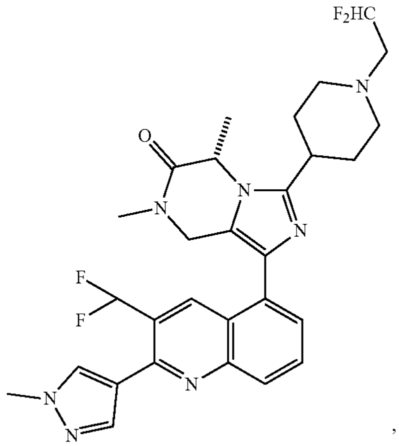
,
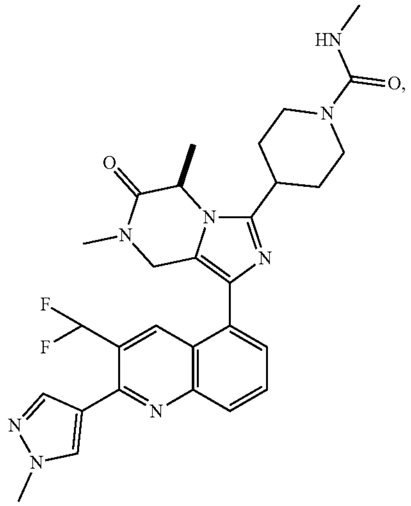
, -continued
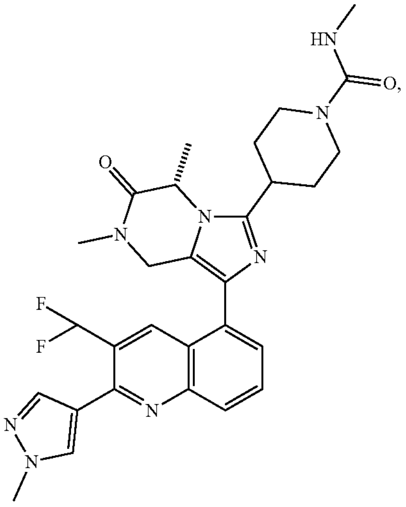
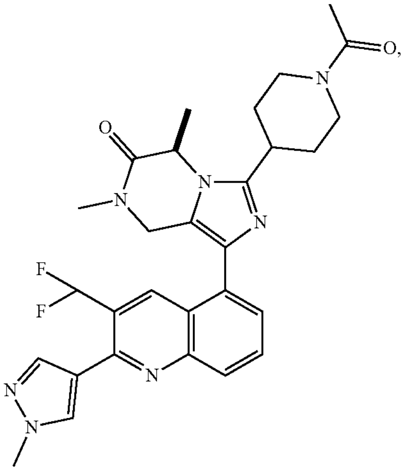
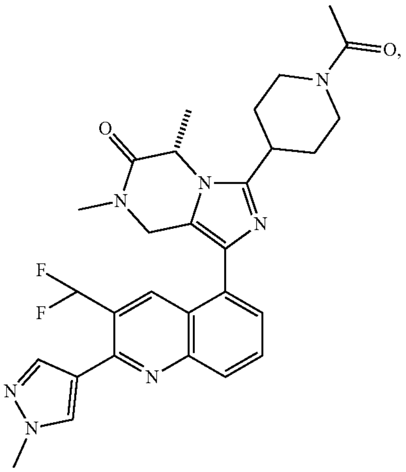
-continued
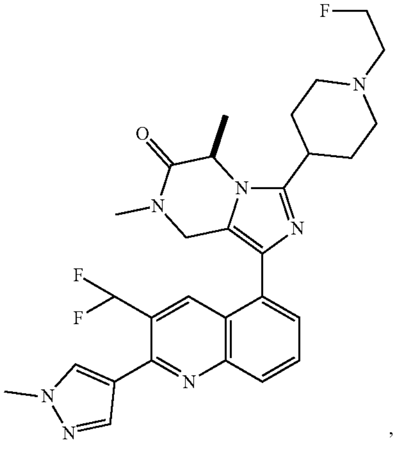
,
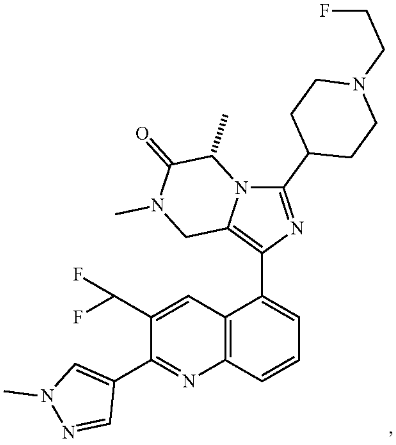
,
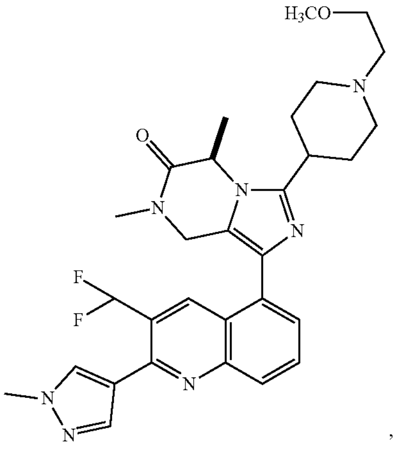
, -continued
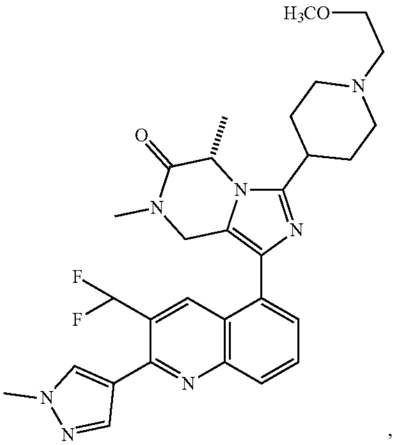
,
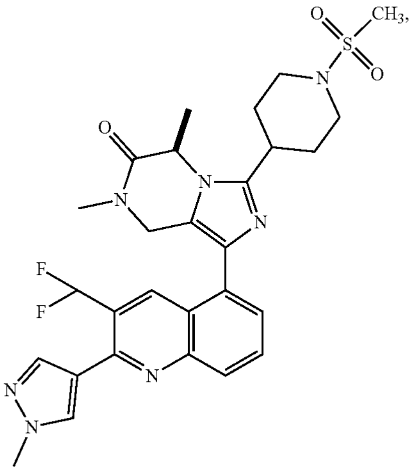
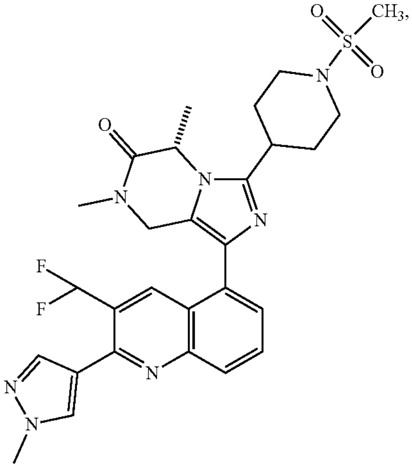
-continued
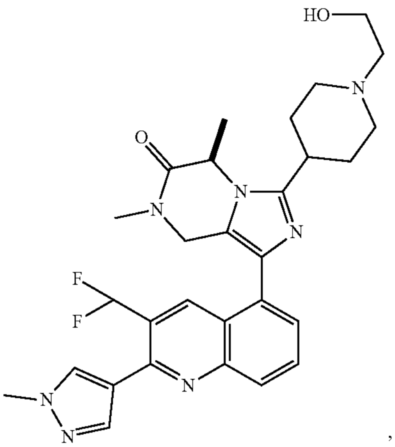
,
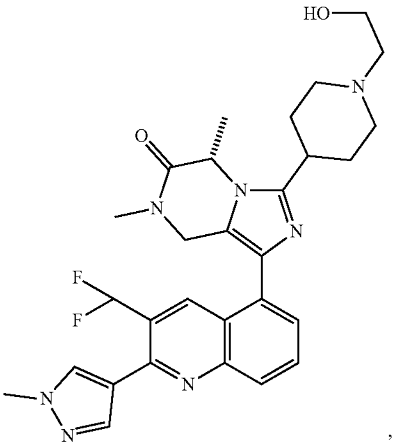
,
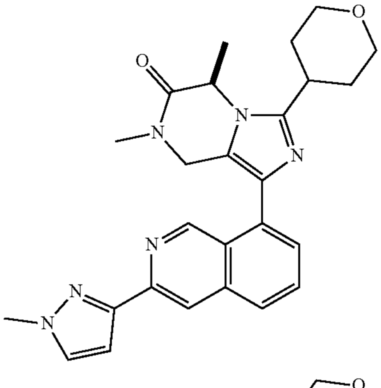
,
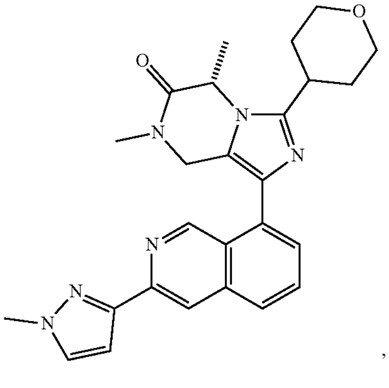
, -continued
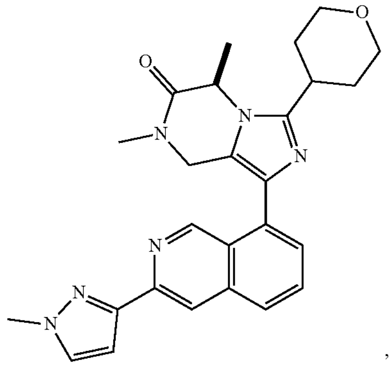
,
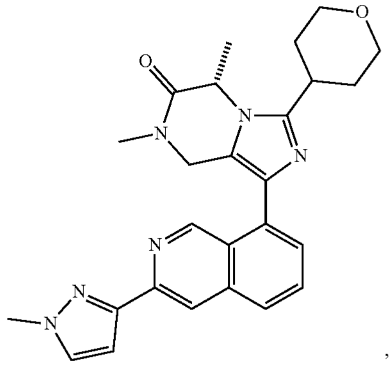
,
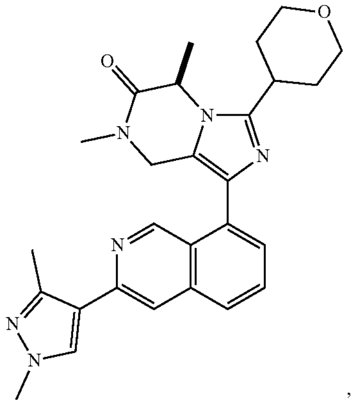
,
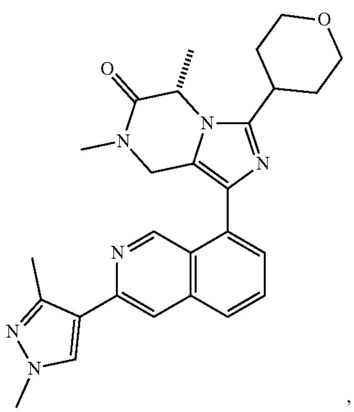
,
-continued
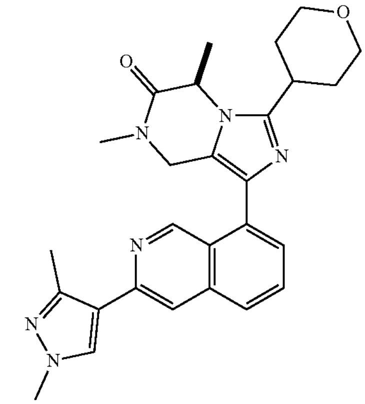
,
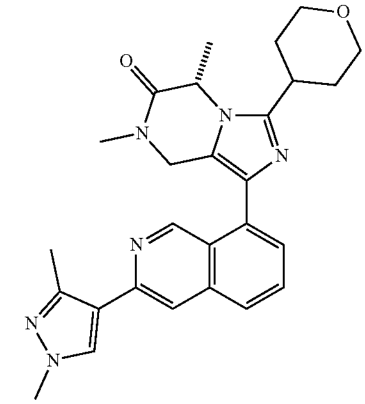
,
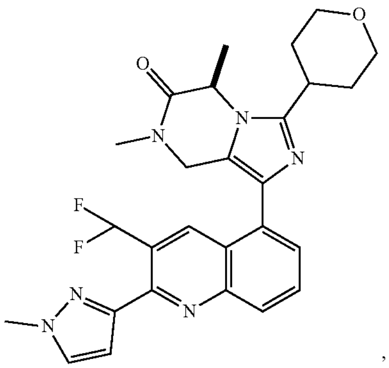
,
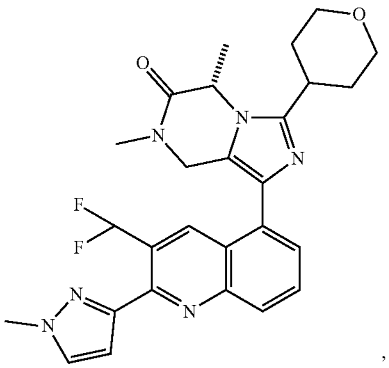
, -continued
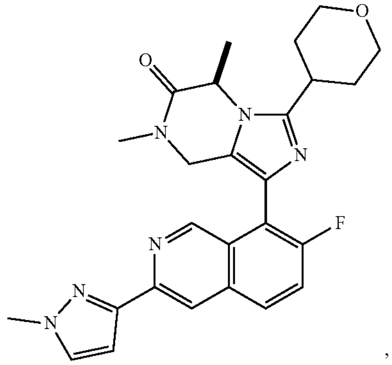
,
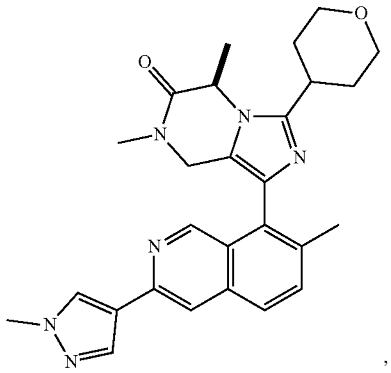
,
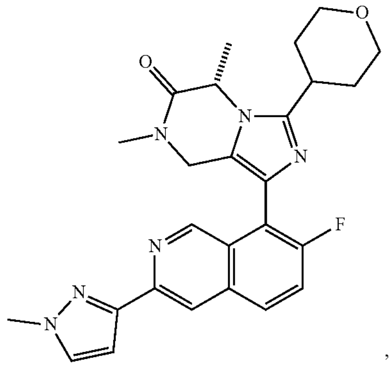
,
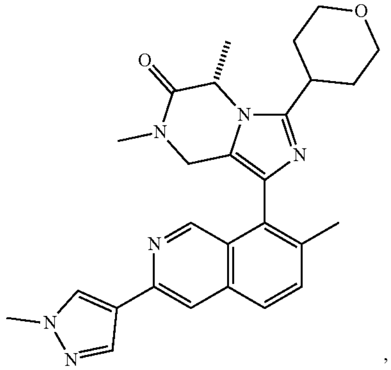
,
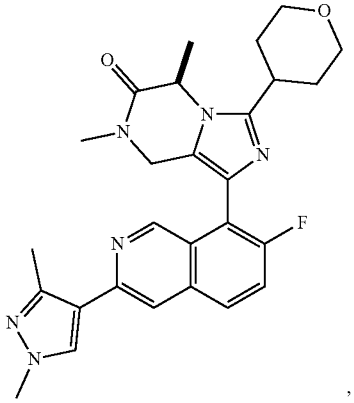
,
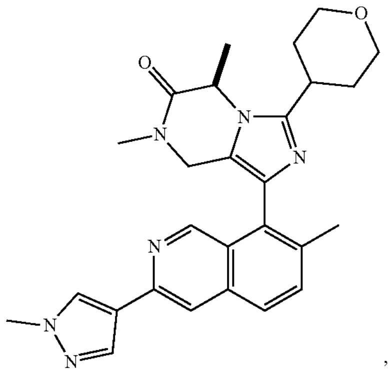
,
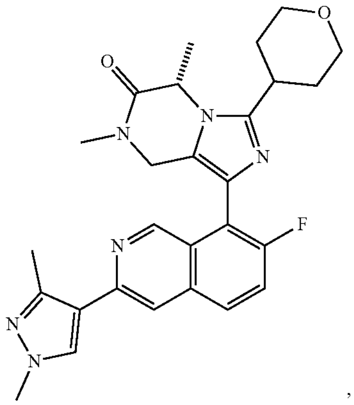
,
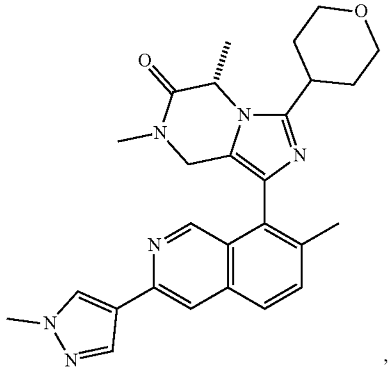
, -continued

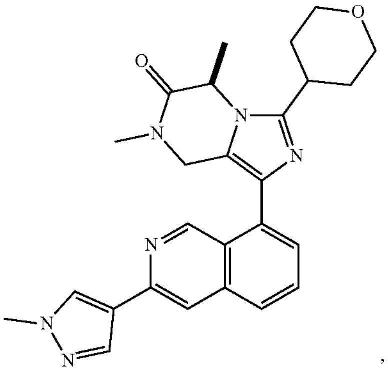

,

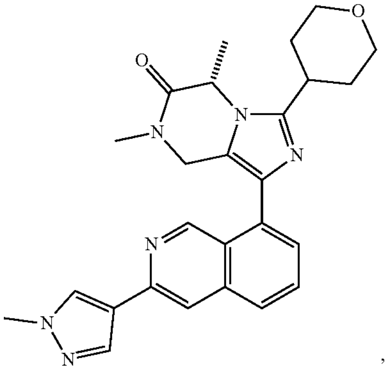

,

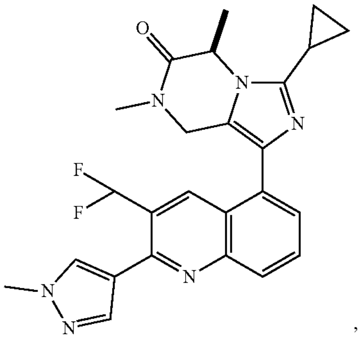

,

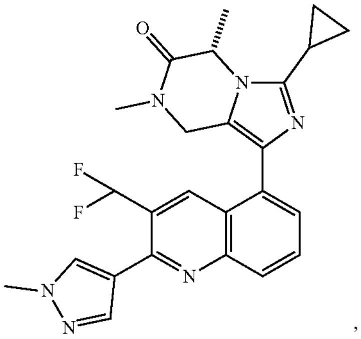

,

-continued

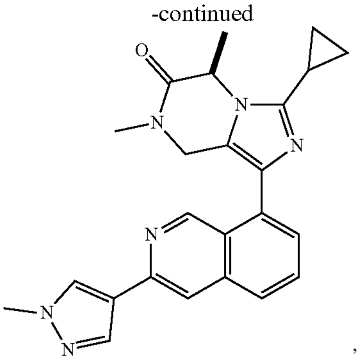

, and

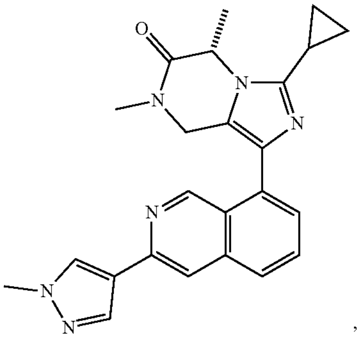

, or a salt thereof.

Also provided is a compound as recited in any preceding embodiment, or a salt thereof, which is selective for CBP and/or P300 over BRD4. In certain embodiments, the compound is at least tenfold selective CBP and/or P300 over BRD4. In certain embodiments, the compound is at least 100-fold selective CBP and/or P300 over BRD4. In certain embodiments, the compound is at least 1000-fold selective CBP and/or P300 over BRD4.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one function of CBP comprising the step of contacting CBP with a compound as described herein. The cell phenotype, cell proliferation, activity of CBP, change in biochemical output produced by active CBP, expression of CBP, or binding of CBP with a natural binding partner may be monitored. Such methods may be modes of treatment of disease, biological assays, cellular assays, biochemical assays, or the like.

The present disclosure also relates to a method of inhibiting at least one function of P300 comprising the step of contacting P300 with a compound as described herein. The cell phenotype, cell proliferation, activity of P300, change in biochemical output produced by active P300, expression of P300, or binding of P300 with a natural binding partner may be monitored. Such methods may be modes of treatment of disease, biological assays, cellular assays, biochemical assays, or the like.

Also provided herein is a method of treatment of a CBP-mediated disease comprising the administration of a therapeutically effective amount of a compound as disclosed herein, or a salt thereof, to a patient in need thereof.

Also provided herein is a method of treatment of a P300-mediated disease comprising the administration of a therapeutically effective amount of a compound as disclosed herein, or a salt thereof, to a patient in need thereof.

In certain embodiments, the disease is a proliferative disease.

In certain embodiments, the disease is cancer.

Also provided herein is a compound as disclosed herein for use as a medicament.

Also provided herein is a compound as disclosed herein for use as a medicament for the treatment of a CBP-mediated disease.

Also provided herein is a compound as disclosed herein for use as a medicament for the treatment of a P300-mediated disease.

Also provided is the use of a compound as disclosed herein as a medicament.

Also provided is the use of a compound as disclosed herein as a medicament for the treatment of a CBP-mediated disease.

Also provided is the use of a compound as disclosed herein as a medicament for the treatment of a P300-mediated disease.

Also provided is a compound as disclosed herein for use in the manufacture of a medicament for the treatment of a CBP-mediated disease.

Also provided is a compound as disclosed herein for use in the manufacture of a medicament for the treatment of a P300-mediated disease.

Also provided is the use of a compound as disclosed herein for the treatment of a CBP-mediated disease.

Also provided is the use of a compound as disclosed herein for the treatment of a P300-mediated disease.

Also provided herein is a method of inhibition of CBP comprising contacting CBP with a compound as disclosed herein, or a salt thereof.

Also provided herein is a method of inhibition of P300 comprising contacting P300 with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the CBP-mediated disease is cancer.

In certain embodiments, the P300-mediated disease is cancer.

Also provided is a method of modulation of a CBP-mediated function in a subject comprising the administration of a therapeutically effective amount of a compound as disclosed herein.

Also provided is a method of modulation of a P300-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

Abbreviations and Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $—C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($—CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene ($—CFH—$), difluoromethylene ($—CF_2—$), chloromethylene ($—CHCl—$) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, $—CH_2—NH—OCH_3$.

The term "heteroaryl", as used herein, alone or in combination, refers to a 3 to 15 membered unsaturated heteromonocyclic ring, or a fused monocyclic, bicyclic, or tricyclic ring system in which all of the fused rings are aromatic, which contains at least one atom chosen from N, O, and S. The term "heteroaryl" thus encompasses, for example, pyridine, thiophene, quinoline, and phenanthridine. The term "heteroaryl" thus does not encompass, for example, indoline, and 2,3-dihydrobenzofuran. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, and wherein heteroaryl rings are fused with other heteroaryl rings. Examples of heteroaryl groups include pyrrolyl, pyrrolinyl, imidazolyl, pyrazolyl, pyridyl, pyrimidinyl, pyrazinyl, pyridazinyl, triazolyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, and the like. Exemplary tricyclic heterocyclic groups include carbazolyl, phenanthrolinyl, dibenzofuranyl, acridinyl, phenanthridinyl, and the like.

The terms "heterocycloalkyl" and, interchangeably, "heterocycle," as used herein, alone or in combination, each refer to a saturated, partially unsaturated, or fully unsaturated (but not fully aromatic) monocyclic, bicyclic, or tricyclic heterocyclic group containing at least one heteroatom as a ring member, wherein each said heteroatom may be independently chosen from nitrogen, oxygen, and sulfur. The term "heterocycloalkyl" thus excludes fully aromatic ring systems such as pyridine, pyrimidine, quinoline, and acridine. The term "heterocycloalkyl" thus includes partially aromatic bicyclic and larger ring systems such as 1,2,3,4-tetrahydroquinoline, 5,6,7,8-tetrahydroquinoline, and indoline. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "7,8-dihydroimidazo[1,5-a]pyrazine-6(5H)-one", as used herein, alone or in combination, refers to the compound having the chemical formula:

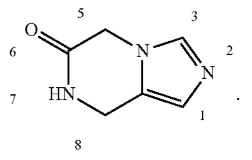

Substituents on the 7,8-dihydroimidazo[1,5-a]pyrazine-6(5H)-one structure can be numbered according to the scheme shown above. The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a $RS(=O)_2NR'$— group with R and R' as defined herein.

The term "S-sulfonamido" refers to a —$S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"CBP inhibitor", as used herein, refers to a compound that binds to and inhibits the bromodomain of CBP with measurable affinity and activity. In certain embodiments, a CBP inhibitor exhibits an IC50 with respect to CBP activity of no more than about 100 μM and more typically not more than about 50 μM, as measured in the CBP (assay name) described generally herein. "IC50" is that concentration of inhibitor which reduces the activity of the bromodomain of CBP to half-maximal level. Certain compounds disclosed herein have been discovered to exhibit inhibition against CBP. In certain embodiments, compounds will exhibit an IC50 with respect to CBP of no more than about 20 μM; in further embodiments, compounds will exhibit an IC50 with respect to CBP of no more than about 5 μM; in yet further embodiments, compounds will exhibit an IC50 with respect to CBP of not more than about 200 nM; in yet further embodiments, compounds will exhibit an IC50 with respect to CBP of not more than about 50 nM; in yet further embodiments, compounds will exhibit an IC50 with respect to CBP of not more than about 10 nM; in yet further embodiments, compounds will exhibit an IC50 with respect to CBP of not more than about 2 nM, as measured in the CBP assay described herein.

"P300 inhibitor", as used herein, refers to a compound that binds to and inhibits the bromodomain of P300 with measurable affinity and activity. In certain embodiments, a P300 inhibitor exhibits an IC50 with respect to P300 activity of no more than about 100 μM and more typically not more than about 50 μM, as measured in the P300 (assay name) described generally herein. "IC50" is that concentration of inhibitor which reduces the activity of the bromodomain of P300 to half-maximal level. Certain compounds disclosed herein have been discovered to exhibit inhibition against P300. In certain embodiments, compounds will exhibit an IC50 with respect to P300 of no more than about 20 μM; in further embodiments, compounds will exhibit an IC50 with respect to P300 of no more than about 5 μM; in yet further embodiments, compounds will exhibit an IC50 with respect to P300 of not more than about 200 nM; in yet further embodiments, compounds will exhibit an IC50 with respect to P300 of not more than about 50 nM; in yet further embodiments, compounds will exhibit an IC50 with respect to P300 of not more than about 10 nM; in yet further embodiments, compounds will exhibit an IC50 with respect to P300 of not more than about 2 nM, as measured in the P300 assay described herein.

In some embodiments, certain compounds disclosed herein interfere with the associating of CBP and/or P300 with histones, in particular acetylated lysines in histones. In some embodiments, certain compounds disclosed herein inhibit binding of CBP and/or P300 to chromatin (e.g., histone associated DNA). In some embodiments, certain compounds disclosed herein inhibit and/or reduces binding of the CBP bromodomain and/or P300 bromodomain to chromatin (e.g., histone associated DNA). In some embodiments, certain compounds disclosed herein do not affect association of other domains of CBP and/or P300 to chromatin. In some embodiments, certain compounds disclosed herein bind to the CBP and/or P300 primarily (e.g., solely)

through contacts and/or interactions with the CBP bromodomain and/or P300 bromodomain. In some embodiments, certain compounds disclosed herein bind to the CBP and/or P300 through contacts and/or interactions with the CBP bromodomain and/or P300 bromodomain as well as additional CBP and/or P300 residues and/or domains. Methods of assaying association with chromatin are known in the art and include, but are not limited to, chromatin fractionation, BRET assay (Promega), FRAP assay, Chromatin Immunoprecipitation (ChIP), biophysical binding assay, and/or Histone Association Assay. See, e.g., Das et al., BioTechniques 37:961-969 (2004).

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a CBP/P300 inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); *vinca* alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN); (8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatininb (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Where a subject is suffering from or at risk of suffering from an inflammatory condition, a CBP/EP300 inhibitor compound described herein is optionally used together with one or more agents or methods for treating an inflammatory condition in any combination. Therapeutic agents/treatments for treating an autoimmune and/or inflammatory condition include, but are not limited to any of the following examples:

(1) corticosteroids, including but not limited to cortisone, dexamethasone, and methylprednisolone;

(2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);

(3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);

(4) CD20 blockers, including but not limited to rituximab (RITUXAN);

(5) Tumor Necrosis Factor (TNF) blockers, including but not limited to etanercept (ENBREL), infliximab (REMICADE) and adalimumab (HUMIRA);

(6) interleukin-1 receptor antagonists, including but not limited to anakinra (KINERET);

(7) interleukin-6 inhibitors, including but not limited to tocilizumab (ACTEMRA);

(8) interleukin-17 inhibitors, including but not limited to AIN457;

(9) Janus kinase inhibitors, including but not limited to tasocitinib; and

(10) syk inhibitors, including but not limited to fostamatinib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating CBP-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of CBP-mediated disorders.

Thus, in another aspect, certain embodiments provide methods for treating P300-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of P300-mediated disorders.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML),) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; $BPin_2$=bis(pinacolato)diboron; Brettphos=2-(dicyclohexylphosphino)3,6-dimethoxy-2',4',6'-triisopropyl-1,1'-biphenyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride dba=dibenzylideneacetone; DBU=1,8-diazabicyclo[5.4.0]undec-7-ene; DCM=dichloromethane; DEAD=diethyl azodicarboxylate; DHP=3,4-dihydro-2H-pyran; DIBAL-H=di-iso-butyl aluminium hydride; DIEA=DIPEA=$iPr_2NEt$=N,N-diisopropylethylamine; DMAP=4-dimethylaminopyridine; DMF=N,N-dimethylformamide; DMP=Dess-Martin periodinane=3,3,3-triacetoxy-3-iodophthalide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC•HCl=EDCI•HCl=1-ethyl-3-(3-dimethylaminopropyl) carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-Pr=isopropyl=2-propyl; i-PrOH=isopropanol; LAH=lithium aluminum hydride; LiHMDS=lithium bis(trimethylsilyl)amide; LDA=lithium diisopropyl amide; mCPBA=3-chloroperbenzoic acid; Me=methyl; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=sodium bis(trimethylsilyl)amide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $PdCl_2(dppf)$=[1,1'-bis(diphenylphosphino)ferrocene]palladium(II) chloride; $Pd(Ph_3)_4$=tetrakis(triphenylphosphine)palladium(0); $Pd_2(dba)_3$=tris(dibenzylideneacetone)-dipalladium(0); $PdCl_2(PPh_3)_2$=bis(triphenylphosphine)palladium(II) dichloride; PG=protecting group; Ph=phenyl; prep-HPLC=preparative high-performance liquid chromatography; PPTS=pyridinium p-toluenesulfonate; PMBCl=para-methoxybenzyl; PMBCl=para-methoxybenzyl chloride; PMBOH=para-methoxybenzyl alcohol; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=propylphosphonic anhydride; tBu=t-Bu=teRT-butyl=1,1-dimethylethyl; TBAF=tetrabutylammonium fluoride; TBDPS=t-butyldiphenylsilyl; TBS=TBDMS=tert-butyldimethylsilyl; TBSCl=TBDMSCl=tert-butyldimethylchlorosilane; TBDPS=tert-butyldiphenylsilyl; TBDPSCL=tert-butyl(chloro)diphenylsilane; TEA=$Et_3N$= triethylamine; TFA=trifluoroacetic acid; TFAA= trifluoroacetic anhydride; THF=tetrahydrofuran; TIPS= triisopropylsilyl; Tol=toluene; TsCl=tosyl chloride; =p-toluenesulfonyl chloride; TosMIC=p-toluenesulfonylmethyl isocyanide; TRT=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl; XPhos Pd G2=chloro(2-dicyclohexylphosphino-2',4',6'-triisopropyl-1,1'-biphenyl) [2-(2'-amino-1,1'-biphenyl)]palladium(II).

General Synthetic Methods for Preparing Compounds

The following schemes can be used to practice the present disclosure.

Scheme I

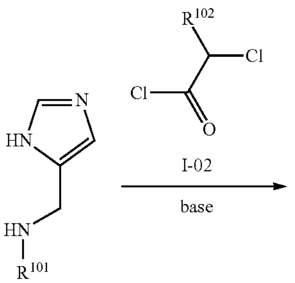

I-02

I-01

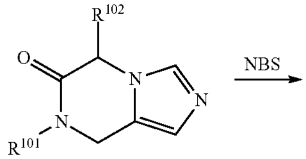

I-03

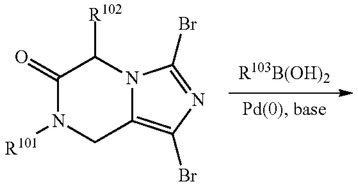

I-04

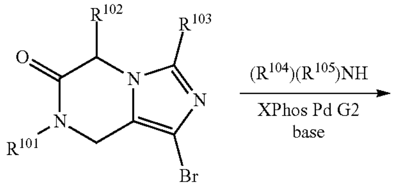

I-05

-continued

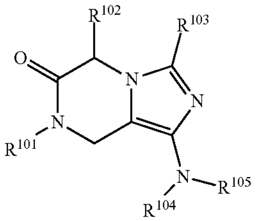

I-06

The Examples can be synthesized using the following general synthetic procedure set forth in Scheme I. Imidazole I-01 is reacted with acid chloride I-02 to give the 7,8-dihydro-imidazo[1,5-a]pyrazine-6(5H)-one compound I-03. Treatment with NBS gives 3,5-dibromo compound I-04. Selective substitution of the 3-bromo moiety gives I-05. Substitution of the remaining bromo moiety with an organic amine using a suitable catalyst gives substitution product I-06.

Scheme II

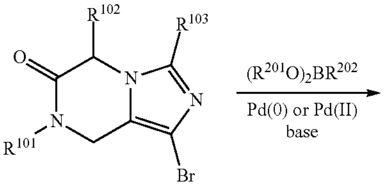

I-05

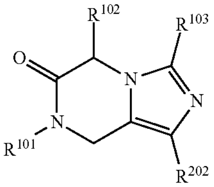

II-01

The Examples can be synthesized using the following general synthetic procedure set forth in Scheme II. Bromo compound I-05, from Scheme I, is reacted with a boronic ester in the presence of a suitable palladium catalyst to give substitution product II-01.

Scheme III

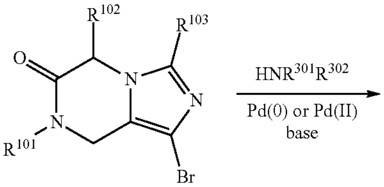

I-05

-continued

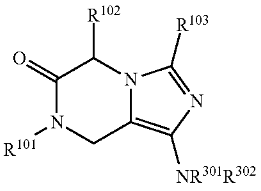

III-01

The Examples can be synthesized using the following general synthetic procedure set forth in Scheme III. Reaction of I-05 under Buchwald coupling conditions provides the substituted amines III-01.

Scheme IV

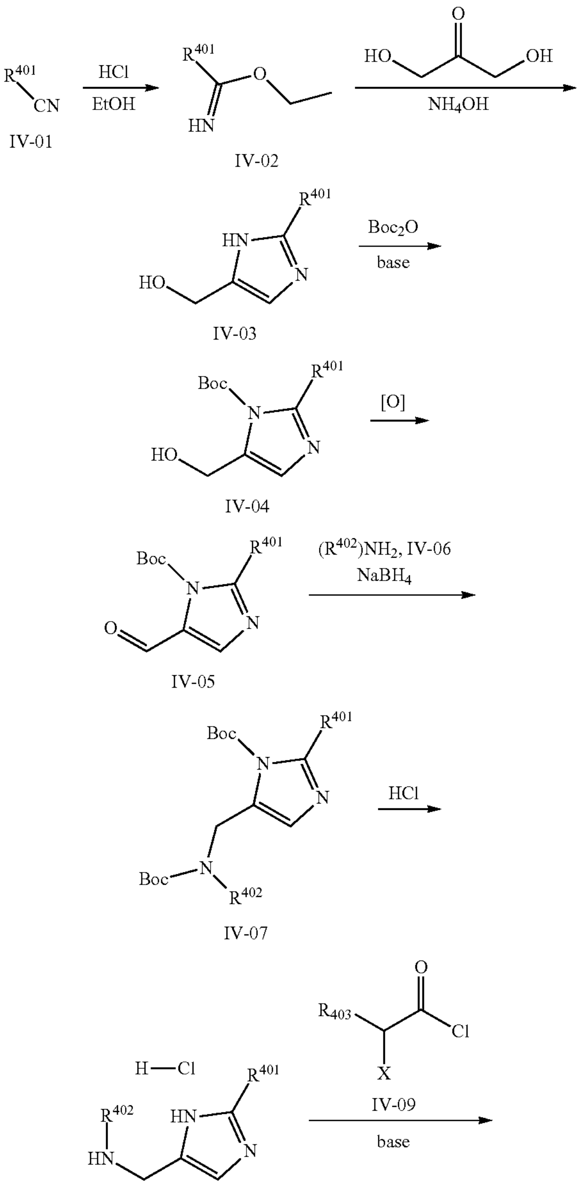

IV-01 IV-02 IV-03 IV-04 IV-05 IV-07 IV-08

-continued

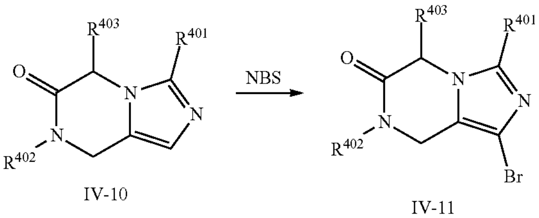

IV-10 IV-11

The Examples can be synthesized using the following general synthetic procedure set forth in Scheme IV. Nitrile IV-01 is reacted with HCl in ethanol to give compound IV-02. Treatment with 1,3-dihydroxypropan-2-one and ammonium hydroxide gives IV-03. Protection of the amine gives IV-04 which is then oxidized with with a suitable oxidant, such as the Dess-Martin periodinane ("DMP") to give aldehyde IV-05. Reductive aminiation with amine IV-06 and sodium borohydride gives IV-07. Deprotection with hydrogen chloride gives the corresponding amine IV-08, which may optionally be carried forth as a salt. IV-08, or a salt thereof, is reacted with acid chloride IV-09 (X=Br, Cl) and base to give IV-10. Treatment with N-bromosuccininmide gives 3-bromo compound IV-11.

Scheme V

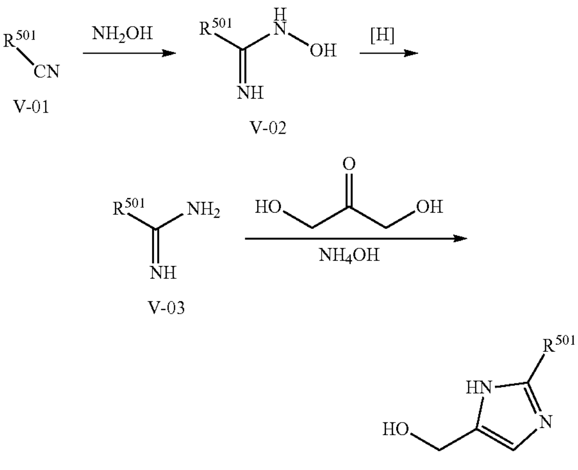

V-01 V-02 V-03 V-04

The Examples can be synthesized using the following general synthetic procedures set forth in Scheme V. Nitrile V-01 is reacted with hydroxylamine to give V-02. Reduction, using for example Raney Ni, gives V-03. Treatment with 1,3-dihydroxypropan-2-one and $NH_4OH$ gives V-04.

Scheme VI

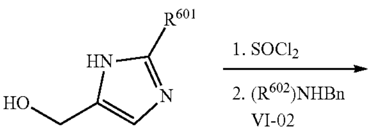

VI-01

-continued

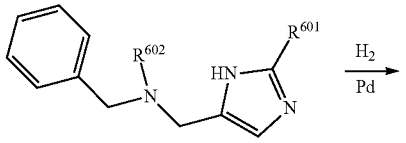

VI-03

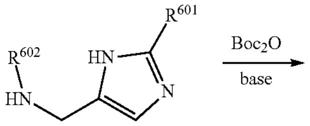

VI-04

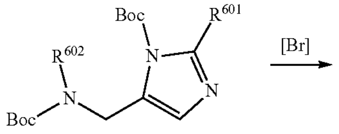

VI-05

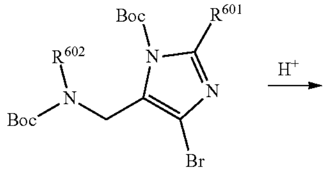

VI-06

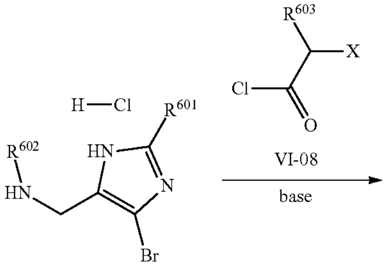

VI-08

VI-07

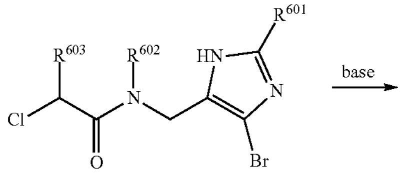

VI-09

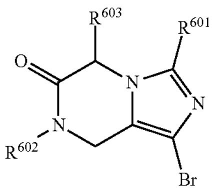

VI-10

The Examples can be synthesized using the following general synthetic procedures set forth in Scheme VI. VI-01 is treated with thionyl chloride followed by VI-02 which gives VI-03. Removal of the benzyl group, for example, with catalytic hydrogenolysis as shown, gives VI-04. Protection of the secondary amines gives VI-05. Bromination, using for example N-bromosuccininimide, gives 3-bromo compound VI-06. Deprotection under acidic conditions gives VI-07. Treatment with acid chloride VI-08 (X=Br, Cl) in the presence of base gives VI-09. Cyclization with base gives VI-10.

The disclosure is further illustrated by the following examples.

Intermediate "A"

1-Bromo-3-cyclopropyl-7-methyl-7,8-dihydroimidazo[1,5-a]pyrazin-6(5H)-one

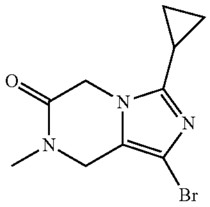

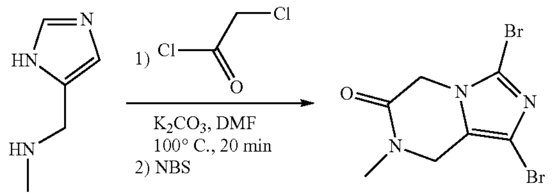

1,3-dibromo-7-methyl-7,8-dihydroimidazo[1,5-al]pyrazin-6(5H)-one

To a solution of 1-(1H-imidazol-5-yl)-N-methylmethanamine (500 mg, 4.50 mmol) in anhydrous DMF (22.5 ml) at −60 OC was added 2-chloroacetyl chloride (358 al, 4.50 mmol) dropwise. The mixture was then warmed to RT and stirred for 2 h. To the mixture was added $K_2CO_3$ powder (1865 mg, 13.50 mmol) and 70 mL of anhydrous degassed DMF. The mixture was then degassed and back-filled with $N_2$ for 3 cycles. The flask was sealed and the mixture was heated to 100° C. and stirred for 15 min. The mixture was allowed to cool to RT, filtered through a frit funnel, then cooled to 0° C. NBS (1842 mg, 10.35 mmol) was added. The mixture was warmed to RT and stirred for 30 min, during which time the mixture turned reddish brown. 20% aq. $Na_2S_2O_3$ (200 uL) was added, and the resulting bright yellow solution was concentrated to ca. 10 ml, diluted with EtOAc (100 mL), and washed with sat. aq. NaCl (100 ml). The organic layer (with some yellow precipitate) was separated and concentrated under reduced pressure. The residue was purified by $SiO_2$ gel chromatography (0% to 20% MeOH in $CH_2Cl_2$) to give the title compound as a yellow solid (450 mg, 32%). MS ($ES^+$) $C_7H_7Br_2N_3O$ requires: 307, found: 308 $[M+H]^+$.

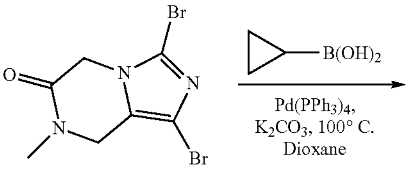

-continued

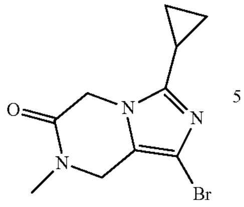

1-bromo-3-cyclopropyl-7-methyl-7,8-dihydroimidazo[1,5-a]pyrazin-6(5H)-one

A mixture of 1,3-dibromo-7-methyl-7,8-dihydroimidazo[1,5-a]pyrazin-6(5H)-one (230 mg, 0.744 mmol), cyclopropylboronic acid (384 mg, 4.47 mmol) and 2.0 M aq. $K_2CO_3$ (3722 al, 7.444 mmol) in dioxane (7444 μl) was degassed with $N_2$ for 5 min. $Pd(PPh_3)_4$(129 mg, 0.112 mmol) was added, and the mixture was degassed with $N_2$ for an additional 5 min. The reaction mixture was heated to 100° C. and stirred for 4 h, then allowed to cool to RT. Another portion of cyclopropylboronic acid (384 mg, 4.47 mmol) and 2.0 M aq. $K_2CO_3$ (3722 al, 7.444 mmol) was added. The reaction was degassed with $N_2$ for 5 min., then stirred at 100° C. for 2 h. The residue was purified by $SiO_2$ gel chromatography (0% to 20% MeOH in $CH_2Cl_2$) to give the title compound as an off-white amorphous material (100 mg, 50%). MS ($ES^+$) $C_{10}H_{12}BrN_3O$ requires: 269, found: 270 $[M+H]^+$.

Intermediate "B"

1-Bromo-3-cyclopropyl-5,7-dimethyl-7,8-dihydroimidazo[1,5-a]pyrazin-6(5H)-one

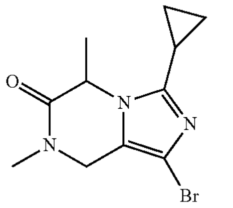 [SMILES: CC1C(=O)N(C)Cc2c(Br)nc(C3CC3)n21]

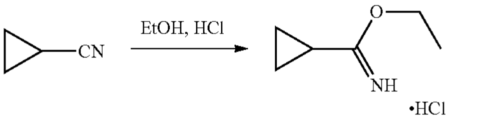

Ethyl Cyclopropanecarbimidate Hydrochloride

To a solution of cyclopropanecarbonitrile (30 g, 447 mmol) in 4.0 M HCl in 1,4-dioxane (300 mL) was added EtOH (35 g, 760 mmol), and the mixture was stirred at RT for 24 h then cooled to 0° C. and treated with $Et_2O$ (1 L). The precipitate that formed was collected by filtration to give the title compound as white solid (60 g, 90%). MS ($ES^+$): $C_6H_{11}NO$ requires: 113, found: 114 $[M+H]^+$.

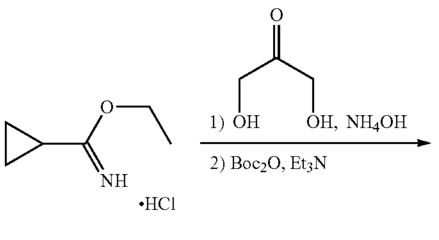

-continued

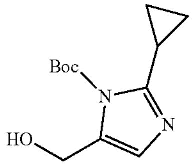

tert-Butyl 2-cyclopropyl-5-(hydroxymethyl)-1H-imidazole-1-carboxylate

A mixture of ethyl cyclopropanecarbimidate hydrochloride (20.0 g, 134 mmol) and 1,3-dihydroxypropan-2-one (12.0 g, 134 mmol) in $NH_4OH$ (80 mL) was stirred in a sealed tube at 90° C. for 4 h. The solution was concentrated under reduced pressure, and the residue was dissolved in DCM (500 mL). To the solution was added TEA (40.6 g, 402 mmol) and $Boc_2O$ (58.4 g, 268 mmol). The mixture was stirred at RT for 24 h, then treated with $H_2O$ (200 mL) and extracted with DCM (200 mL). The organic layer was washed with sat. aq. NaCl (200 mL), dried over $MgSO_4$, filtered and concentrated under reduced pressure. The residue was purified by $SiO_2$ gel chromatography (25% to 100% EtOAc in petroleum ether) to give the title compound (12 g, 37%). MS ($ES^+$): $C_{12}H_{18}N_2O_3$ requires: 238, found: 239 $[M+H]^+$.

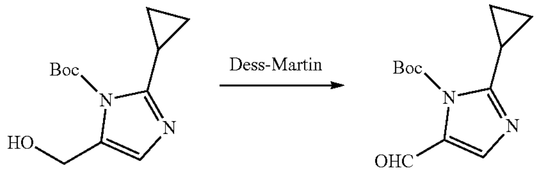 [SMILES: CC(C)(C)OC(=O)n1c(CO)cnc1C1CC1 ; CC(C)(C)OC(=O)n1c(C=O)cnc1C1CC1]

tert-Butyl 2-cyclopropyl-5-formyl-1H-imidazole-1-carboxylate

To a solution of the product from the previous step (17.0 g, 71.4 mmol) in DCM (150 mL) at 0° C. was added DMP (30.0 g, 71.4 mmol). The mixture was stirred at RT for 4 h, then treated with sat. aq. $Na_2SO_3$ solution and extracted with DCM (100 mL×3). The combined organic layers were sequentially washed with sat. aq. $Na_2CO_3$ (145 mL×3) and sat. aq. NaCl (145 mL), dried over $MgSO_4$, filtered and concentrated under reduced pressure. The residue was purified by $SiO_2$ gel chromatography (25% to 75% EtOAc in petroleum ether) to give the title compound as white solid (12 g, 70%). MS ($ES^+$): $C_{12}H_{16}N_2O_3$ requires: 236, found: 237 $[M+H]^+$.

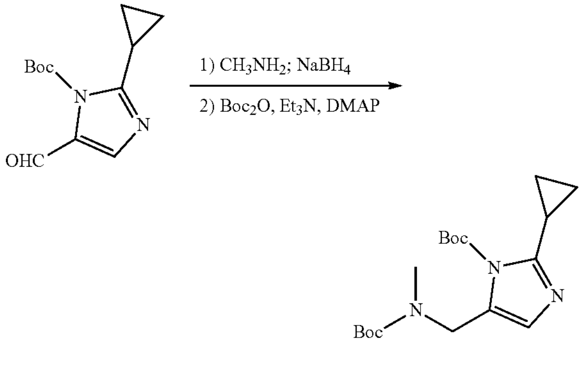

tert-Butyl 5-((tert-butoxycarbonyl(methyl)amino) methyl)-2-cyclopropyl-1H-imidazole-1-carboxylate To a solution of the product from the previous step (25.0 g, 106 mmol) in THF (150 mL) at 0° C. was added a 4 M $CH_3NH_2$ in MeOH solution (133 mL, 530 mmol). The mixture was stirred at RT for 24 h, cooled to 0° C., then treated with $NaBH_4$ (4.10 g, 105 mmol). The mixture was stirred at RT for 2 h, then concentrated under reduced pressure. The residue was dissolved in DCM (300 mL), and the mixture was treated with DMAP (1.23 g, 10.1 mmol) and TEA (42.8 g, 424 mmol), then $Boc_2O$ (69.0 g, 318 mmol) over 1 h. The resulting mixture was stirred at RT overnight, then treated with sat. aq. $Na_2CO_3$ and extracted with DCM (100 mL×3). The combined organic layers were washed with sat. aq. NaCl (200 mL), dried over $MgSO_4$, filtered and concentrated under reduced pressure. The residue was purified by $SiO_2$ gel chromatography (10% to 60% EtOAc in petroleum ether) to give the title compound. MS ($ES^+$): $C_{18}H_{29}N_3O_4$ requires: 351, found: 352 $[M+H]^+$.

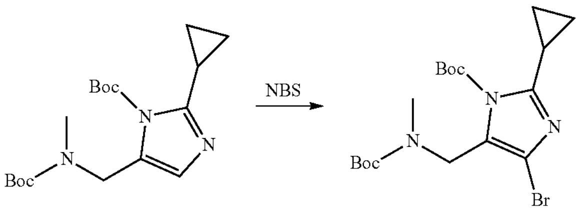

tert-Butyl 4-bromo-5-((tert-butoxycarbonyl(methyl) amino)methyl)-2-cyclopropyl-1H-imidazole-1-carboxylate To a mixture of the product from the previous step (0.90 g, 2.6 mmol) in DCM (20 mL) was added NBS (0.50 g, 2.8 mmol). The mixture was stirred at RT for 30 min, then treated with $H_2O$ and extracted with DCM (40 mL). The organic layer was dried over $Na_2SO_4$, filtered and concentrated under reduced pressure. The residue was purified by $SiO_2$ gel chromatography (20:1 petroleum ether/EtOAc) to give the title compound as a yellow oil (0.98 g, 87%). MS ($ES^+$): $C_{18}H_{28}BrN_3O_4$ requires: 429, found: 430 $[M+H]^+$.

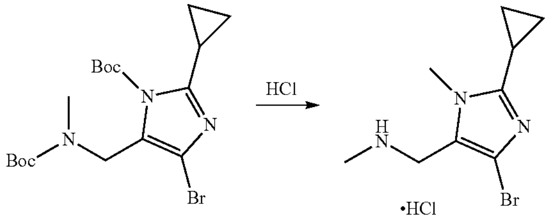 [SMILES: CN(Cc1c(Br)nc(C2CC2)n1C(=O)OC(C)(C)C)C(=O)OC(C)(C)C ; Cl ; CNCc1c(Br)nc(C2CC2)n1C ; Cl]

1-(4-Bromo-2-cyclopropyl-1H-imidazol-5-yl)-N-methylmethanamine hydrochloride. To a mixture of the product from the previous step (1.50 g, 3.49 mmol) in MeOH (10 mL) was added 4 M HCl in MeOH (5 mL). The mixture was stirred at RT overnight, then concentrated under reduced pressure. The residue was washed with diethyl ether (10 mL×2) to give the title compound as a white solid (0.91 g, 98%). MS ($ES^+$): $C_8H_{12}BrN_3$ requires: 229, found: 230 $[M+H]^+$.

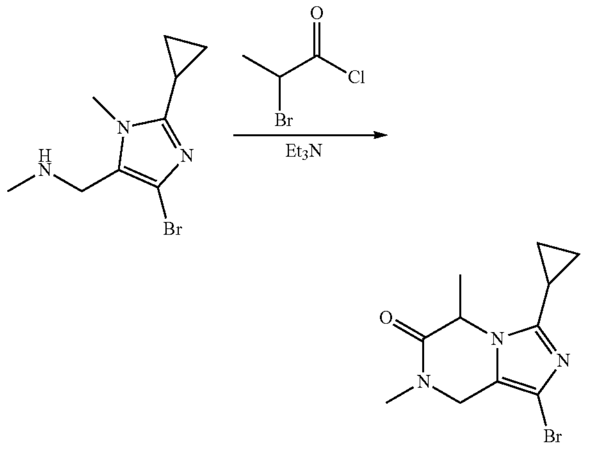

1-Bromo-3-cyclopropyl-5,7-dimethyl-7,8-dihydro-imidazo[1,5-a]pyrazin-6(5H)-one

To a mixture of the product from the previous step (910 mg, 3.41 mmol) and TEA (2.37 mL, 17.1 mmol) in $CHCl_3$ (45 mL) at 0° C. was added 2-bromopropionyl chloride (0.413 mL, 4.10 mmol). The mixture was stirred at 0° C. for 30 min, then concentrated under reduced pressure. To the residue was added $Cs_2CO_3$ (3.32 g, 10.2 mmoles) and MeCN (15 mL). The mixture was stirred at 100° C. overnight, then allowed to cool to RT, filtered and concentrated under reduced pressure. The residue was purified by $SiO_2$ gel chromatography to give the title compound as a yellow oil. MS ($ES^+$): $C_{11}H_{14}BrN_3O$ requires: 283, found: 284 $[M+H]^+$.

Intermediate "C"

1-Bromo-5,7-dimethyl-3-(tetrahydro-2H-pyran-4-yl)-7,8-dihydroimidazo[1,5-a]pyrazin-6(5H)-one

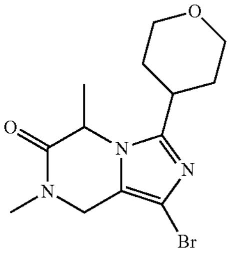 [SMILES: CC1C(=O)N(C)Cc2c(Br)nc(C3CCOCC3)n21]

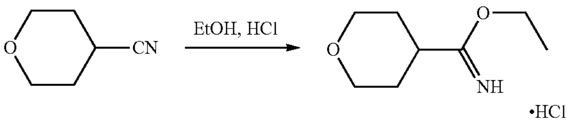

Ethyl tetrahydro-2H-pyran-4-carbimidate hydrochloride

A mixture of tetrahydro-2H-pyran-4-carbonitrile (48.0 g, 432 mmol) and EtOH (30.22 mL, 518.3 mmol) in 4.0 M HCl in 1,4-dioxane (500 mL) was stirred at RT overnight, then treated with diethyl ether (500 mL). Precipitate was isolated by filtration and dried to give the title compound as a white solid (80 g, 96%). MS ($ES^+$): $C_8H_{15}NO_2$ requires: 157, found: 158 $[M+H]^+$.

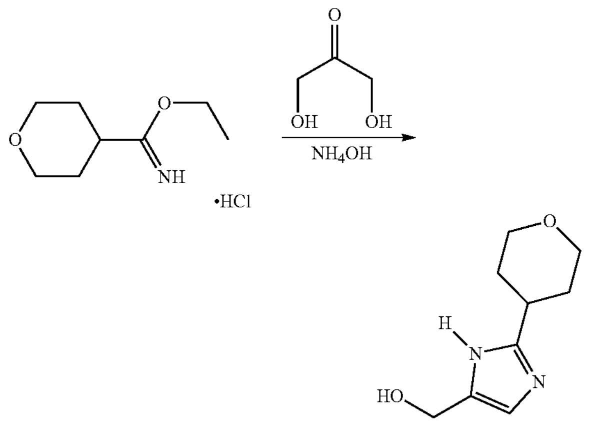

(2-(Tetrahydro-2H-pyran-4-yl)-1H-imidazol-5-yl) methanol

A mixture of ethyl tetrahydro-2H-pyran-4-carbimidate hydrochloride (40.0 g, 207 mmol) and 1,3-dihydroxypropan-2-one (18.60 g, 206.5 mmol) in ammonium hydroxide (159 mL) was stirred in a sealed tube at 90° C. for 4 h, then concentrated under reduced pressure to give the crude title compound as a brown oil (37.5 g, 100%), which was used without further purification. MS ($ES^+$): $C_9H_{14}N_2O_2$ requires: 182, found: 183 $[M+H]^+$.

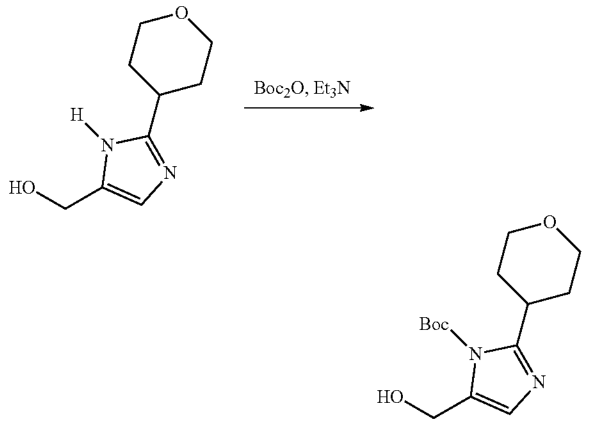

tert-Butyl 5-(hydroxymethyl)-2-(tetrahydro-2H-pyran-4-yl)-1H-imidazole-1-carboxylate To a mixture of the product from the previous step (6.50 g, 35.7 mmol) and $Na_2CO_3$ (9.45 g, 89.2 mmol) in 6:1 1,4-dioxane/$H_2O$ (150 mL) was added $Boc_2O$ (10.88 g, 49.94 mmol). The mixture was stirred at RT overnight, then extracted with DCM (60 mL×3). The combined organic layers were washed with sat. aq. NaCl (45 mL), dried over $MgSO_4$, filtered and concentrated under reduced pressure. The residue was purified by $SiO_2$ gel chromatography (25% to 100% EtOAc in petroleum ether) to give the title compound as a yellow oil (8.20 g, 81%). MS ($ES^+$): $C_{14}H_{22}N_2O_4$ requires: 282, found: 283 $[M+H]^+$.

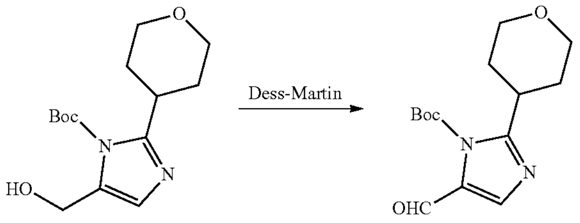 [SMILES: CC(C)(C)OC(=O)n1c(CO)cnc1C1CCOCC1 ; "Dess-Martin" ; CC(C)(C)OC(=O)n1c(C=O)cnc1C1CCOCC1]

tert-Butyl 5-formyl-2-(tetrahydro-2H-pyran-4-yl)-1H-imidazole-1-carboxylate

To a mixture of the product from the previous step (8.20 g, 29.0 mmol) in DCM (120 mL) was added DMP (17.25 g, 40.66 mmol). The mixture was stirred at RT for 2.5 h, then treated with sat. aq $Na_2SO_3$ and extracted with DCM (60 mL×3). The combined organic layers were sequentially washed with sat. aq. $Na_2CO_3$ (45 mL×3) and sat. aq. NaCl (45 mL), dried over $MgSO_4$, filtered and concentrated under reduced pressure. The residue was purified by $SiO_2$ gel chromatography (25% to 75% EtOAc in petroleum ether) to give the title compound as a white solid (6.07 g, 75%). MS ($ES^+$): $C_{14}H_{20}N_2O_4$ requires: 280, found: 281 $[M+H]^+$.

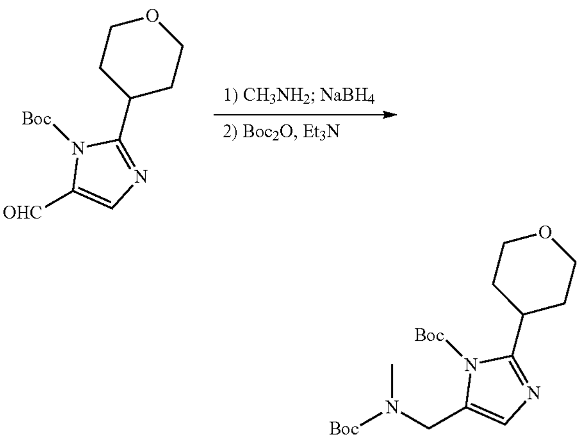

tert-Butyl 5-((tert-butoxycarbonyl(methyl)amino) methyl)-2-(tetrahydro-2H-pyran-4-yl)-1H-imidazole-1-carboxylate A mixture of the product from the previous step (5.00 g, 17.8 mmol) and 2.0 M $CH_3NH_2$ in THF (10.7 mL, 21.4 mmol) in 45 mL of MeOH was stirred at RT for 18 h, cooled to 0° C., then treated portionwise with $NaBH_4$ (809 mg, 21.3 mmol). The resulting mixture was stirred at 0° C. for 30 min, then treated with 1 M aq. NaOH and concentrated under reduced pressure. To the residue was added TEA (6.20 mL, 44.6 mmol) in DCM (90 mL), then $Boc_2O$ (8.55 g, 39.2 mmol). The mixture was stirred at RT overnight, then treated with sat. aq. $Na_2CO_3$ (75 mL) and extracted with DCM (60 mL×3). The combined organic layers were washed with sat.

aq. NaCl (60 mL×1), dried over $MgSO_4$, filtered and concentrated under reduced pressure. The residue was purified by $SiO_2$ gel chromatography (10% to 60% EtOAc in petroleum ether) to give the title compound as a colorless oil (5.55 g, 79%). MS ($ES^+$): $C_{20}H_{33}N_3O_5$ requires: 395, found: 396 $[M+H]^+$.

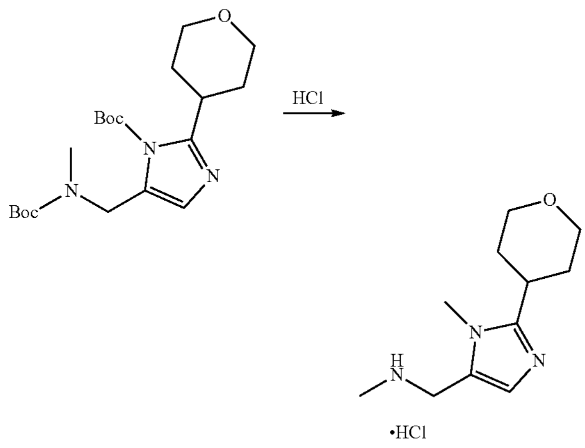

N-Methyl-1-(2-(tetrahydro-2H-pyran-4-yl)-1H-imidazol-5-yl)methanamine hydrochloride A mixture of the product from the previous step (5.55 g, 14.1 mmol) in 2 M HCl in MeOH (45 mL) was stirred at RT overnight, then concentrated under reduced pressure. The residue was washed with diethyl ether (15 mL×2) to give the title compound as a white solid (3.24 g, 100%). MS ($ES^+$): $C_{10}H_{17}N_3O$ requires: 195, found: 196 $[M+H]^+$.

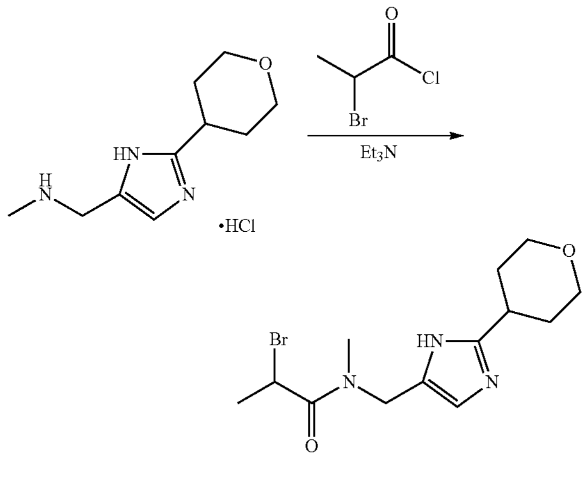

2-Bromo-N-methyl-N-((2-(tetrahydro-2H-pyran-4-yl)-1H-imidazol-5-yl)methyl)propanamide To a mixture of the product from the previous step (10.78 g, 46.52 mmol) and TEA (12.93 mL, 93.04 mmol) in $CHCl_3$ (210 mL) at 0° C. was added 2-bromopropanoyl chloride (4.93 mL. 48.9). The mixture was stirred at 0° C. for 30 min, diluted with DCM (90 mL), then sequentially washed with sat. aq. $Na_2CO_3$ (75 mL×2) and sat. aq. NaCl (90 mL), dried over $MgSO_4$, filtered and concentrated under reduced pressure to give the crude title compound as a yellow oil (14.5 g, 94%), which was used without further purification (14.5 g, 94%). MS ($ES^+$): $C_{13}H_{20}BrN_3O_2$ requires: 329, found: 330 $[M+H]^+$.

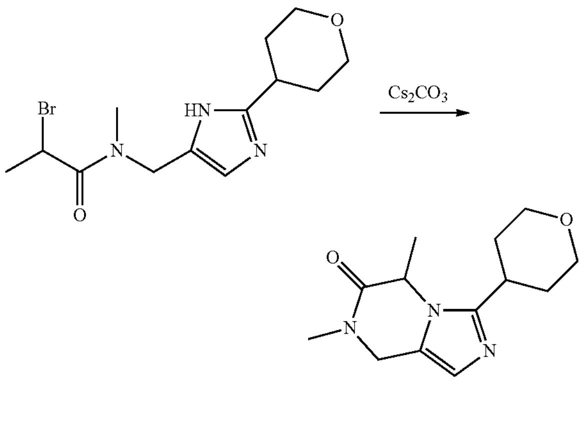

5,7-dimethyl-3-(tetrahydro-2H-pyran-4-yl)-7,8-dihydroimidazo[1,5-al]pyrazin-6(5H)-one A degassed mixture of the product from the previous step (14.5 g, 43.9 mmole) and $Cs_2CO_3$ (21.46 g, 65.86 mmol) in MeCN (120 mL) was stirred at 60° C. for 15 min, then allowed to cool to RT, filtered and concentrated under reduced pressure. The residue was purified by $SiO_2$ gel chromatography (0% to 5% MeOH in EtOAc) to give the title compound as a white solid (7.25 g, 66%). MS ($ES^+$): $C_{13}H_{19}N_3O_2$ requires: 249, found: 250 [M+H]+.

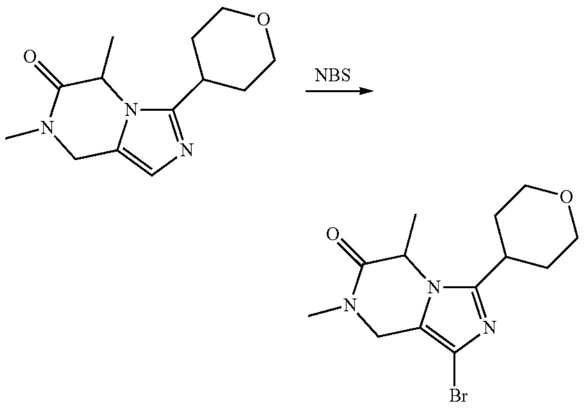

1-Bromo-5,7-dimethyl-3-(tetrahydro-2H-pyran-4-yl)-7,8-dihydroimidazo[1,5-a]pyrazin-6(5H)-one To a mixture of the product from the previous step (341 mg, 1.36 mmol) in 15 mL DCM was added NBS (268 mg, 1.50 mmol). The mixture was stirred at RT for 5 min, then treated with a 1:1 mixture of sat. aq. $Na_2SO_3$ and sat. aq. $Na_2CO_3$ (5 mL) and extracted with DCM (15 mL×3). The combined organic layers were dried over $MgSO_4$, filtered and concentrated under reduced pressure. The residue was purified by $SiO_2$ gel chromatography (0% to 10% MeOH in EtOAc) to give the title compound as a white solid (407 mg, 91%). MS ($ES^+$): $C_{13}H_{18}BrN_3O_2$ requires: 327, found: 328 $[M+H]^+$.

Intermediate "D"

1-bromo-7-methyl-3-(tetrahydro-2H-pyran-4-yl)-7,8-dihydroimidazo[1,5-a]pyrazin-6(5H)-one

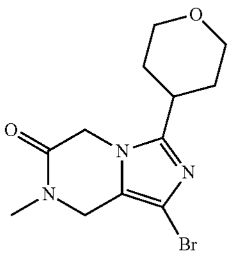 [SMILES: CN1Cc2c(Br)nc(C3CCOCC3)n2CC1=O]

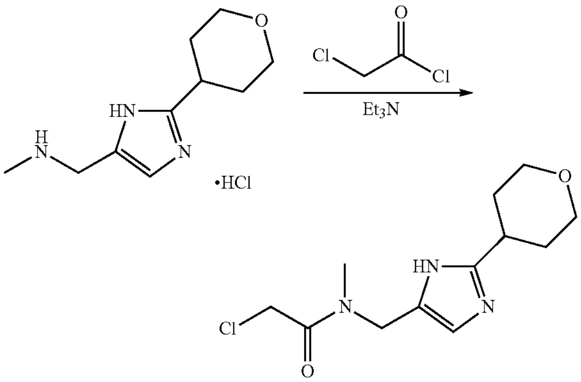

2-Chloro-N-methyl-N-((2-(tetrahydro-2H-pyran-4-yl)-1H-imidazol-5-yl)methyl)acetamide To a mixture of N-methyl-1-(2-(tetrahydro-2H-pyran-4-yl)-1H-imidazol-5-yl)methanamine hydrochloride (1.60 g 6.90 mmol) and TEA (4.80 mL, 34.6 mmol) in chloroform (45 mL) at 0° C. was added chloroacetyl chloride (0.659 mL, 8.29 mmol). The mixture was stirred at 0° C. for 30 min, then treated with sat. aq. $NaHCO_3$ solution and extracted with DCM (25 mL×3). The combined organic layers were dried over $MgSO_4$, filtered and concentrated under reduced pressure to give the crude title compound as a yellow oil (1.68 g, 90%), which was used without further purification. MS ($ES^+$): $C_{12}H_{18}ClN_3O_2$ requires: 271, found: 272 $[M+H]^+$.

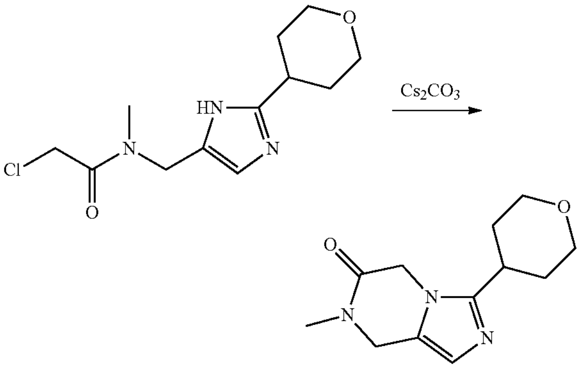

7-methyl-3-(tetrahydro-2H-pyran-4-yl)-7,8-dihydroimidazo[1,5-a]pyrazin-6(5H)-one A degassed mixture of the product from the previous step (1.68 g, 6.18 mmol) and $Cs_2CO_3$ (3.02 g, 9.27 mmol) in MeCN (20 mL) was stirred at 60° C. for 15 min, then allowed to cool to RT, filtered and concentrated under reduced pressure. The residue was purified by $SiO_2$ gel chromatography (0% to 5% MeOH in EtOAc) to give the title compound as a yellow oil (1.15 g, 79%). MS ($ES^+$): $C_{12}H_{17}N_3O_2$ requires: 235, found: 236 $[M+H]^+$.

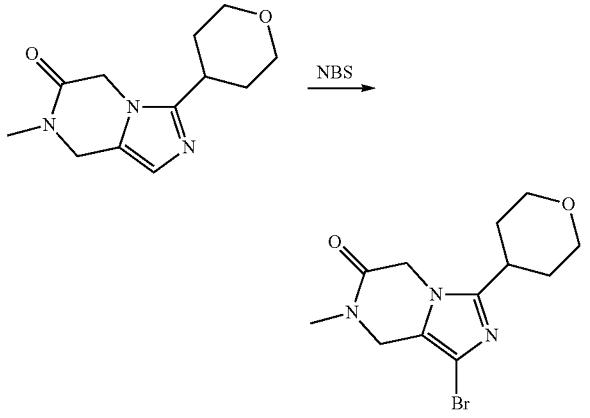

1-bromo-7-methyl-3-(tetrahydro-2H-pyran-4-yl)-7,8-dihydroimidazo[1,5-a]pyrazin-6(5H)-one To a mixture of the product from the previous step (1.15 g, 4.89 mmol) in DCM (25 mL) was added NBS (986.5 mg, 5.38 mmol). The mixture was stirred at RT for 20 min, then treated with a 1:1 mixture of sat. aq. $Na_2SO_3$ and sat. aq. $Na_2CO_3$ (30 mL) and extracted with DCM (25 mL×3). The combined organic layers were washed with sat. aq. NaCl (30 mL), dried over $Na_2SO_4$, filtered and concentrated under reduced pressure. The residue was purified by $SiO_2$ gel chromatography (10% to 60% EtOAc in petroleum ether) to give the title compound as a pale yellow solid. MS ($ES^+$): $C_{12}H_{16}BrN_3O_2$ requires: 313, found: 314 $[M+H]^+$.

Example 1

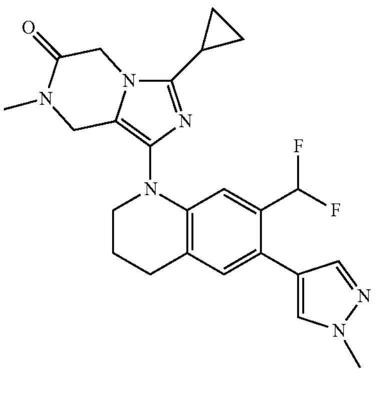 [SMILES: CN1Cc2c(N3CCCc4cc(-c5cnn(C)c5)c(C(F)F)cc43)nc(C3CC3)n2CC1=O]

3-cyclopropyl-1-(7-(difluoromethyl)-6-(1-methyl-1H-pyrazol-4-yl)-3,4-dihydroquinolin-1(2H)-yl)-7-methyl-7,8-dihydroimidazo[1,5-a]pyrazin-6(5H)-one

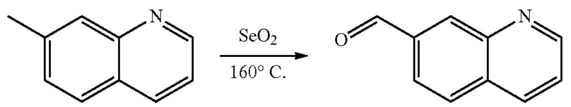

Quinoline-7-carboxaldehyde

To 7-methylquinoline (25.0 g, 17.5 mmol) at 160° C. was added $SeO_2$ (19.2 g, 175 mmol) portionwise over 5 min. The mixture was stirred at 160° C. for 8 h, then allowed to cool to room temperature. DCM (400 mL) was added, and the mixture was filtered through a pad of CELITE®. The filtrate was concentrated under reduced pressure, and the residue was purified by $SiO_2$ gel chromatography (10:1 petroleum ether/EtOAc) to give the title compound as a yellow solid (5 g, 18%). MS($ES^+$): $C_{10}H_7NO$ requires: 157 found: 158 $[M+H]^+$.

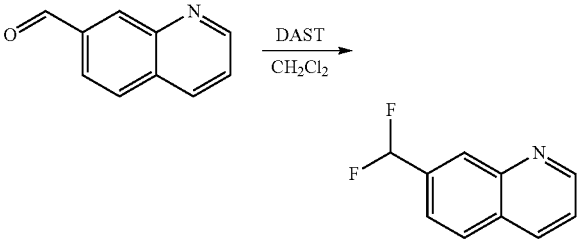

7-(Difluoromethyl)quinoline

To a solution of quinoline-7-carboxaldehyde (5.00 g, 31.8 mmol) in DCM (50 mL) at 0° C. was added diethylaminosulfur trifluoride (23.1 g, 159 mmol) dropwise over 20 min. The mixture was stirred at RT for 16 h. The mixture was poured into sat. aq. $NaHCO_3$(300 mL) at 0° C., and the resulting mixture was extracted with DCM (3×50 mL). The combined organic layers were dried over $Na_2SO_4$, filtered and concentrated under reduced pressure. The residue was purified by $SiO_2$ gel chromatography (10:1 petroleum ether/EtOAc) to give the title compound as a yellow solid (3.4 g, 61%). MS ($ES^+$): $C_{10}H_7F_2N$ requires: 179, found: 180 $[M+H]^+$.

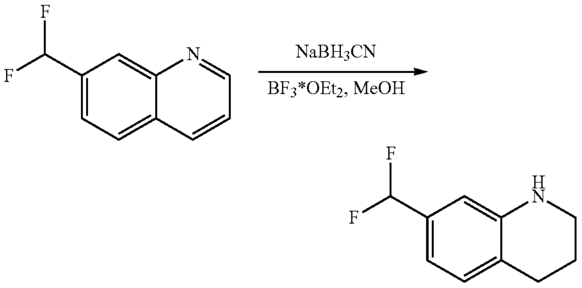

7-(Difluoromethyl)-1,2,3,4-tetrahydroquinoline

To a solution of 7-(difluoromethyl)quinoline (3.4 g, 19 mmol) and $NaBH_3CN$ (6.0 g, 95 mmol) in MeOH (30 mL) at 0° C. was added $BF_3$•$Et_2O$ (4.7 mL, 38 mmol) dropwise over 20 min. The mixture was stirred at 90° C. for 24 h, then allowed to cool to RT. The mixture was poured into sat. aq. $NaHCO_3$(400 mL) at 0° C., and the resulting mixture was extracted with DCM (3×300 mL). The combined organic layers were dried over $Na_2SO_4$, filtered and concentrated under reduced pressure. The residue was purified by $SiO_2$ gel chromatography (20:1 petroleum ether/EtOAc) to give the title compound as a brown oil (1.1 g, 31%). MS ($ES^+$): $C_{10}H_{11}F_2N$ requires: 183, found: 184 $[M+H]^+$.

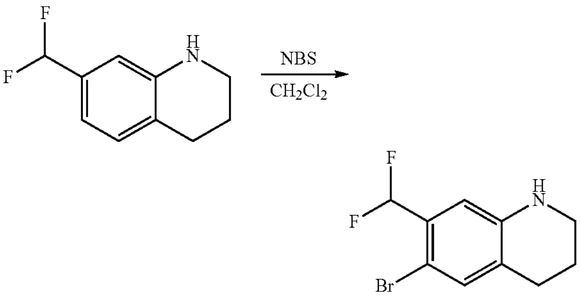

6-Bromo-7-(difluoromethyl)-1,2,3,4-tetrahydroquinoline

To a solution of 7-(difluoromethyl)-1,2,3,4-tetrahydroquinoline (1.1 g, 6.0 mmol) in DCM (20 ml) at 0° C. was added NBS (1.0 g, 5.6 mmol) portionwise over 20 min. The mixture was stirred at room temperature for 16 h. The mixture was poured into water (20 mL) and extracted with DCM (2×40 mL). The combined organic layers were dried over $Na_2SO_4$, filtered and concentrated under reduced pressure. The residue was purified by $SiO_2$ gel chromatography (300:1 petroleum ether/EtOAc) to give the title compound as a yellow oil (1 g, 64%). MS ($ES^+$): $C_{10}H_{10}BrF_2N$ requires: 261, found: 262 $[M+H]^+$.

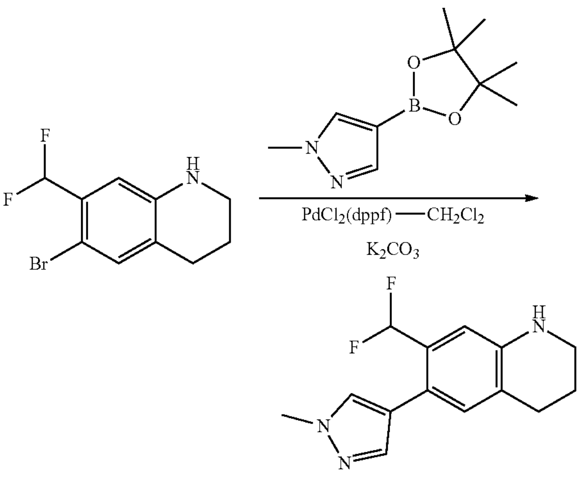

7-(Difluoromethyl)-6-(1-methyl-1H-pyrazol-4-yl)-1,2,3,4-tetrahydroquinoline

To a mixture of 6-bromo-7-(difluoromethyl)-1,2,3,4-tetrahydroquinoline (1.0 g, 3.8 mmol) in 1,4-dioxane (8 mL) and $H_2O$ (2 mL) was added $K_2CO_3$ (1.1 g, 7.6 mmol), [1,1'-bis(diphenylphosphino)ferrocene]dichloropalladium (II) (277 mg, 0.38 mmol) and 1-methyl-4-(4,4,5,5-tetramethyl-1,3,2-dioxaborolan-2-yl)-1H-pyrazole (790 mg, 3.8 mmol). The mixture was stirred at 110° C. for 18 h, then allowed to cool to RT and concentrated under reduced pressure. The residue was purified by $SiO_2$ gel chromatography (40:1 petroleum ether/EtOAc) to give the title compound as a yellow solid (500 mg, 50%). MS ($ES^+$): $C_{14}H_{15}F_2N_3$ requires: 263, found: 264 $[M+H]^+$.

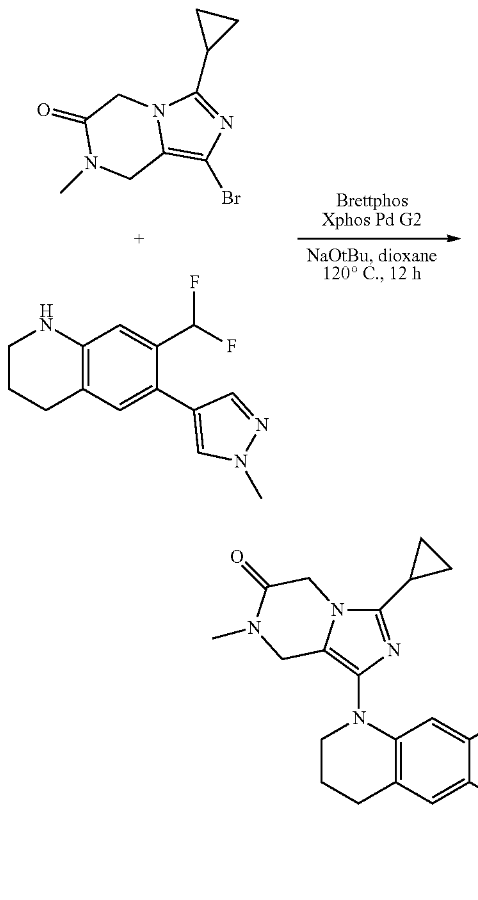

3-Cyclopropyl-1-(7-(difluoromethyl)-6-(1-methyl-1H-pyrazol-4-yl)-3,4-dihydroquinolin-1(2H)-yl)-7-methyl-7,8-dihydroimidazo[1,5-a]pyrazin-6(5H)-one A degassed solution of 7-(difluoromethyl)-6-(1-methyl-1H-pyrazol-4-yl)-1,2,3,4-tetrahydroquinoline (19.49 mg, 0.074 mmol), Intermediate "A" (20 mg, 0.074 mmol), t-BuONa (14.23 mg, 0.148 mmol), Brettphos (3.97 mg, 7.40 µmol) and XPhos Pd G2 (5.83 mg, 7.40 µmol) in dioxane (0.5 ml) was stirred at 120° C. for 16 h. The mixture was concentrated under reduced pressure, and the residue was purified by mass-triggered preparative HPLC (Mobile phase: A=0.1% TFA/H2O, B=0.1% TFA/MeCN; Gradient: B=10% to 40%; 12 min; Column: C18) to give the title compound as a trifluoroacetate salt as an off-white solid (6.5 mg, 16%). MS ($ES^+$) $C_{24}H_{26}F_2N_6O$ requires: 452, found: 453 $[M+H]^+$. $^1H$ NMR ($CD_3OD$) δ: 7.66 (s, 1H), 7.52 (s, 1H), 7.19 (s, 1H), 6.75 (s, 1H), 6.61 (t, 1H, J=55 Hz), 4.92 (s, 2H), 4.47 (s, 2H), 3.93 (s, 3H), 3.63-3.61 (m, 2H), 3.09 (s, 3H), 2.95-2.93 (m, 2H), 2.25-2.53 (m, 1H), 2.23-2.21 (m, 2H), 1.35-1.34 (m, 2H), 1.15-1.13 (m, 2H).

Example 2

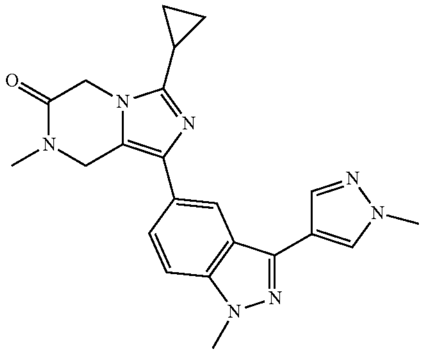 [SMILES: CN1Cc2c(-c3ccc4c(c3)c(-c3cnn(C)c3)nn4C)nc(C3CC3)n2CC1=O]

3-cyclopropyl-7-methyl-1-(1-methyl-3-(1-methyl-1H-pyrazol-4-yl)-1H-indazol-5-yl)-7,8-dihydroimidazo[1,5-a]pyrazin-6(5H)-one

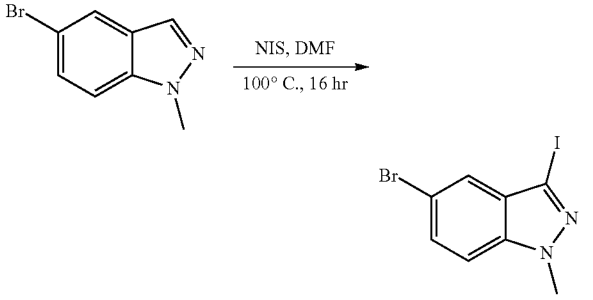

5-Bromo-3-iodo-1-methyl-1H-indazole

To a solution of 5-bromo-1-methyl-1H-indazole (800 mg, 3.79 mmol) in DMF (10 ml) was added NIS (2132 mg, 9.476 mmol), and the resulting mixture was stirred at 100° C. for 16 h. $H_2O$ (30 mL) and sat. aq. $Na_2S_2O_3$ (5 ml) were added, and the layers were separated. The aqueous phase was extracted with EtOAc (3x20 mL), and the combined organic layers were washed with sat. aq. NaCl, dried over $MgSO_4$, filtered and concentrated under reduced pressure. The residue was purified by $SiO_2$ gel chromatography (0% to 25% EtOAc in hexanes) to give the title compound as a white solid (825 mg, 65%). MS ($ES^+$) $C_8H_6BrIN_2$ requires: 336, found: 337 $[M+H]^+$.

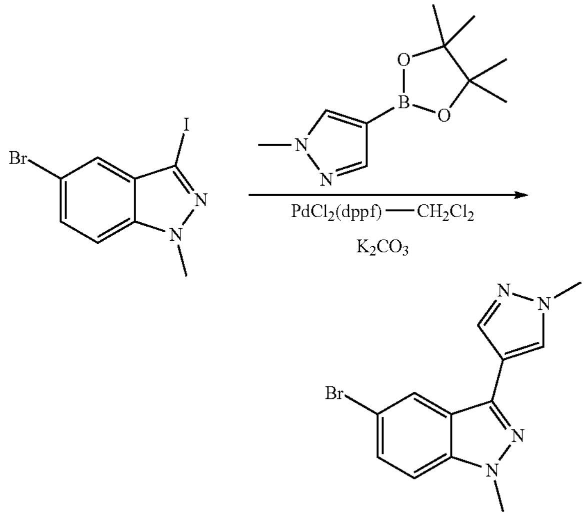

5-Bromo-1-methyl-3-(1-methyl-1H-pyrazol-4-yl)-1H-indazole

To a solution of 5-bromo-3-iodo-1-methyl-1H-indazole (674 mg, 2.00 mmol) in 1,4-dioxane (10 ml) were added 1-methyl-4-(4,4,5,5-tetramethyl-1,3,2-dioxaborolan-2-yl)-1H-pyrazole (458 mg, 2.20 mmol), $PdCl_2(dppf)$-$CH_2Cl_2$ adduct (163 mg, 0.200 mmol) and 2.0 M aq. $K_2CO_3$ (2.00 ml, 4.00 mmol), and the resulting mixture was stirred at 100° C. for 6 h. $H_2O$ (30 mL) was added, and the layers were separated. The aqueous phase was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (20% to 100% EtOAc in hexanes) to give the title compound as a tan solid (360 mg, 62%). MS ($ES^+$) $C_{12}H_{11}BrN_4$ requires: 290, found: 291 $[M+H]^+$.

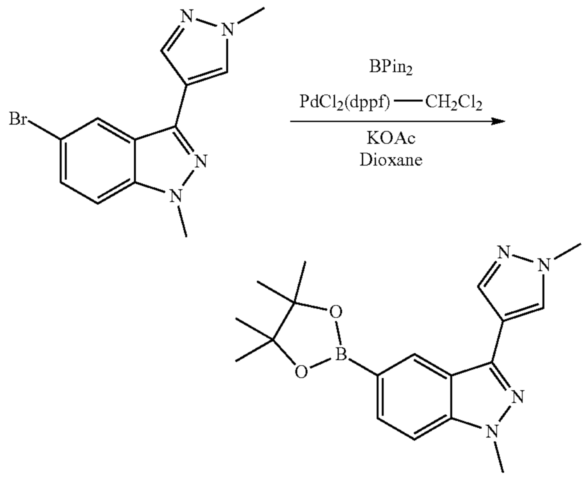

1-Methyl-3-(1-methyl-1H-pyrazol-4-yl)-5-(4,4,5,5-tetramethyl-1,3,2-dioxaborolan-2-yl)-1H-indazole A degassed solution of 5-bromo-1-methyl-3-(1-methyl-1H-pyrazol-4-yl)-1H-indazole (360 mg, 1.24 mmol), $BPin_2$ (377 mg, 1.48 mmol), $PdCl_2(dppf)$-$CH_2Cl_2$ adduct (101 mg, 0.124 mmol) and KOAc (364 mg, 3.71 mmol) in 1,4-dioxane (10 ml) was stirred at 100° C. for 4 h, then allowed to cool to RT. $H_2O$ (50 mL) was added, and the layers were separated. The aqueous phase was extracted with EtOAc (3×30 mL), and the combined organic layers were washed with sat. aq. NaCl, dried over $MgSO_4$, filtered and concentrated under reduced pressure. The residue was purified by $SiO_2$ gel chromatography (0% to 5% MeOH in DCM) to give to give the title compound as on off-white solid (410 mg, 98%). MS ($ES^+$) $C_{18}H_{23}BN_4O_2$ requires: 338, found: 339 $[M+H]^+$.

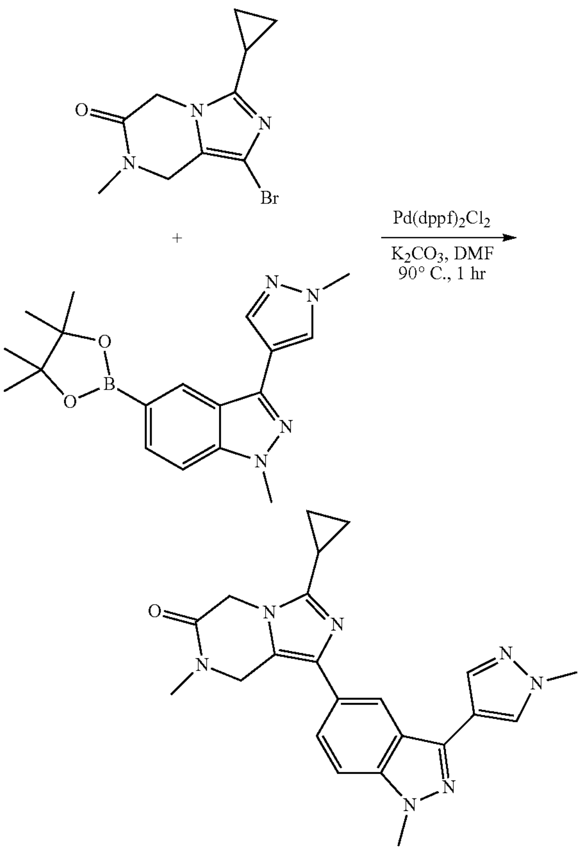

3-Cyclopropyl-7-methyl-1-(1-methyl-3-(1-methyl-1H-pyrazol-4-yl)-1H-indazol-5-yl)-7,8-dihydroimidazo[1,5-a]pyrazin-6(5H)-one A degassed solution of 1-methyl-3-(1-methyl-1H-pyrazol-4-yl)-5-(4,4,5,5-tetramethyl-1,3,2-dioxaborolan-2-yl)-1H-indazole (41.7 mg, 0.074 mmol), Intermediate "A" (20 mg, 0.074 mmol), $PdCl_2(dppf)$-$CH_2Cl_2$ adduct (6.05 mg, 7.40 μmol) and 2.0 M aq. $K_2CO_3$ (74.0 al, 0.148 mmol) in DMF (370 al) was stirred at 90° C. for 1 h. The mixture was concentrated under reduced pressure, and the residue was purified by mass-triggered preparative HPLC (Mobile phase: A=0.1% TFA/H2O, B=0.1% TFA/MeCN; Gradient: B=10% to 40%; 12 min; Column: C18) to give the title compound as the trifluoroacetate salt as a white powder (4.8 mg, 13%). MS ($ES^+$) $C_{22}H_{23}N_7O$ requires: 401, found: 402 $[M+H]^+$. $^1H$ NMR ($CD_3OD$) δ: 8.22 (s, 1H), 8.16 (s, 1H), 8.08 (s, 1H), 7.75 (d, 1H, J=8.9 Hz), 7.59 (d, 1H, J=8.9 Hz), 4.97 (s, 2H), 4.89 (s, 2H), 4.12 (s, 3H), 4.01 (s, 3H), 3.15 (s, 3H), 2.29-2.27 (m, 1H), 1.37-1.35 (m, 2H), 1.27-1.25 (m, 2H).

Example 3

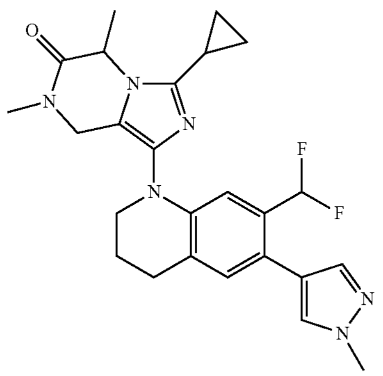 [SMILES: CC1C(=O)N(C)Cc2c(N3CCCc4cc(-c5cnn(C)c5)c(C(F)F)cc43)nc(C3CC3)n21]

3-Cyclopropyl-1-(7-(difluoromethyl)-6-(1-methyl-1H-pyrazol-4-yl)-3,4-dihydroquinolin-1(2H)-yl)-5,7-dimethyl-7,8-dihydroimidazo[1,5-a]pyrazin-6(5H)-one

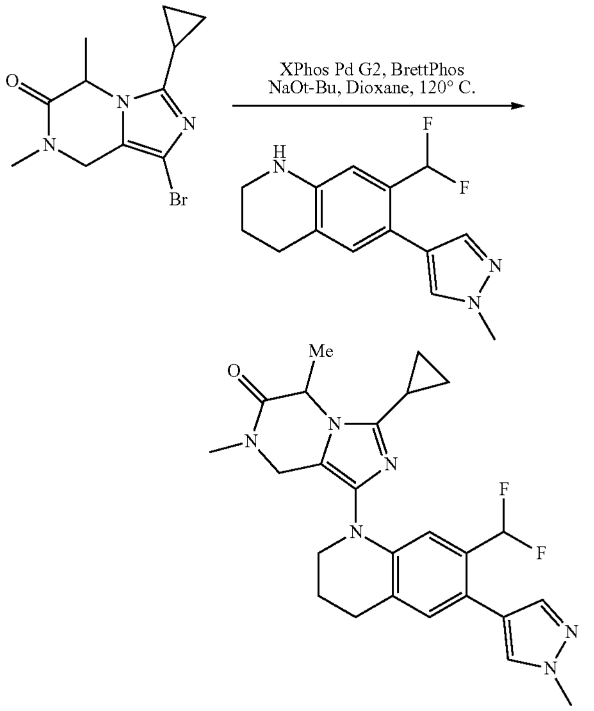

3-Cyclopropyl-1-(7-(difluoromethyl)-6-(1-methyl-1H-pyrazol-4-yl)-3,4-dihydroquinolin-12H)-yl)-5,7-dimethyl-7,8-dihydroimidazo[1,5-a]pyrazin-6(5H)-one A mixture of Intermediate "B" (40 mg, 140 μmol), Brettphos (7.56 mg, 14.1 μmol), XPhos Pd G2(11.08 mg, 14.08 Pd G2 mol), 7-(difluoromethyl)-6-(1-methyl-1H-pyrazol-1-yl)-1,2,3,4-tetrahydroquinoline (37.06 mg, 140.8 μmol) and t-BuONa (27.06 mg, 281.5 μmol) in 1,4-dioxane (2 mL) was degassed and purged with $N_2$ for 3 min, then stirred at 120° C. overnight. The resulting mixture was concentrated under reduced pressure, and the residue was purified by reverse phase preparative HPLC (Mobile phase: A=0.1% TFA/$H_2O$, B=MeCN; Gradient: B=10% to 45% in 18 min; Column: C18) to give the title compound (trifluoroacetate salt) as a yellow solid (36.0 mg, 55%). MS ($ES^+$): $C_{25}H_{28}F_2N_6O$ requires: 466, found: 467 [M+H]+; $^1$H NMR (500 MHz, DMSO-$d_6$) δ 7.77 (s, 1H), 7.51 (s, 1H), 7.16 (s, 1H), 6.96-6.58 (m, 2H), 5.18-5.14 (m, 1H), 4.58-4.48 (m, 1H), 4.56-4.34 (m, 1H), 3.87 (s, 3H), 3.56-3.50 (m, 2H), 2.97 (s, 3H), 2.84 (s, 2H), 2.36-2.25 (m, 1H), 1.99 (s, 2H), 1.63 (d, J=7.0 Hz, 3H), 1.19-0.90 (m, 4H).

Example 4

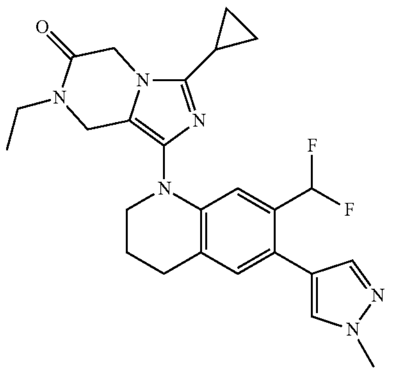 [SMILES: CCN1Cc2c(N3CCCc4cc(-c5cnn(C)c5)c(C(F)F)cc43)nc(C3CC3)n2CC1=O]

3-Cyclopropyl-1-(7-(difluoromethyl)-6-(1-methyl-1H-pyrazol-4-yl)-3,4-dihydroquinolin-1(2H)-yl)-7-ethyl-7,8-dihydroimidazo[1,5-a]pyrazin-6(5H)-one

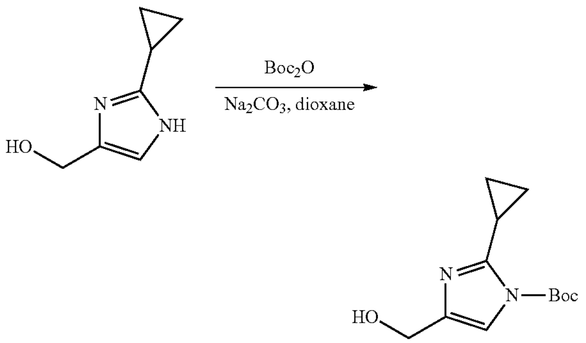

tert-Butyl 2-cyclopropyl-5-(hydroxymethyl)-1H-imidazole-1-carboxylate

To a mixture of 2-cyclopropyl-1H-imidazol-4-yl)methanol (3.0 g, 22 mmol) and $Na_2CO_3$ (5.75 g, 54.3 mmol) in 1,4-dioxane (75 mL) was added $Boc_2O$ (6.63 g, 30.4, mmol). The mixture was stirred at RT for 2 h, then diluted with 100 mL DCM and sequentially washed with water (2×25 mL) and a sat. aq. NaCl solution (25 mL), dried over $MgSO_4$, filtered and concentrated under reduced pressure. The residue was purified by $SiO_2$ gel chromatography (20% to 100% EtOAc/petroleum ether) to give the title compound as a yellow oil (2.50 g, 48%). MS ($ES^+$): $C_{12}H_{18}N_2O_3$ requires: 238, found: 239 $[M+H]^+$.

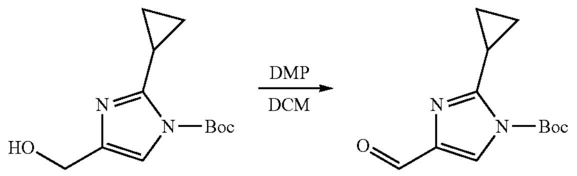

tert-Butyl 2-cyclopropyl-5-formyl-1H-imidazole-1-carboxylate

To a mixture of the product from the previous step (2.5 g, 10.5 mmol) in DCM (45 mL) at 0° C. was added DMP (6.42 g, 14.7 mmol) portionwise, and the resulting mixture was stirred at RT for 2 h. The mixture was filtered and the filtrate was poured into a separatory funnel containing sat. aq. $NaHCO_3$:$Na_2SO_3$ (1:1, 300 mL) then extracted with DCM (4×25 mL). The combined organic phases were dried over $MgSO_4$, filtered, and concentrated under reduced pressure. The residue was purified by $SiO_2$ gel chromatography (20% to 60% EtOAc/petroleum ether) to give the title compound as a white solid (2.10 g, 85%). $^1$H NMR (500 MHz, $CDCl_3$) δ 9.80 (s, 1H), 7.95 (s, 1H), 2.65 (tt, J=8.4, 5.0 Hz, 1H), 1.65 (s, 9H), 1.22-1.14 (m, 2H), 1.07-0.97 (m, 2H).

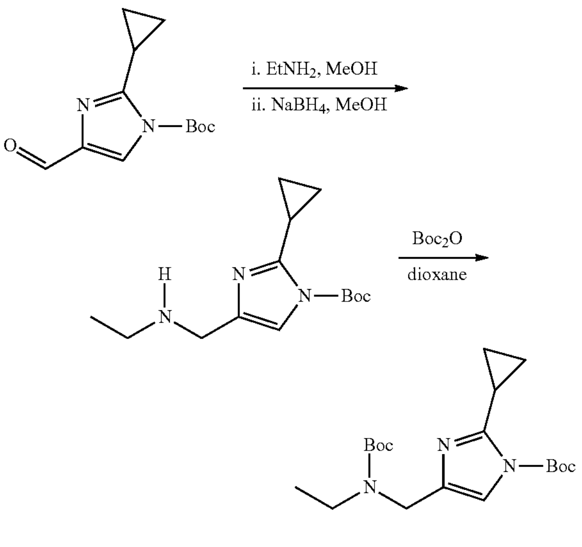

tert-Butyl 5-((tert-butoxycarbonyl(ethyl)amino) methyl)-2-cyclopropyl-1H-imidazole-1-carboxylate A mixture of the product from the previous step (540 mg, 2.24 mmol) and $EtNH_2$ (336.6 mg, 2.240 mmol) in MeOH (10 mL) was stirred at 45° C. overnight, then cooled to 0° C. To the mixture was added $NaBH_4$ (101.7 mg, 2.69 mmol) in portions, and the mixture was stirred at RT for 1 h, treated with a 1 M aq. NaOH solution, and concentrated under reduced pressure to remove organic solvents. To the residue was added 1,4-dioxane (15 mL) then 1 M aq. NaOH dropwise until the pH of the aqueous layer was 9.0. To the mixture was added $Boc_2O$ (978 mg, 4.48 mmol), and the mixture was stirred at RT overnight. The mixture was extracted with EtOAc (3×25 mL), and the combined organic layers were washed with a sat. aq. NaCl solution (25 mL), dried over $Na_2SO_4$, filtered and concentrated under reduced pressure. The residue was purified by $SiO_2$ chromatography (15% to 45% EtOAc/petroleum ether) to give the title compound as a colorless oil (590 mg, 72%) as a colorless oil. MS ($ES^+$): $C_{19}H_{31}N_3O_4$ requires: 365, found: 366 $[M+H]^+$.

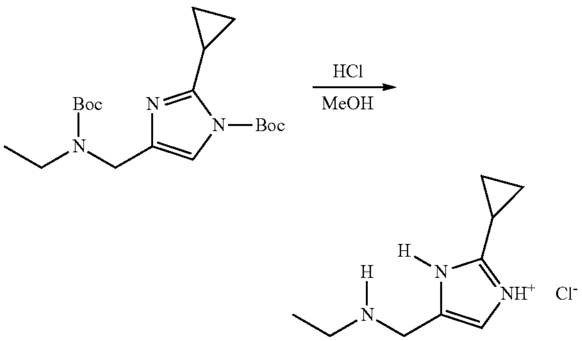

N-((2-cyclopropyl-1H-imidazol-5-yl)methyl) ethanamine hydrochloride

To a solution of the product from the previous step (590 mg, 1.61 mmol) in MeOH (5 mL) was added a 4 N HCl solution in MeOH (5 mL, 20 mmol), and the mixture was stirred at RT overnight then concentrated under reduced pressure to give the title compound as a white solid (320 mg, 98%). MS ($ES^+$): $C_9H_{15}N_3$ requires: 165, found: 166 $[M+H]^+$.

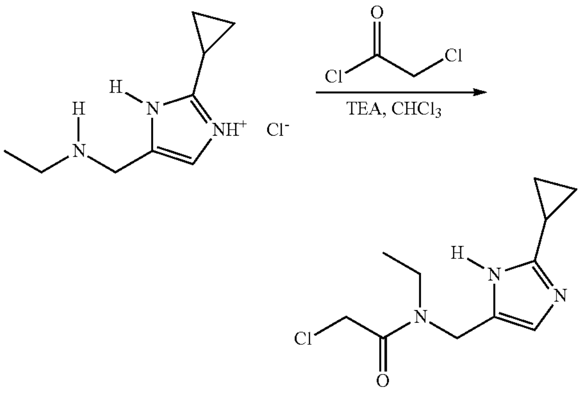

2-Chloro-N-((2-cyclopropyl-1H-imidazol-5-yl) methyl)-N-ethylacetamide

To a mixture of the product from the previous step (320 mg, 1.59 mmol) and triethylamine (1.10 mL, 7.93 mmol) in $CHCl_3$(15 mL) at 0° C. was added chloroacetyl chloride (151 μL, 1.90 mmoles). The mixture was stirred at 0° C. for 30 min, then concentrated under reduced pressure to give crude title compound as a white solid (380 mg, 99%), which was used directly in the next step. MS ($ES^+$): $C_{11}H_{16}ClN_3O$ requires: 241, found: 242 $[M+H]^+$.

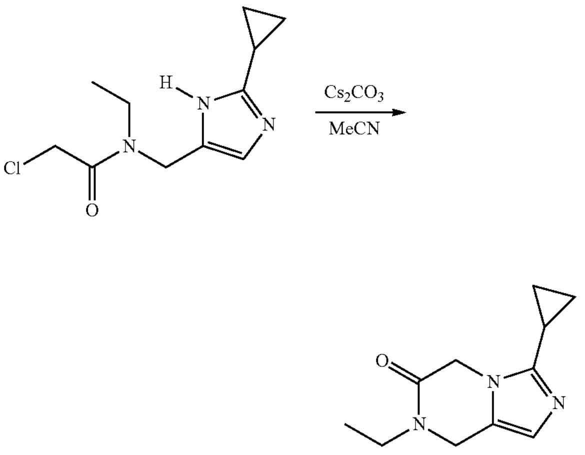

3-Cyclopropyl-1-(7-(difluoromethyl)-6-(1-methyl-1H-pyrazol-4-yl)-3,4-dihydroquinolin-1(2H)-yl)-7-methyl-7,8-dihydroimidazo[1,5-a]pyrazin-6(5H)-one A degassed solution of the product from the previous step (380 mg, 1.57 mmol) and $Cs_2CO_3$ (1.54 g, 4.72 mmol) in $CH_3CN$ (15 mL) was stirred at 100° C. overnight. The mixture was allowed to cool to RT, filtered, and the filtrate concentrated under reduced pressure. The residue was purified by $SiO_2$ gel chromaography (0% to 10% MeOH/EtOAc) to give the title compound as a yellow oil (244 mg, 76%). MS ($ES^+$): $C_{11}H_{15}N_3O$ requires: 205, found: 206 $[M+H]^+$.

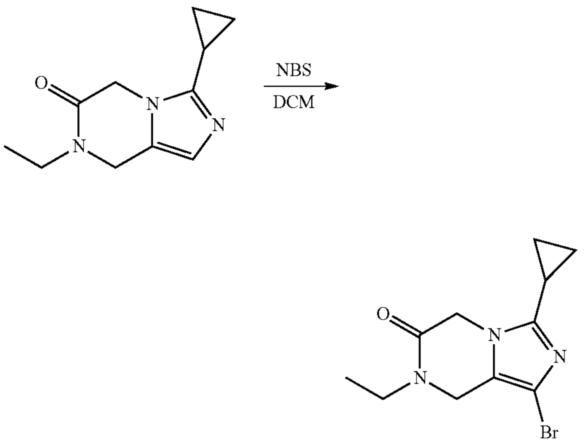

1-Bromo-3-cyclopropyl-7-ethyl-7,8-dihydroimidazo [1,5-al]pyrazin-6(5H)-one

To a mixture of the product from the previous step (244 mg, 1.19 mmol) in DCM (10 mL) was added NBS (250.8 mg, 1.37 mmol), and the mixture was stirred at RT for 30 min. The mixture was treated with 1 mL of a sat. aq. $Na_2SO_3$ solution, diluted with EtOAc (45 mL), washed with a sat. aq. $NaHCO_3$ solution (2×15 mL), dried over $Na_2SO_4$, filtered and concentrated under reduced pressure to give the title compound as a white solid (225 mg, 66%). MS ($ES^+$): $C_{11}H_{14}BrN_3O$ requires: 283, found: 284 $[M+H]^+$. $^1H$ NMR (400 MHz, CDCl3) δ 4.64 (s, 2H), 4.43 (s, 2H), 3.61 (q, J=7.2 Hz, 2H), 1.78-1.68 (m, 1H), 1.25 (t, J=7.2 Hz, 3H), 1.06-0.92 (m, 4H).

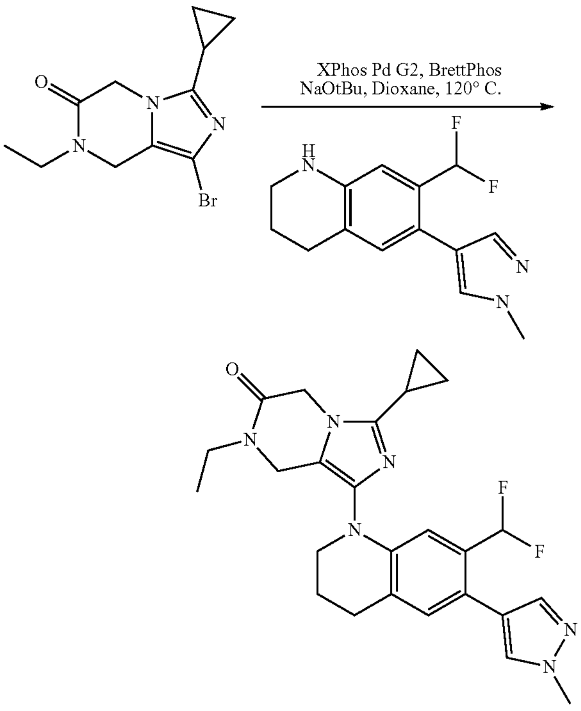

3-Cyclopropyl-1-(7-(difluoromethyl)-6-(1-methyl-1H-pyrazol-4-yl)-3,4-dihydroquinolin-1(2H)-yl)-7-ethyl-7,8-dihydroimidazo[1,5-a]pyrazin-6(5H)-one A mixture of the product from the previous step (40 mg, 141 μmol), BrettPhos (7.56 mg, 14.1 μmol), XPhos Pd G2 (11.08 mg, 14.08 μmol), 7-(difluoromethyl)-6-(1-methyl-1H-pyrazol-4-yl)-1,2,3,4-tetrahydroquinoline (37.06 mg, 140.8 μmol) and t-BuONa (27.06 mg, 281.5 μmol) in 1,4-dioxane (1 mL) was degassed and purged with $N_2$ for 3 min, then stirred at 120° C. overnight. The mixture was concentrated under reduced pressure, and the residue was purified by reverse phase preparative HPLC (Mobile phase: A=0.1% TFA/$H_2O$, B=MeCN; Gradient: B=10% to 45% in 18 min; Column: C18) to give the title compound (trifluoroacetate salt) as an off-white solid (19.0 mg; 29%).

MS ($ES^+$): $C_{25}H_{28}F_2N_6O$ requires: 466, found: 467 $[M+H]^+$.

$^1H$ NMR (500 MHz, $CD_3OD$) δ 7.69 (s, 1H), 7.54 (s, 1H), 7.22 (s, 1H), 6.77 (s, 1H), 6.64 (t, J=55.1 Hz, 1H), 4.94 (s, 2H), 4.50 (s, 2H), 3.96 (s, 3H), 3.69-3.63 (m, 2H), 3.60 (q, J=7.1 Hz, 2H), 2.97 (t, J=5.8 Hz, 2H), 2.30-2.23 (m, 1H), 2.18-2.09 (m, 2H), 1.38-1.30 (m, 2H), 1.19 (t, J=7.2 Hz, 3H), 1.17-1.12 (m, 2H).

Examples 5a/5b (R)-1-(3-(Difluoromethyl)-2-(1-methyl-1H-pyrazol-4-yl)quinolin-5-yl)-5,7-dimethyl-3-(tetrahydro-2H-pyran-4-yl)-7,8-dihydroimidazo[1,5-a]pyrazin-(5H)-one and (S)-1-(3-(difluoromethyl)-2-(1-methyl-1H-pyrazol-4-yl)quinolin-5-yl)-5,7-dimethyl-3-(tetrahydro-2H-pyran-4-yl)-7,8-dihydroimidazo[1,5-a]pyrazin-6(5H)-one 5a

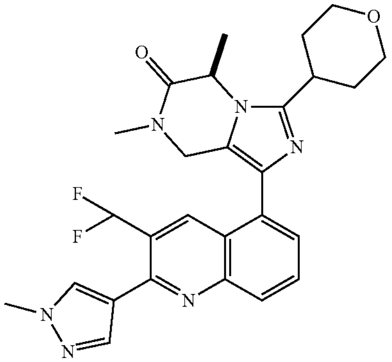

5b

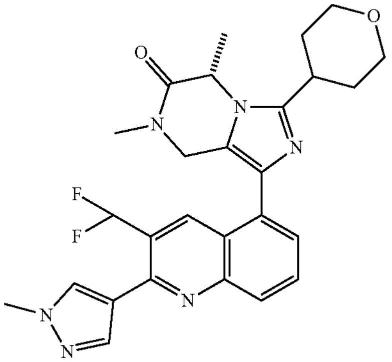

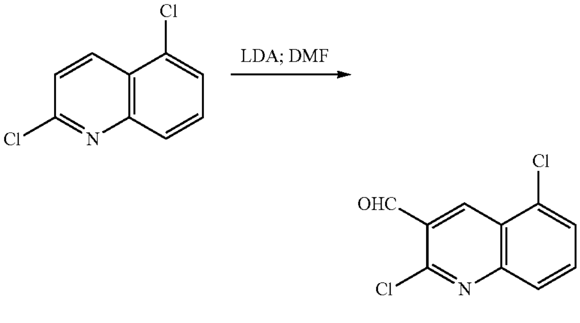

2,5-Dichloroquinoline-3-carbaldehyde

To a solution of $iPr_2NH$ (0.157 mL, 1.10 mmol) in THF (5 mL) at −20 OC was added dropwise a solution of 1.6 M n-BuLi in hexane (0.687 mL, 1.10 mmol). The resulting solution was stirred at 0° C. for 30 min, then cooled to −78° C. To the solution was added dropwise a solution of 2,5-dichloroquinoline (198 mg, 1.00 mmol) in THF (5 mL). The mixture was stirred for 30 min at −78° C., then treated dropwise with DMF (0.116 mL, 1.50 mmol). The mixture was stirred at −78° C. for 30 min, then treated with sat. aq. $NH_4Cl$, allowed to warm to RT, and partitioned between EtOAc (20 mL) and water (10 mL). The organic layer was sequentially washed with water and sat. aq. NaCl, dried over $MgSO_4$, filtered, and concentrated under reduced pressure. The residue was purified by SiO2 gel chromatography (0% to 15% EtOAc in hexanes) to give the title compound as a white solid (108 mg, 48%). MS ($ES^+$) $C_{10}H_5Cl_2NO$ requires: 225, found: 226 $[M+H]^+$.

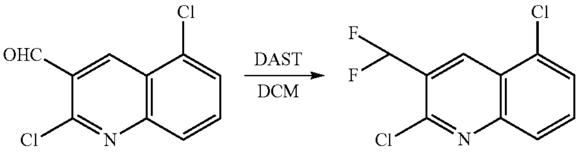

2,5-Dichloro-3-(difluoromethyl)quinoline

To a solution of the product from the previous step (100 mg, 0.442 mmol) in DCM (3 mL) were added DAST (0.175 mL, 1.33 mmol), and the resulting mixture was stirred at 20° C. for 2 h then treated with sat. aq. $NaHCO_3$(10 mL). The layers were separated, and the aqueous layer was extracted with DCM (3×5 mL). The combined organic layers were washed with sat. aq. NaCl, dried over $MgSO_4$, filtered and concentrated under reduced pressure. The residue was purified by $SiO_2$ gel chromatography (0% to 15% EtOAc in hexanes) to give the title compound as an off-white solid (98 mg, 89%). MS ($ES^+$) $C_{10}H_5Cl_2F_2N$ requires: 247, found: 248 $[M+H]^+$.

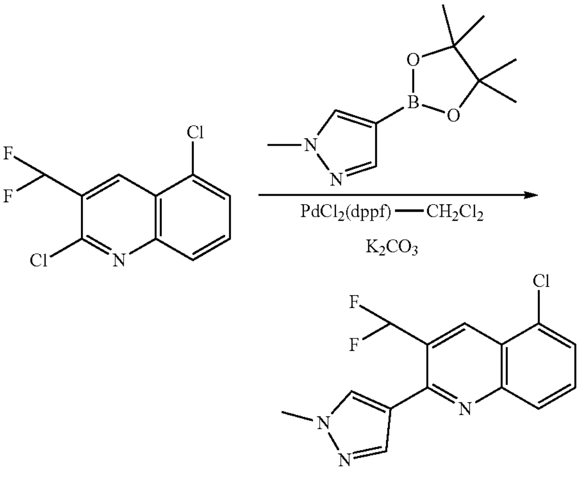

5-Chloro-3-(difluoromethyl)-2-(1-methyl-1H-pyrazol-4-yl)quinoline

A degassed solution of the product from the previous step (112 mg, 0.421 mmol), 1-methyl-4-(4,4,5,5-tetramethyl-1,3,2-dioxaborolan-2-yl)-1H-pyrazole (88 mg, 0.42 mmol), $PdCl_2(dppf)-CH_2Cl_2$ (17.19 mg, 0.021 mmol) and 2.0 M aq. $K_2CO_3$ (0.421 mL, 0.842 mmol) in 1,4-dioxane (4 mL) was stirred at 90° C. for 2 h. $H_2O$ (10 mL) was added, and the layers were separated. The aqueous layer was extracted with EtOAc (3×5 mL), and the combined organic layers were washed with sat. aq. NaCl, dried over $MgSO_4$, filtered and concentrated under reduced pressure. The residue was purified by $SiO_2$ gel chromatography (0% to 5% MeOH in DCM) to give the title compound as an off-white solid (83 mg, 63%). MS ($ES^+$) $C_{14}H_9ClF_2N_3$ requires: 292, found: 293 $[M+H]^+$.

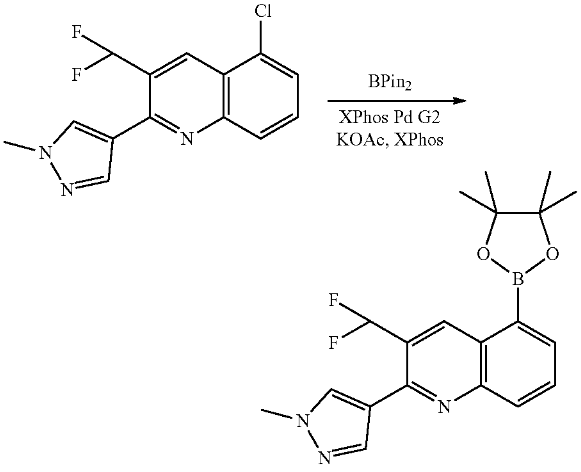

3-(Difluoromethyl)-2-(1-methyl-1H-pyrazol-4-yl)-5-(4,4,5,5-tetramethyl-1,3,2-dioxaborolan-2-yl)quinoline To a degassed solution of the product from the previous step (75 mg, 0.26 mmol) in 1,4-dioxane (2 mL) were added $BPin_2$ (78 mg, 0.31 mmol), KOAc (75 mg, 0.77 mmol), XPhos Pd G2 (20.09 mg, 0.026 mmol), and XPhos (12.17 mg, 0.026 mmol), and the resulting mixture was stirred at 100° C. for 4 h then concentrated under reduced pressure. The residue was purified by $SiO_2$ gel chromatography (0% to 5% MeOH in DCM) to give the title compound as an off-white solid (96 mg, 98%). MS ($ES^+$) $C_{20}H_{22}BF_2N_3O_2$ requires: 385, found: 386 $[M+H]^+$.

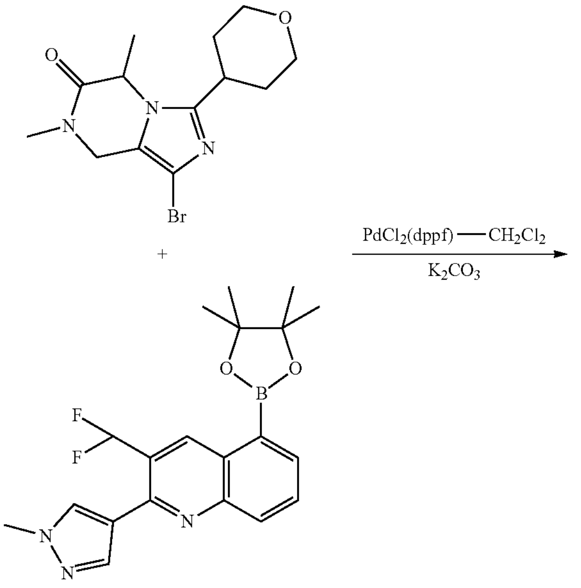

-continued

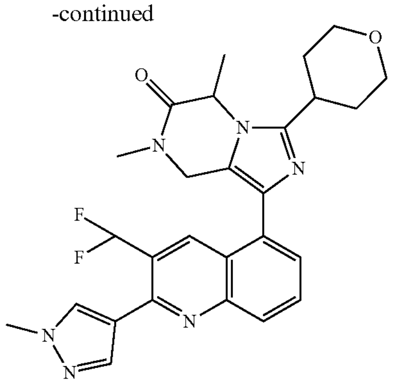

1-(3-(Difluoromethyl)-2-(1-methyl-1H-pyrazol-4-yl)quinolin-5-yl)-5,7-dimethyl-3-(tetrahydro-2H-pyran-4-yl)-7,8-dihydroimidazo[1,5-a]pyrazin-(5H)-one A mixture of Intermediate "C" (75 mg, 0.23 mmol), the product from the previous step (97 mg, 0.25 mmol), and $PdCl_2(dppf)$-$CH_2Cl_2$ (19 mg, 0.023 mmol) in 2 mL DMF (2 mL) was degassed then treated with 2.0 M aq. $K_2CO_3$ (0.34 mL, 0.68 mmol). The mixture was purged with $N_2$ for 3 min, stirred at 100° C. for 1 h, and concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title racemic compound as a white solid (63 mg, 55%). The racemate was separated by chiral HPLC [Instrument: SFC-80 (Thar, Waters); Column: OZ 20*250 mm, 10 um (Daicel); Column temperature: 35° C.; Mobile phase: $CO_2$/MeOH(0.2% 7 M ammonia in MeOH)=30/70; Flow rate: 80 g/min] to give two isomers.

Example 5a was isolated as a white solid (26 mg, 41%). RT=2.28 min.

MS ($ES^+$): $C_{27}H_{28}F_2N_6O_2$ requires: 506, found: 507 $[M+H]^+$.

$^1H$ NMR (500 MHz, MeOD) δ 9.15 (s, 1H), 8.19 (s, 1H), 8.11 (d, J=8.5 Hz, 1H), 8.05 (s, 1H), 7.95-7.87 (m, 1H), 7.61 (d, J=6.4 Hz, 1H), 7.13 (t, J=54.5 Hz, 1H), 5.13 (q, J=7.1 Hz, 1H), 4.95 (d, J=16.0 Hz, 1H), 4.47 (d, J=16.0 Hz, 1H), 4.11-4.08 (m, 2H), 4.05 (s, 3H), 3.67 (appar t, J=11.0 Hz, 2H), 3.27-3.19 (m, 1H), 3.08 (s, 3H), 2.19-2.07 (m, 2H), 1.95-1.89 (m, 2H), 1.74 (d, J=7.1 Hz, 3H). Example 5a was assigned to be the R-enantiomer based on a CBP-bound crystal structure.

Example 5b was isolated as a white solid (26 mg, 41%). RT=4.97 min.

MS ($ES^+$): $C_{27}H_{28}F_2N_6O_2$ requires: 506, found: 507 $[M+H]^+$.

$^1H$ NMR (500 MHz, MeOD) δ 9.15 (s, 1H), 8.19 (s, 1H), 8.11 (d, J=8.6 Hz, 1H), 8.05 (s, 1H), 7.97-7.86 (m, 1H), 7.61 (d, J=6.3 Hz, 1H), 7.13 (t, J=54.5 Hz, 1H), 5.13 (q, J=7.1 Hz, 1H), 4.95 (d, J=16.0 Hz, 1H), 4.47 (d, J=15.9 Hz, 1H), 4.11-4.08 (m, 2H), 4.05 (s, 3H), 3.67 (appar td, J=11.8, 1.7 Hz, 2H), 3.28-3.18 (m, 1H), 3.08 (s, 3H), 2.23-2.07 (m, 2H), 1.95-1.86 (m, 2H), 1.74 (d, J=7.1 Hz, 3H).

Example 6

3-Cyclopropyl-7-(2-hydroxyethyl)-1-(3-(1-methyl-1H-pyrazol-4-yl)isoquinolin-8-yl)-7,8-dihydroimidazo[1,5-a]pyrazin-6(5H)-one

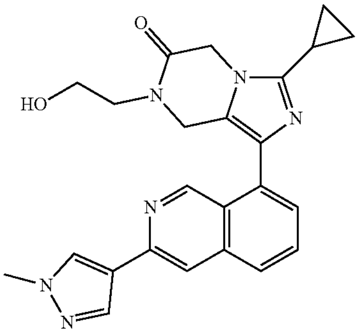 [SMILES: Cn1cc(-c2cc3cccc(-c4nc(C5CC5)n5c4CN(CCO)C(=O)C5)c3cn2)cn1]

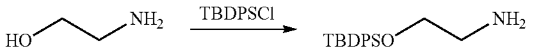

2-(tert-Butyldiphenylsilyloxy)ethanamine

To an ice-cold solution of ethanolamine (18.54 mL, 307.2 mmol) in DCM (15 mL) was added TBDPSCl (4.0 mL, 15 mmol), and the mixture was stirred at RT overnight then diluted with DCM (45 mL). The mixture was sequentially washed with sat. aq. $NaHCO_3$(25 mL×3) and sat. aq. NaCl (25 mL×3), dried over $MgSO_4$, filtered and concentrated under reduced pressure. The residue was purified by $SiO_2$ gel chromatography (20% to 60% EtOAc in petroleum ether) to give the title compound as a colorless oil (4.31 g, 94%). MS ($ES^+$): $C_{18}H_{25}NOSi$ requires: 299, found: 300 $[M+H]^+$.

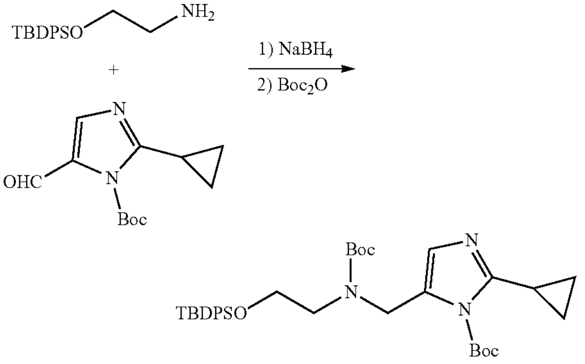

Tert-butyl 5-((tert-butoxycarbonyl(2-(tert-butyldiphenylsilyloxy)ethyl)amino)-methyl)-2-cyclopropyl-1H-imidazole-1-carboxylate A mixture of tert-butyl 2-cyclopropyl-5-formyl-1H-imidazole-1-carboxylate (1.00 g, 4.15 mmol) and the product from the previous step (4.35 g, 4.36 mmoles) in MeOH (25 mL) was stirred at 45° C. overnight. The mixture was cooled to 0° C., then treated with $NaBH_4$ (188.3 g, 4.98 mmol) portionwise. The mixture was stirred at 0° C. for 1 h, then treated with $Boc_2O$ (1.36 g, 6.22 mmol). The mixture was stirred at RT overnight, then extracted with EtOAc (25 mL×3). The combined organic layers were washed with sat. aq. NaCl (25 mL×2), dried over $Na_2SO_4$, filtered and concentrated under reduced pressure. The residue was purified by $SiO_2$ gel chromatography (15% to 45% EtOAc in petroleum ether) to give the title compound as a colorless oil (1.51 g, 59%). MS ($ES^+$): $C_{35}H_{49}N_3O_5Si$ requires: 619, found: 620 $[M+H]^+$.

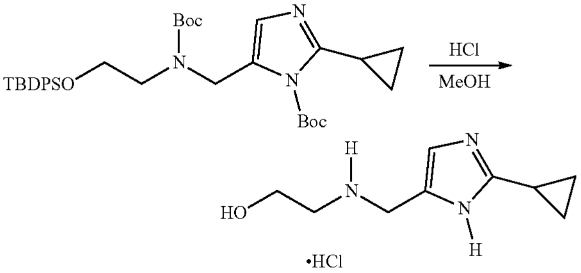

2-((2-Cyclopropyl-1H-imidazol-5-yl)methylamino) ethanol hydrochloride

To a mixture of the product from the previous step (1.51 g, 2.42 mmol) in MeOH (3 mL) was added 4 M HCl in 1,4-dioxane (5 mL). The mixture was stirred at RT overnight, then concentrated under reduced pressure. The residue was washed with $Et_2O$ (10 mL×2) and dried to give the title compound as a white solid (520 mg, 99%). MS ($ES^+$): $C_9H_{15}N_3O$ requires: 181, found: 182 $[M+H]^+$.

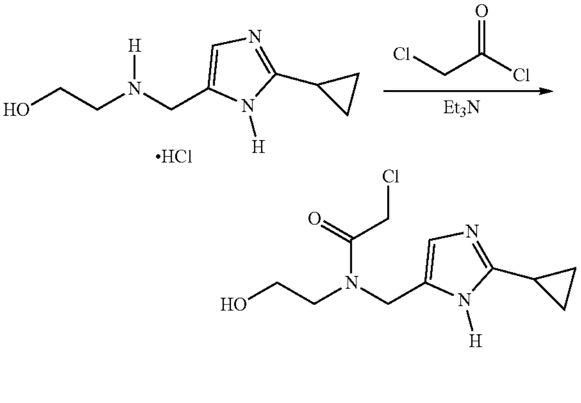

2-Chloro-N-((2-cyclopropyl-1H-imidazol-5-yl) methyl)-N-(2-hydroxyethyl)acetamide To a mixture of the product from the previous step (520 mg, 2.39 mmol) and TEA (1.66 mL, 11.9 mmol) in $CHCl_3$ (15 mL) at 0° C. was added chloroacetyl chloride (0.199 mL, 2.51 mmol). The mixture was stirred at 0° C. for 30 min, then concentrated under reduced pressure to give the crude title compound as a white solid (610 mg, 99%), which was used without further purification. MS ($ES^+$): $C_{11}H_{16}ClN_3O_2$ requires: 257, found: 258 $[M+H]^+$.

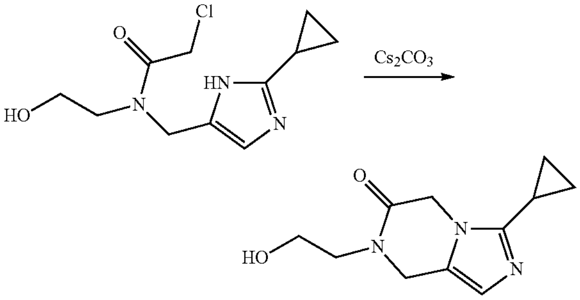

3-cyclopropyl-7-(2-hydroxyethyl)-5,8-dihydroimidazo[1,5-a]pyrazin-6-one

A degassed mixture of the product from the previous step (610 mg, 2.37 mmol) and $Cs_2CO_3$ (2.31 g, 7.10 mmol) in MeCN (10 mL) was stirred at 100° C. for 1 h, then allowed to cool to RT, filtered and the filtrate concentrated under reduced pressure. The residue was purified by $SiO_2$ gel chromatography (0% to 20% MeOH in EtOAc) to give the title compound as a yellow oil (346 mg, 66%). MS ($ES^+$): $C_{11}H_{15}N_3O_2$ requires: 221, found: 222 $[M+H]^+$.

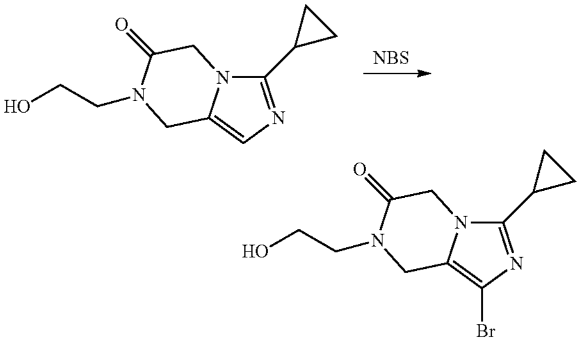

1-Bromo-3-cyclopropyl-7-(2-hydroxyethyl)-7,8-dihydroimidazo[1,5-a]pyrazin-6(5H)-one To a mixture of the product from the previous step (346 mg, 1.56 mmol) in DCM (10 mL) was added NBS (315.63 mg, 1.72 mmoles). The mixture was stirred at RT for 30 min, then treated with sat. aq. $Na_2SO_3$ (2 mL), diluted with EtOAc (45 mL) and washed with sat. aq. $NaHCO_3$(15 mL×2). The organic layer was dried over $Na_2SO_4$, filtered and concentrated under reduced pressure. The residue was purified by $SiO_2$ gel chromatography (0% to 10% MeOH in EtOAc) to give the title compound as a white solid (251 mg, 53%). MS ($ES^+$): $C_{11}H_{14}BrN_3O_2$ requires: 299, found: 300 $[M+H]^+$.

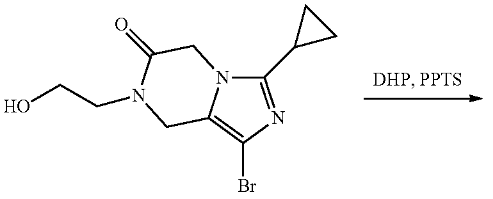

-continued

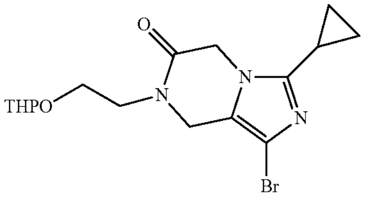

1-Bromo-3-cyclopropyl-7-(2-(tetrahydro-2H-pyran-2-yloxy)ethyl)-7,8-dihydroimidazo[1,5-a]pyrazin-6(5H)-one To a mixture of the product from the previous step (251 mg, 836 mmol) and PPTS (21.02 mg, 83.62 μmol) in DCM (15 mL) was added DHP (0.114 mL, 1.25 mmoles) dropwise. The mixture was stirred at RT overnight, then washed with sat. aq. $NaHCO_3$(15 mL) and the aqueous layer back-extracted with DCM (20 mL×2). The combined organic layers were washed with sat. aq. NaCl (15 mL), dried over $MgSO_4$, filtered and concentrated under reduced pressure. The residue was purified by $SiO_2$ gel chromatography (20% to 100% EtOAc in petroleum ether) to give the title compound as colorless oil (234 mg, 73%). MS ($ES^+$): $C_{16}H_{22}BrN_3O_3$ requires: 383 found: 384 $[M+H]^+$.

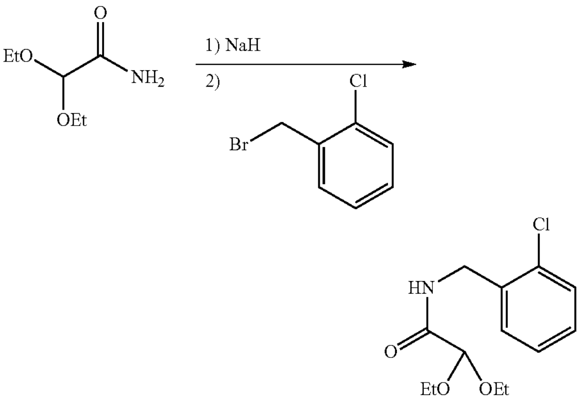

N-(2-Chlorobenzyl)-2,2-diethoxyacetamide

To a suspension of NaH (60% in mineral oil, 192 mg, 4.80 mmol) in THF (15 mL) was added 2,2-diethoxyacetamide (707 mg, 4.80 mmol). The mixture was stirred at 20° C. for 10 min, then treated with 1-(bromomethyl)-2-chlorobenzene (822 mg, 4.00 mmol). The mixture was stirred at 80° C. for 3 h, then treated with sat. aq. $NH_4Cl$ (50 mL). The layers were separated, and the aqueous layer was extracted with EtOAc (30 mL×3). The combined organic layers were washed with sat. aq. NaCl, dried over $MgSO_4$, filtered and concentrated under reduced pressure. The residue was purified by $SiO_2$ gel chromatography (0% to 50% EtOAc in hexanes) to give the title compound as a colorless liquid (468 mg, 43%). MS ($ES^+$) $C_{13}H_{18}ClNO_3$ requires: 271, found: 272 $[M+H]^+$.

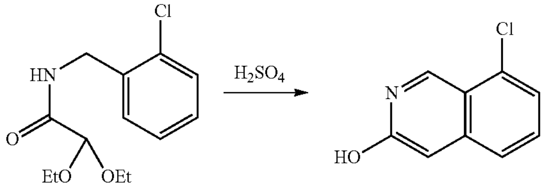

8-Chloroisoquinolin-3-ol

A solution of the product from the previous step (468 mg, 1.722 mmol) in conc. aq. $H_2SO_4$ (2 mL) was stirred at 80° C. for 2 h. The mixture was allowed to cool to RT and poured into ice water. The solution was adjusted to pH 8 using 10% aq. NaOH. The precipitate was isolated by filtration to give the title compound as an off-white solid (280 mg, 91%). MS ($ES^{+}$)$C_9H_6ClNO$ requires: 179, found: 180 $[M+H]^+$.

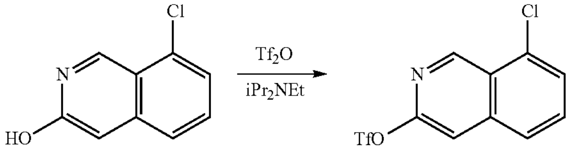 [SMILES: "Tf2O" ; "iPr2NEt" ; Oc1cc2cccc(Cl)c2cn1 ; O=S(=O)(Oc1cc2cccc(Cl)c2cn1)C(F)(F)F]

8-Chloroisoquinolin-3-yl trifluoromethanesulfonate

To a solution of 8-chloroisoquinolin-3-ol (280 mg, 1.56 mmol) in DCM (10 mL) were added $iPr_2NEt$ (0.817 mL, 4.68 mmol) and $Tf_2O$ (0.395 mL, 2.34 mmol). The mixture was stirred at 20° C. for 3 h, then treated with $H_2O$ (30 mL). The layers were separated, and the aqueous layer was extracted with DCM (20 mL×3). The combined organic layers were washed with sat. aq. NaCl, dried over $MgSO_4$, filtered and concentrated under reduced pressure. The residue was purified by $SiO_2$ gel chromatography (0% to 5% MeOH in DCM) to give the title compound as an off-white solid (302 mg, 62%). MS ($ES^+$) $C_{10}H_5ClF_3NO_3S$ requires: 311, found: 312 $[M+H]^+$.

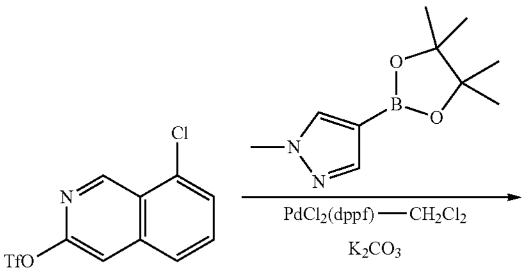

-continued

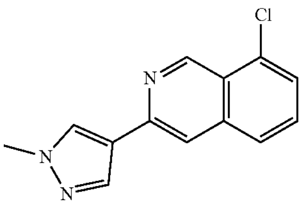

8-Chloro-3-(1-methyl-1H-pyrazol-4-yl)isoquinoline

A degassed mixture of the product from the previous step (300 mg, 0.963 mmol), 1-methyl-4-(4,4,5,5-tetramethyl-1,3,2-dioxaborolan-2-yl)-1H-pyrazole (240 mg, 1.16 mmol), $PdCl_2(dppf)-CH_2Cl_2$ (39.3 mg, 0.048 mmol), and 2.0 M aq. $K_2CO_3$ (0.963 mL, 1.93 mmol) in DMF (5 mL) was stirred at 90° C. for 1 h, then concentrated under reduced pressure. The residue was treated with $H_2O$ (30 mL) and the mixture was extracted with EtOAc (20 mL×3). The combined organic layers were washed with sat. aq. NaCl, dried over $MgSO_4$, filtered and concentrated under reduced pressure. The residue was purified by $SiO_2$ gel chromatography (0% to 5% MeOH in DCM) to give the title compound as an off-white solid (186 mg, 79%). MS ($ES^+$) $C_{13}H_{10}ClN_3$ requires: 243, found: 244 $[M+H]^+$.

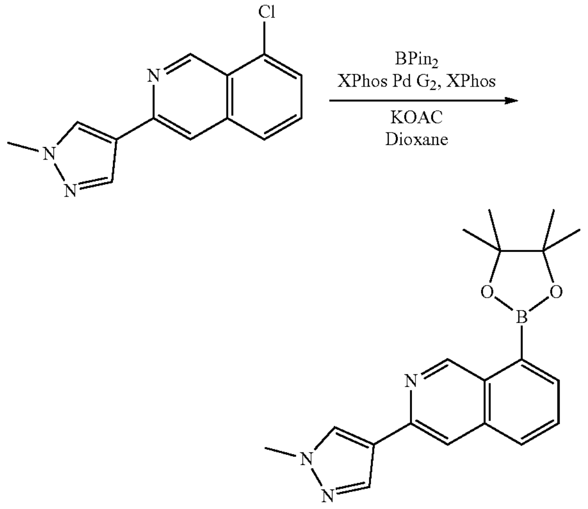

3-(1-Methyl-1H-pyrazol-4-yl)-8-(4,4,5,5-tetramethyl-1,3,2-dioxaborolan-2-yl)isoquinoline To a degassed mixture of the product from the previous step (180 mg, 0.739 mmol) in 1,4-dioxane (5 mL) were added $BPin_2$ (225 mg, 0.886 mmol), KOAc (217 mg, 2.22 mmol), XPhos Pd G2 (58.1 mg, 0.074 mmol), and XPhos (35.2 mg, 0.074 mmol). The resulting mixture was stirred at 100° C. for 4 h, then concentrated under reduced pressure. The residue was purified by $SiO_2$ gel chromatography (0% to 5% MeOH in DCM) to give the title compound as an off-white solid (96 mg, 39%). MS ($ES^+$) $C_{19}H_{22}BN_3O_2$ requires: 335, found: 336 $[M+H]^+$.

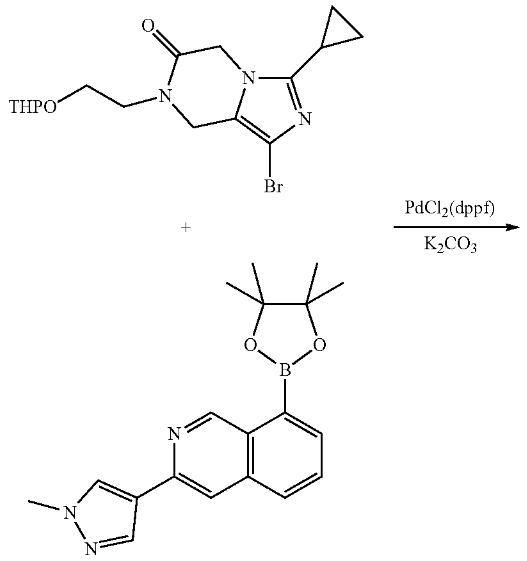

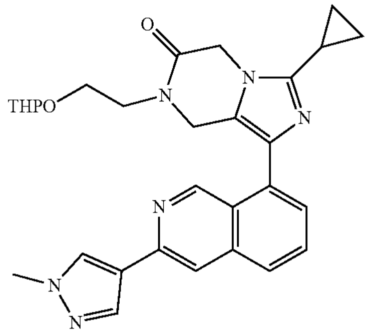

3-Cyclopropyl-1-(3-(1-methyl-1H-pyrazol-4-yl)isoquinolin-8-yl)-7-(2-(tetrahydro-2H-pyran-2-yloxy)ethyl)-7,8-dihydroimidazo[1,5-a]pyrazin-6(5H)-one A mixture of 1-bromo-3-cyclopropyl-7-(2-(tetrahydro-2H-pyran-2-yloxy)ethyl)-7,8-dihydroimidazo[1,5-a]pyrazin-6(5H)-one (50 mg, 0.13 mmol), the product from the previous step (48 mg, 0.14 mmol), and $PdCl_2$(dppf) (10 mg, 0.013 mmol) in DMF (1 mL) was degassed and purged with $N_2$ 3 times, then treated with 2.0 M aq. $K_2CO_3$ (0.195 mL, 0.390 mmol). The mixture was stirred at 100° C. for 1 h, then concentrated under reduced pressure. The residue was purified by $SiO_2$ gel chromatography (0% to 10% MeOH in EtOAc) to give the title compound as a yellow solid (44 mg, 66%). MS ($ES^+$): $C_{29}H_{32}N_6O_3$ requires: 512, found: 513 $[M+H]^+$.

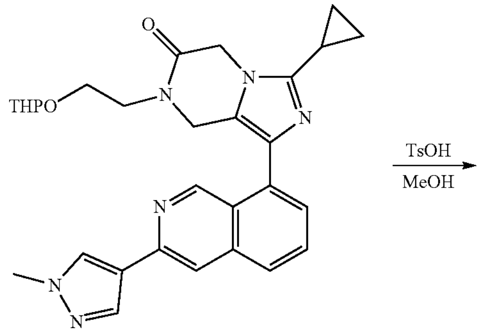

-continued

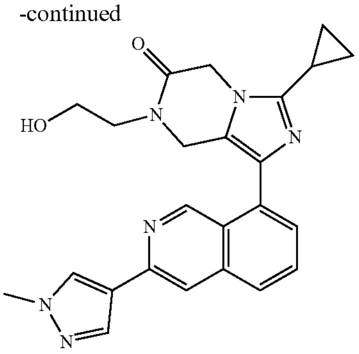

3-Cyclopropyl-7-(2-hydroxyethyl)-1-(3-(1-methyl-1H-pyrazol-4-yl)isoquinolin-8-yl)-7,8-dihydroimidazo[1,5-a]pyrazin-6(5H)-one To a mixture of the product from the previous step (44 mg, 0.086 mmol) in MeOH (2 mL) was added TsOH (3.0 mg, 0.017 mmol). The mixture was stirred at RT overnight, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a white solid (24.3 mg, 66%).

MS ($ES^+$): $C_{24}H_{24}N_6O_2$ requires: 428, found: 429 $[M+H]^+$.

$^1$H NMR (500 MHz, MeOD) δ 9.50 (s, 1H), 8.22 (s, 1H), 8.12 (s, 1H), 8.07 (s, 1H), 7.92 (d, J=8.3 Hz, 1H), 7.82-7.72 (m, 1H), 7.53 (d, J=6.2 Hz, 1H), 4.80 (s, 2H), 4.63 (s, 2H), 4.00 (s, 3H), 3.76 (t, J=5.3 Hz, 2H), 3.64 (t, J=5.3 Hz, 2H), 2.10-2.08 (m, 1H), 1.16-1.04 (m, 4H).

Example 7

3-Cyclopropyl-7-(2-fluoroethyl)-1-(3-(1-methyl-1H-pyrazol-4-yl)isoquinolin-8-yl)-7,8-dihydroimidazo[1,5-a]pyrazin-6(5H)-one

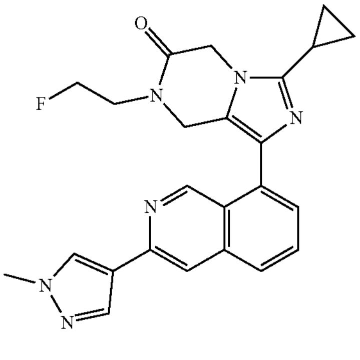 [SMILES: Cn1cc(-c2cc3cccc(-c4nc(C5CC5)n5c4CN(CCF)C(=O)C5)c3cn2)cn1]

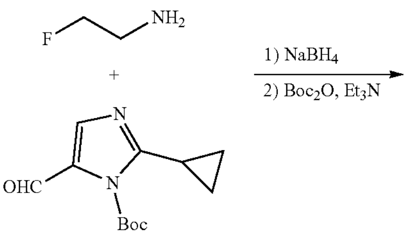

-continued

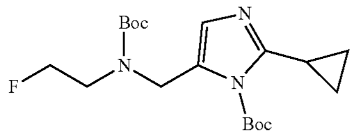

tert-Butyl 5-[(tert-butoxycarbonyl(2-fluoroethyl) amino)methyl]-2-cyclopropyl-imidazole-1-carboxylate A mixture of tert-butyl 2-cyclopropyl-5-formyl-1H-imidazole-1-carboxylate (1.20 g, 4.98 mmol), NaOAc (490 mg, 5.97 mmol) and 2-fluoroethanamine hydrochloride (607 mg, 5.97 mmol) in MeOH (10 mL) was stirred at RT overnight, then cooled to 0° C. and treated portionwise with $NaBH_4$ (188 mg, 4.98 mmol). The mixture was stirred at 0° C. for 30 min, then treated with 1 M aq. NaOH and concentrated under reduced pressure. The residue was treated with TEA (2.42 mL, 17.4 mmol), DCM (30 mL) and $Boc_2O$ (2.17 g, 9.95 mmol). The mixture was stirred at RT overnight, then treated with sat. aq. $Na_2CO_3$ and extracted with DCM (20 mL×3). The combined organic layers were washed with sat. aq. NaCl (20 mL), dried over $Na_2SO_4$, filtered and concentrated under reduced pressure. The residue was purified by $SiO_2$ gel chromatography (0% to 20% MeOH in EtOAc) to give the title compound as a colorless oil (1.08 g, 57%). MS ($ES^+$): $C_{19}H_{30}FN_3O_4$ requires: 383, found: 384 $[M+H]^+$.

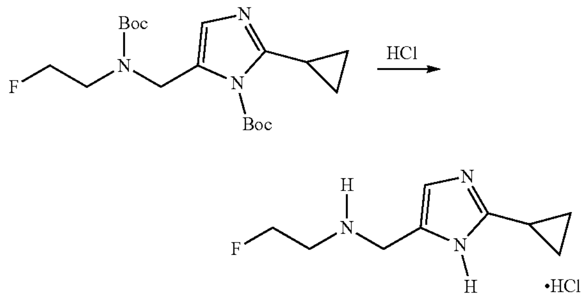

N-((2-cyclopropyl-1H-imidazol-5-yl)methyl)-2-fluoroethanamine hydrochloride

To a mixture of the product from the previous step (1.08 g, 2.82 mmol) in MeOH (5 mL) was added 15 mL of a 2 M HCl in 1,4-dioxane solution. The mixture was stirred at RT overnight, then concentrated under reduced pressure to give the title compound as a white solid (0.618 g, 100%). MS ($ES^+$): $C_9H_{13}FN_3$ requires: 183, found: 184 $[M+H]^+$.

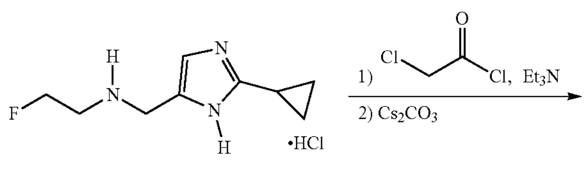

-continued

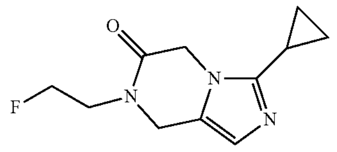

3-Cyclopropyl-7-(2-fluoroethyl)-7,8-dihydroimidazo [1,5-a]pyrazin-6(5H)-one

To a mixture of the product from the previous step (0.618 g, 2.82 mmol) and TEA (0.981 mL, 7.06 mmol) in $CHCl_3$ (20 mL) at 0° C. was added chloroacetyl chloride (0.236 mL, 2.96 mmol). The mixture was stirred at 0° C. for 30 min, then concentrated under reduced pressure to give a white solid (730 mg). The solid was treated with $Cs_2CO_3$ (2.26 g, 6.93 mmol) and MeCN (15 mL). The mixture was stirred at 100° C. for 1 h, allowed to cool to RT, filtered, and the filtrate was concentrated under reduced pressure. The residue was purified by $SiO_2$ gel chromatography (0% to 20% MeOH in EtOAc) to give the title compound as a yellow oil (370 mg, 60%). MS ($ES^+$): $C_{11}H_{14}FN_3O$ requires: 223, found: 224 $[M+H]^+$.

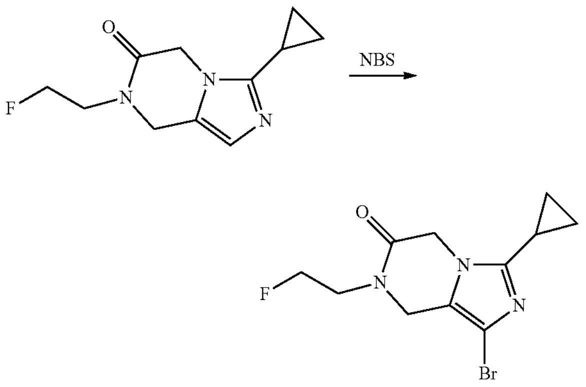

1-Bromo-3-cyclopropyl-7-(2-fluoroethyl)-5,8-dihydroimidazo[1,5-a]pyrazin-6-one

To a mixture of the product from the previous step (346 mg, 1.55 mmol) in DCM (15 mL) was added NBS (313 mg, 1.70 mmol). The mixture was stirred at RT for 30 min, then treated with sat. aq. $Na_2SO_3$ (2 mL) and diluted with EtOAc (45 mL). The mixture was washed with sat. aq. $NaHCO_3$ solution (15 mL×2), dried over $Na_2SO_4$, filtered and concentrated under reduced pressure. The residue was purified by $SiO_2$ gel chromatography (0% to 10% MeOH in EtOAc) to give the title compound as a white solid (438 mg, 94%). MS ($ES^+$): $C_{11}H_{14}BrFN_3O$ requires: 301, found: 302 $[M+H]^+$.

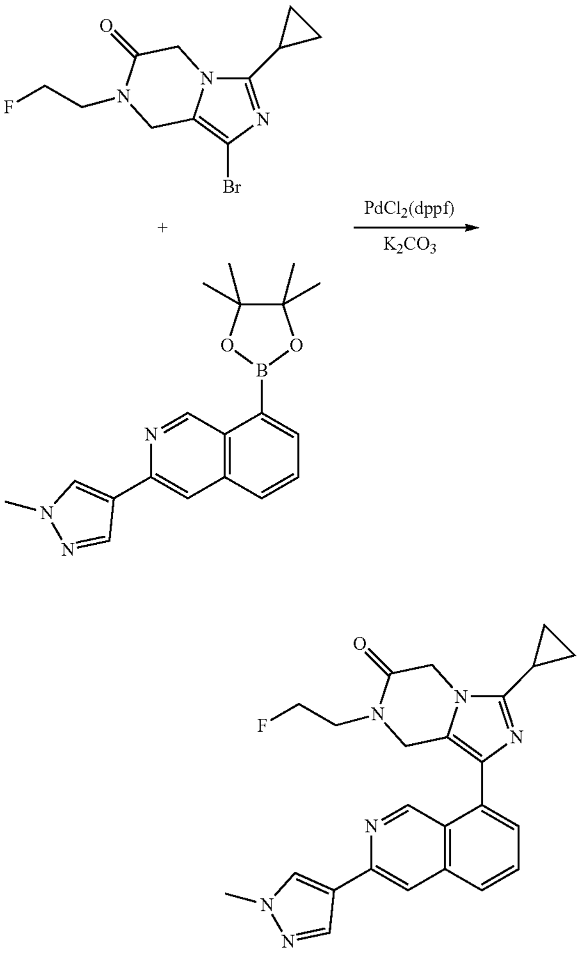

3-Cyclopropyl-7-(2-fluoroethyl)-1-(3-(1-methyl-1H-pyrazol-4-yl)isoquinolin-8-yl)-7,8-dihydroimidazo[1,5-a]pyrazin-6(5H)-one A mixture of the product from the previous step (65.0 mg, 215 μmol), 3-(1-methyl-1H-pyrazol-4-yl)-8-(4,4,5,5-tetramethyl-1,3,2-dioxaborolan-2-yl)isoquinoline (86.54 mg, 258.2 μmol), 2.0 M aq. $K_2CO_3$ (0.322 mL, 644 μmol) and $PdCl_2$(dppf) (26.89 mg, 32.27 μmoles) in DMF (1 mL) was degassed and purged with $N_2$. The mixture was stirred at 90° C. for 1 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as an off-white solid (65 mg, 70%).

MS ($ES^+$): $C_{24}H_{23}FN_6O$ requires: 430, found: 431 $[M+H]^+$.

$^1H$ NMR (500 MHz, MeOD) δ 9.49 (s, 1H), 8.22 (s, 1H), 8.12 (s, 1H), 8.07 (s, 1H), 7.91 (d, J=8.3 Hz, 1H), 7.78 (dd, J=8.2, 7.2 Hz, 1H), 7.51 (d, J=7.0 Hz, 1H), 4.96 (s, 2H), 4.78 (s, 2H), 4.65 (dt, J=45, 4.8 Hz, 2H), 4.00 (s, 3H), 3.84 (dt, J=30.0, 4.8 Hz, 2H), 2.13-2.01 (m, 1H), 1.13-1.06 (m, 4H).

Examples 8a/8b 5-(5,7-dimethyl-6-oxo-3-(tetrahydro-2H-pyran-4-yl)-5,6,7,8-tetrahydroimidazo[1,5-a]pyrazin-1-yl)-2-(1-methyl-1H-pyrazol-4-yl)quinoline-3-carbonitrile

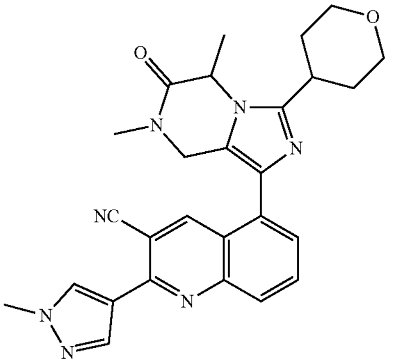 [SMILES: CC1C(=O)N(C)Cc2c(-c3cccc4nc(-c5cnn(C)c5)c(C#N)cc34)nc(C3CCOCC3)n21]

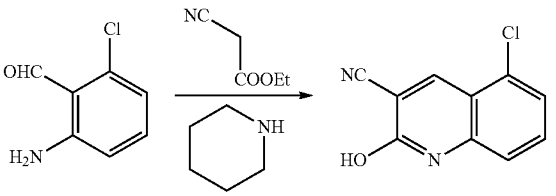

5-Chloro-2-hydroxyquinoline-3-carbonitrile

To a mixture of 2-amino-6-chlorobenzaldehyde (3.5 g, 23 mmol) and ethyl 2-cyanoacetate (3.0 g, 27 mmol) in EtOH (200 mL) was added piperidine (0.50 g, 5.6 mmol). The mixture was stirred at reflux for 5 h, then allowed to cool to RT. The solid was isolated by filtration and washed with EtOH (20 mL) to give the title compound as a white solid (4.1 g, 88%). MS ($ES^+$): $C_{10}H_5ClN_2O$ requires: 204, found: 205 $[M+H]^+$.

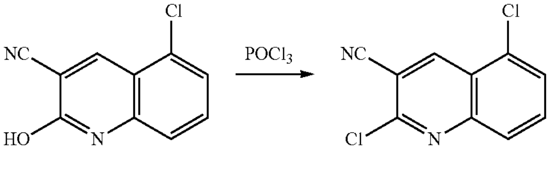

2,5-Dichloroquinoline-3-carbonitrile

A mixture of the product from the previous step (4.1 g, 20 mmol) in $POCl_3$ (100 mL) was stirred at 100° C. for 3 h, then allowed to cool to RT. The mixture was concentrated under reduced pressure, then treated with sat. aq. $NaHCO_3$ until the pH of the mixture was >8. The mixture was extracted with EtOAc (50 mL×4), the combined organic layers were concentrated under reduced pressure, and the residue was purified by $SiO_2$ gel chromatography (0% to 30% EtOAc in petroleum ether) to give the title compound as a light yellow solid (4.0 g, 90%). MS ($ES^+$): $C_{10}H_4Cl_2N_2$ requires: 222, found: 223 $[M+H]^+$.

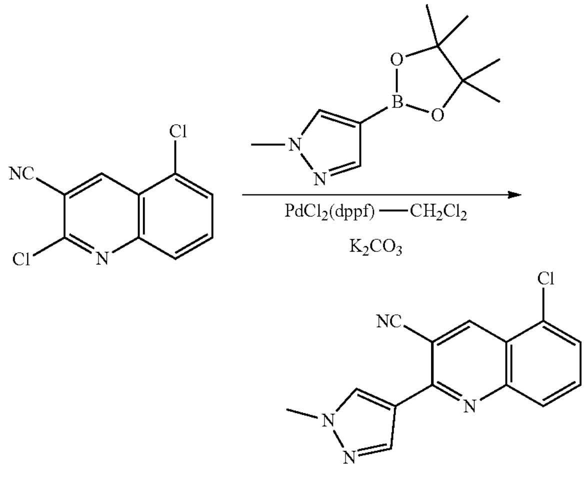

5-Chloro-2-(1-methyl-1H-pyrazol-4-yl)quinoline-3-carbonitrile

A mixture of the product from the previous step (1.1 g, 4.9 mmol), 1-methyl-4-(4,4,5,5-tetramethyl-1,3,2-dioxaborolan-2-yl)-1H-pyrazole (1.1 g, 5.4 mmol), $K_2CO_3$ (2.0 g, 15 mmol) and $PdCl_2$(dppf) (400 mg, 0.49 mmol) in 1,4-dioxane/$H_2O$ (20 mL/4 mL) was degassed and purged with $N_2$, then stirred at 100° C. for 2 h. The mixture was concentrated under reduced pressure, and the residue was purified by $SiO_2$ gel chromatography (0% to 50% EtOAc in petroleum ether) to give the title compound as a tan solid (680 mg, 51%). MS ($ES^+$): $C_{14}H_9ClN_4$ requires: 268, found: 269 $[M+H]^+$.

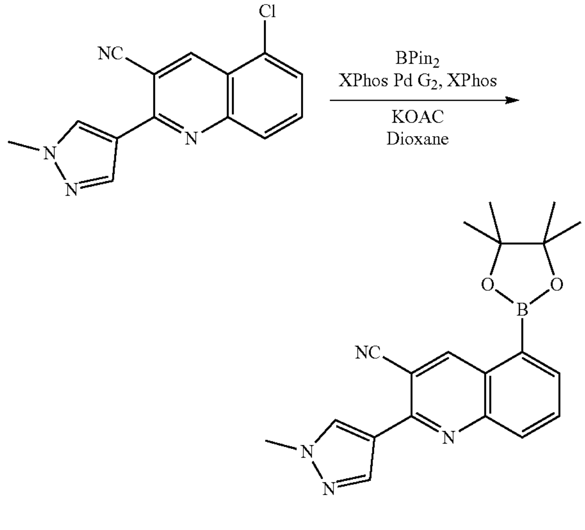

2-(1-methylpyrazol-4-yl)-5-(4,4,5,5-tetramethyl-1,3,2-dioxaborolan-2-yl)quinoline-3-carbonitrile A mixture of the product from the previous step (100 mg, 0.37 mmol), $BPin_2$ (114 mg, 0.45 mmol), KOAc (108 mg, 1.1 mmol), XPhos Pd G2 (29 mg, 0.04 mmol) and XPhos (35 mg, 0.07 mmol) in dry 1,4-dioxane (3 mL) was degassed and purged with Ar, then stirred at 100° C. for 4 h. The reaction was repeated four times, and the combined mixtures were concentrated under reduced pressure. The residue was purified by $SiO_2$ gel chromatography (0% to 50% EtOAc in petroleum ether) to give the crude title compound, which was further washed with DMF (5 mL) to give the title compound as a white solid (375 mg, 69%). MS ($ES^+$): $C_{20}H_{21}BN_4O_2$ requires: 360, found: 361 $[M+H]^+$.

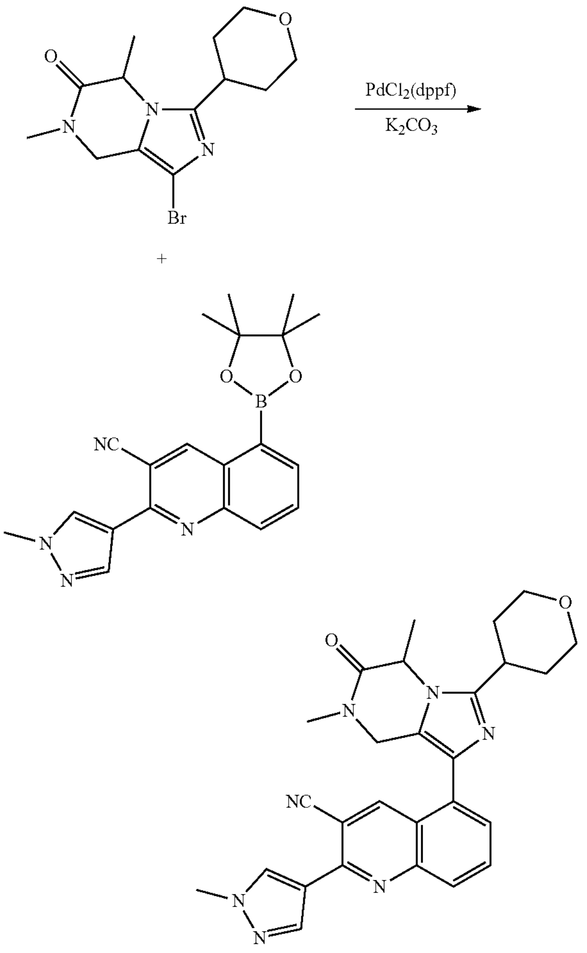

5-(5,7-Dimethyl-6-oxo-3-(tetrahydro-2H-pyran-4-yl)-5,6,7,8-tetrahydroimidazo[1,5-a]pyrazin-1-yl)-2-(1-methyl-1H-pyrazol-4-yl)quinoline-3-carbonitrile (with separation of enantiomers)

A mixture of Intermediate "C" (200 mg, 609 μmol), the product from the previous step (263.41 mg, 731.24 μmol), 2 M aq. $K_2CO_3$ (0.914 mL, 1.83 mmol) and $PdCl_2$(dppf) (50.78 mg, 60.94 moles) in DMF (5 mL) was degassed and purged with $N_2$. The mixture was stirred at 90° C. for 1 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title racemic compound as an off-white solid (51 mg, 17%). The racemate was separated by chiral HPLC [Instrument: SFC-80 (Thar, Waters); Column: OJ 20*250 mm, 10 um (Daicel); Column temperature: 35° C.; Mobile phase: $CO_2$/IPA(0.2% 7 M ammonia in MeOH)=70/30; Flow rate: 80 g/min] to give two isomers.

Example 8a was isolated as a yellow solid (23 mg, 45%). RT=4.07 min.

MS ($ES^+$): $C_{27}H_{27}N_7O_2$ requires: 481, found: 482 $[M+H]^+$.

$^1$H NMR (500 MHz, MeOD) δ 9.14 (s, 1H), 8.44 (s, 1H), 8.27 (s, 1H), 7.96 (d, J=8.5 Hz, 1H), 7.84 (dd, J=8.5, 7.2 Hz, 1H), 7.47 (d, J=7.0 Hz, 1H), 5.00 (q, J=7.0 Hz, 1H), 4.84 (d, J=15.5 Hz, 1H), 4.36 (d, J=15.9 Hz, 1H), 4.01-3.94 (m, 2H), 3.93 (s, 3H), 3.56 (t, J=11.9 Hz, 2H), 3.16-3.06 (m, 1H), 2.97 (s, 3H), 2.10-1.92 (m, 2H), 1.84-1.75 (m, 2H), 1.62 (d, J=7.1 Hz, 3H).

Example 8b was isolated as a yellow solid (24 mg, 47%). RT=5.05 min.

MS ($ES^+$): $C_{27}H_{27}N_7O_2$ requires: 481, found: 482 $[M+H]^+$.

$^1$H NMR (500 MHz, MeOD) δ 9.26 (s, 1H), 8.55 (s, 1H), 8.38 (s, 1H), 8.07 (d, J=8.5 Hz, 1H), 7.95 (appar t, J=7.8 Hz, 1H), 7.59 (d, J=7.1 Hz, 1H), 5.12 (q, J=7.1 Hz, 1H), 4.97 (d, J=16.0 Hz, 1H), 4.49 (d, J=15.9 Hz, 1H), 4.11-4.09 (m, 2H), 4.05 (s, 3H), 3.68 (appar t, J=11.8 Hz, 2H), 3.23 (ddd, J=11.7, 8.0, 3.8 Hz, 1H), 3.09 (s, 3H), 2.19-2.07 (m, 2H), 1.96-1.87 (m, 2H), 1.74 (d, J=7.1 Hz, 3H).

Example 9

3-Cyclopropyl-1-(3-(difluoromethyl)-2-(3,6-dihydro-2H-pyran-4-yl)quinolin-5-yl)-5,7-dimethyl-7,8-dihydroimidazo[1,5-a]pyrazin-6(5H)-one

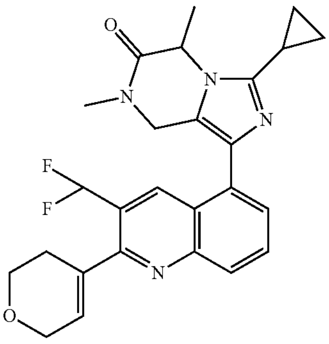 [SMILES: CC1C(=O)N(C)Cc2c(-c3cccc4nc(C5=CCOCC5)c(C(F)F)cc34)nc(C3CC3)n21]

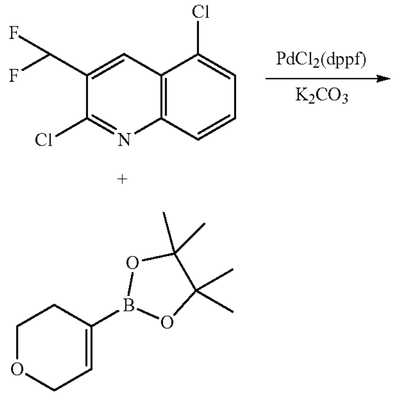

-continued

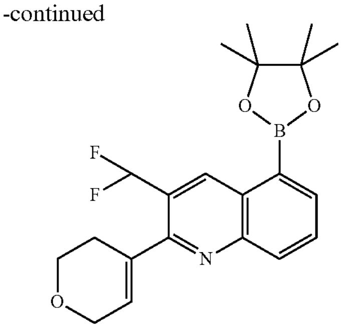

5-Chloro-3-(difluoromethyl)-2-(3,6-dihydro-2H-pyran-4-yl)quinoline

To a degassed solution of 2,5-dichloro-3-(difluoromethyl) quinoline (200 mg, 0.809 mmol) in 1,4-dioxane (2 mL) and $H_2O$ (0.5 mL) were added 2-(3,6-dihydro-2H-pyran-4-yl)-4,4,5,5-tetramethyl-1,3,2-dioxaborolane (170 mg, 0.806 mmol), $K_2CO_3$ (223 mg, 1.62 mmol), and $PdCl_2$(dppf) (66 mg, 0.081 mmol). The mixture was stirred at 100° C. for 2 h, then concentrated under reduced pressure. The residue was purified by $SiO_2$ gel chromatography (0% to 50% EtOAc in petroleum ether) to give the title compound as an off-white solid (140 mg, 59%). MS ($ES^+$) $C_{15}H_{12}ClF_2NO$ requires: 295, found: 296 $[M+H]^+$.

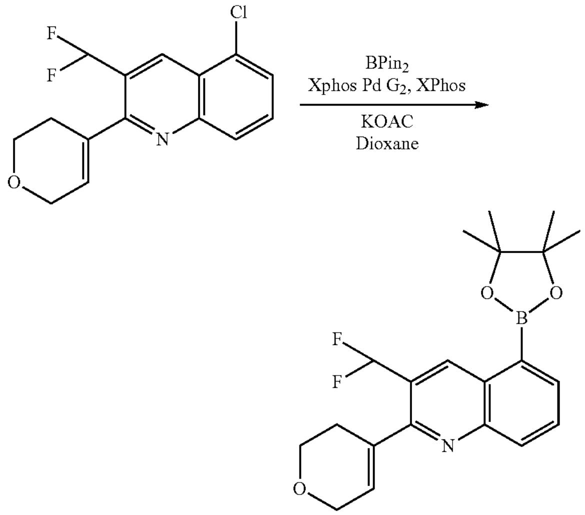

3-(Difluoromethyl)-2-(3,6-dihydro-2H-pyran-4-yl)-5-(4,4,5,5-tetramethyl-1,3,2-dioxaborolan-2-yl)quinoline To a degassed solution of the product from the previous step (140 mg, 0.475 mmol) in 1,4-dioxane (2 mL) were added $BPin_2$ (241 mg, 0.950 mmol), KOAc (92.2 mg, 0.950 mmol), XPhos Pd G2 (46.7 mg, 0.048 mmol), and XPhos (21.1 mg, 0.048 mmol). The mixture was stirred at 100° C. for 4 h, then concentrated under reduced pressure. The residue was purified by $SiO_2$ gel chromatography (0% to 50% EtOAc in petroleum ether) to give the title compound as an off-white solid (100 mg, 54%). MS ($ES^+$) $C_{21}H_{24}BF_2NO_3$ requires: 387, found: 388 $[M+H]^+$.

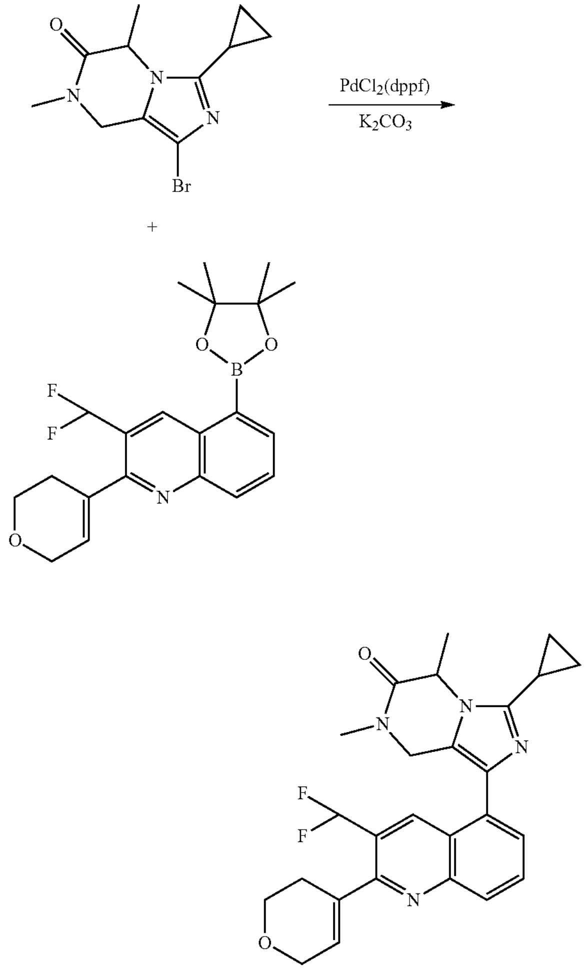

3-Cyclopropyl-1-(3-(difluoromethyl)-2-(3,6-dihydro-2H-pyran-4-yl)quinolin-5-yl)-5,7-dimethyl-7,8-dihydroimidazo[1,5-a]pyrazin-6(5H)-one To a degassed solution of the product from the previous step (100 mg, 0.258 mmol) in 1,4-dioxane (0.7 mL) and $H_2O$ (0.3 mL) were added Intermediate "B" (73.3 mg, 0.258 mmol), $K_2CO_3$ (71.8 mg, 0.516 mmol), and $PdCl_2$(dppf) (21.2 mg, 0.026 mmol). The mixture was stirred at 100° C. for 2 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as an off-white solid (25 mg, 0.054 mmol).

MS ($ES^+$) $C_{26}H_{26}F_2N_4O_2$ requires: 464, found: 465 $[M+H]^+$.

$^1$H NMR (500 MHz, DMSO-$d_6$) δ 9.56 (s, 1H), 8.06-7.95 (m, 1H), 7.93-7.82 (m, 1H), 7.55-7.43 (m, 1H), 7.30 (t, J=54.8 Hz, 1H), 6.03 (appar br s, 1H), 5.15 (q, J=7.0 Hz, 1H), 5.01 (d, J=16.0 Hz, 1H), 4.50 (d, J=16.0 Hz, 1H), 4.38-4.20 (m, 2H), 3.95-3.77 (m, 2H), 2.98 (s, 3H), 2.69-2.55 (m, 2H), 2.26-2.09 (m, 1H), 1.65 (d, J=7.1 Hz, 3H), 1.08-0.93 (m, 3H), 0.94-0.70 (m, 1H).

Example 10

3-Cyclopropyl-1-(3-(difluoromethyl)-2-(tetrahydro-2H-pyran-4-yl)quinolin-5-yl)-5,7-dimethyl-7,8-dihydroimidazo[1,5-a]pyrazin-6(5H)-one

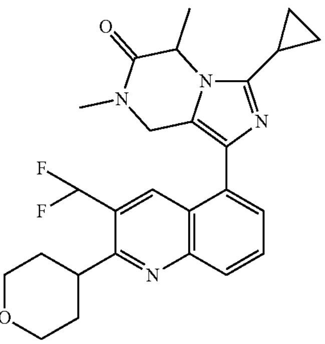

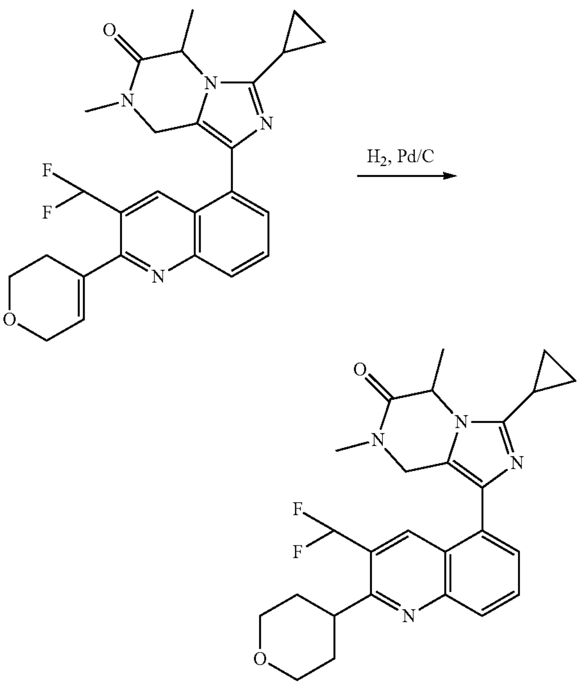

3-Cyclopropyl-1-(3-(difluoromethyl)-2-(tetrahydro-2H-pyran-4-yl)quinolin-5-yl)-5,7-dimethyl-7,8-dihydroimidazo[1,5-a]pyrazin-6(5H)-one To a degassed solution of 3-cyclopropyl-1-(3-(difluoromethyl)-2-(3,6-dihydro-2H-pyran-4-yl)quinolin-5-yl)-5,7-dimethyl-7,8-dihydroimidazo[1,5-a]pyrazin-6(5H)-one (180 mg, 0.388 mmol) in MeOH (10 mL) was added 10% Pd/C (200 mg), and the resulting mixture was stirred at RT under an atmosphere of $H_2$ (balloon) for 5 h. The mixture was filtered, and the filtrate concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as an off-white solid (25 mg, 14%).

MS ($ES^+$) $C_{26}H_{28}F_2N_4O_2$ requires: 466, found: 467 $[M+H]^+$.

$^1H$ NMR (500 MHz, DMSO-$d_6$) δ 9.32 (s, 1H), 7.96-7.92 (m, 1H), 7.89-7.80 (m, 1H), 7.61-7.39 (m, 2H), 5.14 (q, J=7.0 Hz, 1H), 4.98 (d, J=15.5 Hz, 1H), 4.45 (d, J=15.5 Hz, 1H), 4.04-3.93 (m, 2H), 3.53-3.49 (m, 1H), 2.97 (s, 3H), 2.21-2.11 (m, 1H), 2.12-1.98 (m, 2H), 1.79-1.68 (m, 3H), 1.64 (d, J=7.1 Hz, 3H), 1.11-0.93 (m, 4H), 0.92-0.76 (m, 1H).

Example 11

3-cyclopropyl-1-(3-(difluoromethyl)-2-(4-methyl-1H-imidazol-1-yl)quinolin-5-yl)-5,7-dimethyl-7,8-dihydroimidazo[1,5-a]pyrazin-6(5H)-one

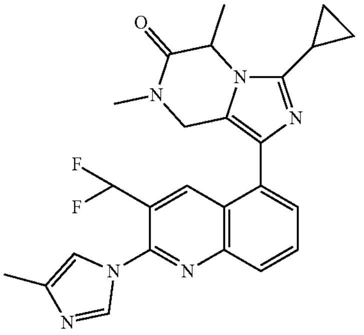 [SMILES: Cc1cn(-c2nc3cccc(-c4nc(C5CC5)n5c4CN(C)C(=O)C5C)c3cc2C(F)F)cn1]

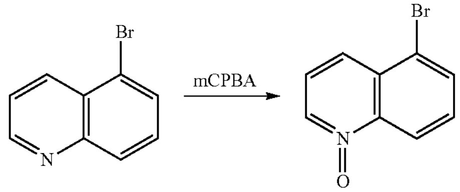

5-Bromoquinoline 1-oxide

To a solution of 5-bromoquinoline (7.5 g, 36 mmol) in DCM (150 mL) at 0° C. was added mCPBA (9.3 g, 54 mmol) slowly. The mixture was stirred at 0° C. for 3 h, then washed with 1.0 M aq. NaOH and concentrated under reduced pressure to give the title compound as a light yellow solid (6.5 g, 81%). MS ($ES^+$) $C_9H_6BrNO$ requires: 223, found: 224 $[M+H]^+$.

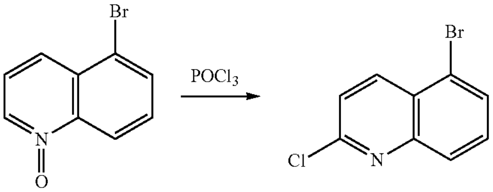

5-Bromo-2-chloroquinoline

To a solution of the product from the previous step (2.0 g, 10 mmol) in DCM (50 mL) was added $POCl_3$ (2 mL) carefully. The mixture was stirred at 45° C. for 4 h, then concentrated under reduced pressure. The residue was partitioned between EtOAc and water, and the organic layer was dried over $Na_2SO_4$, filtered and concentrated under reduced pressure. The residue was purified by $SiO_2$ gel chromatography (20% to 50% EtOAc in petroleum ether) to give the title compound (1.0 g, 37%). MS ($ES^+$) $C_9H_5BrClN$ requires: 241, found: 242 $[M+H]^+$.

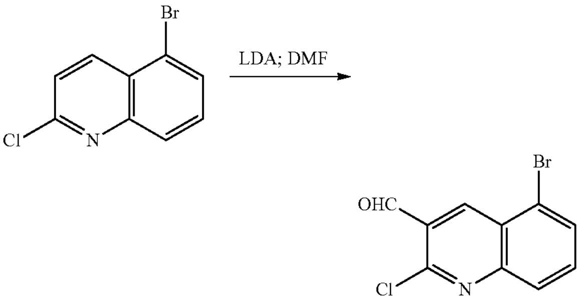

5-Bromo-2-chloroquinoline-3-carbaldehyde

To a solution of the product from the previous step (2.60 g, 10.7 mmol) in THF (25 mL) at −78° C. was added 2.0 M LDA in THF (10.7 mL, 21.4 mmol). The mixture was stirred for 1 h at −78° C., then treated with dry DMF (1.70 g, 23.2 mmol). The mixture was stirred at −78° C. for 1 h, then treated with sat. aq. $NH_4Cl$. The mixture was partitioned between EtOAc and water, and the organic layer was dried over $Na_2SO_4$, filtered and concentrated under reduced pressure. The residue was purified by $SiO_2$ gel chromatography (20% to 50% EtOAc in petroleum ether) to give the title compound (2.0 g, 65%) as a yellow solid. MS ($ES^+$) $C_{10}H_5BrClNO$ requires: 269, found: 270 $[M+H]^+$.

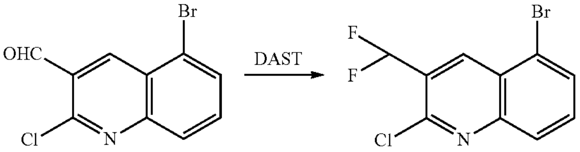

5-Bromo-2-chloro-3-(difluoromethyl)quinoline

To a solution of the product from the previous step (1.4 g, 5.1 mmol) in DCM (10 mL) was added DAST (1.66 g, 10.2 mmol). The mixture was stirred at RT for 3 h, then concentrated under reduced pressure. The residue was purified by $SiO_2$ gel chromatography (20% to 30% EtOAc in petroleum ether) to give the title compound as a yellow solid (1.0 g, 67%). MS ($ES^+$) $C_{10}H_5BrClF_2N$ requires: 291, found: 292 $[M+H]^+$.

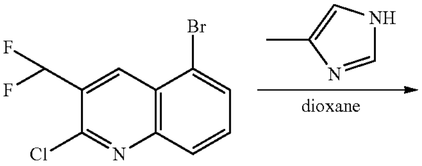

-continued

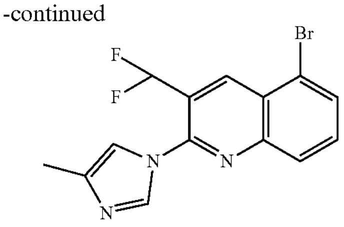

5-Bromo-3-(difluoromethyl)-2-(4-methyl-1H-imidazol-1-yl)quinoline

A mixture of the product from the previous step (150 mg, 0.515 mmol) and 4-methyl-1H-imidazole (1.55 mmol, 128 mg) in 1,4-dioxane (3 mL) was stirred at 105° C. overnight, then poured into water (30 mL) and extracted with $Et_2O$ (30 mL×3). The combined organic layers were dried over $Na_2SO_4$, filtered and concentrated under reduced pressure. The residue was purified by $SiO_2$ gel chromatography (40% to 60% EtOAc in petroleum ether) to give the title compound as a yellow solid (80 mg, 46%). MS ($ES^+$) $C_{14}H_{10}BrF_2N_3$ requires: 337, found: 338 $[M+H]^+$.

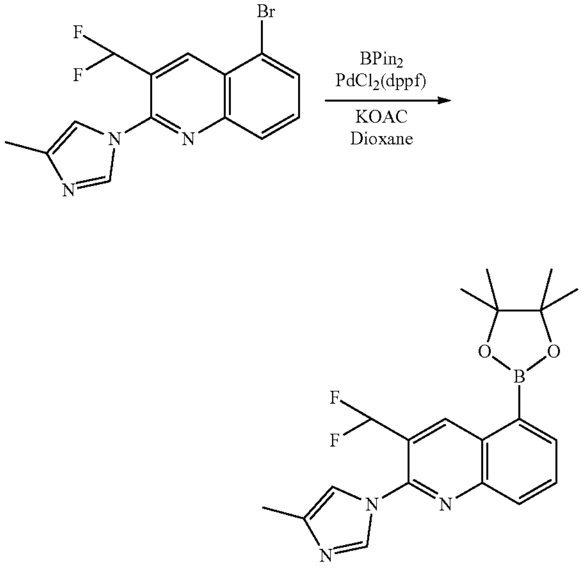

3-(Difluoromethyl)-2-(4-methyl-1H-imidazol-1-yl)-5-(4,4,5,5-tetramethyl-1,3,2-dioxaborolan-2-yl)quinoline A mixture of the product from the previous step (30 mg, 0.089 mmol), $PdCl_2$(dppf) (8 mg, 0.01 mmol), KOAc (27 mg, 0.27 mmol) and $BPin_2$ (34 mg, 0.13 mmol) in 1,4-dioxane (3 mL) was stirred at 95° C. for 2 h, then allowed to cool to RT and concentrated under reduced pressure. The residue was purified by $SiO_2$ gel chromatography (40% to 60% EtOAc in petroleum ether) to give the title compound as a yellow solid (26 mg, 76%). MS ($ES^+$): $C_{20}H_{22}BF_2N_3O_2$ requires: 385, found: 386 $[M+H]^+$.

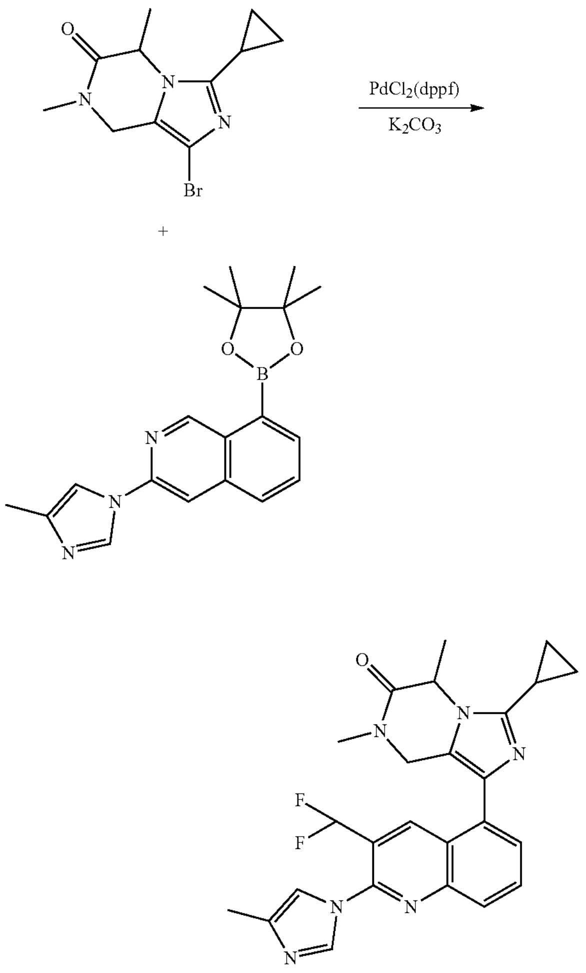

3-Cyclopropyl-1-(3-(difluoromethyl)-2-(4-methyl-1H-imidazol-1-yl)quinolin-5-yl)-5,7-dimethyl-7,8-dihydroimidazo[1,5-a]pyrazin-6(5H)-one A mixture of the product from the previous step (26 mg, 0.068 mmol), Intermediate "B" (23 mg, 0.068 mmol), $PdCl_2$ (dppf) (8 mg, 0.01 mmol), and $K_2CO_3$ (29 mg, 0.20 mmol) in 1,4-dioxane (3 mL) was degassed and purged with $N_2$. The mixture was stirred at 90° C. for 1.5 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a tan solid (3 mg, 10%).

MS ($ES^+$): $C_{25}H_{24}F_2N_6O$ requires: 462, found: 463 $[M+H]^+$.

$^1H$ NMR (500 MHz, $CDCl_3$) δ 9.50 (s, 1H), 8.04-8.02 (m, 2H), 7.87-7.84 (m, 1H), 7.47-7.45 (m, 1H), 7.26 (assumed overlap with solvent peak, 1H), 6.78 (t, J=54.0 Hz, 1H), 5.09 (q, J=7.0 Hz, 1H), 4.83 (d, J=15.5 Hz, 1H), 4.37 (d, J=15.5 Hz, 1H), 3.11 (s, 3H), 2.35 (s, 3H), 1.87-1.85 (m, 1H), 1.79 (d, J=7.5 Hz, 3H), 1.20-1.16 (m, 2H), 1.11-1.08 (m, 2H).

Example 12

3-cyclopropyl-1-(3-(difluoromethyl)-2-(4-methyl-1H-1,2,3-triazol-1-yl)quinolin-5-yl)-5,7-dimethyl-7,8-dihydroimidazo[1,5-a]pyrazin-6(5H)-one

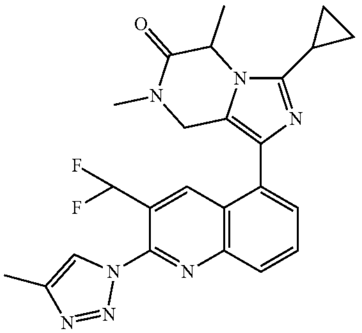 [SMILES: Cc1cn(-c2nc3cccc(-c4nc(C5CC5)n5c4CN(C)C(=O)C5C)c3cc2C(F)F)nn1]

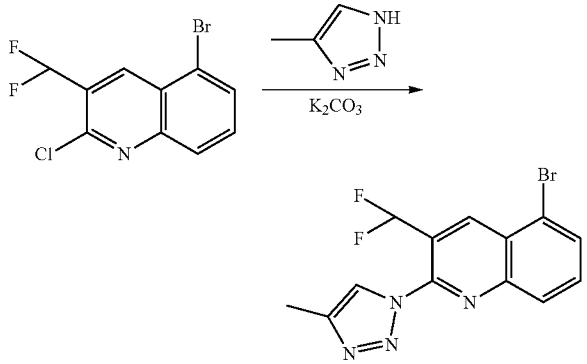

5-Bromo-3-(difluoromethyl)-2-(4-methyl-1H-1,2,3-triazol-1-yl)quinoline

To a mixture of 5-bromo-2-chloro-3-(difluoromethyl)quinoline (115 mg, 0.385 mmol) and 4-methyl-1H-1,2,3-triazole (99 mg, 1.2 mmol) in DMF (3 mL) was added $K_2CO_3$ (164 mg, 1.19 mmol). The mixture was heated at 80° C. overnight, then poured into water (30 mL) and extracted with $Et_2O$ (30 mL×3). The combined organic layers were dried over $Na_2SO_4$, filtered and concentrated under reduced pressure. The residue was purified by $SiO_2$ gel chromatography (60% to 90% EtOAc in petroleum ether) to give the title compound as a yellow solid (109 mg, 84%). MS ($ES^+$): $C_{13}H_9BrF_2N_4$ requires: 338, found: 339 $[M+H]^+$.

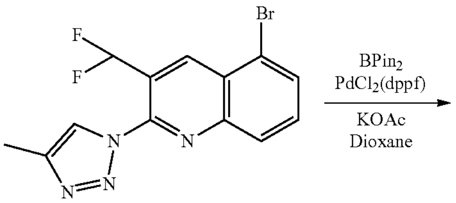

-continued

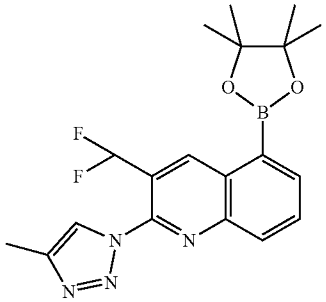

3-(Difluoromethyl)-2-(4-methyl-1H-1,2,3-triazol-1-yl)-5-(4,4,5,5-tetramethyl-1,3,2-dioxaborolan-2-yl)quinoline A mixture of the product from the previous step (30 mg, 0.089 mmol), $PdCl_2(dppf)$ (8 mg, 0.01 mmol), KOAc (27 mg, 0.27 mmol) and $BPin_2$ (34 mg, 0.13 mmol) in 1,4-dioxane (3 mL) was stirred at 95° C. for 2 h, then allowed to cool to RT and concentrated under reduced pressure. The residue was purified by $SiO_2$ gel chromatography (40% to 60% EtOAc in petroleum ether) to give the title compound as a yellow solid (26 mg, 76%). MS ($ES^+$): $C_{19}H_{21}BF_2N_4O_2$ requires: 386, found: 387 $[M+H]^+$.

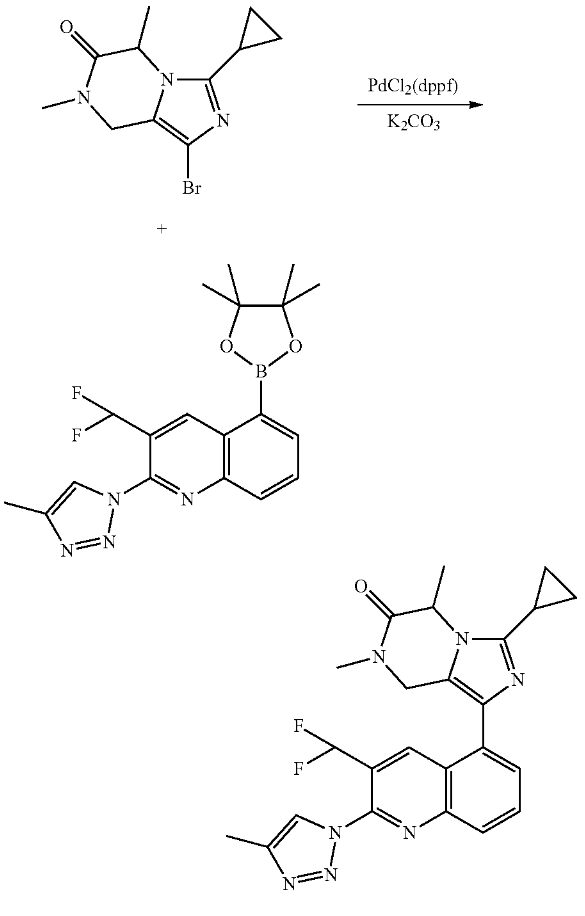

3-Cyclopropyl-1-(3-(difluoromethyl)-2-(4-methyl-1H-1,2,3-triazol-1-yl)quinolin-5-yl)-5,7-dimethyl-7,8-dihydroimidazo[1,5-a]pyrazin-6(5H)-one A mixture of the product from the previous step (26 mg, 0.068 mmol), Intermediate "B" (23 mg, 0.068 mmol), $PdCl_2$ (dppf) (8 mg, 0.01 mmol), and $K_2CO_3$ (29 mg, 0.20 mmol) in 1,4-dioxane (3 mL) was degassed and purged with $N_2$. The mixture was stirred at 90° C. for 1.5 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a tan solid (2 mg, 6%).

MS ($ES^+$): $C_{24}H23F_2N_7O$ requires 463, found: 464 $[M+H]^+$.

$^1H$ NMR (500 MHz, $CD_3OD$) δ 9.37 (s, 1H), 8.18 (d, J=8.5 Hz, 1H), 8.00-7.96 (m, 2H), 7.78-7.67 (m, 2H), 5.19 (q, J=7.3 Hz, 1H), 4.98 (d, J=16.0 Hz, 1H), 4.51 (d, J=16.0 Hz, 1H), 3.10 (s, 3H), 2.52 (s, 3H), 2.16-2.13 (m, 1H), 1.80 (d, J=7.0 Hz, 3H), 1.15-1.09 (m, 4H).

Example 13

3-Cyclopropyl-5,7-dimethyl-1-(3-(2-methylthiazol-5-yl)isoquinolin-8-yl)-7,8-dihydroimidazo[1,5-a]pyrazin-6(5H)-one

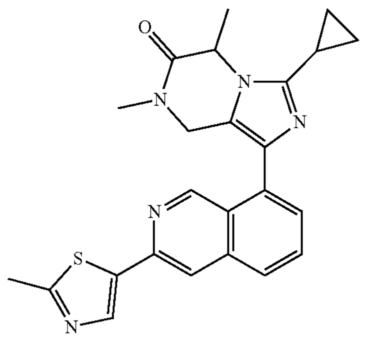 [SMILES: Cc1ncc(-c2cc3cccc(-c4nc(C5CC5)n5c4CN(C)C(=O)C5C)c3cn2)s1]

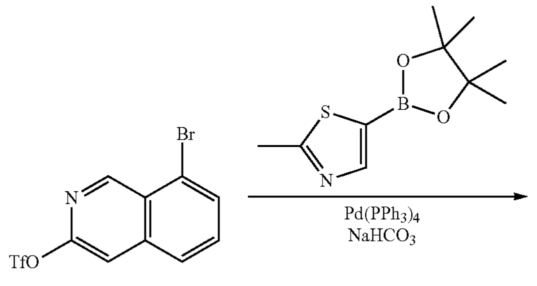

-continued

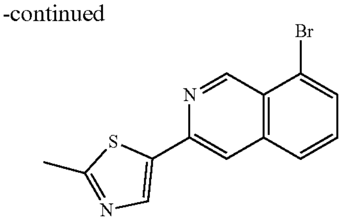

5-(8-Bromoisoquinolin-3-yl)-2-methylthiazole

A mixture of 8-bromoisoquinolin-3-yl trifluoromethanesulfonate (0.90 g, 2.5 mmol), 2-methyl-5-(4,4,5,5-tetramethyl-1,3,2-dioxaborolan-2-yl)thiazole (0.57 g, 2.5 mmol), $NaHCO_3$(0.63 g, 7.5 mmol) and $Pd(PPh_3)_4$(280 mg, 0.25 mmol) in $THF/H_2O$ (20 mL/4 mL) was degassed and purged with $N_2$, then stirred at 50° C. overnight. The mixture was concentrated under reduced pressure, and the residue was purified by $SiO_2$ gel chromatography (0% to 50% EtOAc in petroleum ether) to give the title compound as a yellow solid (450 mg, 60%). MS ($ES^+$): $C_{13}H_9BrN_2S$ requires: 304, found: 305 $[M+H]^+$.

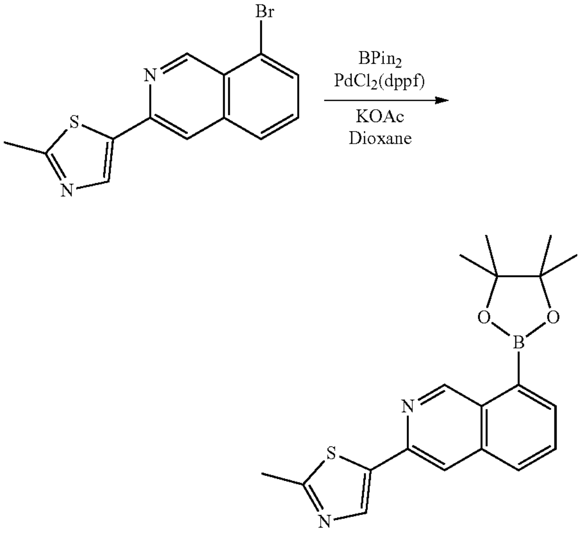

2-Methyl-5-(8-(4,4,5,5-tetramethyl-1,3,2-dioxaborolan-2-yl)isoquinolin-3-yl)thiazole To a mixture of the product from the previous step (450 mg, 1.48 mmol), $BPin_2$ (450 mg, 1.78 mmol) and KOAc (435 mg, 4.44 mmol) in 1,4-dioxane (20 mL) was added $PdCl_2$(dppf) (120 mg, 0.15 mmol). The resulting mixture was purged with $N_2$ for 5 min, then sealed and stirred at 100° C. overnight. The mixture was concentrated under reduced pressure, and the residue was purified by $SiO_2$ gel chromatography (0% to 100% EtOAc in petroleum ether) to give the title compound as a yellow solid (400 mg, 76%). MS ($ES^+$): $C_{19}H_{21}BN_2O_2S$ requires: 352, found: 353 $[M+H]^+$.

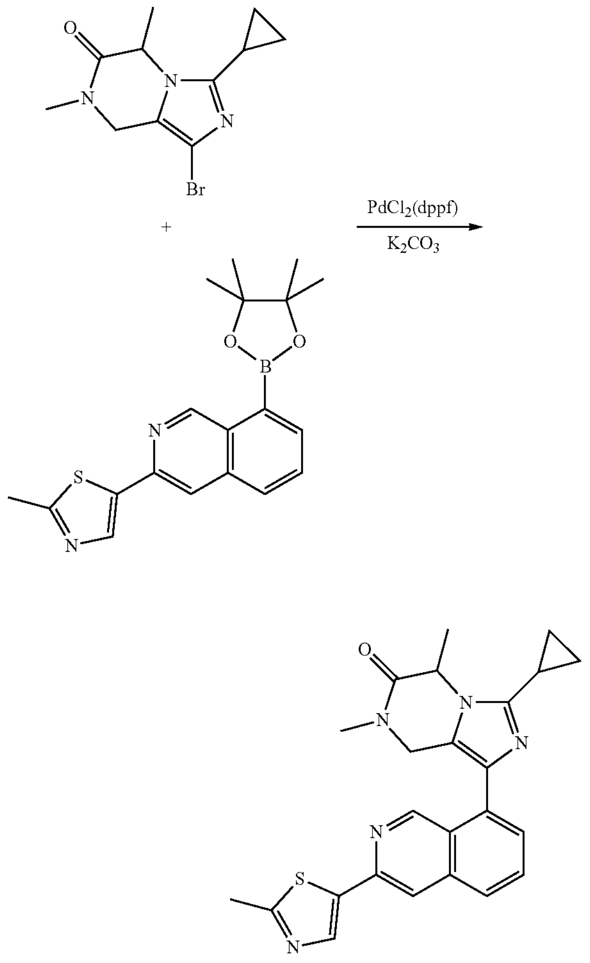

3-Cyclopropyl-5,7-dimethyl-1-(3-(2-methylthiazol-5-yl)isoquinolin-8-yl)-7,8-dihydroimidazo[1,5-a]pyrazin-6(5H)-one A mixture of Intermediate "B" (40 mg, 0.14 mmol), the product from the previous step (50 mg, 0.14 mmol), $K_2CO_3$ (58 mg, 0.42 mmol) and $PdCl_2$(dppf) (11 mg, 0.014 mmol) in 1,4-dioxane/$H_2O$ (2 mL/0.4 mL) was degassed and purged with $N_2$. The mixture was stirred at 100° C. for 2 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a white solid (11 mg, 18%).

MS ($ES^+$): $C_{24}H_{23}N_5OS$ requires: 429, found: 430 $[M+H]^+$.

$^1H$ NMR (500 MHz, MeOD) δ 9.21 (s, 1H), 8.39 (s, 1H), 8.35 (s, 1H), 8.20 (d, J=8.4 Hz, 1H), 7.94 (dd, J=8.3, 7.2 Hz, 1H), 7.81-7.74 (m, 1H), 5.36 (q, J=7.2 Hz, 1H), 4.94 (d, J=16.5 Hz, 1H), 4.49 (d, J=16.3 Hz, 1H), 3.09 (s, 3H), 2.79 (s, 3H), 2.48-2.44 (m, 1H), 1.90 (d, J=7.2 Hz, 3H), 1.46-1.43 (m, 2H), 1.39-1.22 (m, 2H).

Example 14

3-Cyclopropyl-5,7-dimethyl-1-(3-(4-methyl-1H-pyrazol-1-yl)isoquinolin-8-yl)-7,8-dihydroimidazo[1,5-a]pyrazin-6(5H)-one

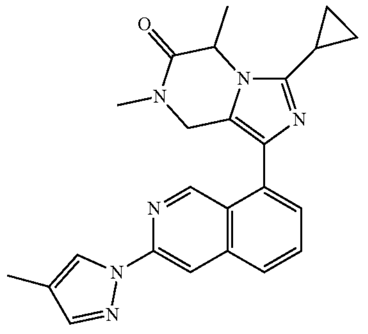 [SMILES: Cc1cnn(-c2cc3cccc(-c4nc(C5CC5)n5c4CN(C)C(=O)C5C)c3cn2)c1]

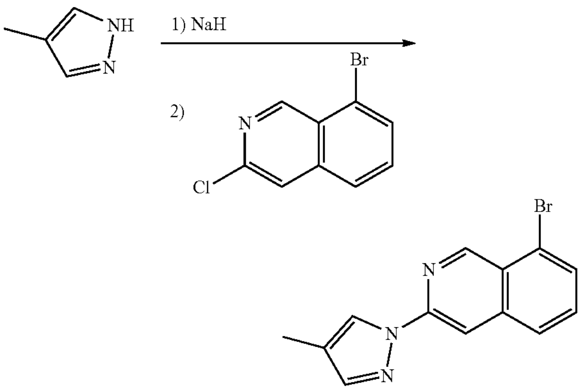

8-Bromo-3-(4-methyl-1H-pyrazol-1-yl)isoquinoline

To a suspension of NaH (60% in mineral oil, 94.01 mg, 2.35 mmol) in DMF (5 mL) was added 4-methyl-1H-pyrazole (203.14 mg, 2.47 mmol). The mixture was stirred at RT for 2 h, then treated with 8-bromo-3-chloroisoquinoline (300 mg, 1.24 mmol) in DMF (3 mL). The mixture was stirred at 90° C. overnight, then allowed to cool to RT and treated with sat. aq. $NH_4Cl$. The mixture was extracted with EtOAc (25 mL×4), and the combined organic layers were washed with sat. aq. NaCl (25 mL×3), dried over $Na_2SO_4$, filtered and concentrated under reduced pressure. The residue was purified by $SiO_2$ gel chromatography (0% to 25% EtOAc in petroleum ether) to give the title compound as a white solid (120 mg, 34%). MS ($ES^+$): $C_{13}H_{10}BrN_3$ requires: 287, found: 288 $[M+H]^+$.

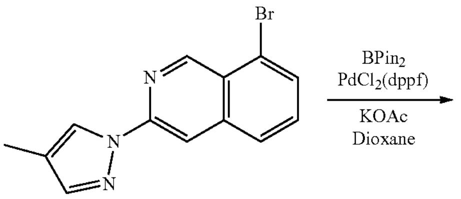

-continued

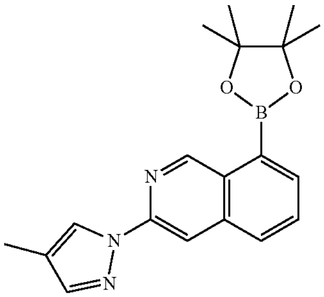

3-(4-methyl-1H-pyrazol-1-yl)-8-(4,4,5,5-tetramethyl-1,3,2-dioxaborolan-2-yl)isoquinoline 3-(4-Methyl-1H-pyrazol-1-yl)-8-(4,4,5,5-tetramethyl-1,3,2-dioxaborolan-2-yl)isoquinoline To a mixture of the product from the previous step (120 mg, 415 μmol), $BPin_2$ (322.64 mg, 1.25 mmol) and KOAc (123.44 mg, 1.25 mmol) in 1,4-dioxane (10 mL) was added $PdCl_2$(dppf) (34.59 mg, 41.50 μmol). The mixture was stirred at 90° C., then concentrated under reduced pressure. The residue was purified by $SiO_2$ gel chromatography (0% to 20% EtOAc in petroleum ether) to give the title compound as a brown oil (139 mg, 100%). MS ($ES^+$): $C_{18}H_{21}BN_4O_2$ requires: 336, found: 337 $[M+H]^+$.

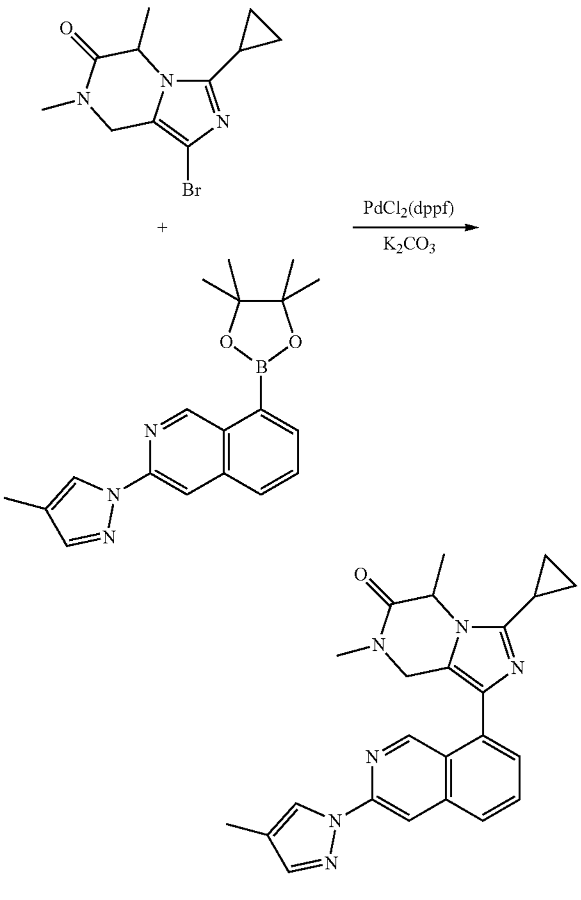

3-Cyclopropyl-5,7-dimethyl-1-(3-(4-methyl-1H-pyrazol-1-yl)isoquinolin-8-yl)-7,8-dihydroimidazo[1,5-a]pyrazin-6(5H)-one A mixture of Intermediate "B" (90.0 mg; 317 μmol), the product from the previous step (138.02 mg, 411.75 μmol), 2.0 M aq. $K_2CO_3$ (0.475 mL, 950 moles) and $PdCl_2$(dppf) (31.67 μmoles; 26.39 mg) in DMF (5 mL) was degassed and purged with $N_2$. The mixture was stirred at 100° C. for 90 min, then concentrated under reduced pressure. The residue was purified by $SiO_2$ gel chromatography (0% to 10% MeOH in EtOAc) to give the title compound as a light yellow solid (39 mg, 30%).

MS ($ES^+$): $C_{24}H_{24}N_6O$ requires: 412, found: 413 $[M+H]^+$.

$^1$H NMR (500 MHz, $CD_3OD$) δ 9.47 (s, 1H), 8.46 (s, 1H), 8.21 (s, 1H), 7.98 (d, J=8.3 Hz, 1H), 7.87-7.76 (m, 1H), 7.65 (s, 1H), 7.52 (d, J=7.0 Hz, 1H), 5.18 (q, J=7.3 Hz, 1H), 4.96 (d, J=15.8 Hz, 1H), 4.45 (d, J=15.8 Hz, 1H), 3.09 (s, 3H), 2.22 (s, 3H), 2.18-2.07 (m, 1H), 1.80 (d, J=7.1 Hz, 3H), 1.17-1.03 (m, 4H).

Examples 15a/15b 5,7-dimethyl-3-(tetrahydro-2H-pyran-4-yl)-1-(3-(tetrahydro-2H-pyran-4-yl)isoquinolin-8-yl)-7,8-dihydroimidazo[1,5-a]pyrazin-6(5H)-one (separated enantiomers)

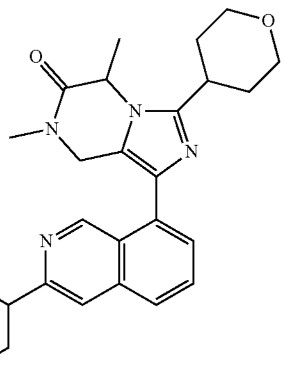

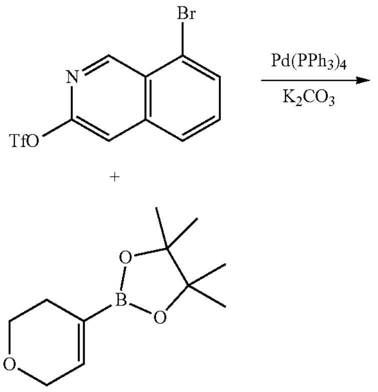

-continued

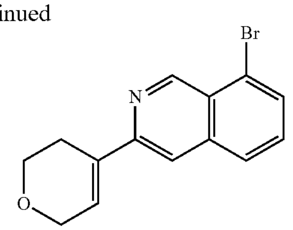

8-Bromo-3-(3,6-dihydro-2H-pyran-4-yl)isoquinoline

A mixture of 8-bromoisoquinolin-3-yl trifluoromethanesulfonate (3.0 g, 8.4 mmol), 2-(3,6-dihydro-2H-pyran-4-yl)-4,4,5,5-tetramethyl-1,3,2-dioxaborolane (1.77 g, 8.45 mmol), $NaHCO_3$(2.1 g, 25 mmol) and $Pd(PPh_3)_4$(920 mg, 0.80 mmol) in 1,4-dioxane/$H_2O$ (20 mL/4 mL) was degassed and purged with $N_2$. The mixture was stirred at 50° C. overnight, then concentrated under reduced pressure. The residue was purified by $SiO_2$ gel chromatography (0% to 50% EtOAc in petroleum ether) to give the title compound as a yellow solid (1.4 g, 57%). MS ($ES^+$): $C_{14}H_{12}BrNO$ requires: 289, found: 290 $[M+H]^+$.

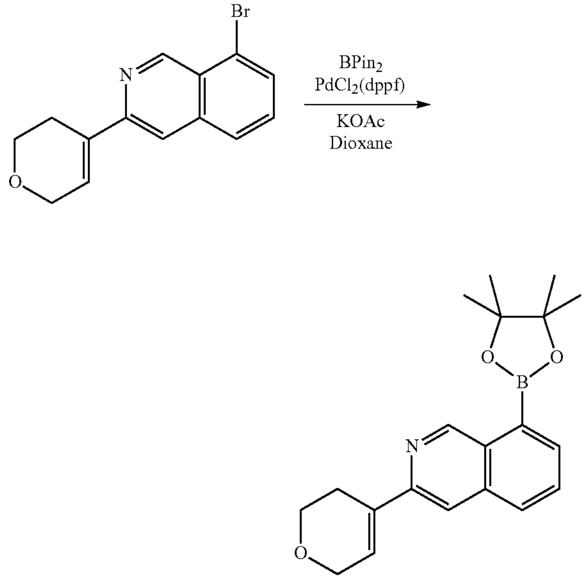

3-(3,6-Dihydro-2H-pyran-4-yl)-8-(4,4,5,5-tetramethyl-1,3,2-dioxaborolan-2-yl)isoquinoline To a mixture of the product from the previous step (1.4 g, 4.8 mmol), $BPin_2$ (1.5 g, 5.8 mmol) and KOAc (1.40 g, 14.4 mmol) in 1,4-dioxane (20 mL) was added $PdCl_2$(dppf) (400 mg, 0.5 mmol). The resulting mixture was purged with $N_2$ for 5 min, then sealed and heated at 100° C. for 5 h. The mixture was concentrated under reduced pressure, and the residue was purified by $SiO_2$ gel chromatography (0% to 60% EtOAc in petroleum ether) to give the title compound as a yellow solid (1.0 g, 62%). MS ($ES^+$): $C_{20}H_{24}BNO_3$ requires: 337, found: 338 $[M+H]^+$.

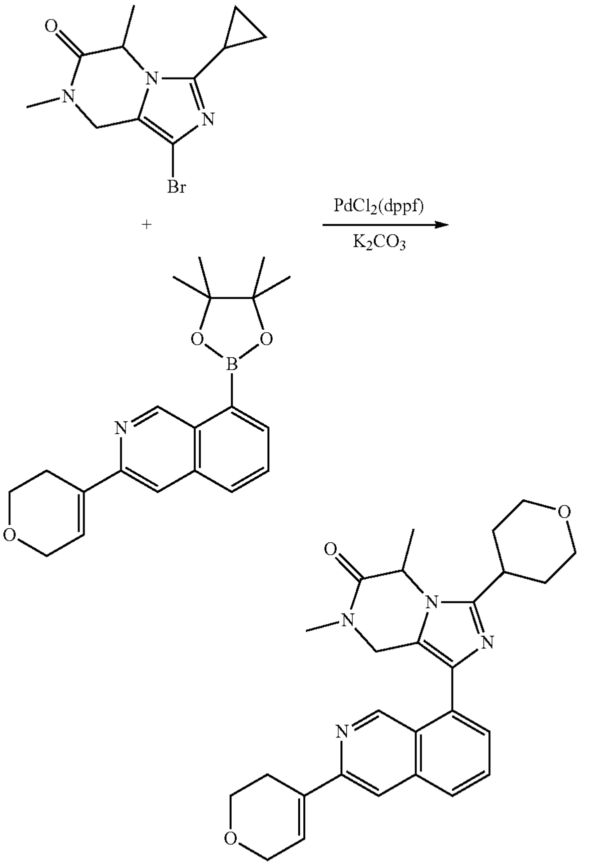

1-(3-(3,6-Dihydro-2H-pyran-4-yl)isoquinolin-8-yl)-5,7-dimethyl-3-(tetrahydro-2H-pyran-4-yl)-7,8-dihydroimidazo[1,5-a]pyrazin-6(5H)-one A mixture of Intermediate "B" (200.0 mg; 609.4 μmol), the product from the previous step (267.14 mg, 792.18 moles), 2.0 M aq. $K_2CO_3$ (0.914 mL, 1.83 mmol) and $PdCl_2$(dppf) (50.78 mg, 60.94 μmol) in DMF (6 mL) was degassed and purged with $N_2$. The mixture was stirred at 100° C. for 90 min, then concentrated under reduced pressure. The residue was purified by $SiO_2$ gel chromatography (25% to 100% EtOAc in petroleum ether) to give the title compound as a light yellow solid (161 mg, 58%). MS ($ES^+$): $C_{25}H_{26}N_6OS$ requires: 458, found: 459 $[M+H]^+$.

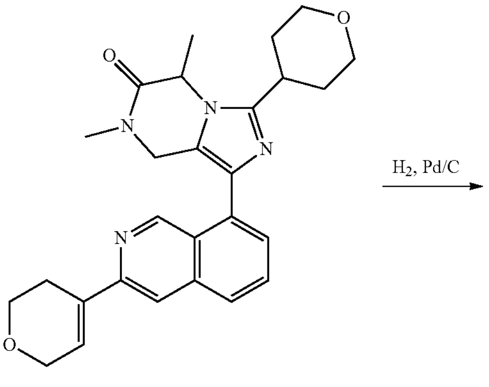

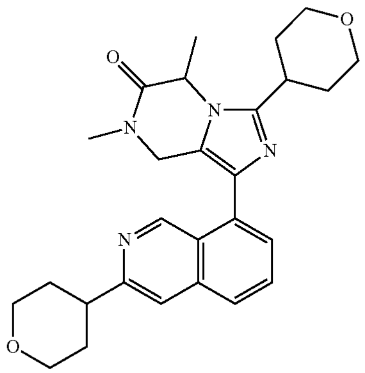 [SMILES: CC1C(=O)N(C)Cc2c(-c3cccc4cc(C5CCOCC5)ncc34)nc(C3CCOCC3)n21]

5,7-dimethyl-3-(tetrahydro-2H-pyran-4-yl)-1-(3-(tetrahydro-2H-pyran-4-yl)isoquinolin-8-yl)-7,8-dihydroimidazo[1,5-a]pyrazin-6(5H)-one (with separation of enantiomers)

A mixture of the product from the previous step (161 mg, 351 μmol) and 10% Pd/C (80 mg) in EtOH (50 mL) was stirred at RT under an atmosphere of $H_2$ (balloon). The mixture was filtered, and the filtrate concentrated under reduced pressure. The residue was purified by reverse phase preparative HPLC (Mobile phase: A=10 mM $NH_4HCO_3$/$H_2O$, B=MeCN; Gradient: B=10% to 45% in 18 min; Column: C18) to give the title racemic compound as a white solid. The racemate was separated by chiral HPLC [Instrument: SFC-80 (Thar, Waters); Column: OJ 20*250 mm, 10 um (Daicel); Column temperature: 35° C.; Mobile phase: $CO_2$/EtOH(1% 7 M ammonia in MeOH)=75/25; Flow rate: 80 g/min] to give two isomers.

Example 15a was isolated as a yellow solid (39 mg, 39%). RT=3.89 min.

MS ($ES^+$): $C_{27}H_{32}N_4O_3$ requires: 460, found: 461 $[M+H]^+$.

$^1$H NMR (500 MHz, MeOD) δ 9.56 (s, 1H), 7.94 (d, J=8.3 Hz, 1H), 7.86-7.77 (m, 1H), 7.74 (s, 1H), 7.57 (d, J=7.0 Hz, 1H), 5.12 (q, J=7.0 Hz, 1H), 4.94 (d, J=15.9 Hz, 1H), 4.43 (d, J=15.9 Hz, 1H), 4.19-4.00 (m, 4H), 3.66 (appar t, J=11.1 Hz, 4H), 3.25-3.10 (m, 2H), 3.06 (s, 3H), 2.21-2.06 (m, 2H), 2.03-1.82 (m, 6H), 1.74 (d, J=7.1 Hz, 3H).

Example 15b was isolated as a yellow solid (38 mg, 38%). RT=6.03 min.

MS ($ES^+$): $C_{27}H_{32}N_4O_3$ requires: 460, found: 461 $[M+H]^+$.

$^1$H NMR (500 MHz, MeOD) δ 9.45 (s, 1H), 7.82 (d, J=8.3 Hz, 1H), 7.74-7.67 (m, 1H), 7.64 (s, 1H), 7.54-7.35 (m, 1H), 5.00 (q, J=7.1 Hz, 1H), 4.82 (d, J=13.6 Hz, 1H), 4.31 (d, J=15.9 Hz, 1H), 4.08-3.84 (m, 4H), 3.54 (appar t, J=11.4 Hz, 4H), 3.17-2.97 (m, 2H), 2.94 (s, 3H), 2.07-1.91 (m, 2H), 1.93-1.71 (m, 6H), 1.61 (d, J=7.1 Hz, 3H).

Examples 16a/16b 5,7-Dimethyl-1-(3-morpholinoisoquinolin-8-yl)-3-(tetrahydro-2H-pyran-4-yl)-7,8-dihydroimidazo[1,5-a]pyrazin-6(5H)-one (separated enantiomers)

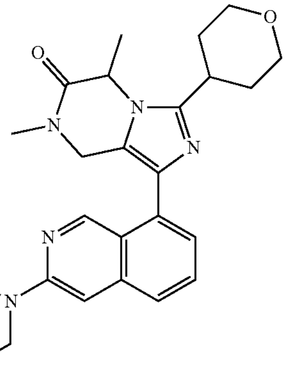

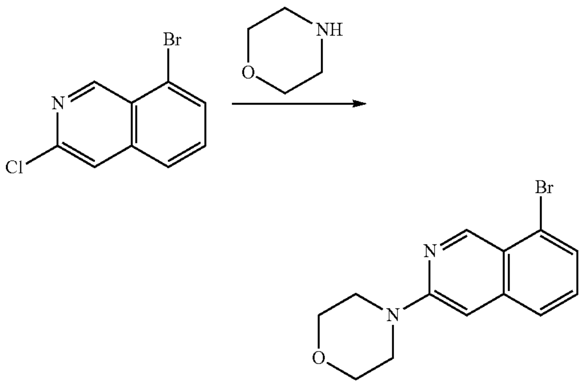

4-(8-Bromoisoquinolin-3-yl)morpholine

A solution of 8-bromo-3-chloroisoquinoline (400 mg, 1.65 mmol) and morpholine (3 mL) in DMSO (5 mL) was stirred at 150° C. for 1 h in a microwave reactor, then allowed to cool to RT. The mixture was diluted with EtOAc (90 mL), washed with sat. aq. NaCl (25 mL×3), dried over $Na_2SO_4$, filtered and concentrated under reduced pressure. The residue was purified by $SiO_2$ gel chromatography (0% to 45% EtOAc in petroleum ether) to give the title compound as a yellow solid (325 mg, 67%). MS ($ES^+$): $C_{13}H_{13}BrN_2O$ requires: 292, found: 293 $[M+H]^+$.

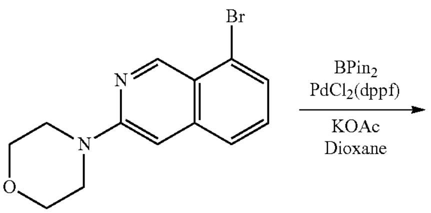

-continued

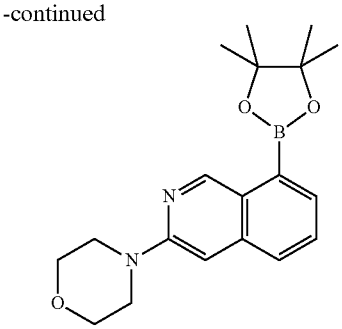

4-(8-(4,4,5,5-Tetramethyl-1,3,2-dioxaborolan-2-yl)isoquinolin-3-yl)morpholine

To a mixture of the product from the previous step (50.0 mg, 171 μmol), $BPin_2$ (110.49 mg, 426.38 μmol) and KOAc (50.73 mg, 511.7 μmol) in 1,4-dioxane (3 mL) was added $PdCl_2$(dppf) (14.21 mg, 17.06 μmol). The mixture was stirred at 90° C. for 3 h, then concentrated under reduced pressure. The residue was purified by $SiO_2$ gel chromatography (0% to 20% EtOAc in petroleum ether) to give the title compound as a yellow solid (58 mg, 100%). MS ($ES^+$): $C_{19}H_{25}BN_2O_3$ requires: 340, found: 341 $[M+H]^+$.

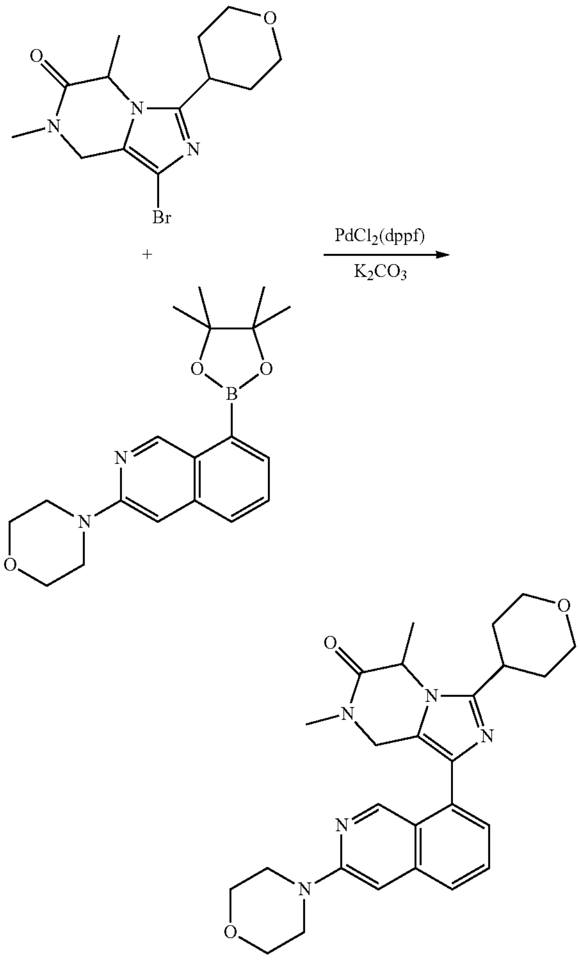

5,7-Dimethyl-1-(3-morpholinoisoquinolin-8-yl)-3-(tetrahydro-2H-pyran-4-yl)-7,8-dihydroimidazo[1,5-a]pyrazin-6(5H)-one (separated enantiomers)

A mixture of Intermediate "B" (160 mg, 487 μmol), the product from the previous step (248.79 mg, 731.24 μmol), 2.0 M aq. $K_2CO_3$ (0.731 mL, 1.46 mmol) and $PdCl_2$(dppf) (40.62 mg, 48.75 μmol) in DMF (6 mL) was degassed and purged with $N_2$. The mixture was stirred at 100° C. for 90 min, then concentrated under reduced pressure. The residue was purified by $SiO_2$ gel chromatography (25% to 100% EtOAc in petroleum ether) to give the title racemic compound as a light yellow solid (95 mg, 42%). The racemate was separated by SFC [Conditions: Instrument: SFC-80 (Thar, Waters); Column: OJ 20*250 mm, 10 um (Daicel); Column temperature: 35° C.; Mobile phase: $CO_2$/MeOH (0.2% 7 M ammonia in MeOH)=45/55; Flow rate: 80 g/min] to give two isomers.

Example 16a was isolated as a white solid (31 mg, 33%). RT=1.25 min.

MS ($ES^+$): $C_{26}H_{31}N_5O_3$ requires: 461, found: 462 $[M+H]^+$.

$^1H$ NMR (500 MHz, $CD_3OD$) δ 9.26 (s, 1H), 7.73 (d, J=8.4 Hz, 1H), 7.67-7.56 (m, 1H), 7.26 (d, J=6.9 Hz, 1H), 7.04 (s, 1H), 5.10 (q, J=7.0 Hz, 1H), 4.93 (d, J=15.8 Hz, 1H), 4.40 (d, J=15.8 Hz, 1H), 4.09-4.06 (m, 2H), 3.94-3.83 (m, 4H), 3.68-3.63 (m, 2H), 3.56-3.53 (m, 4H), 3.23-3.14 (m, 1H), 3.06 (s, 3H), 2.18-2.05 (m, 2H), 1.89-1.84 (m, 2H), 1.72 (d, J=7.1 Hz, 3H).

Example 16b was isolated as a white solid (35 mg, 37%). RT=2.38 min.

MS ($ES^+$): $C_{26}H_{31}N_5O_3$ requires: 461, found: 462 $[M+H]^+$.

$^1H$ NMR (500 MHz, $CD_3OD$) δ 9.14 (s, 1H), 7.60 (d, J=8.4 Hz, 1H), 7.50 (dd, J=8.3, 7.0 Hz, 1H), 7.14 (d, J=6.7 Hz, 1H), 6.91 (s, 1H), 4.98 (q, J=7.1 Hz, 1H), 4.80 (d, J=15.9 Hz, 1H), 4.28 (d, J=15.9 Hz, 1H), 3.97-3.94 (m, 2H), 3.83-3.70 (m, 4H), 3.55-3.51 (m, 2H), 3.43-3.41 (m, 4H), 3.10-3.07 (m, 1H), 2.94 (s, 3H), 2.08-1.89 (m, 2H), 1.79-1.74 (m, 2H), 1.60 (d, J=7.1 Hz, 3H).

Example 17

1-(3-(2H-Tetrazol-5-yl)isoquinolin-8-yl)-3-cyclopropyl-5,7-dimethyl-7,8-dihydroimidazo[1,5-a]pyrazin-6(5H)-one

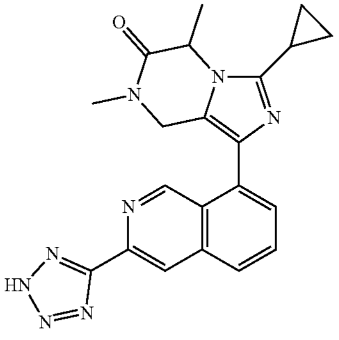 [SMILES: CC1C(=O)N(C)Cc2c(-c3cccc4cc(-c5nn[nH]n5)ncc34)nc(C3CC3)n21]

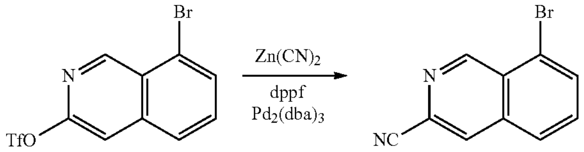

8-Bromoisoquinoline-3-carbonitrile

A mixture of 8-bromoisoquinolin-3-yl trifluoromethanesulfonate (500 mg, 1.4 mmol), $Zn(CN)_2$ (330 mg, 2.8 mmol), dppf (155 mg, 0.28 mmol) and $Pd_2(dba)_3$ (128 mg, 0.14 mmol) in dry DMF (5 mL) was degassed and purged with $N_2$. The mixture was stirred at RT overnight, then concentrated under reduced pressure. The residue was purified by $SiO_2$ gel chromatography (0% to 50% EtOAc in petroleum ether) to give the title compound as a white solid (100 mg, 30%). MS ($ES^+$): $C_{10}H_5BrN_2$ requires: 232, found: 233 $[M+H]^+$.

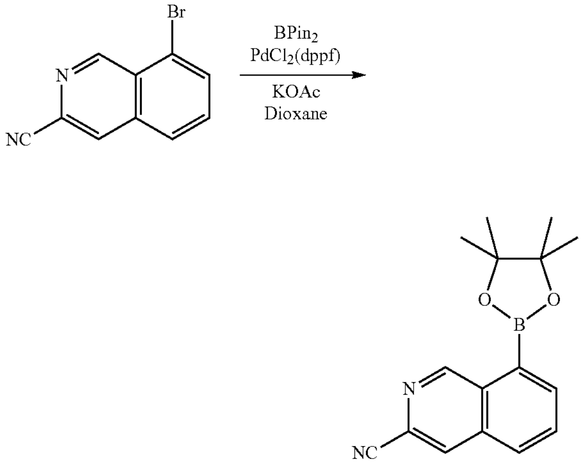

8-(4,4,5,5-Tetramethyl-1,3,2-dioxaborolan-2-yl)isoquinoline-3-carbonitrile

To a mixture of the product from the previous step (100 mg, 0.43 mmol), $BPin_2$ (130 mg, 0.52 mmol) and KOAc (126 mg, 1.29 mmol) in dry 1,4-dioxane (4 mL) was added $PdCl_2(dppf)$ (35 mg, 0.043 mmol). The resulting mixture was purged with $N_2$ for 5 min, then sealed and stirred at 100° C. for 5 h. The mixture was concentrated under reduced pressure, and the residue was purified by $SiO_2$ gel chromatography (0% to 60% EtOAc in petroleum ether) to give the title compound as a tan solid (80 mg, 66%). MS ($ES^+$): $C_{16}H_{17}BN_2O_2$ requires: 280, found: 281 $[M+H]^+$.

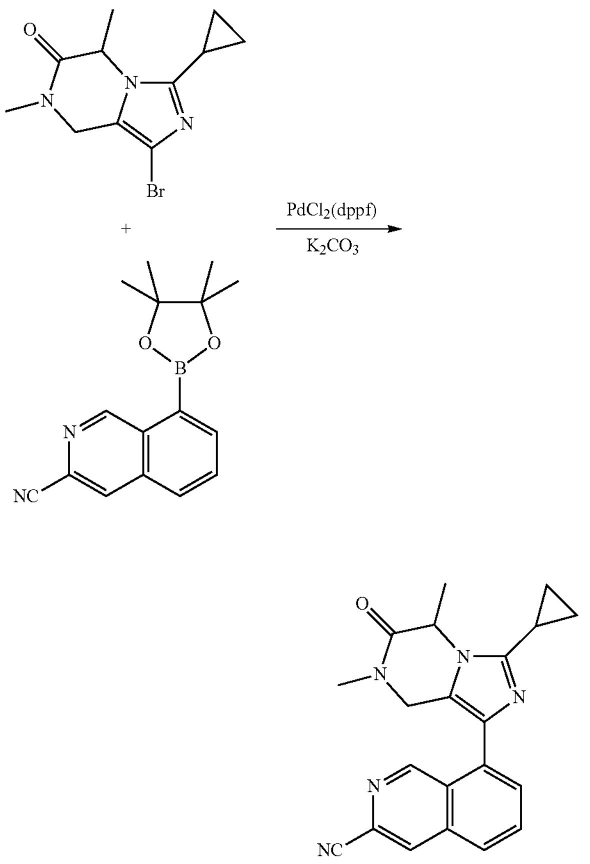

8-(3-Cyclopropyl-5,7-dimethyl-6-oxo-5,6,7,8-tetrahydroimidazo[1,5-al]pyrazin-1-yl)isoquinoline-3-carbonitrile A mixture of Intermediate "B" (75 mg, 0.26 mmol), the product from the previous step (80 mg, 0.28 mmol), $K_2CO_3$ (107 mg, 0.78 mmol) and $PdCl_2(dppf)$ (22 mg, 0.028 mmol) in 1,4-dioxane/$H_2O$ (2 mL/0.4 mL) was degassed and purged with $N_2$. The mixture was stirred at 85° C. for 2 h, then concentrated under reduced pressure. The residue was purified by $SiO_2$ gel chromatography (10% to 80% EtOAc in petroleum ether) to give the title compound as a tan solid (35 mg, 34%). MS ($ES^+$): $C_{21}H_{19}N_5O$ requires: 357, found: 358 $[M+H]^+$.

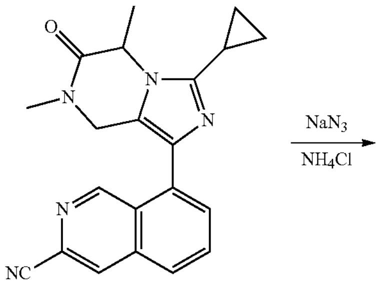

-continued

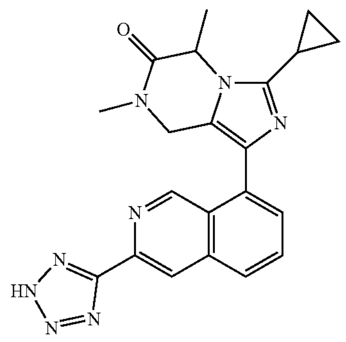

1-(3-(2H-Tetrazol-5-yl)isoquinolin-8-yl)-3-cyclopropyl-5,7-dimethyl-7,8-dihydroimidazo[1,5-a]pyrazin-6(5H)-one A mixture of the product from the previous step (35 mg, 0.1 mmol), $NaN_3$ (32 mg, 0.5 mmol) and $NH_4Cl$ (27 mg, 0.5 mmol) in dry DMF (1 mL) was degassed and purged with $N_2$. The mixture was heated at 120° C. overnight, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a yellow solid (13 mg, 32%).

MS ($ES^+$): $C_{21}H_{20}N_8O$ requires: 400, found: 401 $[M+H]^+$.

$^1$H NMR (500 MHz, DMSO-$d_6$) δ 10.16 (s, 1H), 8.74 (s, 1H), 8.14 (d, J=8.2 Hz, 1H), 7.95-7.84 (m, 1H), 7.59 (d, J=6.8 Hz, 1H), 5.17 (q, J=7.1 Hz, 1H), 5.04 (d, J=15.9 Hz, 1H), 4.53 (d, J=15.8 Hz, 1H), 2.98 (s, 3H), 2.23-2.20 (m, 1H), 1.66 (d, J=7.1 Hz, 3H), 1.07-1.02 (m, 3H), 0.90-0.88 (m, 1H).

Example 18

3-(Azetidin-3-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one

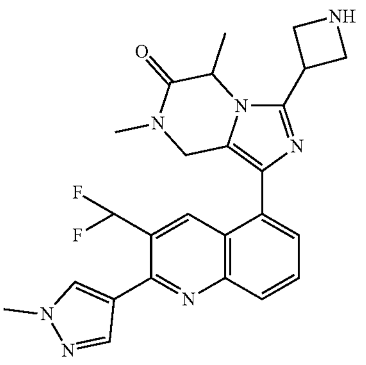 [SMILES: CC1C(=O)N(C)Cc2c(-c3cccc4nc(-c5cnn(C)c5)c(C(F)F)cc34)nc(C3CNC3)n21]

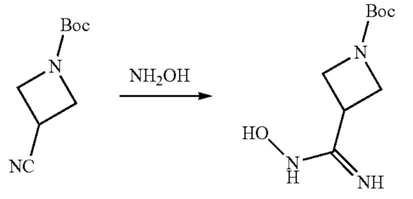 [SMILES: CC(C)(C)OC(=O)N1CC(C#N)C1 ; "NH2OH" ; CC(C)(C)OC(=O)N1CC(C(=N)NO)C1]

tert-Butyl 3-(N-hydroxycarbamimidoyl)azetidine-1-carboxylate

A mixture of tert-butyl 3-cyanoazetidine-1-carboxylate (1.00 g, 5.49 mmol) and 50% aq. $NH_2OH$ (1 mL) in EtOH (25 mL) was stirred at 80° C. for 24 h, then concentrated under reduced pressure to give the crude title compound as a yellow oil (1.15 g, 100%), which was used without further purification. MS ($ES^+$): $C_9H_{17}N_3O_3$ requires: 215, found: 160 $[M-55]^+$.

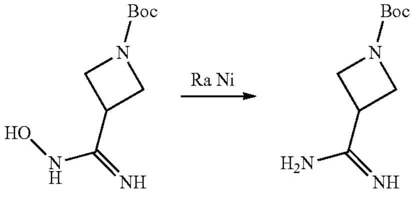 [SMILES: CC(C)(C)OC(=O)N1CC(C(=N)NO)C1 ; "Ra Ni" ; CC(C)(C)OC(=O)N1CC(C(=N)N)C1]

tert-Butyl 3-carbamimidoylazetidine-1-carboxylate

A mixture of the product from the previous step (1.00 g, 4.65 mmol) and Raney Nickel (200 mg wet) in MeOH (25 mL) was stirred at 0° C. for 8 h, then filtered and the filtrate concentrated under reduced pressure to give the crude title compound as a yellow oil (0.92 g, 100%), which was used without further purification. MS ($ES^+$): $C_9H_{17}N_3O_2$ requires: 199, found: 144 $[M-55]^+$.

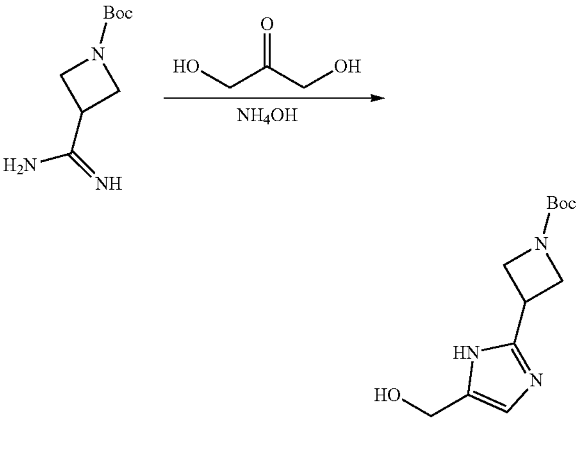

tert-Butyl 3-(5-(hydroxymethyl)-1H-imidazol-2-yl)azetidine-1-carboxylate

A mixture of the product from the previous step (1.0 g, 5.0 mmol) and 1,3-dihydroxypropan-2-one (450 mg, 5 mmol) in $NH_4OH$ (20 mL) was stirred at 90° C. for 4 h, then concentrated under reduced pressure to give the crude title compound as a yellow oil (1.26 g, 100%). MS ($ES^+$): $C12H_{19}N_3O_3$ requires: 253, found: 254 $[M+H]^+$.

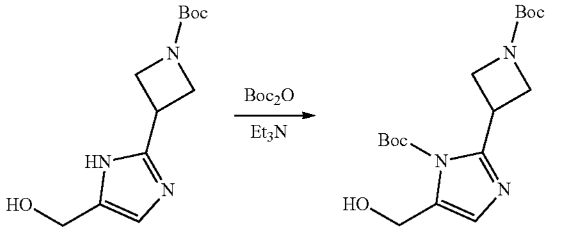 [SMILES: "Boc2O" ; "Et3N" ; CC(C)(C)OC(=O)N1CC(c2ncc(CO)[nH]2)C1 ; CC(C)(C)OC(=O)N1CC(c2ncc(CO)n2C(=O)OC(C)(C)C)C1]

tert-Butyl 2-(1-(tert-butoxycarbonyl)azetidin-3-yl)-5-(hydroxymethyl)-1H-imidazole-1-carboxylate To a mixture of the product from the previous step (1.0 g, 4.0 mmol) in DCM (20 mL) was added TEA (1.2 g, 12 mmol) and $Boc_2O$ (1.74 g, 8.00 mmol). The mixture was stirred at 20° C. for 24 h, then diluted with DCM (20 mL) and washed with $H_2O$ (20 mL×3). The organic layer was dried over $Na_2SO_4$, filtered and concentrated under reduced pressure. The residue was purified by $SiO_2$ gel chromatography (60% to 80% EtOAc in petroleum ether) to give the title compound as an oil (400 mg, 28%). MS ($ES^+$): $C_{17}H_{27}N_3O_5$ requires: 353, found: 354 $[M+H]^+$.

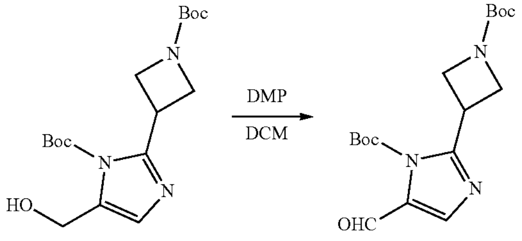

tert-Butyl 2-(1-(tert-butoxycarbonyl)azetidin-3-yl)-5-formyl-1H-imidazole-1-carboxylate To a solution of the product from the previous step (2.0 g, 5.7 mmol) in DCM (50 mL) was added DMP (2.8 g, 6.8 mmol) at 0° C. The mixture was stirred at 20° C. for 4 h, then treated with sat. aq. $Na_2SO_3$ (100 mL) and extracted with DCM (100 mL). The organic layer was washed with $H_2O$ (50 mL×3), dried over $Na_2SO_4$, filtered and concentrated under reduced pressure. The residue was purified by $SiO_2$ gel chromatography (40% to 80% EtOAc in petroleum ether) to give the title compound as an oil (1.5 g, 75%). MS ($ES^+$): $C_{17}H_{25}N_3O_5$ requires: 351, found: 352 $[M+H]^+$.

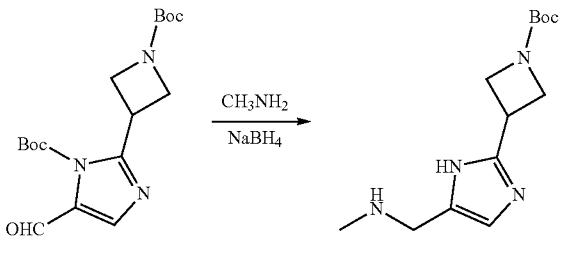 [SMILES: CC(C)(C)OC(=O)N1CC(c2ncc(C=O)n2C(=O)OC(C)(C)C)C1 ; "CH3NH2" ; "NaBH4" ; CNCc1cnc(C2CN(C(=O)OC(C)(C)C)C2)[nH]1]

tert-Butyl 3-(5-((methylamino)methyl)-1H-imidazol-2-yl)azetidine-1-carboxylate

To a solution of the product from the previous step (1.5 g, 4.3 mmol) in THF (25 mL) at 0° C. was added 4 M $CH_3NH_2$ in MeOH (15 mL, 60 mmol). The mixture was stirred at 20° C. for 24 h, then cooled to 0° C. and treated with $NaBH_4$ (160 mg, 4.2 mmol). The mixture was stirred at RT for 2 h, then concentrated under reduced pressure to give the crude title compound (1.13 g, 100%), which was used without further purification. MS ($ES^+$): $C_{13}H_{22}N_4O_2$ requires: 266, found: 267 $[M+H]^+$.

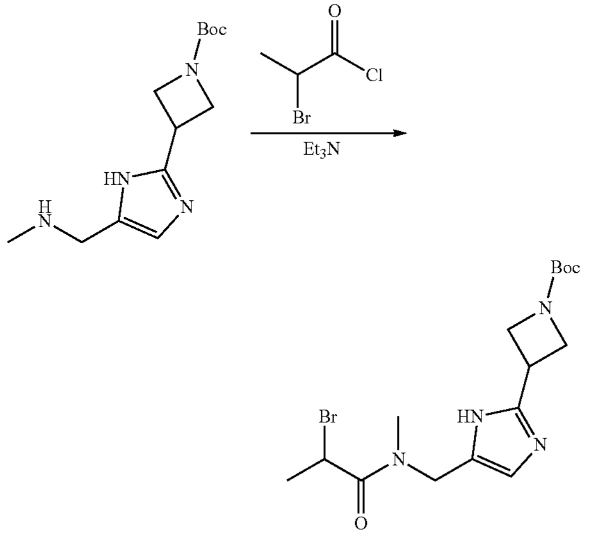

tert-Butyl 3-(5-((2-bromo-N-methylpropanamido)methyl)-1H-imidazol-2-yl)azetidine-1-carboxylate To a solution of the product from the previous step (1.15 g, 4.32 mmol) in DCM (75 mL) at 0° C. was added $Et_3N$ (868 mg, 8.58 mmol) and 2-bromopropanoyl chloride (870 mg, 5.16 mmol). The mixture was stirred at 20° C. for 2 h, then treated with ice water (20 g) and extracted with DCM (100 mL). The organic layer was washed with $H_2O$ (50 mL×3), dried over $Na_2SO_4$, filtered and concentrated under reduced pressure to give the crude title compound as an oil (1.7 g, 100%), which was used without further purification. MS ($ES^+$): $C_{16}H_{25}BrN_4O_3$ requires: 400, found: 401 $[M+H]^+$.

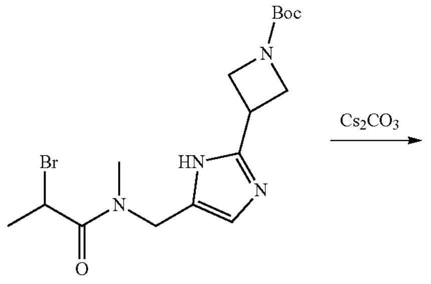

-continued

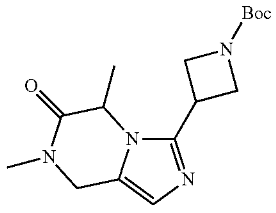

tert-Butyl 3-(5,7-dimethyl-6-oxo-5,6,7,8-tetrahydro-imidazo[1,5-a]pyrazin-3-yl)azetidine-1-carboxylate To a solution of the product from the previous step (1.7 g, 4.4 mmol) in MeCN (75 mL) was added $Cs_2CO_3$ (2.8 g, 8.6 mmol). The mixture was stirred at 60° C. for 1 h, then filtered and the filtrate concentrated under reduced pressure to give the crude title compound as an oil (1.3 g, 100%), which was used without further purification. MS ($ES^+$): $C_{16}H_{24}N_4O_3$ requires: 320, found: 321 $[M+H]^+$.

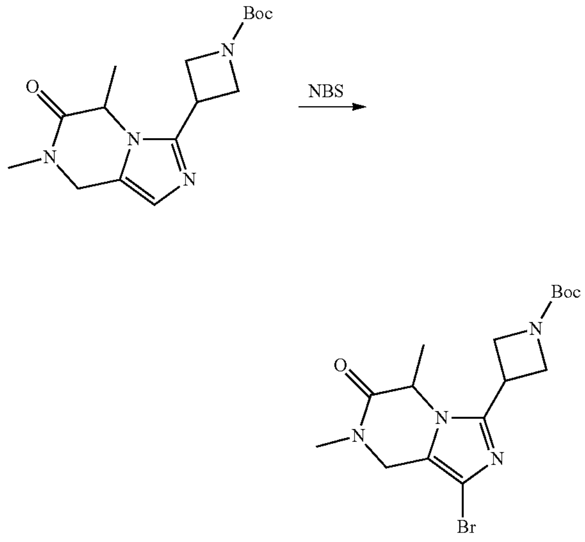

tert-Butyl 3-(1-bromo-5,7-dimethyl-6-oxo-5,6,7,8-tetrahydroimidazo[1,5-a]pyrazin-3-yl)azetidine-1-carboxylate To a solution of the product from the previous step (1.6 g, 5.0 mmol) in DCM (75 mL) was added NBS (890 mg, 5.00 mmol). The mixture was stirred at 20° C. for 1 h, then treated with sat. aq. $Na_2SO_3$ (50 mL) and extracted with DCM (100 mL). The organic layer was washed with $H_2O$ (50 mL×3), dried over $Na_2SO_4$, filtered and concentrated under reduced pressure to give the crude title compound as a yellow solid (2 g, 100%). MS ($ES^+$): $C_{16}H_{23}BrN_4O_3$ requires: 398, found: 399 $[M+H]^+$.

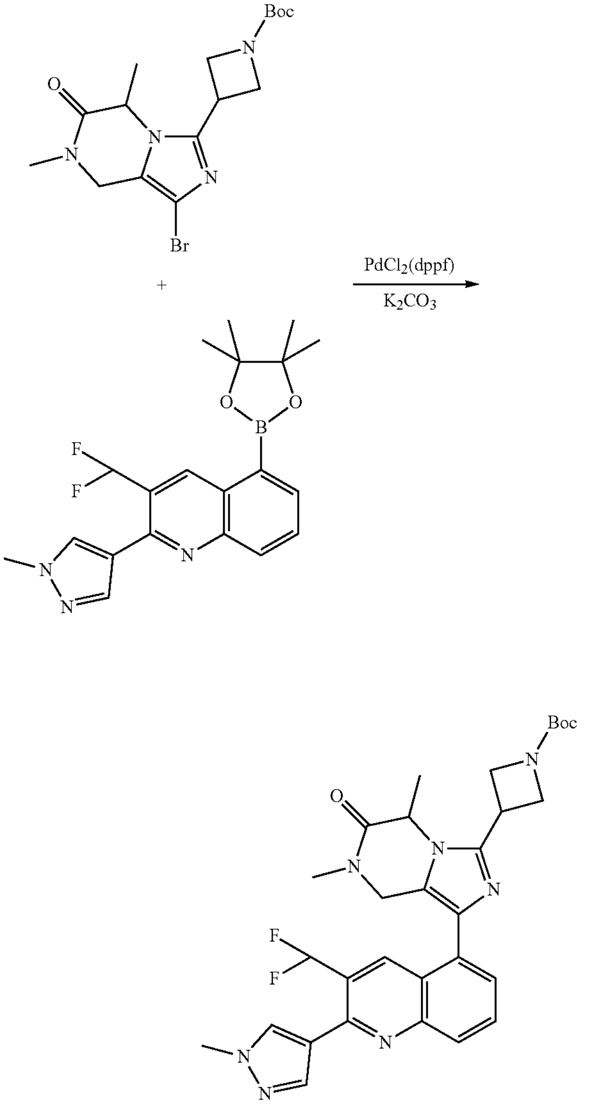

tert-Butyl 3-(1-(3-(difluoromethyl)-2-(1-methyl-1H-pyrazol-4-yl)quinolin-5-yl)-5,7-dimethyl-6-oxo-5,6,7,8-tetrahydroimidazo[1,5-a]pyrazin-3-yl)azetidine-1-carboxylate A mixture of the product from the previous step (400 mg, 1.01 mmol), 3-(difluoromethyl)-2-(1-methyl-1H-pyrazol-4-yl)-5-(4,4,5,5-tetramethyl-1,3,2-dioxaborolan-2-yl)quinoline (400 mg, 1.03 mmol), $PdCl_2(dppf)$ (50 mg, 0.068 mmol) and $K_2CO_3$ (276 mg, 2.00 mmol) in DMF/$H_2O$ (10 mL/4 mL) was stirred at 90° C. for 2 h under Ar. The mixture was concentrated, extracted with EtOAc (60 mL), washed with sat. aq. NaCl (35 mL×2), dried over $Na_2SO_4$, filtered and concentrated under reduced pressure. The residue was purified by $SiO_2$ gel chromatography (40% to 100% EtOAc in petroleum ether) to give the title compound as an oil (120 mg, 21%). MS ($ES^+$): $C_{30}H_{33}F_2N_7O_3$ requires: 577, found: 578 $[M+H]^+$.

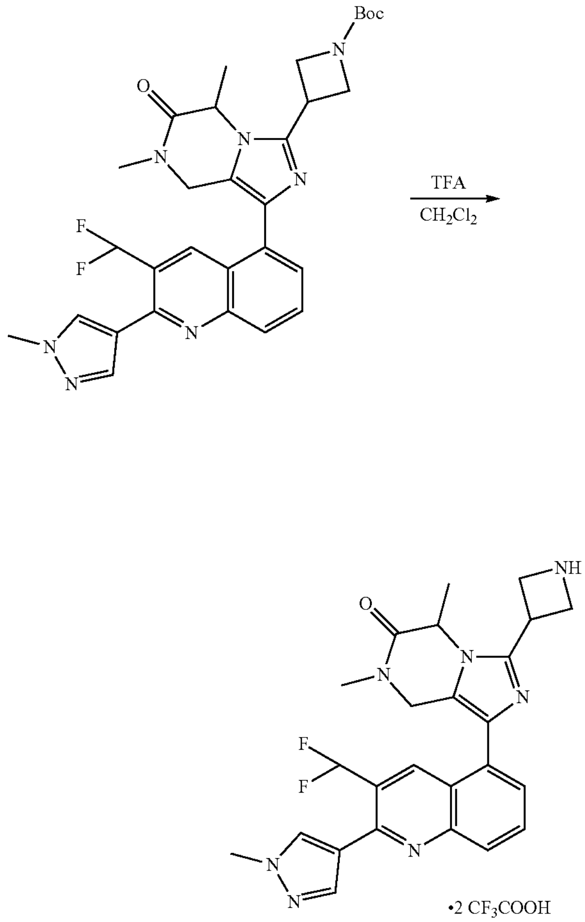

3-(Azetidin-3-yl)-1-(3-(difluoromethyl)-2-(1-methyl-1H-pyrazol-4-yl)quinolin-5-yl)-5,7-dimethyl 7,8-dihydroimidazo[1,5-a]pyrazin-6(5H)-one bis(2,2,2-trifluoroacetate)

To a solution of the product from the previous step (120 mg, 0.208 mmol) in DCM (5 mL) was added TFA (5 mL). The mixture was stirred at 20° C. for 2 h, then concentrated under reduced pressure to give the title compound (120 mg, 82%).

MS ($ES^+$): $C_{25}H_{25}F_2N_7O$ requires: 477, found: 478 $[M+H]^+$.

$^1$H NMR (500 MHz, $CD_3OD$) δ 9.22 (s, 1H), 8.20 (s, 1H), 8.12 (d, J=8.5 Hz, 1H), 8.06 (s, 1H), 7.96-7.92 (m, 1H), 7.64 (d, J=7.1 Hz, 1H), 7.14 (t, J=53.5 Hz, 1H), 5.00-4.94 (m, 2H), 4.49 (d, J=15.9 Hz, 1H), 4.37-4.33 (m, 2H), 4.20-4.09 (m, 1H), 4.05 (s, 3H), 4.02-3.98 (m, 2H), 3.08 (s, 3H), 1.67 (d, J=7.1 Hz, 3H).

Example 19

3-(1-Acetylazetidin-3-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one

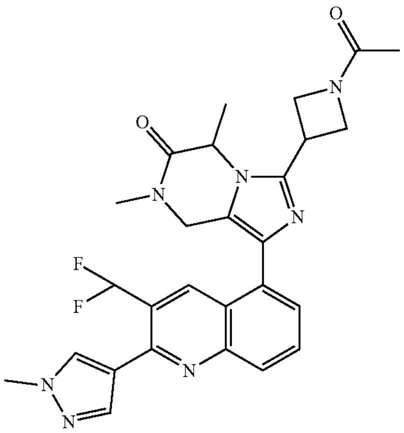 [SMILES: CC(=O)N1CC(c2nc(-c3cccc4nc(-c5cnn(C)c5)c(C(F)F)cc34)c3n2C(C)C(=O)N(C)C3)C1]

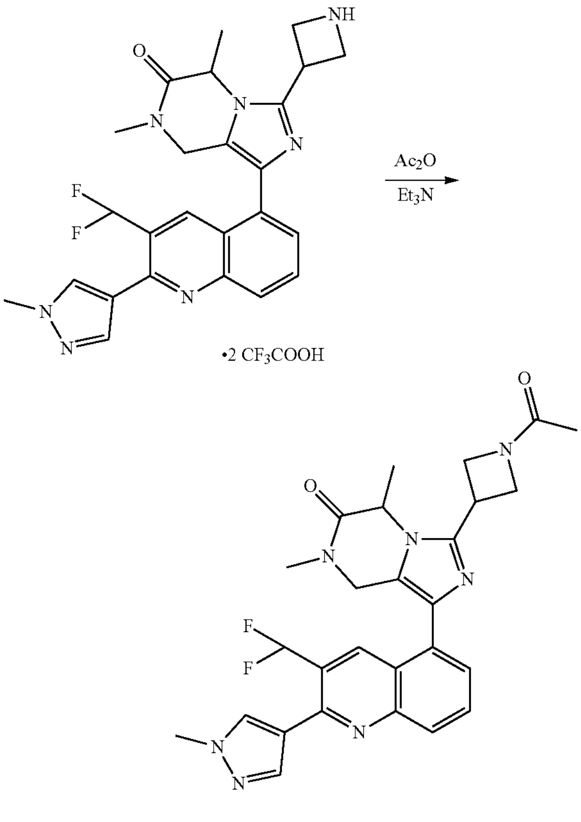

3-(1-Acetylazetidin-3-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one To a solution of the bis(trifluoroacetate) salt of Example 18 (47.7 mg, 0.068 mmol) in DCM (5 mL) were added $Ac_2O$ (20.4 mg, 0.2 mmol) and TEA (0.5 mL). The mixture was stirred at 20° C. for 2 h, then concentrated under reduced pressure. The residue was purified by reverse phase preparative HPLC (Mobile phase: A=10 mM $NH_4HCO_3/H_2O$, B=MeCN; Gradient: B=10% to 50% in 16 min; Column: C18) to give the title compound (5 mg, 14%).

MS ($ES^+$): $C_{27}H_{27}F_2N_7O_2$ requires: 519, found: 520 $[M+H]^+$.

$^1H$ NMR (500 MHz, $CD_3OD$)) δ 9.25 (s, 1H), 8.19 (s, 1H), 8.15-8.09 (m, 1H), 8.06 (s, 1H), 7.97-7.89 (m, 1H), 7.71-7.57 (m, 1H), 7.10 (t, J=54.0 Hz, 1H), 5.12-4.95 (m, 3H), 4.76-4.66 (m, 1H), 4.55-4.39 (m, 3H), 4.31-4.18 (m, 1H), 4.05 (s, 3H), 3.09 (s, 3H), 1.94 (appar d, J=10.4 Hz, 3H), 1.75-1.60 (m, 3H).

Example 20

1-(3-(Difluoromethyl)-2-(1-methyl-1H-pyrazol-4-yl)quinolin-5-yl)-5,7-dimethyl-3-(1-(methylsulfonyl)azetidin-3-yl)-7,8-dihydroimidazo[1,5-a]pyrazin-6(5H)-one

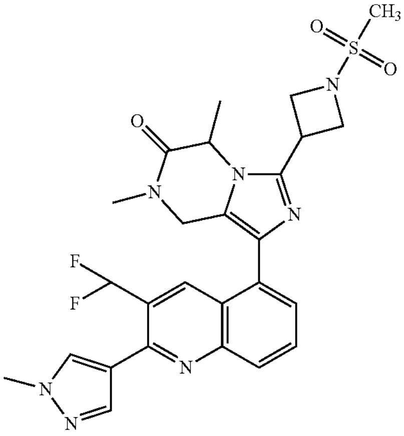 [SMILES: CC1C(=O)N(C)Cc2c(-c3cccc4nc(-c5cnn(C)c5)c(C(F)F)cc34)nc(C3CN(S(C)(=O)=O)C3)n21]

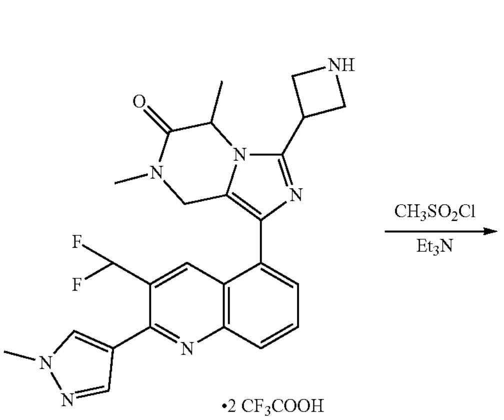

•2 $CF_3COOH$

-continued

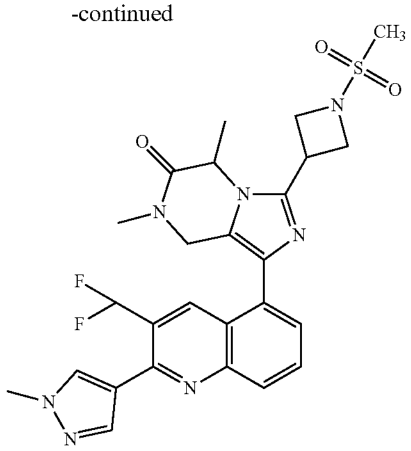

1-(3-(Difluoromethyl)-2-(1-methyl-1H-pyrazol-4-yl)quinolin-5-yl)-5,7-dimethyl-3-(1-(methylsulfonyl)azetidin-3-yl)-7,8-dihydroimidazo[1,5-a]pyrazin-6(5H)-one To a solution of the bis(trifluoroacetate) salt of Example 18 (47.7 mg, 0.068 mmol) in DCM (5 mL) were added $CH_3SO_2C_1$ (22.8 mg, 0.2 mmol) and TEA (0.5 mL). The mixture was stirred at 20° C. for 2 h, then concentrated under reduced pressure. The residue was purified by reverse phase preparative HPLC (Mobile phase: A=10 mM ammonium bicarbonate/water, B=MeCN; Gradient: B=10% to 55% in 18 min; Column: C18) to give the title compound (4 mg, 11%).

MS ($ES^+$): $C_{26}H_{27}F_2N_7O_3S$ requires: 555, found: 556 $[M+H]^+$.

$^1H$ NMR (500 MHz, $CD_3OD$)) δ 9.22 (s, 1H), 8.08 (s, 1H), 7.99 (d, J=8.5 Hz, 1H), 7.94 (s, 1H), 7.80 (d, J=7.1 Hz, 1H), 7.52-7.51 (m, 1H), 7.03 (t, J=54.0 Hz, 1H), 4.90-4.80 (m, 2H), 4.39 (d, J=15.9 Hz, 2H), 4.30-4.13 (m, 4H), 3.93 (s, 3H), 2.97 (s, 3H), 2.94 (s, 3H), 1.56 (d, J=7.1 Hz, 3H).

Example 21

1-(3-(Difluoromethyl)-2-(1-methyl-1H-pyrazol-4-yl)quinolin-5-yl)-5,7-dimethyl-3-(1-(2,2,2-trifluoroethyl)azetidin-3-yl)-7,8-dihydroimidazo[1,5-a]pyrazin-6(5H)-one

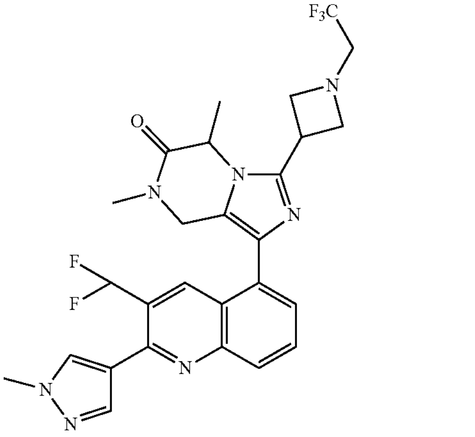 [SMILES: CC1C(=O)N(C)Cc2c(-c3cccc4nc(-c5cnn(C)c5)c(C(F)F)cc34)nc(C3CN(CC(F)(F)F)C3)n21]

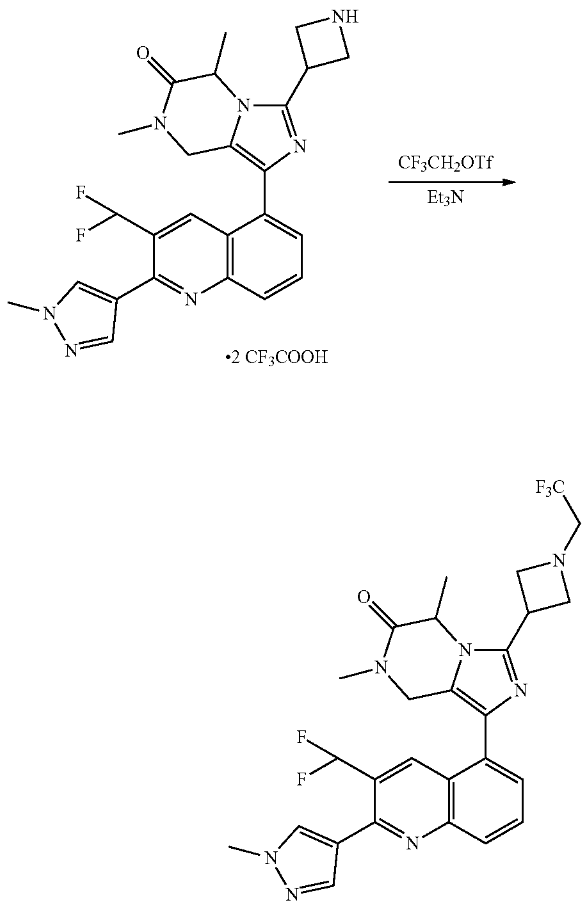

1-(3-(Difluoromethyl)-2-(1-methyl-1H-pyrazol-4-yl)quinolin-5-yl)-5,7-dimethyl-3-(1-(2,2,2-trifluoroethyl)azetidin-3-yl)-7,8-dihydroimidazo[1,5-a]pyrazin-6(5H)-one To a solution of the bis(trifluoroacetate) salt of Example 18 (47.7 mg, 0.068 mmol) in THF (5 mL) were added 2,2,2-trifluoroethyl trifluoromethanesulfonate (69.6 mg, 0.3 mmol) and TEA (0.5 mL). The mixture was stirred at 20° C. for 2 h, then concentrated under reduced pressure. The residue was purified by reverse phase preparative HPLC (Mobile phase: A=10 mM $NH_4HCO_3/H_2O$, B=MeCN; Gradient: B=35% to 75% in 18 min; Column: C18) to give the title compound (4 mg, 11%).

MS (ES$^+$): $C_{27}H_{26}F_5N_7O$ requires: 559, found: 560 $[M+H]^+$.

$^1$H NMR (500 MHz, $CD_3OD$) δ 9.24 (s, 1H), 8.20 (s, 1H), 8.11 (d, J=8.5 Hz, 1H), 8.06 (s, 1H), 7.97-7.91 (m, 1H), 7.64 (d, J=7.1 Hz, 1H), 7.15 (t, J=54.0 Hz, 1H), 5.03-4.90 (m, 2H), 4.48 (d, J=16.0 Hz, 1H), 4.20-4.07 (m, 1H), 4.06-3.99 (m, 5H), 3.85-3.77 (m, 1H), 3.74-3.65 (m, 1H), 3.27 (appar q, J=9.2 Hz, 2H), 3.08 (s, 3H), 1.68 (d, J=7.2 Hz, 3H).

Example 22

3-(1-(2,2-Difluoroethyl)azetidin-3-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one

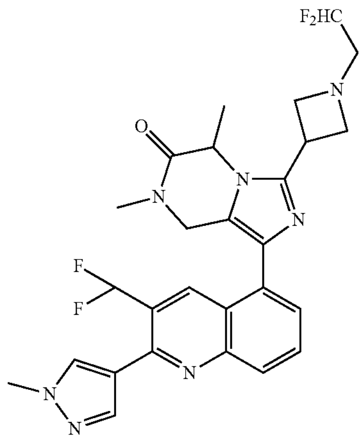 [SMILES: CC1C(=O)N(C)Cc2c(-c3cccc4nc(-c5cnn(C)c5)c(C(F)F)cc34)nc(C3CN(CC(F)F)C3)n21]

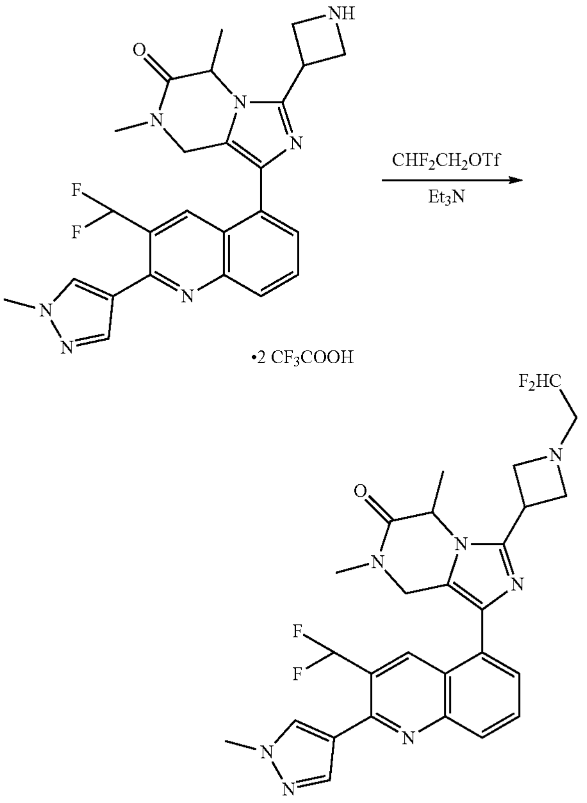

3-(1-(2,2-Difluoroethyl)azetidin-3-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one To a solution of the bis(trifluoroacetate) salt of Example 18) (47.7 mg, 0.068 mmol) in THF (5 mL) was added 2,2-difluoroethyl trifluoromethanesulfonate (64.2 mg, 0.3 mmol) and TEA (0.5 mL). The mixture was stirred at 20° C. for 2 h, then concentrated under reduced pressure. The residue was purified by reverse phase preparative HPLC (Mobile phase: A=10 mM $NH_4HCO_3/H_2O$, B=MeCN; Gradient: B=10% to 60% in 18 min; Column: C18) to give the title compound (5 mg, 14%).

MS ($ES^+$): $C_{27}H_{27}F_4N_7O$ requires: 541, found: 542 $[M+H]^+$.

$^1$H NMR (500 MHz, $CD_3OD$ δ 9.25 (s, 1H), 8.20 (s, 1H), 8.12 (d, J=8.5 Hz, 1H), 8.06 (s, 1H), 7.96-7.91 (m, 1H), 7.63 (d, J=7.1 Hz, 1H), 7.15 (t, J=54.5 Hz, 1H), 6.00-5.75 (m, 1H), 5.01 (q, J=7.2 Hz, 1H), 4.95 (d, J=16.0 Hz, 1H), 4.48 (d, J=16.0 Hz, 1H), 4.12-4.02 (m, 4H), 4.00-3.96 (m, 2H), 3.77 (t, J=7.6 Hz, 1H), 3.65 (t, J=7.7 Hz, 1H), 3.08 (s, 3H), 3.03-2.96 (m, 2H), 1.67 (d, J=7.1 Hz, 3H).

Example 23

1-(3-(Difluoromethyl)-2-(1-methyl-1H-pyrazol-4-yl)quinolin-5-yl)-3-(1-(2-methoxyethyl)azetidin-3-yl)-5,7-dimethyl-7,8-dihydroimidazo[1,5-a]pyrazin-6(5H)-one

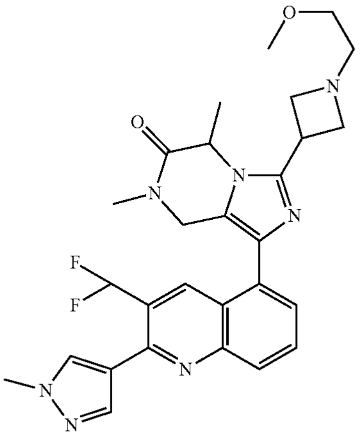 [SMILES: COCCN1CC(c2nc(-c3cccc4nc(-c5cnn(C)c5)c(C(F)F)cc34)c3n2C(C)C(=O)N(C)C3)C1]

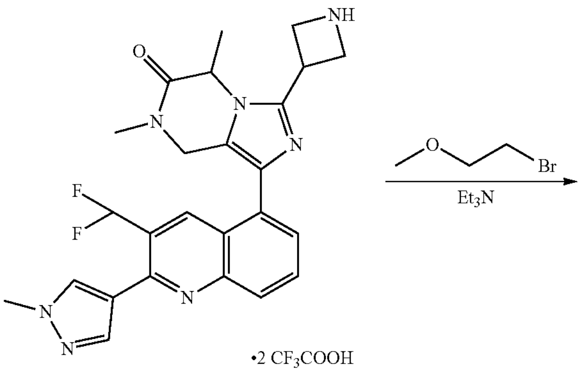

•2 $CF_3COOH$

-continued

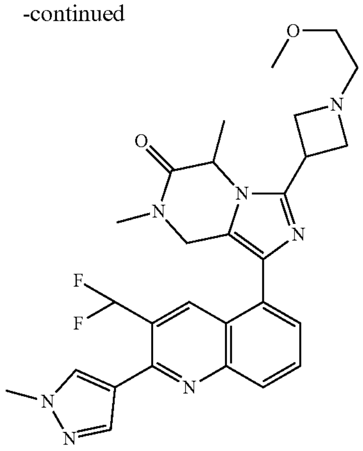

1-(3-(Difluoromethyl)-2-(1-methyl-1H-pyrazol-4-yl)quinolin-5-yl)-3-(1-(2-methoxyethyl)azetidin-3-yl)-5,7-dimethyl-7,8-dihydroimidazo[1,5-a]pyrazin-6(5H)-one To a solution of the bis(trifluoroacetate) salt of Example 18 (47.7 mg, 0.068 mmol) in DMF (5 mL) were added 1-bromo-2-methoxyethane (41.1 mg, 0.3 mmol) and TEA (0.5 mL). The mixture was stirred at 50° C. for 2 h, then concentrated under reduced pressure. The residue was purified by reverse phase preparative HPLC (Mobile phase: A=10 mM $NH_4HCO_3/H_2O$, B=MeCN; Gradient: B=25% to 60% in 18 min; Column: C18) to give the title compound (5 mg, 14%).

MS ($ES^+$): $C_{28}H_{31}F_2N_7O_2$ requires: 535, found: 536 $[M+H]^+$.

$^1$H NMR (500 MHz, $CD_3OD$) δ 9.26 (s, 1H), 8.20 (s, 1H), 8.12 (d, J=8.5 Hz, 1H), 8.06 (s, 1H), 7.97-7.89 (m, 1H), 7.62 (d, J=6.4 Hz, 1H), 7.09 (t, J=54.6 Hz, 1H), 5.03-4.93 (m, 2H), 4.48 (d, J=16.0 Hz, 1H), 4.06-4.02 (m, 4H), 3.98-3.94 (m, 2H), 3.78-3.54 (m, 2H), 3.48 (appar t, J=5.4 Hz, 2H), 3.36 (s, 3H), 3.08 (s, 3H), 2.85-2.83 (m, 2H), 1.68 (d, J=7.1 Hz, 3H).

Example 24

3-(1-(3-(Difluoromethyl)-2-(1-methyl-1H-pyrazol-4-yl)quinolin-5-yl)-5,7-dimethyl-6-oxo-5,6,7,8-tetrahydroimidazo[1,5-a]pyrazin-3-yl)-N-methylazetidine-1-carboxamide

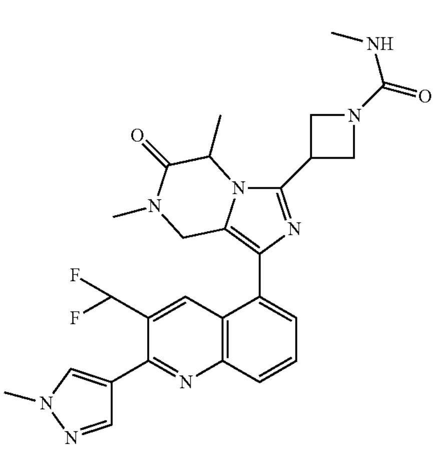 [SMILES: CNC(=O)N1CC(c2nc(-c3cccc4nc(-c5cnn(C)c5)c(C(F)F)cc34)c3n2C(C)C(=O)N(C)C3)C1]

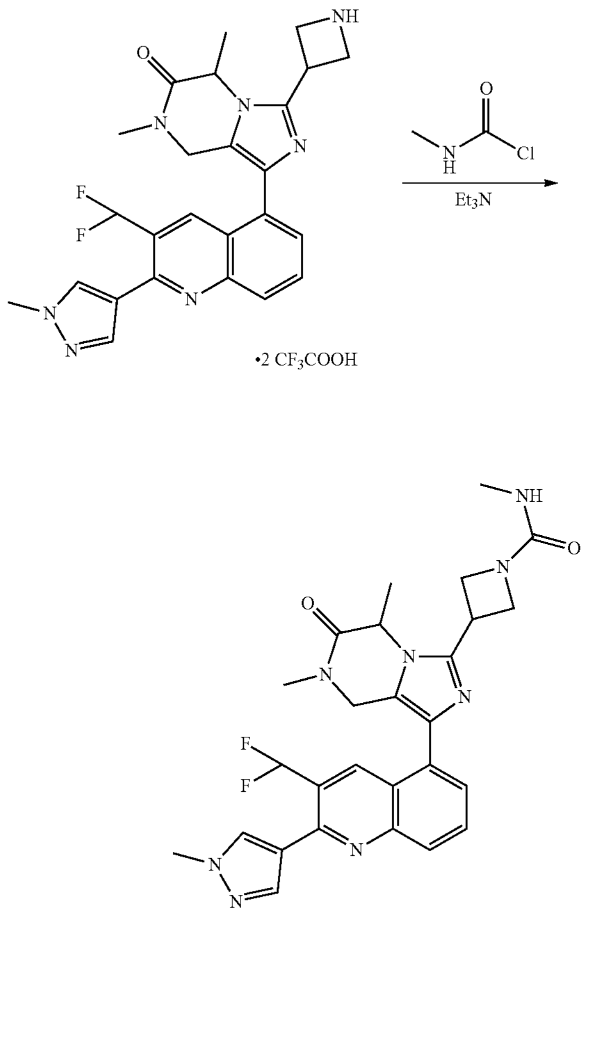

3-(1-(3-(Difluoromethyl)-2-(1-methyl-1H-pyrazol-4-yl)quinolin-5-yl)-5,7-dimethyl-6-oxo-5,6,7,8-tetrahydroimidazo[1,5-a]pyrazin-3-yl)-N-methylazetidine-1-carboxamide To a solution of the bis(trifluoroacetate) salt of Example 18 (47.7 mg, 0.068 mmol) in DCM (5 mL) were added methylcarbamic chloride (11 mg, 0.12 mmol) and TEA (0.5 mL). The mixture was stirred at 20° C. for 2 h, then concentrated under reduced pressure. The residue was purified by reverse phase preparative HPLC (Mobile phase: A=10 mM $NH_4HCO_3/H_2O$, B=MeCN; Gradient: B=25% to 50% in 18 min; Column: C18) to give the title compound (8 mg, 22%).

MS ($ES^+$): $C_{27}H_{28}F_2N_8O_2$ requires: 534, found: 535 $[M+H]^+$.

$^1H$ NMR (500 MHz, $CD_3OD$) δ 9.22 (s, 1H), 8.19 (s, 1H), 8.11 (d, J=8.6 Hz, 1H), 8.06 (s, 1H), 7.95-7.91 (m, 1H), 7.62 (d, J=7.1 Hz, 1H), 7.12 (t, J=54.0 Hz, 1H), 5.01 (q, J=7.1 Hz, 1H) 4.94 (d, J=16.0 Hz, 1H), 4.49 (d, J=16.0 Hz, 2H), 4.44-4.35 (m, 2H), 4.25-4.19 (m, 2H), 4.05 (s, 3H), 3.08 (s, 3H), 2.73 (s, 3H), 1.68 (d, J=7.1 Hz, 3H).

Example 25

1-(3-(Difluoromethyl)-2-(1-methyl-1H-pyrazol-4-yl)quinolin-5-yl)-3-(1-(2-fluoroethyl)azetidin-3-yl)-5,7-dimethyl-7,8-dihydroimidazo[1,5-a]pyrazin-6(5H)-one

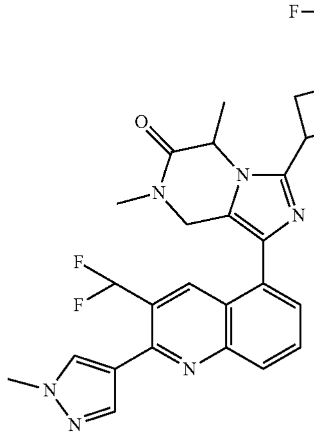

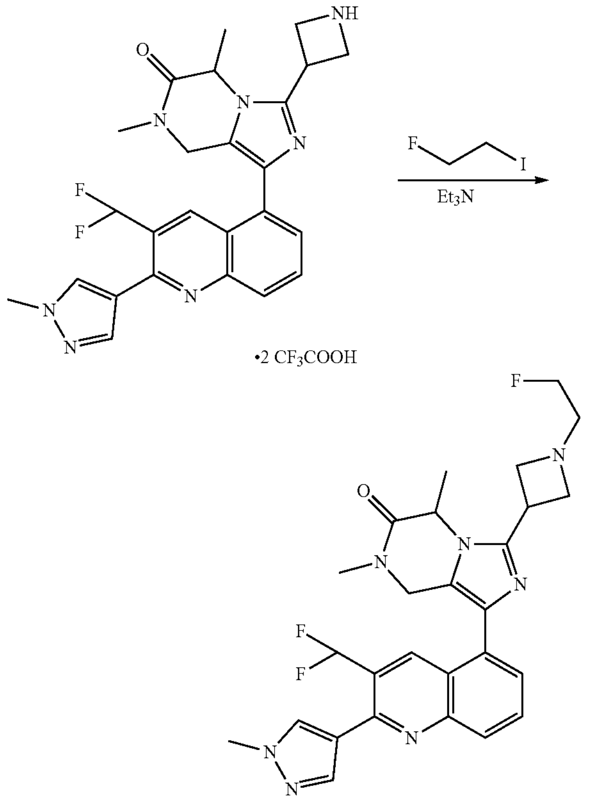

1-(3-(Difluoromethyl)-2-(1-methyl-1H-pyrazol-4-yl)quinolin-5-yl)-3-(1-(2-fluoroethyl)azetidin-3-yl)-5,7-dimethyl-7,8-dihydroimidazo[1,5-a]pyrazin-6(5H)-one To a solution of the bis(trifluoroacetate) salt of Example 18 (47.7 mg, 0.068 mmol) in DMF (5 mL) was added 1-fluoro-2-iodoethane (51 mg, 0.3 mmol) and TEA (0.5 mL). The mixture was stirred at 50° C. for 2 h, then concentrated under reduced pressure. The residue was purified by reverse phase preparative HPLC (Mobile phase: A=10 mM $NH_4HCO_3/H_2O$, B=MeCN; Gradient: B=10% to 60% in 18 min; Column: C18) to give the title compound (15 mg, 42%).

MS (ES$^+$): $C_{27}H_{28}F_3N_7O$ requires: 523, found: 524 $[M+H]^+$.

$^1$H NMR (500 MHz, $CD_3OD$) δ 9.25 (s, 1H), 8.20 (s, 1H), 8.12 (d, J=8.6 Hz, 1H), 8.06 (s, 1H), 7.95-7.91 (m, 1H), 7.63 (d, J=7.1 Hz, 1H), 7.14 (t, J=54.5 Hz, 1H), 5.01 (d, J=7.5 Hz, 1H), 4.95 (d, J=15.5 Hz, 1H), 4.63-4.46 (m, 3H), 4.08-4.05 (m, 4H), 4.00-3.96 (m, 2H), 3.77-3.67 (m, 1H), 3.63-3.55 (m, 1H), 3.08 (s, 3H), 3.00-2.86 (m, 2H), 1.68 (d, J=7.1 Hz, 3H).

Examples 26a/26b 5,7-Dimethyl-1-(2-(1-methyl-1H-pyrazol-4-yl)-3-(trifluoromethyl)quinolin-5-yl)-3-(tetrahydro-2H-pyran-4-yl)-7,8-dihydroimidazo[1,5-a]pyrazin-6(5H)-one

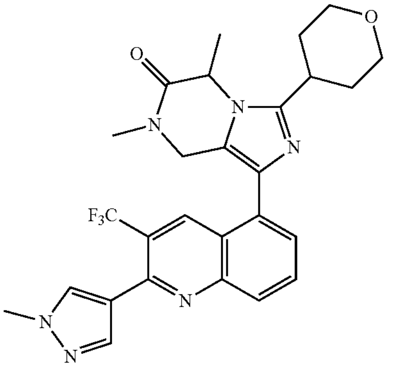 [SMILES: CC1C(=O)N(C)Cc2c(-c3cccc4nc(-c5cnn(C)c5)c(C(F)(F)F)cc34)nc(C3CCOCC3)n21]

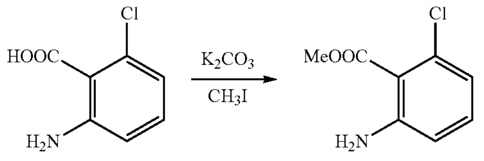

Methyl 2-amino-6-chlorobenzoate

To a solution of 2-amino-6-chlorobenzoic acid (1.0 g, 5.8 mmol) in DMF (10 mL) were added $CH_3I$ (99.5 mg, 7.01 mmol) and $K_2CO_3$ (967 mg, 7.01 mmol). The mixture was stirred at RT overnight, then treated with $H_2O$ (50 mL) and extracted with EtOAc (50 mL×3). The combined organic layers were sequentially washed with water and sat. aq. NaCl, dried over $Na_2SO_4$, filtered and concentrated under reduced pressure. The residue was purified by $SiO_2$ gel chromatography (0% to 15% EtOAc in hexanes) to give the title compound as a yellow oil (800 mg, 93%). MS (ES$^+$) $C_8H_8ClNO_2$ requires: 185, found: 186 $[M+H]^+$.

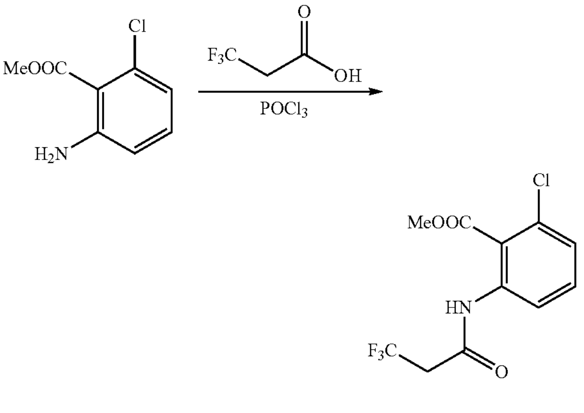

Methyl 2-chloro-6-(3,3,3-trifluoropropanamido)benzoate

To a solution of the product from the previous step (800 mg, 4.32 mmol) in pyridine (8 mL) were added 3,3,3-trifluoropropanoic acid (664 mg, 5.8 mmol) and $POCl_3$ (793 mg, 5.8 mmol). The resulting mixture was stirred at RT for 3 h, then treated with sat. aq. $NaHCO_3$(10 mL). The layers were separated, and the aqueous phase was extracted with EtOAc (3×10 mL). The combined organic layers were washed with sat. aq. NaCl, dried over $Na_2SO_4$, filtered and concentrated under reduced pressure. The residue was purified by $SiO_2$ gel chromatography (0% to 15% EtOAc in hexane) to give the title compound as an off-white solid (500 mg, 39%). MS (ES$^+$) $C_{11}H_9ClF_3NO_3$ requires: 295, found: 296 $[M+H]^+$.

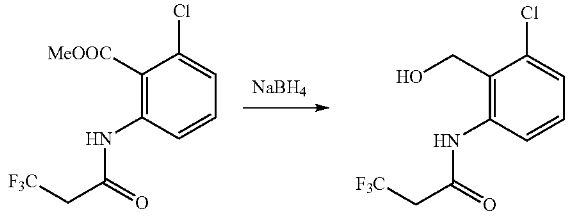 [SMILES: COC(=O)c1c(Cl)cccc1NC(=O)CC(F)(F)F ; "NaBH4" ; O=C(CC(F)(F)F)Nc1cccc(Cl)c1CO]

N-(3-Chloro-2-(hydroxymethyl)phenyl)-3,3,3-trifluoropropanamide

To a degassed solution of the product from the previous step (2000 mg, 6.76 mmol) in THF (20 mL) was added $NaBH_4$ (256.88 mg, 6.76 mmol). The resulting mixture was stirred at RT for 2 h, then concentrated under reduced pressure. The residue was purified by $SiO_2$ gel chromatography (0% to 50% EtOAc in petroleum ether) to give the title compound as an off-white solid (300 mg, 17%). MS (ES$^+$) $C_{10}H_9ClF_3NO_2$ requires: 267, found: 268 $[M+H]^+$.

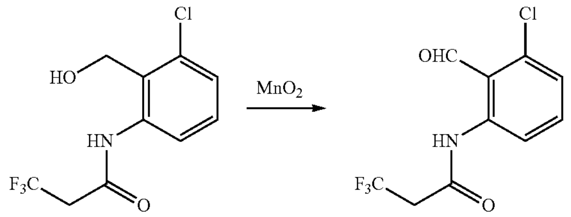

N-(3-Chloro-2-formylphenyl)-3,3,3-trifluoropropanamide

To a degassed solution of the product from the previous step (300 mg, 1.12 mmol) in DCM (10 mL) was added $MnO_2$ (195 mg, 2.24 mmol). The resulting mixture was stirred at RT for 2 h, then filtered and the filtrate concentrated under reduced pressure. The residue was purified by by $SiO_2$ gel chromatography (0% to 50% EtOAc in petroleum ether) to give the title compound as an off-white solid (250 mg, 84%). MS ($ES^+$) $C_{10}H_7ClF_3NO_2$ requires: 265, found: 266 $[M+H]^+$.

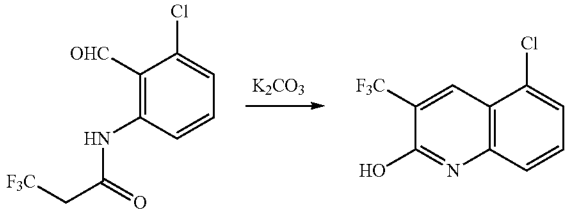

5-Chloro-3-(trifluoromethyl)quinolin-2(1H)-one

To a degassed solution of the product from the previous step (250 mg, 0.943 mmol) in DMF (5 mL) was added $K_2CO_3$ (260 mg, 1.89 mmol) and the resulting mixture was stirred at RT for 2 h, then treated with $H_2O$ (10 mL) and extracted with EtOAc (3×10 mL). The combined organic layers were washed with sat. aq. NaCl, dried over $Na_2SO_4$, filtered and concentrated under reduced pressure. The residue was purified by $SiO_2$ gel chromatography (0% to 30% EtOAc in petroleum ether) to give the title compound as an off-white solid (200 mg, 86%). MS ($ES^+$) $C_{10}H_5ClF_3NO$ requires: 247, found: 248 $[M+H]^+$.

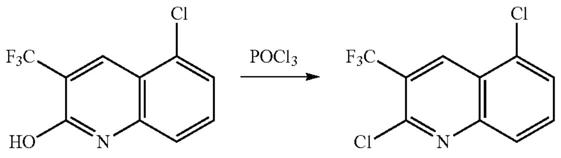

2,5-Dichloro-3-(trifluoromethyl)quinoline

A degassed solution of the product from the previous step (200 mg, 0.810 mmol) in $POCl_3$ (5 mL) was stirred at 100° C. for 3 h. To the mixture was added sat. aq. $NaHCO_3$(10 mL), and layers were separated. The aqueous phase was extracted with EtOAc (3×10 mL), and the combined organic layers were washed with sat. aq. NaCl, dried over $Na_2SO_4$, filtered and concentrated under reduced pressure. The residue was purified by $SiO_2$ gel chromatography (0% to 20% EtOAc in hexane) to give the title compound as an off-white solid (100 mg, 46%). MS ($ES^+$) $C_{10}H_4Cl_2F_3N$ requires: 265, found: 266 $[M+H]^+$.

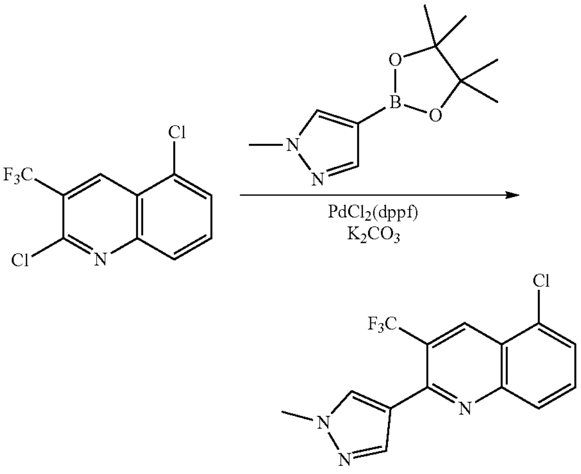

5-Chloro-2-(1-methyl-1H-pyrazol-4-yl)-3(trifluoromethyl)quinoline

To a degassed solution of the product from the previous step (100 mg, 0.376 mmol) in 1,4-dioxane (0.7 mL) and $H_2O$ (0.3 mL) were added 1-methyl-4-(4,4,5,5-tetramethyl-1,3,2-dioxaborolan-2-yl)-1H-pyrazole (93.8 mg, 0.451 mmol), $K_2CO_3$ (103.8 mg, 0.752 mmol), and $Pd(dppf)Cl_2$ (21.2 mg, 0.038 mmol), and the resulting mixture was stirred at 100° C. for 2 h. The mixture was concentrated under reduced pressure, and the residue was purified by $SiO_2$ gel chromatography (0% to 50% EtOAc in hexane) to give the title compound as an off-white solid. (100 mg, 86%). MS ($ES^+$) $C_{14}H_9ClF_3N_3$ requires: 311, found: 312 $[M+H]^+$.

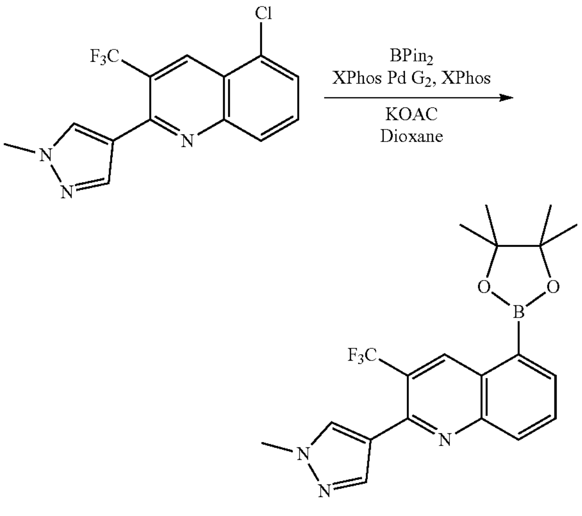

2-(1-Methyl-1H-pyrazol-4-yl)-5-(4,4,5,5-tetramethyl-1,3,2-dioxaborolan-2-yl)-3-(trifluoromethyl) quinoline To a solution of the product from the previous step (100 mg, 0.332 mmol) in 1,4-dioxane (2.0 mL) were added $BPin_2$ (168.7 mg, 0.664 mmol), KOAc (63.3 mg, 0.664 mmol), XPhos Pd G2 (30.2 mg, 0.033 mmol), and XPhos (13.6 mg, 0.033 mmol), and the resulting mixture was stirred at 100° C. for 2 h. The mixture was concentrated under reduced pressure, and the residue was purified by $SiO_2$ gel chromatography (0% to 50% EtOAc in petroleum ether) to give the title compound as an off-white solid (90 mg, 67%). MS ($ES^+$) $C_{20}H_{21}BF_3N_3O_2$ requires: 403, found: 404 $[M+H]^+$.

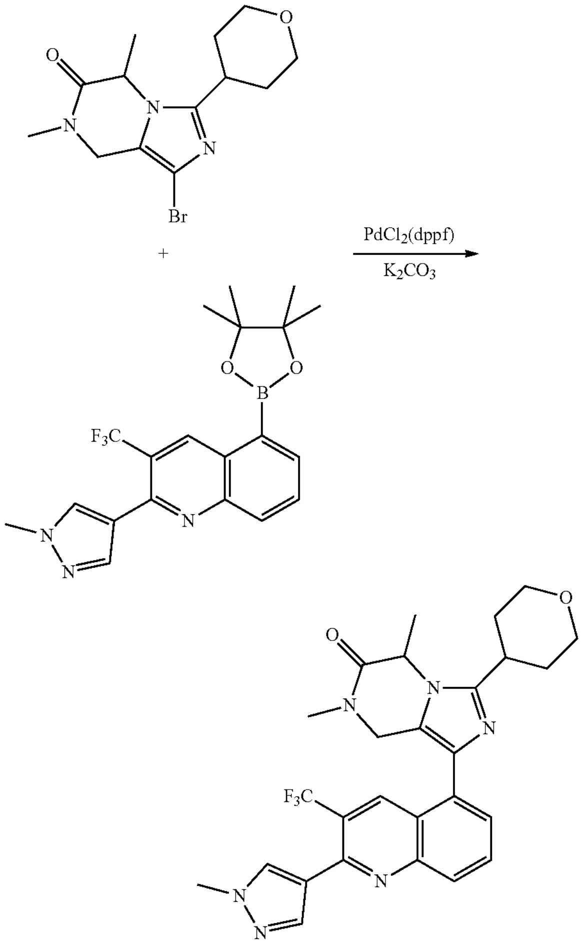

5,7-Dimethyl-1-(2-(1-methyl-1H-pyrazol-4-yl)-3-(trifluoromethyl)quinolin-5-yl)-3-(tetrahydro-2H-pyran-4-yl)-7,8-dihydroimidazo[1,5-a]pyrazin-6(5H)-one (separated enantiomers)

To a degassed solution of the product from the previous step (90.0 mg, 0.223 mmol) in 1,4-dioxane (0.7 mL) and $H_2O$ (0.3 mL) were added Intermediate "C" (87.5 mg, 0.268 mmol), $K_2CO_3$ (61.5 mg, 0.446 mmol), $PdCl_2$(dppf) (20.2 mg, 0.022 mmol). The mixture was stirred at 100° C. for 2 h, then concentrated under reduced pressure. The volatiles were removed under reduced pressure. The residue was purified by reverse phase preparative HPLC (Mobile phase: A=10 mM ammonium bicarbonate/water, B=MeCN; Gradient: B=30% to 65% in 13 min; Column: C18) to give the title racemic compound. The racemate was separated by chiral HPLC [Instrument: SFC-80 (Thar, Waters); Column: OZ 20*250 mm, 10 um (Daicel); Column temperature: 35° C.; Mobile phase: $CO_2$/MeOH(0.2% 7 M ammonia in MeOH)=30/70; Flow rate: 80 g/min] to give two isomers.

Example 26a was isolated as an off-white solid (10 mg, 9%). RT=1.98 min.

MS ($ES^+$) $C_{27}H_{27}F_3N_6O_2$ requires: 524, found: 525 $[M+H]^+$.

$^1$H NMR (500 MHz, DMSO-$d_6$) δ 9.90 (s, 1H), 8.10 (s, 1H), 7.99-7.96 (m, 2H), 7.58-7.49 (m, 2H), 5.10 (d, J=7.0 Hz, 2H), 5.04 (d, J=16.0 Hz, 1H), 4.54 (d, J=16.0 Hz, 1H), 3.96 (s, 3H), 3.5-3.2 (assumed overlap with water peak, 5H), 2.97 (s, 3H), 1.94-1.82 (m, 4H), 1.58 (d, J=7.5 Hz, 3H).

Example 26b was isolated as an off-white solid (10 mg, 9%). RT=4.58 min.

MS ($ES^+$) $C_{27}H_{27}F_3N_6O_2$ requires: 524, found: 525 $[M+H]^+$.

$^1$H NMR (500 MHz, $CD_3OD$) δ 9.27 (s, 1H), 8.07 (s, 1H), 8.15-8.03 (m, 1H), 7.99 (d, J=8.5 Hz, 1H), 7.91 (s, 1H), 7.51 (d, J=7.0 Hz, 1H), 5.00 (d, J=7.5 Hz, 1H), 4.85 (d, J=15.9 Hz, 1H), 4.39 (d, J=16.0 Hz, 1H), 4.03-3.93 (m, 2H), 3.92 (s, 3H), 3.60-3.53 (m, 2H), 3.12-3.08 (m, 1H), 2.97 (s, 3H), 2.03-1.70 (m, 4H), 1.61 (d, J=7.5 Hz, 3H).

Example 27

1-(3-(Difluoromethyl)-2-(1-methyl-1H-pyrazol-4-yl)quinolin-5-yl)-5-fluoro-7-methyl-3-(tetrahydro-2H-pyran-4-yl)-7,8-dihydroimidazo[1,5-a]pyrazin-6(5H)-one

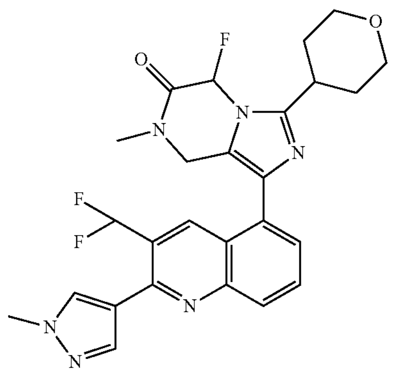 [SMILES: CN1Cc2c(-c3cccc4nc(-c5cnn(C)c5)c(C(F)F)cc34)nc(C3CCOCC3)n2C(F)C1=O]

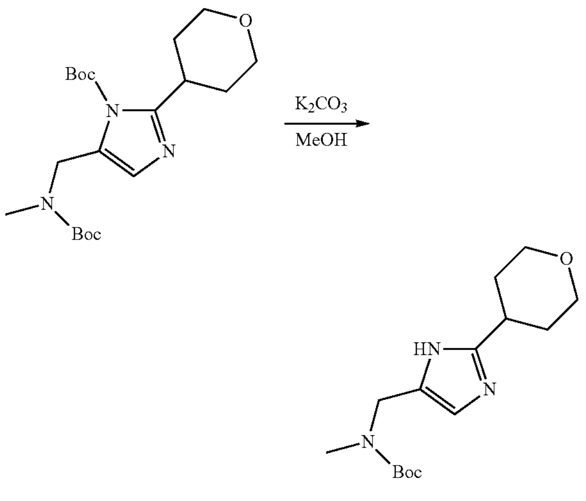

Tert-butyl methyl((2-(tetrahydro-2H-pyran-4-yl)-1H-imidazol-5-yl)methyl)carbamate To a mixture of tert-butyl 5-(((tert-butoxycarbonyl)(methyl)amino)methyl)-2-(tetrahydro-2H-pyran-4-yl)-1H-imidazole-1-carboxylate (2.5 g, 6.3 mmol) in MeOH (45 mL) was added $K_2CO_3$ (1.75 g, 12.6 mmol). The mixture was stirred at RT for 30 min, filtered and concentrated under reduced pressure. The residue was dissolved in DCM (75 mL) and the solution was washed with sat. aq. NaCl (25 mL×2), dried over $MgSO_4$, filtered and concentrated under reduced pressure to give the title compound as a yellow oil (1.86 g, 100%). MS ($ES^+$): $C_{15}H_{25}N_3O_3$ requires: 295, found: 296 $[M+H]^+$.

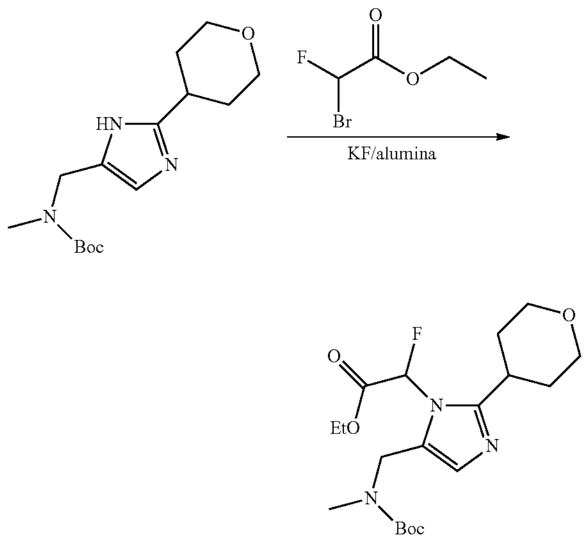

Ethyl 2-(5-(((tert-butoxycarbonyl)(methyl)amino)methyl)-2-(tetrahydro-2H-pyran-4-yl)-1H-imidazol-1-yl)-2-fluoroacetate A degassed mixture of the product from the previous step (1.86 g, 6.30 mmol), ethyl bromofluoroacetate (3.72 mL, 31.5 mmol) and KF/alumina (3.66 g, 25.2 mmol) in MeCN (45 mL) was stirred at reflux for 2 d, allowed to cool to RT and filtered. The filtrate was concentrated under reduced pressure and the residue purified by $SiO_2$ gel chromatography (25% to 75% EtOAc in petroleum ether) to give the title compound as a yellow solid (872 mg, 35%). MS ($ES^+$): $C_{19}H_{30}FN_3O_5$ requires: 399, found: 400 $[M+H]^+$.

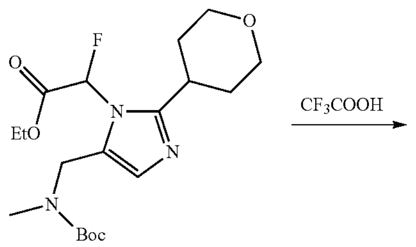

-continued

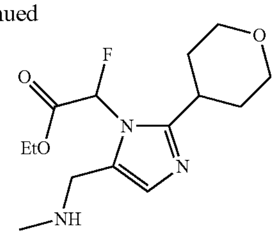

Ethyl 2-fluoro-2-(5-((methylamino)methyl)-2-(tetrahydro-2H-pyran-4-yl)-1H-imidazol-1-yl)acetate To a mixture of the product from the previous step (872 mg, 2.18 mmol) in DCM (15 mL) was added TFA (3 mL). The mixture was stirred at RT for 2 h, concentrated under reduced pressure, and the residue was dissolved in EtOAc (120 mL). The solution was sequentially washed with sat. aq. $NaHCO_3$(10 mL×2) and sat. aq. NaCl (15 mL), dried over $Na_2SO_4$, filtered and concentrated under reduced pressure to give the crude title compound as an oil (486 mg, 74%), which was used without further purification. MS ($ES^+$): $C_{14}H_{22}FN_3O_3$ requires: 299, found: 300 $[M+H]^+$.

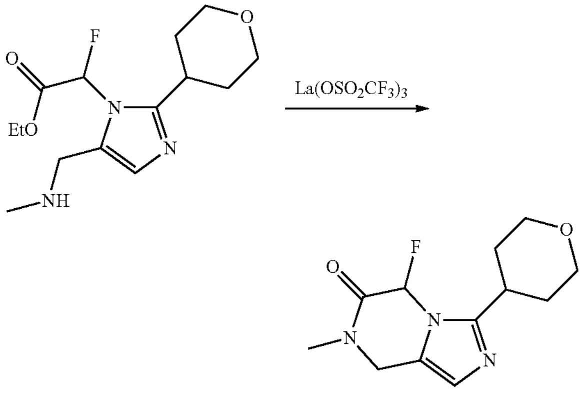

5-Fluoro-7-methyl-3-(tetrahydro-2H-pyran-4-yl)-7,8-dihydroimidazo[1,5-a]pyrazin-6(5H)-one To a mixture of the product from the previous step (486 mg, 1.62 mmol) in DMF (5 mL) at 0° C. was added lanthanum(III) trifluoromethanesulfonate (47.58 mg, 81.18 μmol). The mixture was stirred at 50° C. overnight, then concentrated under reduced pressure. The residue was purified by $SiO_2$ gel chromatography (0% to 10% MeOH in EtOAc) to give the title compound as a yellow oil (54 mg, 13%). MS ($ES^+$): $C_{12}H_{16}FN_3O_2$ requires: 253, found: 254 $[M+H]^+$.

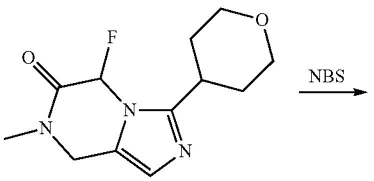

-continued

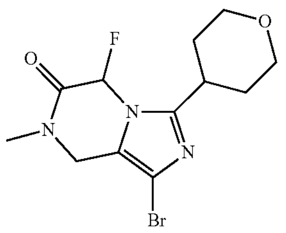

1-Bromo-5-fluoro-7-methyl-3-(tetrahydro-2H-pyran-4-yl)-7,8-dihydroimidazo[1,5-a]pyrazin-6(5H)-one To a mixture of the product from the previous step (72.0 mg; 284 μmol) in DCM (15 mL) was added NBS (57.38 mg, 312.7 μmol). The mixture was stirred at RT for 30 min, then treated with sat. aq. $Na_2CO_3$ (10 mL) and extracted with DCM (15 mL×3). The combined organic layers were washed with sat. aq. NaCl (15 mL), dried over $Na_2SO_4$, filtered and concentrated under reduced pressure to give the title compound as a yellow oil (87 mg, 92%). MS ($ES^+$): $C_{12}H_{15}BrFN_3O_2$ requires: 331, found: 332 $[M+H]^+$.

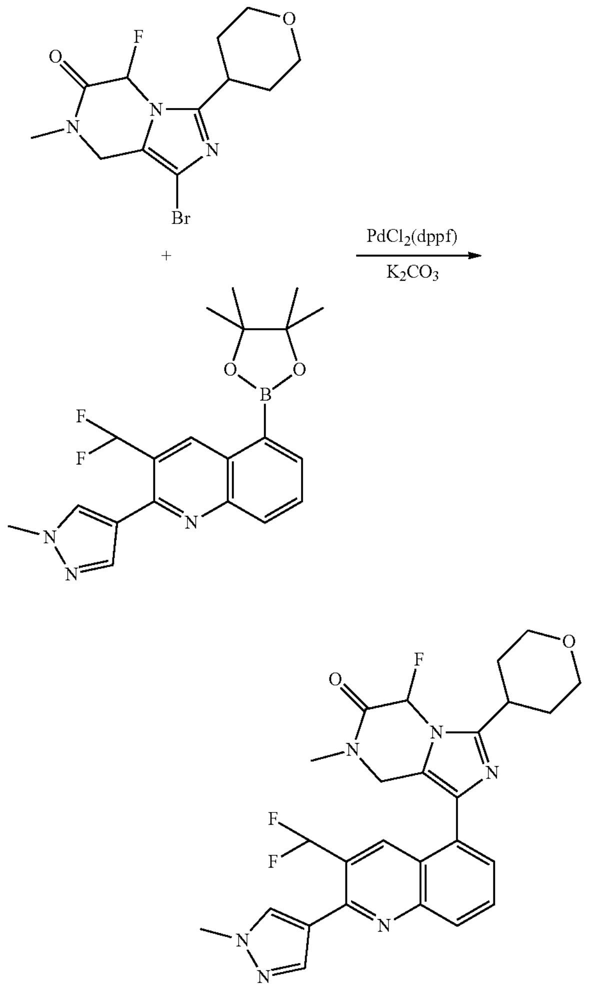

1-(3-(Difluoromethyl)-2-(1-methyl-1H-pyrazol-4-yl)quinolin-5-yl)-5-fluoro-7-methyl-3-(tetrahydro-2H-pyran-4-yl)-7,8-dihydroimidazo[1,5-a]pyrazin-6(5H)-one A mixture of the product from the previous step (87 mg; 260 μmol), 3-(difluoromethyl)-2-(1-methyl-1H-pyrazol-4-yl)-5-(4,4,5,5-tetramethyl-1,3,2-dioxaborolan-2-yl)quinoline (121.07 mg, 314.29 moles), 2.0 M aq. $K_2CO_3$ (0.393 mL, 786 moles) and $PdCl_2(dppf)$ (21.83 mg, 26.19 moles) in DMF (3 mL) was degassed and purged with $N_2$. The mixture was stirred at 80° C. for 1.5 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title compound as a light yellow solid (5 mg, 4%).

MS ($ES^+$): $C_{26}H_{25}F_3N_6O_2$ requires: 510, found: 511 $[M+H]^+$.

$^1$H NMR (500 MHz, $CD_3OD$) δ 9.16 (s, 1H), 8.20 (s, 1H), 8.14 (d, J=8.5 Hz, 1H), 8.06 (s, 1H), 7.99-7.90 (m, 1H), 7.66 (d, J=7.1 Hz, 1H), 7.13 (t, J=54.5 Hz, 1H), 6.75 (d, J=54.9 Hz, 1H), 5.03 (d, J=16.5 Hz, 2H), 4.59 (d, J=16.5 Hz, 1H), 4.16-3.98 (m, 5H), 3.68 (appar t, J=10.8 Hz, 2H), 3.45-3.37 (m, 1H), 3.14 (s, 3H), 2.31-2.14 (m, 1H), 2.05-1.91 (m, 3H).

Example 28

1-(3-(Difluoromethyl)-2-(1-methyl-1H-pyrazol-4-yl)quinolin-5-yl)-3-(1-(2-hydroxyethyl)azetidin-3-yl)-5,7-dimethyl-7,8-dihydroimidazo[1,5-a]pyrazin-6(5H)-one

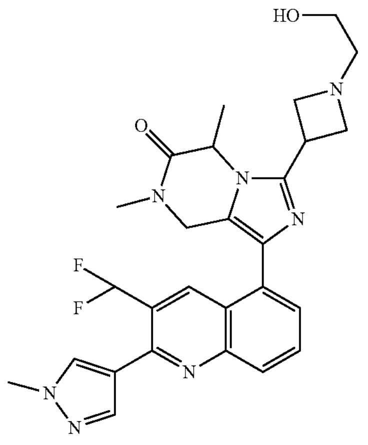 [SMILES: CC1C(=O)N(C)Cc2c(-c3cccc4nc(-c5cnn(C)c5)c(C(F)F)cc34)nc(C3CN(CCO)C3)n21]

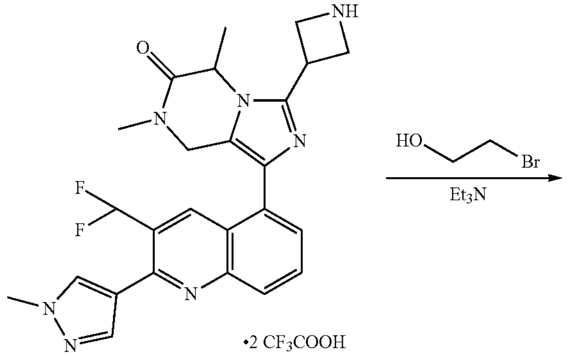

•2 $CF_3COOH$

-continued

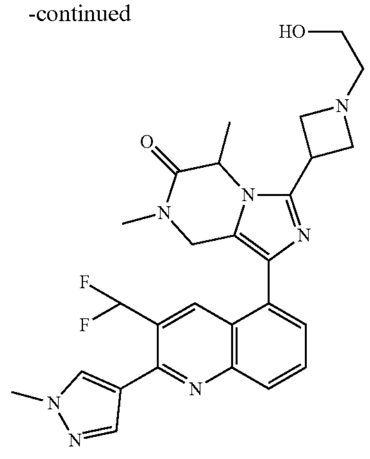

1-(3-(difluoromethyl)-2-(1-methyl-1H-pyrazol-4-yl)quinolin-5-yl)-3-(1-(2-hydroxyethyl)azetidin-3-yl)-5,7-dimethyl-7,8-dihydroimidazo[1,5-a]pyrazin-6(5H)-one To a solution of the bis(trifluoroacetate) salt of Example 18 (47.7 mg, 0.068 mmol) in DMF (5 mL) was added 2-bromoethanol (37 mg, 0.3 mmol) and TEA (0.5 mL). The mixture was stirred at 50° C. for 2 h, then concentrated under reduced pressure. The residue was purified by reverse phase preparative HPLC (Mobile phase: A=10 mM $NH_4HCO_3$/$H_2O$, B=MeCN; Gradient: B=10% to 50% in 18 min; Column: C18) to give the title compound (5 mg, 14%).

MS ($ES^+$): $C_{27}H_{29}F_2N_7O_2$ requires: 521, found: 522 $[M+H]^+$.

$^1H$ NMR (500 MHz, $CD_3OD$) δ 9.23 (s, 1H), 8.20 (s, 1H), 8.12 (d, J=8.5 Hz, 1H), 8.06 (s, 1H), 7.96-7.86 (m, 1H), 7.63 (d, J=7.0 Hz, 1H), 7.14 (t, J=54.3 Hz, 1H), 5.00 (q, J=7.0 Hz, 1H), 4.94 (d, J=15.5 Hz, 1H), 4.47 (d, J=16.0 Hz, 1H), 4.06-4.03 (m, 4H), 3.98-3.90 (m, 2H), 3.69-3.54 (m, 4H), 3.08 (s, 3H), 2.77-2.74 (m, 2H), 1.68 (d, J=7.1 Hz, 3H).

Examples 29a/29b 1-(3-(Difluoromethyl)-2-(1-methyl-1H-pyrazol-4-yl)quinolin-5-yl)-3-(1,1-dioxidotetrahydro-2H-thiopyran-4-yl)-5,7-dimethyl-7,8-dihydroimidazo[1,5-a]pyrazin-6(5H)-one (separated enantiomers)

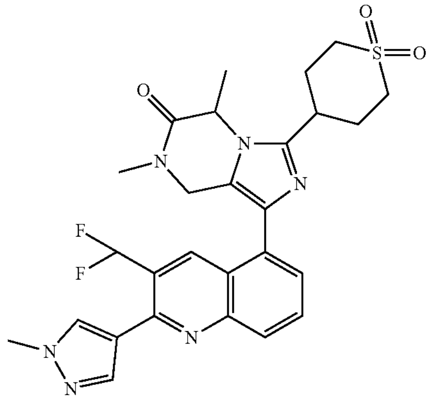

-continued

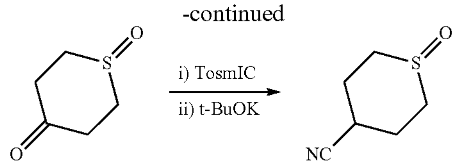

Tetrahydro-2H-thiopyran-4-carbonitrile

To a solution of dihydro-2H-thiopyran-4(3H)-one (10.0 g, 86.2 mmol) and tosylmethyl isocyanide (18.68 g, 94.82 mmol) in 1,2-dimethoxyethane (250 mL) was added a solution of t-BuOK (19.31 g, 172.4 mmol) in 1:1 t-BuOH/1,2-dimethoxyethane (200 mL). The mixture was stirred at RT for 3 h, then diluted with EtOAc and washed with 5% aq. $NaHCO_3$, dried over $Na_2SO_4$, and concentrated under reduced pressure to give the title compound as a brown oil (10.93 g, 100%). MS ($ES^+$): $C_6H_9NS$ requires: 127, found: 128 $[M+H]^+$.

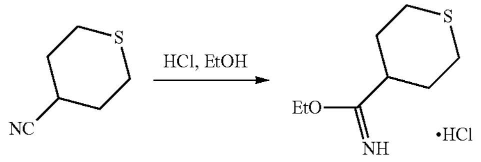

Ethyl tetrahydro-2H-thiopyran-4-carbimidate hydrochloride

A mixture of the product from the previous step (10.93 g, 86 mmol) and EtOH (4.34 g, 103 mmol) in a 4 M HCl in 1,4-dioxane solution (200 mL) was stirred at RT overnight, then diluted with ether (500 mL). The solid that formed was isolated by filtration and dried to give the title compound as a brown solid (15 g, 83%). MS ($ES^+$): $C_8H_{15}NOS$ requires: 173, found: 174 $[M+H]^+$.

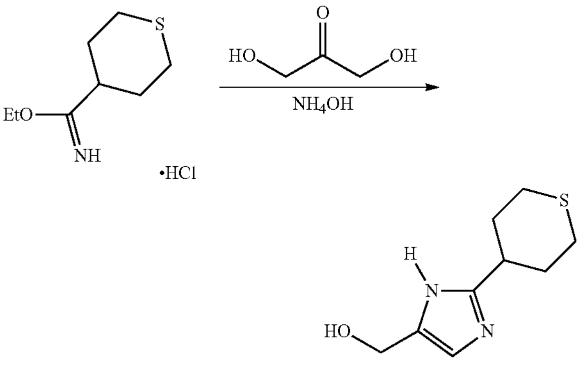

(2-(Tetrahydro-2H-thiopyran-4-yl)-1H-imidazol-5-yl)methanol

A mixture of the product from the previous step (7.5 g, 36 mmol) and 1,3-dihydroxypropan-2-one (3.23 g, 35.9 mmol) in $NH_4OH$ (101 mL. 1.35 mol) was stirred at 90° C. for 4 h in a sealed tube, then concentrated to give the crude title compound as a brown oil (6.48 g, 91%), which was used without further purification. MS ($ES^+$): $C_9H_{14}N_2OS$ requires: 198, found: 119 $[M+H]^+$.

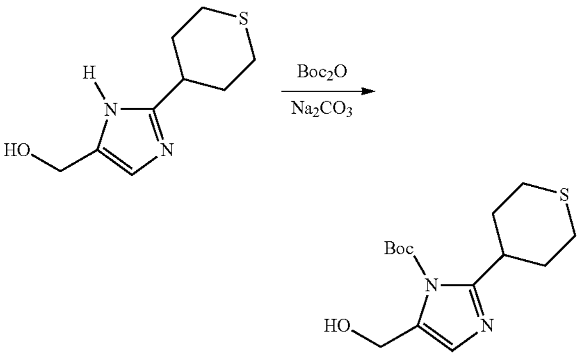

Tert-butyl 5-(hydroxymethyl)-2-(tetrahydro-2H-thiopyran-4-yl)-1H-imidazole-1-carboxylate To a mixture of the product from the previous step (6.48 g, 32.7 mmol) and $Na_2CO_3$ (8.67 g, 81.8 mmol) in 6:1 THF-$H_2O$ (150 mL) was added $Boc_2O$ (10.7 g, 49.1 mmol). The mixture was stirred at RT overnight, then extracted with DCM (60 mL×3). The combined organic layers were washed with sat. aq. NaCl (45 mL), dried over $MgSO_4$, filtered and concentrated under reduced pressure. The residue was purified by $SiO_2$ gel chromatography (25% to 100% EtOAc in petroleum ether) to give the title compound as a yellow oil (4.8 g, 49%). MS ($ES^+$): $C_{14}H_{22}N_2O_3S$ requires: 298, found: 299 $[M+H]^+$.

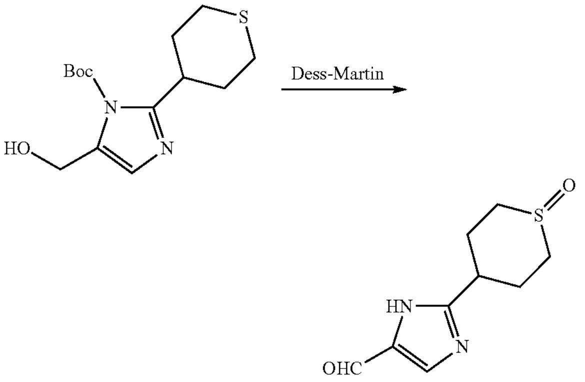

2-(1-Oxidotetrahydro-2H-thiopyran-4-yl)-1H-imidazole-5-carbaldehyde

To a solution of the product from the previous step (4.8 g, 16 mmol) in DCM (120 mL) was added DMP (9.56 g, 22.5 mmol). The mixture was stirred at RT for 2.5 h, then treated with sat. aq. $Na_2SO_3$ and extracted with with DCM (60 mL×3). The combined organic layers were sequentially washed with sat. aq. $Na_2CO_3$ (45 mL×3) and sat. aq. NaCl (45 mL), dried over $MgSO_4$, filtered and concentrated under reduced pressure. The residue was purified by $SiO_2$ gel chromatography (25% to 75% EtOAc in petroleum ether) to give the title compound as a white solid (3.30 g, 97%). MS ($ES^+$): $C_9H_{12}N_2O_2S$ requires: 212, found: 213 $[M+H]^+$.

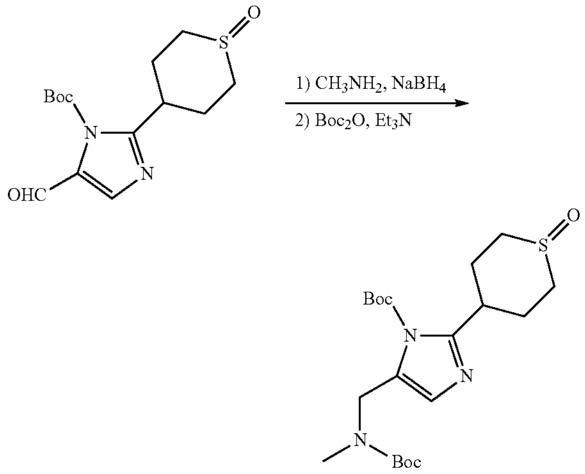

Tert-butyl 5-(((tert-butoxycarbonyl)(methyl)amino)methyl)-2-(1-oxidotetrahydro-2H-thiopyran-4-yl)-1H-imidazole-1-carboxylate A mixture of the product from the previous step (3.30 g, 15.6 mmol) and 2.0 M $CH_3NH_2$ in THF (15.6 mL, 31.1 mmol) in MeOH (45 mL) was stirred at RT for 18 h, then cooled to 0° C. and treated with $NaBH_4$ (1.21 g, 31.1 mmol) portionwise. The mixture was stirred at 0° C. for 30 min, then treated with 1 M aq. NaOH and concentrated under reduced pressure. To the residue was added TEA (4.72 g, 46.7 mmol) in DCM (90 mL), then $Boc_2O$ (10.18 g, 46.71 mmol). The mixture was stirred at RT overnight, then treated with sat. aq. $Na_2CO_3$ (75 mL) and extracted with DCM (60 mL×3). The combined organic layers were washed with sat. aq. NaCl (60 mL), dried over $MgSO_4$, filtered and concentrated under reduced pressure. The residue was purified by $SiO_2$ gel chromatography (10% to 60% EtOAc in petroleum ether) to give the title compound as a colorless oil (2.20 g, 33%). MS ($ES^+$): $C_{20}H_{33}N_3O_5S$ requires: 427, found: 428 $[M+H]^+$.

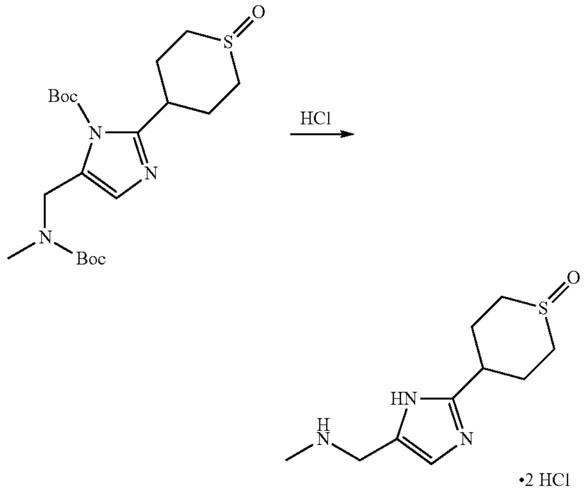

4-(5-((methylamino)methyl)-1H-imidazol-2-yl)tetrahydro-2H-thiopyran 1-oxide bis(hydrochloride)

A mixture of the product from the previous step (2.20 g, 5.15 mmol) in 2.0 M HCl in MeOH (30 mL) was stirred at RT overnight, then concentrated under reduced pressure. The solid was washed with $Et_2O$ (15 mL×2) and dried to give the title compound as a white solid (1.4 g, 91%). MS ($ES^+$): $C_{10}H_{17}N_3OS$ requires: 227, found: 228 $[M+H]^+$.

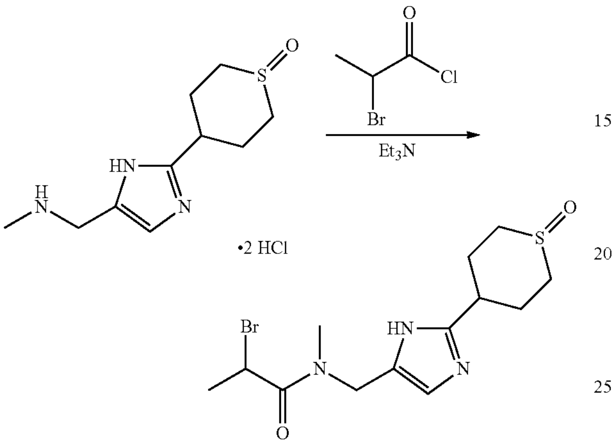

2-Bromo-N-methyl-N-((2-(1-oxidotetrahydro-2H-thiopyran-4-yl)-1H-imidazol-5-yl)methyl)propanamide To a mixture of the product from the previous step (1.4 g, 4.7 mmol) and TEA (1.62 g, 15.96 mmol) in $CHCl_3$ (20 mL) at 0° C. was added 2-bromopropanoyl chloride (758 mg, 4.43 mmol). The mixture was stirred at 0° C. for 30 min, then diluted with DCM (40 mL). The solution was sequentially washed with sat. aq. $Na_2CO_3$ (40 mL×2) and sat. aq. NaCl (45 mL), dried over $MgSO_4$, filtered and concentrated under reduced pressure to give the crude title compound as a yellow oil (700 mg, 41%), which was used without further purification. MS ($ES^+$): $C_{13}H_{20}BrN_3O_2S$ requires: 361, found: 362 $[M+H]^+$.

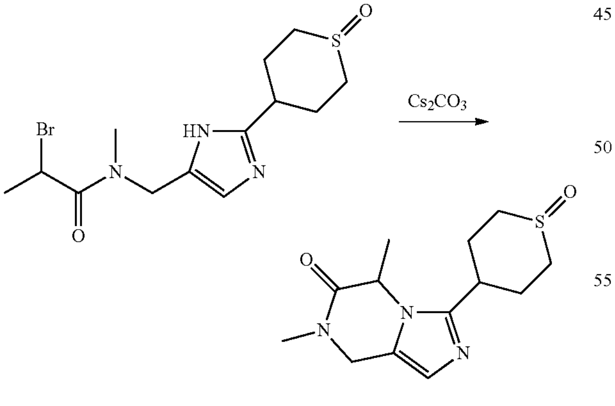

5,7-Dimethyl-3-(1-oxidotetrahydro-2H-thiopyran-4-yl)-7,8-dihydroimidazo[1,5-a]pyrazin-6(5H)-one A degassed solution of the product from the previous step (700 mg, 1.93 mmol) and $Cs_2CO_3$ (1.13 g, 3.47 mmol) in MeCN (20 mL) was stirred at 60° C. for 15 min, then allowed to cool to RT, filtered and the filtrate concentrated under reduced pressure. The residue was purified by $SiO_2$ gel chromatography (0% to 5% MeOH in EtOAc) to give the title compound as a white solid (253 mg, 47%). MS ($ES^+$): $C_{13}H_{19}N_3O_2S$ requires: 281, found: 282 $[M+H]^+$.

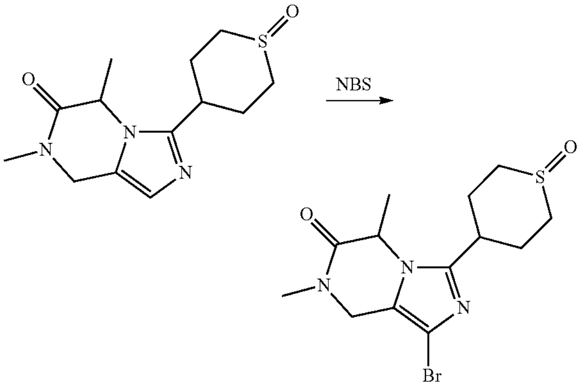

1-bromo-5,7-dimethyl-3-(1-oxidotetrahydro-2H-thiopyran-4-yl)-7,8-dihydroimidazo[1,5-a]pyrazin-6(5H)-one 1-Bromo-3-(1-oxidotetrahydro-2H-thiopyran-4-yl)-5,7-dimethyl-7,8-dihydroimidazo[1,5-a]pyrazin-6(5H)-one To a solution of the product from the previous step (253 mg, 0.900 mmol) in DCM (15 mL) was added NBS (179 mg, 1.01 mmol). The mixture was stirred at RT for 5 min, treated with 1:1 sat. aq. $Na_2SO_3$/sat. aq. $Na_2CO_3$ (5 mL), and extracted with DCM (15 mL×3). The combined organic layers were dried over $MgSO_4$, filtered and concentrated under reduced pressure. The residue was purified by reverse phase preparative HPLC to give the title compound as a white solid (68 mg, 21%). MS ($ES^+$): $C_{13}H_{18}BrN_3O_2S$ requires: 359, found: 360 $[M+H]^+$.

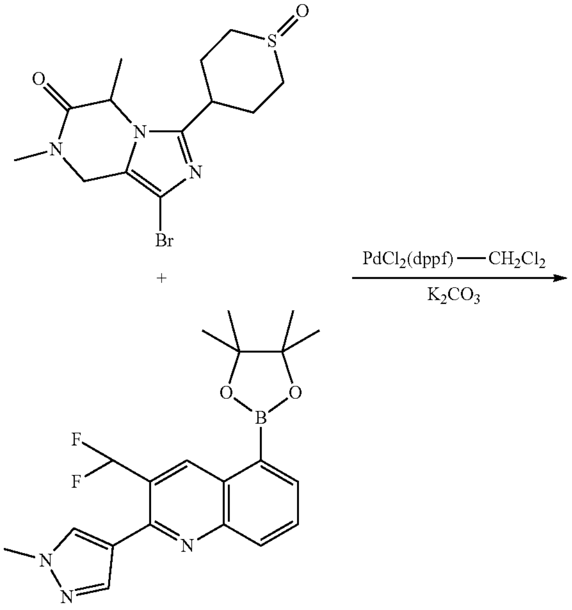

-continued

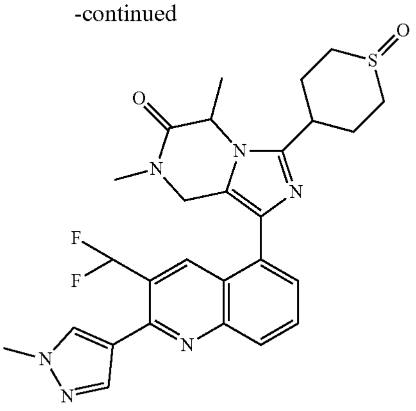

1-(3-(Difluoromethyl)-2-(1-methyl-1H-pyrazol-4-yl)quinolin-5-yl)-5,7-dimethyl-3-(1-oxidotetrahydro-2H-thiopyran-4-yl)-7,8-dihydroimidazo[1,5-a]pyrazin-6(5H)-one To a degassed mixture of the product from the previous step (68 mg, 0.19 mmol), 3-(difluoromethyl)-2-(1-methyl-1H-pyrazol-4-yl)-5-(4,4,5,5-tetramethyl-1,3,2-dioxaborolan-2-yl)quinoline (88 mg, 0.23 mmol) and $PdCl_2(dppf)$-$CH_2Cl_2$ in DMF (2 mL) was added 2.0 M aq. $K_2CO_3$ (0.29 mL, 0.58 mmol). The mixture was purged with $N_2$ for 3 min, stirred at 100° C. for 1 h, and concentrated under reduced pressure. The residue was purified by reverse phase preparative HPLC to give the title compound as a white solid (61 mg, 60%). MS ($ES^+$): $C_{27}H_{28}F_2N_6O_2S$ requires: 538, found: 539.

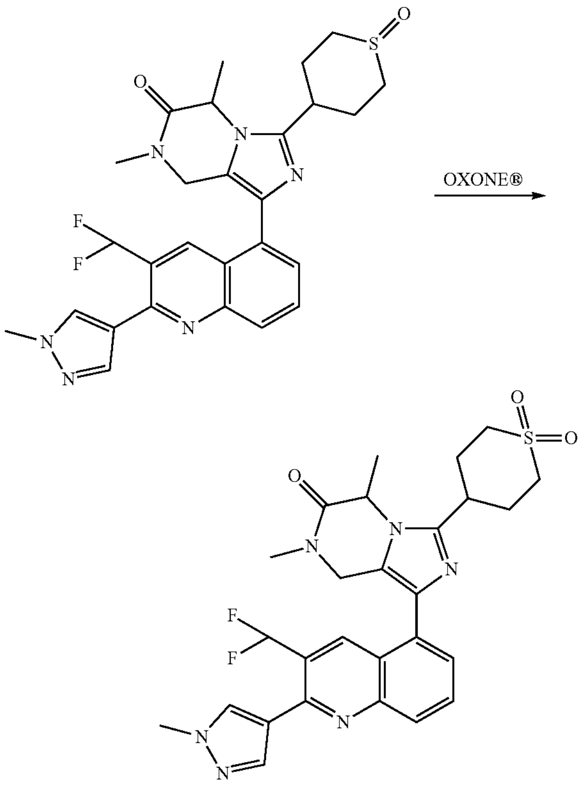

1-(3-(Difluoromethyl)-2-(1-methyl-1H-pyrazol-4-yl)quinolin-5-yl)-3-(1,1-dioxidotetrahydro-2H-thiopyran-4-yl)-5,7-dimethyl-7,8-dihydroimidazo[1,5-a]pyrazin-6(5H)-one (separated enantiomers)

To a mixture of the product from the previous step (61 mg, 0.11 mmol) in acetone (4 mL) and $H_2O$ (1 mL) was added OXONE® (561 mg, 0.912 mmol). The mixture was stirred at RT overnight, then filtered and extracted with DCM (15 mL×3). The combined organic layers were dried over $MgSO_4$, filtered and concentrated under reduced pressure. The residue was purified by reverse phase preparative HPLC (Mobile phase: A=10 mM $NH_4HCO_3/H_2O$+0.01% ammonium hydroxide, B=MeCN; Gradient: B=10% to 38% in 22 min; Column: C18) to give the title racemic compound as a white solid. The racemate was separated by chiral HPLC [Instrument: SFC-80 (Thar, Waters); Column: IG 20*250 mm, 10 um (Daicel); Column temperature: 35° C.; Mobile phase: $CO_2$/MeOH(0.2% 7 M ammonia in MeOH)=30/70; Flow rate: 80 g/min] to give two isomers.

Example 29a was isolated as a white solid (16 mg, 36%). RT=1.38 min.

MS ($ES^+$): $C_{27}H_{28}F_2N_6O_3S$ requires: 554, found: 555 $[M+H]^+$.

$^1H$ NMR (500 MHz, $CD_3OD$ δ 9.05 (s, 1H), 8.07 (s, 1H), 7.98 (d, J=8.5 Hz, 1H), 7.94 (s, 1H), 7.82-7.78 (m, 1H), 7.47 (d, J=6.5 Hz, 1H), 7.01 (t, J=54.3 Hz, 1H), 5.01 (q, J=7.0 Hz, 1H), 4.85 (d, J=16.0 Hz, 1H), 4.37 (d, J=15.5 Hz, 1H), 3.93 (s, 3H), 3.30-3.24 (m, 5H), 2.96 (s, 3H), 2.48-2.42 (m, 2H), 2.33-2.77 (m, 2H), 1.62 (d, J=7.5 Hz, 3H).

Example 29b was isolated as a white solid (18 mg, 40%). RT=2.55 min.

MS ($ES^+$): $C_{27}H_{28}F_2N_6O_3S$ requires: 554, found: 555 $[M+H]^+$.

$^1H$ NMR (500 MHz, $CD_3OD$) δ 9.17 (s, 1H), 8.19 (s, 1H), 8.10 (d, J=8.0 Hz, 1H), 8.06 (s, 1H), 7.93-7.91 (m, 1H), 7.60 (d, J=6.5 Hz, 1H), 7.13 (t, J=54.5 Hz, 1H), 5.13 (q, J=7.5 Hz, 1H), 4.97 (d, J=16.0 Hz, 1H), 4.49 (d, J=16.5 Hz, 1H), 4.05 (s, 3H), 3.40-3.2 (m, 5H), 3.07 (s, 3H), 2.59-2.55 (m, 2H), 2.44-2.36 (m, 2H), 1.74 (d, J=7.0 Hz, 3H).

Examples 30a/30b 5,7-dimethyl-1-(3-(4-methyl-1H-imidazol-1-yl)isoquinolin-8-yl)-3-(tetrahydro-2H-pyran-4-yl)-7,8-dihydroimidazo[1,5-a]pyrazin-6(5H)-one

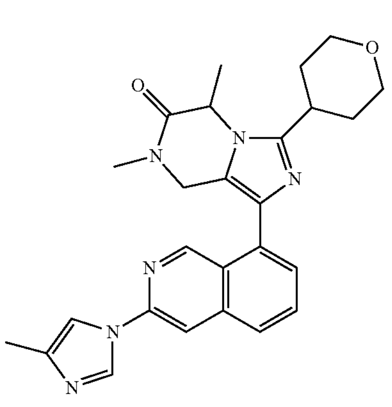 [SMILES: Cc1cn(-c2cc3cccc(-c4nc(C5CCOCC5)n5c4CN(C)C(=O)C5C)c3cn2)cn1]

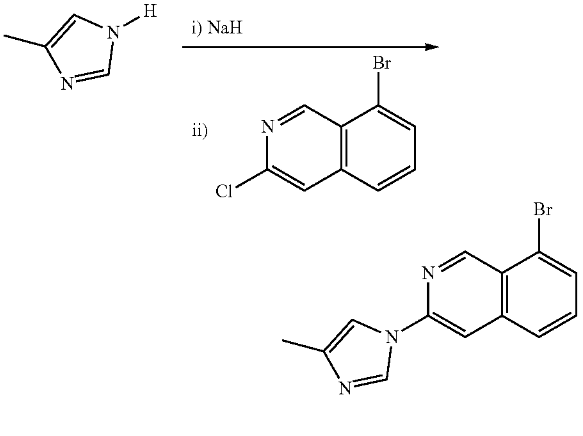

8-Bromo-3-(4-methyl-1H-imidazol-1-yl)isoquinoline

To a mixture of NaH (60% in mineral oil, 94.01 mg, 2.35 mmol) in DMF (5 mL) was added 4-methyl-1H-imidazole (203.14 mg, 2.47 mmol). The mixture was stirred at RT for 2 h, then treated with 8-bromo-3-chloroisoquinoline (300 mg, 1.24 mmol) in DMF (3 mL). The mixture was stirred at 120° C. overnight, then concentrated under reduced pressure. The residue was purified by $SiO_2$ gel chromatography (10% to 60% EtOAc in petroleum ether) to give the title compound as a pale yellow solid (88 mg, 25%). MS ($ES^+$): $C_{13}H_{10}BrN_3$ requires: 287, found: 288 $[M+H]^+$.

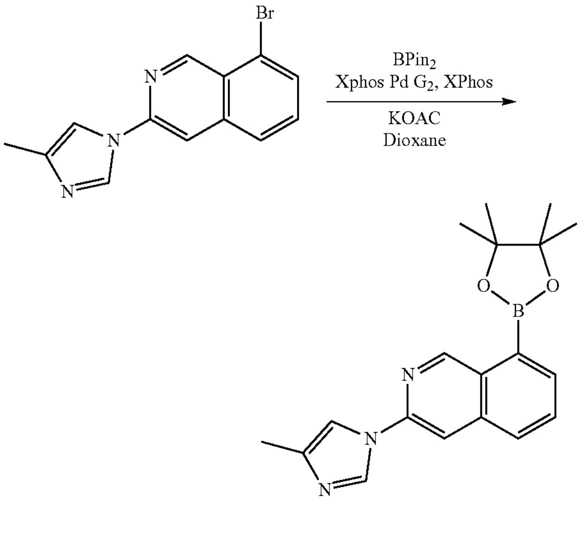

3-(4-Methyl-1H-imidazol-1-yl)-8-(4,4,5,5-tetramethyl-1,3,2-dioxaborolan-2-yl)isoquinoline To a degassed solution of the product from the previous step (85.0 mg, 0.285 mmol) in 1,4-dioxane (2 mL) were added $BPin_2$ (86.9 mg, 0.342 mmol), KOAc (54.4 mg, 0.57 mmol), XPhos Pd G2 (26.6 mg, 0.029 mmol) and XPhos (12.0 mg, 0.029 mmol). The mixture was stirred at 90° C. for 4 h, then concentrated under reduced pressure. The residue was purified by $SiO_2$ gel chromatography (0% to 50% EtOAc in petroleum ether) to give the title compound as an off-white solid (100 mg, 99%). MS ($ES^+$) $C_{19}H_{22}BN_3O_2$ requires: 335, found: 336 $[M+H]^+$.

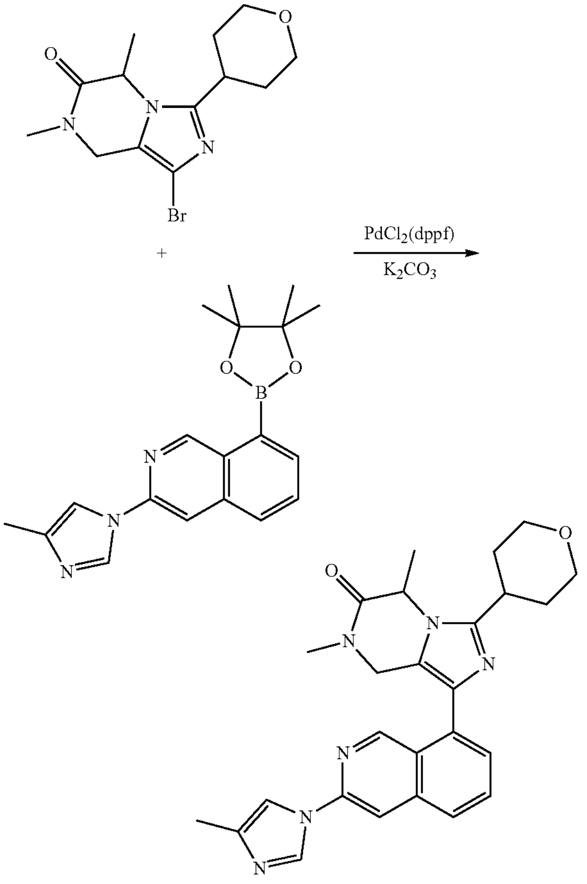

5,7-dimethyl-1-(3-(4-methyl-1H-imidazol-1-yl)isoquinolin-8-yl)-3-(tetrahydro-2H-pyran-4-yl)-7,8-dihydroimidazo[1,5-a]pyrazin-6(5H)-one (separated enantiomers)

To a degassed solution of the product from the previous step (100 mg, 0.299 mmol) in DMF (2 mL) and $H_2O$ (0.5 mL) were added Intermediate "C" (117.8 mg, 0.359 mmol), $K_2CO_3$ (82.5 mg, 0.598 mmol), and $PdCl_2$(dppf) (24.4 mg, 0.030 mmol). The mixture was stirred at 100° C. for 1.5 h, then concentrated under reduced pressure. The residue was purified by reverse phase preparative HPLC (Mobile phase: A=10 mM $NH_4HCO_3/H_2O$, B=MeCN; Gradient: B=40% to 70% in 9 min then 95% for 4 min; Column: C18) to give the title racemic compound. The racemate was separated by chiral HPLC [Instrument: SFC-80 (Thar, Waters); Column: OJ 20*250 mm, 10 um (Daicel); Column temperature: 35° C.; Mobile phase: $C_{02}$/MeOH (0.2% 7 M $NH_3$ in MeOH)=60/40; Flow rate: 80 g/min] to give two isomers.

Example 30a was isolated as an off-white solid (25 mg, 18%). RT=2.88 min.

MS ($ES^+$) $C_{26}H_{28}N_6O_2$ requires: 456, found: 467 $[M+H]^+$.

$^1H$ NMR (500 MHz, DMSO-$d_6$) δ 9.98 (s, 1H), 8.54 (s, 1H), 8.27 (s, 1H), 8.01 (d, J=8.5 Hz, 1H), 7.87-7.73 (m, 1H), 7.68 (s, 1H), 7.42 (d, J=7.0 Hz, 1H), 5.10 (q, J=7.0 Hz, 1H), 5.03 (d, J=16.0 Hz, 1H), 4.50 (d, J=16.0 Hz, 1H), 4.00-3.89 (m, 2H), 3.58-3.45 (m, 2H), 3.24-3.14 (m, 1H), 2.96 (s, 3H), 2.14 (s, 3H), 1.97-1.84 (m, 3H), 1.80-1.71 (m, 1H), 1.60 (d, J=7.0 Hz, 3H).

Example 30b was isolated as an off-white solid (25 mg, 18%). RT=4.13 min.

MS ($ES^+$) $C_{26}H_{28}N_6O_2$ requires: 456, found: 467 $[M+H]^+$.

$^1H$ NMR (500 MHz, DMSO-$d_6$) δ 9.98 (s, 1H), 8.54 (s, 1H), 8.27 (s, 1H), 8.01 (d, J=8.0 Hz, 1H), 7.87-7.73 (m, 1H), 7.68 (s, 1H), 7.42 (d, J=6.5 Hz, 1H), 5.10 (q, J=7.0 Hz, 1H), 5.03 (d, J=16.0 Hz, 1H), 4.50 (d, J=15.5 Hz, 1H), 4.00-3.89 (m, 2H), 3.58-3.45 (m, 2H), 3.24-3.14 (m, 1H), 2.96 (s, 3H), 2.14 (s, 3H), 1.97-1.84 (m, 3H), 1.80-1.71 (m, 1H), 1.60 (d, J=7.0 Hz, 3H).

Examples 31a/31b 5,7-Dimethyl-1-(3-(2-methylthiazol-5-yl)isoquinolin-8-yl)-3-(tetrahydro-2H-pyran-4-yl)-7,8-dihydroimidazo[1,5-a]pyrazin-6(5H)-one (separated enantiomers)

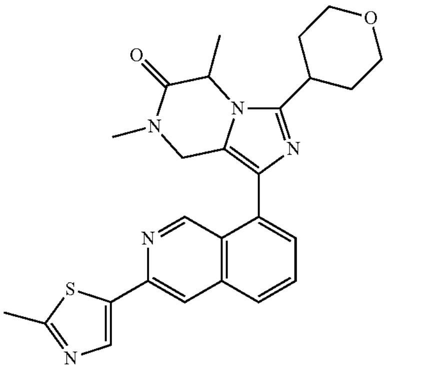 [SMILES: Cc1ncc(-c2cc3cccc(-c4nc(C5CCOCC5)n5c4CN(C)C(=O)C5C)c3cn2)s1]

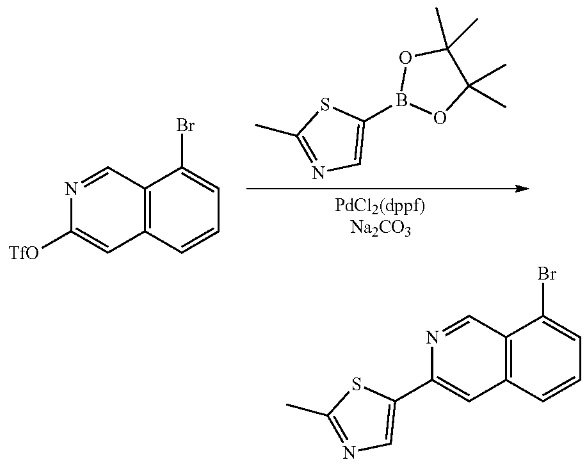

5-(8-Bromoisoquinolin-3-yl)-2-methylthiazole

To a mixture of 8-bromoisoquinolin-3-yl trifluoromethanesulfonate (800 mg, 2.24 mmoles) and 2-methyl-5-(4,4,5,5-tetramethyl-1,3,2-dioxaborolan-2-yl)thiazole (500 mg, 2.24 mmol) in 3:1 THF/$H_2O$ (10 mL) were added $Na_2CO_3$ (700 mg, 6.72 mmol) and $PdCl_2$(dppf) (100 mg, 0.22 mmol). The system was evacuated and then filled with $N_2$ gas. The mixture was stirred at RT overnight, then partitioned between EtOAc (30 mL) and sat. aq. NaCl (30 mL). The organic layer concentrated under reduced pressure, and the residue was purified by $SiO_2$ gel chromatography (0% to 40% EtOAc in petroleum ether) to give the title compound as a white solid (200 mg, 28%). MS ($ES^+$): $C_{13}H_9BrN_2S$ requires: 304, found: 305 $[M+H]^+$.

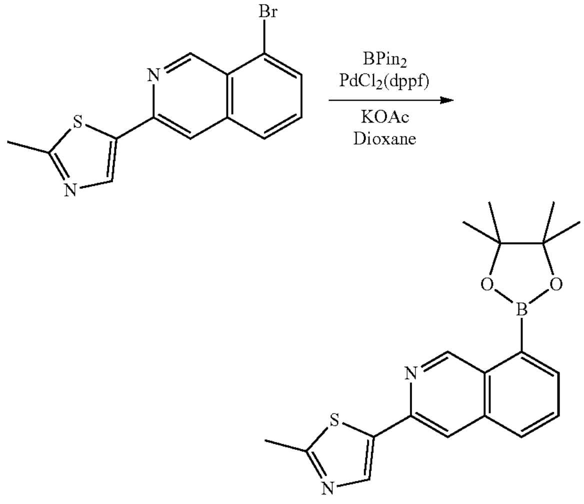

2-Methyl-5-(8-(4,4,5,5-tetramethyl-1,3,2-dioxaborolan-2-yl)isoquinolin-3-yl)thiazole To a mixture of the product from the previous step (200 mg, 0.66 mmol) in 1,4-dioxane (8 mL) and $BPin_2$ (500 mg, 1.98 mmol) were added $PdCl_2$(dppf) (51 mg, 0.063 mmol) and KOAc (258 mg, 2.64 mmol). The mixture was stirred at 100° C. overnight under Ar, then partitioned between EtOAc (30 mL) and sat. aq. NaCl (30 mL). The organic layer was concentrated under reduced pressure, and the residue was purified by $SiO_2$ gel chromatography (0% to 70% EtOAc in petroleum ether) to give the title compound as a white solid (100 mg, 43%). MS ($ES^+$): $C_{19}H_{21}BN_2O_2S$ requires 352, found: 353 $[M+H]^+$.

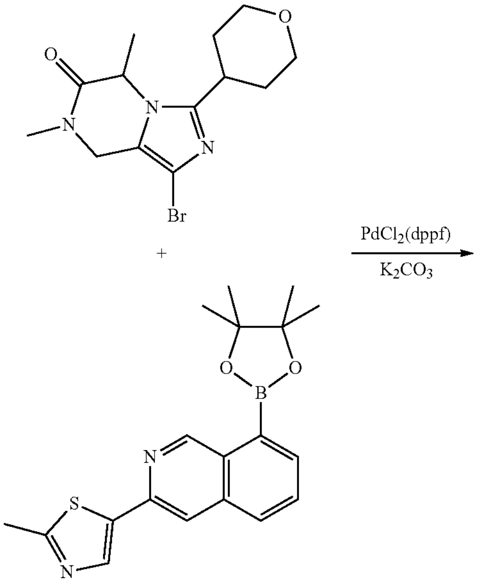

-continued

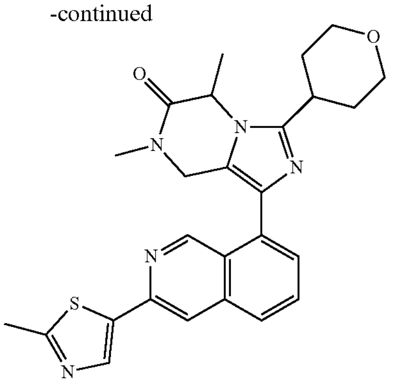

5,7-dimethyl-1-(3-(2-methylthiazol-5-yl)isoquinolin-8-yl)-3-(tetrahydro-2H-pyran-4-yl)-7,8-dihydroimidazo[1,5-a]pyrazin-6(5H)-one (separated enantiomers)

To a mixture of the product from the previous step (353 mg, 1.00 mmoles) and Intermediate "C" (328 mg, 1.00 mmol) in 3:1 DMF/$H_2O$ (10 mL) were added $PdCl_2$(dppf) (50 mg, 0.062 mmol) and $K_2CO_3$ (276 mg; 2.00 mmols). The mixture was stirred at 90° C. for 3 h under Ar, then partitioned between EtOAc (20 mL) and sat. aq. NaCl (20 mL). The organic layer was concentrated under reduced pressure, and the residue was purified by reverse phase preparative HPLC (Mobile phase: A=10 mM $NH_4HCO_3$/$H_2O$, B=MeCN; Gradient: B=10% to 60% in 18 min; Column: C18) to give the title racemic compound as a white solid (100 mg, 21%).

The racemate was separated by chiral HPLC [Instrument: SFC-80 (Thar, Waters); Column: OJ 20*250 mm, 10 um (Daicel); Column temperature: 35° C.; Mobile phase: $CO_2$/MeOH(0.2% 7 M ammonia in MeOH)=60/40; Flow rate: 80 g/min] to give two isomers.

Example 31a was isolated as a white solid (25 mg, 25%). RT=2.57 min.

MS ($ES^+$): $C_{26}H_{27}N_5O_2S$ requires: 473, found: 474 $[M+H]^+$.

$^1H$ NMR (500 MHz, $CD_3OD$) δ 9.59 (s, 1H), 8.30 (s, 1H), 8.27 (s, 1H), 7.99 (d, J=8.4 Hz, 1H), 7.94-7.80 (m, 1H), 7.60 (d, J=6.2 Hz, 1H), 5.12 (q, J=7.1 Hz, 1H), 4.96 (d, J=15.9 Hz, 1H), 4.45 (d, J=15.9 Hz, 1H), 4.10-4.06 (m, 2H), 3.69-3.65 (m, 2H), 3.27-3.14 (m, 1H), 3.07 (s, 3H), 2.78 (s, 3H), 2.23-2.05 (m, 2H), 1.96-1.83 (m, 2H), 1.74 (d, J=7.1 Hz, 3H).

Example 31b was isolated as a white solid (25 mg, 25%). RT=4.75 min.

MS ($ES^+$): $C_{26}H_{27}N_5O_2S$ requires: 473, found: 474 $[M+H]^+$.

$^1H$ NMR (500 MHz, $CD_3OD$) δ 9.49 (s, 1H), 8.31 (appar s, 2H), 8.06 (d, J=8.4 Hz, 1H), 7.94-7.80 (m, 1H), 7.66 (d, J=6.2 Hz, 1H), 5.18 (q, J=7.1 Hz, 1H), 4.95 (d, J=15.9 Hz, 1H), 4.46 (d, J=15.9 Hz, 1H), 5.01-4.07 (m, 2H), 3.70-3.66 (m, 2H), 3.34-3.33 (assumed overlap with solvent peak, 1H), 3.08 (s, 3H), 2.78 (s, 3H), 2.23-2.05 (m, 2H), 2.00-1.83 (m, 2H), 1.77 (d, J=7.1 Hz, 3H).

Examples 32a/32b 1-(3-(Difluoromethyl)-2-(1-methyl-1H-pyrazol-4-yl)quinolin-5-yl)-5,7-dimethyl-3-(4-methyltetrahydro-2H-pyran-4-yl)-7,8-dihydroimidazo[1,5-a]pyrazin-6(5H)-one (separated enantiomers)

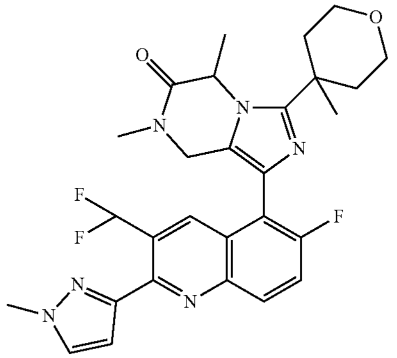

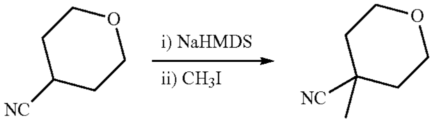

4-Methyltetrahydro-2H-pyran-4-carbonitrile

To a solution of tetrahydro-2H-pyran-4-carbonitrile (10 g, 90 mmol) in dry THF (100 mL) at 0° C. was added dropwise 1.0 M NaHDMS in THF (108 mL, 108 mmol). The mixture was stirred for 1.5 h at 0° C., then treated with $CH_3I$ (38 g, 270 mmol) slowly. The mixture was stirred at RT for 16 h, then cooled to 0° C. and treated with 1 M aq. HCl (150 mL) and extracted with EtOAc (300 mL). The organic layer was washed with sat. aq. NaCl (80 mL×3), dried over $MgSO_4$, filtered and concentrated under reduced pressure to give the title compound as a pale yellow liquid (10 g, 87%). $^1H$ NMR ($CDCl_3$) δ 3.98-3.92 (m, 2H), 3.74-3.65 (m, 2H), 1.89-1.82 (m, 2H), 1.66-1.56 (m, 2H), 1.42 (s, 3H).

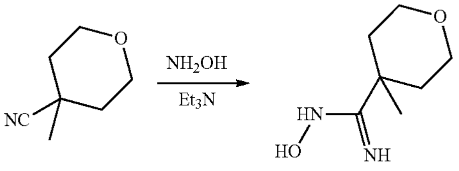

N-Hydroxy-4-methyltetrahydro-2H-pyran-4-carboximidamide

A mixture of the product from the previous step (3.75 g, 30 mmol), hydroxylamine hydrochloride (4.14 g, 60 mmol) and TEA (6.06 g, 60 mmol) in EtOH (50 mL) was stirred at 100° C. overnight under Ar, then concentrated under reduced pressure to give the crude title compound as a white solid (4.74 g, 100%), which was used without further purification. MS ($ES^+$): $C_7H_{14}N_2O_2$ requires: 158, found: 159 $[M+H]^+$.

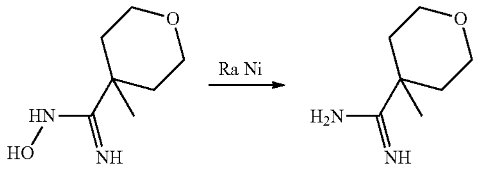

4-Methyltetrahydro-2H-pyran-4-carboximidamide

A mixture of the product from the previous step (4.74 g, 30 mmol), Raney Nickel (1 g, wet) and TEA (6.06 g, 60 mmol) in MeOH (50 mL) was stirred at RT under an atmosphere of $H_2$ overnight. The mixture was filtered and the filtrate concentrated under reduced pressure to give the crude title compound as an oil (4.26 g, 100%), which was used without further purification. MS ($ES^+$): $C_7H_{14}N_2O$ requires: 142, found: 143 $[M+H]^+$.

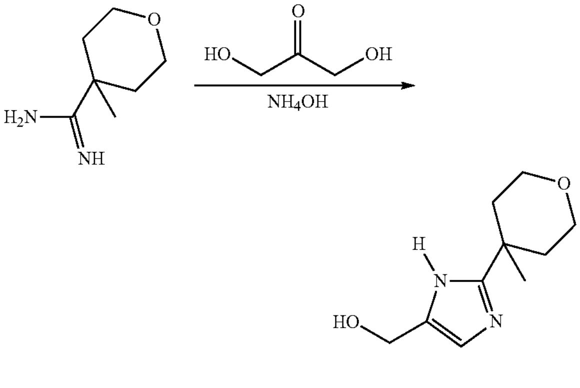

(2-(4-Methyltetrahydro-2H-pyran-4-yl)-1H-imidazol-5-yl)methanol

A mixture of the product from the previous step (4.26 g, 30 mmol) and 1,3-dihydroxypropan-2-one (2.70 g, 30 mmol) in $NH_4OH$ (60 mL) was stirred at 100° C. for 4 h in a sealed tube, then concentrated under reduced pressure. The residue was purified by reverse phase preparative HPLC (Mobile phase: A=10 mM $NH_4HCO_3/H_2O$, B=MeCN; Column: C18) to give the title compound as a yellow solid (2 g, 34%). MS ($ES^+$): $C_{10}H_{16}N_2O_2$ requires: 196, found: 197 $[M+H]^+$.

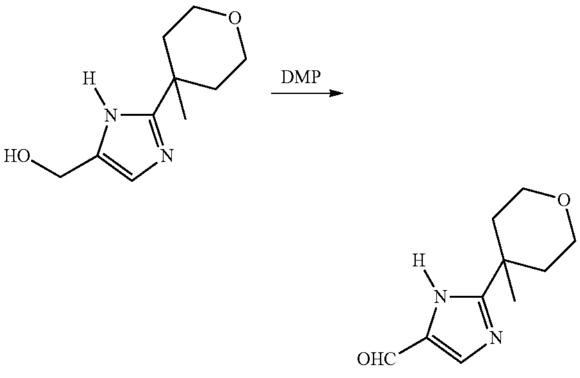

2-(4-Methyltetrahydro-2H-pyran-4-yl)-1H-imidazole-5-carbaldehyde

To a mixture of the product from the previous step (1.3 g, 6.6 mmol) in DCM/DMF (130 mL/30 mL) at 0° C. was added DMP (5.6 g, 13 mmol). The mixture was stirred at RT for 18 h, then treated with sat. aq. $Na_2SO_3$ (100 mL) and sat. aq. $Na_2CO_3$ (100 mL) and extracted with DCM (100 mL). The organic layer was washed with water, dried over $MgSO_4$, filtered and concentrated under reduced pressure to give the crude title compound as a yellow oil (1.3 g, 100%). MS ($ES^+$): $C_{10}H_{14}N_2O_2$ requires: 194, found: 195 $[M+H]^+$.

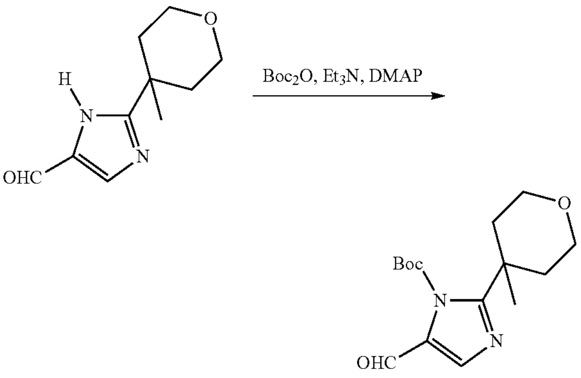

Tert-butyl 5-formyl-2-(4-methyltetrahydro-2H-pyran-4-yl)-1H-imidazole-1-carboxylate To a mixture of the product from the previous step (1.0 g, 5.1 mmol) in DCM (80 mL) at 0° C. was added DMAP (0.20 g, 1.6 mmol), TEA (2.2 mL, 15 mmol), and $Boc_2O$ (2.18 g, 10.0 mmol). The solution was stirred for 18 h at RT, then washed with water, dried over $MgSO_4$, filtered and concentrated under reduced pressure. The residue was purified by $SiO_2$ gel chromatography (3:1 EtOAc/petroleum ether) to give the title compound as a yellow oil (410 mg, 28%). MS ($ES^+$): $C_{15}H_{22}N_2O_4$ requires: 294, found: 295 $[M+H]^+$.

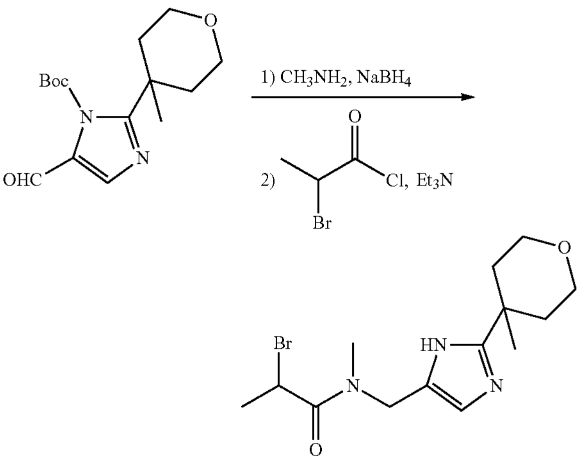

2-Bromo-N-methyl-N-((2-(4-methyltetrahydro-2H-pyran-4-yl)-1H-imidazol-5-yl)methyl)propanamide To a solution of the product from the previous step (410 mg, 1.4 mmol) in MeOH (4 mL) at 0° C. was added 2.0 M $CH_3NH_2$ in THF (3.5 mL, 7.0 mmol). The solution was stirred at RT for 18 h, then cooled to 0° C. and treated with $NaBH_4$ (53 mg, 1.4 mmol). The mixture was stirred at RT for 0.5 h, then concentrated under reduced pressure to give a yellow oil (290 mg), which was treated with DCM (40 mL). The resulting mixture was cooled to 0° C., then treated with TEA (2 mL) and 2-bromopropanoyl chloride (46 mg, 2.8 mmol). The mixture was stirred at RT for 2 h, then washed with sat. aq. $Na_2CO_3$, and the aqueous layer back-extracted with DCM (50 mL). The combined organic layers were dried over $MgSO_4$, filtered and concentrated under reduced pressure to give the crude title compound as a yellow oil (480 mg, 100%), which was used without further purification. MS ($ES^+$): $C_{14}H_{22}BrN_3O_2$ requires: 343, found: 344 $[M+H]^+$.

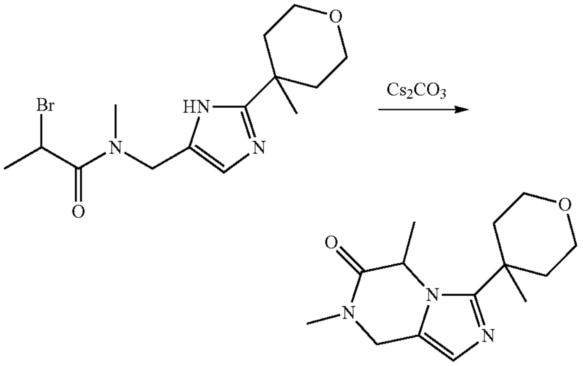

5,7-Dimethyl-3-(4-methyltetrahydro-2H-pyran-4-yl)-7,8-dihydroimidazo[1,5-a]pyrazin-6(5H)-one A mixture of the product from the previous step (233 mg, 0.68 mmoles) and $Cs_2CO_3$ (444 mg, 1.36 mmol) in MeCN (10 mL) was stirred at reflux for 2 h, then filtered and the filtrate concentrated under reduced pressure to give the crude title compound as a yellow oil (178 mg, 100%). MS ($ES^+$): $C_{14}H_{21}N_3O_2$ requires: 263, found: 264 $[M+H]^+$.

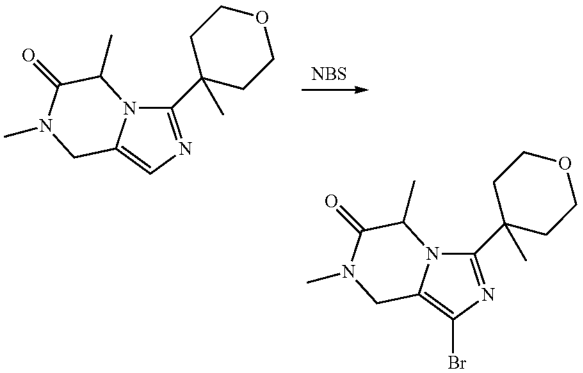

1-Bromo-5,7-dimethyl-3-(4-methyltetrahydro-2H-pyran-4-yl)-7,8-dihydroimidazo[1,5-a]pyrazin-6(5H)-one To a solution of the product from the previous step (178 mg, 0.68 mmol) in DCM (10 mL) was added NBS (121 mg, 0.68 mmol). The mixture was stirred at RT for 2 h, then treated with sat. aq. $Na_2SO_3$ and washed with water, back-extracting with DCM (30 mL). The combined organic layers were dried over $MgSO_4$, filtered and concentrated under reduced pressure to give the crude title compound as a yellow oil (232 mg, 100%). MS ($ES^+$): $C_{14}H_{20}BrN_3O_2$ requires: 341, found: 342 $[M+H]^+$.

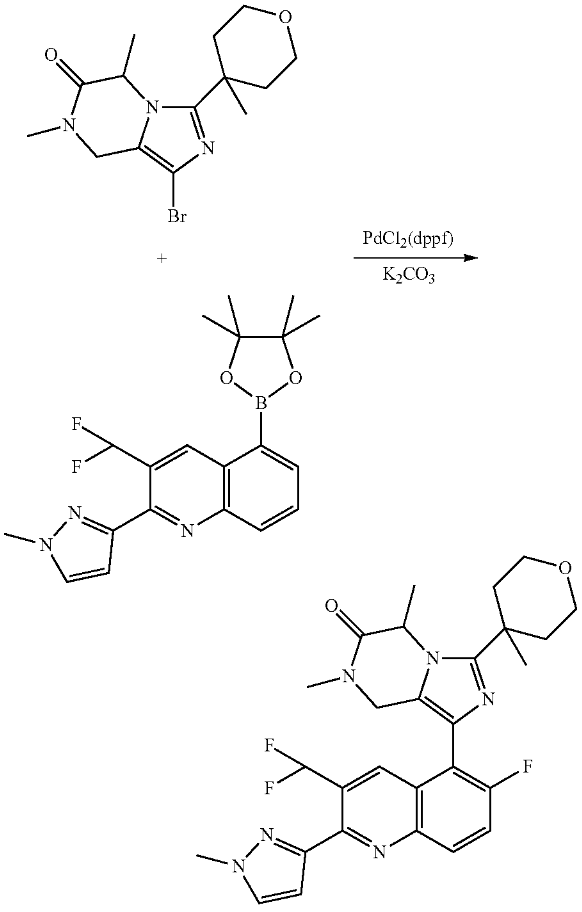

1-(3-(Difluoromethyl)-2-(1-methyl-1H-pyrazol-4-yl)quinolin-5-yl)-5,7-dimethyl-3-(4-methyltetrahydro-2H-pyran-4-yl)-7,8-dihydroimidazo[1,5-al]pyrazin-6(5H)-one (separated enantiomers)

To a mixture of the product from the previous step (100 mg, 0.29 mmol) and 3-(difluoromethyl)-2-(1-methyl-1H-pyrazol-4-yl)-5-(4,4,5,5-tetramethyl-1,3,2-dioxaborolan-2-yl)quinoline (115 mg, 0.29 mmol) in 2:1 DMF/$H_2O$ (10 mL) was added $PdCl_2(dppf)$ (30 mg, 0.03 mmol) and $K_2CO_3$ (100 mg, 0.7 mmol). The mixture was stirred at 90° C. for 3 h under Ar gas, then partitioned between EtOAc (20 mL) and sat. aq. NaCl (20 mL). The organic layer was concentrated under reduced pressure, and the residue was purified by reverse phase preparative HPLC (Mobile phase: A=10 mM $NH_4HCO_3/H_2O$, B=MeCN; Gradient: B=35% to 65% in 18 min; Column: C18) to give the title racemic compound as a white solid (35 mg, 24%).

The racemate was separated by chiral HPLC [Instrument: SFC-80 (Thar, Waters); Column: OJ 20*250 mm, 10 um (Daicel); Column temperature: 35° C.; Mobile phase: $CO_2$/MeOH(0.2% 7 M ammonia in MeOH)=50/50; Flow rate: 80 g/min] to give two isomers.

Example 32a (15 mg, 42%). RT=1.14 min.

MS ($ES^+$): $C_{28}H_{30}F_2N_6O_2$ requires: 520, found: 521 $[M+H]^+$.

$^1$H NMR (500 MHz, $CD_3OD$) δ 9.33 (s, 1H), 8.18 (s, 1H), 8.10 (d, J=8.5 Hz, 1H), 8.05 (s, 1H), 7.95-7.91 (m, 1H), 7.60 (d, J=7.0 Hz, 1H), 7.13 (t, J=15.9 Hz, 1H), 5.21 (q, J=7.0 Hz, 1H), 4.99 (d, J=16.0 Hz, 1H), 4.47 (d, J=16.0 Hz, 1H), 4.05 (s, 3H), 3.88-3.84 (m, 4H), 3.07 (s, 3H), 2.54-2.36 (m, 2H), 2.02-1.83 (m, 2H), 1.74 (d, J=7.0 Hz, 3H), 1.52 (s, 3H).

Example 32b (15 mg, 42%). RT=2.18 min.

MS ($ES^+$): $C_{28}H_{30}F_2N_6O_2$ requires: 520, found: 521 $[M+H]^+$.

$^1$H NMR (500 MHz, $CD_3OD$) δ 9.33 (s, 1H), 8.18 (s, 1H), 8.10 (d, J=8.5 Hz, 1H), 8.05 (s, 1H), 7.95-7.91 (m, 1H), 7.60 (d, J=7.0 Hz, 1H), 7.13 (t, J=15.9 Hz, 1H), 5.21 (q, J=7.0 Hz, 1H), 4.99 (d, J=16.0 Hz, 1H), 4.47 (d, J=16.0 Hz, 1H), 4.05 (s, 3H), 3.88-3.84 (m, 4H), 3.07 (s, 3H), 2.54-2.36 (m, 2H), 2.02-1.83 (m, 2H), 1.74 (d, J=7.0 Hz, 3H), 1.52 (s, 3H).

Examples 33a/33b 1-(7-fluoro-3-(4-methyl-1H-imidazol-1-yl)isoquinolin-8-yl)-5,7-dimethyl-3-(tetrahydro-2H-pyran-4-yl)-7,8-dihydroimidazo[1,5-a]pyrazin-6(5H)-one (separated enantiomers)

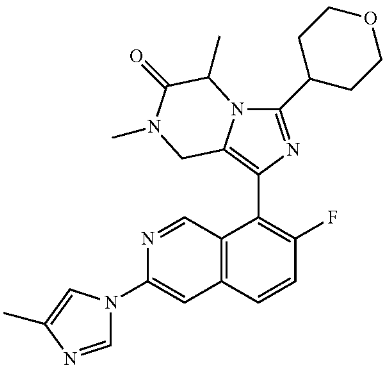 [SMILES: Cc1cn(-c2cc3ccc(F)c(-c4nc(C5CCOCC5)n5c4CN(C)C(=O)C5C)c3cn2)cn1]

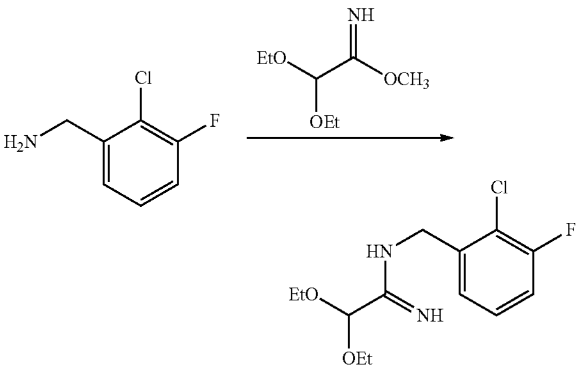

N-(2-Chloro-3-fluorobenzyl)-2,2-diethoxyacetimidamide

A mixture of (2-chloro-3-fluorophenyl)methanamine (5.00 g, 31.3 mmole) and methyl 2,2-diethoxyacetimidate (6.06 g, 37.6 mmoles) in MeOH (60 mL) was stirred at RT for 3 h, then concentrated under reduced pressure. The residue was diluted with DCM (210 mL) and washed with sat. aq. NaCl (90 mL×3), dried over $Na_2SO_4$, filtered and concentrated under reduced pressure. The resulting oil was allowed to stand for 3 h to give the title compound as a white solid (8.1 g, 90%). MS ($ES^+$): $C_{13}H_{18}ClFN_2O_2$ requires: 288, found: 289 $[M+H]^+$.

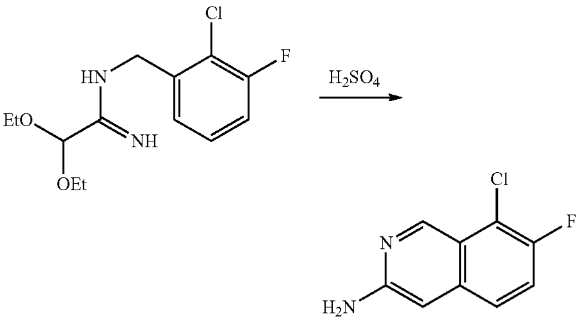

8-Chloro-7-fluoroisoquinolin-3-amine

To the product from the previous step (3.00 g, 10.4 mmol) at 0° C. was added cone. aq. sulfuric acid (25 g). The mixture was stirred at 0° C. for 30 min, then at 80° C. for 3 h, then allowed to cool to RT and poured into ice water. The mixture was adjusted to pH=12.0 using 10 M aq. NaOH at 0° C. Precipitate was collected by filtration and dried to give the title compound as a yellow solid (1.87 g, 92%). MS ($ES^+$): $C_9H_6ClFN_2$ requires: 196, found: 197 $[M+H]^+$.

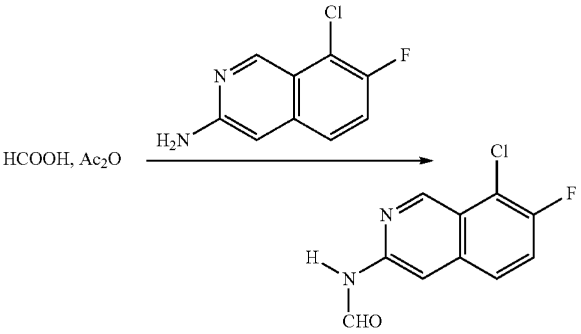

N-(8-Chloro-7-fluoroisoquinolin-3-yl)formamide

A mixture of formic acid (4.50 mL, 117 mmol) and acetic anhydride (3 mL) was stirred at RT for 45 min, then treated dropwise with the product from the previous step (1.50 g, 7.63 mmol) in THF (10 mL). The mixture was stirred at 60° C. for 3 h, then allowed to cool to RT and poured into ice-water. The precipitate was collected by filtration to give the title compound as a yellow solid (1.56 g, 91%). MS ($ES^+$): $C_{10}H_6ClFN_2O$ requires: 224, found: 225 $[M+H]^+$.

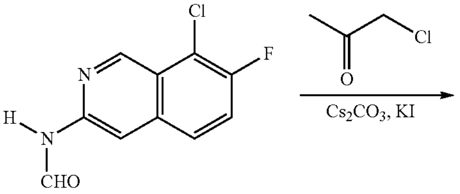

-continued

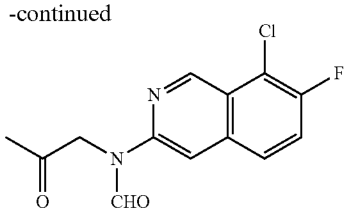

N-(8-Chloro-7-fluoroisoquinolin-3-yl)-N-(2-oxopropyl)formamide

A mixture of the product from the previous step (1.50 g, 6.68 mmol), chloroacetone (1.33 mL, 16.7 mmol), KI (110.85 mg, 667.79 μmoles) and $Cs_2CO_3$ (7.62 g, 23.4 mmol) in DMF (25 mL) was stirred at RT overnight, then poured into ice-water and extracted with EtOAc (60 mL×3). The combined organic layers were washed with sat. aq. NaCl (25 mL×3), dried over $Na_2SO_4$, filtered and concentrated under reduced pressure to give the title compound as a pale yellow solid (1.26 g, 67%). MS ($ES^+$): $C_{13}H_{10}ClFN_2O_2$ requires: 280, found: 281 $[M+H]^+$.

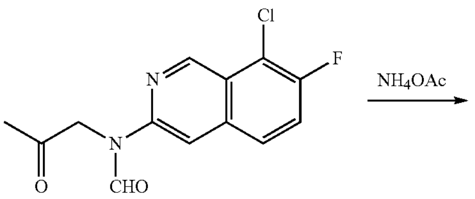

-continued

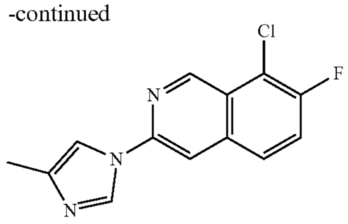

8-Chloro-7-fluoro-3-(4-methyl-1H-imidazol-1-yl) isoquinoline

A mixture of the product from the previous step (1.26 g, 4.49 mmol) and $NH_4OAc$ (1.73 g, 22.5 mmol) in AcOH (15 mL) was stirred at 130° C. for 5 h, allowed to cool to RT and poured into ice-water. The mixture was adjusted to pH=9.0 using 50% w/v aq. NaOH, then extracted with EtOAc (45 mL×3). The combined organic layers were washed with sat. aq. NaCl (50 mL), dried over $Na_2SO_4$, filtered and concentrated under reduced pressure. The residue was purified by $SiO_2$ gel chromatography (45% to 100% EtOAc in petroleum ether) to give the title compound as a pale yellow solid (830 mg, 71%). MS ($ES^+$): $C_{13}H_9ClFN_3$ requires: 261, found: 262 $[M+H]^+$.

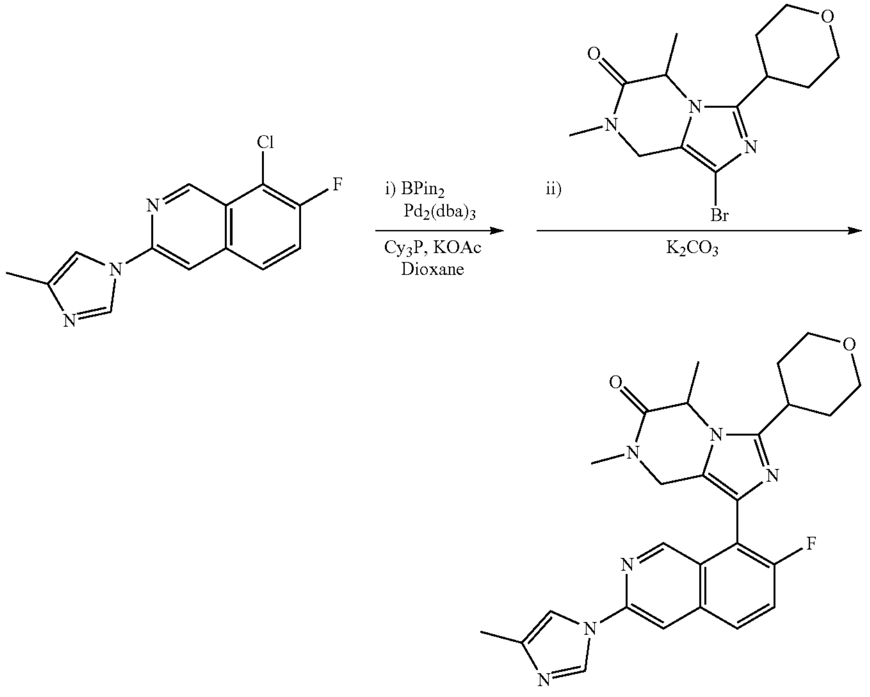

1-(7-Fluoro-3-(4-methyl-1H-imidazol-1-yl)isoquinolin-8-yl)-5,7-dimethyl-3-(tetrahydro-2H-pyran-4-yl)-7,8-dihydroimidazo[1,5-a]pyrazin-6(5H)-one (separated enantiomers)

A mixture of $Pd_2(dba)_3$ (214.25 mg, 229.28 μmol) and tricyclohexylphosphine (257.19 mg, 917.13 mmoles) in 1,4-dioxane (20 mL) was stirred at RT under $N_2$ for 30 min. To the mixture were added the product from the previous step (300 mg, 1.15 mmoles), $BPin_2$ (445.60 mg, 1.72 mmoles) and KOAc (340.98 mg, 3.44 mmol). The mixture was purged with $N_2$, then sealed and stirred at 120° C. overnight. The mixture was allowed to cool to RT, filtered and concentrated under reduced pressure. To the residue was added 1,4-dioxane (25 mL), Intermediate "C" (200 mg; 609.37 mmoles), 2.0 M aq $K_2CO_3$ (0.914 mL, 1.83 mmoles) and $PdCl_2$(dppf) (50.78 mg, 60.94 μmol). The mixture was degassed and purged with $N_2$, stirred at 90° C. for 1.5 h, and concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title racemic compound as a light yellow solid (96 mg, 33%).

The racemate was separated by chiral HPLC [Instrument: SFC-80 (Thar, Waters); Column: OJ 20*250 mm, 10 um (Daicel); Column temperature: 35° C.; Mobile phase: $C_{02}$/EtOH(0.1% 7 M $NH_3$ in MeOH)=75/25; Flow rate: 80 g/min] to give two isomers.

Example 33a was isolated as a white solid (29 mg, 30%). RT=2.46 min.

MS ($ES^+$): $C_{26}H_{27}FN_6O_2$ requires: 474, found: 475 $[M+H]^+$.

$^1H$ NMR (500 MHz, $CD_3OD$) δ 9.44 (s, 1H), 8.53 (s, 1H), 8.21-8.01 (m, 2H), 7.75 (appar t, J=9.4 Hz, 1H), 7.70 (s, 1H), 5.14 (q, J=7.0 Hz, 1H), 4.82 (d, J=16.0 Hz, 1H), 4.40 (d, J=16.1 Hz, 1H), 4.18-3.98 (m, 2H), 3.67 (appar t, J=11.7 Hz, 2H), 3.29-3.18 (m, 1H), 3.08 (s, 3H), 2.31 (s, 3H), 2.17-2.04 (m, 2H), 1.96-1.88 (m, 2H), 1.74 (d, J=7.1 Hz, 3H).

Example 33b was isolated as a white solid (31 mg, 32%).

MS ($ES^+$): $C_{26}H_{27}FN_6O_2$ requires: 474, found: 475 $[M+H]^+$.

$^1H$ NMR (500 MHz, $CD_3OD$) δ 9.44 (s, 1H), 8.52 (s, 1H), 8.22-8.04 (m, 2H), 7.77-7.73 (m, 1H), 7.70 (s, 1H), 5.14 (q, J=7.0 Hz, 1H), 4.81 (d, J=16.1 Hz, 1H), 4.40 (d, J=16.1 Hz, 1H), 4.18-4.05 (m, 2H), 3.67 (appar t, J=11.7 Hz, 2H), 3.29-3.18 (m, 1H), 3.08 (s, 3H), 2.31 (s, 3H), 2.20-2.04 (m, 2H), 1.96-1.88 (m, 2H), 1.74 (d, J=7.1 Hz, 3H).

Examples 34a/34b

1-(7-Fluoro-3-(tetrahydro-2H-pyran-4-yl)isoquinolin-8-yl)-5,7-dimethyl-3-(tetrahydro-2H-pyran-4-yl)-7,8-dihydroimidazo[1,5-a]pyrazin-6(5H)-one (separated enantiomers)

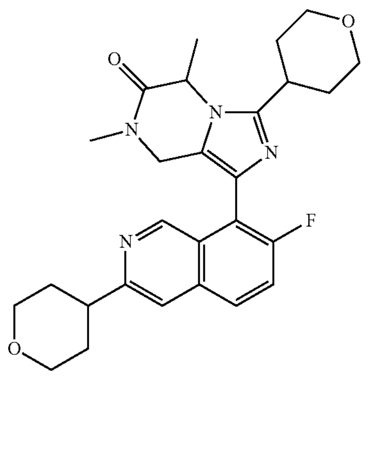 [SMILES: CC1C(=O)N(C)Cc2c(-c3c(F)ccc4cc(C5CCOCC5)ncc34)nc(C3CCOCC3)n21]

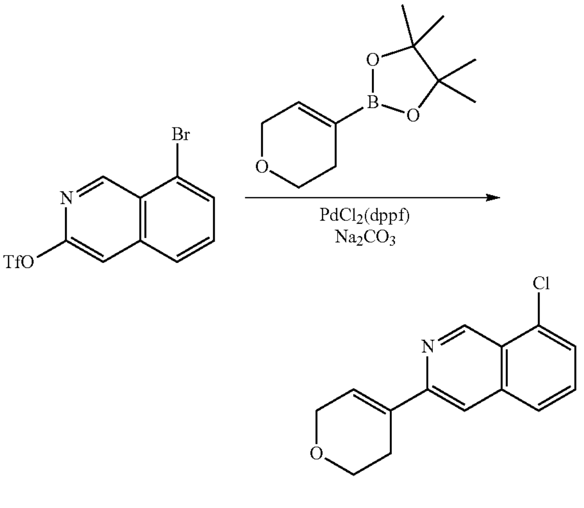

8-chloro-3-(3,6-dihydro-2H-pyran-4-yl)-7-fluoroisoquinoline

A mixture of 8-chloro-7-fluoroisoquinolin-3-yl trifluoromethanesulfonate (2.0 g, 6.0 mmol), 2-(3,6-dihydro-2H-pyran-4-yl)-4,4,5,5-tetramethyl-1,3,2-dioxaborolane (1.5 g, 7.3 mmol), $K_2CO_3$ (2.5 g, 18 mmol) and $PdCl_2$(dppf) (490 mg, 0.6 mmol) in THF/$H_2O$ (20 mL/4 mL) was degassed and purged with $N_2$. The mixture was stirred at 80° C. for 4 h, then concentrated under reduced pressure. The residue was purified by $SiO_2$ gel chromatography (0% to 50% EtOAc in petroleum ether) to give the title compound as a white solid (1.1 g, 69%). MS ($ES^+$): $C_{14}H_{11}ClFNO$ requires: 263, found: 264 $[M+H]^+$.

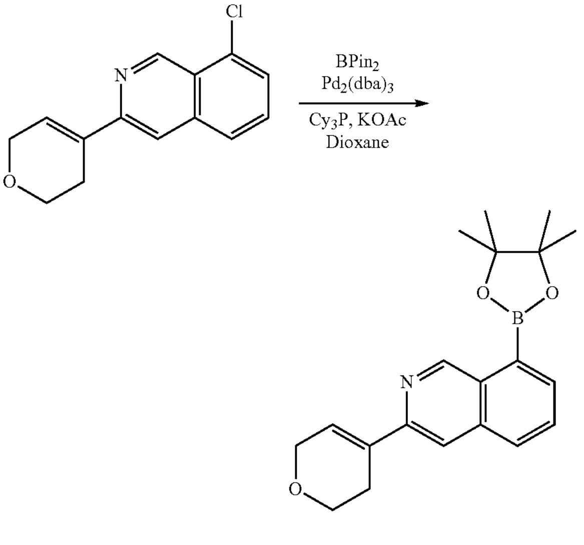

3-(3,6-Dihydro-2H-pyran-4-yl)-7-fluoro-8-(4,4,5,5-tetramethyl-1,3,2-dioxaborolan-2-yl)isoquinoline A mixture of $Pd_2(dba)_3$ (37 mg, 0.04 mmol) and tricyclohexylphosphine (42 mg, 0.15 mmol) in dry 1,4-dioxane (3 mL) was stirred at RT under $N_2$ for 30 min, then treated with the product from the previous step (100 mg, 0.38 mmol), $BPin_2$ (125 mg, 0.49 mmol) and KOAc (125 mg, 1.14 mmol). The resulting mixture was purged with $N_2$ for 5 min, then sealed and stirred at 120° C. overnight. The mixture was allowed to cool to RT, then concentrated under reduced pressure to give the crude title compound, which was used directly in the next step. MS ($ES^+$): $C_{20}H_{23}BFNO_3$ requires: 355, found: 356 $[M+H]^+$.

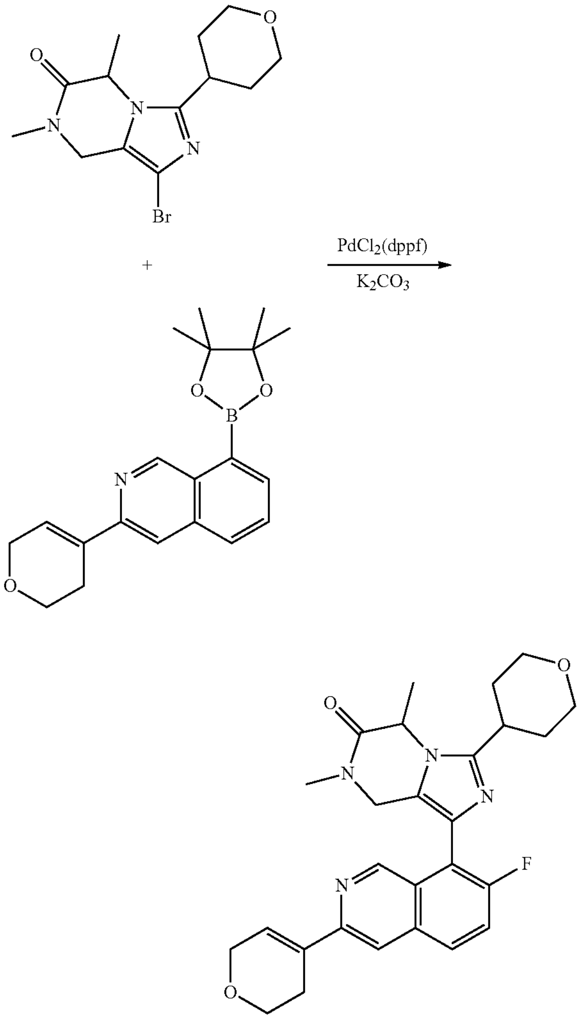

1-(3-(3,6-Dihydro-2H-pyran-4-yl)-7-fluoroisoquinolin-8-yl)-5,7-dimethyl-3-(tetrahydro-2H-pyran-4-yl)-7,8-dihydroimidazo[1,5-al]pyrazin-6(5H)-one A mixture of Intermediate "C" (80 mg, 0.24 mmol), the product from the previous step (crude, 0.38 mmol), 2.0 M $K_2CO_3$ (0.36 mL, 0.72 mmol) and $PdCl_2(dppf)$ (25 mg, 0.03 mmol) in 1,4-dioxane (3 mL) was degassed and purged with $N_2$. The mixture was stirred at 100° C. for 2 h. This reaction was repeated 5 times, and the crude mixtures combined and concentrated under reduced pressure. The residue was purified by $SiO_2$ gel chromatography (0% to 10% MeOH/EtOAc) to give the title compound as a dark yellow solid (330 mg, 58%). MS ($ES^+$): $C_{27}H_{29}FN_4O_3$ requires: 476, found: 477 $[M+H]^+$.

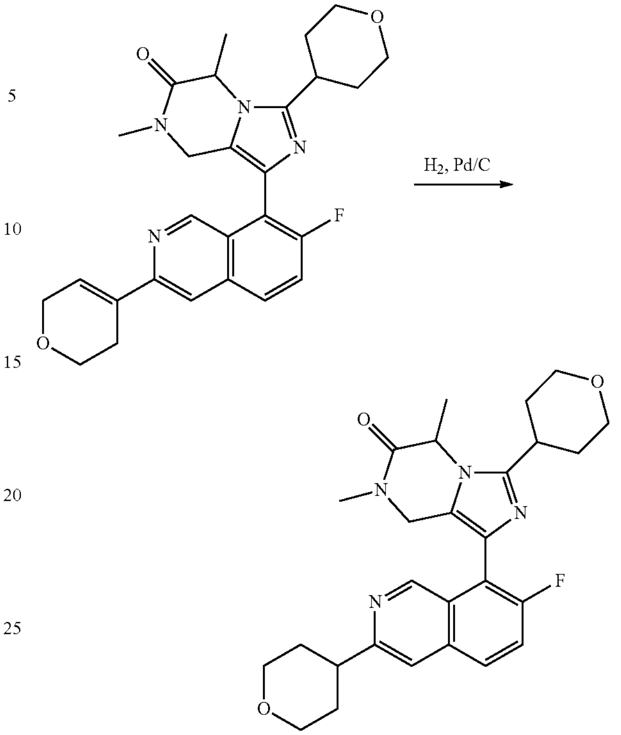

1-(7-Fluoro-3-(tetrahydro-2H-pyran-4-yl)isoquinolin-8-yl)-5,7-dimethyl-3-(tetrahydro-2H-pyran-4-yl)-7,8-dihydroimidazo[1,5-al]pyrazin-6(5H)-one (separated enantiomers)

A mixture of the product from the previous step (330 mg, 0.69 mmol) and 10% Pd/C (200 mg) in EtOH (25 mL) was degassed and purged with $H_2$, then stirred at RT under an atmosphere of $H_2$ overnight. The mixture was filtered and the filtrate concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the title racemic compound as a light yellow solid.

The racemate was separated by chiral HPLC [Instrument: SFC-80 (Thar, Waters); Column: OJ 20*250 mm, 10 um (Daicel); Column temperature: 35° C.; Mobile phase: $CO_2$/EtOH(0.1% 7 M ammonia in MeOH)=75/25; Flow rate: 80 g/min] to give two isomers.

Example 34a was isolated as a white solid (61 mg, 24%). RT=1.71 min.

MS ($ES^+$): $C_{27}H_{31}FN_4O_3$ requires: 478, found: 479 $[M+H]^+$.

$^1H$ NMR (500 MHz, DMSO-$d_6$) δ 9.59 (s, 1H), 8.07-8.04 (m, 1H), 7.88-7.70 (m, 2H), 5.12 (q, J=7.0 Hz, 1H), 4.76 (d, J=15.8 Hz, 1H), 4.33 (d, J=15.9 Hz, 1H), 4.07-3.92 (m, 4H), 3.56-3.48 (m, 4H), 3.26-3.21 (m, 1H), 3.12-3.04 (m, 1H), 2.94 (s, 3H), 1.95-1.78 (m, 8H), 1.61 (d, J=7.1 Hz, 3H).

Example 34b was isolated as a white solid (49 mg, 20%). RT=2.54 min.

MS ($ES^+$): $C_{27}H_{31}FN_4O_3$ requires: 478, found: 479 $[M+H]^+$.

$^1H$ NMR (500 MHz, DMSO-$d_6$) δ 9.59 (s, 1H), 8.08-8.05 (m, 1H), 7.85-7.73 (m, 2H), 5.12 (q, J=7.0 Hz, 1H), 4.77 (d, J=15.9 Hz, 1H), 4.33 (d, J=15.9 Hz, 1H), 4.02-3.91 (m, 4H), 3.55-3.45 (m, 4H), 3.27-3.21 (m, 1H), 3.14-3.03 (m, 1H), 2.94 (s, 3H), 1.91-1.79 (m, 8H), 1.61 (d, J=7.1 Hz, 3H).

Example 35

1-(6-Fluoro-2-(1-methyl-1H-pyrazol-4-yl)-3-(trifluoromethyl)quinolin-5-yl)-5,7-dimethyl-3-(tetrahydro-2H-pyran-4-yl)-7,8-dihydroimidazo[1,5-a]pyrazin-6(5H)-one

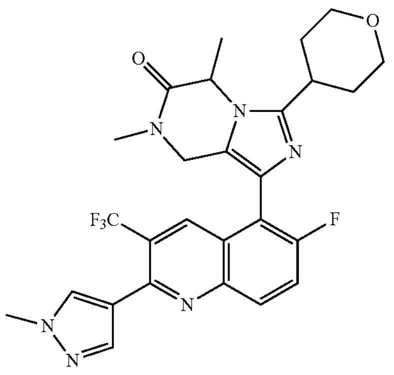 [SMILES: CC1C(=O)N(C)Cc2c(-c3c(F)ccc4nc(-c5cnn(C)c5)c(C(F)(F)F)cc34)nc(C3CCOCC3)n21]

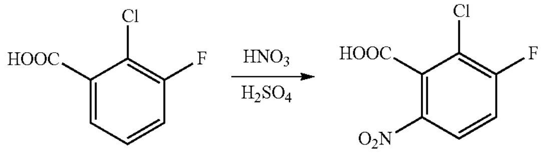

2-Chloro-3-fluoro-6-nitrobenzoic acid

To a solution of 2-chloro-3-fluorobenzoic acid (5.00 g, 28.7 mmol) in conc. aq. $H_2SO_4$ (50 mL) at 0° C. was added conc. aq. $HNO_3$ (1.54 mL, 34.5 mmol) dropwise. The mixture was stirred at 0° C. for 1.5 h, then poured onto ice water. The precipitate was collected by filtration to give the title compound as a white solid (5.0 g, 80%). MS ($ES^+$) $C_7H_3ClFNO_4$ requires: 219, found: 220 $[M+H]^+$.

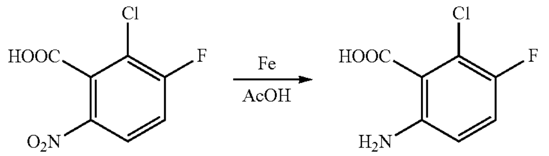

6-Amino-2-chloro-3-fluorobenzoic acid

To a solution of the product from the previous step (5.0 g, 23 mmol) in AcOH (50 mL) was added Fe (25.5 mg, 45.6 mmol). The reaction mixture was stirred at RT overnight, then sequentially treated with aq. HCl (20 mL) and aq. NaOH (20 mL). The mixture was extracted with DCM (100 mL×3). The combined organic layers were sequentially washed with water and sat. aq. NaCl, dried over $Na_2SO_4$, filtered and concentrated under reduced pressure. The residue was purified by $SiO_2$ gel chromatography (0% to 15% MeOH in DCM) to give the title compound as a yellow oil (2.5 g, 58%). MS ($ES^+$) $C_7H_5ClFNO_2$ requires: 189, found: 190 $[M+H]^+$.

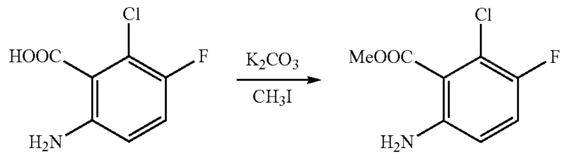

Methyl 6-amino-2-chloro-3-fluorobenzoate

To a solution of the product from the previous step (2.00 g, 10.6 mmol) in DMF (10 mL) was added $CH_3I$ (1.80 g, 12.7 mmol) and $K_2CO_3$ (2.90 g, 21.2 mmol). The reaction mixture was stirred at RT overnight, then washed with $H_2O$ (50 mL) and extracted with EtOAc (50 mL×3). The combined organic layers were sequentially washed with water and sat. aq. NaCl, dried over $Na_2SO_4$, filtered and concentrated under reduced pressure. The residue was purified by $SiO_2$ gel chromatography (0% to 15% EtOAc in hexanes) to give the title compound as a yellow oil (1.3 g, 93%). MS ($ES^+$) $C_8H_7ClFNO_2$ requires: 203, found: 204 $[M+H]^+$.

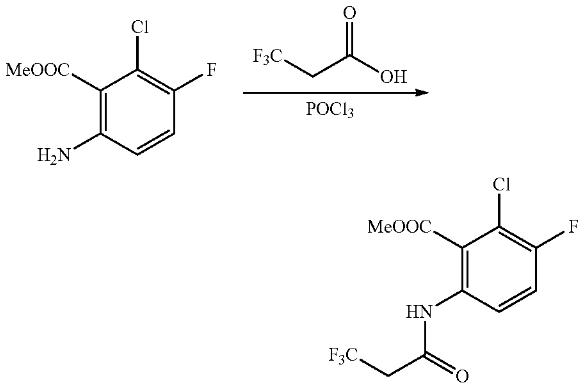

Methyl 2-chloro-3-fluoro-6-(3,3,3-trifluoropropanamido)benzoate

To a solution of the product from the previous step (1300 mg, 6.40 mmol) in pyridine (13 mL) were added 3,3,3-trifluoropropanoic acid (880 mg, 7.68 mmol) and $POCl_3$ (1050 mg, 7.68 mmol). The mixture was stirred at RT for 3 h, then treated with sat. aq. $NaHCO_3$(10 mL). The aqueous layer was extracted with EtOAc (3×10 mL), and the combined organic layers were washed with sat. aq. NaCl, dried over $Na_2SO_4$, filtered and concentrated under reduced pressure. The residue was purified by $SiO_2$ gel chromatography (0% to 15% EtOAc in hexanes) to give the title compound as an off-white solid (1500 mg, 75%). MS ($ES^+$) $C_{11}H_8ClF_4NO_3$ requires: 313, found: 314 $[M+H]^+$.

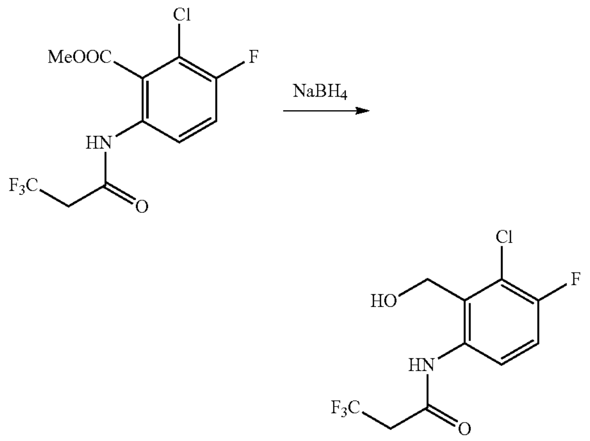

N-(3-Chloro-4-fluoro-2-(hydroxymethyl)phenyl)-3,3,3-trifluoropropanamide

To a solution of the product from the previous step (1.50 g, 4.79 mmol) in THF (20 mL) was added $NaBH_4$ (256.88 mg, 6.76 mmol), and the resulting mixture was stirred at RT for 2 h then concentrated under reduced pressure. The residue was purified by $SiO_2$ gel chromatography (0% to 50% EtOAc in petroleum ether) to give the title compound as an off-white solid (500 mg, 37%). MS ($ES^+$) $C_{10}H_8ClF_4NO_2$ requires: 285, found: 286 $[M+H]^+$.

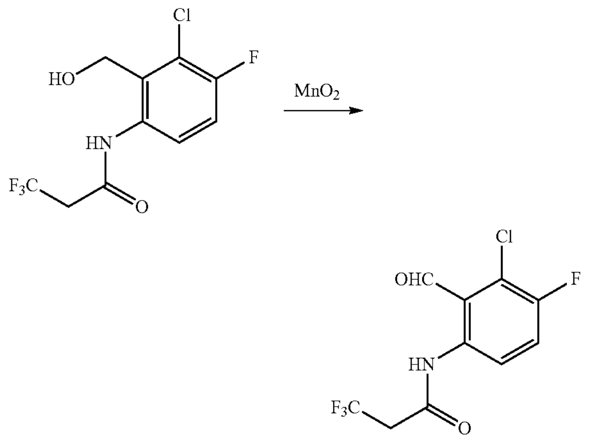

N-(3-chloro-4-fluoro-2-formylphenyl)-3,3,3-trifluoropropanamide

To a degassed solution of the product from the previous step (500 mg, 1.75 mmol) in DCM (10 mL) was added $MnO_2$ (195 mg, 2.24 mmol). The resulting mixture was stirred at RT for 2 h, then concentrated under reduced pressure. The residue was purified by $SiO_2$ gel chromatography (0% to 50% EtOAc in petroleum ether) to give the title compound as an off-white solid (450 mg, 91%). MS ($ES^+$) $C_{10}H_6ClF_4NO_2$ requires: 283, found: 284 $[M+H]^+$.

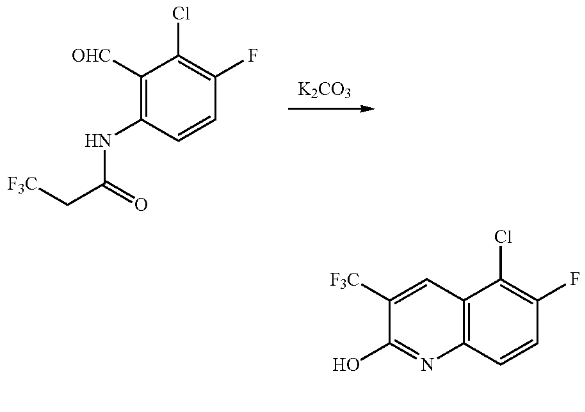

5-Chloro-6-fluoro-3-(trifluoromethyl)quinolin-2(1H)-one

To a solution of the product from the previous step (450 mg, 1.59 mmol) in DMF (5 mL) was added $K_2CO_3$ (260 mg, 1.89 mmol). The mixture was stirred at RT for 2 h, then treated with $H_2O$ (10 mL) and extracted with EtOAc (3×10 mL). The combined organic layers were washed with sat. aq. NaCl, dried over $Na_2SO_4$, filtered and concentrated under reduced pressure. The residue was purified by $SiO_2$ gel chromatography (0% to 30% EtOAc in petroleum ether) to give the title compound as an off-white solid (400 mg, 95%). MS ($ES^+$) $C_{10}H_4ClF_4NO$ requires: 265, found: 266 $[M+H]^+$.

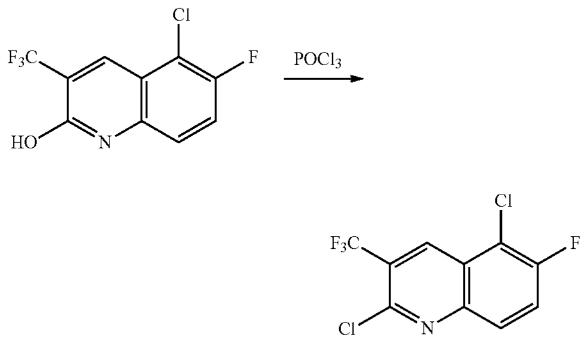

2,5-Dichloro-6-fluoro-3-(trifluoromethyl)quinoline

A degassed mixture of the product from the previous step (400 mg, 1.51 mmol) in $POCl_3$ (5 mL) was stirred at 100° C. for 3 h, then treated with sat. aq. $NaHCO_3$(10 mL) and the layers were separated. The aqueous layer was extracted with EtOAc (3×10 mL), and the combined organic layers were washed with sat. aq. NaCl, dried over $Na_2SO_4$, filtered and concentrated under reduced pressure. The residue was purified by $SiO_2$ gel chromatography (0% to 20% EtOAc in hexanes) to give the title compound as an off-white solid (400 mg, 93%). MS ($ES^+$) $C_{10}H_3Cl_2F_4N$ requires: 283, found: 284 $[M+H]^+$.

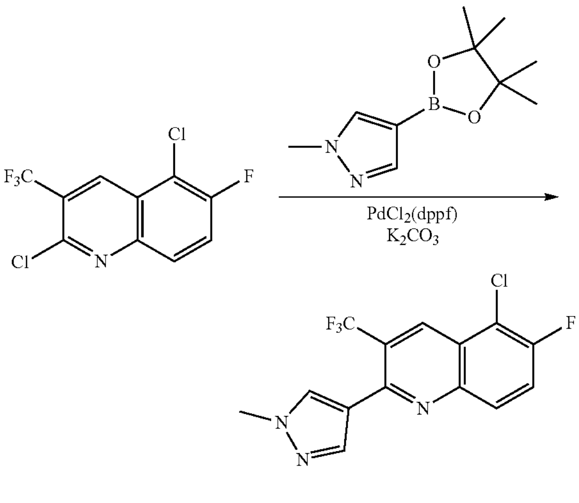

5-Chloro-6-fluoro-2-(1-methyl-1H-pyrazol-4-yl)-3-(trifluoromethyl) quinoline

To a degassed mixture of the product from the previous step (400 mg, 1.41 mmol) in 1,4-dioxane (3 mL) and $H_2O$ (1 mL) were added 1-methyl-4-(4,4,5,5-tetramethyl-1,3,2-dioxaborolan-2-yl)-1H-pyrazole (294 mg, 1.41 mmol), $K_2CO_3$ (389 mg, 2.82 mmol), and $PdCl_2$(dppf) (78.7 mg, 0.141 mmol). The mixture was stirred at 100° C. for 2 h, then concentrated under reduced pressure. The residue was purified by $SiO_2$ gel chromatography(0% to 50% EtOAc in hexanes) to give the title compound as an off-white solid (360 mg, 78%). MS ($ES^{+}$)$C_{14}H_8ClF_4N_3$ requires: 329, found: 330 $[M+H]^+$.

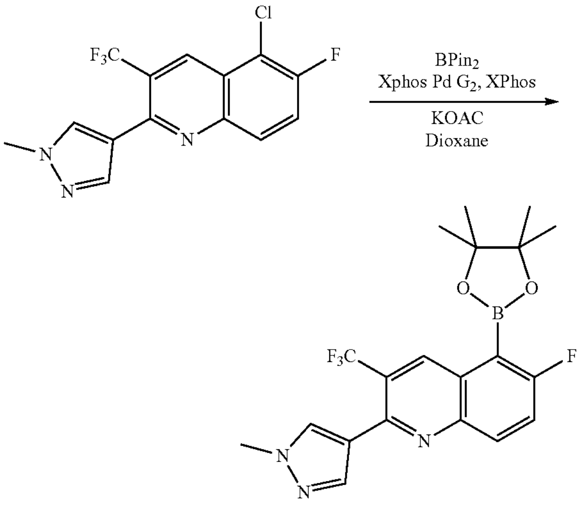

6-Fluoro-2-(1-methyl-1H-pyrazol-4-yl)-5-(4,4,5,5-tetramethyl-1,3,2-dioxaborolan-2-yl)-3-(trifluoromethyl)quinoline To a solution of the product from the previous step (360 mg, 1.09 mmol) in 1,4-dioxane (4 mL) were added $BPin_2$ (554 mg, 2.18 mmol), KOAc (208 mg, 2.18 mmol), XPhos Pd G2 (99.2 mg, 0.11 mmol) and XPhos (45.5 mg, 0.11 mmol). The resulting mixture was stirred at 100° C. for 2 h, then concentrated under reduced pressure. The residue was purified by $SiO_2$ gel chromatography (0% to 50% EtOAc in petroleum ether) to give the title compound as an off-white solid (400 mg, 87%). MS ($ES^+$) $C_{20}H_{20}BF_4N_3O_2$ requires: 421, found: 422 $[M+H]^+$.

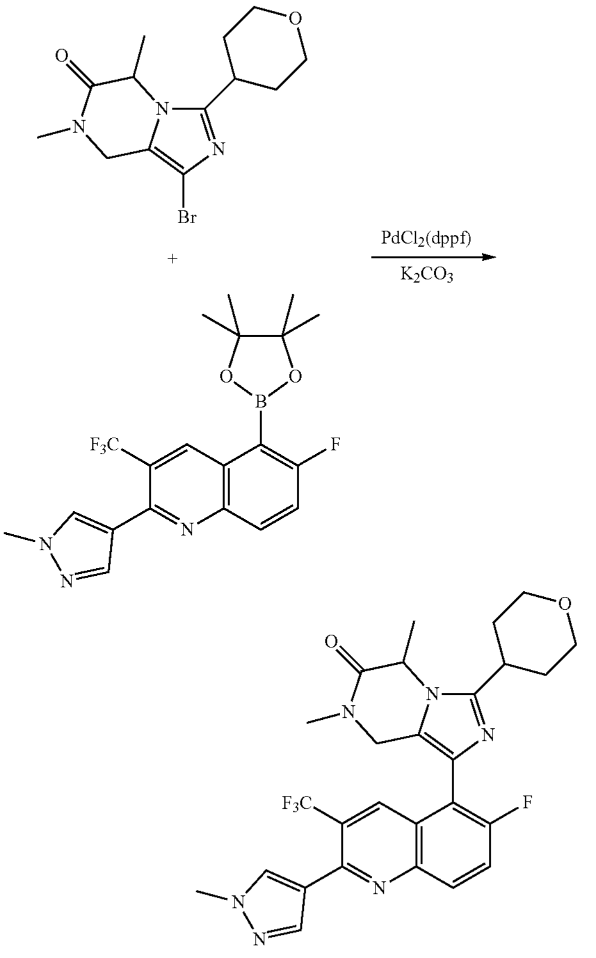

1-(6-Fluoro-2-(1-methyl-1H-pyrazol-4-yl)-3-(trifluoromethyl)quinolin-5-yl)-5,7-dimethyl-3-(tetrahydro-2H-pyran-4-yl)-7,8-dihydroimidazo[1,5-a]pyrazin-6 (5H)-one To a degassed mixture of the product from the previous step (400 mg, 0.950 mmol) in 1,4-dioxane (3 mL) and $H_2O$ (1 mL) were added Intermediate "C" (372 mg, 1.14 mmol), $K_2CO_3$ (262 mg, 1.90 mmol), and $PdCl_2$(dppf) (87.2 mg, 0.095 mmol). The resulting mixture was stirred at 100° C. for 2 hr then concentrated under reduced pressure. The residue was purified by reverse phase preparative HPLC (Mobile phase: A=10 mM $NH_4HCO_3/H_2O$, B=MeCN; Column: C18) to give the title compound as an off-white solid (10 mg, 2%).

MS ($ES^+$) $C_{27}H_{26}F_4N_6O_2$ requires: 542, found: 543 $[M+H]^+$.

$^1H$ NMR (500 MHz, $CD_3OD$) δ 9.10 (s, 1H), 8.23-8.19 (m, 1H), 8.03 (s, 1H), 7.91-7.79 (m, 1H), 5.14 (q, J=6.5 Hz, 1H), 4.83 (d, J=16.5 Hz, 1H), 4.43 (d, J=16.5 Hz, 1H), 4.13-4.06 (m, 2H), 4.03 (s, 3H), 3.72-3.63 (m, 2H), 3.25-3.18 (m, 1H), 3.09 (s, 3H), 2.16-2.03 (m, 2H), 1.99-1.82 (m, 2H), 1.73 (d, J=7.0 Hz, 3H).

Examples 36a/36b 1-(3-(Difluoromethyl)-6-fluoro-2-(1-methyl-1H-pyrazol-4-yl)quinolin-5-yl)-5,7-dimethyl-3-(tetra-hydro-2H-pyran-4-yl)-7,8-dihydroimidazo[1,5-a]pyrazin-6(5H)-one (separated enantiomers)

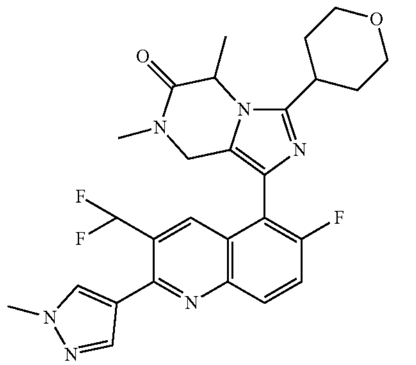

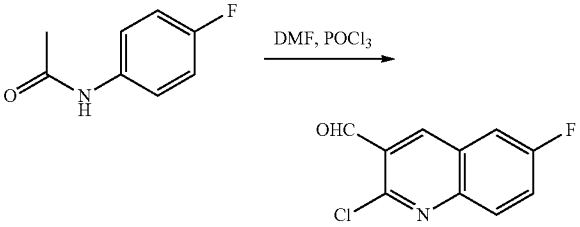

2-Chloro-6-fluoroquinoline-3-carbaldehyde

To DMF (18.94 mL, 18.94 mL) at 0° C. was added $POCl_3$ (63.90 mL, 685.6 mmol) dropwise, then N-(4-fluorophenyl) acetamide (15.00 g, 97.94 mmol) portionwise. The mixture was stirred at 0° C. for 20 min, then at 82° C. overnight. The mixture was allowed to cool to RT then poured into ice-water. Precipitate was collected by filtration and and dried to give the title compound as a yellow solid (3.16 g, 15%). MS ($ES^+$): $C_{10}H_5ClFNO$ requires: 209, found: 210 $[M+H]^+$.

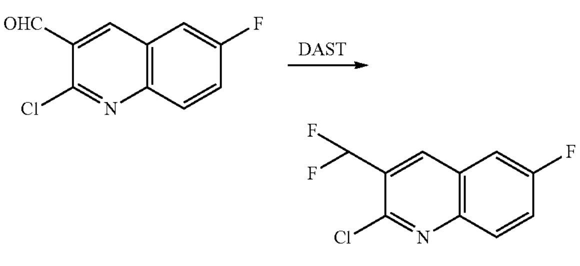

2-Chloro-3-(difluoromethyl)-6-fluoroquinoline

To a mixture of the product from the previous step (3.14, 15.0 mmol) in DCM (120 mL) at 0° C. was added DAST (5.50 mL, 44.9 mmol). The mixture was stirred at RT for 3 h, then treated with sat. aq. $NaHCO_3$ and extracted with DCM (45 mL×2). The combined organic layers were washed with sat. aq. NaCl (25 mL), dried over $MgSO_4$, filtered and concentrated under reduced pressure. The residue was purified by $SiO_2$ gel chromatography (0% to 15% EtOAc in petroleum ether) to give the title compound as a white solid (2.97 g, 86%). MS ($ES^+$): $C_{10}H_5ClF_3N$ requires: 231, found: 232 $[M+H]^+$.

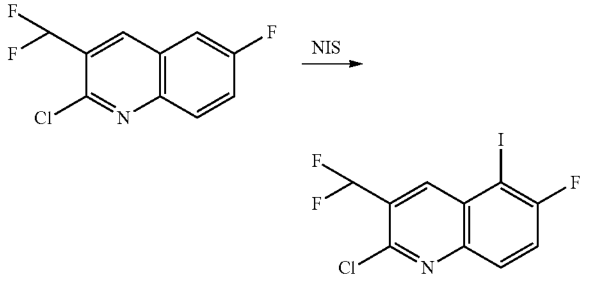

2-Chloro-3-(difluoromethyl)-6-fluoro-5-iodoquinoline

To a mixture of the product from the previous step (2.97 g, 12.8 mmol) in trifluoromethanesulphonic acid (17.08 mL, 192.4 mmol) was added NIS (14.43 g, 64.12 mmol). The mixture was stirred at RT for 2 d, poured onto ice, and diluted with water. Precipitate was collected by filtration, and dissolved in DCM (120 mL). The solution was sequentially washed with sat. aq. $NaHCO_3$(45 mL×2), sat. aq. $Na_2SO_3$ (45 mL) and sat. aq. NaCl (45 mL), dried over $Na_2SO_4$, filtered and concentrated under reduced pressure. The residue was purified by $SiO_2$ gel chromatography (0% to 25% EtOAc in petroleum ether) to give the title compound as a white solid (3.64 g, 79%). MS ($ES^+$): $C_{10}H_4ClF_3IN$ requires: 357, found: 358 $[M+H]^+$.

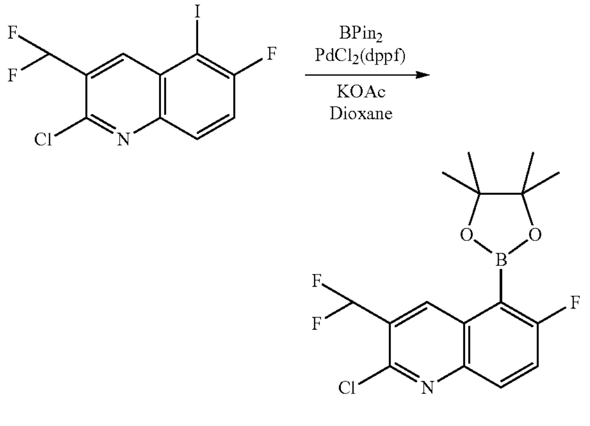

2-Chloro-3-(difluoromethyl)-6-fluoro-5-(4,4,5,5-tetramethyl-1,3,2-dioxaborolan-2-yl)quinoline To a mixture of the product from the previous step (2.00 g, 5.59 mmol), $BPin_2$ (2.17 g, 8.39 mmoles) and KOAc (1.39 g, 14.0 mmoles) in 1,4-dioxane (50 mL) was added $PdCl_2$ (dppf) (466.19 mg, 559.44 mmoles). The mixture was stirred at 148° C. for 2 h, filtered and the filtrate concentrated under reduced pressure. The residue was purified by $SiO_2$ gel chromatography (0% to 25% EtOAc in petroleum ether) to give the title compound as a white solid (1.21 g, 60%). MS ($ES^+$): $C_{16}H_{16}BClF_3NO_2$ requires: 357, found: 358 $[M+H]^+$.

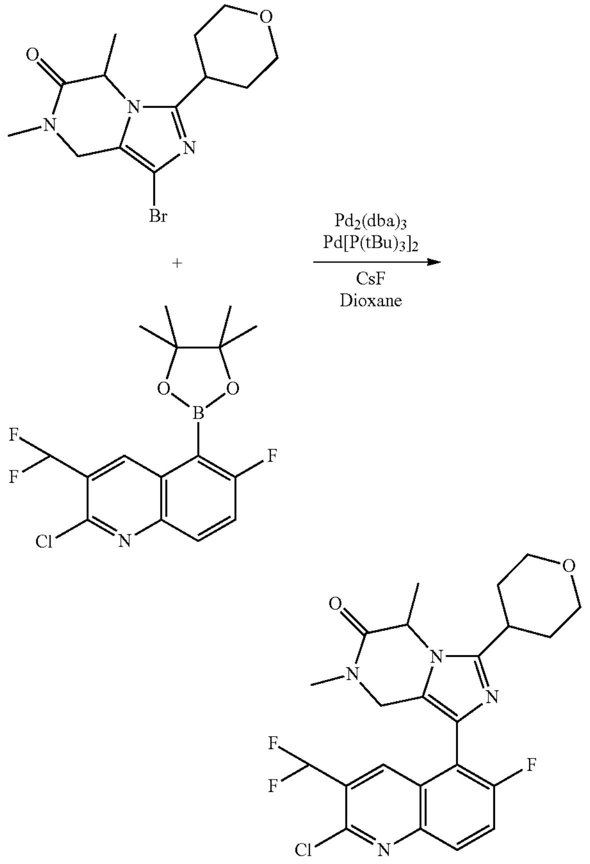

1-(2-Chloro-3-(difluoromethyl)-6-fluoroquinolin-5-yl)-5,7-dimethyl-3-(tetrahydro-2H-pyran-4-yl)-7,8-dihydroimidazo[1,5-a]pyrazin-6(5H)-one A mixture of the product from the previous step (352.98 mg, 987.18 μmol), Intermediate "C" (240 mg, 731 μmol), $Pd_2(dba)_3$ (34.16 mg, 36.56 μmol), bis(tri-tert-butylphosphine)palladium (37.37 mg, 73.12 μmol) and CsF (1.21 g, 2.41 mmol) in 1,4-dioxane (15 mL) was stirred at RT for 45 min, then filtered and concentrated under reduced pressure to give the crude title compound as a brown oil, which was used directly in the next step (assumed as 731 μmol, 100%). MS ($ES^+$): $C_{23}H_{22}ClF_3N_4O_2$ requires: 478, found: 479 $[M+H]^+$.

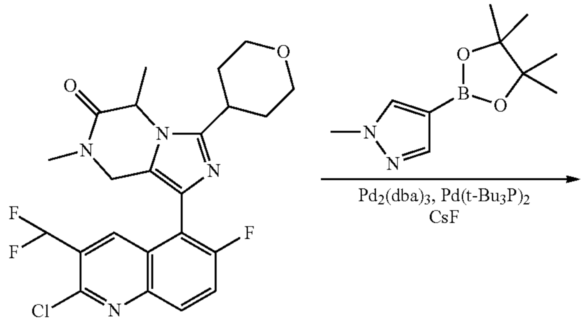

-continued

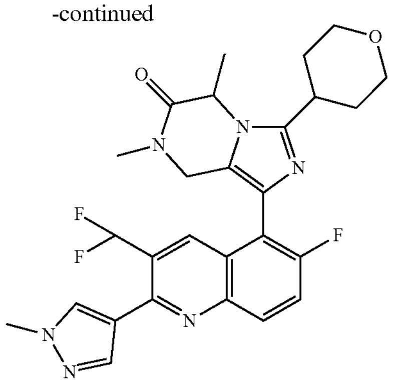

1-(3-(Difluoromethyl)-6-fluoro-2-(1-methyl-1H-pyrazol-4-yl)quinolin-5-yl)-5,7-dimethyl-3-(tetrahydro-2H-pyran-4-yl)-7,8-dihydroimidazo[1,5-al]pyrazin-6(5H)-one (separated enantiomers)

A mixture of the product from the previous step (350 mg, 731 μmol), 1-methyl-4-(4,4,5,5-tetramethyl-1,3,2-dioxaborolan-2-yl)-1H-pyrazole (crude, 731 μmol), $Pd_2(dba)_3$ (34.15 mg, 36.54 μmol), $Pd(t\text{-}Bu_3P)_2$ (37.35 mg, 73.08 μmol) and CsF (1.21 g, 2.41 mmol) in 1,4-dioxane (5 mL) was degassed and purged with $N_2$ 3 times. The mixture was stirred at 60° C. overnight, allowed to cool to RT, filtered and concentrated under reduced pressure. The residue was purified by $SiO_2$ gel chromatography (0% to 10% MeOH in EtOAc) to give the title racemic compound as a white solid (75 mg, 20%).

The racemate was separated by chiral HPLC [Instrument: SFC-80 (Thar, Waters); Column: OD 20*250 mm, 10 um (Daicel); Column temperature: 35° C.; Mobile phase: $CO_2$/MeOH(0.2% 7 M ammonia in MeOH)=75/25; Flow rate: 80 g/min] to give two isomers.

Example 36a was isolated as a white solid (31 mg, 41%). RT=3.37 min.

MS ($ES^+$): $C_{27}H_{27}F_3N_6O_2$ requires: 524, found: 525 $[M+H]^+$.

$^1$H NMR (500 MHz, $CD_3OD$) δ 9.01 (s, 1H), 8.24-8.12 (m, 2H), 8.05 (s, 1H), 7.79 (appar t, J=9.4 Hz, 1H), 7.13 (t, J=54.4 Hz, 1H), 5.14 (q, J=7.0 Hz, 1H), 4.81 (d, J=16.1 Hz, 1H), 4.40 (d, J=16.0 Hz, 1H), 4.12-4.07 (m, 2H), 4.04 (s, 3H), 3.67 (appar t, J=11.3 Hz, 2H), 3.28-3.20 (m, 1H), 3.08 (s, 3H), 2.17-2.01 (m, 2H), 1.96-1.88 (m, 2H), 1.74 (d, J=7.1 Hz, 3H).

Example 36b was isolated as a white solid (30 mg, 40%). RT=4.11 min.

MS ($ES^+$): $C_{27}H_{27}F_3N_6O_2$ requires: 524, found: 525 $[M+H]^+$.

$^1$H NMR (500 MHz, $CD_3OD$) δ 8.88 (s, 1H), 8.10-8.00 (m, 2H), 7.92 (s, 1H), 7.67 (appar t, J=9.5 Hz, 1H), 7.01 (t, J=54.4 Hz, 1H), 5.02 (q, J=7.0 Hz, 1H), 4.69 (d, J=16.1 Hz, 1H), 4.28 (d, J=16.0 Hz, 1H), 4.00-3.92 (m, 2H), 3.92 (s, 3H), 3.55 (appar t, J=11.3 Hz, 2H), 3.13-3.11 (m, 1H), 2.96 (s, 3H), 2.07-1.91 (m, 2H), 1.84-1.75 (m, 2H), 1.61 (d, J=7.1 Hz, 3H).

Examples 37a/37b 1-(7-Fluoro-3-(2-methylthiazol-5-yl)isoquinolin-8-yl)-5,7-dimethyl-3-(tetrahydro-2H-pyran-4-yl)-7,8-dihydroimidazo[1,5-a]pyrazin-6(5H)-one (separated enantiomers)

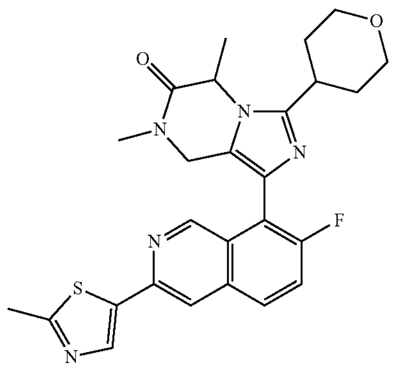

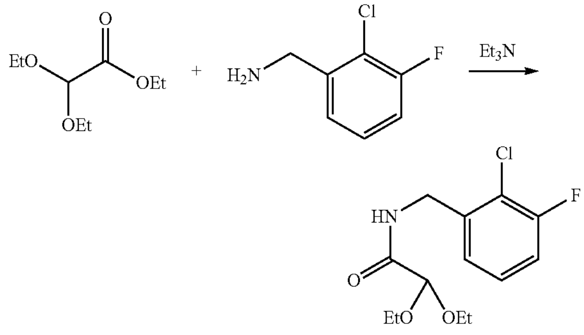

N-(2-Chloro-3-fluorobenzyl)-2,2-diethoxyacetamide

To a mixture of (2-chloro-3-fluorophenyl)methanamine (12 g, 75 mmol) and ethyl 2,2-diethoxyacetate (19.93 g, 113.2 mmol) in MeOH (120 mL) was added TEA (22.87 g, 226.4 mmol), and the mixture was stirred at 80° C. overnight then concentrated under reduced pressure. The residual oil was poured into water (150 mL) and the mixture was extracted with $Et_2O$ (150 mL×3). The combined organic layers were dried over $Na_2SO_4$, filtered and concentrated under reduced pressure. The residue was purified by $SiO_2$ gel chromatography (40% to 60% EtOAc in petroleum ether) to give the title compound as a yellow solid (17.3 g, 79%). MS ($ES^+$) $C_{13}H_{17}ClFNO_3$ requires: 289, found: 290 $[M+H]^+$.

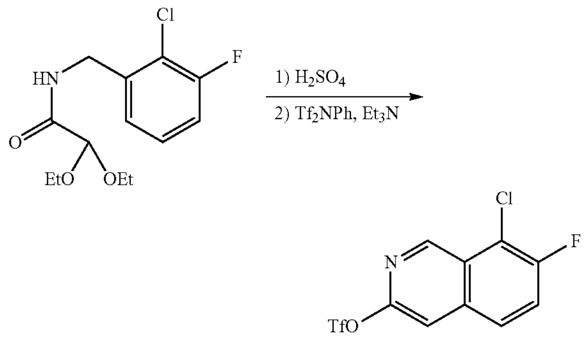

8-Chloro-7-fluoroisoquinolin-3-yl trifluoromethanesulfonate

The product from the previous step (17.3 g, 59.9 mmol) was dissolved in conc. aq. $H_2SO_4$ (200 mL), and the mixture was stirred at RT overnight. The mixture was poured into ice water (400 mL), the pH was adjusted to 7, and the mixture was extracted with $Et_2O$ (400 mL×3). The combined organic layers were dried over $Na_2SO_4$, filtered and concentrated under reduced pressure to give crude 8-chloro-7-fluoroisoquinolin-3-ol as a yellow solid (15.8 g). A mixture of 8-chloro-7-fluoroisoquinolin-3-ol (15.8 g, 80.2 mmol), 1,1,1-trifluoro-N-phenyl-N-(trifluoromethylsulfonyl)methanesulfonamide (34.36 g, 96.24 mmol), and TEA (24.3 g, 241 mmol) in DCM (500 mL) was stirred at RT for 3 h, then poured into water (500 mL) and extracted with DCM (500 mL×3). The combined organic layers were dried over $Na_2SO_4$, filtered and concentrated under reduced pressure. The residue was purified by $SiO_2$ gel chromatography (3% to 5% EtOAc in petroleum ether) to give the title compound as a yellow solid (14.7 g, 75%). MS ($ES^+$) $C_{10}H_4ClF_4NO_3S$ requires: 329, found: 330 $[M+H]^+$.

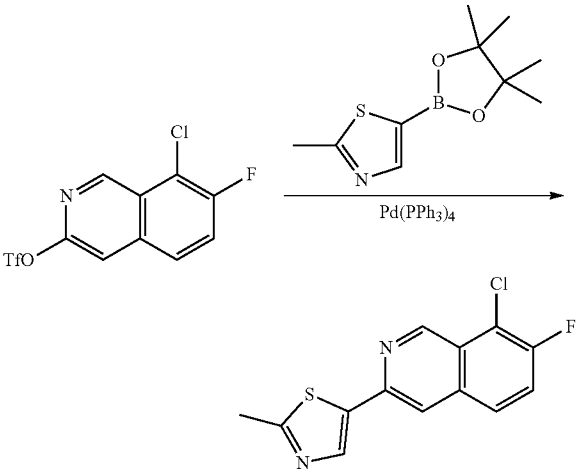

5-(8-Chloro-7-fluoroisoquinolin-3-yl)-2-methylthiazole

A mixture of the product from the previous step (500 mg, 1.52 mmol), 2-methyl-5-(4,4,5,5-tetramethyl-1,3,2-dioxaborolan-2-yl)thiazole (412 mg, 1.83 mmol), $Pd(dppf)Cl_2$ (110 mg, 0.15 mmol), and $K_2CO_3$ (630 mg, 4.56 mmol) in 1,4-dioxane (15 mL) and $H_2O$ (3 mL) was stirred at 80° C. for 2 h. The mixture was poured into water (40 mL) and extracted with EtOAc (40 mL×3). The combined organic layers were dried over $Na_2SO_4$, filtered and concentrated under reduced pressure. The residue was purified by $SiO_2$ gel chromatography (70% to 100% EtOAc in petroleum ether) to give the title compound as a gray solid (460 mg, 100%). MS ($ES^+$) $C_{13}H_8ClFN_2S$ requires: 278, found: 279 $[M+H]^+$.

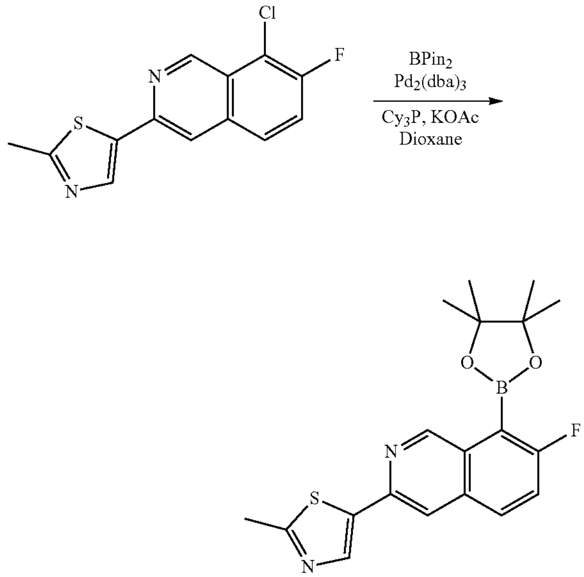

5-(7-Fluoro-8-(4,4,5,5-tetramethyl-1,3,2-dioxaborolan-2-yl)isoquinolin-3-yl)-2-methylthiazole A mixture of the product from the previous step (70 mg, 0.25 mmol) and $Pd_2(dba)_3$ (28 mg, 0.03 mmol), $Cy_3P$ (23 mg, 0.08 mmol), KOAc (106 mg, 1.08 mmol) and $BPin_2$ (97 mg, 0.38 mmol) in 1,4-dioxane (3 mL) was stirred at 120° C. overnight. The mixture was allowed to cool to RT, filtered, and the filtrate concentrated to give the crude title compound (63 mg, 68%), which was used without further purification. MS ($ES^+$) $C_{19}H_{20}BFN_2O_2S$ requires: 370, found: 371 [M+H].

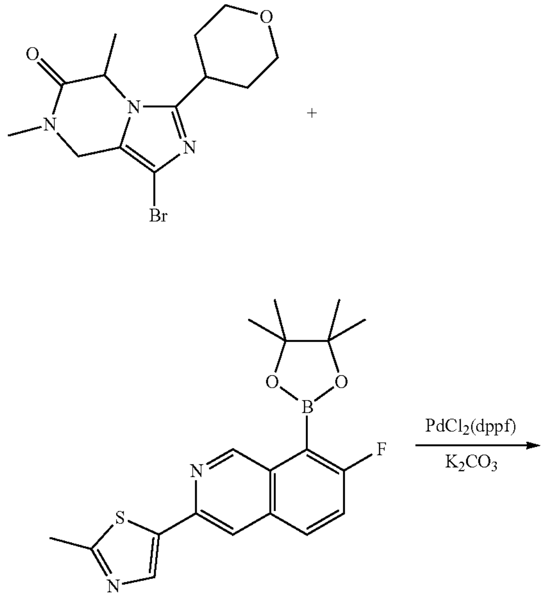

-continued

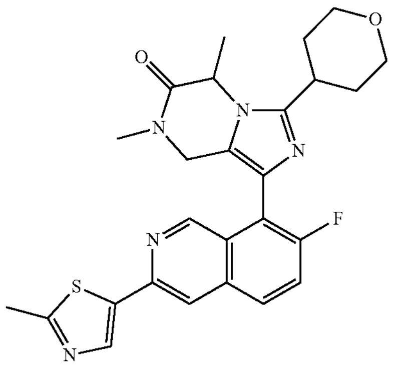

(7-Fluoro-3-(2-methylthiazol-5-yl)isoquinolin-8-yl)-5,7-dimethyl-3-(tetrahydro-2H-pyran-4-yl)-7,8-dihydroimidazo[1,5-a]pyrazin-6(5H)-one (separated enantiomers)

A mixture of the product from the previous step (63 mg, 0.17 mmol), Intermediate "C" (56 mg, 0.17 mmol), Pd(dppf)$Cl_2$ (15 mg, 0.02 mmol), and 2.0 M aq. $K_2CO_3$ (0.272 mL, 0.544 mmol) in 1,4-dioxane (3 mL) was degassed and purged with $N_2$. The mixture was stirred at 90° C. for 1.5 h, then concentrated under reduced pressure. The residue was purified by reverse phase preparative HPLC (Mobile phase: A=10 mM $NH_4HCO_3/H_2O$, B=MeCN; Gradient: B=10% to 45% in 18 min; Column: C18) to give the racemic title compound as a white solid (45 mg, 53%). The racemate was separated by chiral HPLC to obtain two isomers. Instrument: SFC-80 (Thar, Waters); Column: OJ 20*250 mm, 10 um (Daicel); Column temperature: 35° C.; Mobile phase: $CO_2$/MeOH (0.2% 7 M $NH_3$ in MeOH)=70/30; Flow rate: 80 g/min] to give two isomers.

Example 37a was isolated as a white solid (11 mg, 24%). RT=1.46 min.

MS ($ES^+$): $C_{26}H_{26}FN_5O_2S$ requires: 491, found: 492 $[M+H]^+$.

$^1H$ NMR (500 MHz, DMSO-$d_6$) δ 9.65 (s, 1H), 8.43 (s, 1H), 8.36 (s, 1H), 8.06-8.03 (m, 1H), 7.82 (appar t, J=9.8 Hz, 1H), 5.11 (q, J=7.0 Hz, 1H), 4.76 (d, J=15.5 Hz, 1H), 4.36 (d, J=14.5 Hz, 1H), 3.98-3.94 (m, 2H), 3.54-3.49 (m, 2H), 3.21-3.17 (m, 1H), 2.93 (s, 3H), 2.70 (s, 3H), 1.89-1.74 (m, 4H), 1.59 (d, J=7.5 Hz, 3H).

Example 37b was isolated as a white solid (10 mg, 22%). RT=2.52 min.

MS ($ES^+$): $C_{26}H_{26}FN_5O_2S$ requires: 491, found: 492 $[M+H]^+$.

$^1H$ NMR (500 MHz, DMSO-$d_6$) δ 9.65 (s, 1H), 8.43 (s, 1H), 8.36 (s, 1H), 8.06-8.03 (m, 1H), 7.82 (appar t, J=9.8 Hz, 1H), 5.11 (q, J=7.0 Hz, 1H), 4.76 (d, J=15.5 Hz, 1H), 4.36 (d, J=14.5 Hz, 1H), 3.98-3.94 (m, 2H), 3.54-3.49 (m, 2H), 3.21-3.17 (m, 1H), 2.93 (s, 3H), 2.70 (s, 3H), 1.89-1.74 (m, 4H), 1.59 (d, J=7.5 Hz, 3H).

Examples 38a/38b 5,7-Dimethyl-1-(7-methyl-3-(2-methylthiazol-5-yl)isoquinolin-1-yl)-3-(tetrahydro-2H-pyran-4-yl)-7,8-dihydroimidazo[1,5-a]pyrazin-6(5H)-one

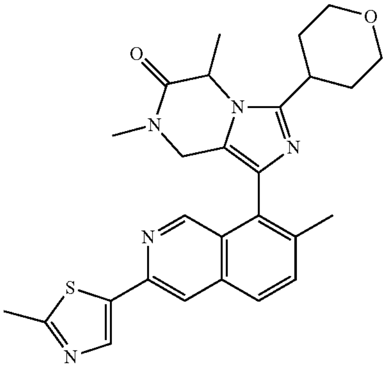 [SMILES: Cc1ncc(-c2cc3ccc(C)c(-c4nc(C5CCOCC5)n5c4CN(C)C(=O)C5C)c3cn2)s1]

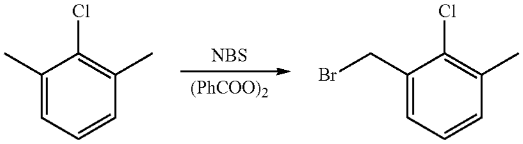

1-(Bromomethyl)-2-chloro-3-methylbenzene

A mixture of 2-chloro-m-xylene (30.0 g, 214 mmol), NBS (38.0 g, 214 mmol), and benzoyl peroxide (500 mg) in $CCl_4$ (300 mL) was stirred at reflux for 6 h, then allowed to cool to RT, filtered and the filtrate concentrated under reduced pressure. The residue was purified by $SiO_2$ gel chromatography (5% EtOAc in petroleum ether) to give the title compound (17 g, 36%). $^1H$ NMR (300 MHz, $CDCl_3$) δ 7.30-7.25 (m, 1H), 7.23-7.08 (m, 2H), 4.61 (s, 2H), 2.39 (s, 3H).

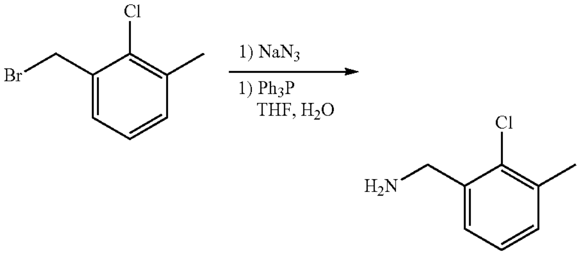

(2-Chloro-3-methylphenyl)methanamine)

A mixture of the product from the previous step (17.0 g, 77.9 mmol) and $NaN_3$ (6.10 g, 93.6 mmol) in DMF (170 mL) was stirred at RT for 14 h, then diluted with water and extracted with $Et_2O$ (3×300 mL). The combined organic layers were sequentially washed with $H_2O$ (3×150 mL) and sat. aq. NaCl (150 mL), dried over $MgSO_4$, filtered and concentrated under reduced pressure. The residue was dissolved in 3:1 THF/$H_2O$ (400 mL) and the mixture was treated with $Ph_3P$ (20.0 g, 77.9 mmol). The mixture was stirred for 72 h, then acidified with conc. aq. HCl to pH=1. The resulting mixture was washed with $Et_2O$ and the aqueous layer was adjusted to pH=14 with 1 M aq. NaOH and extracted with $Et_2O$ (6×200 mL). The combined organic layers were sequentially washed with $H_2O$ (3×100 mL) and sat. aq. NaCl (100 mL), dried over $MgSO_4$, filtered and concentrated under reduced pressure to give the title compound (8.0 g, 67%). MS ($ES^+$): $C_8H_{10}ClN$ requires: 155, found: 156 $[M+H]^+$.

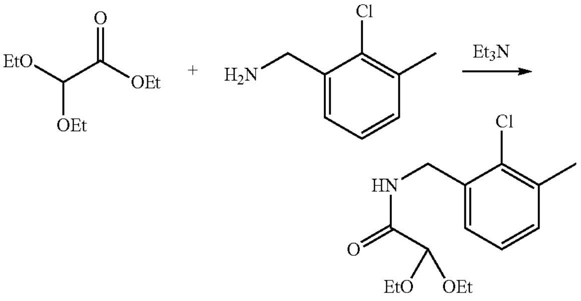

N-(2-Chloro-3-methylbenzyl)-2,2-dimethoxyacetamide

A mixture of the product from the previous step (6.0 g, 39 mmol), methyl 2,2-dimethoxyacetate (6.2 g, 46 mmol) and TEA (6.0 g, 59 mmol) was stirred at 70° C. for 72 h, then concentrated under reduced pressure. The residue was purified by $SiO_2$ gel chromatography (50% EtOAc in petroleum ether) to give the title compound as a yellow oil (6.0 g, 60%). MS ($ES^+$): $C_{12}H_{16}ClNO_3$ requires: 257, found: 258 $[M+H]^+$.

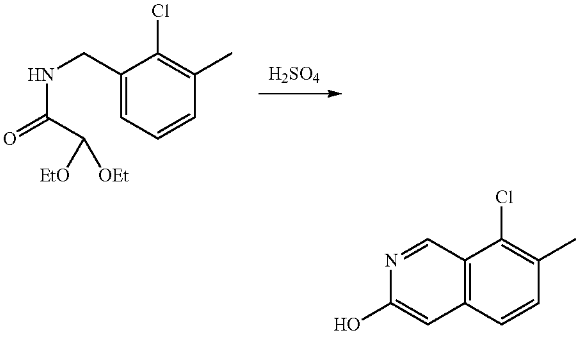

8-chloro-7-methylisoquinolin-3-ol

A mixture of the product from the previous step (2.5 g, 9.7 mmol) and conc. aq. $H_2SO_4$ (20 mL) was stirred at RT for 24 h, then poured into ice-water (100 mL). Precipitate was collected by filtration to give the title compound as a yellow solid (1.9 g, 100%). MS ($ES^+$): $C_{10}H_8ClNO$ requires: 193, found: 194 $[M+H]^+$.

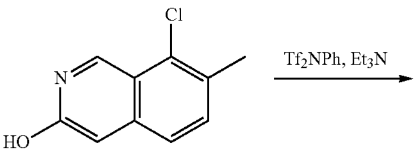

-continued

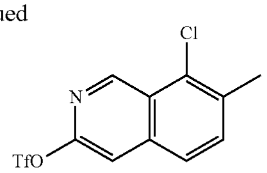

8-Chloro-7-methylisoquinolin-3-yl trifluoromethanesulfonate

To a mixture of the product from the previous step (400 mg, 2.1 mmol) in DCM (20 mL) was added TEA (0.4 g, 4 mmol) and $Tf_2NPh$ (1.1 g, 3.1 mmol). The mixture was stirred at RT for 24 h, then diluted with DCM (20 mL) and washed with water (20 mL×3). The organic layer was dried over $Na_2SO_4$ and concentrated under reduced pressure. The residue was purified by $SiO_2$ gel chromatography (20% EtOAc in petroleum ether) to give the title compound as a white solid (250 mg, 37%). MS ($ES^+$): $C_{11}H_7ClF_3NO_3S$ requires: 325, found: 326 $[M+H]^+$.

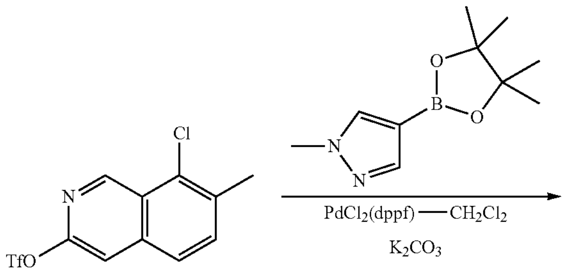

-continued

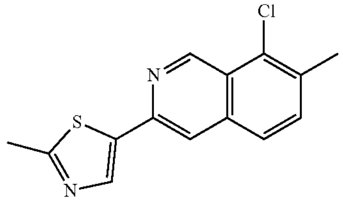

5-(8-Chloro-7-methylisoquinolin-3-yl)-2-methylthiazole

A mixture the product from the previous step (250 mg, 0.76 mmol), 2-methyl-5-(4,4,5,5-tetramethyl-1,3,2-dioxaborolan-2-yl)thiazole (173 mg, 0.76 mmol), $PdCl_2(dppf)$ (26 mg, 32 μmoles) and 2.0 M aq. $K_2CO_3$ (1.0 mL, 2.0 mmol) in THF (3 mL) was stirred at 70° C. for 3 h, then concentrated under reduced pressure. The residue was purified by $SiO_2$ gel chromatography (50% EtOAc in petroleum ether) to give the title compound as a yellow solid (150 mg, 72%). MS ($ES^+$): $C_{14}H_{11}ClN_2S$ requires: 274, found: 275 $[M+H]^+$.

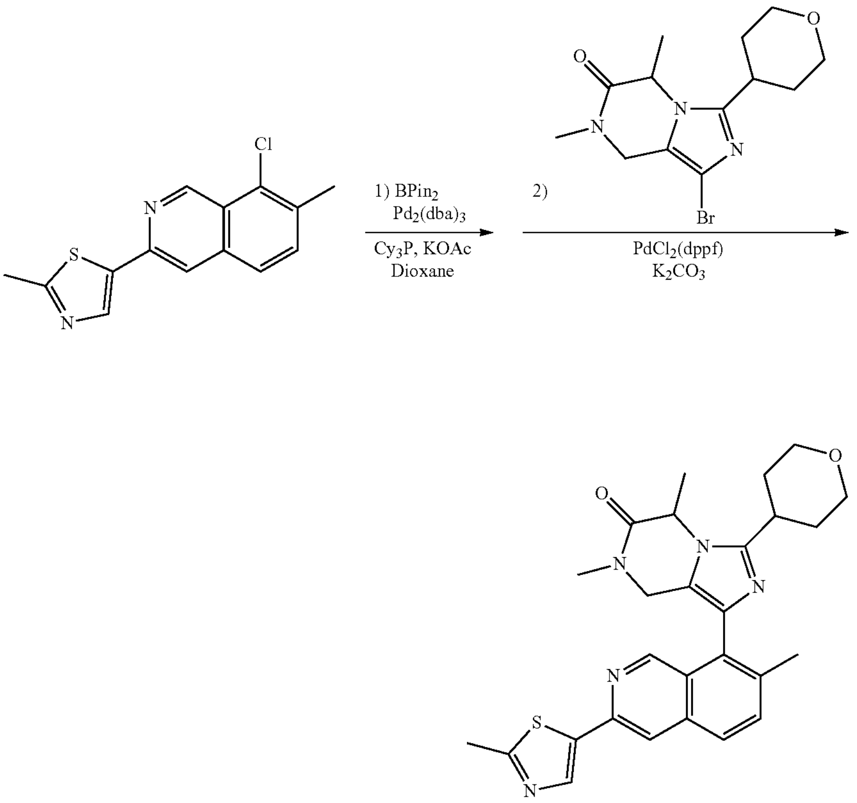

5,7-Dimethyl-1-(7-methyl-3-(2-methylthiazol-5-yl)isoquinolin-1-yl)-3-(tetrahydro-2H-pyran-4-yl)-7,8-dihydroimidazo[1,5-a]pyrazin-6(5H)-one (separated enantiomers)

A mixture of the product from the previous step (150 mg, 0.55 mmol), $BPin_2$ (189 mg, 0.75 mmol) $Pd_2(dba)_3$ (42 mg, 45 μmol), $Cy_3P$ (50.0 mg, 183 μmoles), and KOAc (100 mg, 1.02 mmol) in 1,4-dioxane (5 mL) was stirred at 120° C. under Ar overnight. The mixture was allowed to cool to RT, filtered and concentrated under reduced pressure. To the residue was added 1,4-dioxane (5 mL), Intermediate "C" (132 mg, 400 μmol), 2.0 M aq. $K_2CO_3$ (0.777 mL, 1.55 mmol) and $PdCl_2$(dppf) (43.16 mg, 51.80 μmol). The mixture was degassed and purged with $N_2$ 3 times, stirred at 90° C. for 1.5 h, and concentrated under reduced pressure. The residue was purified by reverse phase preparative HPLC (Mobile phase: A=10 mM $NH_4HCO_3/H_2O$, B=MeCN; Gradient: B=10% to 65% in 18 min; Column: C18) to give the title racemic compound as a white solid (30 mg, 13%). The racemate was separated by chiral HPLC [Instrument: SFC-80 (Thar, Waters); Column: OD 20*250 mm, 10 um (Daicel); Column temperature: 35° C.; Mobile phase: $CO_2$/MeOH(0.2% 7 M ammonia in MeOH)=60/40; Flow rate: 80 g/min] to give two isomers.

Example 38a was isolated as a white solid (9 mg, 30%). RT=1.16 min.

MS ($ES^+$): $C_{27}H_{29}N_5O_2S$ requires: 487, found: 488 $[M+H]^+$.

$^1$H NMR (500 MHz, $CD_3OD$) (apparent 1:1 mixture of atropisomers) δ 8.90 (s, 0.5H), 8.81 (s, 0.5H), 8.27-8.24 (m, 2H), 7.99-7.96 (m, 1H), 7.80-7.77 (m, 1H), 5.17-5.14 (m, 1H), 4.69 (d, J=16.0 Hz, 0.5H), 4.63 (d, J=1.5 Hz, 0.5H), 4.16-4.06 (m, 3H), 3.69-3.64 (m, 2H), 3.30-3.19 (m, 1H), 3.04 (s, 1.5H), 3.02 (s, 1.5H), 2.78 (appar s, 3H), 2.41 (appar d, J=3 Hz, 3H), 2.20-1.80 (m, 4H), 1.77 (d, J=7.1 Hz, 1.5H), 1.73 (d, J=7.1 Hz, 1.5H).

Example 38b was isolated as a white solid (9 mg, 30%). RT=1.80 min.

MS ($ES^+$): $C_{27}H_{29}N_5O_2S$ requires: 487, found: 488 $[M+H]^+$.

$^1$H NMR (500 MHz, $CD_3OD$) (apparent 1:1 mixture of atropisomers) δ 8.90 (s, 0.5H), 8.82 (s, 0.5H), 8.26-8.24 (m, 2H), 7.99-7.96 (m, 1H), 7.80-7.77 (m, 1H), 5.17-5.15 (m, 1H), 4.69 (d, J=16.0 Hz, 0.5H), 4.63 (d, J=1.5 Hz, 0.5H), 4.16-4.06 (m, 3H), 3.69-3.64 (m, 2H), 3.30-3.19 (m, 1H), 3.04 (s, 1.5H), 3.02 (s, 1.5H), 2.78 (appar s, 3H), 2.41 (appar d, J=3 Hz, 3H), 2.20-1.80 (m, 4H), 1.77 (d, J=7.1 Hz, 1.5H), 1.73 (d, J=7.1 Hz, 1.5H).

Example 39

3-Cyclopropyl-7-methyl-1-(6-(1-methyl-1H-pyrazol-4-yl)-7-(trifluoromethyl)-3,4-dihydro-1,5-naphthyridin-1(2H)-yl)-7,8-dihydroimidazo[1,5-a]pyrazin-6(5H)-one

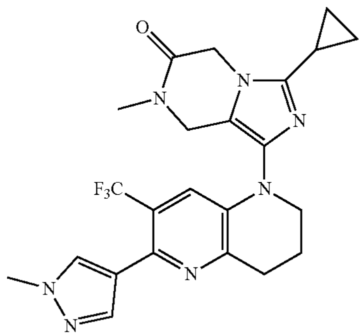

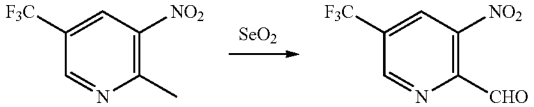

3-Nitro-5-(trifluoromethyl)picolinaldehyde

To a solution of 2-methyl-3-nitro-5-(trifluoromethyl)pyridine (1.00 g, 4.85 mmol) in 1,4-dioxane (20 mL) was added selenium dioxide (1.077 g, 9.70 mmol) and the resulting mixture was stirred at 100° C. for 6 h, then allowed to cool to RT. The mixture was filtered through CELITE®, and the filtrate was concentrated under reduced pressure. The residue was purified by $SiO_2$ gel chromatography (0% to 60% EtOAc in hexanes) to give the title compound as a yellow solid (912 mg, 85%). MS ($ES^+$) $C_7H_3F_3N_2O_3$ requires: 220, found: 221 $[M+H]^+$.

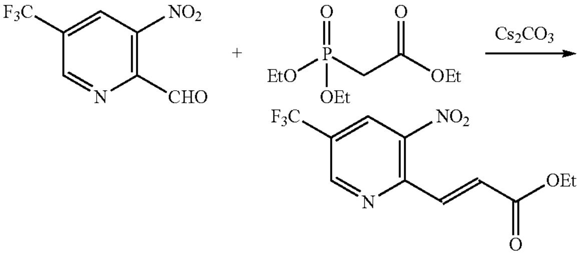

(E)-Ethyl 3-(3-nitro-5-(trifluoromethyl)pyridin-2-yl)acrylate

To a solution of the product from the previous step (725 mg, 3.29 mmol) in THF (30 mL) were added ethyl 2-(diethoxyphosphoryl)acetate (886 mg, 3.95 mmol) and $Cs_2CO_3$ (1288 mg, 3.95 mmol) and the resulting mixture was stirred at 20° C. for 0.5 h. The reaction mixture was filtered through CELITE®, and the filtrate was concentrated under reduced pressure. The residue was purified by $SiO_2$ gel chromatography (0% to 15% EtOAc in hexanes) to give the title compound as a colorless liquid (624 mg, 65%). MS ($ES^+$) $C_{11}H_9F_3N_2O_4$ requires: 290, found: 291 $[M+H]^+$.

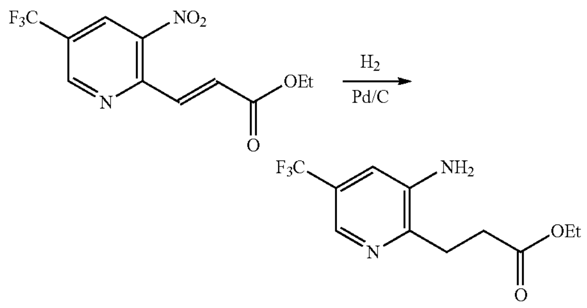

Ethyl 3-(3-amino-5-(trifluoromethyl)pyridin-2-yl)propanoate

A reaction vessel was charged with the product from the previous step (620 mg, 2.14 mmol), 10% Pd/C (227 mg) and EtOH (10 mL) under a nitrogen atmosphere. The suspension was degassed by bubbling nitrogen through for 2 min, then purged with $H_2$ for 2 min. The reaction mixture was stirred under an atmosphere of $H_2$ at 1 atm for 1 h. The reaction mixture was then purged with nitrogen, filtered through CELITE® and concentrated under reduced pressure to give the title compound as a colorless liquid (502 mg, 90%), which was used without further purification. MS ($ES^+$) $C_{11}H_{11}F_3N_2O_4$ requires: 262, found: 263 [M+H]+.

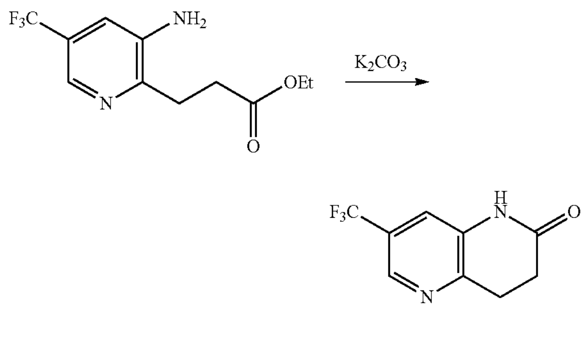

7-(Trifluoromethyl)-3,4-dihydro-1,5-naphthyridin-2(1H)-one

To a solution of the product from the previous step (500 mg, 1.91 mmol) in DMF (10 mL) was added $K_2CO_3$ (791 mg, 5.72 mmol), and the resulting mixture was stirred at 80° C. for 4 h, allowed to cool to RT, then concentrated under reduced pressure. The residue was purified by $SiO_2$ gel chromatography (0% to 5% MeOH in DCM) to give the title compound as a white solid (388 mg, 94%). MS ($ES^+$) $C_9H_7F_3N_2O$ requires: 216, found: 217 $[M+H]^+$.

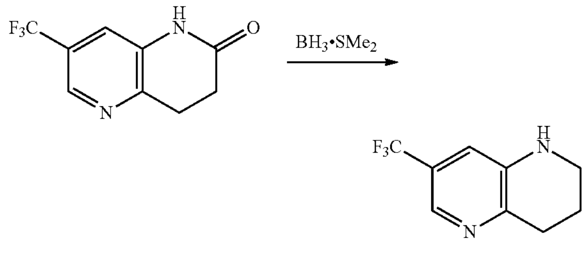

7-(Trifluoromethyl)-1,2,3,4-tetrahydro-1,5-naphthyridine

To a solution of the product from the previous step (385 mg, 1.78 mmol) in THF (10 mL) was added $BH_3{\cdot}SMe_2$ (0.169 mL, 1.78 mmol), and the resulting mixture was stirred at 60° C. for 2 h then allowed to cool to RT. MeOH (10 mL) was added dropwise and the resulting mixture was stirred at 60° C. for 1 h then concentrated under reduced pressure. The residue was purified by $SiO_2$ gel chromatography (0% to 5% MeOH in DCM) to give the title compound as a white solid (325 mg, 90%). MS ($ES^+$) $C_9H_9F_3N_2$ requires: 202, found: 203 $[M+H]^+$.

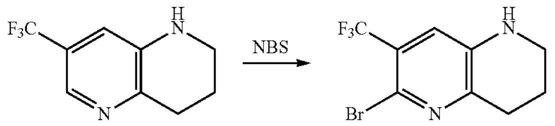

6-Bromo-7-(trifluoromethyl)-1,2,3,4-tetrahydro-1,5-naphthyridine

To a solution of the product from the previous step (300 mg, 1.48 mmol) in THF (10 mL) was added NBS (291 mg, 1.63 mmol), and the resulting mixture was stirred at 20° C. for 1 h. $H_2O$ (20 mL) was added, and the layers were separated. The aqueous layer was extracted with EtOAc (3×10 mL), and the combined organic layers were washed with sat. aq. NaCl, dried over $MgSO_4$, filtered and concentrated under reduced pressure. The residue was purified by $SiO_2$ gel chromatography (0% to 40% EtOAc in hexanes) to give the title compound as a white solid (344 mg, 82%). MS ($ES^+$) $C_9H_8BrF_3N_2$ requires: 280, found: 281 $[M+H]^+$.

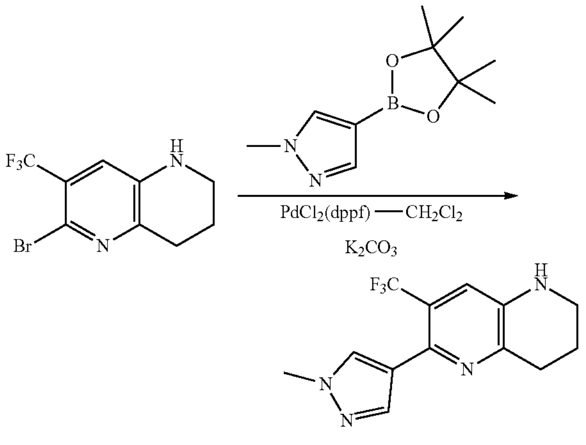

6-(1-Methyl-1H-pyrazol-4-yl)-7-(trifluoromethyl)-1,2,3,4-tetrahydro-1,5-naphthyridine A degassed solution of the product from the previous step (250 mg, 0.889 mmol), 1-methyl-4-(4,4,5,5-tetramethyl-1,3,2-dioxaborolan-2-yl)-1H-pyrazole (222 mg, 1.07 mmol), $PdCl_2(dppf)$-$CH_2Cl_2$ (72.6 mg, 0.089 mmol) and $K_2CO_3$ (0.889 mL, 1.78 mmol) in DMF (5 mL) was stirred at 90° C. for 1 h, then concentrated under reduced pressure. The residue was purified by $SiO_2$ gel chromatography (0% to 5%

MeOH in DCM) to give the title compound as an off-white solid (186 mg, 74%). MS ($ES^+$) $C_{13}H_{13}F_3N_4$ requires: 282, found: 283 $[M+H]^+$.

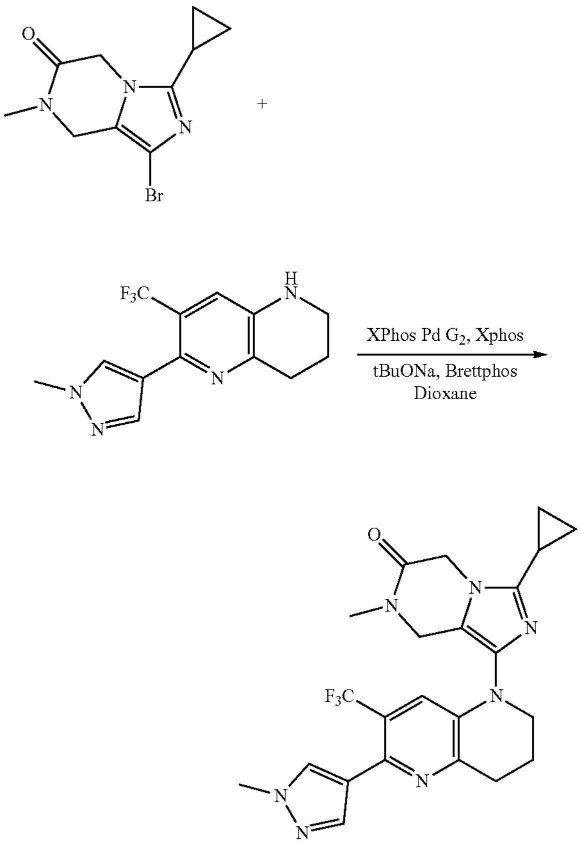

3-Cyclopropyl-7-methyl-1-(6-(1-methyl-1H-pyrazol-4-yl)-7-(trifluoromethyl)-3,4-dihydro-1,5-naphthyridin-1(2H)-yl)-7,8-dihydroimidazo[1,5-a]pyrazin-6(5H)-one bis(2,2,2)-trifluoroacetate A degassed solution of Intermediate "A" (20 mg, 0.074 mmol), the product from the previous step (20.9 mg, 0.074 mmol), t-BuONa (14.23 mg, 0.148 mmol), Brettphos (3.97 mg, 7.40 μmol) and XPhos Pd G2 (5.83 mg, 7.40 μmol) in 1,4-dioxane (0.5 mL) was stirred at 120° C. for 5 h, then concentrated under reduced pressure. The residue was purified by reverse phase preparative HPLC (Mobile phase: A=0.1% TFA/$H_2O$, B=0.1% TFA/MeCN; Gradient: B=10% to 40%; 12 min; Column: C18) to give the title compound as an off-white solid (15 mg, 29%).

MS ($ES^+$) $C_{23}H_{24}F_3N_7O$ requires: 471, found: 472 $[M+H]^+$.

$^1H$ NMR ($CD_3OD$) δ 7.90 (s, 1H), 7.73 (s, 1H), 7.18 (s, 1H), 4.89 (s, 2H), 4.53 (s, 2H), 3.95 (s, 3H), 3.65 (t, J=5.5 Hz, 2H), 3.12-3.07 (m, 5H), 2.25-2.17 (m, 3H), 1.31-1.26 (m, 2H), 1.12-1.08 (m, 2H).

Example 40

5,7-Dimethyl-1-(1-methyl-3-(1-methyl-1H-pyrazol-4-yl)-1H-indazol-5-yl)-3-(tetrahydro-2H-pyran-4-yl)-7,8-dihydroimidazo[1,5-a]pyrazin-6(5H)-one

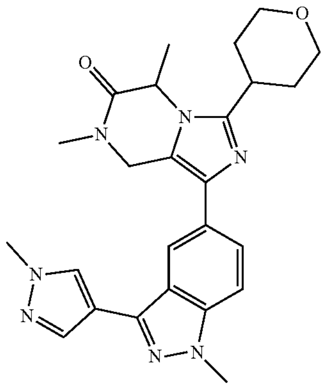 [SMILES: CC1C(=O)N(C)Cc2c(-c3ccc4c(c3)c(-c3cnn(C)c3)nn4C)nc(C3CCOCC3)n21]

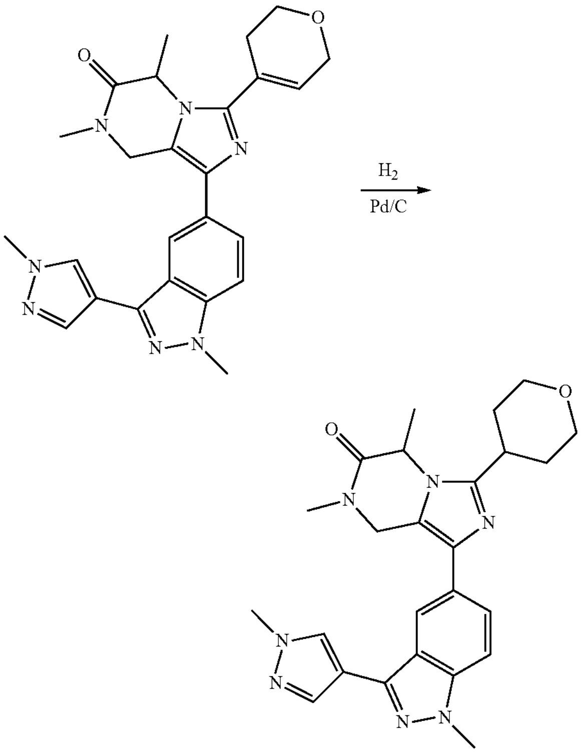

5,7-Dimethyl-1-(1-methyl-3-(1-methyl-1H-pyrazol-4-yl)-1H-indazol-5-yl)-3-(tetrahydro-2H-pyran-4-yl)-7,8-dihydroimidazo[1,5-al]pyrazin-6(5H)-one A suspension of the Example 41 compound (below) (50.0 mg, 0.109 mmol) and 10% Pd/C (106 mg) in methanol (5 mL) was degassed by bubbling with $N_2$ for 5 min, then evacuated and backfilled with $H_2$ via a balloon. The mixture was stirred at RT overnight under an atmosphere of $H_2$ (balloon), then filtered through CELITE®. The filtrate was concentrated under reduced pressure, and the residue was purified by $SiO_2$ gel chromatography (0% to 25% MeOH in DCM) to give the title compound as an off-white solid (23.5 mg, 48%).

MS ($ES^+$) $C_{25}H_{29}N_7O_2$ requires: 459, found: 460 $[M+H]^+$.

$^1H$ NMR (500 MHz, $CD_3OD$) δ 8.25 (s, 1H), 8.08 (s, 1H), 8.03 (s, 1H), 7.66-7.58 (m, 2H), 5.10-4.99 (m, 2H), 4.66-4.56 (m, 2H), 4.12-4.02 (m, 4H), 4.01 (s, 3H), 3.67-3.58 (m, 1H), 3.10 (s, 3H), 2.22-2.04 (m, 4H), 1.85-1.76 (m, 2H), 1.66 (d, J=7.1 Hz, 3H).

Example 41

3-(3,6-Dihydro-2H-pyran-4-yl)-5,7-dimethyl-1-(1-methyl-3-(1-methyl-1H-pyrazol-4-yl)-1H-indazol-5-yl)-7,8-dihydroimidazo[1,5-a]pyrazin-6(5H)-one

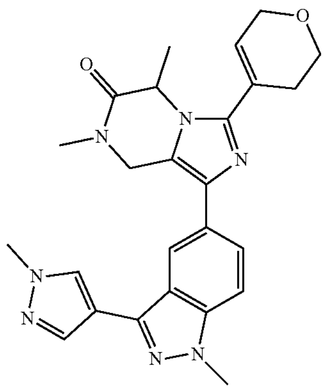 [SMILES: CC1C(=O)N(C)Cc2c(-c3ccc4c(c3)c(-c3cnn(C)c3)nn4C)nc(C3=CCOCC3)n21]

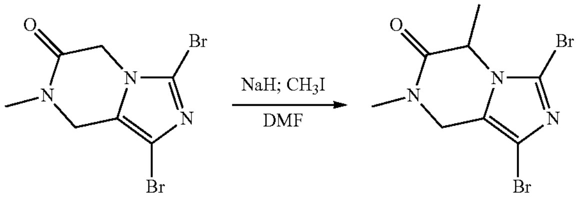

1,3-Dibromo-5,7-dimethyl-7,8-dihydroimidazo[1,5-a]pyrazin-6(5H)-one

A suspension of 1,3-dibromo-7-methyl-7,8-dihydroimidazo[1,5-a]pyrazin-6(5H)-one (1.31 g, 4.24 mmol) in DMF (21.20 mL) was purged by bubbling with $N_2$ for 5 min. The mixture was then capped and cooled to 0-5° C. To the mixture was added NaH (60% in mineral oil, 0.509 g, 12.7 mmol) in one portion. The mixture was stirred for 5 min at 0-5° C., then treated with methyl iodide (0.530 mL, 8.48 mmol) and stirred for 30 min. The reaction was then poured onto ice, the ice was allowed to melt, and the resulting mixture was diluted with EtOAc (50 mL) and washed with a sat. aq. $NH_4Cl$ solution. The organic layer was concentrated under reduced pressure. The residue was purified by $SiO_2$ gel chromatography (0% to 100% EtOAc in hexanes) to give the title compound as a white solid (1.2 g, 88%). MS ($ES^+$) $C_8H_9Br_2N_3O$ requires: 321, found: 322 $[M+H]^+$.

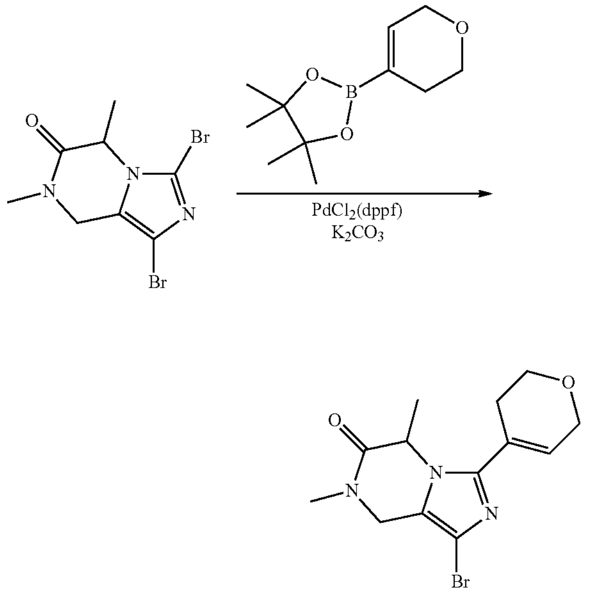

1-Bromo-3-(3,6-dihydro-2H-pyran-4-yl)-5,7-dimethyl-7,8-dihydroimidazo[1,5-a]pyrazin-6(5H)-one A stirring suspension of the product from the previous step (100 mg, 0.310 mmol), 2-(3,6-dihydro-2H-pyran-4-yl)-4,4,5,5-tetramethyl-1,3,2-dioxaborolane (71.5 mg, 0.341 mmol), $Pd(PPh_3)_4$(53.7 mg, 0.046 mmol), and 2.0 M aq. $K_2CO_3$ (0.774 mL, 1.55 mmol) in 1,4-dioxane (3 mL) was purged by bubbling with $N_2$ for 20 min. The reaction mixture was then sealed, heated to 100° C., and stirred for 2 h. The mixture was concentrated under reduced pressure, and the residue was purified by $SiO_2$ gel chromatography (0% to 100% EtOAc in hexanes) to give the title compound as a yellow solid (85 mg, 84%). MS ($ES^+$) $C_{13}H_{16}BrN_3O_2$ requires: 325, found: 326 $[M+H]^+$.

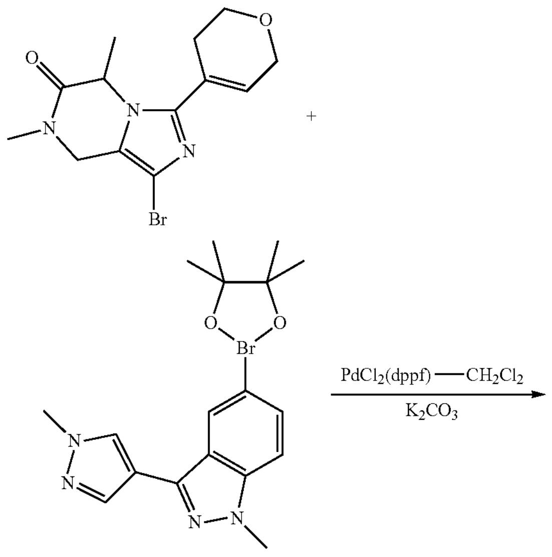

-continued

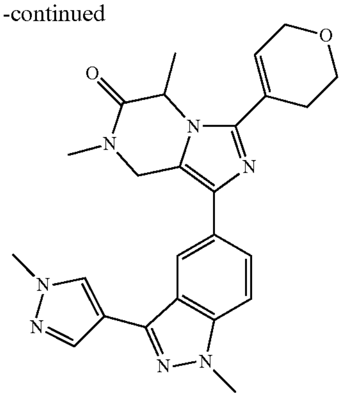

3-(3,6-Dihydro-2H-pyran-4-yl)-5,7-dimethyl-1-(1-methyl-3-(1-methyl-1H-pyrazol-4-yl)-1H-indazol-5-yl)-7,8-dihydroimidazo[1,5-a]pyrazin-6(5H)-one A mixture of the product from the previous step (50 mg, 0.15 mmol), 1-methyl-3-(1-methyl-1H-pyrazol-4-yl)-5-(4,4,5,5-tetramethyl-1,3,2-dioxaborolan-2-yl)-1H-indazole (95 mg, 0.17 mmol), $PdCl_2$(dppf)-$CH_2Cl_2$ (18.78 mg, 0.023 mmol) and 2.0 M aq. $K_2CO_3$ (250 μl, 0.500 mmol) in 1,4-dioxane (1.2 mL) was degassed by bubbling with $N_2$ for 5 min, then stirred at 100° C. for 2 h. The mixture was concentrated under reduced pressure, and the residue was purified by $SiO_2$ gel chromatography (0% to 25% MeOH in DCM) to give the title compound as an off-white solid (65 mg, 93%).

MS ($ES^+$) $C_{25}H_{27}N_7O_2$ requires: 457, found: 458 $[M+H]^+$.

$^1$H NMR (500 MHz, $CD_3OD$) δ 8.25 (s, 1H), 8.11 (s, 1H), 8.07 (s, 1H), 7.68-7.64 (m, 1H), 7.63-7.60 (m, 1H), 6.26-6.23 (m, 1H), 5.11 (d, J=15.9 Hz, 1H), 5.04 (q, J=7.1 Hz, 1H), 4.70 (d, J=15.9 Hz, 1H), 4.36 (appar q, J=2.8 Hz, 2H), 4.09 (s, 3H), 4.01 (s, 3H), 3.95 (appar t, J=5.4 Hz, 2H), 3.11 (s, 3H), 2.64-2.60 (m, 2H), 1.66 (d, J=7.0 Hz, 3H).

Example 42

3-(3,6-Dihydro-2H-pyran-4-yl)-1-(6-fluoro-1-methyl-3-(1-methyl-1H-pyrazol-4-yl)-1H-indazol-5-yl)-5,7-dimethyl-7,8-dihydroimidazo[1,5-a]pyrazin-6(5H)-one

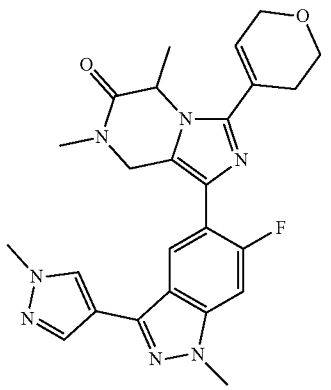 [SMILES: CC1C(=O)N(C)Cc2c(-c3cc4c(-c5cnn(C)c5)nn(C)c4cc3F)nc(C3=CCOCC3)n21]

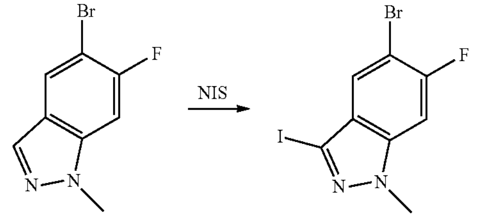

5-Bromo-6-fluoro-3-iodo-1-methyl-1H-indazole

To a solution of 5-bromo-6-fluoro-1-methyl-1H-indazole (500 mg, 2.18 mmol) in DMSO (5 mL) was added NIS (982 mg, 4.37 mmol) and the resulting mixture was stirred at 90° C. for 16 h. $H_2O$ (30 mL) and sat. aq. $Na_2S_2O_3$ (3 mL) were added, the mixture was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (0% to 15% EtOAc in hexanes) to give the title compound as a white solid (688 mg, 89%). MS ($ES^+$) $C_8H_5BrFIN_2$ requires: 354, found: 355 $[M+H]^+$.

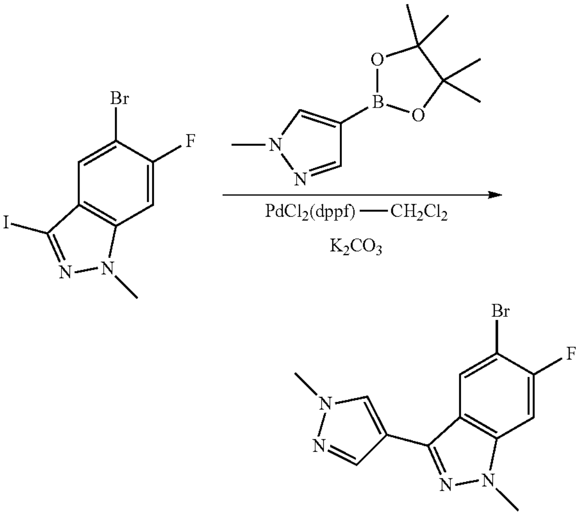

5-Bromo-6-fluoro-1-methyl-3-(1-methyl-1H-pyrazol-4-yl)-1H-indazole

To a solution of the product from the previous step (674 mg, 1.90 mmol) in 1,4-dioxane (10 mL) were added 1-methyl-4-(4,4,5,5-tetramethyl-1,3,2-dioxaborolan-2-yl)-1H-pyrazole (435 mg, 2.09 mmol), $PdCl_2$(dppf)-$CH_2Cl_2$ (155 mg, 0.190 mmol) and 2.0 M aq. $K_2CO_3$ (1.899 mL, 3.80 mmol), and the resulting mixture was stirred at 100° C. for 6 h. $H_2O$ (30 mL) was added, and the layers were separated. The aqueous layer was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (20% to 100% EtOAc in hexanes) to give the title compound as a tan solid (360 mg, 61%). MS ($ES^+$) $C_{12}H_{10}BrFN_4$ requires: 308, found: 309 $[M+H]^+$.

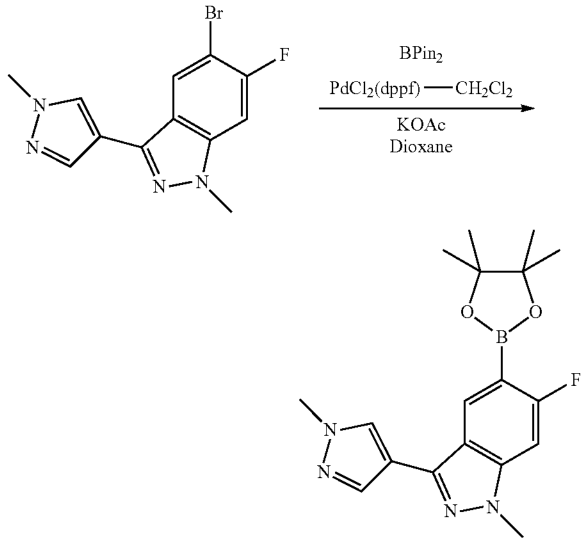

6-Fluoro-1-methyl-3-(1-methyl-1H-pyrazol-4-yl)-5-(4,4,5,5-tetramethyl-1,3,2-dioxaborolan-2-yl)-1H-indazole A degassed mixture of the product from the previous step (360 mg, 1.16 mmol), BPin$_2$ (355 mg, 1.40 mmol), PdCl$_2$(dppf)-CH$_2$Cl$_2$ (95 mg, 0.12 mmol) and KOAc (343 mg, 3.49 mmol) in 1,4-dioxane (10 mL) was stirred at 100° C. for 4 h, then allowed to cool to RT. $H_2O$ (20 mL) was added, and the layers were separated. The aqueous layer was extracted with EtOAc (3×10 mL), and the combined organic layers were washed with sat. aq. NaCl, dried over $MgSO_4$, filtered and concentrated under reduced pressure. The residue was purified by $SiO_2$ gel chromatography (0% to 5% MeOH in DCM) to give the title compound as a tan solid (288 mg, 69%). MS ($ES^+$) $C_{18}H_{22}BFN_4O_2$ requires: 356, found: 357 $[M+H]^+$.

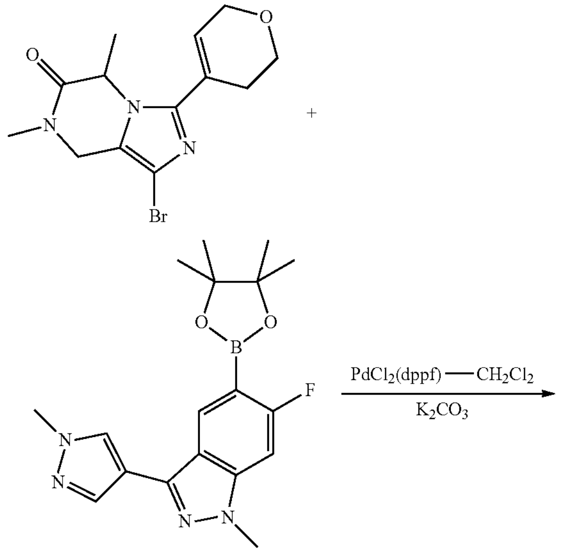

-continued

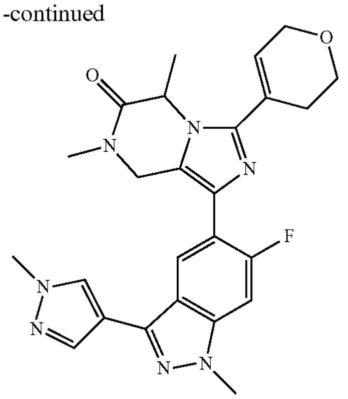

3-(3,6-Dihydro-2H-pyran-4-yl)-1-(6-fluoro-1-methyl-3-(1-methyl-1H-pyrazol-4-yl)-1H-indazol-5-yl)-5,7-dimethyl-7,8-dihydroimidazo[1,5-al]pyrazin-6(5H)-one A mixture of 1-bromo-3-(3,6-dihydro-2H-pyran-4-yl)-5,7-dimethyl-7,8-dihydroimidazo[1,5-a]pyrazin-6(5H)-one (40.0 mg, 0.123 mmol), the product from the previous step (43.7 mg, 0.123 mmol), PdCl$_2$(dppf)-CH$_2$Cl$_2$ (10.01 mg, 0.012 mmol) and 2.0 M aq. $K_2CO_3$ (0.123, 0.146 mmol) in 1,4-dioxane (0.5 mL) was degassed by bubbling with $N_2$ for 5 min, then stirred at 90° C. for 2 h. The mixture was concentrated under reduced pressure, and the residue was purified by $SiO_2$ gel chromatography (0% to 30% MeOH in DCM) to give the title compound as a brown solid (40 mg, 69%).

MS ($ES^+$) $C_{25}H_{26}FN_7O_2$ requires: 475, found: 476 $[M+H]^+$.

$^1H$ NMR (600 MHz, $CD_3OD$) δ 8.23 (s, 1H), 8.16 (d, J=6.8 Hz, 1H), 8.03 (s, 1H), 7.41 (d, J=10.8 Hz, 1H), 6.26 (s, 1H), 5.05 (q, J=7.1 Hz, 1H), 4.89 (overlaps with solvent peak, assigned 1H), 4.50 (d, J=16.2 Hz, 1H), 4.36 (appar t, J=2.7 Hz, 2H), 4.04 (s, 3H), 3.99 (s, 3H), 3.98-3.96 (m, 2H), 3.08 (s, 3H), 2.65-2.56 (m, 2H), 1.66 (d, J=7.2 Hz, 3H).

Example 43

1-(6-Fluoro-1-methyl-3-(1-methyl-1H-pyrazol-4-yl)-1H-indazol-5-yl)-5,7-dimethyl-3-(tetrahydro-2H-pyran-4-yl)-7,8-dihydroimidazo[1,5-a]pyrazin-6(5H)-one 2,2,2-trifluoroacetate

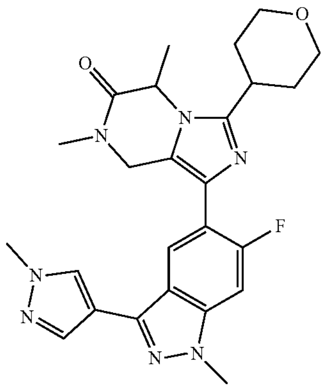 [SMILES: CC1C(=O)N(C)Cc2c(-c3cc4c(-c5cnn(C)c5)nn(C)c4cc3F)nc(C3CCOCC3)n21]

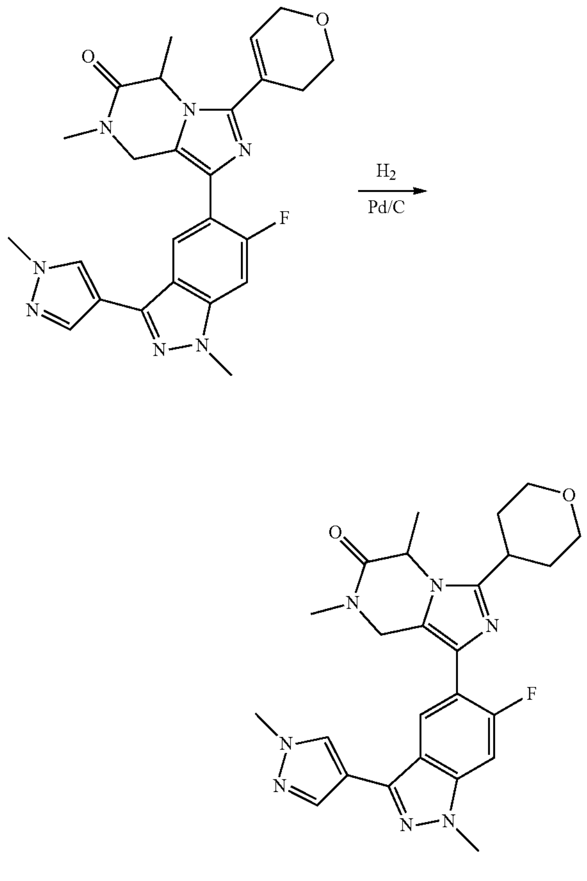

1-(6-Fluoro-1-methyl-3-(1-methyl-1H-pyrazol-4-yl)-1H-indazol-5-yl)-5,7-dimethyl-3-(tetrahydro-2H-pyran-4-yl)-7,8-dihydroimidazo[1,5-a]pyrazin-6(5H)-one 2,2,2-trifluoroacetate A suspension of 3-(3,6-dihydro-2H-pyran-4-yl)-1-(6-fluoro-1-methyl-3-(1-methyl-1H-pyrazol-4-yl)-1H-indazol-5-yl)-5,7-dimethyl-7,8-dihydroimidazo[1,5-a]pyrazin-6(5H)-one (30.0 mg, 0.047 mmol) and 10% Pd/C (50.0 mg) in MeOH (10 mL) was degassed by evacuation for 1 min, and backfilled with $H_2$ via a balloon. The mixture was stirred at RT overnight under am atmosphere of $H_2$ (balloon), then filtered through CELITE®. The filtrate was concentrated under reduced pressure, and the residue was purified by reverse phase preparative HPLC ((Mobile phase: A=0.1% TFA/$H_2O$, B=0.1% TFA/MeCN; Gradient: B=10% to 30%; 12 min; Column: C18) to give the title compound as a white solid (8.3 mg, 22%).

MS ($ES^+$) $C_{25}H_{28}FN_7O_2$ requires: 477, found: 478 $[M+H]^+$.

$^1H$ NMR (600 MHz, $CD_3OD$) δ 8.24-8.18 (m, 2H), 8.08 (s, 1H), 7.60 (d, J=10.7 Hz, 1H), 5.31 (q, J=7.2 Hz, 1H), 4.97 (d, J=16.3 Hz, 1H), 4.59 (d, J=16.4 Hz, 1H), 4.11-4.06 (m, 5H), 4.00 (s, 3H), 3.68-3.61 (m, 2H), 3.61-3.53 (m, 1H), 3.10 (s, 3H), 2.09-1.92 (m, 4H), 1.77 (d, J=7.2 Hz, 3H).

Examples 44a/44b 3-(8-(3-Cyclopropyl-5,7-dimethyl-6-oxo-5,6,7,8-tetrahydroimidazo[1,5-a]pyrazin-1-yl)isoquinolin-3-yl)-1,2,4-oxadiazol-5(4H)-one (separated enantiomers)

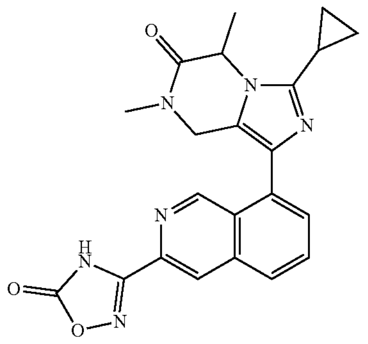 [SMILES: CC1C(=O)N(C)Cc2c(-c3cccc4cc(-c5noc(=O)[nH]5)ncc34)nc(C3CC3)n21]

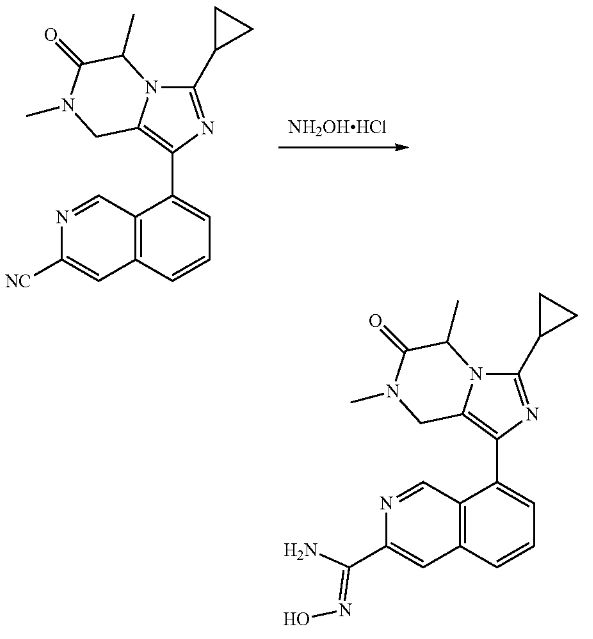

8-(3-Cyclopropyl-5,7-dimethyl-6-oxo-5,6,7,8-tetrahydroimidazo[1,5-al]pyrazin-1-yl)-N-hydroxyisoquinoline-3-carboximidamide To a solution of 8-(3-cyclopropyl-5,7-dimethyl-6-oxo-5,6,7,8-tetrahydroimidazo[1,5-a]pyrazin-1-yl)isoquinoline-3-carbonitrile (420 mg, 1.17 mmol) in EtOH (10 mL) was added hydroxylamine hydrochloride (242 mg, 3.52 mmol) in water (0.5 mL) and the resulting mixture was stirred at 80° C. for 2 h. The mixture was concentrated under reduced pressure, and the residue was purified by $SiO_2$ gel chromatography (0% to 10% MeOH in DCM) to give the title compound as a brown solid (440 mg, 96%). MS ($ES^+$): $C_{21}H_{22}N_6O_2$ requires: 390, found: 391 $[M+H]^+$.

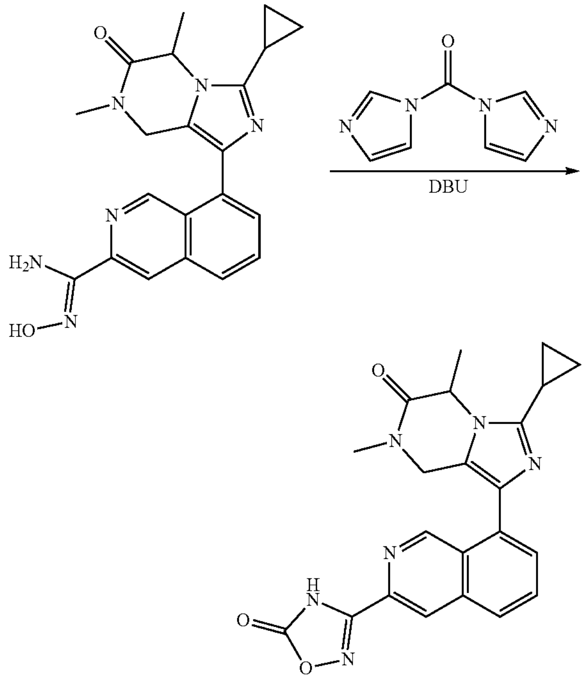

3-(8-(3-Cyclopropyl-5,7-dimethyl-6-oxo-5,6,7,8-tetrahydroimidazo[1,5-a]pyrazin-1-yl)isoquinolin-3-yl)-1,2,4-oxadiazol-5(4H)-one (separated enantiomers)

To a solution of the product from the previous step (250 mg, 0.64 mmol) in DMSO (10 mL) was added CDI (311 mg, 1.92 mmol) and DBU (107 mg, 0.70 mmol), and the resulting mixture was stirred at RT for 18 h. The mixture was concentrated under reduced pressure and the residue was purified by reverse phase preparative HPLC (Mobile phase: A=10 mM ammonium bicarbonate/water, B=MeCN; Gradient: B=7% to 39% in 18 min; Column: C18) to give the title racemic compound as a light yellow solid (28 mg, 11%). The racemate was separated by chiral HPLC [Instrument: SFC-80 (Thar, Waters); Column: IG 20*250 mm, 10 um (Daicel); Column temperature: 35° C.; Mobile phase: $CO_2$/EtOH(0.5% 7 M ammonia in MeOH)=30/70; Flow rate: 80 g/min] to give two isomers.

Example 44a was isolated as a white solid (9.4 mg, 37%). RT=1.41 min.

MS ($ES^+$): $C_{22}H_{20}N_6O_3$ requires: 416, found: 417 $[M+H]^+$. $^1H$ NMR (400 MHz, DMSO-$d_6$) δ 10.02 (s, 1H), 8.43 (s, 1H), 8.06 (d, J=7.6 Hz, 1H), 7.88-7.84 (m, 1H), 7.57 (d, J=6.6 Hz, 1H), 5.16 (q, J=6.9 Hz, 1H), 5.02 (d, J=16.0 Hz, 1H), 4.50 (d, J=16.0 Hz, 1H), 2.97 (s, 3H), 2.34-2.31 (m, 1H), 1.65 (d, J=7.1 Hz, 3H), 1.05-1.01 (m, 3H), 0.89-0.86 (m, 1H).

Example 44b was isolated as a white solid (10.3 mg, 41%). RT=2.31 min.

MS ($ES^+$): $C_{22}H_{20}N_6O_3$ requires: 416, found: 417 $[M+H]^+$.

$^1H$ NMR (400 MHz, DMSO-$d_6$) δ 10.03 (s, 1H), 8.44 (s, 1H), 8.06-8.04 (m, 1H), 7.88-7.86 (m, 1H), 7.58-7.56 (m, 1H), 5.18-5.15 (m, 1H), 5.03 (d, J=15.9 Hz, 1H), 4.50 (d, J=15.9 Hz, 1H), 2.97 (s, 3H), 2.22-2.20 (m, 1H), 1.65 (d, J=6.7 Hz, 3H), 1.05-1.02 (m, 3H), 0.87-0.85 (m, 1H).

Examples 45a/45b 3-(5-(3-Cyclopropyl-5,7-dimethyl-6-oxo-5,6,7,8-tetrahydroimidazo[1,5-a]pyrazin-1-yl)-3-(difluoromethyl)quinolin-2-yl)-1,2,4-oxadiazol-5(4H)-one (separated enantiomers)

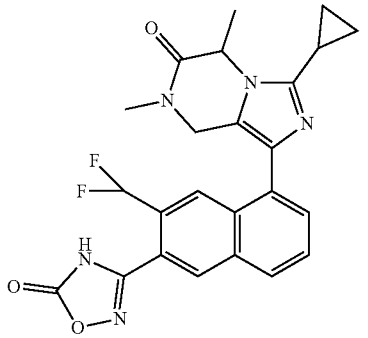 [SMILES: CC1C(=O)N(C)Cc2c(-c3cccc4cc(-c5noc(=O)[nH]5)c(C(F)F)cc34)nc(C3CC3)n21]

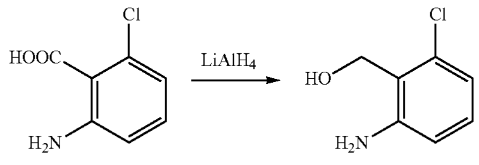 [SMILES: Nc1cccc(Cl)c1C(=O)O ; "LiAlH4" ; Nc1cccc(Cl)c1CO]

(2-Amino-6-chlorophenyl)methanol

To a solution of 2-amino-6-chlorobenzoic acid (15.0 g, 87.7 mmol) in THF (200 mL) at 0° C. was added dropwise a solution of $LiAlH_4$ (3.33 g, 87.7 mmol) in THF (50 mL), and the resulting mixture was stirred at RT for 2 h. The mixture was treated with sat. aq. $NH_4Cl$ (100 mL) and the layers were separated. The aqueous phase was extracted with EtOAc (3×500 mL), and the combined organic layers were sequentially washed with water (100 mL) and sat. aq. NaCl (100 mL), dried over $Na_2SO_4$, filtered and concentrated under reduced pressure. The residue was purified by $SiO_2$ gel chromatography (0% to 50% EtOAc in hexane) to give the title compound as a yellow solid (12.0 g, 87%). MS ($ES^+$) $C_7H_8ClNO$ requires: 157, found: 158 $[M+H]^+$.

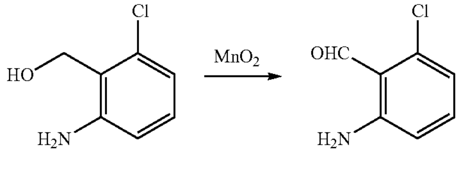

2-Amino-6-chlorobenzaldehyde

To a solution of the product from the previous step (12.0 g, 75.9 mmol) in DCM (500 mL) was added $MnO_2$ (33.0 g, 380 mmol) and the resulting mixture was stirred at RT for 5 h. The mixture was filtered through CELITE® and concentrated under reduced pressure to give the title compound as a yellow solid (12 g, 100%). MS ($ES^+$) $C_7H_6ClNO$ requires: 155, found: 156 $[M+H]^+$.

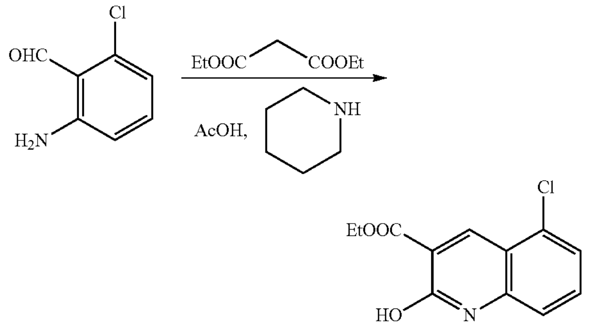

Ethyl 5-chloro-2-oxo-1,2-dihydroquinoline-3-carboxylate

To a degassed solution of the product from the previous step (12.0 g, 75.9 mmol) in MeOH (150 mL) was added dimethyl malonate (20.0 g, 152 mmol), AcOH (4.63 g, 75.9 mmol), and piperidine (6.45 g, 75.9 mmol). The mixture was stirred at 60° C. for 18 h, then concentrated under reduced pressure. The residue was purified by $SiO_2$ gel chromatography (0% to 50% EtOAc in PE) to give the title compound as a yellow solid (12.0 g, 63%). MS ($ES^{+}$)$C_{12}H_{10}ClNO_3$ requires: 251, found: 252 $[M+H]^+$.

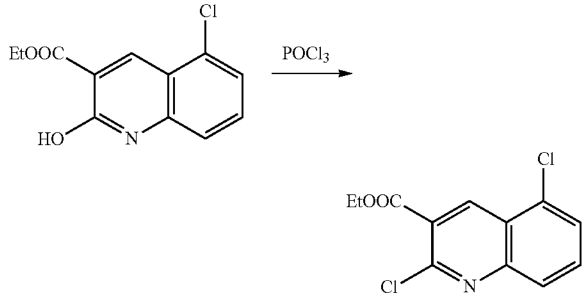

Ethyl 2,5-dichloroquinoline-3-carboxylate

To a degassed solution of the product from the previous step (12.0 g, 47.8 mmol) was added $POCl_3$ (100 mL) and the resulting mixture was stirred at 90° C. for 4 h then concentrated under reduced pressure. The residue was treated with sat. aq. $NaHCO_3$ (200 mL) and extracted with EtOAc (3×500 mL). The combined organic layers were dried over $Na_2SO_4$, filtered, and concentrated under reduced pressure. The residue was purified by SiO2 gel chromatography (0% to 30% EtOAc in PE) to give the title compound as a white solid (10 g, 78%). MS ($ES^{+}$)$C_{12}H_9Cl_2NO_2$ requires: 270, found: 271 $[M+H]^+$.

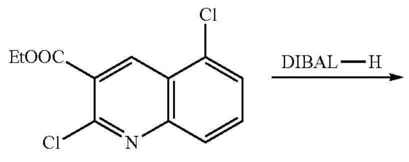

-continued

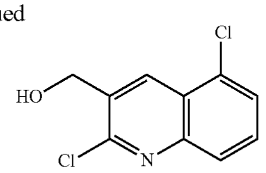

(2,5-Dichloroquinolin-3-yl)methanol

To a degassed solution of the product from the previous step (10.0 g, 37.0 mmol) in DCM (100 mL) was added 1.0 M DIBAL-H in THF (111.0 mL, 111.0 mmol) dropwise. The mixture was stirred at RT for 4 h, then treated with 1.0 M aq. HCl (5 mL) and the layers separated. The organic layer was dried over $MgSO_4$, filtered, and concentrated under reduced pressure to give the title compound as a yellow solid (7.0 g, 83%). MS ($ES^+$) $C_{10}H_7Cl_2NO$ requires: 228, found: 229 $[M+H]^+$.

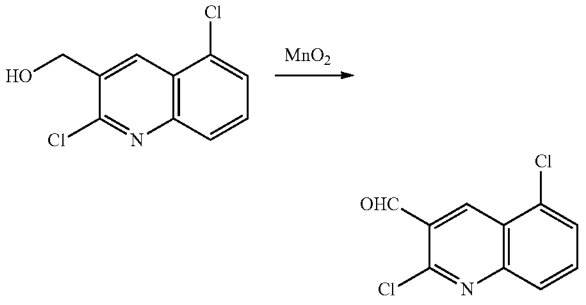

2,5-Dichloroquinoline-3-carbaldehyde

To a solution of the product from the previous step (6.0 g, 26 mmol) in DCM (200 mL) was added $MnO_2$ (11.4 g, 132 mmol) and the resulting mixture was stirred at RT for 5 h. The reaction mixture was filtered through sintered glass paper, and the collected solid was dried under reduced pressure to give the title compound as a yellow solid (6.0 g, 100%). MS ($ES^{+}$)$C_{10}H_5Cl_2NO$ requires: 226, found: 227 $[M+H]^+$.

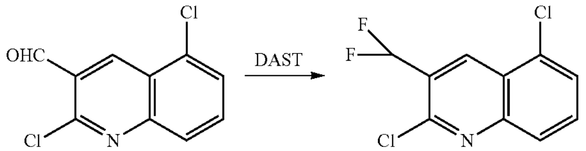

2,5-Dichloro-3-(difluoromethyl)quinoline

To a solution of the product from the previous step (6.0 g, 26.3 mmol) in DCM (60 mL) was added DAST (10.4 mL, 78.9 mmol), and the resulting mixture was stirred at 20° C. for 2 h. The mixture was washed with sat. aq. $NaHCO_3$(200 mL), and the aqueous layer was back-extracted with DCM (3×200 mL). The combined organic layers were washed with sat. aq. NaCl (200 mL), dried over $Na_2SO_4$, filtered and concentrated under reduced pressure. The residue was purified by $SiO_2$ gel chromatography (0% to 15% EtOAc in hexane) to give the title compound as a yellow solid (4.5 g, 69%). MS (ES) $C_{10}H_5Cl_2F_2N$ requires: 246, found: 247 $[M+H]^+$.

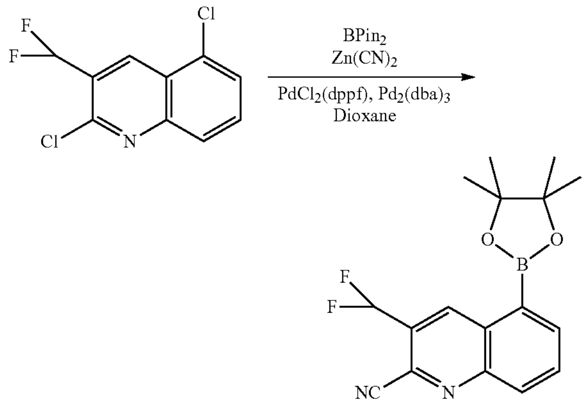

5-Chloro-3-(difluoromethyl)quinoline-2-carbonitrile

To a degassed solution of the product from the previous step (2.0 g, 8.1 mmol) in DMF (20 mL) were added $Zn(CN)_2$ (1.28 g, 12.2 mmol), $PdCl_2$(dppf) (66 mg, 0.081 mmol), and $Pd_2dba_3$ (74 mg, 0.081 mmol). The resulting mixture was stirred at 100° C. for 18 h, then concentrated under reduced pressure. The residue was purified by $SiO_2$ gel chromatography (0% to 50% EtOAc in petroleum ether) to give the title compound as a yellow solid (1.6 g, 83%). MS ($ES^+$) $C_{11}H_5ClF_2N_2$ requires: 238, found: 239 $[M+H]^+$.

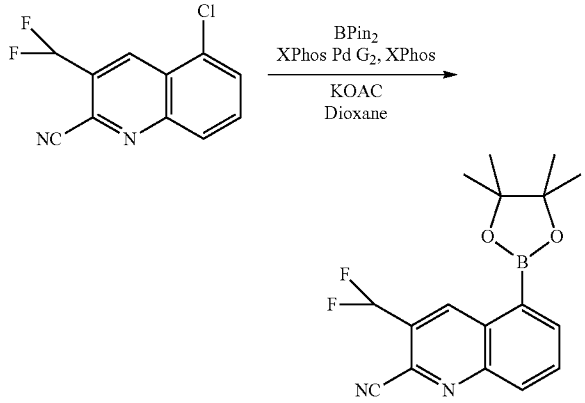

3-(Difluoromethyl)-5-(4,4,5,5-tetramethyl-1,3,2-dioxaborolan-2-yl)quinoline-2-carbonitrile To a degassed solution of the product from the previous step (500 mg, 2.10 mmol) in 1,4-dioxane (2 mL) were added $BPin_2$ (1.07 g, 4.20 mmol), KOAc (407 mg, 4.20 mmol), XPhos Pd G2 (152 mg, 0.210 mmol), and XPhos (115 mg, 0.210 mmol) The resulting mixture was stirred at 100° C. for 4 h, then concentrated under reduced pressure. The residue was purified by $SiO_2$ gel chromatography (0% to 50% EA in PE) to give the title compound as a yellow solid (300 mg, 43%). MS ($ES^+$) $C_{17}H_{17}BF_2N_2O_2$ requires: 330, found: 331 $[M+H]^+$.

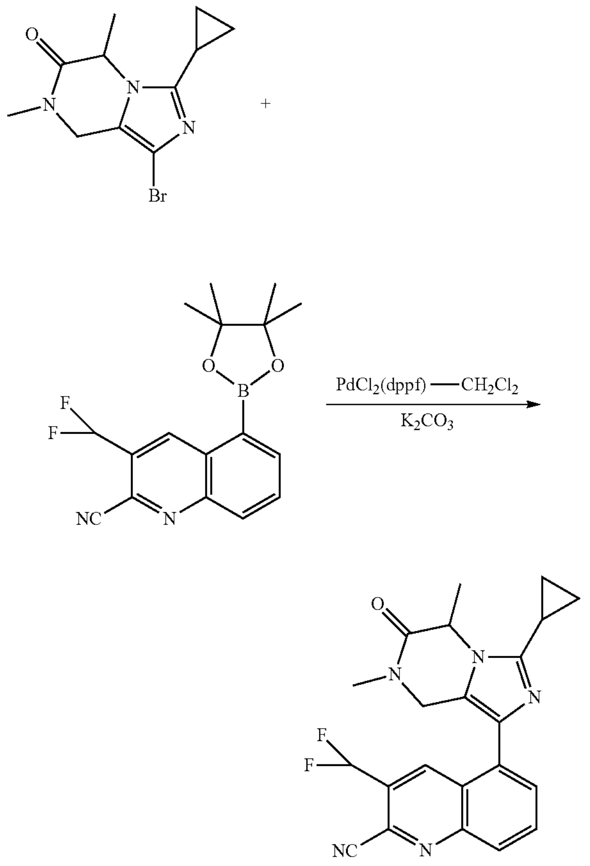

5-(3-Cyclopropyl-5,7-dimethyl-6-oxo-5,6,7,8-tetrahydroimidazo[1,5-a]pyrazin-1-yl)-3-(difluoromethyl)quinoline-2-carbonitrile To a degassed solution of the product from the previous step (300 mg, 0.909 mmol) in 1,4-dioxane (3.0 mL) and $H_2O$ (1.0 mL) was added Intermediate "B" (257 mg, 0.909 mmol), $K_2CO_3$ (251 mg, 1.82 mmol), and $PdCl_2$(dppf) (0.091 mg, 74 mmol). The resulting mixture was stirred at 100° C. for 2 h, then concentrated under reduced pressure. The residue was purified by $SiO_2$ gel chromatography (0% to 50% EtOAc in petroleum ether) to give the title compound as a yellow solid (300 mg, 81%). MS ($ES^+$) $C_{22}H_{19}F_2N_5O$ requires: 407, found: 408 [M+H]+.

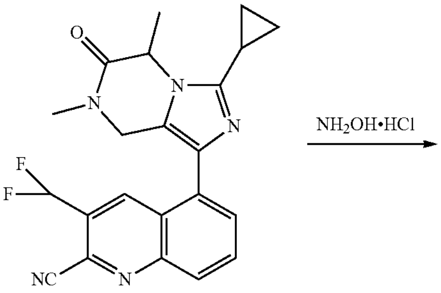

-continued

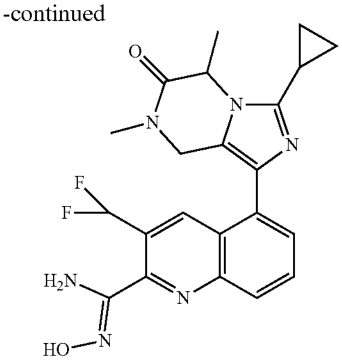

5-(3-Cyclopropyl-5,7-dimethyl-6-oxo-5,6,7,8-tetrahydroimidazo[1,5-al]pyrazin-1-yl)-3-(difluoromethyl)-N-hydroxyquinoline-2-carboximidamide To a degassed solution of the product from the previous step (300 mg, 0.737 mmol) in EtOH (3.0 mL) and $H_2O$ (0.5 mL) was added hydroxylamine hydrochloride (73.0 mg, 2.21 mmol). The mixture was stirred at 80° C. for 3 h, then concentrated under reduced pressure. The residue was purified by $SiO_2$ gel chromatography (0% to 20% MeOH in DCM) to give the title compound as an off-white solid (300 mg, 93%). MS ($ES^+$) $C_{22}H_{22}F_2N_6O_2$ requires: 440, found: 441 $[M+H]^+$.

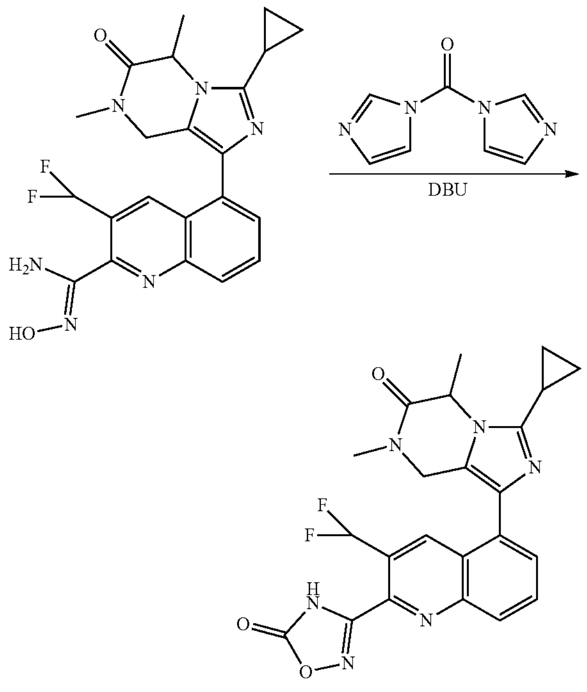

3-(5-(3-Cyclopropyl-5,7-dimethyl-6-oxo-5,6,7,8-tetrahydroimidazo[1,5-a]pyrazin-1-yl)-3-(difluoromethyl)quinolin-2-yl)-1,2,4-oxadiazol-5(4H)-one (separated enantiomers)

To a degassed solution of the product from the previous step (150 mg, 0.341 mmol) in DMSO (3.0 mL) were added CDI (166 mg, 1.02 mmol) and DBU (51.8 mg, 0.341 mmol). The resulting mixture was stirred at 80° C. for 4 h, then concentrated under reduced pressure. The residue was purified by reverse phase preparative HPLC (Mobile phase: A=10 mM ammonium bicarbonate/water, B=MeCN; Gradient: B=13% to 42% in 18 min; Column: C18) to give the title racemic compound. The racemate was separated by chiral HPLC [Instrument: SFC-80 (Thar, Waters); Column: SC 20*250 mm, 10 um (Daicel); Column temperature: 35° C.; Mobile phase: $CO_2$/MeOH(0.2% 7 M ammonia in MeOH)=50/50; Flow rate: 80 g/min] to give two isomers.

Example 45a was isolated as a yellow solid (8.0 mg, 5%). RT=3.36 min.

MS ($ES^+$) $C_{23}H_{20}F_2N_6O_3$ requires: 466, found: 467 $[M+H]^+$.

$^1H$ NMR (400 MHz, DMSO-$d_6$) δ 9.79 (s, 1H), 8.10 (d, J=8.8 Hz, 1H), 7.99 (dd, J=8.4, 7.2 Hz, 1H), 7.71 (t, J=54.0 Hz, 1H) 7.63 (d, J=7.2 Hz, 1H), 5.17 (q, J=7.2 Hz, 1H), 5.04 (d, J=16.0 Hz, 1H), 4.56 (d, J=16.0 Hz, 1H), 2.99 (s, 3H), 2.29-2.15 (m, 1H), 1.65 (d, J=7.0 Hz, 3H), 1.10-0.98 (m, 3H), 0.91-0.79 (m, 1H).

Example 45b was isolated as a yellow solid (8.0 mg, 5%). RT=4.48 min.

MS ($ES^+$) $C_{23}H_{20}F_2N_6O_3$ requires: 466, found: 467 $[M+H]^+$.

$^1H$ NMR (400 MHz, DMSO-$d_6$) δ 9.76 (s, 1H), 8.08 (d, J=8.4 Hz, 1H), 7.99 (dd, J=8.0, 7.6 Hz, 1H), 7.76 (t, J=54.8 Hz, 1H), 7.60 (d, J=7.2 Hz, 1H), 5.18 (q, J=7.2 Hz, 1H), 5.04 (d, J=16.0 Hz, 1H), 4.55 (d, J=16.0 Hz, 1H), 2.98 (s, 3H), 2.27-2.17 (m, 1H), 1.65 (d, J=7.2 Hz, 3H), 1.10-0.97 (m, 3H), 0.96-0.80 (m, 1H).

Example 46

3-(5-(3-Cyclopropyl-5,7-dimethyl-6-oxo-5,6,7,8-tetrahydroimidazo[1,5-a]pyrazin-1-yl)-3-(difluoromethyl)quinolin-2-yl)-1,2,4-thiadiazol-5(4H)-one

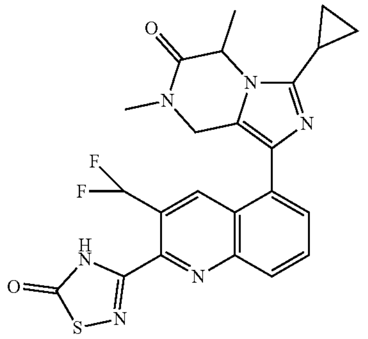 [SMILES: CC1C(=O)N(C)Cc2c(-c3cccc4nc(-c5nsc(=O)[nH]5)c(C(F)F)cc34)nc(C3CC3)n21]

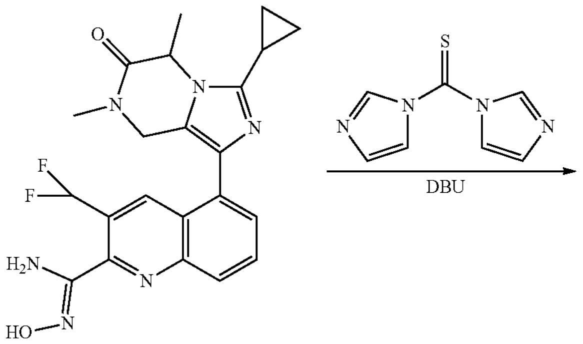

-continued

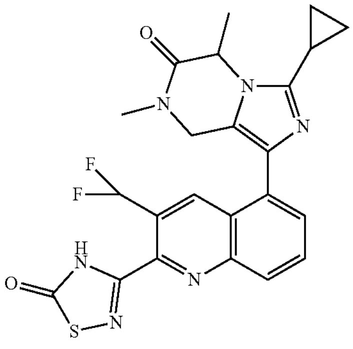

3-(5-(3-Cyclopropyl-5,7-dimethyl-6-oxo-5,6,7,8-tetrahydroimidazo[1,5-a]pyrazin-1-yl)-3-(difluoromethyl)quinolin-2-yl)-1,2,4-thiadiazol-5(4H)-one To a degassed solution of 5-(3-cyclopropyl-5,7-dimethyl-6-oxo-5,6,7,8-tetrahydroimidazo[1,5-a]pyrazin-1-yl)-3-(difluoromethyl)-N-hydroxyquinoline-2-carboximidamide (150 mg, 0.341 mmol) in DMSO (3.0 mL) were added thiocarbonyl diimidazole (182 mg, 1.02 mmol) and DBU (51.8 mg, 0.341 mmol). The resulting mixture was stirred at 80° C. for 4 h, then concentrated under reduced pressure. The residue was purified by reverse phase preparative HPLC (Mobile phase: A=10 mM $NH_4HCO_3/H_2O$, B=MeCN; Gradient: B=12% to 42% in 18 min; Column: C18) to give the title compound as a yellow solid (30.0 mg, 18%).

MS ($ES^+$) $C_{23}H_{20}F_2N_6O_2S$ requires: 482, found: 483 $[M+H]^+$.

$^1H$ NMR (400 MHz, DMSO-$d_6$) δ 9.79 (s, 1H), 8.14 (d, J=8.4 Hz, 1H), 7.96 (dd, J=8.2, 7.2 Hz, 1H), 7.58 (d, J=7.2 Hz, 1H), 7.07 (t, J=51.2 Hz, 1H), 5.16 (q, J=7.6 Hz, 1H), 5.03 (d, J=16.0 Hz, 1H), 4.55 (d, J=16.0 Hz, 1H), 2.93 (s, 3H), 2.23-2.19 (m, 1H), 1.65 (d, J=7.6 Hz, 3H), 1.06-0.99 (m, 3H), 0.96-0.82 (m, 1H).

Example 47

3-(8-(3-Cyclopropyl-5,7-dimethyl-6-oxo-5,6,7,8-tetrahydroimidazo[1,5-a]pyrazin-1-yl)isoquinolin-3-yl)-1,2,4-thiadiazol-5(4H)-one

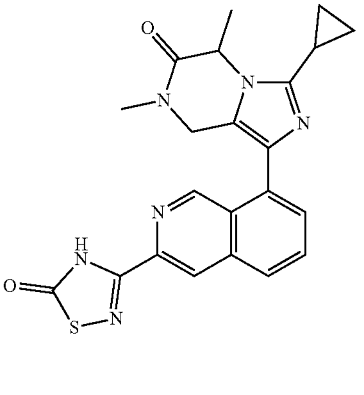

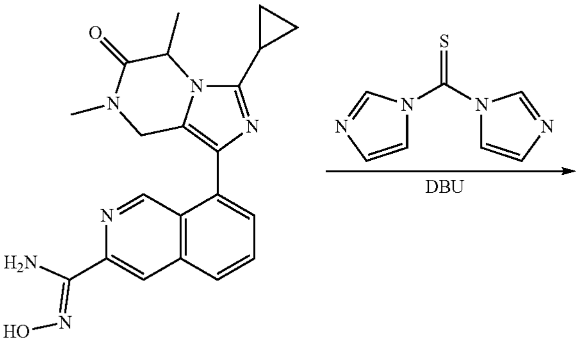

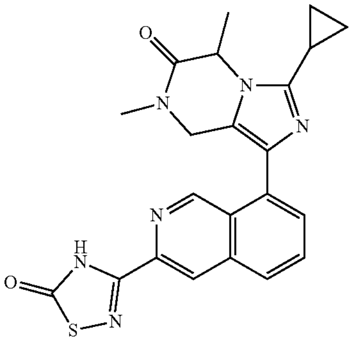

3-(8-(3-Cyclopropyl-5,7-dimethyl-6-oxo-5,6,7,8-tetrahydroimidazo[1,5-a]pyrazin-1-yl)isoquinolin-3-yl)-1,2,4-thiadiazol-5(4H)-one To a degassed solution of 8-(3-cyclopropyl-5,7-dimethyl-6-oxo-5,6,7,8-tetrahydroimidazo[1,5-a]pyrazin-1-yl)-N-hydroxyisoquinoline-3-carboximidamide (150 mg, 0.38 mmol) in DMSO (2 mL) were added thiocarbonyl diimidazole (203 mg, 1.14 mmol) and DBU (116 mg, 0.76 mmol). The mixture was stirred at RT for 18 h, then concentrated under reduced pressure. The residue was purified by reverse phase preparative HPLC (Mobile phase: A=10 mM $NH_4HCO_3/H_2O$, B=MeCN; Gradient: B=10% to 42% in 18 min; Column: C18) to give the title compound as a yellow solid (19 mg, 11%).

MS ($ES^+$): $C_{22}H_{20}N_6O_2S$ requires: 432, found: 433 $[M+H]^+$.

$^1H$ NMR (400 MHz, DMSO) δ 9.99 (s, 1H), 8.54 (s, 1H), 8.11-8.07 (m, 1H), 7.93-7.88 (m, 1H), 7.66-7.59 (m, 1H), 5.23-5.13 (m, 1H), 5.02 (d, J=16.0 Hz, 1H), 4.50 (d, J=16.0 Hz, 1H), 2.97 (s, 3H), 2.23-2.19 (m, 1H), 1.67 (d, J=6.9 Hz, 3H), 1.04 (s, 3H), 0.96-0.83 (m, 1H).

TABLE 1

Example compounds 48 to 111

| Ex. | Structure | IUPAC Name | MWt/[M + H] | |
|---|---|---|---|---|
| 48 | 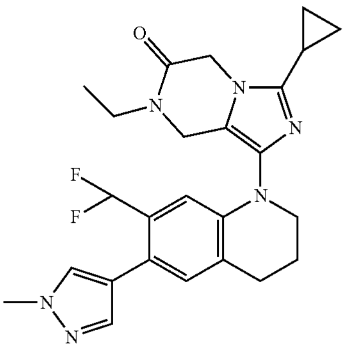 [SMILES: CCN1Cc2c(N3CCCc4cc(-c5cnn(C)c5)c(C(F)F)cc43)nc(C3CC3)n2CC1=O] | 3-cyclopropyl-1-(7-(difluoromethyl)-6-(1-methyl-1H-pyrazol-4-yl)-3,4-dihydroquinolin-1(2H)-yl)-7-ethyl-7,8-dihydroimidazo[1,5-a]pyrazin-6(5H)-one | 466/467 | 48 |
| 49 | 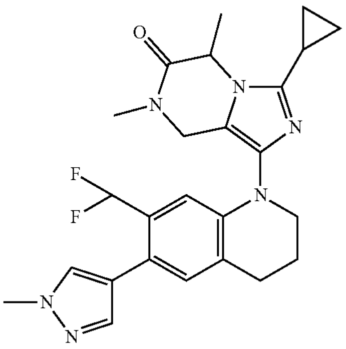 [SMILES: CC1C(=O)N(C)Cc2c(N3CCCc4cc(-c5cnn(C)c5)c(C(F)F)cc43)nc(C3CC3)n21] | 3-cyclopropyl-1-(7-(difluoromethyl)-6-(1-methyl-1H-pyrazol-4-yl)-3,4-dihydroquinolin-1(2H)-yl)-5,7-dimethyl-7,8-dihydroimidazo[1,5-a]pyrazin-6(5H)-one | 466/467 | 49 |
| 50 | 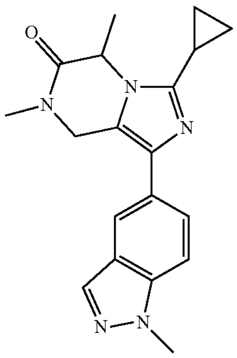 [SMILES: CC1C(=O)N(C)Cc2c(-c3ccc4c(cnn4C)c3)nc(C3CC3)n21] | 3-cyclopropyl-5,7-dimethyl-1-(1-methyl-1H-indazol-5-yl)-7,8-dihydroimidazo[1,5-a]pyrazin-6(5H)-one | 335/336 | 109 |
| 51 | 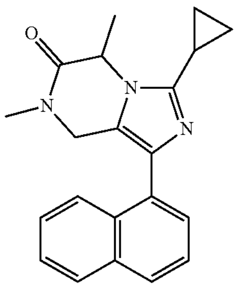 [SMILES: CC1C(=O)N(C)Cc2c(-c3cccc4ccccc34)nc(C3CC3)n21] | 3-cyclopropyl-5,7-dimethyl-1-(naphthalen-2-yl)-7,8-dihydroimidazo[1,5-a]pyrazin-6(5H)-one | 331/332 | 5 |

TABLE 1-continued

| Example compounds 48 to 111 | | | | |
|---|---|---|---|---|
| Ex. | Structure | IUPAC Name | MWt/[M + H] | |
| 52 | 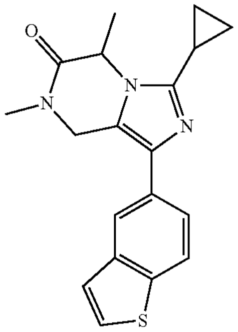 [SMILES: CC1C(=O)N(C)Cc2c(-c3ccc4sccc4c3)nc(C3CC3)n21] | 1-(benzo[b]thiophen-5-yl)-3-cyclopropyl-5,7-dimethyl-7,8-dihydroimidazo[1,5-a]pyrazin-6(5H)-one | 337/338 | 109 |
| 53 | 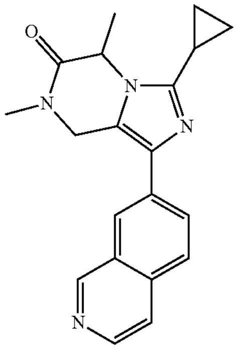 [SMILES: CC1C(=O)N(C)Cc2c(-c3ccc4ccncc4c3)nc(C3CC3)n21] | 3-cyclopropyl-1-(isoquinolin-7-yl)-5,7-dimethyl-7,8-dihydroimidazo[1,5-a]pyrazin-6(5H)-one | 332/333 | 109 |
| 54 | 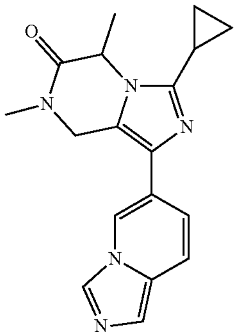 [SMILES: CC1C(=O)N(C)Cc2c(-c3ccc4cncn4c3)nc(C3CC3)n21] | 3-cyclopropyl-1-(imidazo[1,5-a]pyridin-6-yl)-5,7-dimethyl-7,8-dihydroimidazo[1,5-a]pyrazin-6(5H)-one | 321/322 | 109 |
| 55 | 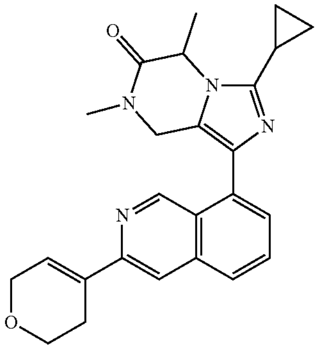 [SMILES: CC1C(=O)N(C)Cc2c(-c3cccc4cc(C5=CCOCC5)ncc34)nc(C3CC3)n21] | 3-cyclopropyl-l-(3-(3,6-dihydro-2H-pyran-4-yl)isoquinolin-8-yl)-5,7-dimethyl-7,8-dihydroimidazo[1,5-a]pyrazin-6(5H)-one | 414/415 | |

TABLE 1-continued

| Ex. | Structure | IUPAC Name | MWt/[M + H] |
|---|---|---|---|
| Example compounds 48 to 111 | | | |
| 56a | 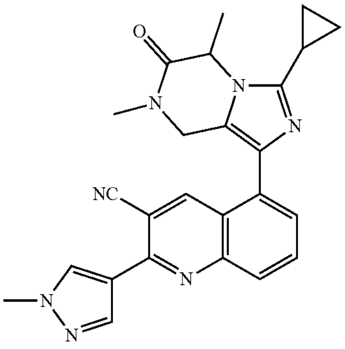 [SMILES: CC1C(=O)N(C)Cc2c(-c3cccc4nc(-c5cnn(C)c5)c(C#N)cc34)nc(C3CC3)n21] | 5-(3-cyclopropyl-5,7-dimethyl-6-oxo-5,6,7,8-tetrahydroimidazo[1,5-a]pyrazin-1-yl)-2-(1-methyl-1H-pyrazol-4-yl)quinoline-3-carbonitrile | 437/438 |
| 56b | 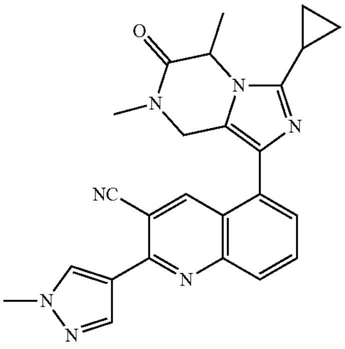 [SMILES: CC1C(=O)N(C)Cc2c(-c3cccc4nc(-c5cnn(C)c5)c(C#N)cc34)nc(C3CC3)n21] | 5-(3-cyclopropyl-5,7-dimethyl-6-oxo-5,6,7,8-tetrahydroimidazo[1,5-a]pyrazin-1-yl)-2-(1-methyl-1H-pyrazol-4-yl)quinoline-3-carbonitrile | 437/438 |
| 57 | 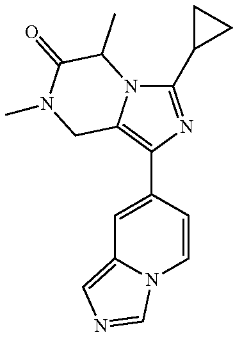 [SMILES: CC1C(=O)N(C)Cc2c(-c3ccn4cncc4c3)nc(C3CC3)n21] | 3-cyclopropyl-1-(imidazo[1,5-a]pyridin-7-yl)-5,7-dimethyl-7,8-dihydroimidazo[1,5-a]pyrazin-6(5H)-one | 321/322 |
| 58 | 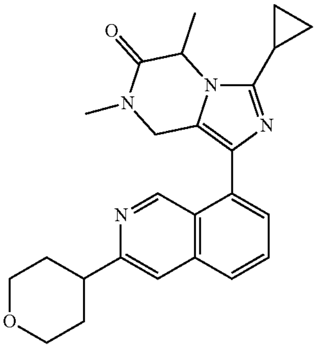 [SMILES: CC1C(=O)N(C)Cc2c(-c3cccc4cc(C5CCOCC5)ncc34)nc(C3CC3)n21] | 3-cyclopropyl-5,7-dimethyl-1-(3-(tetrahydro-2H-pyran-4-yl)isoquinolin-8-yl)-7,8-dihydroimidazo[1,5-a]pyrazin-6(5H)-one | 416/417 |

TABLE 1-continued

| Example compounds 48 to 111 | | | |
|---|---|---|---|
| Ex. | Structure | IUPAC Name | MWt/[M + H] |
| 59 | 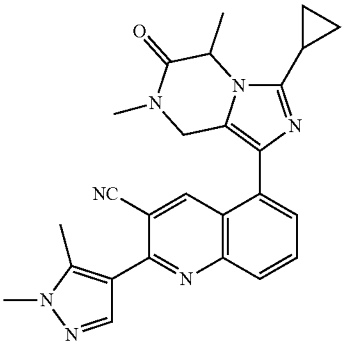 [SMILES: Cc1c(-c2nc3cccc(-c4nc(C5CC5)n5c4CN(C)C(=O)C5C)c3cc2C#N)cnn1C] | 3-cyclopropyl-1-(3-(1,5-dimethyl-1H-pyrazol-4-yl)isoquinolin-8-yl)-5,7-dimethyl-7,8-dihydroimidazo[1,5-a] pyrazin-6(5H)-one | 426/427 |
| 60 | 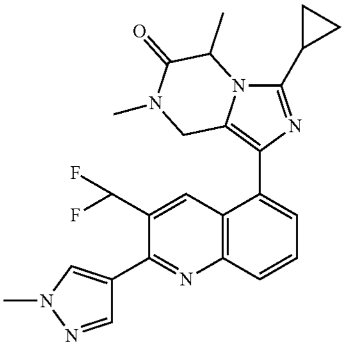 | 3-cyclopropyl-1-(3-(difluoromethyl)-2-(1 methyl-1H-pyrazol-3-yl)quinolin-5-yl)-5,7-dimethyl-7,8-dihydroimidazo[1,5-a] pyrazin-6(5H)-one | 462/463 |
| 61 | 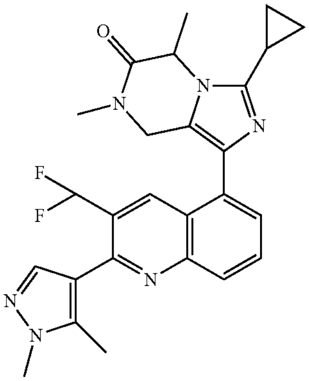 [SMILES: Cc1c(-c2nc3cccc(-c4nc(C5CC5)n5c4CN(C)C(=O)C5C)c3cc2C(F)F)cnn1C] | 3-cyclopropyl-1-(3-(difluoromethyl)-2-(1,5-dimethyl-1H-pyrazol-4-yl)quinolin-5-yl)-5,7-dimethyl-7,8-dihydroimidazo[1,5-a] pyrazin-6(5H)-one | 476/477 |
| 62 | 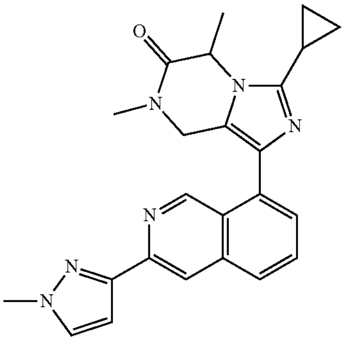 [SMILES: CC1C(=O)N(C)Cc2c(-c3cccc4cc(-c5ccn(C)n5)ncc34)nc(C3CC3)n21] | 3-cyclopropyl-5,7-dimethyl-1-(3-(l-methyl-1H-pyrazol-3-yl)isoquinolin-8-yl)-7,8-dihydroimidazo[1,5-a] pyrazin-6(5H)-one | 412/413 |

TABLE 1-continued

| Example compounds 48 to 111 | | | |
|---|---|---|---|
| Ex. | Structure | IUPAC Name | MWt/[M + H] |
| 63 | 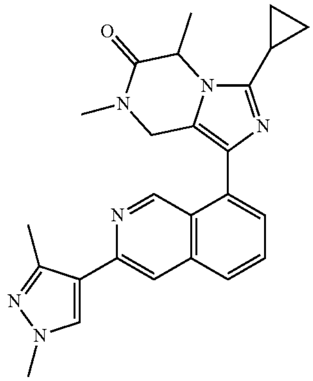 [SMILES: Cc1nn(C)cc1-c1cc2cccc(-c3nc(C4CC4)n4c3CN(C)C(=O)C4C)c2cn1] | 3-cyclopropyl-1-(3-(1,3-dimethyl-1H-pyrazol-4-yl)isoquinolin-8-yl)-5,7-dimethyl-7,8-dihydroimidazo[1,5-a]pyrazin-6(5H)-one | 426/427 |
| 64a | 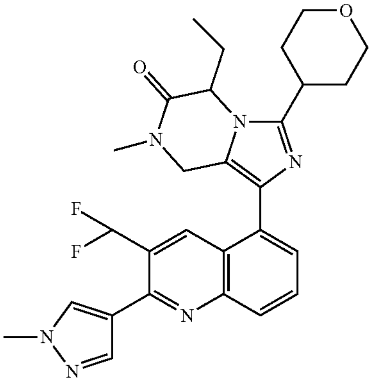 [SMILES: CCC1C(=O)N(C)Cc2c(-c3cccc4nc(-c5cnn(C)c5)c(C(F)F)cc34)nc(C3CCOCC3)n21] | 1-(3-(difluoromethyl)-2-(1-methyl-1H-pyrazol-4-yl)quinolin-5-yl)-5-ethyl-7-methyl-3-(tetrahydro-2H-pyran-4-yl)-7,8-dihydroimidazo[1,5-a]pyrazin-6(5H)-one | 520/521 |
| 64b | 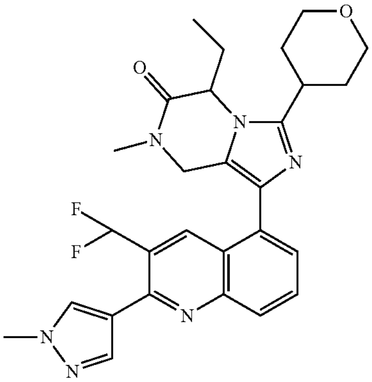 [SMILES: CCC1C(=O)N(C)Cc2c(-c3cccc4nc(-c5cnn(C)c5)c(C(F)F)cc34)nc(C3CCOCC3)n21] | 1-(3-(difluoromethyl)-2-(1-methyl-1H-pyrazol-4-yl)quinolin-5-yl)-5-ethyl-7-methyl-3-(tetrahydro-2H-pyran-4-yl)-7,8-dihydroimidazo[1,5-a]pyrazin-6(5H)-one | 520/521 |
| 65 | 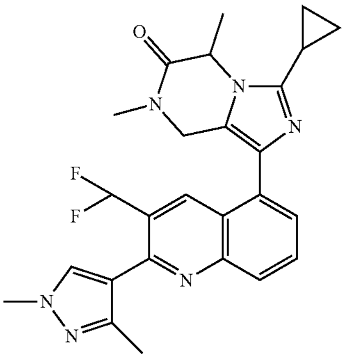 [SMILES: Cc1nn(C)cc1-c1nc2cccc(-c3nc(C4CC4)n4c3CN(C)C(=O)C4C)c2cc1C(F)F] | 3-cyclopropyl-1-(3-(difluoromethyl)-2-(1,3-dimethyl-1H-pyrazol-4-yl)quinolin-5-yl)-5,7-dimethyl-7,8-dihydroimidazo[1,5-a]pyrazin-6(5H)-one | 476/477 |

TABLE 1-continued

| Example compounds 48 to 111 | | | |
|---|---|---|---|
| Ex. | Structure | IUPAC Name | MWt/[M + H] |
| 66 | 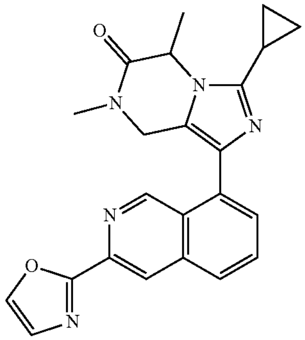 [SMILES: CC1C(=O)N(C)Cc2c(-c3cccc4cc(-c5ncco5)ncc34)nc(C3CC3)n21] | 3-cyclopropyl-5,7-dimethyl-1-(3-(oxazol-2-yl)isoquinolin-8-yl)-7,8-dihydroimidazo[1,5-a] pyrazin-6(5H)-one | 399/400 |
| 67 | 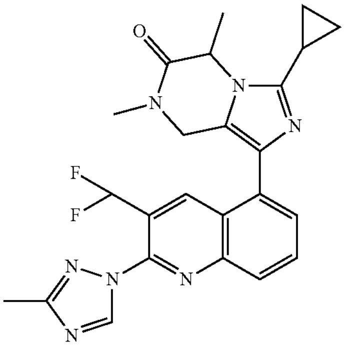 [SMILES: Cc1ncn(-c2nc3cccc(-c4nc(C5CC5)n5c4CN(C)C(=O)C5C)c3cc2C(F)F)n1] | 3-cyclopropyl-1-(3-(difluoromethyl)-2-(3-methyl-1H-1,2,4-triazol-1-yl)quinolin-5-yl)-5,7-dimethyl-7,8-dihydroimidazo[1,5-a] pyrazin-6(5H)-one | 463/464 |
| 68 | 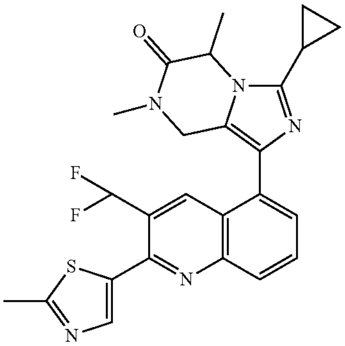 [SMILES: Cc1ncc(-c2nc3cccc(-c4nc(C5CC5)n5c4CN(C)C(=O)C5C)c3cc2C(F)F)s1] | 3-cyclopropyl-1-(3-(difluoromethyl)-2-(2-methylthiazol-5-yl)quinolin-5-yl)-5,7-dimethyl-7,8-dihydroimidazo[1,5-a] pyrazin-6(5H)-one | 479/480 |
| 69 | 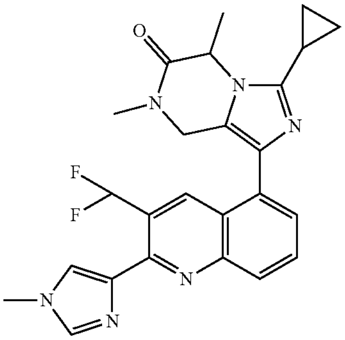 [SMILES: CC1C(=O)N(C)Cc2c(-c3cccc4nc(-c5cn(C)cn5)c(C(F)F)cc34)nc(C3CC3)n21] | 3-cyclopropyl-1-(3-(difluoromethyl)-2-(1-methyl-1H-imidazol-4-yl)quinolin-5-yl)-5,7-dimethyl-7,8-dihydroimidazo[1,5-a] pyrazin-6(5H)-one | 462/463 |

TABLE 1-continued

| Example compounds 48 to 111 | | | |
|---|---|---|---|
| Ex. | Structure | IUPAC Name | MWt/[M + H] |
| 70 | 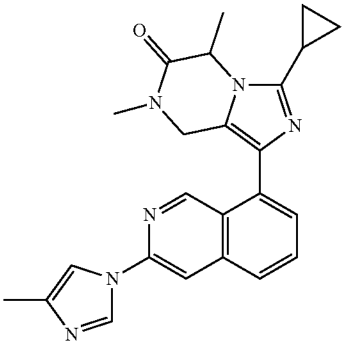 [SMILES: Cc1cn(-c2cc3cccc(-c4nc(C5CC5)n5c4CN(C)C(=O)C5C)c3cn2)cn1] | 3-cyclopropyl-5,7-dimethyl-1-(3-(4-methyl-1H-imidazol-1-yl)isoquinolin-8-yl)-7,8-dihydroimidazo[1,5-a]pyrazin-6(5H)-one | 412/413 |
| 71 | 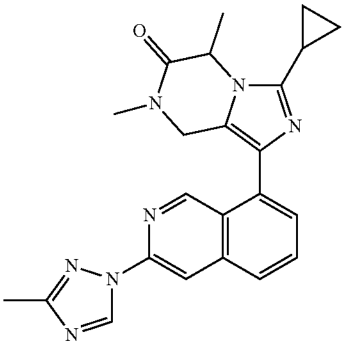 [SMILES: Cc1ncn(-c2cc3cccc(-c4nc(C5CC5)n5c4CN(C)C(=O)C5C)c3cn2)n1] | 3-cyclopropyl-5,7-dimethyl-1-(3-(3-methyl-1H-1,2,4-triazol-1-yl)isoquinolin-8-yl)-7,8-dihydroimidazo[1,5-a]pyrazin-6(5H)-one | 413/414 |
| 72 | 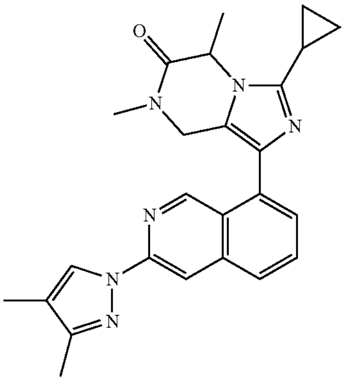 [SMILES: Cc1cn(-c2cc3cccc(-c4nc(C5CC5)n5c4CN(C)C(=O)C5C)c3cn2)nc1C] | 3-cyclopropyl-1-(3-(3,4-dimethyl-1H-pyrazol-1-yl)isoquinolin-8-yl)-5,7-dimethyl-7,8-dihydroimidazo[1,5-a]pyrazin-6(5H)-one | 426/427 |
| 73 | 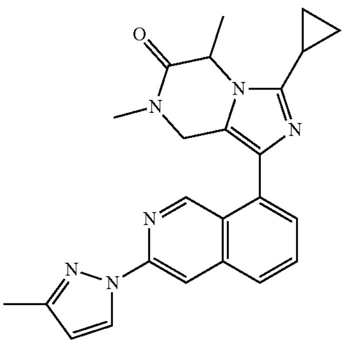 [SMILES: Cc1ccn(-c2cc3cccc(-c4nc(C5CC5)n5c4CN(C)C(=O)C5C)c3cn2)n1] | 3-cyclopropyl-5,7-dimethyl-1-(3-(3-methyl-1H-pyrazol-1-yl)isoquinolin-8-yl)-7,8-dihydroimidazo[1,5-a]pyrazin-6(5H)-one | 412/413 |

TABLE 1-continued

| Example compounds 48 to 111 | | | |
|---|---|---|---|
| Ex. | Structure | IUPAC Name | MWt/[M + H] |
| 74 | 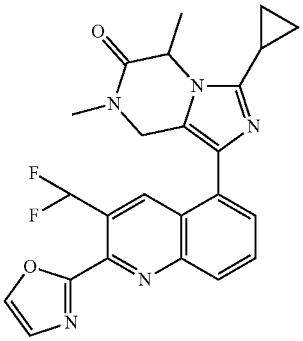 [SMILES: CC1C(=O)N(C)Cc2c(-c3cccc4nc(-c5ncco5)c(C(F)F)cc34)nc(C3CC3)n21] | 3-cyclopropyl-1-(3-(difluoromethyl)-2-(oxazol-2-yl)quinolin-5-yl)-5,7-dimethyl-7,8-dihydroimidazo[1,5-a]pyrazin-6(5H)-one | 449/450 |
| 75 | 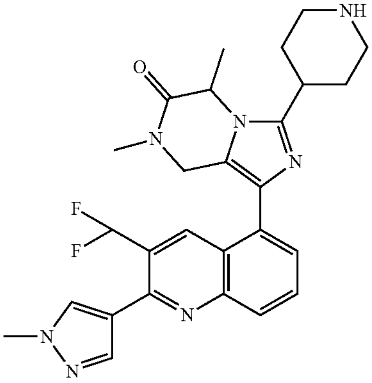 [SMILES: CC1C(=O)N(C)Cc2c(-c3cccc4nc(-c5cnn(C)c5)c(C(F)F)cc34)nc(C3CCNCC3)n21] | 1-(3-(difluoromethyl)-2-(1-methyl-1H-pyrazol-4-yl)quinolin-5-yl)-5,7-dimethyl-3-(piperidin-4-yl)-7,8-dihydroimidazo[1,5-a]pyrazin-6(5H)-one | 505/506 |
| 76 | 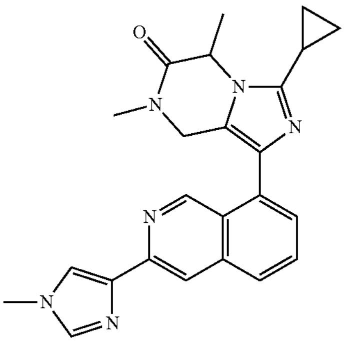 [SMILES: CC1C(=O)N(C)Cc2c(-c3cccc4cc(-c5cn(C)cn5)ncc34)nc(C3CC3)n21] | 3-cyclopropyl-5,7-dimethyl-1-(3-(1-methyl-1H-imidazol-4-yl)isoquinolin-8-yl)-7,8-dihydroimidazo[1,5-a]pyrazin-6(5H)-one | 412/413 |
| 77 | 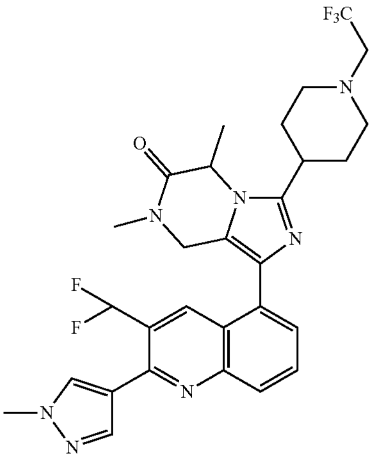 [SMILES: CC1C(=O)N(C)Cc2c(-c3cccc4nc(-c5cnn(C)c5)c(C(F)F)cc34)nc(C3CCN(CC(F)(F)F)CC3)n21] | 1-(3-(difluoromethyl)-2-(1-methyl-1H-pyrazol-4-yl)quinolin-5-yl)-5,7-dimethyl-3-(1-(2,2,2-trifluoroethyl)piperidin-4-yl)-7,8-dihydroimidazo[1,5-a]pyrazin-6(5H)-one | 587/588 |

TABLE 1-continued

| Example compounds 48 to 111 | | | |
|---|---|---|---|
| Ex. | Structure | IUPAC Name | MWt/[M + H] |
| 78 | 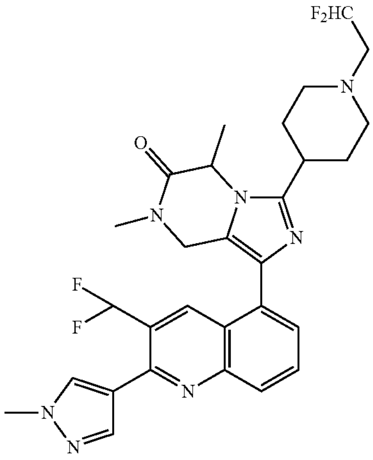 | 3-(1-(2,2-difluoroethyl)piperidin-4-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one | 569/570 |
| 79 | 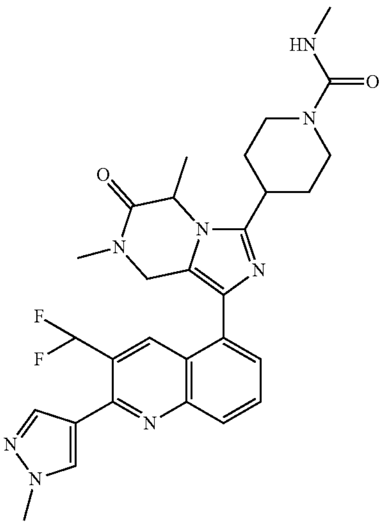 [SMILES: CNC(=O)N1CCC(c2nc(-c3cccc4nc(-c5cnn(C)c5)c(C(F)F)cc34)c3n2C(C)C(=O)N(C)C3)CC1] | 4-(1-(3-(difluoromethyl)-2-(1-methyl-1H-pyrazol-4-yl)quinolin-5-yl)-5,7-dimethyl-6-oxo-5,6,7,8-tetrahydroimidazo[1,5-a]pyrazin-3-yl)-N-methylpiperidine-1-carboxamide | 562/563 |
| 80 | 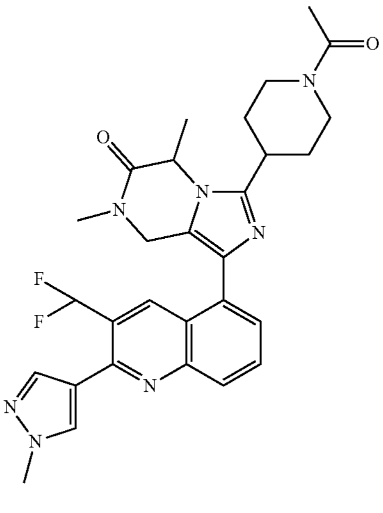 [SMILES: CC(=O)N1CCC(c2nc(-c3cccc4nc(-c5cnn(C)c5)c(C(F)F)cc34)c3n2C(C)C(=O)N(C)C3)CC1] | 3-(1-acetylpiperidin-4-yl)-1-(3-(difluoromethyl)-2-(1-methyl-1H-pyrazol-4-yl)quinolin-5-yl)-5,7-dimethyl-7,8-dihydroimidazo[1,5-a]pyrazin-6(5H)-one | 547/548 |

TABLE 1-continued

| Example compounds 48 to 111 | | | |
|---|---|---|---|
| Ex. | Structure | IUPAC Name | MWt/[M + H] |
| 81 | 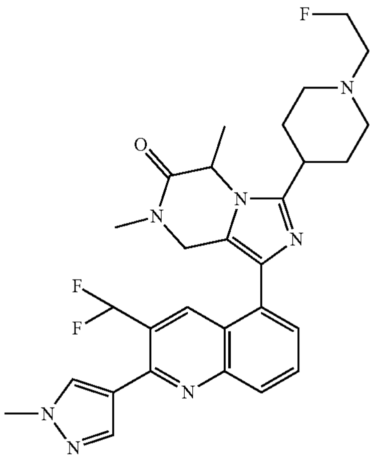 [SMILES: CC1C(=O)N(C)Cc2c(-c3cccc4nc(-c5cnn(C)c5)c(C(F)F)cc34)nc(C3CCN(CCF)CC3)n21] | 1-(3-(difluoromethyl)-2-(1-methyl-1H-pyrazol-4-yl)quinolin-5-yl)-3-(1-(2-fluoroethyl)piperidin-4-yl)-5,7-dimethyl-7,8-dihydroimidazo[1,5-a] pyrazin-6(5H)-one | 551/552 |
| 82 | 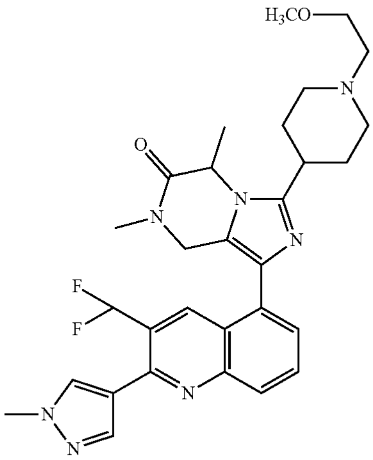 [SMILES: COCCN1CCC(c2nc(-c3cccc4nc(-c5cnn(C)c5)c(C(F)F)cc34)c3n2C(C)C(=O)N(C)C3)CC1] | 1-(3-(difluoromethyl)-2-(1-methyl-1H-pyrazol-4-yl)quinolin-5-yl)-3-(1-(2-methoxyethyl)piperidin-4-yl)-5,7-dimethyl-7,8-dihydroimidazo[1,5-a] pyrazin-6(5H)-one | 563/564 |
| 83 | 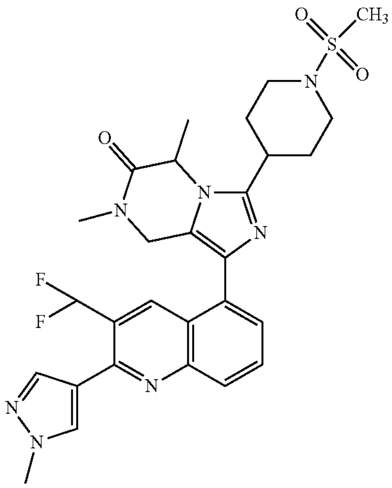 [SMILES: CC1C(=O)N(C)Cc2c(-c3cccc4nc(-c5cnn(C)c5)c(C(F)F)cc34)nc(C3CCN(S(C)(=O)=O)CC3)n21] | 1-(3-(difluoromethyl)-2-(1-methyl-1H-pyrazol-4-yl)quinolin-5-yl)-5,7-dimethyl-3-(1-(methylsulfonyl)piperidin-4-yl)-7,8-dihydroimidazo[1,5-a] pyrazin-6(5H)-one | 583/584 |

TABLE 1-continued

| Example compounds 48 to 111 | | | |
|---|---|---|---|
| Ex. | Structure | IUPAC Name | MWt/[M + H] |
| 84 | 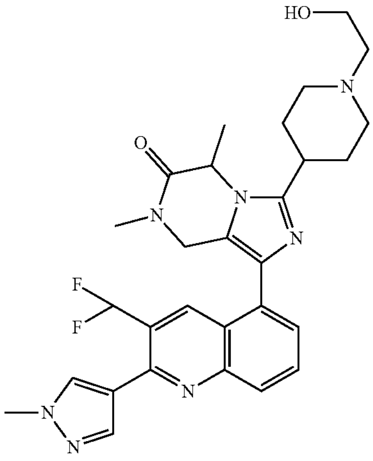 [SMILES: CC1C(=O)N(C)Cc2c(-c3cccc4nc(-c5cnn(C)c5)c(C(F)F)cc34)nc(C3CCN(CCO)CC3)n21] | 1-(3-(difluoromethyl)-2-(1-methyl-1H-pyrazol-4-yl)quinolin-5-yl)-3-(1-(2-hydroxyethyl)piperidin-4-yl)-5,7-dimethyl-7,8-dihydroimidazo[1,5-a]pyrazin-6(5H)-one | 549/550 |
| 85 | 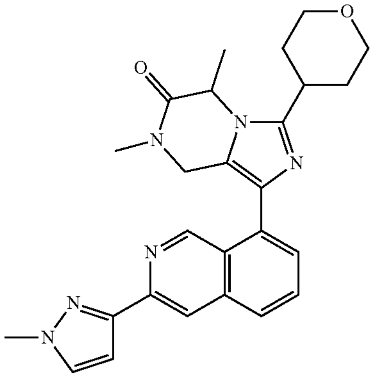 [SMILES: CC1C(=O)N(C)Cc2c(-c3cccc4cc(-c5ccn(C)n5)ncc34)nc(C3CCOCC3)n21] | 5,7-dimethyl-1-(3-(1-methyl-1H-pyrazol-3-yl)isoquinolin-8-yl)-3-(tetrahydro-2H-pyran-4-yl)-7,8-dihydroimidazo[1,5-a]pyrazin-6(5H)-one | 456/457 |
| 86 | 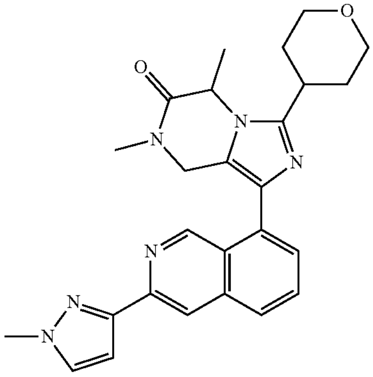 [SMILES: CC1C(=O)N(C)Cc2c(-c3cccc4cc(-c5ccn(C)n5)ncc34)nc(C3CCOCC3)n21] | 5,7-dimethyl-1-(3-(1-methyl-1H-pyrazol-3-yl)isoquinolin-8-yl)-3-(tetrahydro-2H-pyran-4-yl)-7,8-dihydroimidazo[1,5-a]pyrazin-6(5H)-one | 456/457 |

TABLE 1-continued

| Example compounds 48 to 111 | | | |
|---|---|---|---|
| Ex. | Structure | IUPAC Name | MWt/[M + H] |
| 87 | 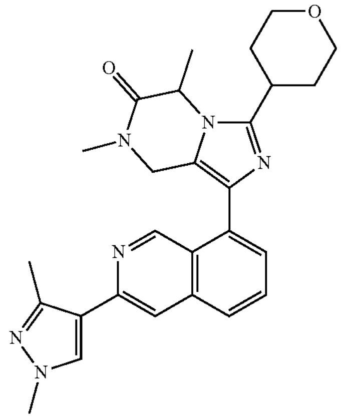 [SMILES: Cc1nn(C)cc1-c1cc2cccc(-c3nc(C4CCOCC4)n4c3CN(C)C(=O)C4C)c2cn1] | 1-(3-(1,3-dimethyl-1H-pyrazol-4-yl)isoquinolin-8-yl)-5,7-dimethyl-3-(tetrahydro-2H-pyran-4-yl)-7,8-dihydroimidazo[1,5-a]pyrazin-6(5H)-one | 470/471 |
| 88 | 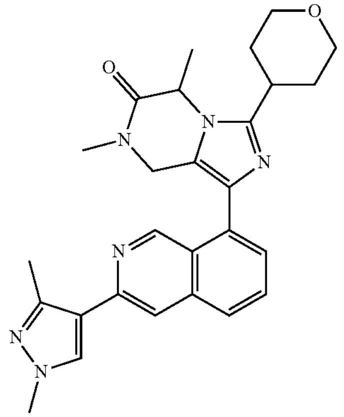 [SMILES: Cc1nn(C)cc1-c1cc2cccc(-c3nc(C4CCOCC4)n4c3CN(C)C(=O)C4C)c2cn1] | 1-(3-(1,3-dimethyl-1H-pyrazol-4-yl)isoquinolin-8-yl)-5,7-dimethyl-3-(tetrahydro-2H-pyran-4-yl)-7,8-dihydroimidazo[1,5-a]pyrazin-6(5H)-one | 470/471 |
| 89a | 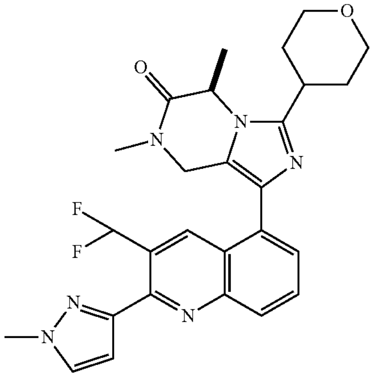 [SMILES: C[C@@H]1C(=O)N(C)Cc2c(-c3cccc4nc(-c5ccn(C)n5)c(C(F)F)cc34)nc(C3CCOCC3)n21] | (R)-1-(3-(difluoromethyl)-2-(1-methyl-1H-pyrazol-3-yl)quinolin-5-yl)-5,7-dimethyl-3-(tetrahydro-2H-pyran-4-yl)-7,8-dihydroimidazo[1,5-a]pyrazin-6(5H)-one | 506/507 |

TABLE 1-continued

| Example compounds 48 to 111 | | | |
|---|---|---|---|
| Ex. | Structure | IUPAC Name | MWt/[M + H] |
| 89b | 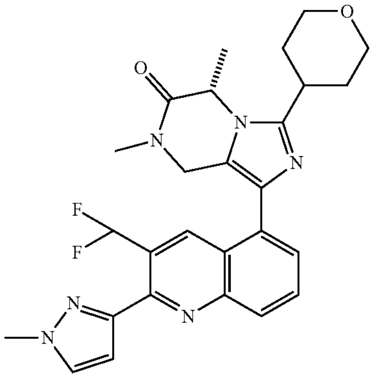 [SMILES: C[C@H]1C(=O)N(C)Cc2c(-c3cccc4nc(-c5ccn(C)n5)c(C(F)F)cc34)nc(C3CCOCC3)n21] | (S)-1-(3-(difluoromethyl)-2-(1-methyl-1H-pyrazol-3-yl)quinolin-5-yl)-5,7-dimethyl-3-(tetrahydro-2H-pyran-4-yl)-7,8-dihydroimidazo[1,5-a] pyrazin-6(5H)-one | 506/507 |
| 90a | 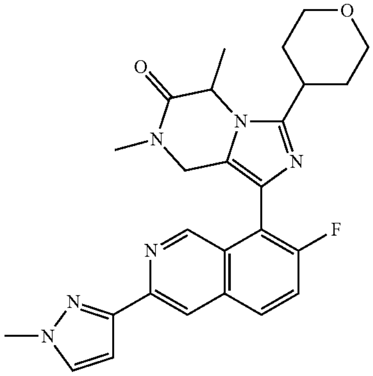 [SMILES: CC1C(=O)N(C)Cc2c(-c3c(F)ccc4cc(-c5ccn(C)n5)ncc34)nc(C3CCOCC3)n21] | 1-(7-fluoro-3-(1-methyl-1H-pyrazol-3-yl)isoquinolin-8-yl)-5,7-dimethyl-3-(tetrahydro-2H-pyran-4-yl)-7,8-dihydroimidazo[1,5a] pyrazin-6(5H)-one | 474/475 |
| 90b | 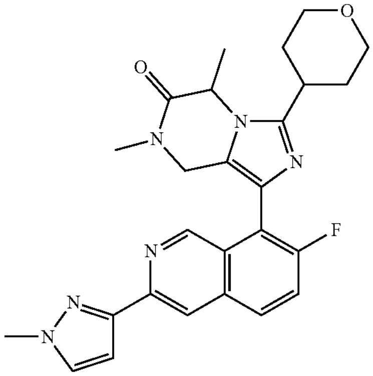 [SMILES: CC1C(=O)N(C)Cc2c(-c3c(F)ccc4cc(-c5ccn(C)n5)ncc34)nc(C3CCOCC3)n21] | 1-(7-fluoro-3-(1-methyl-1H-pyrazol-3-yl)isoquinolin-8-yl)-5,7-dimethyl-3-(tetrahydro-2H-pyran-4-yl)-7,8-dihydroimidazo[1,5a] pyrazin-6(5H)-one | 474/475 |
| 91a | 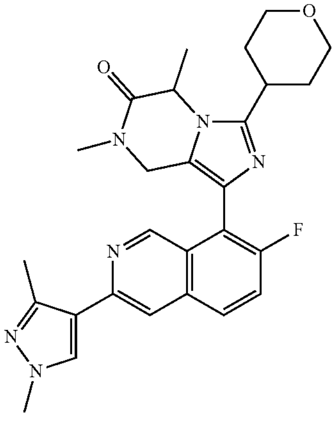 [SMILES: Cc1nn(C)cc1-c1cc2ccc(F)c(-c3nc(C4CCOCC4)n4c3CN(C)C(=O)C4C)c2cn1] | 1-(3-(1,3-dimethyl-1H-pyrazol-4-yl)-7-fluoroisoquinolin-8-yl)-5,7-dimethyl-3-(tetrahydro-2H-pyran-4-yl)-7,8-dihydroimidazo[1,5-a] pyrazin-6(5H)-one | 488/489 |

TABLE 1-continued

| Example compounds 48 to 111 | | | |
|---|---|---|---|
| Ex. | Structure | IUPAC Name | MWt/[M + H] |
| 91b | 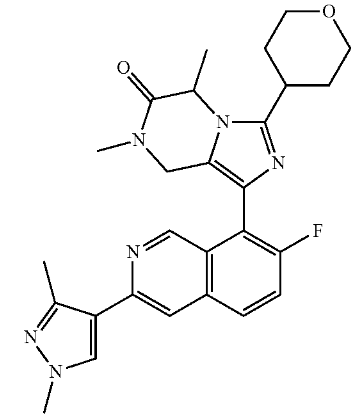 | 1-(3-(1,3-dimethyl-1H-pyrazol-4-yl)-7-fluoroisoquinolin-8-yl)-5,7-dimethyl-3-(tetrahydro-2H-pyran-4-yl)-7,8-dihydroimidazo[1,5-a] pyrazin-6(5H)-one | 488/489 |
| 92 | 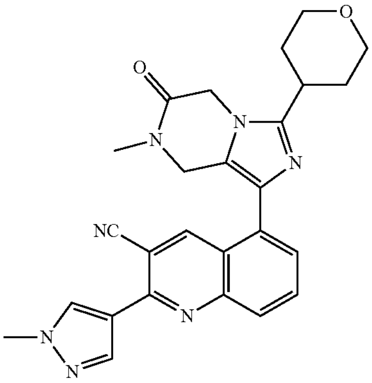 [SMILES: CN1Cc2c(-c3cccc4nc(-c5cnn(C)c5)c(C#N)cc34)nc(C3CCOCC3)n2CC1=O] | 2-(1-methyl-1H-pyrazol-4-yl)-5-(7-methyl-6-oxo-3-(tetrahydro-2H-pyran-4-yl)-5,6,7,8-tetrahydroimidazo[1,5-a] pyrazin-1-yl)quinoline-3-carbonitrile | 467/468 |
| 93 | 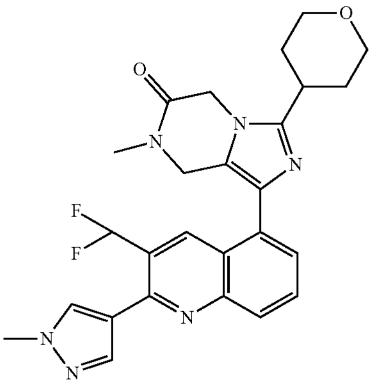 [SMILES: CN1Cc2c(-c3cccc4nc(-c5cnn(C)c5)c(C(F)F)cc34)nc(C3CCOCC3)n2CC1=O] | 1-(3-(difluoromethyl)-2-(1-methyl-1H-pyrazol-4-yl)quinolin-5-yl)-7-methyl-3-(tetrahydro-2H-pyran-4-yl)-7,8-dihydroimidazo [1,5-a] pyrazin-6(5H)-one | 492/493 |

TABLE 1-continued

| Example compounds 48 to 111 | | | |
|---|---|---|---|
| Ex. | Structure | IUPAC Name | MWt/[M + H] |
| 94 | 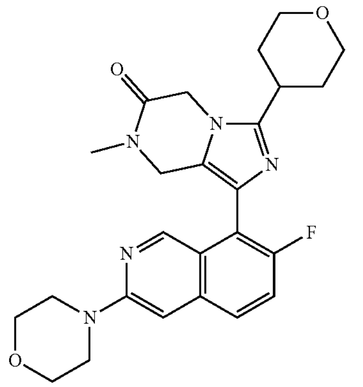 [SMILES: CN1Cc2c(-c3c(F)ccc4cc(N5CCOCC5)ncc34)nc(C3CCOCC3)n2CC1=O] | 7-methyl-1-(3-morpholinoisoquinolin-8-yl)-3-(tetrahydro-2H-pyran-4-yl)-7,8-dihydroimidazo[1,5-a] pyrazin-6(5H)-one | 447/448 |
| 95 | 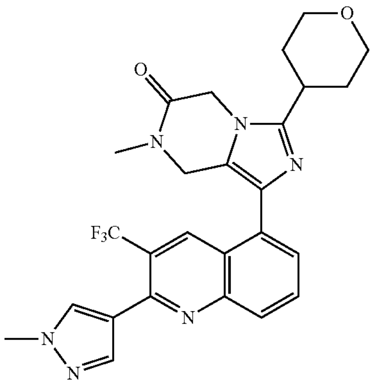 [SMILES: CN1Cc2c(-c3cccc4nc(-c5cnn(C)c5)c(C(F)(F)F)cc34)nc(C3CCOCC3)n2CC1=O] | 7-methyl-1-(2-(1-methyl-1H-pyrazol-4-yl)-3-(trifluoromethyl)quinolin-5-yl)-3-(tetrahydro-2H-pyran-4-yl)-7,8-dihydroimidazo[1,5-a] pyrazin-6(5H)-one | 510/511 |
| 96 | 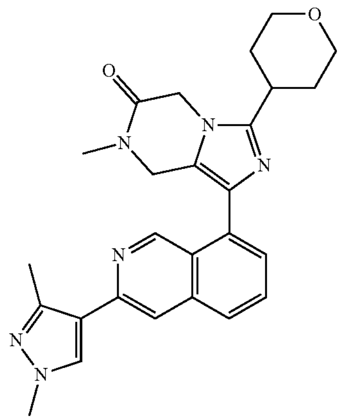 [SMILES: Cc1nn(C)cc1-c1cc2cccc(-c3nc(C4CCOCC4)n4c3CN(C)C(=O)C4)c2cn1] | 1-(3-(1,3-dimethyl-1H-pyrazol-4-yl)isoquinolin-8-yl)-7-methyl-3-(tetrahydro-2H-pyran-4-yl)-7,8-dihydroimidazo[1,5-a] pyrazin-6(5H)-one | 456/457 |

TABLE 1-continued

| Example compounds 48 to 111 | | | |
|---|---|---|---|
| Ex. | Structure | IUPAC Name | MWt/[M + H] |
| 97 | 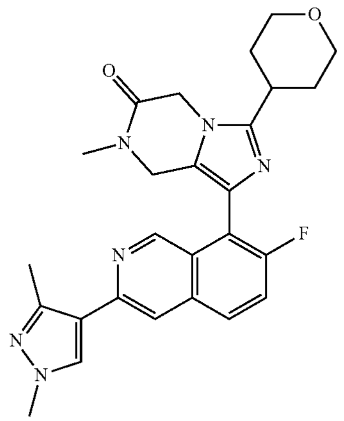 [SMILES: Cc1nn(C)cc1-c1cc2ccc(F)c(-c3nc(C4CCOCC4)n4c3CN(C)C(=O)C4)c2cn1] | 1-(3-(1,3-dimethyl-1H-pyrazol-4-yl)-7-fluoroisoquinolin-8-yl)-7-methyl-3-(tetrahydro-2H-pyran-4-yl)-7,8-dihydroimidazo[1,5-a]pyrazin-6(5H)-one | 474/475 |
| 98 | 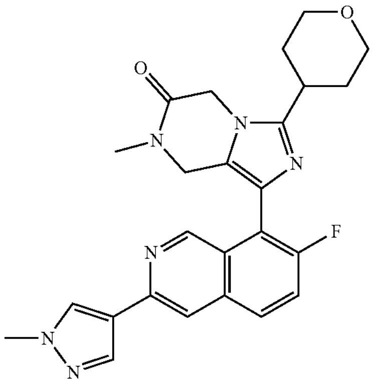 [SMILES: CN1Cc2c(-c3c(F)ccc4cc(-c5cnn(C)c5)ncc34)nc(C3CCOCC3)n2CC1=O] | 1-(7-fluoro-3-(1-methyl-1H-pyrazol-3-yl)isoquinolin-8-yl)-7-methyl-3-(tetrahydro-2H-pyran-4-yl)-7,8-dihydroimidazo[1,5-a]pyrazin-6(5H)-one | 460/461 |
| 99 | 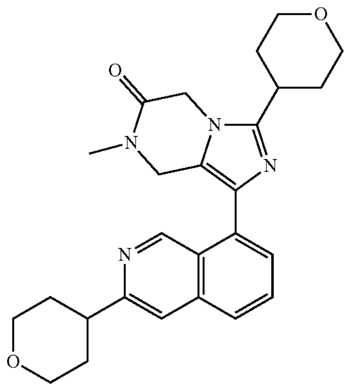 [SMILES: CN1Cc2c(-c3cccc4cc(C5CCOCC5)ncc34)nc(C3CCOCC3)n2CC1=O] | 7-methyl-3-(tetrahydro-2H-pyran-4-yl)-1-(3-(tetrahydro-2H-pyran-4-yl)isoquinolin-8-yl)-7,8-dihydroimidazo[1,5-a]pyrazin-6(5H)-one | 446/47 |

TABLE 1-continued

| Example compounds 48 to 111 | | | |
|---|---|---|---|
| Ex. | Structure | IUPAC Name | MWt/[M + H] |
| 100 | 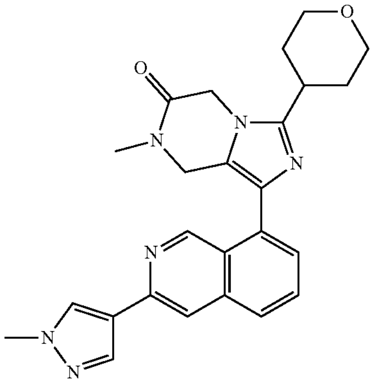 [SMILES: CN1Cc2c(-c3cccc4cc(-c5cnn(C)c5)ncc34)nc(C3CCOCC3)n2CC1=O] | 7-methyl-1-(3-(1-methyl-1H-pyrazol-3-yl)isoquinolin-8-yl)-3-(tetrahydro-2H-pyran-4-yl)-7,8-dihydroimidazo[1,5-a]pyrazin-6(5H)-one | 442/443 |
| 101 | 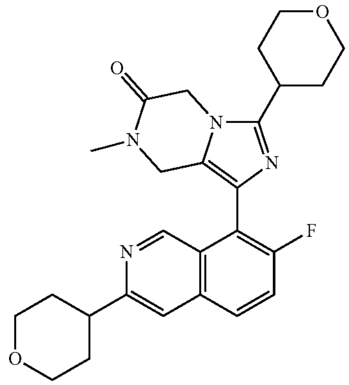 [SMILES: CN1Cc2c(-c3c(F)ccc4cc(C5CCOCC5)ncc34)nc(C3CCOCC3)n2CC1=O] | 1-(7-fluoro-3-(tetrahydro-2H-pyran-4-yl)isoquinolin-8-yl)-7-methyl-3-(tetrahydro-2H-pyran-4-yl)-7,8-dihydroimidazo[1,5-a]pyrazin-6(5H)-one | 464/465 |
| 102 | 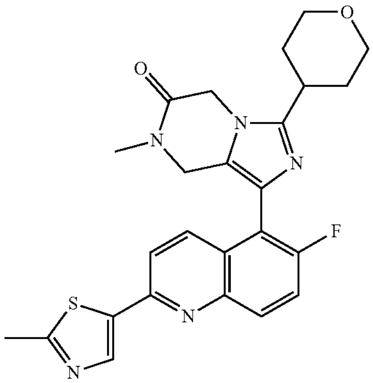 [SMILES: Cc1ncc(-c2ccc3c(-c4nc(C5CCOCC5)n5c4CN(C)C(=O)C5)c(F)ccc3n2)s1] | 1-(7-fluoro-3-(2-methylthiazol-5-yl)isoquinolin-8-yl)-7-methyl-3-(tetrahydro-2H-pyran-4-yl)-7,8-dihydroimidazo[1,5-a]pyrazin-6(5H)-one | 477/478 |
| 103 | 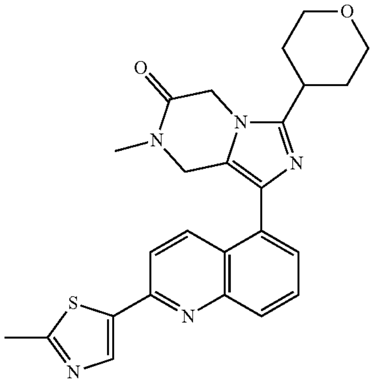 [SMILES: Cc1ncc(-c2ccc3c(-c4nc(C5CCOCC5)n5c4CN(C)C(=O)C5)cccc3n2)s1] | 7-methyl-1-(3-(2-methylthiazol-5-yl)isoquinolin-8-yl)-3-(tetrahydro-2H-pyran-4-yl)-7,8-dihydroimidazo[1,5-a]pyrazin-6(5H)-one | 459/460 |

TABLE 1-continued

| Example compounds 48 to 111 | | | | |
|---|---|---|---|---|
| Ex. | Structure | IUPAC Name | MWt/[M + H] | |
| 104 | 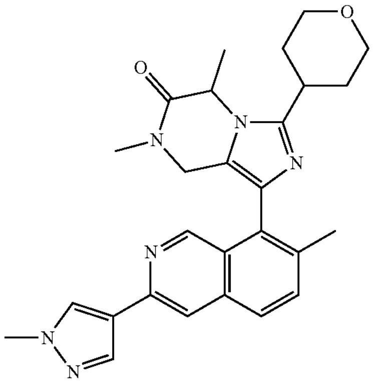 [SMILES: Cc1ccc2cc(-c3cnn(C)c3)ncc2c1-c1nc(C2CCOCC2)n2c1CN(C)C(=O)C2C] | 5,7-dimethyl-1-(7-methyl-3-(1-methyl-1H-pyrazol-3-yl)isoquinolin-8-yl)-3-(tetrahydro-2H-pyran-4-yl)-7,8-dihydroimidazo[1,5-a] pyrazin-6(5H)-one | 470/471 | |
| 105 | 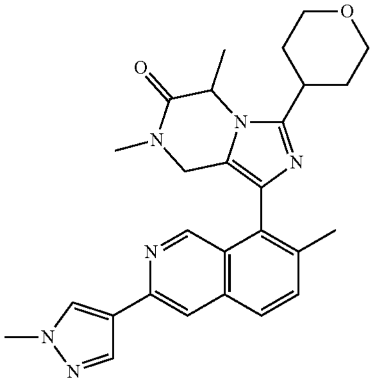 [SMILES: Cc1ccc2cc(-c3cnn(C)c3)ncc2c1-c1nc(C2CCOCC2)n2c1CN(C)C(=O)C2C] | 5,7-dimethyl-1-(7-methyl-3-(1-methyl-1H-pyrazol-3-yl)isoquinolin-8-yl)-3-(tetrahydro-2H-pyran-4-yl)-7,8-dihydroimidazo[1,5-a] pyrazin-6(5H)-one | 470/471 | |
| 106 | 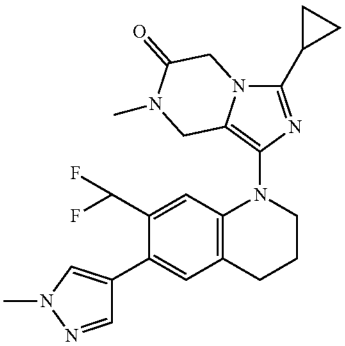 [SMILES: CN1Cc2c(N3CCCc4cc(-c5cnn(C)c5)c(C(F)F)cc43)nc(C3CC3)n2CC1=O] | 3-cyclopropyl-1-(7-(difluoromethyl)-6-(1-methyl-1H-pyrazol-4-yl)-3,4-dihydroquinolin-1(2H)-yl)-7-methyl-7,8-dihydroimidazo[1,5-a] pyrazin-6(5H)-one | 452/453 | 106 |
| 107 | 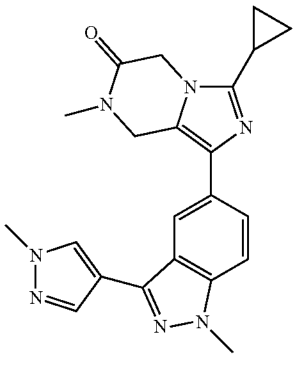 [SMILES: CN1Cc2c(-c3ccc4c(c3)c(-c3cnn(C)c3)nn4C)nc(C3CC3)n2CC1=O] | 3-cyclopropyl-7-methyl-1-(1-methyl-3-(1-methyl-1H-pyrazol-4-yl)-1H-indazol-5-yl)-7,8-dihydroimidazo [1,5-a] pyrazin-6(5H)-one | 401/402 | 107 |

TABLE 1-continued

Example compounds 48 to 111

| Ex. | Structure | IUPAC Name | MWt/[M + H] |
|---|---|---|---|
| 108 | 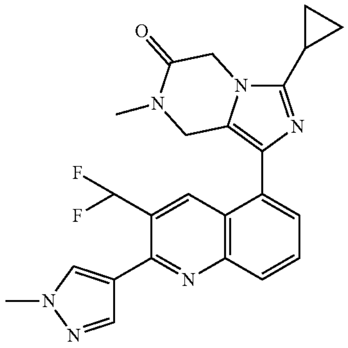 [SMILES: CN1Cc2c(-c3cccc4nc(-c5cnn(C)c5)c(C(F)F)cc34)nc(C3CC3)n2CC1=O] | 3-cyclopropyl-1-(3-(difluoromethyl)-2-(1-methyl-1H-pyrazol-4-yl)quinolin-5-yl)-7-methyl-7,8-dihydroimidazo[1,5-a]pyrazin-6(5H)-one | 448/449 |
| 109 | 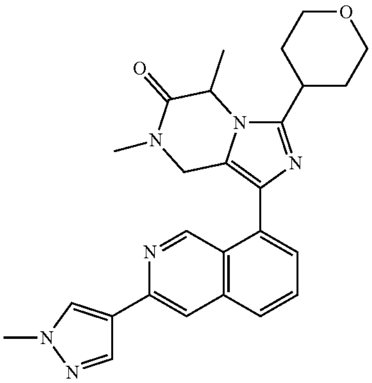 [SMILES: CC1C(=O)N(C)Cc2c(-c3cccc4cc(-c5cnn(C)c5)ncc34)nc(C3CCOCC3)n21] | 5,7-dimethyl-1-(3-(1-methyl-1H-pyrazol-4-yl)isoquinolin-8-yl)-3-(tetrahydro-2H-pyran-4-yl)-7,8-dihydroimidazo[1,5-a]pyrazin-6(5H)-one | 456/457 109 |
| 110a | 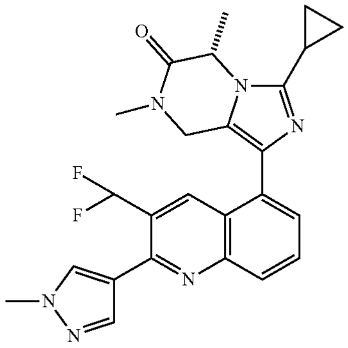 [SMILES: C[C@H]1C(=O)N(C)Cc2c(-c3cccc4nc(-c5cnn(C)c5)c(C(F)F)cc34)nc(C3CC3)n21] | (S)-3-cyclopropyl-1-(3 (difluoromethyl)-2-(1-methyl-1H-pyrazol-4-yl)quinolin-5-yl)-5,7-dimethyl-7,8-dihydroimidazo[1,5-a]pyrazin-6(5H)-one | 462/463 |
| 110b | 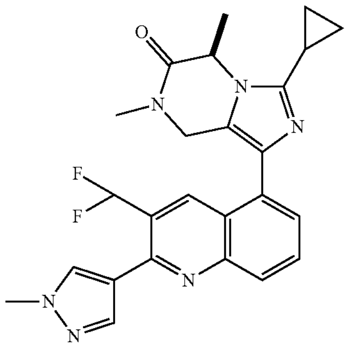 [SMILES: C[C@@H]1C(=O)N(C)Cc2c(-c3cccc4nc(-c5cnn(C)c5)c(C(F)F)cc34)nc(C3CC3)n21] | (R)-3-cyclopropyl-1-(3 (difluoromethyl)-2-(1-methyl-1H-pyrazol-4-yl)quinolin-5-yl)-5,7-dimethyl-7,8-dihydroimidazo[1,5-a]pyrazin-6(5H)-one | 462/463 |

TABLE 1-continued

Example compounds 48 to 111

| Ex. | Structure | IUPAC Name | MWt/[M + H] | |
|---|---|---|---|---|
| 111a | 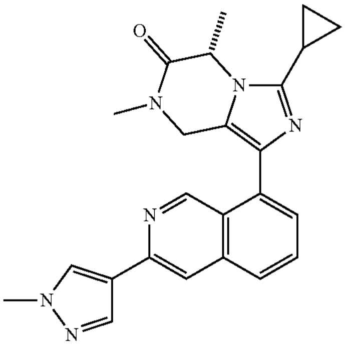 [SMILES: C[C@H]1C(=O)N(C)Cc2c(-c3cccc4cc(-c5cnn(C)c5)ncc34)nc(C3CC3)n21] | (S)-3-cyclopropyl-5,7-dimethyl-1-(3-(1-methyl-1H-pyrazol-4-yl)isoquinolin-8-yl)-7,8-dihydroimidazo[1,5-a] pyrazin-6(5H)-one | 412/413 | 111 |
| 111b | 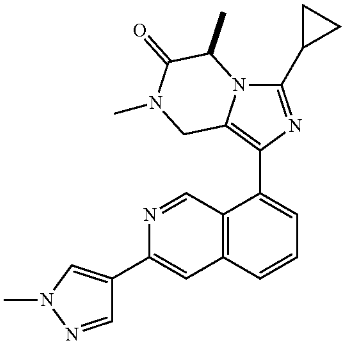 [SMILES: C[C@@H]1C(=O)N(C)Cc2c(-c3cccc4cc(-c5cnn(C)c5)ncc34)nc(C3CC3)n21] | (R)-3-cyclopropyl-5,7-dimethyl-1-(3-(1-methyl-1H-pyrazol-4-yl)isoquinolin-8-yl)-7,8-dihydroimidazo[1,5-a] pyrazin-6(5H)-one | 412/413 | 111 |

The following compounds can generally be made using the methods described above. It is expected that these compounds when made will have activity similar to those that have been made in the examples above.

| Structure | Name | SMILES |
|---|---|---|
| 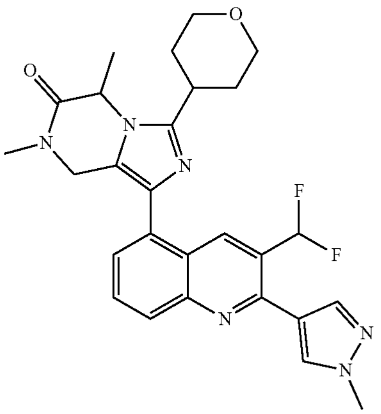 [SMILES: CC1C(=O)N(C)Cc2c(-c3cccc4nc(-c5cnn(C)c5)c(C(F)F)cc34)nc(C3CCOCC3)n21] | 1-(7-(Difluoromethyl)-6-(1-methyl-1H-pyrazol-4-yl)-3,4-dihydroquinolin-1(2H)-yl)-5,7-dimethyl-3-(tetrahydro-2H-pyran-4-yl)-7,8-dihydro-imidazo[1,5-a]pyrazin-6(5H)-one | CN(N=C1)C=C1C(C(C(F)F)=C2)=CC3=C2N(C4=C5N(C(C)C(N(C)C5)=O)C(C6CCOCC6)=N4)CCC3 |

-continued

| Structure | Name | SMILES |
|---|---|---|
| 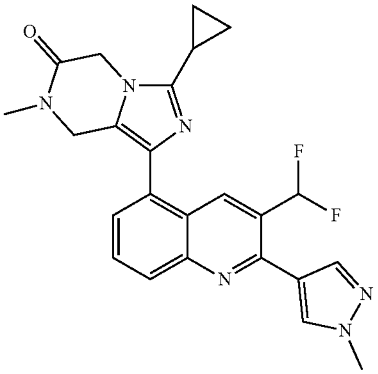 [SMILES: CN1Cc2c(-c3cccc4nc(-c5cnn(C)c5)c(C(F)F)cc34)nc(C3CC3)n2CC1=O] | 3-Cyclopropyl-1-(3-(difluoromethyl)-2-(1-methyl-1H-pyrazol-4-yl)quinolin-5-yl)-7-methyl-7,8-dihydroimidazo[1,5-a]pyrazin-6(5H)-one | CN(C1)C(CN2C1=C(C3=C4C(N=C(C5=CN(C)N=C5)C(C(F)F)=C4)=CC=C3)N=C2C6CC6)=O |
| 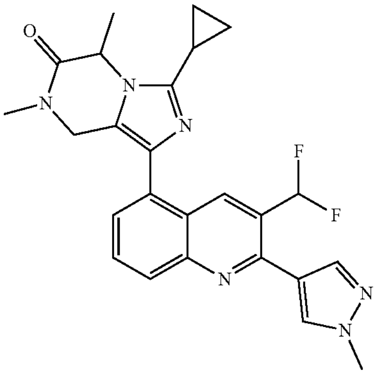 [SMILES: CC1C(=O)N(C)Cc2c(-c3cccc4nc(-c5cnn(C)c5)c(C(F)F)cc34)nc(C3CC3)n21] | 3-Cyclopropyl-1-(3-(difluoromethyl)-2-(1-methyl-1H-pyrazol-4-yl)quinolin-5-yl)-5,7-dimethyl-7,8-dihydro-imidazo[1,5-a]pyrazin-6(5/H)-one | CN(C1)C(C(C)N2C1=C(C3=C4C(N=C(C5=CN(C)N=C5)C(C(F)F)=C4)=CC=C3)N=C2C6CC6)=O |
| 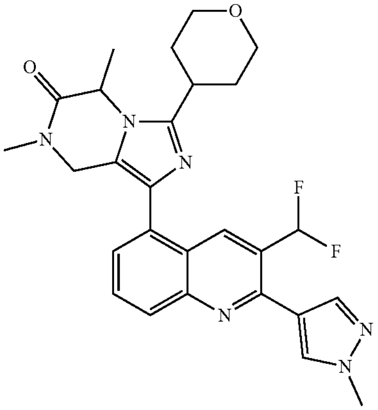 [SMILES: CC1C(=O)N(C)Cc2c(-c3cccc4nc(-c5cnn(C)c5)c(C(F)F)cc34)nc(C3CCOCC3)n21] | 1-(3-(Difluoromethyl)-2-(1-methyl-1H-pyrazol-4-yl)-quinolin-5-yl)-5,7-dimethyl-3-(tetrahydro-2H-pyran-4-yl)-7,8-dihydroimidazo[1,5-a]pyrazin-6(5H)-one | CN(C1)C(C(C)N2C1=C(C3=C4C(N=C(C5=CN(C)N=C5)C(C(F)F)=C4)=CC=C3)N=C2C6CCOCC6)=O |
| 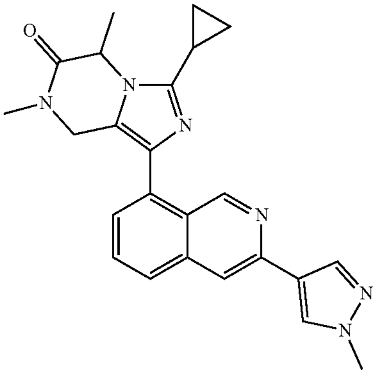 [SMILES: CC1C(=O)N(C)Cc2c(-c3cccc4cc(-c5cnn(C)c5)ncc34)nc(C3CC3)n21] | 3-Cyclopropyl-5,7-dimethyl-1-(3-(1-methyl-1H-pyrazol-4-yl)isoquinolin-8-yl)-7,8-dihydroimidazo[1,5-a]-pyrazin-6(5H)-one | CN(C1)C(C(C)N2C1=C(C3=C4C(C=C(C5=CN(C)N=C5)N=C4)=CC=C3)N=C2C6CC6)=O |

-continued

| Structure | Name | SMILES |
|---|---|---|
| 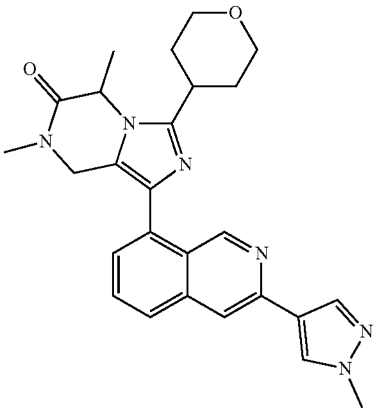 [SMILES: CC1C(=O)N(C)Cc2c(-c3cccc4cc(-c5cnn(C)c5)ncc34)nc(C3CCOCC3)n21] | 5,7-Dimethyl-1-(3-(1-methyl-1H-pyrazol-4-yl)isoquinolin-8-yl)-3-(tetrahydro-2H-pyran-4-yl)-7,8-dihydro-imidazo[1,5-a]pyrazin-6(5H)-one | CN(C1)C(C(C)N2C1=C(C3=C4C(C=C(C5=CN(C)N=C5)N=C4)=CC=C3)N=C2C6CCOCC6)=O |
| 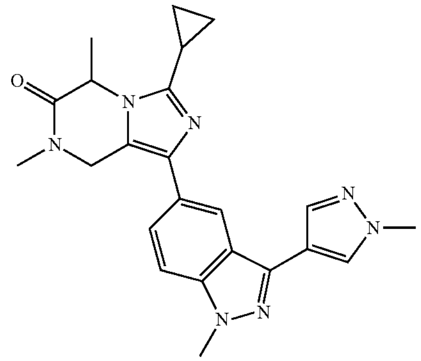 [SMILES: CC1C(=O)N(C)Cc2c(-c3ccc4c(c3)c(-c3cnn(C)c3)nn4C)nc(C3CC3)n21] | 3-Cyclopropyl-5,7-dimethyl-1-(1-methyl-3-(1-methyl-1H-pyrazol-4-yl)-1H-indazol-5-yl)-7,8-dihydroimidazo[1,5-a]pyrazin-6(5H)-one | CN(C1)C(C(C)N2C1=C(C3=CC4=C(N(C)N=C4C5=CN(C)N=C5)C=C3)N=C2C6CC6)=O |
| 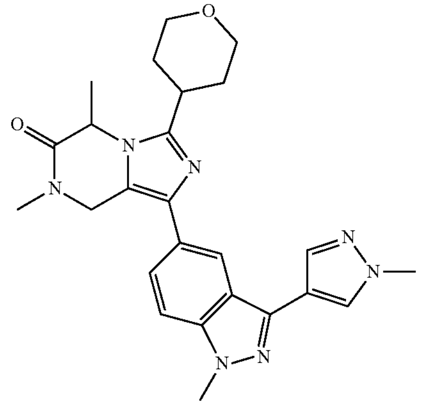 [SMILES: CC1C(=O)N(C)Cc2c(-c3ccc4c(c3)c(-c3cnn(C)c3)nn4C)nc(C3CCOCC3)n21] | 5,7-dimethyl-1-(1-methyl-3-(1-methyl-1H-pyrazol-4-yl)-1H-indazol-5-yl)-3-(tetrahydro-2H-pyran-4-yl)-7,8-dihydroimidazo[1,5-a]pyrazin-6(5H)-one | CN(C1)C(C(C)N2C1=C(C3=CC4=C(N(C)N=C4C5=CN(C)N=C5)C=C3)N=C2C6CCOCC6)=O |

The activity of the compounds in Examples 1-3 as inhibitors of CBP and BRD4 is illustrated in the following assays. The other compounds listed above, which have not yet been made and/or tested, are predicted to have activity in these assays as well.

Biological Activity Assay

Specific binding of the CBP or BRD4 bromodomain to the acetylated peptide derived from the H4 histone substrate (tetra acetylated H4(1-21) Ac-K5/8/12/16) was measured in absence or presence of inhibitors. The GST tagged bromodomains of CBP (1081-1197) and BRD4 (49-170) were obtained from BPS Bioscience and binding to the biotinylated H4(1-21) Ac-K5/8/12/16 (AnaSpec. 64989) was assessed via AlphaScreen technology (Perkin Elmer).

CBP AlphaScreen Assay:

5 nM GST-CBP(1081-1197) and 20 nM biotin-H4(1-21) Ac-K5/8/12/16 (AnaSpec. 64989) were incubated with varying concentrations of CBP inhibitors in 15 μL of buffer containing 50 mM HEPES 7.5, 100 nM NaCl, 1 mM TCEP, and 0.003% Tween-20. After 30 minutes incubation at room temperature, 15 μL of detection buffer (BPS Bio. 33006) containing 7 μg/mL of Glutathione AlphaLisa acceptor beads (Perkin Elmer AL109) and 14 μg/mL of Streptavidin donor beads (Perkin Elmer 676002) was then added to the previous mixture. The reaction was incubated for an additional 2 hours at at room temperature, and the AlphaScreen signal was quantified using the Envision Multilabel plate reader. As negative control, GST-CBP(1081-1197) was incubated with the non-acetylated biotin-H4(1-21) peptide (AnaSpec. 62555) and in presence of 0.25% of final DMSO concentration.

BRD4 AlphaScreen Assay:

the binding of 2.5 nM of BRD4(49-170) to 10 nM biotin-H4(1-21) Ac-K5/8/12/16 (AnaSpec. 64989) was assessed following the same procedure described for the CBP assay. The standard dose response curves were fitted by Genedata Screener software using the variable-slope model:

$$Signal=Signal_{negative\ control}+(Signal_{DMSO\ control}-Signal_{negative\ control})/(1+(IC_{50}/Dose)^{\wedge}Hill\ slope).$$

Only Signal and Dose in the equation were treated as know values.

TABLE 2

Biological Activity

| Ex. No | Avg CBP IC50, nM | Avg BRD4 IC50, nM |
|---|---|---|
| 1 | 7 | 8810 |
| 2 | 29 | 6815 |
| 3 | 1 | 332 |
| 4 | 6 | 17614 |
| 5a | 4 | 353 |
| 5b | 2668 | 25000 |
| 6 | 2252 | 25000 |
| 7 | 19 | 4969 |
| 8a | 513 | 25000 |
| 8b | 2 | 332 |
| 9 | 3 | 366 |
| 10 | 2 | 51 |
| 11 | 4 | 268 |
| 12 | 3 | 130 |
| 13 | 2 | 187 |
| 14 | 3 | 440 |
| 15a | 170 | 19698 |
| 15b | 2 | 195 |
| 16a | 1122 | 25000 |
| 16b | 3 | 353 |
| 17 | 2 | 3027 |
| 18 | 50 | 17488 |
| 19 | 41 | 5903 |
| 20 | 37 | 8571 |
| 21 | 13 | 6157 |
| 22 | 11 | 4339 |
| 23 | 94 | 24579 |
| 24 | 81 | 4886 |
| 25 | 26 | 11612 |
| 26a | 2 | 193 |
| 26b | 271 | 11701 |
| 27 | 43 | 8941 |
| 28 | 123 | 9366 |
| 29a | 6503 | 25000 |
| 29b | 32 | 592 |
| 30a | 1 | 96 |
| 30b | 373 | 18570 |
| 31a | 38 | 2686 |
| 31b | 2 | 106 |
| 32a | 490 | 25000 |
| 32b | 2 | 351 |
| 33a | 1614 | 25000 |
| 33b | 6 | 2125 |
| 34a | 2463 | 25000 |
| 34b | 8 | 1233 |
| 35 | 1198 | 25000 |
| 36a | 2 | 624 |
| 36b | 144 | 25000 |
| 37a | 1 | 215 |
| 37b | 647 | 25000 |
| 38a | 8 | 1814 |
| 38b | 302 | 4864 |
| 39 | 185 | 25000 |
| 40 | 9 | 1036 |
| 41 | 14 | 1615 |
| 42 | 28 | 3334 |
| 43 | 6 | 1435 |
| 44a | 68 | >25000 |
| 44b | 1 | 1460 |
| 45a | 1 | 112 |
| 45b | 29 | 5399 |
| 46 | 2 | 341 |
| 47 | 2 | 1458 |
| 48 | 18 | 17614 |
| 49 | 1 | 332 |
| 50 | 155 | 1181 |
| 51 | 80 | 688 |
| 52 | 94 | 487 |
| 53 | 159 | 2965 |
| 54 | 751 | 2102 |
| 55 | 2 | 392 |
| 56a | 424 | 25000 |
| 56b | 1 | 132 |
| 57 | 1066 | 2611 |
| 58 | 2 | 188 |
| 59 | 4 | 496 |
| 60 | 2 | 160 |
| 61 | 4 | 511 |
| 62 | 2 | 164 |
| 63 | 1 | 76 |
| 64a | 2430 | 25000 |
| 64b | 46 | 729 |
| 65 | 17 | 426 |
| 66 | 11 | 1590 |
| 67 | 3 | 319 |
| 68 | 5 | 163 |
| 69 | 13 | 1527 |
| 70 | 2 | 667 |
| 71 | 4 | 868 |
| 72 | 2 | 297 |
| 73 | 3 | 408 |
| 74 | 4 | 179 |
| 75 | 172 | 11951 |
| 76 | 2 | 384 |
| 77 | 34 | 2889 |
| 78 | 41 | 3766 |
| 79 | 39 | 2431 |
| 80 | 45 | 2564 |
| 81 | 153 | 9627 |
| 82 | 227 | 12331 |
| 83 | 42 | 3226 |
| 84 | 230 | 11690 |
| 85 | 78 | 24084 |
| 86 | 1 | 232 |
| 87 | 77 | 10738 |
| 88 | 1 | 101 |
| 89a | 1 | 101 |
| 89b | 482 | 20750 |
| 90a | 1005 | 25000 |
| 90b | 4 | 879 |
| 91a | 3608 | 25000 |
| 91b | 3 | 287 |
| 92 | 63 | 25000 |
| 93 | 357 | 25000 |
| 94 | 145 | 25000 |
| 95 | 31 | 10571 |
| 96 | 181 | 12629 |
| 97 | 323 | 25000 |
| 98 | 282 | 25000 |
| 99 | 45 | 18092 |
| 100 | 21 | 4156 |
| 101 | 219 | 25000 |
| 102 | 49 | 21309 |
| 103 | 10 | 4026 |
| 104 | 3147 | 25000 |
| 105 | 27 | 3485 |
| 106 | 9 | 5703 |
| 107 | 29 | 6815 |
| 108 | 114 | 18267 |
| 109 | 2 | 341 |
| 110a | 453 | 9254 |
| 110b | 1 | 407 |
| 111a | 510 | 25000 |

TABLE 2-continued

| Biological Activity | | |
|---|---|---|
| Ex. No | Avg CBP IC50, nM | Avg BRD4 IC50, nM |
| 111b | 1 | 89 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula I (I)

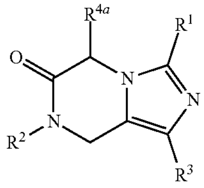

or a salt thereof, wherein:

$R^1$ is chosen from alkyl, cycloalkyl, and heterocycloalkyl, any either of which is optionally substituted with 1, 2, or 3 $R^5$ groups;

$R^2$ is H or is chosen from alkyl, heteroalkyl, and haloalkyl, any of which is optionally substituted with 1, 2, or 3 $R^6$ groups;

$R^3$ is chosen from alkyl, cycloalkyl, heterocycloalkyl, aryl, and heteroaryl, any of which is:

(a) optionally substituted with 1, 2, or 3 $R^7$ groups, and (b) optionally substituted with 1 $R^8$ group;

$R^{4a}$ is chosen from H, halo, and alkyl;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ and $R^7$ is independently chosen from alkyl, alkoxy, cyano, carboxy, halo, haloalkyl, hydroxy, and oxo;

$R^8$ is chosen from heterocycloalkyl, aryl and heteroaryl, either of which is optionally substituted with 1, 2, or 3 $R^{10}$ groups; and each $R^{10}$ is independently chosen from alkyl, alkoxy, cyano, carboxy, halo, haloalkyl, and hydroxy.

2. The compound as recited in claim 1, wherein $R^{4a}$ is H.

3. The compound as recited in claim 2, wherein $R^2$ is chosen from alkyl and heteroalkyl, any of which is optionally substituted with 1 or 2 $R^6$ groups.

4. The compound as recited in claim 3, wherein $R^2$ is alkyl.

5. The compound as recited in claim 4, wherein $R^3$ is chosen from aryl and heteroaryl, either of which is optionally substituted with 1, 2, or 3 $R^7$ groups, and either of which is optionally substituted with 1 $R^8$ group.

6. The compound as recited in claim 5, wherein $R^3$ is chosen from aryl and heteroaryl, either of which is:

(a) optionally substituted with 1, 2, or 3 $R^7$ groups, and (b) substituted with 1 $R^8$ group;

$R^8$ is chosen from heterocycloalkyl, aryl and heteroaryl, either of which is optionally substituted with 1, 2, or 3 $R^{10}$ groups; and each $R^{10}$ is independently chosen from alkyl and alkoxy.

7. The compound as recited in claim 6, wherein each $R^7$ is independently chosen from alkyl, alkoxy, and haloalkyl.

8. The compound as recited in claim 7, wherein $R^1$ is $C_{3-7}$cycloalkyl.

9. The compound as recited in claim 8, wherein $R^1$ is cyclopropyl.

10. The compound as recited in claim 9, wherein $R^3$ is a monocyclic or bicyclic heteroaryl, either of which is:

(a) optionally substituted with 1, 2, or 3 $R^7$ groups, and (b) substituted with 1 $R^8$ group.

11. The compound as recited in claim 10, wherein $R^8$ is a monocyclic aryl or heteroaryl, either of which is optionally substituted with 1 or 2 $R^{10}$ groups.

12. The compound as recited in claim 11, wherein $R^8$ is chosen from pyrrolyl, imidazolyl, and pyrazolyl, any of which is optionally substituted with 1 or 2 $R^{10}$ groups.

13. The compound as recited in claim 12, wherein $R^{10}$ is $C_{1-4}$alkyl.

14. The compound as recited in claim 1, having structural Formula II:

(II)

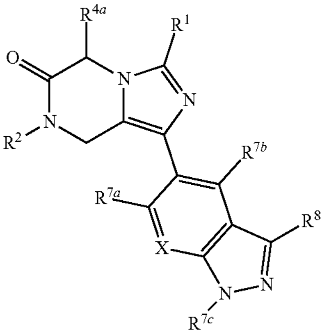

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, heteroalkyl, and haloalkyl, any of which is optionally substituted with 1, 2, or 3 $R^6$ groups;

$R^{4a}$ is chosen from H, halo, and alkyl;

X is chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$, $R^{7b}$, and $R^{7c}$ are independently chosen from H, alkyl, alkoxy, cyano, carboxy, halo, haloalkyl, and hydroxy;

$R^8$ is chosen from heterocycloalkyl, aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

15. The compound as recited in claim 14, wherein $R^1$ is $C_{3-7}$cycloalkyl;

$R^2$ is chosen from alkyl and cycloalkyl;

$R^{7a}$, $R^{7b}$, and $R^{7c}$ are independently chosen from H, cyano, and halo; and $R^8$ is monocyclic heteroaryl and is optionally substituted with 1 or 2 $R^{10}$ groups.

16. The compound as recited in claim 1, having structural Formula III:

(III)

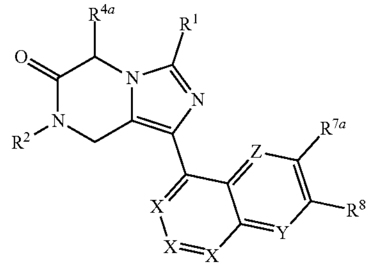

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, heteroalkyl, and haloalkyl, any of which is optionally substituted with 1, 2, or 3 $R^6$ groups;

$R^{4a}$ is chosen from H, halo, and alkyl;

each X is independently chosen from CH and N;

Y and Z are independently chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, and hydroxy;

$R^8$ is chosen from heterocycloalkyl, aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

17. The compound as recited in claim 16, wherein $R^1$ is $C_{3-7}$cycloalkyl;

$R^2$ is chosen from alkyl and cycloalkyl;

$R^{7a}$ is chosen from H, cyano, and halo; and $R^8$ is monocyclic heteroaryl and is optionally substituted with 1 or 2 $R^{10}$ groups.

18. The compound as recited in claim 1, having structural Formula III:

(IIIa)

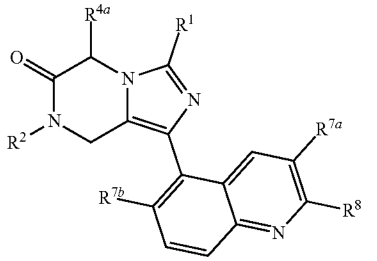

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, and haloalkyl, any of which is optionally substituted with 1, 2, or 3 $R^6$ groups;

$R^{4a}$ is chosen from H, halo, and alkyl;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, hydroxy, and oxo;

$R^{7b}$ is chosen from H and fluoro;

$R^8$ is chosen from heterocycloalkyl, aryl, and heteroaryl, any of which is optionally substituted with 1 or 2 $R^{10}$ groups; and each $R^{10}$ is independently chosen from alkyl, alkoxy, cyano, carboxy, halo, haloalkyl, and hydroxy.

19. The compound as recited in claim 18, wherein $R^1$ is chosen from

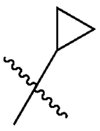

and

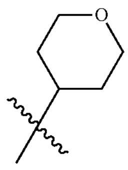

;

$R^2$ is methyl.

20. The compound as recited in claim 19, wherein $R^{7b}$ is H.

21. The compound as recited in claim 20, wherein $R^{7a}$ is chosen from alkyl, cyano, and haloalkyl; and $R^8$ is pyrazol-4-yl, and is optionally substituted with 1 $R^{10}$ group.

22. The compound as recited in claim 21, wherein $R^8$ is

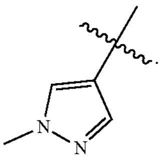 [SMILES: *c1cnn(C)c1]

23. The compound as recited in claim 1, having structural Formula IV:

(IV)

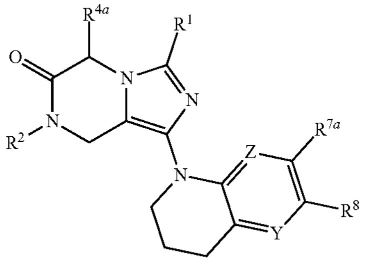

or a salt thereof, wherein:

$R^1$ is chosen from alkyl, cycloalkyl, and heterocycloalkyl, any of which is optionally substituted with 1 or 2 $R^5$ groups;

$R^2$ is H or is chosen from alkyl, heteroalkyl, and haloalkyl, any of which is optionally substituted with 1, 2, or 3 $R^6$ groups;

$R^{4a}$ is chosen from H, halo, and alkyl;

Y and Z are independently chosen from CH and N;

each $R^5$ is independently chosen from alkyl, alkoxy, alkoxyalkyl, alkylcarbonyl, alkylsulfonyl, amino, aminocarbonyl, cyano, carboxy, halo, haloalkoxy, haloalkyl, hydroxy, hydroxyalkyl, and oxo;

each $R^6$ is independently chosen from alkyl, alkoxy, cyano, carboxy, halo, haloalkyl, hydroxy, and oxo;

$R^{7a}$ is chosen from H, alkyl, alkoxy, cyano, carboxy, halo, haloalkyl, and hydroxy;

$R^8$ is chosen from aryl and heteroaryl, either of which is optionally substituted with 1 or 2 $R^{10}$ groups; and each $R^{10}$ is independently chosen from alkyl, alkoxy, cyano, carboxy, halo, haloalkyl, and hydroxy.

24. The compound as recited in claim 23, wherein $R^1$ is $C_{3-7}$cycloalkyl;

$R^2$ is chosen from alkyl and cycloalkyl;

$R^{7a}$ is chosen from H, cyano, and halo; and $R^8$ is monocyclic heteroaryl and is optionally substituted with 1 or 2 $R^{10}$ groups.

25. The compound as recited in claim 1, chosen from:

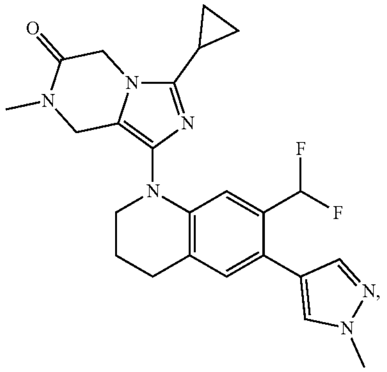

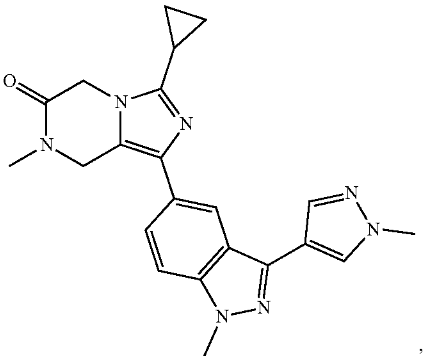

,

-continued

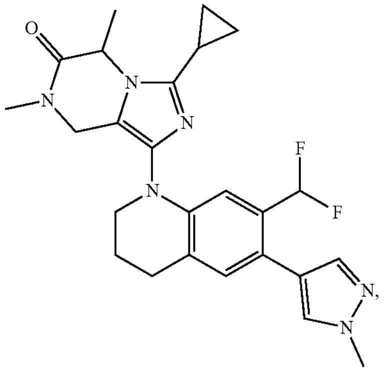

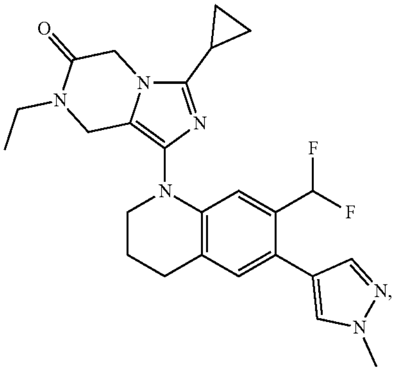

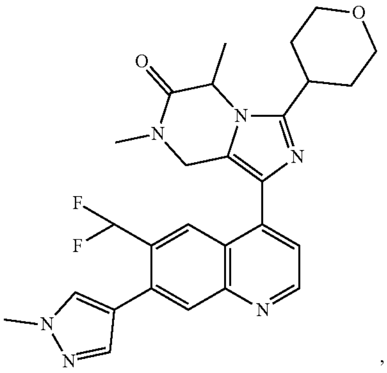

,

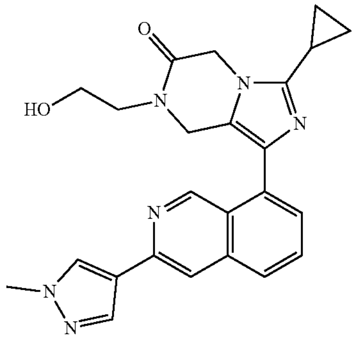

,

-continued
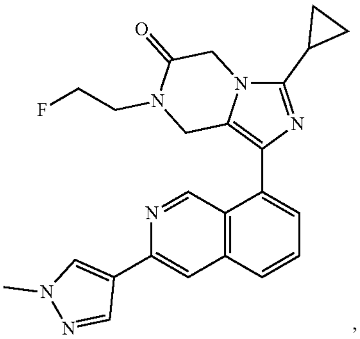
,
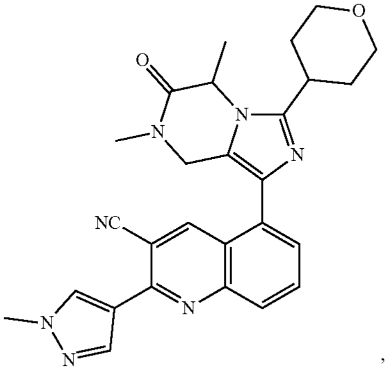
,
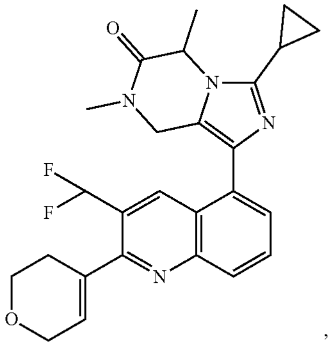
,
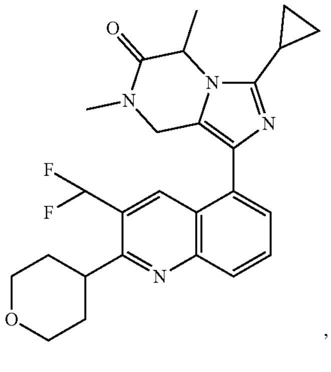
,
-continued
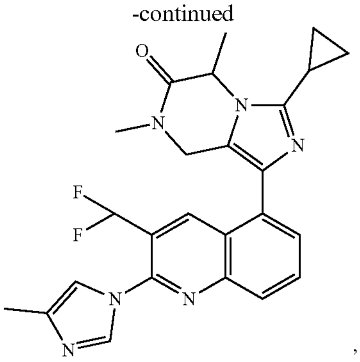
,
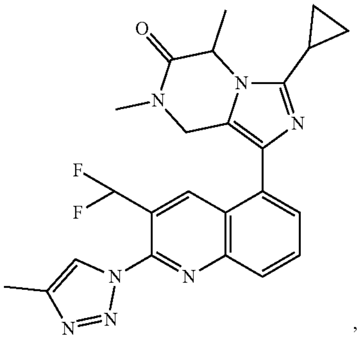
,
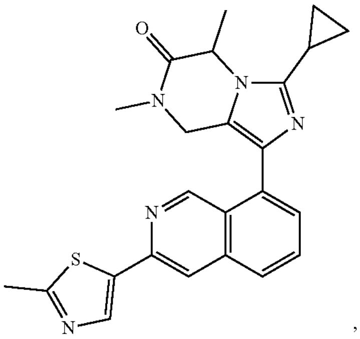
,
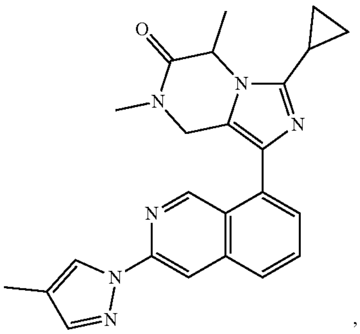
,
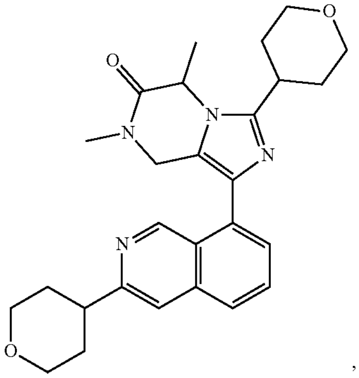
, -continued
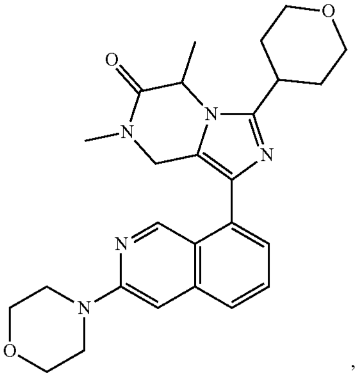
,
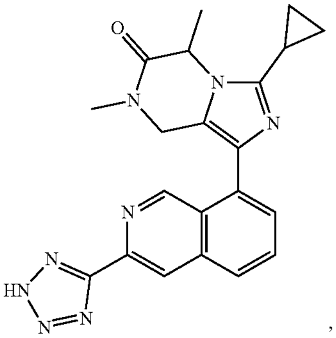
,
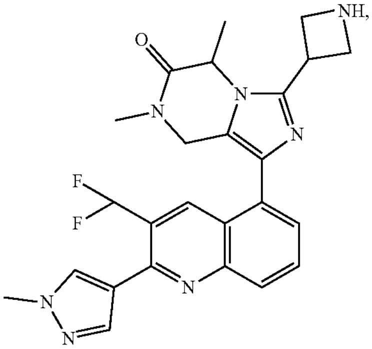
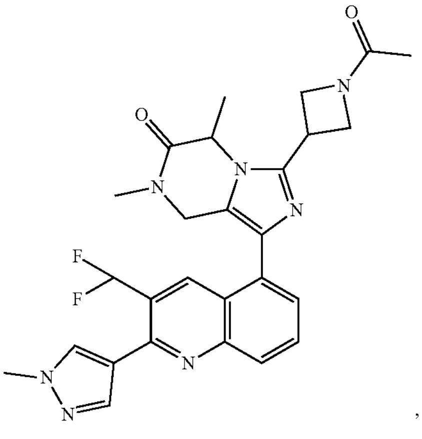
,
-continued
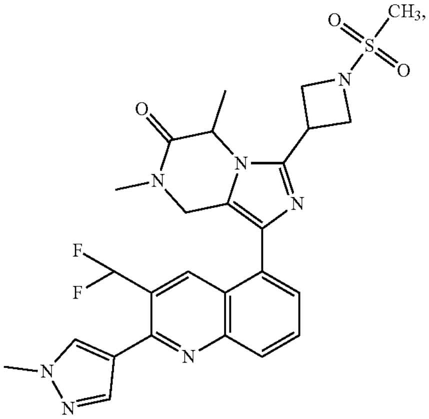
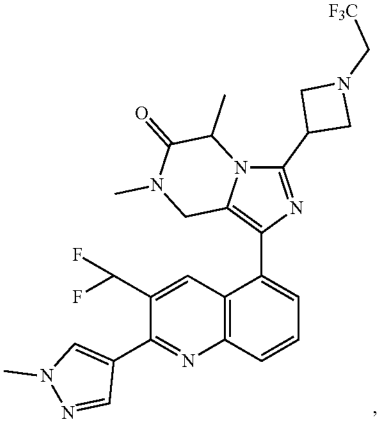
,
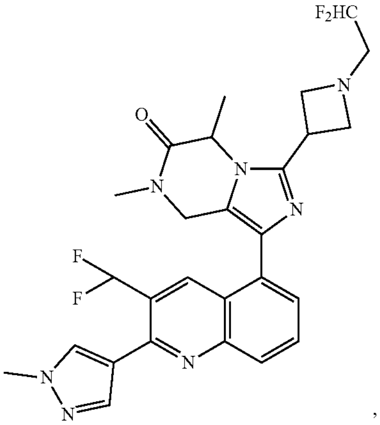
,
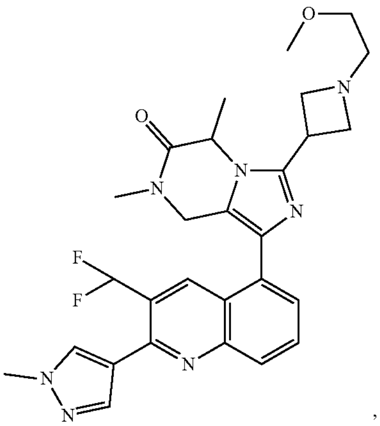
, -continued
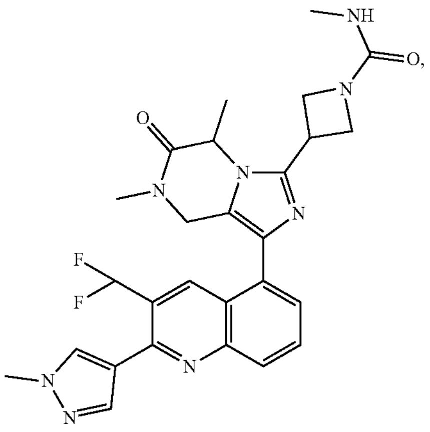
,
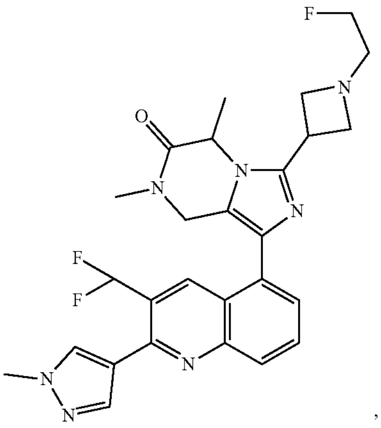
,
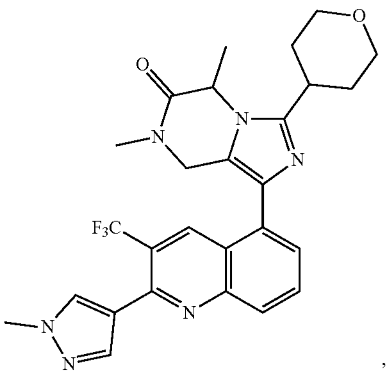
,
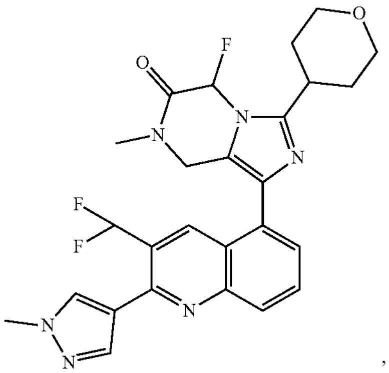
,
-continued
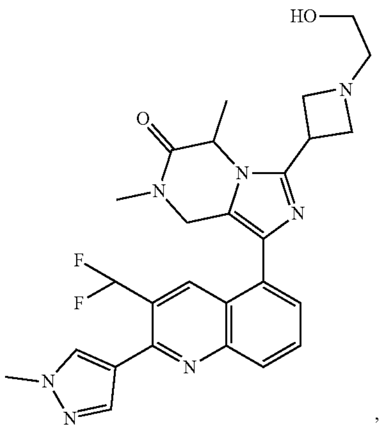
,
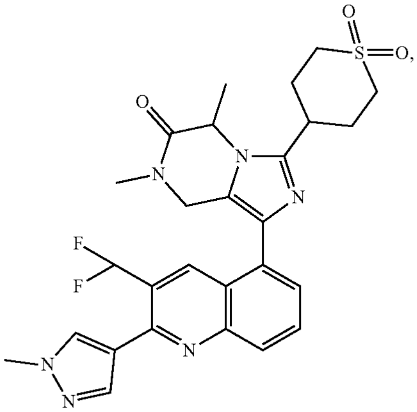
,
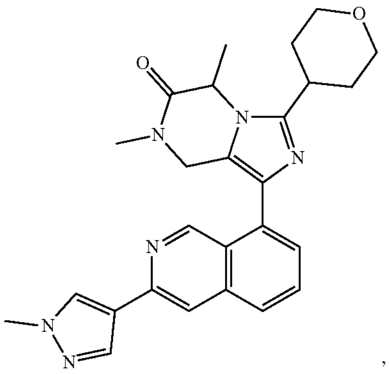
,
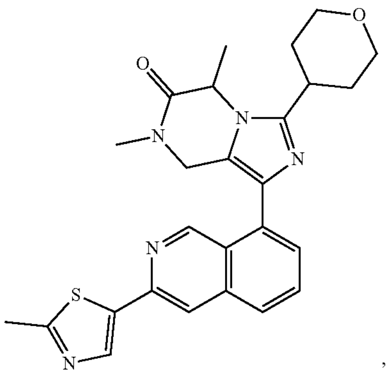
, -continued
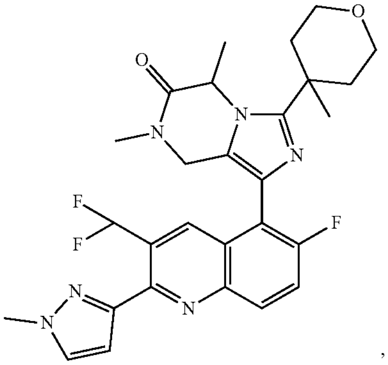
,
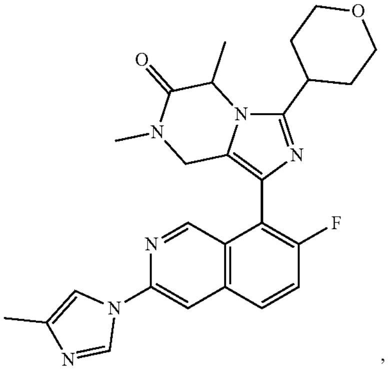
,
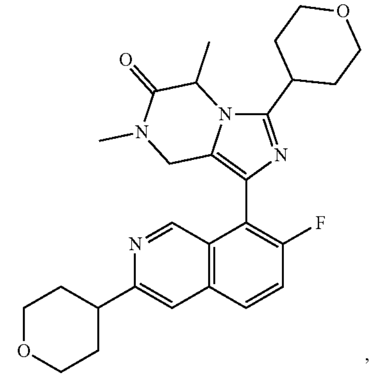
,
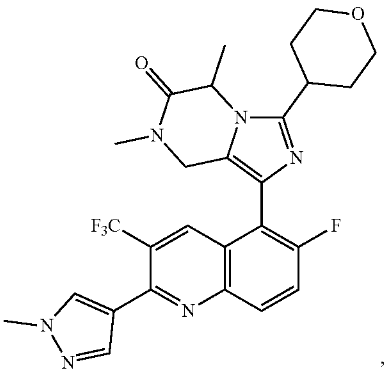
,
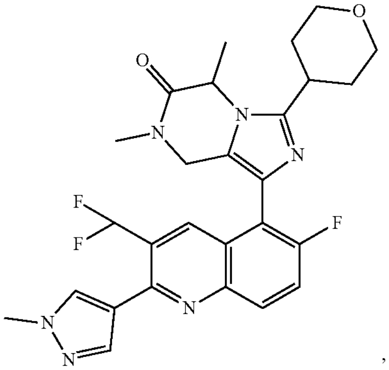
,
-continued
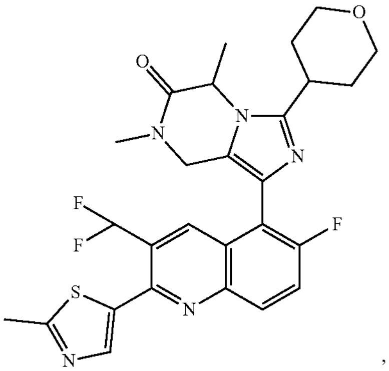
,
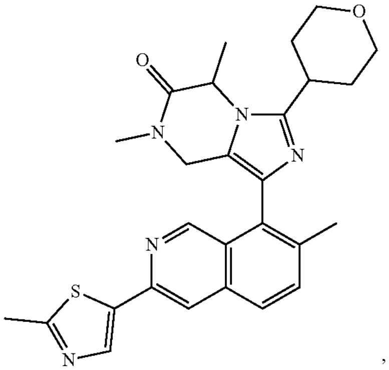
,
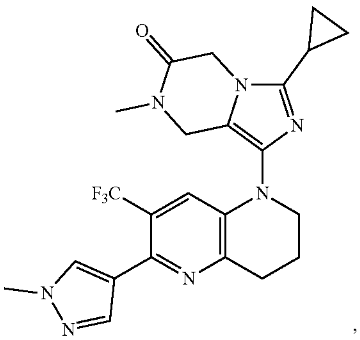
,

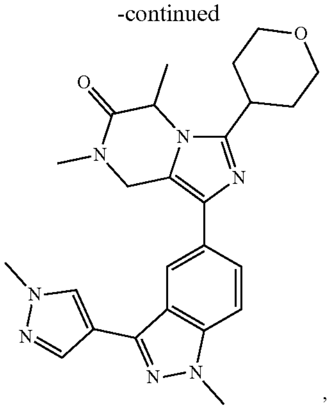
,
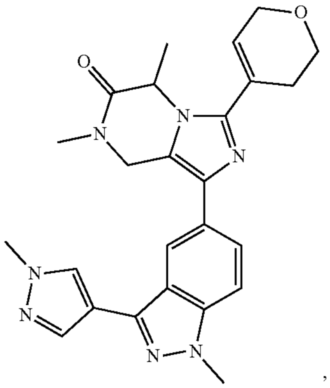
,
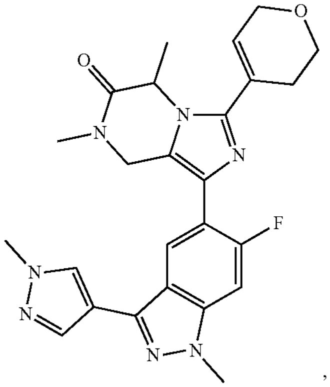
,
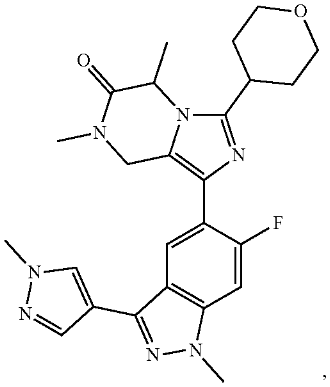
,
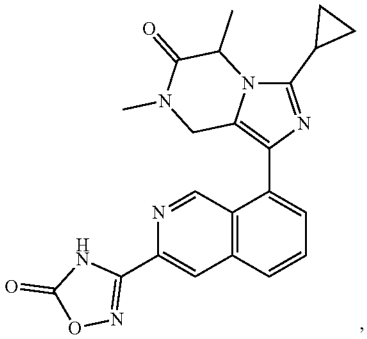
,
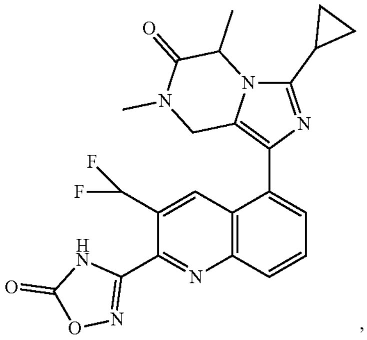
,
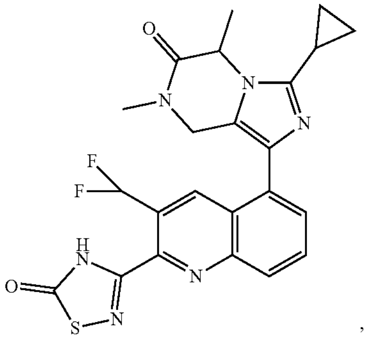
,
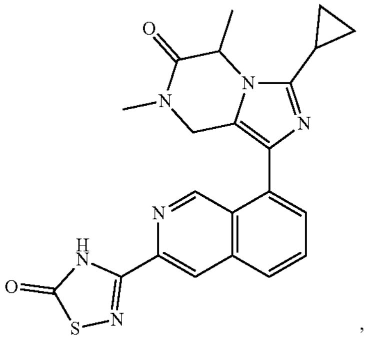
,
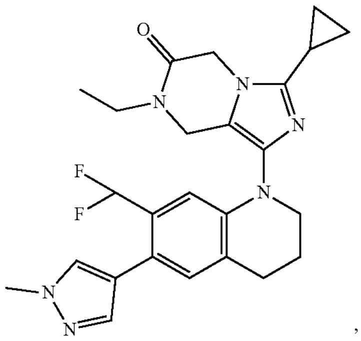
, -continued
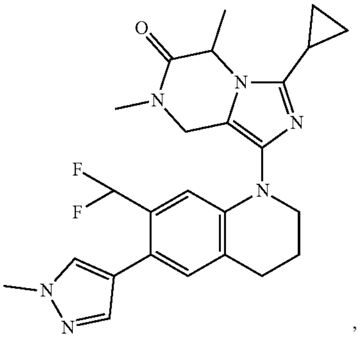
,
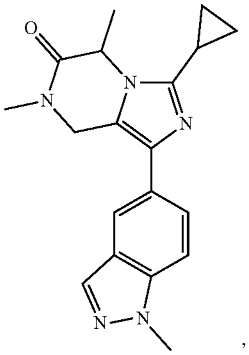
,
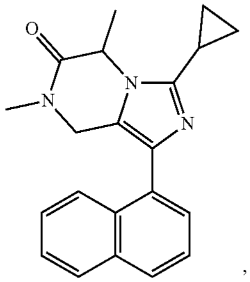
,
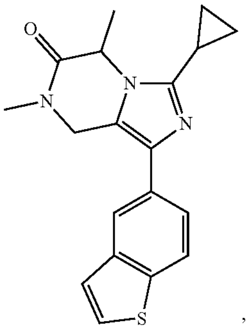
,
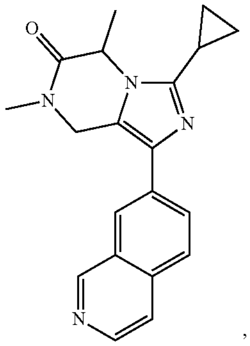
,
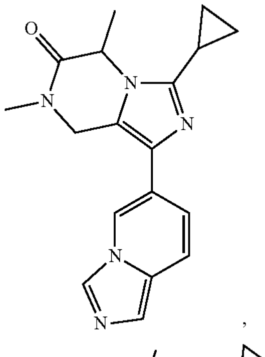
,
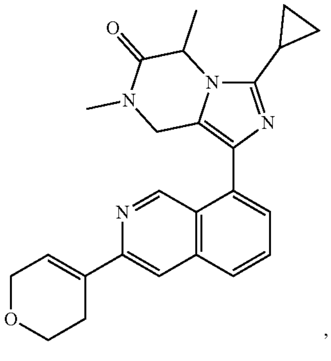
,
-continued
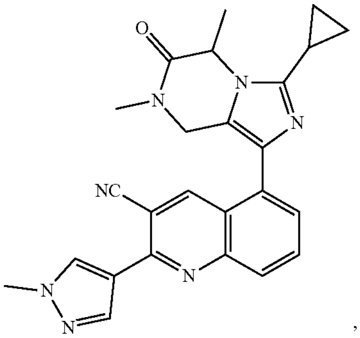
,
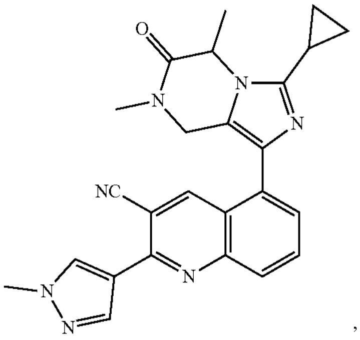
,
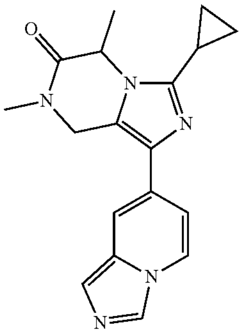
,
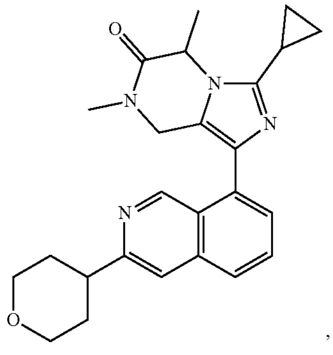
,
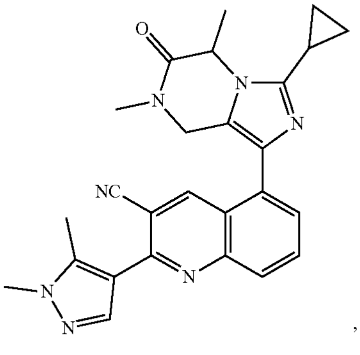
, -continued
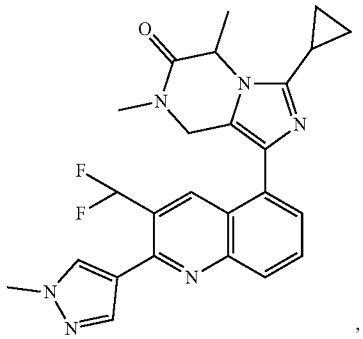
,
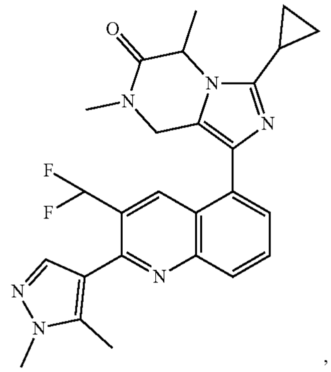
,
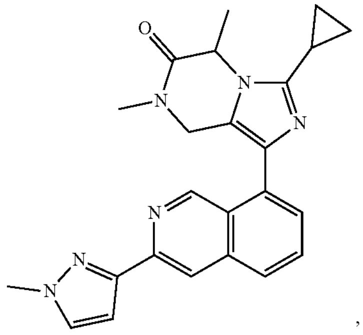
,
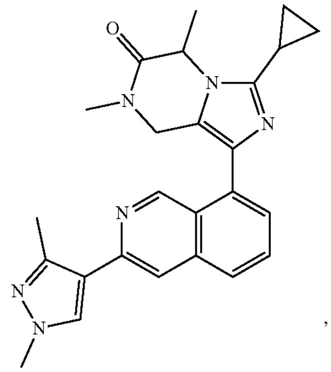
,
-continued
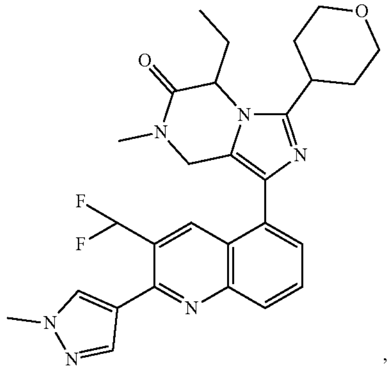
,
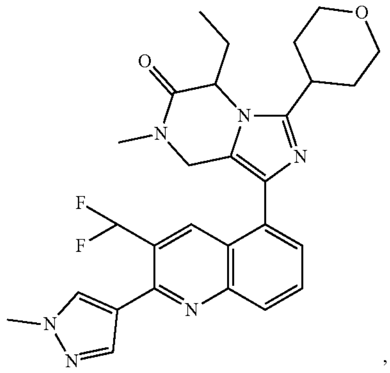
,
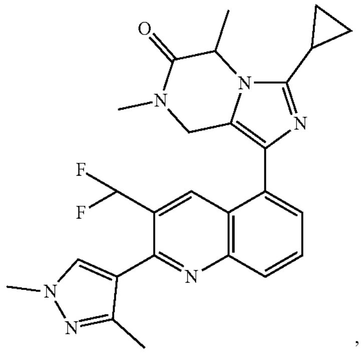
,
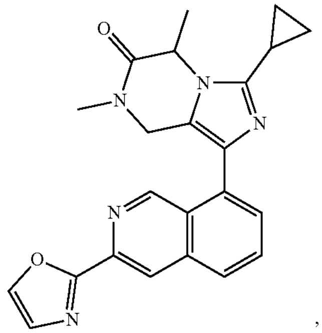
, -continued
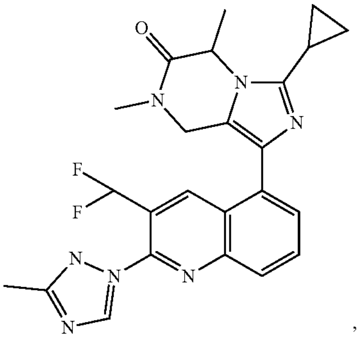
,
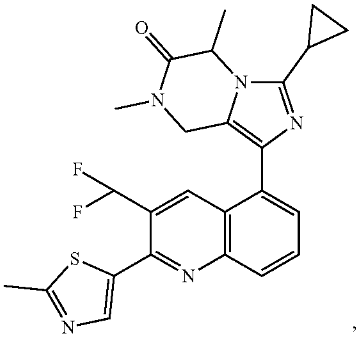
,
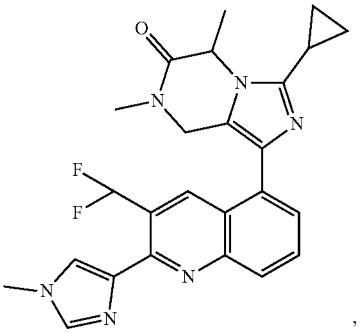
,
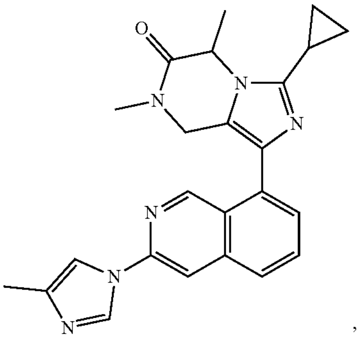
,
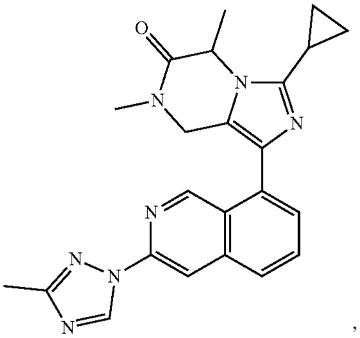
,
-continued
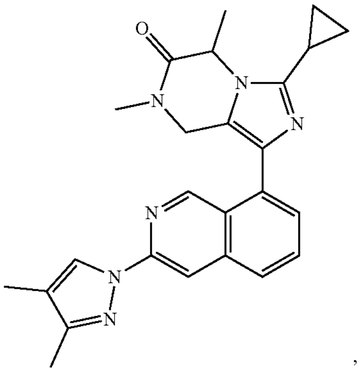
,
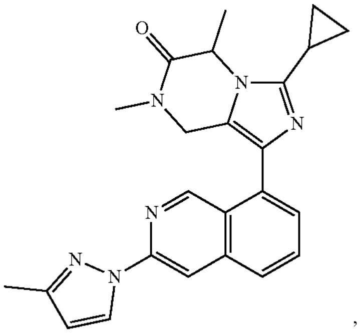
,
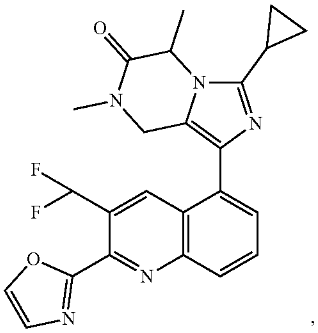
,
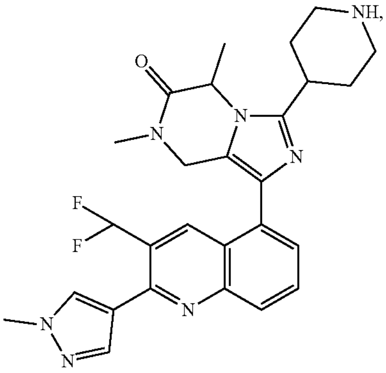
, -continued
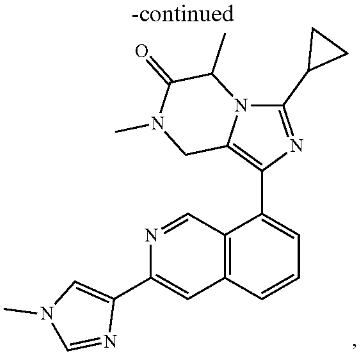
,
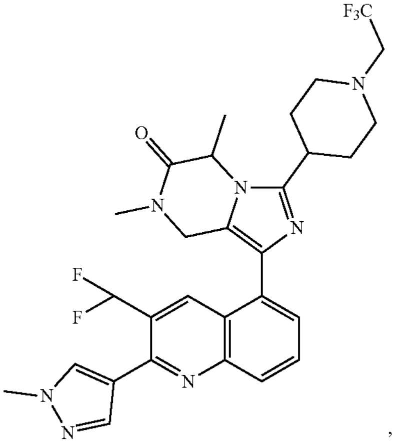
,
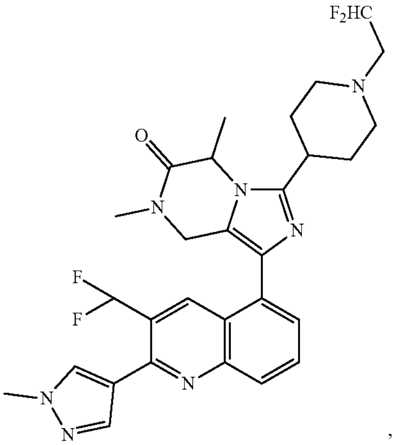
,
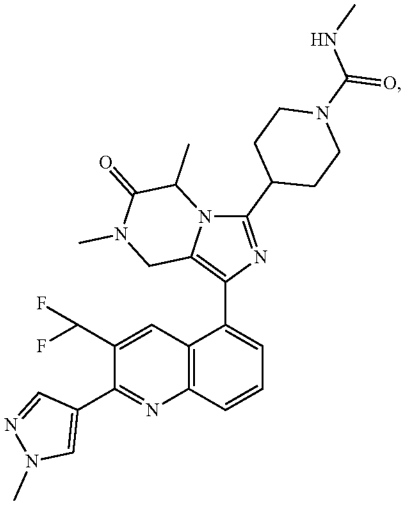
-continued
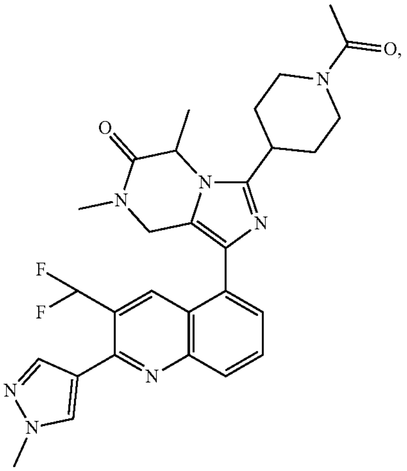
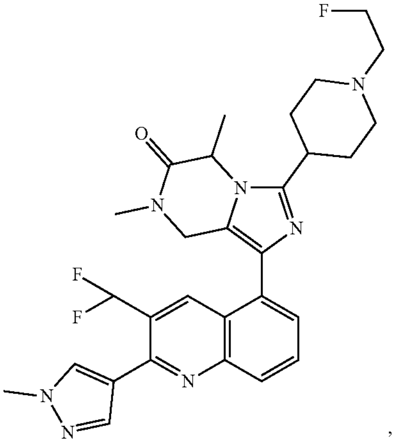
,
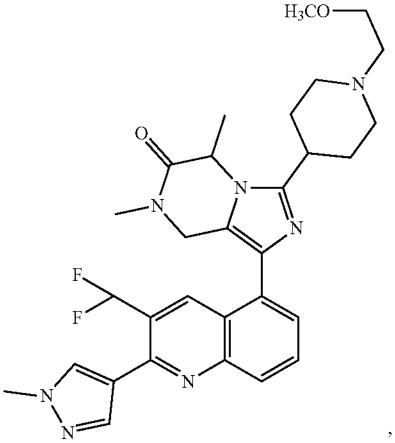
, -continued
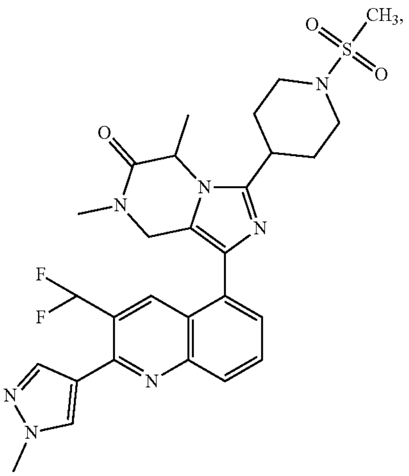
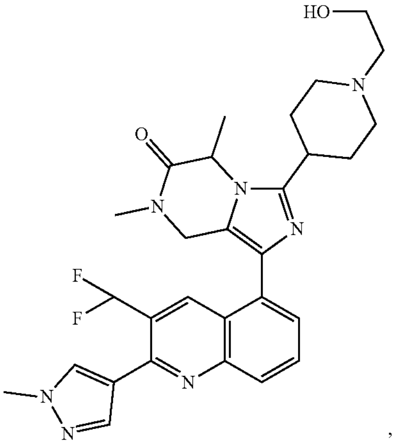
,
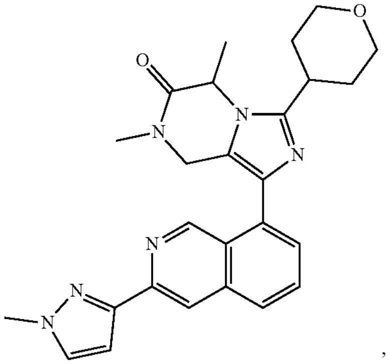
,
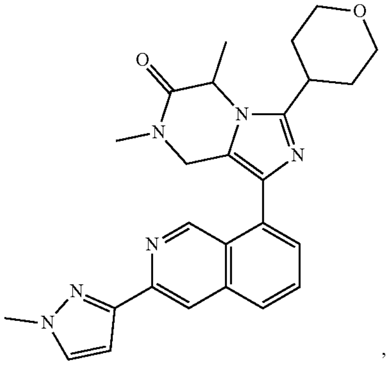
,
-continued
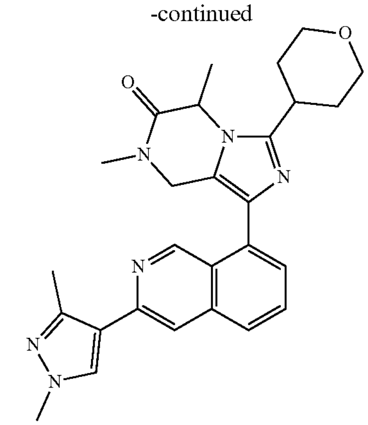
,
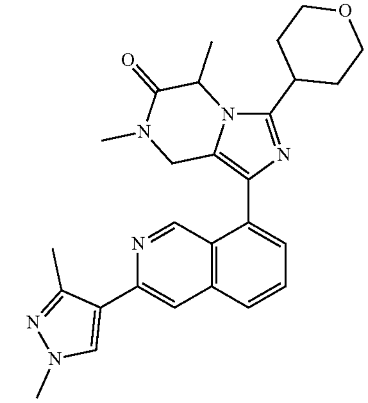
,
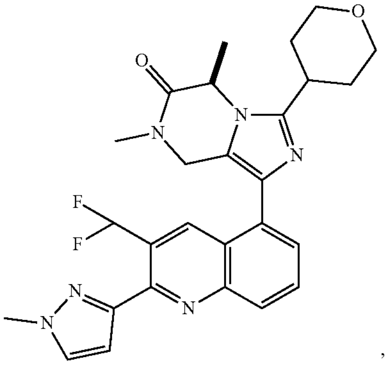
,
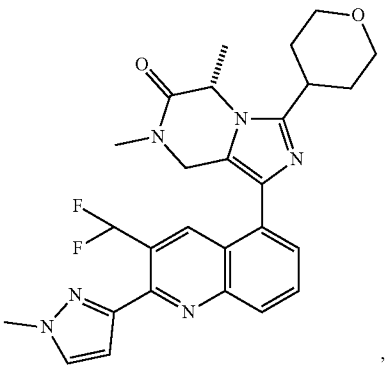
, -continued
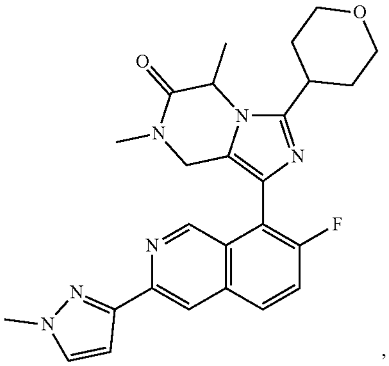
,
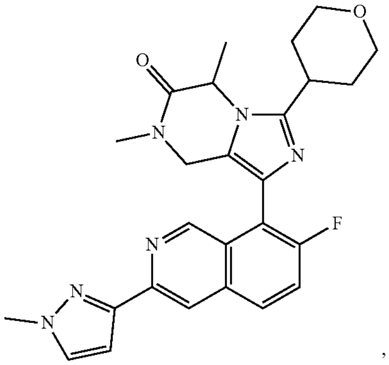
,
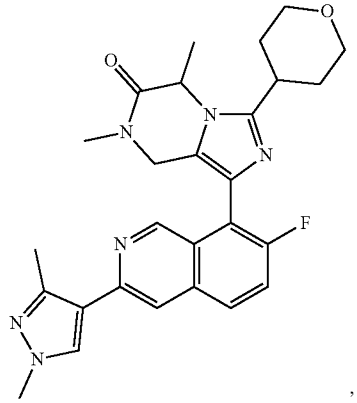
,
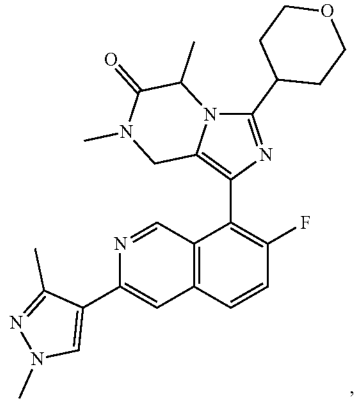
,
-continued
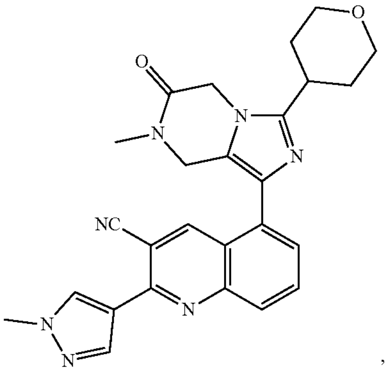
,
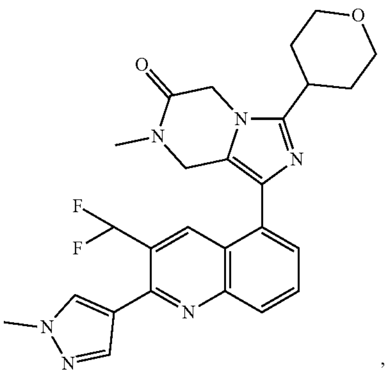
,
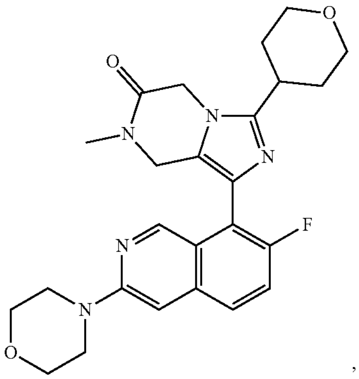
,
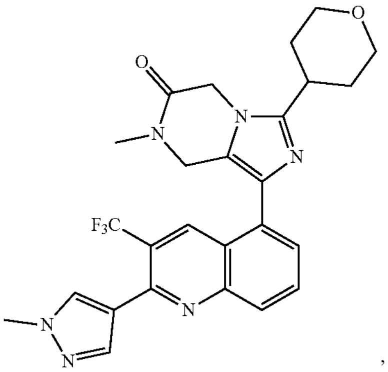
, -continued
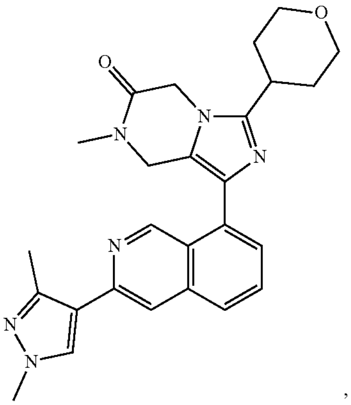
,
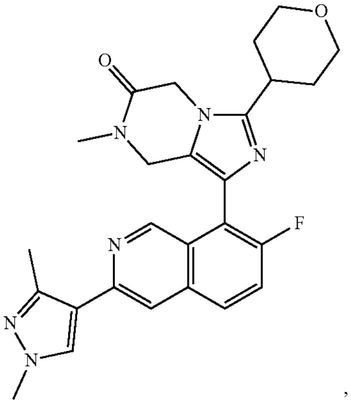
,
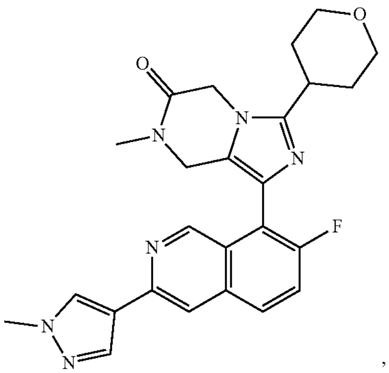
,
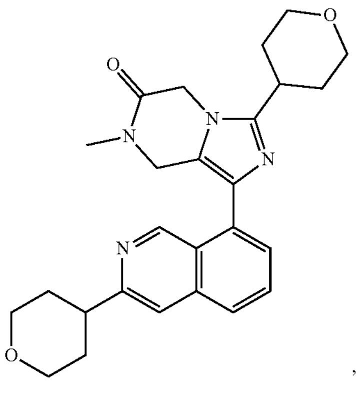
,
-continued
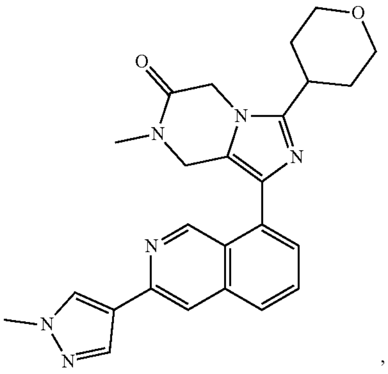
,
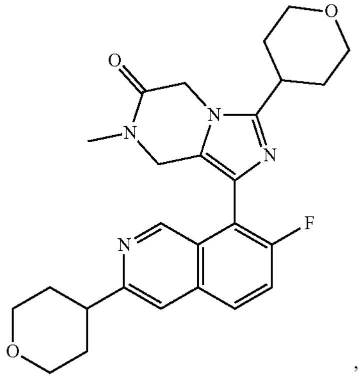
,
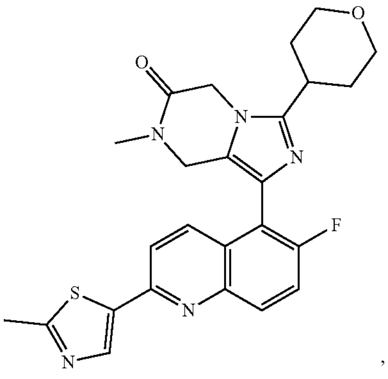
,
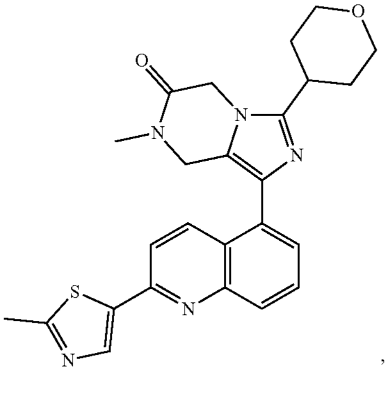
, -continued
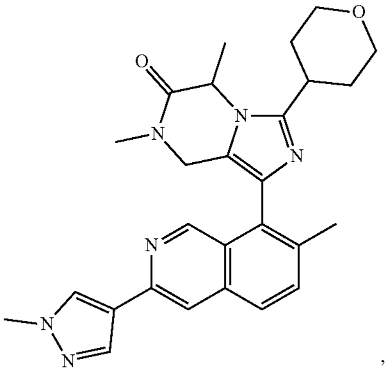
,
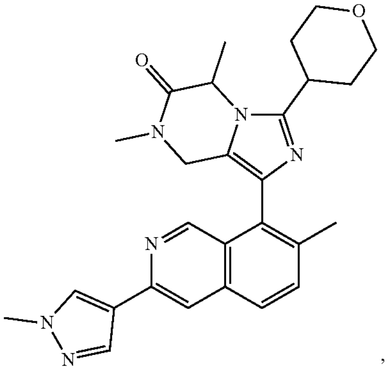
,
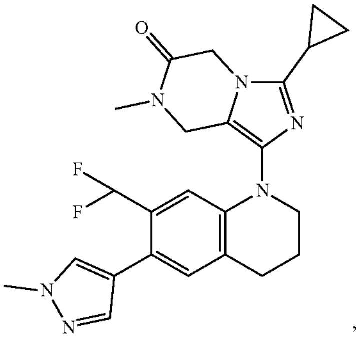
,
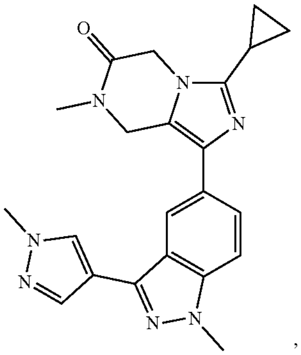
,
-continued
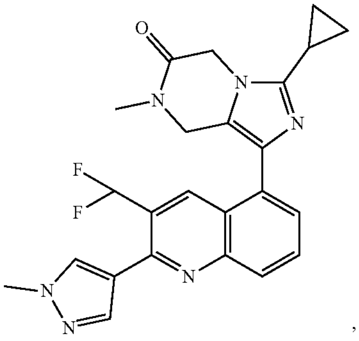
,
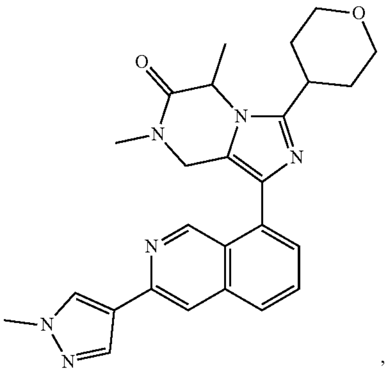
,
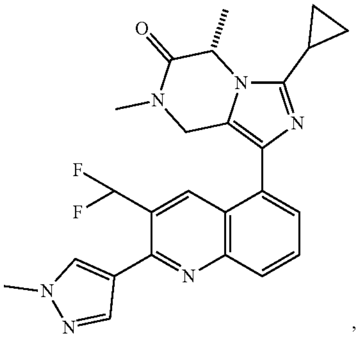
,
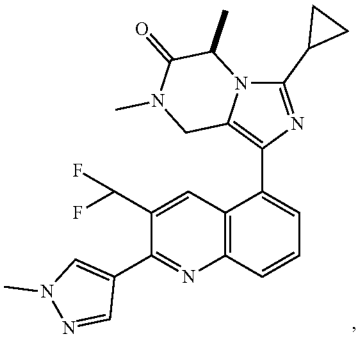
,
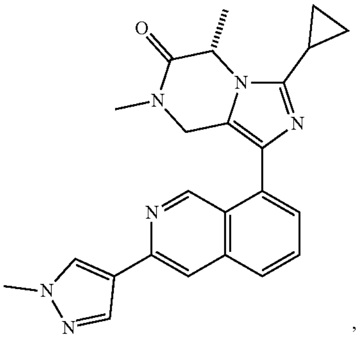
, and -continued
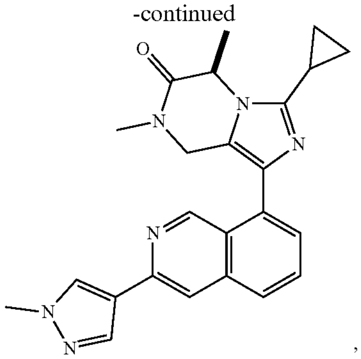
,
or a salt thereof.
26. A pharmaceutical composition comprising a compound as recited in claim 1 together with a pharmaceutically acceptable carrier.
* * * * *